United States Patent
Hagihara et al.

(10) Patent No.: US 8,450,319 B2
(45) Date of Patent: May 28, 2013

(54) PYRROLOPYRIDAZINONE COMPOUND

(75) Inventors: Masahiko Hagihara, Ube (JP); Masayuki Tanaka, Ube (JP); Tetsushi Katsube, Ube (JP); Makoto Okudo, Ube (JP); Noriaki Iwase, Ube (JP); Manabu Shigetomi, Ube (JP); Tomoko Kanda, Ube (JP); Takayuki Nakanishi, Ube (JP)

(73) Assignee: Ube Industries, Ltd., Ube-Shi, Yamaguchi (JP)

(*) Notice: Subject to any disclaimer, the term of this patent is extended or adjusted under 35 U.S.C. 154(b) by 0 days.

(21) Appl. No.: 12/087,864

(22) PCT Filed: Jan. 16, 2007

(86) PCT No.: PCT/JP2007/050533
§ 371 (c)(1),
(2), (4) Date: Jul. 16, 2008

(87) PCT Pub. No.: WO2007/081030
PCT Pub. Date: Jul. 19, 2007

(65) Prior Publication Data
US 2009/0036453 A1 Feb. 5, 2009

(30) Foreign Application Priority Data
Jan. 16, 2006 (JP) .................................. 2006-006981

(51) Int. Cl.
C07D 487/04 (2006.01)
A61K 31/5025 (2006.01)
A61P 29/00 (2006.01)

(52) U.S. Cl.
USPC ........................................ 514/248; 544/236

(58) Field of Classification Search
USPC ........................................ 544/236; 514/248
See application file for complete search history.

(56) References Cited

U.S. PATENT DOCUMENTS
2009/0192156 A1* 7/2009 Menear et al. ............. 514/234.5

FOREIGN PATENT DOCUMENTS
WO WO-01/96336 A2 12/2001
WO WO-2004/058729 A1 7/2004

OTHER PUBLICATIONS

Europ. Respiratory Soc., Feb. 13, 2007, http://www.newtocopd.com/currentaffairsnews/list751_item17680.aspx, downloaded Jan. 16, 2008.*
Foey, et al., Implications for Rheumatoid Arthritis, downloaded Jan. 17, 2008, http://www.medscape.com/viewarticle/464104.*
Prehn, et al., J. Clin. Immunol., vol. 21, No. 5, 2001, pp. 357-364.*
Walker, http://www.medpagetoday.com/Pulmonology/SmokingCOPD/19448, Medpage Today, Apr. 7, 2010.*
Wu, et al., Ann. Surg., Mar. 2007; 245(3): 480-486.*
Rovin, et al., J. Am. Soc. Nephrol., 12:1659-1667, 2001.*
Huang, et al., Curr. Opin. Chem. Biol., vol. 5, # 4, Aug. 8, 2001, 432-438.*
Sullivank, CHEST Physician Article, 03.05.11.*
Soares, et al., Brit. J. Pharmacol., Nov. 2003; 140(5): 855-862.*
Seybold, et al., Blood, 2005, 105:3569-3576.*
Monge, A. et al., Journal of Medicinal Chemistry, 1991, vol. 34, No. 10, pp. 3023-3029.
Murineddu et al., "Synthesis and Cytotoxic Activities of Pyrrole[2,3-d]pyridazin-4-one Derivatives", Chem. Pharm. Bull., vol. 50, No. 6, pp. 754-759, (2002).
Yamasaki et al., "A New Synthetic Approach to fused 1,4-Dihydropyridazines", Heterocycles, vol. 43, No. 9, pp. 1863-1871, (1996).
R'kyek et al., "5-Alkynyl-4-Chloro- and 4-Alkynyl-5-Chloro-2-Methylpyridazin-3(2H)-Ones: Convenient Precursors for The Preparation of 2-Substituted Pyrrolo[2,3-d]Pyridazinones", Heterocycles, vol. 60, No. 11, pp. 2471-2483, (2003).
Karlsson et al., "Phosphodiesterase 4 Inhibitors for the treatment of asthma", Expert Opinion on Therapeutic Patents, vol. 7, No. 9, pp. 989-1003, (1997).
Compton et al., "Cilomilast, a selective phosphodiesterase-4 inhibitor for treatment of patients with chronic obstructive pulmonary disease: a randomised, dose-ranging study", The Lancet, vol. 358, pp. 265-270, (Jul. 28, 2001).
Schmidt et al., "The phosphodiesterase 4 inhibitor roflumilast is effective in the treatment of allergic rhinitis", J, Allergy Clin. Immunol., vol. 108, No. 4, pp. 530-536, (Oct. 2001).
Harbinson et al., "The effect of a novel orally active selective PDE4 isoenzyme inhibitor (CDP840) on allergen-induced responses in asthmatic subjects", European Respiratory Journal, vol. 10, pp. 1008-1014, (1997).

* cited by examiner

Primary Examiner — Susanna Moore
Assistant Examiner — Cecilia M Jaisle
(74) Attorney, Agent, or Firm — Birch, Stewart, Kolasch & Birch, LLP

(57) ABSTRACT

The present invention discloses a pyrrolopyridazinone compound represented by the formula (1):

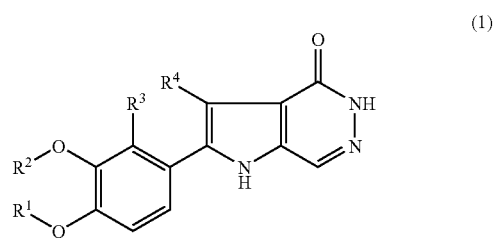

useful, for example, as an anti-inflammatory agent or an inhibitor of respiratory tract contraction.

14 Claims, No Drawings

PYRROLOPYRIDAZINONE COMPOUND

TECHNICAL FIELD

The present invention relates to a novel pyrrolopyridazinone compound and a pharmaceutically acceptable salt thereof useful as a medicine, and a pharmaceutical composition containing these.

The pyrrolopyridazinone compound according to the present invention has a potent phosphodiesterase 4 (hereinafter abbreviated to as PDE4) inhibiting action, and controls function of cells restrainingly by causing increase in a cyclic adenosine monophosphate (cAMP) concentration in cells. PDE4 localizes in cells which participate in an inflammatory reaction, and further exists in bronchial smooth muscle cells, so that it causes restraint of functions of inflammatory cells and relaxation of bronchial smooth muscle, whereby it is useful, for example, as an anti-inflammatory agent or an inhibitor of respiratory tract contraction.

BACKGROUND ART

It has been known pyrrolopyridazinone compounds similar to the compound of the present invention (see Patent literature 1 and Non-patent literatures 1 to 3), but it has been not known that these compounds have a PDE4 inhibitory activity.

As a PDE4 inhibitor, it has already been known compounds such as xanthine derivatives, Rolipram analogues, or nitroquazone derivatives, etc., but these inhibitors could not be used clinically since they causes severe vomit or nausea as side effects (see Non-patent literature 4). In recent years, PDE4 inhibitors improved in side effects such as vomit and nausea have been reported that they are useful for treatment of asthma, chronic obstructive pulmonary disease (hereinafter also referred to as COPD) and allergic coryza (see Non-patent literatures 5 to 7).

However, it cannot be said that they have a clinically sufficient effects even in compounds in which vomit or nausea as side effects are improved with a certain extent.

Patent literature 1: WO 01/96336 pamphlet
Non-patent literature 1: Chem. Pharm. Bull., 50, 754 (2002)
Non-patent literature 2: Heterocycles, 43, 1863 (1996)
Non-patent literature 3: Heterocycles, 60, 2471 (2003)
Non-patent literature 4: Exp. Opin. Ther. Patents, 7, 989 (1997)
Non-patent literature 5: Lancet, 358, 265 (2001)
Non-patent literature 6: J. Allergy Clin. Immunol., 108, 530 (2001)
Non-patent literature 7: Eur. Respir. J., 10, 1008 (1997)

DISCLOSURE OF THE INVENTION

Problems to be Solved by the Invention

The present inventors have intensively studied on syntheses and pharmacological effects of compounds having PDE4 inhibitory activity and less side effects, and as a result, they have found that a novel pyrrolopyridazinone compound is a compound having a potent PDE4 inhibitory activity, excellent oral absorbability and continuity of action, and causing less vomit or nausea as side effects, whereby the present invention has been accomplished. Accordingly, the present invention is to provide a novel pyrrolopyridazinone compound and a pharmaceutically acceptable salt thereof having a potent PDE4 inhibitory activity, excellent oral absorbability and continuity of action, and causing less vomit or nausea as side effects, and a pharmaceutical composition containing these.

Means to Solve the Problems

The present invention relates to a novel pyrrolopyridazinone compound and a pharmaceutically acceptable salt thereof, having a potent PDE4 inhibitory activity, excellent oral absorbability and continuity of action, and causing less vomit or nausea as side effects.

The "pyrrolopyridazinone compound" of the present invention means a compound represented by the following formula (1).

A pyrrolopyridazinone compound represented by

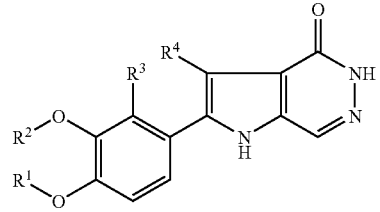

wherein $R^1$ represents a $C_1$-$C_2$ alkyl group or a halogeno $C_1$-$C_2$ alkyl group, $R^2$ represents a $C_3$-$C_5$ cycloalkyl group, a ($C_3$-$C_5$ cycloalkyl)$C_1$-$C_2$ alkyl group or a $C_1$-$C_3$ alkyl group, $R^3$ represents a hydrogen atom, or a methylene group or a cis-vinylene group each of which is a group for constituting a substituted oxygen-containing heterocyclic ring in combination with the group —O—$R^2$, $R^4$ represents a hydrogen atom, a halogen atom, a $C_1$-$C_8$ alkyl group, a $C_2$-$C_6$ alkenyl group, a $C_2$-$C_6$ alkynyl group, a hydroxy $C_3$-$C_6$ alkenyl group, a hydroxy $C_3$-$C_6$ alkynyl group, a $C_1$-$C_6$ alkyl group substituted by a substituent(s) selected from Substituent group (a), a $C_3$-$C_6$ cycloalkyl group which may be substituted by a substituent(s) selected from Substituent group (b), "a $C_1$-$C_3$ alkyl group which is substituted by a $C_3$-$C_6$ cycloalkyl group which may be substituted by a substituent(s) selected from Substituent group (b), and which may be substituted by a hydroxy group", an aromatic ring group or heteroaromatic ring group each of which may be substituted by a substituent(s) selected from Substituent group (c), or "$C_1$-$C_2$ alkyl group which is substituted by an aromatic ring group or heteroaromatic ring group each of which may be substituted by a substituent(s) selected from Substituent group (c), and which may be substituted by a hydroxy group", Substituent group (a) represents a halogen atom, a hydroxy group, a cyano group, a carboxy group, a $C_1$-$C_5$ alkoxy group, a halogeno $C_1$-$C_4$ alkoxy group, a $C_3$-$C_6$ cycloalkoxy group, a ($C_3$-$C_6$ cycloalkyl) $C_1$-$C_2$ alkoxy group, a $C_1$-$C_4$ alkoxycarbonyl group, a $C_2$-$C_4$ alkanoyl group, a $C_2$-$C_4$ alkanoyloxy group or a $C_1$-$C_4$ alkyl-substituted amino group, Substituent group (b) represents a hydroxy group or a halogen atom, Substituent group (c) represents a halogen atom, a hydroxy group, a cyano group, a nitro group, a carboxy group, a $C_1$-$C_5$ alkoxy group, a $C_1$-$C_4$ alkoxycarbonyl group, a $C_2$-$C_4$ alkanoyloxy group, a $C_1$-$C_4$ alkyl-substituted amino group or a $C_1$-$C_4$ alkyl group which may be substituted by a substituent(s) selected from the group consisting of (a halogen atom, a hydroxy group and a carboxy group), or a pharmaceutically acceptable salt thereof.

BEST MODE TO CARRY OUT THE INVENTION

In the compound represented by the above-mentioned formula (1), a "$C_1$-$C_2$ alkyl group", and a "$C_1$-$C_2$ alkyl group portion" of the halogeno $C_1$-$C_2$ alkyl group represented by $R^1$, a "$C_1$-$C_2$ alkyl group portion" of the ($C_3$-$C_4$ cycloalkyl)-$C_1$-$C_2$ alkyl group represented by $R^2$, and a "$C_1$-$C_2$ alkyl group portion" in the "$C_1$-$C_2$ alkyl group which is substituted by an aromatic ring group or heteroaromatic ring group each of which may be substituted by a substituent(s) selected from Substituent group (c), and may be substituted by a hydroxy group" represented by $R^4$ each means the "$C_1$-$C_2$ alkyl group" having the same meaning, and such a "$C_1$-$C_2$ alkyl group" may be mentioned, for example, a methyl or ethyl group, preferably a methyl group.

The "halogeno portion" of the halogeno $C_1$-$C_2$ alkyl group represented by $R^1$ means a halogen atom such as a fluorine or chlorine atom, etc., preferably a fluorine atom.

As the "halogeno $C_1$-$C_2$ alkyl group" represented by $R^1$, there may be mentioned, for example, a fluoromethyl, difluoromethyl, trifluoromethyl, 2-fluoroethyl, 2,2-difluoroethyl, 2,2,2-trifluoroethyl, chloromethyl, dichloromethyl, trichloromethyl, 2-chloroethyl, 2,2-dichloroethyl or 2,2,2-trichloroethyl group, etc., preferably a fluoromethyl, difluoromethyl, chloromethyl or dichloromethyl group, more preferably a difluoromethyl group.

As $R^1$, there may be preferably mentioned a methyl or difluoromethyl group, more preferably difluoromethyl group.

As the "$C_3$-$C_5$ cycloalkyl group" represented by $R^2$, there may be mentioned, for example, a cyclopropyl, cyclobutyl or cyclopentyl group, preferably a cyclopropyl or cyclobutyl group.

As the "($C_3$-$C_5$ cycloalkyl)$C_1$-$C_2$ alkyl group" represented by $R^2$, there may be mentioned, for example, a cyclopropylmethyl, 1-cyclopropylethyl, 2-cyclopropylethyl, cyclobutylmethyl, 1-cyclobutylethyl, 2-cyclobutylethyl, cyclopentylmethyl, 1-cyclopentylethyl or 2-cyclopentylethyl group, preferably a cyclopropylmethyl or cyclobutylmethyl group.

As the "$C_1$-$C_3$ alkyl group" represented by $R^2$, there may be mentioned, for example, a straight or branched $C_1$-$C_3$ alkyl group such as a methyl, ethyl, propyl or isopropyl group, preferably an ethyl or isopropyl group.

As $R^2$, there may be preferably mentioned a cyclopropyl, cyclobutyl, cyclopentyl, cyclopropylmethyl, cyclobutylmethyl, ethyl or isopropyl group, more preferably a cyclopropyl, cyclobutyl, cyclopentyl, cyclopropylmethyl or isopropyl group, particularly preferably a cyclopropyl or cyclopropylmethyl group.

$R^3$ represents a hydrogen atom, or a methylene group or a cis-vinylene group for constituting a substituted oxygen-containing heterocyclic ring in combination with the group —O—$R^2$.

The substituted oxygen-containing hetero ring formed by $R^3$ in combination with the group —O—$R^2$ is a substituted oxygen-containing hetero ring constituted by a tetrahydrofuran ring or 3,6-dihydro-2H-pyran ring, and as a substituent(s) on the ring, there may be mentioned, for example, a 1,2-ethylene, 1,3-propylene, 1,4-butylene, cyclopropyl, cyclobutyl or a methyl group, etc.

A substituted position on the ring is at the carbon atom which directly binds to an oxygen atom of the group —O—$R^2$. A number of the substituent(s) on the ring is 1 or 2, and when the substituents are of a plural number, they may be the same or different from each other.

As the substituted oxygen-containing hetero ring formed by $R^3$ in combination with the group —O—$R^2$, there may be preferably mentioned a 2,2-(1,2-ethylene)-tetrahydrofuran ring, 2,2-(1,3-propylene)-tetrahydrofuran ring, 2,2-(1,4-butylene)-tetrahydrofuran ring, 2-cyclopropyl-tetrahydrofuran ring, 2-cyclobutyl-tetrahydrofuran ring, 2,2-dimethyl-tetrahydrofuran ring, 6,6-(1,2-ethylene)-3,6-dihydro-2H-pyran ring, 6,6-(1,3-propylene)-3,6-dihydro-2H-pyran ring, 6,6-(1,4-butylene)-3,6-dihydro-2H-pyran ring, 6-cyclopropyl-3,6-dihydro-2H-pyran ring, 6-cyclobutyl-3,6-dihydro-2H-pyran ring or 6,6-dimethyl-3,6-dihydro-2H-pyran ring, more preferably a 2,2-(1,4-butylene)-tetrahydrofuran ring, 6,6-(1,3-propylene)-3,6-dihydro-2H-pyran ring, 6,6-(1,4-butylene)-3,6-dihydro-2H-pyran ring, 6-cyclopropyl-3,6-dihydro-2H-pyran ring or 6,6-dimethyl-3,6-dihydro-2H-pyran ring.

As the "halogen atom" which is a substituent(s) of $R^4$, there may be mentioned, for example, a fluorine, chlorine, bromine or iodine atom, preferably a chlorine, bromine or iodine atom, more preferably a chlorine or bromine atom.

The halogen atoms which are a substituent(s) in Substituent group (a), Substituent group (b) and Substituent group (c) represented by $R^4$, and the halogen atom in "a $C_1$-$C_4$ alkyl group which may be substituted by a substituent(s) selected from the group consisting of (a halogen atom, a hydroxy group, and a carboxy group)" of Substituent group (c) each means "a halogen atom" having the same meanings, and such a halogen atom may be mentioned, for example, a fluorine, chlorine, bromine or iodine atom, preferably a fluorine, chlorine or bromine atom, more preferably a fluorine or chlorine atom.

As the "$C_1$-$C_8$ alkyl group" of $R^4$, there may be mentioned, for example, a straight or branched $C_1$-$C_8$ alkyl group such as a methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, 1-ethylpropyl, hexyl, 1-methylpentyl, 2-methylpentyl, 3-methylpentyl, 4-methylpentyl, 1-ethylbutyl, 2-ethylbutyl, 1,1-dimethylbutyl, 2,2-dimethylbutyl, 3,3-dimethylbutyl, 1,3-dimethylbutyl, 2,3-dimethylbutyl, heptyl, 1-methylhexyl, 2-methylhexyl, 3-methylhexyl, 4-methylhexyl, 5-methylhexyl, 1-ethylpentyl, 2-ethylpentyl, 3-ethylpentyl, 1,2-dimethylpentyl, 1,3-dimethylpentyl, 1,4-dimethylpentyl, 2,3-dimethylpentyl, 2,4-dimethylpentyl, 3,4-dimethylpentyl, 1,1-dimethylpentyl, 2,2-dimethylpentyl, 3,3-dimethylpentyl, 4,4-dimethylpentyl, 1-methyl-2-ethylbutyl, 1-methylheptyl, 2-methylheptyl, 3-methylheptyl, 4-methylheptyl, 5-methylheptyl, 6-methylheptyl, 1-ethylhexyl, 2-ethylhexyl, 3-ethylhexyl, 4-ethylhexyl, 1,2-dimethylhexyl, 1,3-dimethylhexyl, 1,4-dimethylhexyl, 1,5-dimethylhexyl, 2,3-dimethylhexyl, 2,4-dimethylhexyl, 2,5-dimethylhexyl, 3,4-dimethylhexyl, 3,5-dimethylhexyl, 1,1-dimethylhexyl, 2,2-dimethylhexyl, 3,3-dimethylhexyl, 4,4-dimethylhexyl, 5,5-dimethylhexyl, 1-methyl-3-ethylpentyl, 2-methyl-3-ethylpentyl, 2-propylpentyl or 2,2,3,3-tetramethylbutyl group, etc., preferably a methyl, ethyl, propyl, isopropyl, butyl, isobutyl, pentyl, isopentyl, neopentyl, 2-methylbutyl, hexyl, 2-methylpentyl, 3-methylpentyl, 4-methylpentyl, 2-ethylbutyl, 2,2-dimethylbutyl, 3,3-dimethylbutyl, 2,3-dimethylbutyl, heptyl, 2-methylhexyl, 3-methylhexyl, 4-methylhexyl, 5-methylhexyl, 2,3-dimethylpentyl, 2,4-dimethylpentyl, 3,4-dimethylpentyl, 2,2-dimethylpentyl, 3,3-dimethylpentyl, 4,4-dimethylpentyl, octyl, 2-methylheptyl, 3-methylheptyl, 4-methylheptyl, 5-methylheptyl, 6-methylheptyl, 2-ethylhexyl, 3-ethylhexyl, 4-ethylhexyl, 2,3-dimethylhexyl, 2,4-dimethylhexyl, 2,5-dimethylhexyl, 3,4-dimethylhexyl, 3,5-dimethylhexyl, 2,2-dimethylhexyl, 3,3-dimethylhexyl, 4,4-dimethylhexyl, 5,5-dimethylhexyl, 2-methyl-3-ethylpentyl, 2-propylpentyl or 2,2,3,3-tetramethylbutyl group, more preferably a methyl, ethyl, propyl, isopropyl, butyl, isobutyl, pentyl, isopentyl, neopentyl, hexyl, 2-ethylbutyl, 2,2-dimethylbutyl, 3,3-dimethylbutyl, heptyl, 2,2-dimethylpentyl, 3,3-dimethylpentyl, 4,4-dimethylpentyl, octyl, 4-ethylhexyl, 2,2-dimethylhexyl, 3,3-dimethylhexyl, 4,4-dimethylhexyl, 5,5-dimethylhexyl, 2-propylpentyl or 2,2,3,3-tetramethylbutyl group, particularly preferably a methyl, ethyl, propyl, isopropyl, butyl, isobutyl, pentyl, isopentyl, neopentyl, hexyl, 2-ethylbutyl, 2,2-dimethylbutyl and 3,3-dimethylbutyl group.

The "$C_1$-$C_5$ alkoxy group"s in Substituent group (a) and Substituent group (c) each means a "$C_1$-$C_5$ alkoxy group" having the same meanings, and such a "$C_1$-$C_5$ alkoxy group" may be mentioned a straight or branched $C_1$-$C_5$ alkoxy group such as a methoxy, ethoxy, propoxy, isopropoxy, butoxy, isobutoxy, sec-butoxy, tert-butoxy, pentoxy, isopentoxy, neopentoxy, tert-pentoxy, 1,2-dimethylpropoxy, 1-ethylpropoxy, 1-methylbutoxy and 2-methylbutoxy group.

As the "halogeno $C_1$-$C_4$ alkoxy group" in Substituent group (a), there may be mentioned a straight or branched halogeno $C_1$-$C_4$ alkoxy group such as a difluoromethoxy, dichloromethoxy, dibromomethoxy, diiodomethoxy, trifluoromethoxy, trichloromethoxy, 2-fluoroethoxy, 2-chloroethoxy, 2-bromoethoxy, 2,2-difluoroethoxy, 2,2,2-trifluoroethoxy, perfluoroethoxy, 2,2-dichloroethoxy, 2,2,2-trichloroethoxy, 2-fluoropropoxy, 3-fluoropropoxy, 3,3,3-trifluoropropoxy, perfluoropropoxy, 2-fluoro-1-methylethoxy, 2,2-difluoro-1-methylethoxy, 2,2,2-trifluoro-1-methylethoxy, 4-fluorobutoxy and perfluorobutoxy group, etc.

As the "$C_3$-$C_6$ cycloalkoxy group" in Substituent group (a), there may be mentioned, for example, a cyclopropoxy, cyclobutoxy, cyclopentoxy or cyclohexyloxy group.

As the "($C_3$-$C_6$ cycloalkyl)$C_1$-$C_2$ alkoxy group" in Substituent group (a), there may be mentioned, for example, a cyclopropylmethoxy, 1-cyclopropylethoxy, 2-cyclopropylethoxy, cyclobutylmethoxy, 1-cyclobutylethoxy, 2-cyclobutylethoxy, cyclopentylmethoxy, 1-cyclopentylethoxy, 2-cyclopentylethoxy, cyclohexylmethoxy, 1-cyclohexylethoxy or 2-cyclohexylethoxy group.

The "$C_1$-$C_4$ alkoxycarbonyl group"s in Substituent group (a) and Substituent group (c) each means a "$C_1$-$C_4$ alkoxycarbonyl group" having the same meanings, and such a "$C_1$-$C_4$ alkoxycarbonyl group" may be mentioned, for example, a straight or branched $C_1$-$C_4$ alkoxycarbonyl group such as a methoxycarbonyl, ethoxycarbonyl, propoxycarbonyl, isopropoxycarbonyl, butoxycarbonyl, isobutoxycarbonyl, sec-butoxycarbonyl and tert-butoxycarbonyl group.

As the "$C_2$-$C_4$ alkanoyl group" in Substituent group (a), there may be mentioned, for example, a straight or branched $C_2$-$C_4$ alkanoyl group such as an acetyl, propionyl, butyryl and isobutyryl group.

The "$C_2$-$C_4$ alkanoyloxy group"s in Substituent group (a) and Substituent group (c) each means a "$C_2$-$C_4$ alkanoyloxy group" having the same meanings, and such a "$C_2$-$C_4$ alkanoyloxy group" may be mentioned, for example, a straight or branched $C_2$-$C_4$ alkanoyloxy group such as an acetyloxy, propionyloxy, butyryloxy and isobutyryloxy group.

The $C_1$-$C_4$ alkyl-substituted amino groups in Substituent group (a) and Substituent group (c) are an amino group which is substituted by 1 or 2 alkyl groups selected from a straight or branched $C_1$-$C_4$ alkyl group such as a methyl, ethyl, propyl, isopropyl, butyl, isobutyl, sec-butyl and tert-butyl group (when 2 substituents are substituted, the respective alkyl groups may be the same or different from each other), and there may be mentioned, for example, a methylamino, ethylamino, propylamino, isopropylamino, butylamino, isobutylamino, sec-butylamino, tertbutylamino, dimethylamino, diethylamino, dipropylamino, dibutylamino, diisopropylamino, diisobutylamino, ethylmethylamino, methylpropylamino, butylmethylamino, isopropylmethylamino or isobutylmethylamino group, etc., preferably a dimethylamino, diethylamino, dipropylamino, dibutylamino, diisopropylamino, diisobutylamino, ethylmethylamino, methylpropylamino, butylmethylamino, isopropylmethylamino or isobutylmethylamino group, more preferably a dimethylamino, diethylamino, dipropylamino, dibutylamino or diisopropylamino group.

As Substituent group (a), they are preferably a fluorine atom, chlorine atom, hydroxy, cyano, carboxy, methoxy, ethoxy, propoxy, isopropoxy, butoxy, isobutoxy, sec-butoxy, tert-butoxy, 1-ethylpropoxy, 2-fluoroethoxy, 2,2-difluoroethoxy, 2,2,2-trifluoroethoxy, cyclopropoxy, cyclobutoxy, cyclopropylmethoxy, 1-cyclopropylethoxy, 2-cyclopropylethoxy, cyclobutylmethoxy, methoxycarbonyl, ethoxycarbonyl, propoxycarbonyl, isopropoxycarbonyl, butoxycarbonyl, isobutoxycarbonyl, acetyl, propionyl, butyryl, isobutyryl, acetyloxy, propionyloxy, butyryloxy, isobutyryloxy, dimethylamino, diethylamino, dipropylamino, dibutylamino, diisopropylamino, diisobutylamino, ethylmethylamino, methylpropylamino, butylmethylamino, isopropylmethylamino or isobutylmethylamino group, more preferably a fluorine atom, chlorine atom, hydroxy, cyano, carboxy, methoxy, ethoxy, propoxy, isopropoxy, butoxy, isobutoxy, sec-butoxy, tert-butoxy, 1-ethylpropoxy, 2-fluoroethoxy, 2,2,2-trifluoroethoxy, cyclopropoxy, cyclobutoxy, cyclopropylmethoxy, cyclobutylmethoxy, methoxycarbonyl, ethoxycarbonyl, propoxycarbonyl, isopropoxycarbonyl, butoxycarbonyl, isobutoxycarbonyl, dimethylamino, diethylamino, dipropylamino, dibutylamino, diisopropylamino or diisobutylamino group, particularly preferably a fluorine atom, chlorine atom, hydroxy, carboxy, methoxy, ethoxy, propoxy, isopropoxy, butoxy, isobutoxy, sec-butoxy, tert-butoxy, 1-ethylpropoxy, 2-fluoroethoxy, cyclobutoxy, cyclopropylmethoxy, methoxycarbonyl, ethoxycarbonyl, propoxycarbonyl, isopropoxycarbonyl or butoxycarbonyl group.

A number of these substituent(s) of the $C_1$-$C_6$ alkyl group substituted by a substituent(s) selected from Substituent group (a) is, for example, 1 to 4, preferably 1 to 3, and when they are a plural number, these substituents may be the same or different from each other.

As the "$C_1$-$C_6$ alkyl group" of the $C_1$-$C_6$ alkyl group substituted by a substituent(s) selected from Substituent group (a) of $R^4$, there may be mentioned, for example, a straight or branched $C_1$-$C_6$ alkyl group such as a methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, 1-ethylpropyl, hexyl, 1-methylpentyl, 2-methylpentyl, 3-methylpentyl, 4-methylpentyl, 1-ethylbutyl, 2-ethylbutyl, 1,1-dimethylbutyl, 2,2-dimethylbutyl, 3,3-dimethylbutyl, 1,3-dimethylbutyl and 2,3-dimethylbutyl group, etc., preferably methyl, ethyl, propyl, isopropyl, butyl, isobutyl, pentyl, isopentyl, 2-methylbutyl, hexyl, 2-methylpentyl, 3-methylpentyl, 4-methylpentyl or 2-ethylbutyl group, more preferably methyl, ethyl, propyl, isopropyl, butyl, isobutyl, pentyl, isopentyl, hexyl or 2-ethylbutyl group, particularly preferably methyl, ethyl, propyl, isopropyl, butyl, isobutyl, isopentyl or 2-ethylbutyl group.

As the "$C_1$-$C_6$ alkyl group substituted by a substituent(s) selected from Substituent group (a)" of $R^4$, there may be mentioned, for example, trifluoromethyl, 2,2,2-trifluoroethyl, 3,3,3-trifluoropropyl, 2-chloroethyl, 2,2-dichloroethyl, 2,2,2-trichloroethyl, hydroxymethyl, 1-hydroxyethyl, 2-hydroxyethyl, 1-hydroxypropyl, 2-hydroxypropyl, 3-hydroxypropyl, 1-hydroxybutyl, 2-hydroxybutyl, 3-hydroxybutyl, 4-hydroxybutyl, 1-hydroxypentyl, 5-hydroxypentyl, 1-hydroxyhexyl, 6-hydroxyhexyl, 1-hydroxy-2-methylpropyl, 2-hydroxy-2-methylpropyl, 1-hydroxy-3-methylbutyl, 3-hydroxy-3-methylbutyl, 1-hydroxy-4-methylpentyl, 4-hydroxy-4-methylpentyl, 2-ethyl-2-hydroxybutyl, cyanomethyl, 1-cyanoethyl, 2-cyanoethyl, 1-cyanopropyl, 2-cyanopropyl, 3-cyanopropyl, 1-cyanobutyl, 2-cyanobutyl, 3-cyanobutyl, 4-cyanobutyl, 1-cyanopentyl, 5-cyanopentyl, 1-cyanohexyl, 6-cyanohexyl, 1-cyano-2-methylpropyl, 2-cyano-2-methylpropyl, 1-cyano-3-methylbutyl, 3-cyano-3-methylbutyl, 1-cyano-4-methylpentyl, 4-cyano-4-methylpentyl, 2-cyano-2-ethylbutyl, carboxymethyl, 1-carboxyethyl, 2-carboxyethyl, 1-carboxypropyl, 2-carboxypropyl, 3-carboxypropyl, 1-carboxybutyl, 2-carboxybutyl, 3-carboxybutyl, 4-carboxybutyl, 1-carboxypentyl, 5-carboxypentyl, 1-carboxyhexyl, 6-carboxyhexyl, 1-carboxy-2-methylpropyl, 2-carboxy-2-methylpropyl, 1-carboxy-3-methylbutyl, 3-carboxy-3-methylbutyl, 1-carboxy-4-methylpentyl, 4-carboxy-4-methylpentyl, 2-carboxy-2-ethylbutyl, methoxymethyl, 1-methoxyethyl, 2-methoxyethyl, 1-methoxypropyl, 2-methoxypropyl, 3-methoxypropyl, 1-methoxybutyl, 2-methoxybutyl, 3-methoxybutyl, 4-methoxybutyl, 1-methoxypentyl, 5-methoxypentyl, 1-methoxyhexyl, 6-methoxyhexyl, 1-methoxy-2-methylpropyl, 2-methoxy-2-methylpropyl, 1-methoxy-3-methylbutyl, 3-methoxy-3-methylbutyl, 1-methoxy-4-methylpentyl, 4-methoxy-4-methylpentyl, 2-ethyl-2-methoxybutyl, ethoxymethyl, 1-ethoxyethyl, 2-ethoxyethyl, 1-ethoxypropyl, 2-ethoxypropyl, 3-ethoxypropyl, 1-ethoxybutyl, 2-ethoxybutyl, 3-ethoxybutyl, 4-ethoxybutyl, 1-ethoxypentyl, 5-ethoxypentyl, 1-ethoxyhexyl, 6-ethoxyhexyl, 1-ethoxy-2-methylpropyl, 2-ethoxy-2-methylpropyl, 1-ethoxy-3-methylbutyl, 3-ethoxy-3-methylbutyl, 1-ethoxy-4-methylpentyl, 4-ethoxy-4-methylpentyl, 2-ethoxy-2-ethylbutyl, propoxymethyl, 1-propoxyethyl, 2-propoxyethyl, 1-propoxypropyl, 2-propoxypropyl, 3-propoxypropyl, 1-propoxybutyl, 2-propoxybutyl, 3-propoxybutyl, 4-propoxybutyl, 1-propoxypentyl, 5-propoxypentyl, 1-propoxyhexyl, 6-propoxyhexyl, 2-methyl-1-propoxypropyl, 2-methyl-2-propoxypropyl, 3-methyl-1-propoxybutyl, 3-methyl-3-propoxybutyl, 4-methyl-1-propoxypentyl, 4-methyl-4-propoxypentyl, 2-ethyl-2-propoxybutyl, butoxymethyl, 1-butoxyethyl, 2-butoxyethyl, 1-butoxypropyl, 2-butoxypropyl, 3-butoxypropyl, 1-butoxybutyl, 2-butoxybutyl, 3-butoxybutyl, 4-butoxybutyl, 1-butoxypentyl, 5-butoxypentyl, 1-butoxyhexyl, 6-butoxyhexyl, 1-butoxy-2-methylpropyl, 2-butoxy-2-methylpropyl, 1-butoxy-3-methylbutyl, 3-butoxy-3-methylbutyl, 1-butoxy-4-methylpentyl, 4-butoxy-4-methylpentyl, 2-butoxy-2-ethylbutyl, isopropoxymethyl, 1-isopropoxyethyl, 2-isopropoxyethyl, 1-isopropoxypropyl, 2-isopropoxypropyl, 3-isopropoxypropyl, 1-isopropoxybutyl, 2-isopropoxybutyl, 3-isopropoxybutyl, 4-isopropoxybutyl, 1-isopropoxypentyl, 5-isopropoxypentyl, 1-isopropoxyhexyl, 6-isopropoxyhexyl, 1-isopropoxy-2-methylpropyl, 2-isopropoxy-2-methylpropyl, 1-isopropoxy-3-methylbutyl, 3-isopropoxy-3-methylbutyl, 1-isopropoxy-4-methylpentyl, 4-isopropoxy-4-methylpentyl, 2-ethyl-2-isopropoxybutyl, isobutoxymethyl, 1-isobutoxyethyl, 2-isobutoxyethyl, sec-butoxymethyl, 1-(sec-butoxy)ethyl, 2-(sec-butoxy)ethyl, tert-butoxymethyl, 1-(tert-butoxy)ethyl, 2-(tert-butoxy)ethyl, 1-ethylpropoxymethyl, 1-(1-ethylpropoxy)ethyl, 2-(1-ethylpropoxy)ethyl, 2-fluoroethoxymethyl, 1-(2-fluoroethoxy)ethyl, 2-(2-fluoroethoxy)ethyl, 1-(2-fluoroethoxy)propyl, 2-(2-fluoroethoxy) propyl, 3-(2-fluoroethoxy)propyl, 1-(2-fluoroethoxy)butyl, 2-(2-fluoroethoxy)butyl, 3-(2-fluoroethoxy)butyl, 4-(2-fluoroethoxy)butyl, 1-(2-fluoroethoxy)pentyl, 5-(2-fluoroethoxy)pentyl, 1-(2-fluoroethoxy)hexyl, 6-(2-fluoroethoxy) hexyl, 1-(2-fluoroethoxy)-2-methylpropyl, 2-(2-fluoroethoxy)-2-methylpropyl, 1-(2-fluoroethoxy)-3-methylbutyl, 3-(2-fluoroethoxy)-3-methylbutyl, 1-(2-fluoroethoxy)-4-methylpentyl, 4-(2-fluoroethoxy)-4-methylpentyl, 2-ethyl-2-(2-fluoroethoxy)butyl, (2,2-difluoroethoxy)methyl, 1-(2,2-difluoroethoxy)ethyl, 2-(2,2-difluoroethoxy)ethyl, 1-(2,2-difluoroethoxy)propyl, 2-(2,2-difluoroethoxy)propyl, 3-(2,2-difluoroethoxy)propyl, 1-(2,2-difluoroethoxy)butyl, 2-(2,2-difluoroethoxy)butyl, 3-(2,2-difluoroethoxy)butyl, 4-(2,2-difluoroethoxy)butyl, 1-(2,2-difluoroethoxy)pentyl, 5-(2,2-difluoroethoxy)pentyl, 1-(2,2-difluoroethoxy)hexyl, 6-(2,2-difluoroethoxy)hexyl, 1-(2,2-difluoroethoxy)-2-methylpropyl, 2-(2,2-difluoroethoxy)-2-methylpropyl, 1-(2,2-difluoroethoxy)-3-methylbutyl, 3-(2,2-difluoroethoxy)-3-methylbutyl, 1-(2,2-difluoroethoxy)-4-methylpentyl, 4-(2,2-difluoroethoxy)-4-methylpentyl, 2-ethyl-2-(2,2-difluoroethoxy)butyl, (2,2,2-trifluoroethoxy)methyl, 1-(2,2,2-trifluoroethoxy)ethyl, 2-(2,2,2-trifluoroethoxy)ethyl, 1-(2,2,2-trifluoroethoxy)propyl, 2-(2,2,2-trifluoroethoxy)propyl, 3-(2,2,2-trifluoroethoxy)propyl, 1-(2,2,2-trifluoroethoxy)butyl, 2-(2,2,2-trifluoroethoxy)butyl, 3-(2,2,2-trifluoroethoxy)butyl, 4-(2,2,2-trifluoroethoxy)butyl, 1-(2,2,2-trifluoroethoxy)pentyl, 5-(2,2,2-trifluoroethoxy)pentyl, 1-(2,2,2-trifluoroethoxy)hexyl, 6-(2,2,2-trifluoroethoxy)hexyl, 1-(2,2,2-trifluoroethoxy)-2-methylpropyl, 2-(2,2,2-trifluoroethoxy)-2-methylpropyl, 1-(2,2,2-trifluoroethoxy)-3-methylbutyl, 3-(2,2,2-trifluoroethoxy)-3-methylbutyl, 1-(2,2,2-trifluoroethoxy)-4-methylpentyl, 4-(2,2,2-trifluoroethoxy)-4-methylpentyl, 2-ethyl-2-(2,2,2-trifluoroethoxy)butyl, cyclopropoxymethyl, 1-cyclopropoxyethyl, 2-cyclopropoxyethyl, 1-cyclopropoxypropyl, 2-cyclopropoxypropyl, 3-cyclopropoxypropyl, 1-cyclopropoxybutyl, 2-cyclopropoxybutyl, 3-cyclopropoxybutyl, 4-cyclopropoxybutyl, 1-cyclopropoxypentyl, 5-cyclopropoxypentyl, 1-cyclopropoxyhexyl, 6-cyclopropoxyhexyl, 1-cyclopropoxy-2-methylpropyl, 2-cyclopropoxy-2-methylpropyl, 1-cyclopropoxy-3-methylbutyl, 3-cyclopropoxy-3-methylbutyl, 1-cyclopropoxy-4-methylpentyl, 4-cyclopropoxy-4-methylpentyl, 2-cyclopropoxy-2-ethylbutyl, cyclobutoxymethyl, 1-cyclobutoxyethyl, 2-cyclobutoxyethyl, 1-cyclobutoxypropyl, 2-cyclobutoxypropyl, 3-cyclobutoxypropyl, 1-cyclobutoxybutyl, 2-cyclobutoxybutyl, 3-cyclobutoxybutyl, 4-cyclobutoxybutyl, 1-cyclobutoxypentyl, 5-cyclobutoxypentyl, 1-cyclobutoxyhexyl, 6-cyclobutoxyhexyl, 1-cyclobutoxy-2-methylpropyl, 2-cyclobutoxy-2-methylpropyl, 1-cyclobutoxy-3-methylbutyl, 3-cyclobutoxy-3-methylbutyl, 1-cyclobutoxy-4-methylpentyl, 4-cyclobutoxy-4-methylpentyl, 2-cyclobutoxy-2-ethylbutyl, cyclopropylmethoxymethyl, 1-cyclopropylmethoxyethyl, 2-cyclopropylmethoxyethyl, 1-cyclopropylmethoxypropyl, 2-cyclopropylmethoxypropyl, 3-cyclopropylmethoxypropyl, 1-cyclopropylmethoxybutyl, 2-cyclopropylmethoxybutyl, 3-cyclopropylmethoxybutyl, 4-cyclopropylmethoxybutyl, 1-cyclopropylmethoxypentyl, 5-cyclopropylmethoxypentyl, 1-cyclopropylmethoxyhexyl, 6-cyclopropylmethoxyhexyl, 1-cyclopropylmethoxy-2-methylpropyl, 2-cyclopropylmethoxy-2-methylpropyl, 1-cyclopropylmethoxy-3-methylbutyl, 3-cyclopropylmethoxy-3-methylbutyl, 1-cyclopropylmethoxy-4-methylpentyl, 4-cyclopropylmethoxy-4-methylpentyl, 2-cyclopropylmethoxy-2-ethylbutyl, cyclobutylmethoxymethyl, 1-cyclobutylmethoxyethyl, 2-cyclobutylmethoxyethyl, 1-cyclobutylmethoxypropyl, 2-cyclobutylmethoxypropyl, 3-cyclobutylmethoxypropyl, 1-cyclobutylmethoxybutyl, 2-cyclobutylmethoxybutyl, 3-cyclobutylmethoxybutyl, 4-cyclobutylmethoxybutyl, 1-cyclobutylmethoxypentyl, 5-cyclobutylmethoxypentyl, 1-cyclobutylmethoxyhexyl, 6-cyclobutylmethoxyhexyl, 1-cyclobutylmethoxy-2-methylpropyl, 2-cyclobutylmethoxy-2-methylpropyl, 1-cyclobutylmethoxy-3-methylbutyl, 3-cyclobutylmethoxy-3-methylbutyl, 1-cyclobutylmethoxy-4-methylpentyl, 4-cyclobutylmethoxy-4-methylpentyl, 2-cyclobutylmethoxy-2-ethylbutyl, (1-cyclopropylethoxy)methyl, 2-(1-cyclopropylethoxy)ethyl, 2-(1-cyclopropylethoxy)propyl, 3-(1-cyclopropylethoxy)propyl, 4-(1-cyclopropylethoxy)butyl, 5-(1-cyclopropylethoxy)pentyl, 6-(1-cyclopropylethoxy)hexyl, 2-(1-cyclopropylethoxy)-2-methylpropyl, 3-(1-cyclopropylethoxy)-3-methylbutyl, 4-(1-cyclopropylethoxy)-4-methylpentyl, 2-(1-cyclopropylethoxy)-2-ethylbutyl, (2-cyclopropylethoxy)methyl, 2-(2-cyclopropylethoxy)ethyl, 2-(2-cyclopropylethoxy)propyl, 3-(2-cyclopropylethoxy)propyl, 4-(2-cyclopropylethoxy)butyl, 5-(2-cyclopropylethoxy)pentyl, 6-(2-cyclopropylethoxy)hexyl, 2-(2-cyclopropylethoxy)-2-methylpropyl, 3-(2-cyclopropylethoxy)-3-methylbutyl, 4-(2-cyclopropylethoxy)-4-methylpentyl, 2-(2-cyclopropylethoxy)-2-ethylbutyl, methoxycarbonylmethyl, 1-methoxycarbonylethyl, 2-methoxycarbonylethyl, 1-methoxycarbonylpropyl, 2-methoxycarbonylpropyl, 3-methoxycarbonylpropyl, 1-methoxycarbonylbutyl, 2-methoxycarbonylbutyl, 3-methoxycarbonylbutyl, 4-methoxycarbonylbutyl, 1-methoxycarbonylpentyl, 5-methoxycarbonylpentyl, 1-methoxycarbonylhexyl, 6-methoxycarbonylhexyl, 1-methoxycarbonyl-2-methylpropyl, 2-methoxycarbonyl-2-methylpropyl, 1-methoxycarbonyl-3-methylbutyl, 3-methoxycarbonyl-3-methylbutyl, 1-methoxycarbonyl-4-methylpentyl, 4-methoxycarbonyl-4-methylpentyl, 2-ethyl-2-methoxycarbonylbutyl, ethoxycarbonylmethyl, 1-ethoxycarbonylethyl, 2-ethoxycarbonylethyl, 1-ethoxycarbonylpropyl, 2-ethoxycarbonylpropyl, 3-ethoxycarbonylpropyl, 1-ethoxycarbonylbutyl, 2-ethoxycarbonylbutyl, 3-ethoxycarbonylbutyl, 4-ethoxycarbonylbutyl, 1-ethoxycarbonylpentyl, 5-ethoxycarbonylpentyl, 1-ethoxycarbonylhexyl, 6-ethoxycarbonylhexyl, 1-ethoxycarbonyl-2-methylpropyl, 2-ethoxycarbonyl-2-methylpropyl, 1-ethoxycarbonyl-3-methylbutyl, 3-ethoxycarbonyl-3-methylbutyl, 1-ethoxycarbonyl-4-methylpentyl, 4-ethoxycarbonyl-4-methylpentyl, 2-ethoxycarbonyl-2-ethylbutyl, propoxycarbonylmethyl, 1-propoxycarbonylethyl, 2-propoxycarbonylethyl, 1-propoxycarbonylpropyl, 2-propoxycarbonylpropyl, 3-propoxycarbonylpropyl, 1-propoxycarbonylbutyl, 2-propoxycarbonylbutyl, 3-propoxycarbonylbutyl, 4-propoxycarbonylbutyl, 1-propoxycarbonylpentyl, 5-propoxycarbonylpentyl, 1-propoxycarbonylhexyl, 6-propoxycarbonylhexyl, 2-methyl-1-propoxycarbonylpropyl, 2-methyl-2-propoxycarbonylpropyl, 3-methyl-1-propoxycarbonylbutyl, 3-methyl-3-propoxycarbonylbutyl, 4-methyl-1-propoxycarbonylpentyl, 4-methyl-4-propoxycarbonylpentyl, 2-ethyl-2-propoxycarbonylbutyl, butoxycarbonylmethyl, 1-butoxycarbonylethyl, 2-butoxycarbonylethyl, 1-butoxycarbonylpropyl, 2-butoxycarbonylpropyl, 3-butoxycarbonylpropyl, 1-butoxycarbonylbutyl, 2-butoxycarbonylbutyl, 3-butoxycarbonylbutyl, 4-butoxycarbonylbutyl, 1-butoxycarbonylpentyl, 5-butoxycarbonylpentyl, 1-butoxycarbonylhexyl, 6-butoxycarbonylhexyl, 1-butoxycarbonyl-2-methylpropyl, 2-butoxycarbonyl-2-methylpropyl, 1-butoxycarbonyl-3-methylbutyl, 3-butoxycarbonyl-3-methylbutyl, 1-butoxycarbonyl-4-methylpentyl, 4-butoxycarbonyl-4-methylpentyl, 2-butoxycarbonyl-2-ethylbutyl, isopropoxycarbonylmethyl, 1-isopropoxycarbonylethyl, 2-isopropoxycarbonylethyl, 1-isopropoxycarbonylpropyl, 2-isopropoxycarbonylpropyl, 3-isopropoxycarbonylpropyl, 1-isopropoxycarbonylbutyl, 2-isopropoxycarbonylbutyl, 3-isopropoxycarbonylbutyl, 4-isopropoxycarbonylbutyl, 1-isopropoxycarbonylpentyl, 5-isopropoxycarbonylpentyl, 1-isopropoxycarbonylhexyl, 6-isopropoxycarbonylhexyl, 1-isopropoxycarbonyl-2-methylpropyl, 2-isopropoxycarbonyl-2-methylpropyl, 1-isopropoxycarbonyl-3-methylbutyl, 3-isopropoxycarbonyl-3-methylbutyl, 1-isopropoxycarbonyl-4-methylpentyl, 4-isopropoxycarbonyl-4-methylpentyl, 2-ethyl-2-isopropoxycarbonylbutyl, isobutoxycarbonylmethyl, 1-isobutoxycarbonylethyl, 2-isobutoxycarbonylethyl, 1-isobutoxycarbonylpropyl, 2-isobutoxycarbonylpropyl, 3-isobutoxycarbonylpropyl, 1-isobutoxycarbonylbutyl, 2-isobutoxycarbonylbutyl, 3-isobutoxycarbonylbutyl, 4-isobutoxycarbonylbutyl, 1-isobutoxycarbonylpentyl, 5-isobutoxycarbonylpentyl, 1-isobutoxycarbonylhexyl, 6-isobutoxycarbonylhexyl, 1-isobutoxycarbonyl-2-methylpropyl, 2-isobutoxycarbonyl-2-methylpropyl, 1-isobutoxycarbonyl-3-methylbutyl, 3-isobutoxycarbonyl-3-methylbutyl, 1-isobutoxycarbonyl-4-methylpentyl, 4-isobutoxycarbonyl-4-methylpentyl, 2-ethyl-2-isobutoxycarbonylbutyl, acetyloxymethyl, 1-acetyloxyethyl, 2-acetyloxyethyl, 1-acetyloxypropyl, 2-acetyloxypropyl, 3-acetyloxypropyl, 1-acetyloxybutyl, 2-acetyloxybutyl, 3-acetyloxybutyl, 4-acetyloxybutyl, 1-acetyloxypentyl, 5-acetyloxypentyl, 1-acetyloxyhexyl, 6-acetyloxyhexyl, 1-acetyloxy-2-methylpropyl, 2-acetyloxy-2-methylpropyl, 1-acetyloxy-3-methylbutyl, 3-acetyloxy-3-methylbutyl, 1-acetyloxy-4-methylpentyl, 4-acetyloxy-4-methylpentyl, 2-acetyloxy-2-ethylbutyl, propionyloxymethyl, 1-propionyloxyethyl, 2-propionyloxyethyl, 1-propionyloxypropyl, 2-propionyloxypropyl, 3-propionyloxypropyl, 1-propionyloxybutyl, 2-propionyloxybutyl, 3-propionyloxybutyl, 4-propionyloxybutyl, 1-propionyloxypentyl, 5-propionyloxypentyl, 1-propionyloxyhexyl, 6-propionyloxyhexyl, 2-methyl-1-propionyloxypropyl, 2-methyl-2-propionyloxypropyl, 3-methyl-1-propionyloxybutyl, 3-methyl-3-propionyloxybutyl, 4-methyl-1-propionyloxypentyl, 4-methyl-4-propionyloxypentyl, 2-ethyl-2-propionyloxybutyl, butyryloxymethyl, 1-butyryloxyethyl, 2-butyryloxyethyl, 1-butyryloxypropyl, 2-butyryloxypropyl, 3-butyryloxypropyl, 1-butyryloxybutyl, 2-butyryloxybutyl, 3-butyryloxybutyl, 4-butyryloxybutyl, 1-butyryloxypentyl, 5-butyryloxypentyl, 1-butyryloxyhexyl, 6-butyryloxyhexyl, 1-butyryloxy-2-methylpropyl, 2-butyryloxy-2-methylpropyl, 1-butyryloxy-3-methylbutyl, 3-butyryloxy-3-methylbutyl, 1-butyryloxy-4-methylpentyl, 4-butyryloxy-4-methylpentyl, 2-butyryloxy-2-ethylbutyl, acetylmethyl, 1-acetylethyl, 2-acetylethyl, 1-acetylpropyl, 2-acetylpropyl, 3-acetylpropyl, 1-acetylbutyl, 2-acetylbutyl, 3-acetylbutyl, 4-acetylbutyl, 1-acetylpentyl, 5-acetylpentyl, 1-acetylhexyl, 6-acetylhexyl, 1-acetyl-2-methylpropyl, 2-acetyl-2-methylpropyl, 1-acetyl-3-methylbutyl, 3-acetyl-3-methylbutyl, 1-acetyl-4-methylpentyl, 4-acetyl-4-methylpentyl, 2-acetyl-2-ethylbutyl, propionylmethyl, 1-propionylethyl, 2-propionylethyl, 1-propionylpropyl, 2-propionylpropyl, 3-propionylpropyl, 1-propionylbutyl, 2-propionylbutyl, 3-propionylbutyl, 4-propionylbutyl, 1-propionylpentyl, 5-propionylpentyl, 1-propionylhexyl, 6-propionylhexyl, 2-methyl-1-propionylpropyl, 2-methyl-2-propionylpropyl, 3-methyl-1-propionylbutyl, 3-methyl-3-propionylbutyl, 4-methyl-1-propionylpentyl, 4-methyl-4-propionylpentyl, 2-ethyl-2-propionylbutyl, butyrylmethyl, 1-butyrylethyl, 2-butyrylethyl, 1-butyrylpropyl, 2-butyrylpropyl, 3-butyrylpropyl, 1-butyrylbutyl, 2-butyrylbutyl, 3-butyrylbutyl, 4-butyrylbutyl, 1-butyrylpentyl, 5-butyrylpentyl, 1-butyrylhexyl, 6-butyrylhexyl, 1-butyryl-2-methylpropyl, 2-butyryl-2-methylpropyl, 1-butyryl-3-methylbutyl, 3-butyryl-3-methylbutyl, 1-butyryl-4-methylpentyl, 4-butyryl-4-methylpentyl, 2-butyryl-2-ethylbutyl, dimethylaminomethyl, 2-dimethylaminoethyl, 3-dimethylaminopropyl, 4-dimethylaminobutyl, 5-dimethylaminopentyl, 6-dimethylaminohexyl, diethylaminomethyl, 2-diethylaminoethyl, 3-diethylaminopropyl, 4-diethylaminobutyl, 5-diethylaminopentyl, 6-diethylaminohexyl, dipropylaminomethyl, 2-dipropylaminoethyl, 3-dipropylaminopropyl, 4-dipropylaminobutyl, 5-dipropylaminopentyl, 6-dipropylaminohexyl, dibutylaminomethyl, 2-dibutylaminoethyl, 3-dibutylaminopropyl, 4-dibutylaminobutyl, 5-dibutylaminopentyl, 6-dibutylaminohexyl, diisopropylaminomethyl, 2-diisopropylaminoethyl, 3-diisopropylaminopropyl, 4-diisopropylaminobutyl, 5-diisopropylaminopentyl or 6-diisopropylaminohexyl group, etc., preferably a trifluoromethyl, 2,2,2-trifluoroethyl, 3,3,3-trifluoropropyl, 2-chloroethyl, hydroxymethyl, 1-hydroxyethyl, 2-hydroxyethyl, 1-hydroxypropyl, 3-hydroxypropyl, 1-hydroxybutyl, 4-hydroxybutyl, 1-hydroxypentyl, 5-hydroxypentyl, 1-hydroxyhexyl, 6-hydroxyhexyl, 1-hydroxy-2-methylpropyl, 2-hydroxy-2-methylpropyl, 1-hydroxy-3-methylbutyl, 3-hydroxy-3-methylbutyl, 1-hydroxy-4-methylpentyl, 4-hydroxy-4-methylpentyl, 2-ethyl-2-hydroxybutyl, cyanomethyl, 2-cyanoethyl, 3-cyanopropyl, 4-cyanobutyl, 5-cyanopentyl, 6-cyanohexyl, 2-cyano-2-methylpropyl, 3-cyano-3-methylbutyl, 4-cyano-4-methylpentyl, 2-cyano-2-ethylbutyl, carboxymethyl, 2-carboxyethyl, 3-carboxypropyl, 4-carboxybutyl, 5-carboxypentyl, 6-carboxyhexyl, 2-carboxy-2-methylpropyl, 3-carboxy-3-methylbutyl, 4-carboxy-4-methylpentyl, 2-carboxy-2-ethylbutyl, methoxymethyl, 2-methoxyethyl, 2-methoxypropyl, 3-methoxypropyl, 4-methoxybutyl, 5-methoxypentyl, 6-methoxyhexyl, 2-methoxy-2-methylpropyl, 3-methoxy-3-methylbutyl, 4-methoxy-4-methylpentyl, 2-ethyl-2-methoxybutyl, ethoxymethyl, 2-ethoxyethyl, 2-ethoxypropyl, 3-ethoxypropyl, 4-ethoxybutyl, 5-ethoxypentyl, 6-ethoxyhexyl, 2-ethoxy-2-methylpropyl, 3-ethoxy-3-methylbutyl, 4-ethoxy-4-methylpentyl, 2-ethoxy-2-ethylbutyl, propoxymethyl, 2-propoxyethyl, 3-propoxypropyl, 4-propoxybutyl, 5-propoxypentyl, 6-propoxyhexyl, 2-methyl-2-propoxypropyl, 3-methyl-3-propoxybutyl, 4-methyl-4-propoxypentyl, 2-ethyl-2-propoxybutyl, butoxymethyl, 2-butoxyethyl, 3-butoxypropyl, 4-butoxybutyl, 5-butoxypentyl, 6-butoxyhexyl, 2-butoxy-2-methylpropyl, 3-butoxy-3-methylbutyl, 4-butoxy-4-methylpentyl, 2-butoxy-2-ethylbutyl, isopropoxymethyl, 2-isopropoxyethyl, 3-isopropoxypropyl, 4-isopropoxybutyl, 5-isopropoxypentyl, 6-isopropoxyhexyl, 2-isopropoxy-2-methylpropyl, 3-isopropoxy-3-methylbutyl, 4-isopropoxy-4-methylpentyl, 2-ethyl-2-isopropoxybutyl, isobutoxymethyl, 2-isobutoxyethyl, sec-butoxymethyl, 2-(sec-butoxy)ethyl, tert-butoxymethyl, 2-(tert-butoxy)ethyl, 1-ethylpropoxymethyl, 2-(1-ethylpropoxy)ethyl, 2-fluoroethoxymethyl, 2-(2-fluoroethoxy)ethyl, 2-(2-fluoroethoxy)propyl, 3-(2-fluoroethoxy)propyl, 4-(2-fluoroethoxy)butyl, 5-(2-fluoroethoxy)pentyl, 6-(2-fluoroethoxy)hexyl, 2-(2-fluoroethoxy)-2-methylpropyl, 3-(2-fluoroethoxy)-3-methylbutyl, 4-(2-fluoroethoxy)-4-methylpentyl, 2-ethyl-2-(2-fluoroethoxy)butyl, (2,2,2-trifluoroethoxy)methyl, 2-(2,2,2-trifluoroethoxy)ethyl, 2-(2,2,2-trifluoroethoxy)propyl, 3-(2,2,2-trifluoroethoxy)propyl, 4-(2,2,2-trifluoroethoxy)butyl, 5-(2,2,2-trifluoroethoxy)pentyl, 6-(2,2,2-trifluoroethoxy)hexyl, 2-(2,2,2-trifluoroethoxy)-2-methylpropyl, 3-(2,2,2-trifluoroethoxy)-3-methylbutyl, 4-(2,2,2-trifluoroethoxy)-4-methylpentyl, 2-ethyl-2-(2,2,2-trifluoroethoxy)butyl, cyclopropoxymethyl, 2-cyclopropoxyethyl, 2-cyclopropoxypropyl, 3-cyclopropoxypropyl, 4-cyclopropoxybutyl, 5-cyclopropoxypentyl, 6-cyclopropoxyhexyl, 2-cyclopropoxy-2-methylpropyl, 3-cyclopropoxy-3-methylbutyl, 4-cyclopropoxy-4-methylpentyl, 2-cyclopropoxy-2-ethylbutyl, cyclobutoxymethyl, 2-cyclobutoxyethyl, 2-cyclobutoxypropyl, 3-cyclobutoxypropyl, 4-cyclobutoxybutyl, 5-cyclobutoxypentyl, 6-cyclobutoxyhexyl, 2-cyclobutoxy-2-methylpropyl, 3-cyclobutoxy-3-methylbutyl, 4-cyclobutoxy-4-methylpentyl, 2-cyclobutoxy-2-ethylbutyl, cyclopropylmethoxymethyl, 2-cyclopropylmethoxyethyl, 2-cyclopropylmethoxypropyl, 3-cyclopropylmethoxypropyl, 4-cyclopropylmethoxybutyl, 5-cyclopropylmethoxypentyl, 6-cyclopropylmethoxyhexyl, 2-cyclopropylmethoxy-2-methylpropyl, 3-cyclopropylmethoxy-3-methylbutyl, 4-cyclopropylmethoxy-4-methylpentyl, 2-cyclopropylmethoxy-2-ethylbutyl, cyclobutylmethoxymethyl, 2-cyclobutylmethoxyethyl, 2-cyclobutylmethoxypropyl, 3-cyclobutylmethoxypropyl, 4-cyclobutylmethoxybutyl, 5-cyclobutylmethoxypentyl, 6-cyclobutylmethoxyhexyl, 2-cyclobutylmethoxy-2-methylpropyl, 3-cyclobutylmethoxy-3-methylbutyl, 4-cyclobutylmethoxy-4-methylpentyl, 2-cyclobutylmethoxy-2-ethylbutyl, methoxycarbonylmethyl, 2-methoxycarbonylethyl, 3-methoxycarbonylpropyl, 4-methoxycarbonylbutyl, 5-methoxycarbonylpentyl, 6-methoxycarbonylhexyl, 2-methoxycarbonyl-2-methylpropyl, 3-methoxycarbonyl-3-methylbutyl, 4-methoxycarbonyl-4-methylpentyl, 2-ethyl-2-methoxycarbonylbutyl, ethoxycarbonylmethyl, 2-ethoxycarbonylethyl, 3-ethoxycarbonylpropyl, 4-ethoxycarbonylbutyl, 5-ethoxycarbonylpentyl, 6-ethoxycarbonylhexyl, 2-ethoxycarbonyl-2-methylpropyl, 3-ethoxycarbonyl-3-methylbutyl, 4-ethoxycarbonyl-4-methylpentyl, 2-ethoxycarbonyl-2-ethylbutyl, propoxycarbonylmethyl, 2-propoxycarbonylethyl, 3-propoxycarbonylpropyl, 4-propoxycarbonylbutyl, 5-propoxycarbonylpentyl, 6-propoxycarbonylhexyl, 2-methyl-2-propoxycarbonylpropyl, 3-methyl-3-propoxycarbonylbutyl, 4-methyl-4-propoxycarbonylpentyl, 2-ethyl-2-propoxycarbonylbutyl, butoxycarbonylmethyl, 2-butoxycarbonylethyl, 3-butoxycarbonylpropyl, 4-butoxycarbonylbutyl, 5-butoxycarbonylpentyl, 6-butoxycarbonylhexyl, 2-butoxycarbonyl-2-methylpropyl, 3-butoxycarbonyl-3-methylbutyl, 4-butoxycarbonyl-4-methylpentyl, 2-butoxycarbonyl-2-ethylbutyl, isopropoxycarbonylmethyl, 2-isopropoxycarbonylethyl, 3-isopropoxycarbonylpropyl, 4-isopropoxycarbonylbutyl, 5-isopropoxycarbonylpentyl, 6-isopropoxycarbonylhexyl, 2-isopropoxycarbonyl-2-methylpropyl, 3-isopropoxycarbonyl-3-methylbutyl, 4-isopropoxycarbonyl-4-methylpentyl, 2-ethyl-2-isopropoxycarbonylbutyl, isobutoxycarbonylmethyl, 2-isobutoxycarbonylethyl, 3-isobutoxycarbonylpropyl, 4-isobutoxycarbonylbutyl, 5-isobutoxycarbonylpentyl, 6-isobutoxycarbonylhexyl, 2-isobutoxycarbonyl-2-methylpropyl, 3-isobutoxycarbonyl-3-methylbutyl, 4-isobutoxycarbonyl-4-methylpentyl, 2-ethyl-2-isobutoxycarbonylbutyl, acetyloxymethyl, 2-acetyloxyethyl, 3-acetyloxypropyl, 4-acetyloxybutyl, 5-acetyloxypentyl, 6-acetyloxyhexyl, 2-acetyloxy-2-methylpropyl, 3-acetyloxy-3-methylbutyl, 4-acetyloxy-4-methylpentyl, 2-acetyloxy-2-ethylbutyl, propionyloxymethyl, 2-propionyloxyethyl, 3-propionyloxypropyl, 4-propionyloxybutyl, 5-propionyloxypentyl, 6-propionyloxyhexyl, 2-methyl-2-propionyloxypropyl, 3-methyl-3-propionyloxybutyl, 4-methyl-4-propionyloxypentyl, 2-ethyl-2-propionyloxybutyl, butyryloxymethyl, 2-butyryloxyethyl, 3-butyryloxypropyl, 4-butyryloxybutyl, 5-butyryloxypentyl, 6-butyryloxyhexyl, 2-butyryloxy-2-methylpropyl, 3-butyryloxy-3-methylbutyl, 4-butyryloxy-4-methylpentyl, 2-butyryloxy-2-ethylbutyl, acetylmethyl, 2-acetylethyl, 3-acetylpropyl, 4-acetylbutyl, 5-acetylpentyl, 6-acetylhexyl, 2-acetyl-2-methylpropyl, 3-acetyl-3-methylbutyl, 4-acetyl-4-methylpentyl, 2-acetyl-2-ethylbutyl, propionylmethyl, 2-propionylethyl, 3-propionylpropyl, 4-propionylbutyl, 5-propionylpentyl, 6-propionylhexyl, 3-methyl-3-propionylbutyl, 4-methyl-4-propionylpentyl, 2-ethyl-2-propionylbutyl, butyrylmethyl, 2-butyrylethyl, 3-butyrylpropyl, 4-butyrylbutyl, 5-butyrylpentyl, 6-butyrylhexyl, 2-butyryl-2-methylpropyl, 3-butyryl-3-methylbutyl, 4-butyryl-4-methylpentyl, 2-butyryl-2-ethylbutyl, dimethylaminomethyl, 2-dimethylaminoethyl, 3-dimethylaminopropyl, 4-dimethylaminobutyl, diethylaminomethyl, 2-diethylaminoethyl, 3-diethylaminopropyl, 4-diethylaminobutyl, dipropylaminomethyl, 2-dipropylaminoethyl, 3-dipropylaminopropyl, 4-dipropylaminobutyl, dibutylaminomethyl, 2-dibutylaminoethyl, 3-dibutylaminopropyl, 4-dibutylaminobutyl, diisopropylaminomethyl, 2-diisopropylaminoethyl, 3-diisopropylaminopropyl or 4-diisopropylaminobutyl group, more preferably 2,2,2-trifluoroethyl, 3,3,3-trifluoropropyl, 2-chloroethyl, hydroxymethyl, 2-hydroxyethyl, 3-hydroxypropyl, 4-hydroxybutyl, 5-hydroxypentyl, 6-hydroxyhexyl, 2-hydroxy-2-methylpropyl, 3-hydroxy-3-methylbutyl, 4-hydroxy-4-methylpentyl, 2-ethyl-2-hydroxybutyl, 2-cyano-2-methylpropyl, 3-cyano-3-methylbutyl, 4-cyano-4-methylpentyl, 2-cyano-2-ethylbutyl, 2-carboxy-2-methylpropyl, 3-carboxy-3-methylbutyl, 4-carboxy-4-methylpentyl, 2-carboxy-2-ethylbutyl, methoxymethyl, 2-methoxyethyl, 3-methoxypropyl, 4-methoxybutyl, 5-methoxypentyl, 6-methoxyhexyl, 2-methoxy-2-methylpropyl, 3-methoxy-3-methylbutyl, 4-methoxy-4-methylpentyl, 2-ethyl-2-methoxybutyl, ethoxymethyl, 2-ethoxyethyl, 3-ethoxypropyl, 4-ethoxybutyl, 5-ethoxypentyl, 6-ethoxyhexyl, 2-ethoxy-2-methylpropyl, 3-ethoxy-3-methylbutyl, 4-ethoxy-4-methylpentyl, 2-ethoxy-2-ethylbutyl, propoxymethyl, 2-propoxyethyl, 3-propoxypropyl, 4-propoxybutyl, 2-methyl-2-propoxypropyl, 3-methyl-3-propoxybutyl, 4-methyl-4-propoxypentyl, 2-ethyl-2-propoxybutyl, butoxymethyl, 2-butoxyethyl, 3-butoxypropyl, 4-butoxybutyl, 2-butoxy-2-methylpropyl, 3-butoxy-3-methylbutyl, 4-butoxy-4-methylpentyl, 2-butoxy-2-ethylbutyl, isopropoxymethyl, 2-isopropoxyethyl, 3-isopropoxypropyl, 4-isopropoxybutyl, isobutoxymethyl, sec-butoxymethyl, tert-butoxymethyl, 1-ethylpropoxymethyl, 2-fluoroethoxymethyl, 2-(2-fluoroethoxy)ethyl, 3-(2-fluoroethoxy)propyl, 4-(2-fluoroethoxy)butyl, 5-(2-fluoroethoxy)pentyl, 6-(2-fluoroethoxy)hexyl, 2-(2-fluoroethoxy)-2-methylpropyl, 3-(2-fluoroethoxy)-3-methylbutyl, 4-(2-fluoroethoxy)-4-methylpentyl, 2-ethyl-2-(2-fluoroethoxy)butyl, (2,2,2-trifluoroethoxy)methyl, cyclopropoxymethyl, cyclobutoxymethyl, 2-cyclobutoxyethyl, 3-cyclobutoxypropyl, 4-cyclobutoxybutyl, 5-cyclobutoxypentyl, 6-cyclobutoxyhexyl, 2-cyclobutoxy-2-methylpropyl, 3-cyclobutoxy-3-methylbutyl, 4-cyclobutoxy-4-methylpentyl, 2-cyclobutoxy-2-ethylbutyl, cyclopropylmethoxymethyl, 2-cyclopropylmethoxyethyl, 3-cyclopropylmethoxypropyl, 4-cyclopropylmethoxybutyl, 5-cyclopropylmethoxypentyl, 6-cyclopropylmethoxyhexyl, 2-cyclopropylmethoxy-2-methylpropyl, 3-cyclopropylmethoxy-3-methylbutyl, 4-cyclopropylmethoxy-4-methylpentyl, 2-cyclopropylmethoxy-2-ethylbutyl, cyclobutylmethoxymethyl, methoxycarbonylmethyl, 2-methoxycarbonylethyl, 3-methoxycarbonylpropyl, 4-methoxycarbonylbutyl, 2-methoxycarbonyl-2-methylpropyl, 3-methoxycarbonyl-3-methylbutyl, 4-methoxycarbonyl-4-methylpentyl, 2-ethyl-2-methoxycarbonylbutyl, ethoxycarbonylmethyl, 2-ethoxycarbonylethyl, 3-ethoxycarbonylpropyl, 4-ethoxycarbonylbutyl, 2-ethoxycarbonyl-2-methylpropyl, 3-ethoxycarbonyl-3-methylbutyl, 4-ethoxycarbonyl-4-methylpentyl, 2-ethoxycarbonyl-2-ethylbutyl, propoxycarbonylmethyl, 2-propoxycarbonylethyl, 3-propoxycarbonylpropyl, 4-propoxycarbonylbutyl, 2-methyl-2-propoxycarbonylpropyl, 3-methyl-3-propoxycarbonylbutyl, 4-methyl-4-propoxycarbonylpentyl, 2-ethyl-2-propoxycarbonylbutyl, butoxycarbonylmethyl, 2-butoxycarbonylethyl, 3-butoxycarbonylpropyl, 4-butoxycarbonylbutyl, 2-butoxycarbonyl-2-methylpropyl, 3-butoxycarbonyl-3-methylbutyl, 4-butoxycarbonyl-4-methylpentyl, 2-butoxycarbonyl-2-ethylbutyl, isopropoxycarbonylmethyl, 2-isopropoxycarbonylethyl, 3-isopropoxycarbonylpropyl, 4-isopropoxycarbonylbutyl, 2-isopropoxycarbonyl-2-methylpropyl, 3-isopropoxycarbonyl-3-methylbutyl, 4-isopropoxycarbonyl-4-methylpentyl, 2-ethyl-2-isopropoxycarbonylbutyl, isobutoxycarbonylmethyl, 2-isobutoxycarbonylethyl, 3-isobutoxycarbonylpropyl, 4-isobutoxycarbonylbutyl, acetyloxymethyl, 2-acetyloxyethyl, 3-acetyloxypropyl, 4-acetyloxybutyl, 5-acetyloxypentyl, 6-acetyloxyhexyl, 2-acetyloxy-2-methylpropyl, 3-acetyloxy-3-methylbutyl, 4-acetyloxy-4-methylpentyl, 2-acetyloxy-2-ethylbutyl, propionyloxymethyl, 2-propionyloxyethyl, 3-propionyloxypropyl, 4-propionyloxybutyl, 5-propionyloxypentyl, acetylmethyl, 2-acetylethyl, 3-acetylpropyl, 4-acetylbutyl, 5-acetylpentyl, 6-acetylhexyl, 2-acetyl-2-methylpropyl, 3-acetyl-3-methylbutyl, 4-acetyl-4-methylpentyl, 2-acetyl-2-ethylbutyl, propionylmethyl, 2-propionylethyl, 3-propionylpropyl, 4-propionylbutyl, 5-propionylpentyl, dimethylaminomethyl, 2-dimethylaminoethyl, diethylaminomethyl, 2-diethylaminoethyl, dipropylaminomethyl, 2-dipropylaminoethyl, 2-dibutylaminoethyl, 3-dibutylaminopropyl, diisopropylaminomethyl or 2-diisopropylaminoethyl group, particularly preferably 2,2,2-trifluoroethyl, 3,3,3-trifluoropropyl, 2-chloroethyl, hydroxymethyl, 2-hydroxy-2-methylpropyl, 3-hydroxy-3-methylbutyl, 4-hydroxy-4-methylpentyl, 2-ethyl-2-hydroxybutyl, 2-cyano-2-methylpropyl, 3-cyano-3-methylbutyl, 2-carboxy-2-methylpropyl, 3-carboxy-3-methylbutyl, 4-carboxy-4-methylpentyl, methoxymethyl, 2-methoxyethyl, ethoxymethyl, 2-ethoxyethyl, isopropoxymethyl, 2-isopropoxyethyl, isobutoxymethyl, sec-butoxymethyl, tert-butoxymethyl, 1-ethylpropoxymethyl, 2-fluoroethoxymethyl, cyclobutoxymethyl, cyclopropylmethoxymethyl or dimethylamino group.

The "$C_3$-$C_6$ cycloalkyl group" of the $C_3$-$C_6$ cycloalkyl group which may be substituted by a substituent(s) selected from Substituent group (b) and the "$C_3$-$C_6$ cycloalkyl group" of the $C_1$-$C_3$ alkyl group which is substituted by a $C_3$-$C_6$ cycloalkyl group which may be substituted by a substituent(s) selected from Substituent group (b), and may be substituted by a hydroxy group of $R^4$ each mean a "$C_3$-$C_6$ cycloalkyl group" having the same meaning, and such a "$C_3$-$C_6$ cycloalkyl group" may be mentioned, for example, a cyclopropyl, cyclobutyl, cyclopentyl or cyclohexyl group.

As Substituent group (b), there may be mentioned, for example, a hydroxy group, a fluorine, chlorine, bromine or iodine atom, preferably a hydroxy group, a fluorine, chlorine or bromine atom, more preferably a hydroxy group, a fluorine or chlorine atom.

A number of substituents of the $C_3$-$C_6$ cycloalkyl group substituted by these substituent(s) selected from Substituent group (b) is, for example, 1 to 5, preferably 1 to 3, and the substituents in the case of a plural numer may be the same or different from each other.

As the $C_3$-$C_6$ cycloalkyl group which may be substituted by a substituent(s) selected from Substituent group (b), there may be mentioned, for example, a cyclopropyl, 1-hydroxycyclopropyl, cyclobutyl, 1-hydroxycyclobutyl, cyclopentyl, 3,3-difluoro-1-hydroxycyclopentyl, cyclohexyl, 3,3-difluoro-1-hydroxycyclohexyl or 4,4-difluoro-1-hydroxycyclohexyl group, etc., preferably a cyclopropyl, 1-hydroxycyclopropyl, cyclobutyl or 1-hydroxycyclobutyl group.

As the "$C_1$-$C_3$ alkyl group portion" of the "$C_1$-$C_3$ alkyl group which is substituted by a $C_3$-$C_6$ cycloalkyl group which may be substituted by a substituent(s) selected from Substituent group (b), and may be substituted by a hydroxy group" of $R^4$, there may be mentioned, for example, a straight or branched $C_1$-$C_3$ alkyl group such as a methyl, ethyl, propyl and isopropyl group, preferably a methyl, ethyl or propyl group.

As the "$C_1$-$C_3$ alkyl group which is substituted by a $C_3$-$C_6$ cycloalkyl group which may be substituted by a substituent(s) selected from Substituent group (b), and may be substituted by a hydroxy group" of $R^4$, there may be mentioned, for example, a cyclopropylmethyl, (1-hydroxycyclopropyl)methyl, cyclobutylmethyl, (1-hydroxycyclobutyl)methyl, cyclopentylmethyl, (3,3-difluoro-1-hydroxycyclopentyl)methyl, cyclohexylmethyl, (3,3-difluoro-1-hydroxycyclohexyl)methyl, (4,4-difluoro-1-hydroxycyclohexyl)methyl, cyclopropylhydroxymethyl, hydroxy(1-hydroxycyclopropyl)methyl, cyclobutylhydroxymethyl, hydroxy(1-hydroxycyclobutyl)methyl, cyclopentylhydroxymethyl, (3,3-difluoro-1-hydroxycyclopentyl)hydroxymethyl, cyclohexylhydroxymethyl, (3,3-difluoro-1-hydroxycyclohexyl)hydroxymethyl, (4,4-difluoro-1-hydroxycyclohexyl)hydroxymethyl, 1-cyclopropylethyl, 2-cyclopropylethyl, 1-(1-hydroxycyclopropyl)ethyl, 2-(1-hydroxycyclopropyl)ethyl, 1-cyclobutylethyl, 2-cyclobutylethyl, 1-(1-hydroxycyclobutyl)ethyl, 2-(1-hydroxycyclobutyl)ethyl, 1-cyclopentylethyl, 2-cyclopentylethyl, 1-(3,3-difluoro-1-hydroxycyclopentyl)ethyl, 2-(3,3-difluoro-1-hydroxycyclopentyl)ethyl, 1-cyclohexylethyl, 2-cyclohexylethyl, 1-(3,3-difluoro-1-hydroxycyclohexyl)ethyl, 2-(3,3-difluoro-1-hydroxycyclohexyl)ethyl, 1-(4,4-difluoro-1-hydroxycyclohexyl)ethyl, 2-(4,4-difluoro-1-hydroxycyclohexyl)ethyl, 1-cyclopropylpropyl, 3-cyclopropylpropyl, 1-(1-hydroxycyclopropyl)propyl, 3-(1-hydroxycyclopropyl)propyl, 1-cyclobutylpropyl, 3-cyclobutylpropyl, 1-(1-hydroxycyclobutyl)propyl, 3-(1-hydroxycyclobutyl)propyl, 1-cyclopentylpropyl, 3-cyclopentylpropyl, 1-(3,3-difluoro-1-hydroxycyclopentyl)propyl, 3-(3,3-difluoro-1-hydroxycyclopentyl)propyl, 1-cyclohexylpropyl, 3-cyclohexylpropyl, 1-(3,3-difluoro-1-hydroxycyclohexyl)propyl, 3-(3,3-difluoro-1-hydroxycyclohexyl)propyl, 1-(4,4-difluoro-1-hydroxycyclohexyl)propyl, 3-(4,4-difluoro-1-hydroxycyclohexyl)propyl, 1-cyclopropyl-1-hydroxyethyl, 2-cyclopropyl-2-hydroxyethyl, 1-hydroxy-1-(1-hydroxycyclopropyl)ethyl, 2-hydroxy-2-(1-hydroxycyclopropyl)ethyl, 1-cyclobutyl-1-hydroxyethyl, 2-cyclobutyl-2-hydroxyethyl, 1-hydroxy-1-(1-hydroxycyclobutyl)ethyl, 2-hydroxy-2-(1-hydroxycyclobutyl)ethyl, 1-cyclopentyl-1-hydroxyethyl, 2-cyclopentyl-2-hydroxyethyl, 1-(3,3-difluoro-1-hydroxycyclopentyl)-1-hydroxyethyl, 2-(3,3-difluoro-1-hydroxycyclopentyl)-2-hydroxyethyl, 1-cyclohexyl-1-hydroxyethyl, 2-cyclohexyl-2-hydroxyethyl, 1-(3,3-difluoro-1-hydroxycyclohexyl)-1-hydroxyethyl, 2-(3,3-difluoro-1-hydroxycyclohexyl)-2-hydroxyethyl, 1-(4,4-difluoro-1-hydroxycyclohexyl)-1-hydroxyethyl, 2-(4,4-difluoro-1-hydroxycyclohexyl)-2-hydroxyethyl, 1-cyclopropyl-1-hydroxypropyl, 3-cyclopropyl-3-hydroxypropyl, 1-hydroxy-1-(1-hydroxycyclopropyl)propyl, 3-hydroxy-3-(1-hydroxycyclopropyl)propyl, 1-cyclobutyl-1-hydroxypropyl, 3-cyclobutyl-3-hydroxypropyl, 1-hydroxy-1-(1-hydroxycyclobutyl)propyl, 3-hydroxy-3-(1-hydroxycyclobutyl)propyl, 1-cyclopentyl-1-hydroxypropyl, 3-cyclopentyl-3-hydroxypropyl, 1-(3,3-difluoro-1-hydroxycyclopentyl)-1-hydroxypropyl, 3-(3,3-difluoro-1-hydroxycyclopentyl)-3-hydroxypropyl, 1-cyclohexyl-1-hydroxypropyl, 3-cyclohexyl-3-hydroxypropyl, 1-(3,3-difluoro-1-hydroxycyclohexyl)-1-hydroxypropyl, 3-(3,3-difluoro-1-hydroxycyclohexyl)-3-hydroxypropyl, 1-(4,4-difluoro-1-hydroxycyclohexyl)-1-hydroxypropyl, 3-(4,4-difluoro-1-hydroxycyclohexyl)-3-hydroxypropyl, 1-cyclopropyl-1-methylethyl, 2-cyclopropyl-1-methylethyl, 1-cyclobutyl-1-methylethyl, 2-cyclobutyl-1-methylethyl, 1-(1-hydroxycyclopropyl)-1-methylethyl or 2-cyclopropyl-2-hydroxy-1-methylethyl group, etc., preferably a cyclopropylmethyl, (1-hydroxycyclopropyl)methyl, cyclobutylmethyl, (1-hydroxycyclobutyl)methyl, cyclopropylhydroxymethyl, hydroxy(1-hydroxycyclopropyl)methyl, cyclobutylhydroxymethyl, hydroxy(1-hydroxycyclobutyl)methyl, 2-cyclopropylethyl, 2-(1-hydroxycyclopropyl)ethyl, 2-cyclobutylethyl, 2-(1-hydroxycyclobutyl)ethyl, 3-cyclopropylpropyl, 3-(1-hydroxycyclopropyl)propyl, 3-cyclobutylpropyl, 3-(1-hydroxycyclobutyl)propyl, 2-cyclopropyl-2-hydroxyethyl, 2-hydroxy-2-(1-hydroxycyclopropyl)ethyl, 2-cyclobutyl-2-hydroxyethyl, 2-hydroxy-2-(1-hydroxycyclobutyl)ethyl, 3-cyclopropyl-3-hydroxypropyl, 3-hydroxy-3-(1-hydroxycyclopropyl)propyl, 3-cyclobutyl-3-hydroxypropyl or 3-hydroxy-3-(1-hydroxycyclobutyl)propyl group, more preferably cyclopropylmethyl, (1-hydroxycyclopropyl)methyl, cyclobutylmethyl, (1-hydroxycyclobutyl)methyl, cyclopropylhydroxymethyl, hydroxy(1-hydroxycyclopropyl)methyl, cyclobutylhydroxymethyl, hydroxy(1-hydroxycyclobutyl)methyl, 2-cyclopropylethyl, 2-(1-hydroxycyclopropyl)ethyl, 2-cyclobutylethyl or 2-(1-hydroxycyclobutyl)ethyl group.

As the "$C_2$-$C_6$ alkenyl group" of $R^4$, there may be mentioned, for example, a straight or branched $C_2$-$C_6$ alkenyl group such as vinyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-methyl-1-propenyl, 2-methyl-1-propenyl, 1-methyl-2-propenyl, 2-methyl-2-propenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl and 2,3-dimethyl-2-butenyl group, etc., preferably 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, 2-methyl-2-butenyl, 3-methyl-2-butenyl, 2-methyl-3-butenyl, 3-methyl-3-butenyl, 2-methyl-2-pentenyl, 3-methyl-2-pentenyl, 4-methyl-2-pentenyl, 2-methyl-3-pentenyl, 3-methyl-3-pentenyl, 4-methyl-3-pentenyl, 2-methyl-4-pentenyl, 3-methyl-4-pentenyl, 4-methyl-4-pentenyl or 2,3-dimethyl-2-butenyl group, more preferably 2-propenyl, 2-butenyl, 2-pentenyl, 2-hexenyl, 2-methyl-2-propenyl, 2-methyl-2-butenyl, 3-methyl-2-butenyl, 2-methyl-2-pentenyl, 3-methyl-2-pentenyl, 4-methyl-2-pentenyl or 2,3-dimethyl-2-butenyl group, particularly preferably 2-propenyl, 2-butenyl, 2-methyl-2-propenyl, 2-methyl-2-butenyl, 3-methyl-2-butenyl and 2,3-dimethyl-2-butenyl group.

As the "$C_2$-$C_6$ alkynyl group" of $R^4$, there may be mentioned, for example, a straight or branched $C_2$-$C_6$ alkynyl group such as an ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 3-methyl-1-butynyl, 1-methyl-2-butynyl, 1-methyl-3-butynyl, 2-methyl-3-butynyl, 1-hexynyl, 2-hexynyl, 3-hexynyl, 4-hexynyl, 5-hexynyl, 3-methyl-1-hexynyl, 4-methyl-1-pentynyl, 1-methyl-2-pentynyl, 4-methyl-2-pentynyl, 1-methyl-3-pentynyl, 2-methyl-3-pentynyl, 1-methyl-4-pentynyl, 2-methyl-4-pentynyl, 3-methyl-4-pentynyl and 2,2-dimethyl-3-butynyl group, etc., preferably an ethynyl, 2-propynyl, 2-butynyl, 3-butynyl, 2-pentynyl, 3-pentynyl, 4-pentynyl, 2-methyl-3-butynyl, 2-hexynyl, 3-hexynyl, 4-hexynyl, 5-hexynyl, 4-methyl-2-pentynyl, 2-methyl-3-pentynyl, 2-methyl-4-pentynyl, 3-methyl-4-pentynyl or 2,2-dimethyl-3-butynyl group, more preferably an ethynyl, 2-propynyl, 2-butynyl, 2-pentynyl, 2-hexynyl or 4-methyl-2-pentynyl group, particularly preferably an ethynyl, 2-propynyl, 2-butynyl and 4-methyl-2-pentynyl group.

The "hydroxy $C_3$-$C_5$ alkenyl group" of $R^4$ means a $C_3$-$C_6$ alkenyl group in which a hydroxy group is substituted on a carbon which is other carbon atoms than those constituting a double bond, and there may be mentioned, for example, a 3-hydroxy-1-propenyl, 1-hydroxy-2-propenyl, 3-hydroxy-1-butenyl, 4-hydroxy-1-butenyl, 1-hydroxy-2-butenyl, 4-hydroxy-2-butenyl, 1-hydroxy-3-butenyl, 2-hydroxy-3-butenyl, 3-hydroxy-1-pentenyl, 1-hydroxy-2-pentenyl, 2-hydroxy-3-pentenyl, 3-hydroxy-4-pentenyl, 3-hydroxy-1-hexenyl, 1-hydroxy-2-hexenyl, 2-hydroxy-3-hexenyl, 3-hydroxy-4-hexenyl or 4-hydroxy-5-hexenyl group, etc., preferably a 1-hydroxy-2-propenyl, 1-hydroxy-2-butenyl, 2-hydroxy-3-butenyl, 1-hydroxy-2-pentenyl, 2-hydroxy-3-pentenyl, 3-hydroxy-4-pentenyl, 1-hydroxy-2-hexenyl, 2-hydroxy-3-hexenyl, 3-hydroxy-4-hexenyl or 4-hydroxy-5-hexenyl group, more preferably a 1-hydroxy-2-propenyl, 1-hydroxy-2-butenyl, 1-hydroxy-2-pentenyl or 1-hydroxy-2-hexenyl group, particularly preferably a 1-hydroxy-2-propenyl or 1-hydroxy-2-butenyl group.

The "hydroxy $C_3$-$C_6$ alkynyl group" of $R^4$ means a $C_3$-$C_6$ alkynyl group in which a hydroxy group is substituted on a carbon which is other carbon atoms than those constituting a triple bond, and there may be mentioned, for example, a 3-hydroxy-1-propynyl, 1-hydroxy-2-propynyl, 3-hydroxy-1-butynyl, 4-hydroxy-1-butynyl, 1-hydroxy-2-butynyl, 4-hydroxy-2-butynyl, 1-hydroxy-3-butynyl, 2-hydroxy-3-butynyl, 3-hydroxy-1-pentynyl, 1-hydroxy-2-pentynyl, 2-hydroxy-3-pentynyl, 3-hydroxy-4-pentynyl, 3-hydroxy-1-hexynyl, 1-hydroxy-2-hexynyl, 2-hydroxy-3-hexynyl, 3-hydroxy-4-hexynyl or 4-hydroxy-5-hexynyl group, etc., preferably a 1-hydroxy-2-propynyl, 1-hydroxy-2-butynyl, 2-hydroxy-3-butynyl, 1-hydroxy-2-pentynyl, 2-hydroxy-3-pentynyl, 3-hydroxy-4-pentynyl, 1-hydroxy-2-hexynyl, 2-hydroxy-3-hexynyl, 3-hydroxy-4-hexynyl or 4-hydroxy-5-hexynyl group, more preferably a 1-hydroxy-2-propynyl, 1-hydroxy-2-butynyl, 1-hydroxy-2-pentynyl or 1-hydroxy-2-hexynyl group, particularly preferably a 1-hydroxy-2-propynyl or 1-hydroxy-2-butynyl group.

The "aromatic ring group or heteroaromatic ring group" of the aromatic ring group or heteroaromatic ring group which may be substituted by a substituent(s) selected from Substituent group (c) of $R^4$, there may be mentioned, for example, a phenyl, naphthyl, thienyl, oxazolyl, isoxazolyl, thiazolyl, isothiazolyl, imidazolyl, pyrazolyl, pyridyl, pyridazinyl, pyrimidinyl or pyrazinyl group, etc., preferably a phenyl, thienyl, thiazolyl, pyrazolyl, pyridyl, pyridazinyl or pyrimidinyl group, more preferably a phenyl, thienyl, thiazolyl, pyrazolyl or pyridyl group.

A number of substituent(s) of the $C_1$-$C_4$ alkyl group substituted by a substituent(s) selected from (a halogen atom, a hydroxy group or a carboxy group) in the "$C_1$-$C_4$ alkyl group which may be substituted by a substituent(s) selected from the group consisting of (a halogen atom, a hydroxy group and a carboxy group)" of Substituent group (c) is, for example, 1 to 9, preferably 1 to 6, more preferably 1 to 3, and the substituents in the case of a plural number may be the same or different from each other.

As the "$C_1$-$C_4$ alkyl group portion" in the $C_1$-$C_4$ alkyl group which may be substituted by a substituent(s) selected from the group consisting of (a halogen atom, a hydroxy group and a carboxy group) of Substituent group (c), there may be mentioned, for example, a methyl, ethyl, propyl, isopropyl, butyl, isobutyl, sec-butyl or tert-butyl group, preferably a methyl, ethyl, propyl or isopropyl group.

As the "$C_1$-$C_4$ alkyl group which may be substituted by a substituent(s) selected from the group consisting of (a halogen atom, a hydroxy group and a carboxy group)" of Substituent group (c), there may be mentioned, for example, a trifluoromethyl, 2,2,2-trifluoroethyl, 3,3,3-trifluoropropyl, 2-chloroethyl, 2,2-dichloroethyl, 2,2,2-trichloroethyl, hydroxymethyl, 1-hydroxyethyl, 2-hydroxyethyl, 1-hydroxypropyl, 2-hydroxypropyl, 3-hydroxypropyl, 2,2,2-trifluoro-1-hydroxy-1-trifluoromethylethyl, 1-hydroxy-1-methylethyl, 1-hydroxybutyl, 2-hydroxybutyl, 3-hydroxybutyl, 4-hydroxybutyl, 1-hydroxy-2-methylpropyl, 2-hydroxy-2-methylpropyl, carboxymethyl, 1-carboxyethyl, 2-carboxyethyl, 1-carboxypropyl, 2-carboxypropyl, 3-carboxypropyl, 1-carboxybutyl, 2-carboxybutyl, 3-carboxybutyl, 4-carboxybutyl, 1-carboxy-2-methylpropyl or 2-carboxy-2-methylpropyl group, etc., preferably a trifluoromethyl, 2,2,2-trifluoroethyl, 2-chloroethyl, 2,2-dichloroethyl, hydroxymethyl, 2-hydroxyethyl, 2-hydroxypropyl, 3-hydroxypropyl, 2,2,2-trifluoro-1-hydroxy-1-trifluoromethylethyl, 1-hydroxy-1-methylethyl, 2-hydroxybutyl, 3-hydroxybutyl, 4-hydroxybutyl, 1-hydroxy-2-methylpropyl, 2-hydroxy-2-methylpropyl, carboxymethyl, 2-carboxyethyl, 2-carboxypropyl, 3-carboxypropyl, 2-carboxybutyl, 3-carboxybutyl, 4-carboxybutyl or 2-carboxy-2-methylpropyl group, more preferably a trifluoromethyl, 2,2,2-trifluoroethyl, hydroxymethyl, 2-hydroxyethyl, 3-hydroxypropyl, 2,2,2-trifluoro-1-hydroxy-1-trifluoromethylethyl, 1-hydroxy-1-methylethyl, 3-hydroxybutyl, 4-hydroxybutyl, 1-hydroxy-2-methylpropyl, 2-hydroxy-2-methylpropyl, carboxymethyl, 2-carboxyethyl, 3-carboxypropyl, 3-carboxybutyl, 4-carboxybutyl or 2-carboxy-2-methylpropyl group.

A number of the substituent(s) of the aromatic ring group or heteroaromatic ring group each of which is substituted by a substituent(s) selected from Substituent group (c) is, for example, 1 to 4, preferably 1 to 3, and the substituents in a plural number may be the same or different from each other.

As the "aromatic ring group or heteroaromatic ring group which may be substituted by a substituent(s) selected from Substituent group (c)" of $R^4$, there may be mentioned, for example, a phenyl, 2-fluorophenyl, 3-fluorophenyl, 4-fluorophenyl, 2,4-difluorophenyl, 2,6-difluorophenyl, 3,4-difluorophenyl, 2,4,6-trifluorophenyl, 2-chlorophenyl, 3-chlorophenyl, 4-chlorophenyl, 2,4-dichlorophenyl, 2,6-dichlorophenyl, 3,4-dichlorophenyl, 2,4,6-trichlorophenyl, 2-hydroxyphenyl, 3-hydroxyphenyl, 4-hydroxyphenyl, 2,6-dihydroxyphenyl, 2,4-dihydroxyphenyl, 3,4-dihydroxyphenyl, 2,4,6-trihydroxyphenyl, 3,4,5-trihydroxyphenyl, 2-cyanophenyl, 3-cyanophenyl, 4-cyanophenyl, 2-nitrophenyl, 3-nitrophenyl, 4-nitrophenyl, 2-carboxyphenyl, 3-carboxyphenyl, 4-carboxyphenyl, 2-methylphenyl, 3-methylphenyl, 4-methylphenyl, 2,6-dimethylphenyl, 2,4-dimethylphenyl, 3,4-dimethylphenyl, 2,4,6-trimethylphenyl, 2-trifluoromethylphenyl, 3-trifluoromethylphenyl, 4-trifluoromethylphenyl, 3-ethylphenyl, 4-ethylphenyl, 3-propylphenyl, 4-propylphenyl, 3-isopropylphenyl, 4-isopropylphenyl, 3-butylphenyl, 4-butylphenyl, 3-isobutylphenyl, 4-isobutylphenyl, 3-(1-hydroxy-1-methylethyl)phenyl, 4-(1-hydroxy-1-methylethyl)phenyl, 3-(2,2,2-trifluoro-1-hydroxy-1-ethyl)phenyl, 4-(2,2,2-trifluoro-1-hydroxy-1-trifluoromethylethyl)phenyl, 3-(1-carboxy-1-methylethyl)phenyl, 4-(1-carboxy-1-methylethyl)phenyl, 2-methoxyphenyl, 3-methoxyphenyl, 4-methoxyphenyl, 2,6-dimethoxyphenyl, 2,4-dimethoxyphenyl, 3,4-dimethoxyphenyl, 2,4,6-trimethoxyphenyl, 3,4,5-trimethoxyphenyl, 2-ethoxyphenyl, 3-ethoxyphenyl, 4-ethoxyphenyl, 2,6-diethoxyphenyl, 2,4-diethoxyphenyl, 3,4-diethoxyphenyl, 2-propoxyphenyl, 3-propoxyphenyl, 4-propoxyphenyl, 2-butoxyphenyl, 3-butoxyphenyl, 4-butoxyphenyl, 2-isopropoxyphenyl, 3-isopropoxyphenyl, 4-isopropoxyphenyl, 2-methoxycarbonylphenyl, 3-methoxycarbonylphenyl, 4-methoxycarbonylphenyl, 2,6-dimethoxycarbonylphenyl, 2,4-dimethoxycarbonylphenyl, 3,4-dimethoxycarbonylphenyl, 2,4,6-trimethoxycarbonylphenyl, 3,4,5-trimethoxycarbonylphenyl, 2-ethoxycarbonylphenyl, 3-ethoxycarbonylphenyl, 4-ethoxycarbonylphenyl, 2,6-diethoxycarbonylphenyl, 2,4-diethoxycarbonylphenyl, 3,4-diethoxycarbonylphenyl, 2-propoxycarbonylphenyl, 3-propoxycarbonylphenyl, 4-propoxycarbonylphenyl, 2-butoxycarbonylphenyl, 3-butoxycarbonylphenyl, 4-butoxycarbonylphenyl, 2-isopropoxycarbonylphenyl, 3-isopropoxycarbonylphenyl, 4-isopropoxycarbonylphenyl, 3-acetoxyphenyl, 4-acetoxyphenyl, 3-propionyloxyphenyl, 4-propionyloxyphenyl, 3-butyryloxyphenyl, 4-butyryloxyphenyl, 3-dimethylaminophenyl, 4-dimethylaminophenyl, 3-diethylaminophenyl, 4-diethylaminophenyl, 3-dipropylaminophenyl, 4-dipropylaminophenyl, 3-dibutylaminophenyl, 4-dibutylaminophenyl, 3-diisopropylaminophenyl, 4-diisopropylaminophenyl, 1-naphthyl, 2-naphthyl, 2-thienyl, 3-cyano-2-thienyl, 4-cyano-2-thienyl, 5-cyano-2-thienyl, 3-carboxy-2-thienyl, 4-carboxy-2-thienyl, 5-carboxy-2-thienyl, 3-methyl-2-thienyl, 4-methyl-2-thienyl, 5-methyl-2-thienyl, 3-trifluoromethyl-2-thienyl, 4-trifluoromethyl-2-thienyl, 5-trifluoromethyl-2-thienyl, 3,4-dimethyl-2-thienyl, 3,5-dimethyl-2-thienyl, 4,5-dimethyl-2-thienyl, 4-ethyl-2-thienyl, 5-ethyl-2-thienyl, 4-propyl-2-thienyl, 5-propyl-2-thienyl, 4-isopropyl-2-thienyl, 5-isopropyl-2-thienyl, 4-butyl-2-thienyl, 5-butyl-2-thienyl, 4-isobutyl-2-thienyl, 5-isobutyl-2-thienyl, 4-(1-hydroxy-1-methylethyl)-2-thienyl, 5-(1-hydroxy-1-methylethyl)-2-thienyl, 4-(2,2,2-trifluoro-1-hydroxy-1-trifluoromethylethyl)-2-thienyl, 5-(2,2,2-trifluoro-1-hydroxy-1-trifluoromethylethyl)-2-thienyl, 4-(1-carboxy-1-methylethyl)-2-thienyl, 5-(1-carboxy-1-methylethyl)-2-thienyl, 3-methoxycarbonyl-2-thienyl, 4-methoxycarbonyl-2-thienyl, 5-methoxycarbonyl-2-thienyl, 3-ethoxycarbonyl-2-thienyl, 4-ethoxycarbonyl-2-thienyl, 5-ethoxycarbonyl-2-thienyl, 3-propoxycarbonyl-2-thienyl, 4-propoxycarbonyl-2-thienyl, 5-propoxycarbonyl-2-thienyl, 3-butoxycarbonyl-2-thienyl, 4-butoxycarbonyl-2-thienyl, 5-butoxycarbonyl-2-thienyl, 3-isopropoxycarbonyl-2-thienyl, 4-isopropoxycarbonyl-2-thienyl, 5-isopropoxycarbonyl-2-thienyl, 3-thienyl, 2-cyano-3-thienyl, 4-cyano-3-thienyl, 5-cyano-3-thienyl, 2-carboxy-3-thienyl, 4-carboxy-3-thienyl, 5-carboxy-3-thienyl, 2-methyl-3-thienyl, 4-methyl-3-thienyl, 5-methyl-3-thienyl, 2-trifluoromethyl-3-thienyl, 4-trifluoromethyl-3-thienyl, 5-trifluoromethyl-3-thienyl, 2,4-dimethyl-3-thienyl, 2,5-dimethyl-3-thienyl, 4,5-dimethyl-3-thienyl, 5-ethyl-3-thienyl, 5-propyl-3-thienyl, 5-isopropyl-3-thienyl, 5-butyl-3-thienyl, 5-isobutyl-3-thienyl, 5-(1-hydroxy-1-methylethyl)-3-thienyl, 5-(2,2,2-trifluoro-1-hydroxy-1-trifluoromethylethyl)-3-thienyl, 5-(1-carboxy-1-methylethyl)-3-thienyl, 5-methoxycarbonyl-3-thienyl, 5-ethoxycarbonyl-3-thienyl, 5-propoxycarbonyl-3-thienyl, 5-butoxycarbonyl-3-thienyl, 5-isopropoxycarbonyl-3-thienyl, 4-oxazolyl, 5-oxazolyl, 4-isoxazolyl, 5-isoxazolyl, 4-thiazolyl, 2-cyano-4-thiazolyl, 2-carboxy-4-thiazolyl, 2-methyl-4-thiazolyl, 2-ethyl-4-thiazolyl, 2-propyl-4-thiazolyl, 2-isopropyl-4-thiazolyl, 2-trifluoromethyl-4-thiazolyl, 2-(1-hydroxy-1-methylethyl)-4-thiazolyl, 2-(2,2,2-trifluoro-1-hydroxy-1-trifluoromethylethyl)-4-thiazolyl, 2-(1-carboxy-1-methylethyl)-4-thiazolyl, 2-methoxycarbonyl-4-thiazolyl, 2-ethoxycarbonyl-4-thiazolyl, 2-propoxycarbonyl-4-thiazolyl, 2-isopropoxycarbonyl-4-thiazolyl, 5-thiazolyl, 2-cyano-5-thiazolyl, 2-carboxy-5-thiazolyl, 2-methyl-5-thiazolyl, 2-ethyl-5-thiazolyl, 2-propyl-5-thiazolyl, 2-isopropyl-5-thiazolyl, 2-trifluoromethyl-5-thiazolyl, 2-(1-hydroxy-1-methylethyl)-5-thiazolyl, 2-(2,2,2-trifluoro-1-hydroxy-1-trifluoromethylethyl)-5-thiazolyl, 2-(1-carboxy-1-methylethyl)-5-thiazolyl, 2-methoxycarbonyl-5-thiazolyl, 2-ethoxycarbonyl-5-thiazolyl, 2-propoxycarbonyl-5-thiazolyl, 2-isopropoxycarbonyl-5-thiazolyl, 4-isothiazolyl, 5-isothiazolyl, 2-imidazolyl, 4-imidazolyl, 4-pyrazolyl, 1-methyl-4-pyrazolyl, 1-ethyl-4-pyrazolyl, 1-propyl-4-pyrazolyl, 1-isopropyl-4-pyrazolyl, 1-butyl-4-pyrazolyl, 3-pyrazolyl, 1-methyl-3-pyrazolyl, 1-ethyl-3-pyrazolyl, 1-propyl-3-pyrazolyl, 1-isopropyl-3-pyrazolyl, 1-butyl-3-pyrazolyl, 2-pyridyl, 6-cyano-2-pyridyl, 6-carboxy-2-pyridyl, 6-trifluoromethyl-2-pyridyl, 6-methoxy-2-pyridyl, 6-ethoxy-2-pyridyl, 6-propoxy-2-pyridyl, 6-isopropoxy-2-pyridyl, 6-butoxy-2-pyridyl, 6-methoxycarbonyl-2-pyridyl, 6-ethoxycarbonyl-2-pyridyl, 6-propoxycarbonyl-2-pyridyl, 6-isopropoxycarbonyl-2-pyridyl, 6-butoxycarbonyl-2-pyridyl, 6-(1-hydroxy-1-methylethyl)-2-pyridyl, 6-(2,2,2-trifluoro-1-hydroxy-1-trifluoromethylethyl)-2-pyridyl, 6-(1-carboxy-1-methylethyl)-2-pyridyl, 3-pyridyl, 6-cyano-3-pyridyl, 6-carboxy-3-pyridyl, 6-trifluoromethyl-3-pyridyl, 6-methoxy-3-pyridyl, 6-ethoxy-3-pyridyl, 6-propoxy-3-pyridyl, 6-isopropoxy-3-pyridyl, 6-butoxy-3-pyridyl, 6-methoxycarbonyl-3-pyridyl, 6-ethoxycarbonyl-3-pyridyl, 6-propoxycarbonyl-3-pyridyl, 6-isopropoxycarbonyl-3-pyridyl, 6-butoxycarbonyl-3-pyridyl, 6-(1-hydroxy-1-methylethyl)-3-pyridyl, 6-(2,2,2-trifluoro-1-hydroxy-1-trifluoromethylethyl)-3-pyridyl, 6-(1-carboxy-1-methylethyl)-3-pyridyl, 2-cyano-3-pyridyl, 2-carboxy-3-pyridyl, 2-trifluoromethyl-3-pyridyl, 2-methoxy-3-pyridyl, 2-ethoxy-3-pyridyl, 2-propoxy-3-pyridyl, 2-isopropoxy-3-pyridyl, 2-butoxy-3-pyridyl, 2-methoxycarbonyl-3-pyridyl, 2-ethoxycarbonyl-3-pyridyl, 2-propoxycarbonyl-3-pyridyl, 2-isopropoxycarbonyl-3-pyridyl, 2-butoxycarbonyl-3-pyridyl, 2-(1-hydroxy-1-methylethyl)-3-pyridyl, 2-(2,2,2-trifluoro-1-hydroxy-1-trifluoromethylethyl)-3-pyridyl, 2-(1-carboxy-1-methylethyl)-3-pyridyl, 4-pyridyl, 2-cyano-4-pyridyl, 2-carboxy-4-pyridyl, 2-trifluoromethyl-4-pyridyl, 2-methoxy-4-pyridyl, 2-ethoxy-4-pyridyl, 2-propoxy-4-pyridyl, 2-isopropoxy-4-pyridyl, 2-butoxy-4-pyridyl, 2-methoxycarbonyl-4-pyridyl, 2-ethoxycarbonyl-4-pyridyl, 2-propoxycarbonyl-4-pyridyl, 2-isopropoxycarbonyl-4-pyridyl, 2-butoxycarbonyl-4-pyridyl, 2-(1-hydroxy-1-methylethyl)-4-pyridyl, 2-(2,2,2-trifluoro-1-hydroxy-1-trifluoromethylethyl)-4-pyridyl, 2-(1- carboxy-1-methylethyl)-4-pyridyl, 3-pyridazinyl, 4-pyridazinyl, 2-pyrimidinyl, 4-pyrimidinyl, 5-pyrimidinyl or 2-pyrazinyl group, etc., preferably a phenyl, 2-fluorophenyl, 3-fluorophenyl, 4-fluorophenyl, 2,4-difluorophenyl, 2,6-difluorophenyl, 3,4-difluorophenyl, 2,4,6-trifluorophenyl, 2-chlorophenyl, 3-chlorophenyl, 4-chlorophenyl, 2,4-dichlorophenyl, 2,6-dichlorophenyl, 3,4-dichlorophenyl, 2,4,6-trichlorophenyl, 3-hydroxyphenyl, 4-hydroxyphenyl, 3-cyanophenyl, 4-cyanophenyl, 3-nitrophenyl, 4-nitrophenyl, 3-carboxyphenyl, 4-carboxyphenyl, 3-methylphenyl, 4-methylphenyl, 3-trifluoromethylphenyl, 4-trifluoromethylphenyl, 3-ethylphenyl, 4-ethylphenyl, 3-propylphenyl, 4-propylphenyl, 3-isopropylphenyl, 4-isopropylphenyl, 3-(1-hydroxy-1-methylethyl)phenyl, 4-(1-hydroxy-1-methylethyl)phenyl, 3-(2,2,2-trifluoro-1-hydroxy-1-trifluoromethylethyl)phenyl, 4-(2,2,2-trifluoro-1-hydroxy-1-trifluoromethylethyl)phenyl, 3-(1-carboxy-1-methylethyl)phenyl, 4-(1-carboxy-1-methylethyl)phenyl, 3-methoxyphenyl, 4-methoxyphenyl, 3-ethoxyphenyl, 4-ethoxyphenyl, 3-propoxyphenyl, 4-propoxyphenyl, 3-butoxyphenyl, 4-butoxyphenyl, 3-isopropoxyphenyl, 4-isopropoxyphenyl, 3-methoxycarbonylphenyl, 4-methoxycarbonylphenyl, 3-ethoxycarbonylphenyl, 4-ethoxycarbonylphenyl, 3-acetoxyphenyl, 4-acetoxyphenyl, 3-dimethylaminophenyl, 4-dimethylaminophenyl, 3-diethylaminophenyl, 4-diethylaminophenyl, 3-dipropylaminophenyl, 4-dipropylaminophenyl, 2-thienyl, 4-cyano-2-thienyl, 5-cyano-2-thienyl, 4-carboxy-2-thienyl, 5-carboxy-2-thienyl, 4-methyl-2-thienyl, 5-methyl-2-thienyl, 4-trifluoromethyl-2-thienyl, 5-trifluoromethyl-2-thienyl, 4-ethyl-2-thienyl, 5-ethyl-2-thienyl, 4-propyl-2-thienyl, 5-propyl-2-thienyl, 4-isopropyl-2-thienyl, 5-isopropyl-2-thienyl, 4-(1-hydroxy-1-methylethyl)-2-thienyl, 5-(1-hydroxy-1-methylethyl)-2-thienyl, 4-(2,2,2-trifluoro-1-hydroxy-1-trifluoromethylethyl)-2-thienyl, 5-(2,2,2-trifluoro-1-hydroxy-1-trifluoromethylethyl)-2-thienyl, 4-(1-carboxy-1-methylethyl)-2-thienyl, 5-(1-carboxy-1-methylethyl)-2-thienyl, 4-methoxycarbonyl-2-thienyl, 5-methoxycarbonyl-2-thienyl, 4-ethoxycarbonyl-2-thienyl, 5-ethoxycarbonyl-2-thienyl, 4-propoxycarbonyl-2-thienyl, 5-propoxycarbonyl-2-thienyl, 4-butoxycarbonyl-2-thienyl, 5-butoxycarbonyl-2-thienyl, 4-isopropoxycarbonyl-2-thienyl, 5-isopropoxycarbonyl-2-thienyl, 3-thienyl, 4-cyano-3-thienyl, 5-cyano-3-thienyl, 4-carboxy-3-thienyl, 5-carboxy-3-thienyl, 4-methyl-3-thienyl, 5-methyl-3-thienyl, 4-trifluoromethyl-3-thienyl, 5-trifluoromethyl-3-thienyl, 5-ethyl-3-thienyl, 5-propyl-3-thienyl, 5-isopropyl-3-thienyl, 5-(1-hydroxy-1-methylethyl)-3-thienyl, 5-(2,2,2-trifluoro-1-hydroxy-1-trifluoromethylethyl)-3-thienyl, 5-(1-carboxy-1-methylethyl)-3-thienyl, 5-methoxycarbonyl-3-thienyl, 5-ethoxycarbonyl-3-thienyl, 4-thiazolyl, 2-cyano-4-thiazolyl, 2-carboxy-4-thiazolyl, 2-methyl-4-thiazolyl, 2-ethyl-4-thiazolyl, 2-propyl-4-thiazolyl, 2-isopropyl-4-thiazolyl, 2-trifluoromethyl-4-thiazolyl, 2-(1-hydroxy-1-methylethyl)-4-thiazolyl, 2-(2,2,2-trifluoro-1-hydroxy-1-trifluoromethylethyl)-4-thiazolyl, 2-(1-carboxy-1-methylethyl)-4-thiazolyl, 2-methoxycarbonyl-4-thiazolyl, 2-ethoxycarbonyl-4-thiazolyl, 5-thiazolyl, 2-cyano-5-thiazolyl, 2-carboxy-5-thiazolyl, 2-methyl-5-thiazolyl, 2-ethyl-5-thiazolyl, 2-propyl-5-thiazolyl, 2-isopropyl-5-thiazolyl, 2-trifluoromethyl-5-thiazolyl, 2-(1-hydroxy-1-methylethyl)-5-thiazolyl, 2-(2,2,2-trifluoro-1-hydroxy-1-trifluoromethylethyl)-5-thiazolyl, 2-(1-carboxy-1-methylethyl)-5-thiazolyl, 2-methoxycarbonyl-5-thiazolyl, 2-ethoxycarbonyl-5-thiazolyl, 2-propoxycarbonyl-5-thiazolyl, 2-isopropoxycarbonyl-5-thiazolyl, 4-pyrazolyl, 1-methyl-4-pyrazolyl, 1-ethyl-4-pyrazolyl, 3-pyrazolyl, 1-methyl-3-pyrazolyl, 1-ethyl-3-pyrazolyl, 6-cyano-2-pyridyl, 6-carboxy-2-pyridyl, 6-trifluoromethyl-2-pyridyl, 6-methoxy-2-pyridyl, 6-ethoxy-2-pyridyl, 6-methoxycarbonyl-2-pyridyl, 6-ethoxycarbonyl-2-pyridyl, 6-(1-hydroxy-1-methylethyl)-2-pyridyl, 6-(2,2,2-trifluoro-1-hydroxy-1-trifluoromethylethyl)-2-pyridyl, 6-(1-carboxy-1-methylethyl)-2-pyridyl, 6-cyano-3-pyridyl, 6-carboxy-3-pyridyl, 6-trifluoromethyl-3-pyridyl, 6-methoxy-3-pyridyl, 6-ethoxy-3-pyridyl, 6-methoxycarbonyl-3-pyridyl, 6-ethoxycarbonyl-3-pyridyl, 6-(1-hydroxy-1-methylethyl)-3-pyridyl, 6-(2,2,2-trifluoro-1-hydroxy-1-trifluoromethylethyl)-3-pyridyl, 6-(1-carboxy-1-methylethyl)-3-pyridyl, 2-cyano-3-pyridyl, 2-carboxy-3-pyridyl, 2-trifluoromethyl-3-pyridyl, 2-methoxy-3-pyridyl, 2-ethoxy-3-pyridyl, 2-propoxy-3-pyridyl, 2-methoxycarbonyl-3-pyridyl, 2-ethoxycarbonyl-3-pyridyl, 2-propoxycarbonyl-3-pyridyl, 2-(1-hydroxy-1-methylethyl)-3-pyridyl, 2-(2,2,2-trifluoro-1-hydroxy-1-trifluoromethylethyl)-3-pyridyl, 2-(1-carboxy-1-methylethyl)-3-pyridyl, 2-cyano-4-pyridyl, 2-carboxy-4-pyridyl, 2-trifluoromethyl-4-pyridyl, 2-methoxy-4-pyridyl, 2-ethoxy-4-pyridyl, 2-propoxy-4-pyridyl, 2-methoxycarbonyl-4-pyridyl, 2-ethoxycarbonyl-4-pyridyl, 2-(1-hydroxy-1-methylethyl)-4-pyridyl, 2-(2,2,2-trifluoro-1-hydroxy-1-trifluoromethylethyl)-4-pyridyl or 2-(1-carboxy-1-methylethyl)-4-pyridyl group, more preferably a phenyl, 2-fluorophenyl, 3-fluorophenyl, 4-fluorophenyl, 2,4-difluorophenyl, 2,6-difluorophenyl, 3,4-difluorophenyl, 2-chlorophenyl, 3-chlorophenyl, 4-chlorophenyl, 2,4-dichlorophenyl, 2,6-dichlorophenyl, 3,4-dichlorophenyl, 3-cyanophenyl, 4-cyanophenyl, 3-nitrophenyl, 4-nitrophenyl, 3-carboxyphenyl, 4-carboxyphenyl, 3-trifluoromethylphenyl, 4-trifluoromethylphenyl, 3-(1-hydroxy-1-methylethyl)phenyl, 4-(1-hydroxy-1-methylethyl)phenyl, 3-(2,2,2-trifluoro-1-hydroxy-1-trifluoromethylethyl)phenyl, 4-(2,2,2-trifluoro-1-hydroxy-1-trifluoromethylethyl)phenyl, 3-(1-carboxy-1-methylethyl)phenyl, 4-(1-carboxy-1-methylethyl)phenyl, 3-methoxyphenyl, 4-methoxyphenyl, 3-ethoxyphenyl, 4-ethoxyphenyl, 3-methoxycarbonylphenyl, 4-methoxycarbonylphenyl, 3-ethoxycarbonylphenyl, 4-ethoxycarbonylphenyl, 2-thienyl, 4-cyano-2-thienyl, 5-cyano-2-thienyl, 4-carboxy-2-thienyl, 5-carboxy-2-thienyl, 4-methyl-2-thienyl, 5-methyl-2-thienyl, 4-trifluoromethyl-2-thienyl, 5-trifluoromethyl-2-thienyl, 4-(1-hydroxy-1-methylethyl)-2-thienyl, 5-(1-hydroxy-1-methylethyl)-2-thienyl, 4-(2,2,2-trifluoro-1-hydroxy-1-trifluoromethylethyl)-2-thienyl, 5-(2,2,2-trifluoro-1-hydroxy-1-trifluoromethylethyl)-2-thienyl, 4-(1-carboxy-1-methylethyl)-2-thienyl, 5-(1-carboxy-1-methylethyl)-2-thienyl, 3-thienyl, 4-cyano-3-thienyl, 5-cyano-3-thienyl, 4-carboxy-3-thienyl, 5-carboxy-3-thienyl, 4-methyl-3-thienyl, 5-methyl-3-thienyl, 4-trifluoromethyl-3-thienyl, 5-trifluoromethyl-3-thienyl, 5-ethyl-3-thienyl, 5-(1-hydroxy-1-methylethyl)-3-thienyl, 5-(2,2,2-trifluoro-1-hydroxy-1-trifluoromethylethyl)-3-thienyl, 5-(1-carboxy-1-methylethyl)-3-thienyl, 5-methoxycarbonyl-3-thienyl, 4-thiazolyl, 2-cyano-4-thiazolyl, 2-carboxy-4-thiazolyl, 2-methyl-4-thiazolyl, 2-ethyl-4-thiazolyl, 2-propyl-4-thiazolyl, 2-isopropyl-4-thiazolyl, 2-trifluoromethyl-4-thiazolyl, 2-(1-hydroxy-1-methylethyl)-4-thiazolyl, 2-(2,2,2-trifluoro-1-hydroxy-1-trifluoromethylethyl)-4-thiazolyl, 2-(1-carboxy-1-methylethyl)-4-thiazolyl, 2-methoxycarbonyl-4-thiazolyl, 5-thiazolyl, 2-cyano-5-thiazolyl, 2-carboxy-5-thiazolyl, 2-methyl-5-thiazolyl, 2-ethyl-5-thiazolyl, 2-trifluoromethyl-5-thiazolyl, 2-(1-hydroxy-1-methylethyl)-5-thiazolyl, 2-(2,2,2-trifluoro-1-hydroxy-1-trifluoromethylethyl)-5-thiazolyl, 2-(1-carboxy-1-methylethyl)-5-thiazolyl, 2-methoxycarbonyl-5-thiazolyl, 2-ethoxycarbonyl-5-thiazolyl, 2-propoxycarbonyl-5-thiazolyl, 2-isopropoxycarbonyl-5-thiazolyl, 4-pyrazolyl, 6-cyano-2-pyridyl, 6-carboxy-2-pyridyl, 6-trifluoromethyl-2-pyridyl, 6-methoxy-2-pyridyl, 6-ethoxy-2-pyridyl, 6-methoxycarbonyl-2-pyridyl, 6-ethoxycarbonyl-2-pyridyl, 6-(1-hydroxy-1-methylethyl)-2-pyridyl, 6-(2,2,2-trifluoro-1-hydroxy-1-trifluoromethylethyl)-2-pyridyl, 6-(1-carboxy-1-methylethyl)-2-pyridyl, 6-cyano-3-pyridyl, 6-carboxy-3-pyridyl, 6-trifluoromethyl-3-pyridyl, 6-methoxy-3-pyridyl, 6-ethoxy-3-pyridyl, 6-methoxycarbonyl-3-pyridyl, 6-ethoxycarbonyl-3-pyridyl, 6-(1-hydroxy-1-methylethyl)-3-pyridyl, 6-(2,2,2-trifluoro-1-hydroxy-1-trifluoromethylethyl)-3-pyridyl, 6-(1-carboxy-1-methylethyl)-3-pyridyl,
2-cyano-3-pyridyl, 2-carboxy-3-pyridyl, 2-trifluoromethyl-3-pyridyl, 2-methoxy-3-pyridyl, 2-ethoxy-3-pyridyl, 2-propoxy-3-pyridyl, 2-methoxycarbonyl-3-pyridyl, 2-ethoxycarbonyl-3-pyridyl, 2-propoxycarbonyl-3-pyridyl, 2-(1-hydroxy-1-methylethyl)-3-pyridyl, 2-(2,2,2-trifluoro-1-hydroxy-1-trifluoromethylethyl)-3-pyridyl, 2-(1-carboxy-1-methylethyl)-3-pyridyl, 2-cyano-4-pyridyl, 2-carboxy-4-pyridyl, 2-trifluoromethyl-4-pyridyl, 2-methoxy-4-pyridyl, 2-ethoxy-4-pyridyl, 2-propoxy-4-pyridyl, 2-methoxycarbonyl-4-pyridyl, 2-ethoxycarbonyl-4-pyridyl, 2-(1-hydroxy-1-methylethyl)-4-pyridyl, 2-(2,2,2-trifluoro-1-hydroxy-1-trifluoromethylethyl)-4-pyridyl or 2-(1-carboxy-1-methylethyl)-4-pyridyl group,
particularly preferably a phenyl, 2-fluorophenyl, 4-fluorophenyl, 2,4-difluorophenyl, 2-chlorophenyl, 4-chlorophenyl, 4-cyanophenyl, 4-nitrophenyl, 4-carboxyphenyl, 4-trifluoromethylphenyl, 3-methoxyphenyl, 4-methoxyphenyl, 4-methoxycarbonylphenyl, 2-thienyl, 5-cyano-2-thienyl, 5-carboxy-2-thienyl, 5-methyl-2-thienyl, 5-trifluoromethyl-2-thienyl, 3-thienyl, 5-cyano-3-thienyl, 5-carboxy-3-thienyl, 5-methyl-3-thienyl, 5-trifluoromethyl-3-thienyl, 4-thiazolyl, 2-cyano-4-thiazolyl, 2-carboxy-4-thiazolyl, 2-methyl-4-thiazolyl, 2-trifluoromethyl-4-thiazolyl, 2-(1-hydroxy-1-methylethyl)-4-thiazolyl, 2-(2,2,2-trifluoro-1-hydroxy-1-trifluoromethylethyl)-4-thiazolyl, 5-thiazolyl, 2-cyano-5-thiazolyl, 2-carboxy-5-thiazolyl, 2-methyl-5-thiazolyl, 2-trifluoromethyl-5-thiazolyl, 2-(1-hydroxy-1-methylethyl)-5-thiazolyl, 2-(2,2,2-trifluoro-1-hydroxy-1-trifluoromethylethyl)-5-thiazolyl, 4-pyrazolyl, 6-cyano-2-pyridyl, 6-carboxy-2-pyridyl, 6-trifluoromethyl-2-pyridyl, 6-methoxy-2-pyridyl, 6-(1-hydroxy-1-methylethyl)-2-pyridyl, 6-(2,2,2-trifluoro-1-hydroxy-1-trifluoromethylethyl)-2-pyridyl, 6-cyano-3-pyridyl, 6-carboxy-3-pyridyl, 6-trifluoromethyl-3-pyridyl, 6-methoxy-3-pyridyl, 6-(1-hydroxy-1-methylethyl)-3-pyridyl, 6-(2,2,2-trifluoro-1-hydroxy-1-trifluoromethylethyl)-3-pyridyl,
2-cyano-4-pyridyl, 2-carboxy-4-pyridyl, 2-trifluoromethyl-4-pyridyl, 2-methoxy-4-pyridyl, 2-(1-hydroxy-1-methylethyl)-4-pyridyl or 2-(2,2,2-trifluoro-1-hydroxy-1-trifluoromethylethyl)-4-pyridyl group.

As the "$C_1$-$C_2$ alkyl group which is substituted by an aromatic ring group or heteroaromatic ring group each of which may be substituted by a substituent(s) selected from Substituent group (c), and may be substituted by a hydroxy group" of $R^4$, there may be mentioned, for example, a benzyl, 2-fluorobenzyl, 3-fluorobenzyl, 4-fluorobenzyl, 2,4-difluorobenzyl, 2,6-difluorobenzyl, 3,4-difluorobenzyl, 2-chlorobenzyl, 3-chlorobenzyl, 4-chlorobenzyl, 2,4-dichlorobenzyl, 2,6-dichlorobenzyl, 3,4-dichlorobenzyl, 2-cyanobenzyl, 3-cyanobenzyl, 4-cyanobenzyl, 3-nitrobenzyl, 4-nitrobenzyl, 3-carboxybenzyl, 4-carboxybenzyl, 3-trifluoromethylbenzyl, 4-trifluoromethylbenzyl, 3-(1-hydroxy-1-methylethyl) benzyl, 4-(1-hydroxy-1-methylethyl)benzyl, 3-(2,2,2-trifluoro-1-hydroxy-1-trifluoromethylethyl)benzyl, 4-(2,2,2-trifluoro-1-hydroxy-1-trifluoromethylethyl)benzyl, 3-(1-carboxy-1-methylethyl)benzyl, 4-(1-carboxy-1-methylethyl)benzyl, 3-methoxybenzyl, 4-methoxybenzyl, 3-ethoxybenzyl, 4-ethoxybenzyl, 3-methoxycarbonylbenzyl, 4-methoxycarbonylbenzyl, 3-ethoxycarbonylbenzyl, 4-ethoxycarbonylbenzyl, 1-naphthylmethyl, 2-naphthylmethyl, 2-thienylmethyl, 4-cyano-2-thienylmethyl, 5-cyano-2-thienylmethyl, 4-carboxy-2-thienylmethyl, 5-carboxy-2-thienylmethyl, 4-methyl-2-thienylmethyl, 5-methyl-2-thienylmethyl, 4-trifluoromethyl-2-thienylmethyl, 5-trifluoromethyl-2-thienylmethyl, 4-(1-hydroxy-1-methylethyl)-2-thienylmethyl, 5-(1-hydroxy-1-methylethyl)-2-thienylmethyl, 4-(2,2,2-trifluoro-1-hydroxy-1-trifluoromethylethyl)-2-thienylmethyl, 5-(2,2,2-trifluoro-1-hydroxy-1-trifluoromethylethyl)-2-thienylmethyl, 4-(1-carboxy-1-methylethyl)-2-thienylmethyl, 5-(1-carboxy-1-methylethyl)-2-thienylmethyl,
3-thienylmethyl, 4-cyano-3-thienylmethyl, 5-cyano-3-thienylmethyl, 4-carboxy-3-thienylmethyl, 5-carboxy-3-thienylmethyl, 4-methyl-3-thienylmethyl, 5-methyl-3-thienylmethyl, 4-trifluoromethyl-3-thienylmethyl, 5-trifluoromethyl-3-thienylmethyl, 5-ethyl-3-thienylmethyl, 5-(1-hydroxy-1-methylethyl)-3-thienylmethyl, 5-(2,2,2-trifluoro-1-hydroxy-1-trifluoromethylethyl)-3-thienylmethyl, 5-(1-carboxy-1-methylethyl)-3-thienylmethyl, 5-methoxycarbonyl-3-thienylmethyl, 4-oxazolylmethyl, 5-oxazolylmethyl, 4-isoxazolylmethyl, 5-isoxazolylmethyl, 4-thiazolylmethyl, 2-cyano-4-thiazolylmethyl, 2-carboxy-4-thiazolylmethyl, 2-methyl-4-thiazolylmethyl, 2-ethyl-4-thiazolylmethyl, 2-propyl-4-thiazolylmethyl, 2-isopropyl-4-thiazolylmethyl, 2-trifluoromethyl-4-thiazolylmethyl, 2-(1-hydroxy-1-methylethyl)-4-thiazolylmethyl, 2-(2,2,2-trifluoro-1-hydroxy-1-trifluoromethylethyl)-4-thiazolylmethyl, 2-(1-carboxy-1-methylethyl)-4-thiazolylmethyl, 2-methoxycarbonyl-4-thiazolylmethyl, 5-thiazolylmethyl, 2-cyano-5-thiazolylmethyl, 2-carboxy-5-thiazolylmethyl, 2-methyl-5-thiazolylmethyl, 2-ethyl-5-thiazolylmethyl, 2-trifluoromethyl-5-thiazolylmethyl, 2-(1-hydroxy-1-methylethyl)-5-thiazolylmethyl, 2-(2,2,2-trifluoro-1-hydroxy-1-trifluoromethylethyl)-5-thiazolylmethyl, 2-(1-carboxy-1-methylethyl)-5-thiazolylmethyl, 2-methoxycarbonyl-5-thiazolylmethyl, 2-ethoxycarbonyl-5-thiazolylmethyl, 2-propoxycarbonyl-5-thiazolylmethyl, 2-isopropoxycarbonyl-5-thiazolylmethyl, 4-isothiazolylmethyl, 5-isothiazolylmethyl, 2-imidazolylmethyl, 4-imidazolylmethyl, 3-pyrazolylmethyl, 4-pyrazolylmethyl,
2-pyridylmethyl, 6-cyano-2-pyridylmethyl, 6-carboxy-2-pyridylmethyl, 6-trifluoromethyl-2-pyridylmethyl, 6-methoxy-2-pyridylmethyl, 6-ethoxy-2-pyridylmethyl, 6-methoxycarbonyl-2-pyridylmethyl, 6-ethoxycarbonyl-2-pyridylmethyl, 6-(1-hydroxy-1-methylethyl)-2-pyridylmethyl, 6-(2,2,2-trifluoro-1-hydroxy-1-trifluoromethylethyl)-2-pyridylmethyl, 6-(1-carboxy-1-methylethyl)-2-pyridylmethyl, 3-pyridylmethyl, 6-cyano-3-pyridylmethyl, 6-carboxy-3-pyridylmethyl, 6-trifluoromethyl-3-pyridylmethyl, 6-methoxy-3-pyridylmethyl, 6-ethoxy-3-pyridylmethyl, 6-methoxycarbonyl-3-pyridylmethyl, 6-ethoxycarbonyl-3-pyridylmethyl, 6-(1-hydroxy-1-methylethyl)-3-pyridylmethyl, 6-(2,2,2-trifluoro-1-hydroxy-1-trifluoromethylethyl)-3-pyridylmethyl, 6-(1-carboxy-1-methylethyl)-3-pyridylmethyl, 2-cyano-3-pyridylmethyl, 2-carboxy-3-pyridylmethyl, 2-trifluoromethyl-3-pyridylmethyl, 2-methoxy-3-pyridylmethyl, 2-ethoxy-3-pyridylmethyl, 2-propoxy-3-pyridylmethyl, 2-methoxycarbonyl-3-pyridylmethyl, 2-ethoxycarbonyl-3-pyridylmethyl, 2-propoxycarbonyl-3-pyridylmethyl, 2-(1-hydroxy-1-methylethyl)-3-pyridylmethyl, 2-(2,2,2-trifluoro-1-hydroxy-1-trifluoromethylethyl)-3-pyridylmethyl, 2-(1-carboxy-1-methylethyl)-3-pyridylmethyl, 4-pyridylmethyl, 2-cyano-4-pyridylmethyl, 2-carboxy-4-pyridylmethyl, 2-trifluoromethyl-4-pyridylmethyl, 2-methoxy-4-pyridylmethyl, 2-ethoxy-4-pyridylmethyl, 2-propoxy-4-pyridylmethyl, 2-methoxycarbonyl-4-pyridylmethyl, 2-ethoxycarbonyl-4-pyridylmethyl, 2-(1-hydroxy-1-methylethyl)-4-pyridylmethyl, 2-(2,2,2-trifluoro-1-hydroxy-1-trifluoromethylethyl)-4-pyridylmethyl, 2-(1-carboxy-1-methylethyl)-4-pyridylmethyl, 3-pyridazinylmethyl, 4-pyridazinylmethyl, 2-pyrimidinylmethyl, 4-pyrimidinylmethyl, 5-pyrimidinylmethyl, 2-pyrazinylmethyl, phenethyl, 2-fluorophenethyl, 3-fluorophenethyl, 4-fluorophenethyl, 2,4-difluorophenethyl, 2,6-difluorophenethyl, 3,4-difluorophenethyl, 2-chlorophenethyl, 3-chlorophenethyl, 4-chlorophenethyl, 2,4-dichlorophenethyl, 2,6-dichlorophenethyl, 3,4-dichlorophenethyl, 3-cyanophenethyl, 4-cyanophenethyl, 3-nitrophenethyl, 4-nitrophenethyl, 3-carboxyphenethyl, 4-carboxyphenethyl, 3-trifluoromethylphenethyl, 4-trifluoromethylphenethyl, 3-(1-hydroxy-1-methylethyl)phenethyl, 4-(1-hydroxy-1-methylethyl)phenethyl, 3-(2,2,2-trifluoro-1-hydroxy-1-trifluoromethylethyl)phenethyl, 4-(2,2,2-trifluoro-1-hydroxy-1-trifluoromethylethyl)phenethyl, 3-(1-carboxy-1-methylethyl)phenethyl, 4-(1-carboxy-1-methylethyl)phenethyl, 3-methoxyphenethyl, 4-methoxyphenethyl, 3-ethoxyphenethyl, 4-ethoxyphenethyl, 3-methoxycarbonylphenethyl, 4-methoxycarbonylphenethyl, 3-ethoxycarbonylphenethyl, 4-ethoxycarbonylphenethyl, 2-(2-thienyl)ethyl, 2-(4-cyano-2-thienyl)ethyl, 2-(5-cyano-2-thienyl)ethyl, 2-(4-carboxy-2-thienyl)ethyl, 2-(5-carboxy-2-thienyl)ethyl, 2-(4-methyl-2-thienyl)ethyl, 2-(5-methyl-2-thienyl)ethyl, 2-(4-trifluoromethyl-2-thienyl)ethyl, 2-(5-trifluoromethyl-2-thienyl)ethyl, 2-(4-(1-hydroxy-1-methylethyl)-2-thienyl)ethyl, 2-(5-(1-hydroxy-1-methylethyl)-2-thienyl)ethyl, 2-(4-(2,2,2-trifluoro-1-hydroxy-1-trifluoromethylethyl)-2-thienyl)ethyl, 2-(5-(2,2,2-trifluoro-1-hydroxy-1-trifluoromethylethyl)-2-thienyl)ethyl, 2-(4-(1-carboxy-1-methylethyl)-2-thienyl)ethyl, 2-(5-(1-carboxy-1-methylethyl)-2-thienyl)ethyl, 2-(3-thienyl)ethyl, 2-(4-cyano-3-thienyl)ethyl, 2-(5-cyano-3-thienyl)ethyl, 2-(4-carboxy-3-thienyl)ethyl, 2-(5-carboxy-3-thienyl)ethyl, 2-(4-methyl-3-thienyl)ethyl, 2-(5-methyl-3-thienyl)ethyl, 2-(4-trifluoromethyl-3-thienyl)ethyl, 2-(5-trifluoromethyl-3-thienyl)ethyl, 2-(5-ethyl-3-thienyl)ethyl, 2-(5-(1-hydroxy-1-methylethyl)-3-thienyl)ethyl, 2-(5-(2,2,2-trifluoro-1-hydroxy-1-trifluoromethylethyl)-3-thienyl)ethyl, 2-(5-(1-carboxy-1-methylethyl)-3-thienyl)ethyl, 2-(5-methoxycarbonyl-3-thienyl)ethyl, 2-(4-thiazolyl)ethyl, 2-(2-cyano-4-thiazolyl)ethyl, 2-(2-carboxy-4-thiazolyl)ethyl, 2-(2-methyl-4-thiazolyl)ethyl, 2-(2-ethyl-4-thiazolyl)ethyl, 2-(2-propyl-4-thiazolyl)ethyl, 2-(2-isopropyl-4-thiazolyl)ethyl, 2-(2-trifluoromethyl-4-thiazolyl)ethyl, 2-(2-(1-hydroxy-1-methylethyl)-4-thiazolyl)ethyl, 2-(2-(2,2,2-trifluoro-1-hydroxy-1-trifluoromethylethyl)-4-thiazolyl)ethyl, 2-(2-(1-carboxy-1-methylethyl)-4-thiazolyl)ethyl, 2-(2-methoxycarbonyl-4-thiazolyl)ethyl, 2-(5-thiazolyl)ethyl, 2-(2-cyano-5-thiazolyl)ethyl, 2-(2-carboxy-5-thiazolyl)ethyl, 2-(2-methyl-5-thiazolyl)ethyl, 2-(2-ethyl-5-thiazolyl)ethyl, 2-(2-trifluoromethyl-5-thiazolyl)ethyl, 2-(2-(1-hydroxy-1-methylethyl)-5-thiazolyl)ethyl, 2-(2-(2,2,2-trifluoro-1-hydroxy-1-trifluoromethylethyl)-5-thiazolyl)ethyl, 2-(2-(1-carboxy-1-methylethyl)-5-thiazolyl)ethyl, 2-(2-methoxycarbonyl-5-thiazolyl)ethyl, 2-(2-ethoxycarbonyl-5-thiazolyl)ethyl, 2-(2-propoxycarbonyl-5-thiazolyl)ethyl, 2-(2-isopropoxycarbonyl-5-thiazolyl)ethyl, 2-(4-pyrazolyl)ethyl, 2-(6-cyano-2-pyridyl)ethyl, 2-(6-carboxy-2-pyridyl)ethyl, 2-(6-trifluoromethyl-2-pyridyl)ethyl, 2-(6-methoxy-2-pyridyl)ethyl, 2-(6-ethoxy-2-pyridyl)ethyl, 2-(6-methoxycarbonyl-2-pyridyl)ethyl, 2-(6-ethoxycarbonyl-2-pyridyl)ethyl, 2-(6-(1-hydroxy-1-methylethyl)-2-pyridyl)ethyl, 2-(6-(2,2,2-trifluoro-1-hydroxy-1-trifluoromethylethyl)-2-pyridyl)ethyl, 2-(6-(1-carboxy-1-methylethyl)-2-pyridyl)ethyl, 2-(6-cyano-3-pyridyl)ethyl, 2-(6-carboxy-3-pyridyl)ethyl, 2-(6-trifluoromethyl-3-pyridyl)ethyl, 2-(6-methoxy-3-pyridyl)ethyl, 2-(6-ethoxy-3-pyridyl)ethyl, 2-(6-methoxycarbonyl-3-pyridyl)ethyl, 2-(6-ethoxycarbonyl-3-pyridyl)ethyl, 2-(6-(1-hydroxy-1-methylethyl)-3-pyridyl)ethyl, 2-(6-(2,2,2-trifluoro-1-hydroxy-1-trifluoromethylethyl)ethyl, 2-(6-(1-carboxy-1-methylethyl)-3-pyridyl)ethyl, 2-(2-cyano-3-pyridyl)ethyl, 2-(2-carboxy-3-pyridyl)ethyl, 2-(2-trifluoromethyl-3-pyridyl)ethyl, 2-(2-methoxy-3-pyridyl)ethyl, 2-(2-ethoxy-3-pyridyl)ethyl, 2-(2-propoxy-3-pyridyl)ethyl, 2-(2-methoxycarbonyl-3-pyridyl)ethyl, 2-(2-ethoxycarbonyl-3-pyridyl)ethyl, 2-(2-propoxycarbonyl-3-pyridyl)ethyl, 2-(2-(1-hydroxy-1-methylethyl)-3-pyridyl)ethyl, 2-(2-(2,2,2-trifluoro-1-hydroxy-1-trifluoromethylethyl)ethyl, 2-(2-(1-carboxy-1-methylethyl)-3-pyridyl)ethyl, 2-(2-cyano-4-pyridyl)ethyl, 2-(2-carboxy-4-pyridyl)ethyl, 2-(2-trifluoromethyl-4-pyridyl)ethyl, 2-(2-methoxy-4-pyridyl)ethyl, 2-(2-ethoxy-4-pyridyl)ethyl, 2-(2-propoxy-4-pyridyl)ethyl, 2-(2-methoxycarbonyl-4-pyridyl)ethyl, 2-(2-ethoxycarbonyl-4-pyridyl)ethyl, 2-(2-(1-hydroxy-1-methylethyl)-4-pyridyl)ethyl, 2-(2-(2,2,2-trifluoro-1-hydroxy-1-trifluoromethylethyl)-4-pyridyl)ethyl, 2-(2-(1-carboxy-1-methylethyl)-4-pyridyl)ethyl, hydroxyphenylmethyl, (2-fluorophenyl)hydroxymethyl, (3-fluorophenyl)hydroxymethyl, (4-fluorophenyl)hydroxymethyl, (2,4-difluorophenyl)hydroxymethyl, (2,6-difluorophenyl)hydroxymethyl, (3,4-difluorophenyl)hydroxymethyl, (2-chlorophenyl)hydroxymethyl, (3-chlorophenyl)hydroxymethyl, (4-chlorophenyl)hydroxymethyl, (2,4-dichlorophenyl)hydroxylmethyl, (2,6-dichlorophenyl)hydroxymethyl, (3,4-dichlorophenyl)hydroxymethyl, (3-cyanophenyl)hydroxymethyl, (4-cyanophenyl)hydroxymethyl, hydroxy(3-nitrophenyl)methyl, hydroxy(4-nitrophenyl)methyl, (3-carboxyphenyl)hydroxymethyl, (4-carboxyphenyl)hydroxymethyl, hydroxy(3-trifluoromethylphenyl)methyl, hydroxy(4-trifluoromethylphenyl)methyl, hydroxy(3-methoxyphenyl)methyl, hydroxy(4-methoxyphenyl)methyl, (3-ethoxyphenyl)hydroxymethyl, (4-ethoxyphenyl)hydroxymethyl, hydroxy(3-methoxycarbonylphenyl)methyl, hydroxy(4-methoxycarbonylphenyl)methyl, (3-ethoxycarbonylphenyl)hydroxymethyl, (4-ethoxycarbonylphenyl)hydroxymethyl, hydroxy(2-thienyl)methyl, hydroxy(5-methyl-2-thienyl)methyl or hydroxy(5-trifluoromethyl-2-thienyl) methyl group, etc., preferably a benzyl, 2-fluorobenzyl, 3-fluorobenzyl, 4-fluorobenzyl, 2,4-difluorobenzyl, 2,6-difluorobenzyl, 3,4-difluorobenzyl, 2-chlorobenzyl, 3-chlorobenzyl, 4-chlorobenzyl, 2,4-dichlorobenzyl, 2,6-dichlorobenzyl, 3,4-dichlorobenzyl, 2-cyanobenzyl, 3-cyanobenzyl, 4-cyanobenzyl, 3-nitrobenzyl, 4-nitrobenzyl, 3-carboxybenzyl, 4-carboxybenzyl, 3-trifluoromethylbenzyl, 4-trifluoromethylbenzyl, 3-(1-hydroxy-1-methylethyl)benzyl, 4-(1-hydroxy-1-methylethyl)benzyl, 3-(2,2,2-trifluoro-1-hydroxy-1-trifluoromethylethyl)benzyl, 4-(2,2,2-trifluoro-1-hydroxy-1-trifluoromethylethyl)benzyl, 3-(1-carboxy-1-methylethyl)benzyl, 4-(1-carboxy-1-methylethyl)benzyl, 3-methoxybenzyl, 4-methoxybenzyl, 3-ethoxybenzyl, 4-ethoxybenzyl, 3-methoxycarbonylbenzyl, 4-methoxycarbonylbenzyl, 3-ethoxycarbonylbenzyl, 4-ethoxycarbonylbenzyl, 2-thienylmethyl, 4-cyano-2-thienylmethyl, 5-cyano-2-thienylmethyl, 4-carboxy-2-thienylmethyl, 5-carboxy-2-thienylmethyl, 4-methyl-2-thienylmethyl, 5-methyl-2-thienylmethyl, 4-trifluoromethyl-2-thienylmethyl, 5-trifluoromethyl-2-thienylmethyl, 4-(1-hydroxy-1-methylethyl)-2-thienylmethyl, 5-(1-hydroxy-1-methylethyl)-2-thienylmethyl, 4-(2,2,2-trifluoro-1-hydroxy-1-trifluoromethylethyl)-2-thienylmethyl, 5-(2,2,2-trifluoro-1-hydroxy-1-trifluoromethylethyl)-2-thienylmethyl, 4-(1-carboxy-1-methylethyl)-2-thienylmethyl, 5-(1-carboxy-1-methylethyl)-2-thienylmethyl, 3-thienylmethyl, 4-cyano-3-thienylmethyl, 5-cyano-3-thienylmethyl, 4-carboxy-3-thienylmethyl, 5-carboxy-3-thienylmethyl, 4-methyl-3-thienylmethyl, 5-methyl-3-thienylmethyl, 4-trifluoromethyl-3-thienylmethyl, 5-trifluoromethyl-3-thienylmethyl, 5-ethyl-3-thienylmethyl, 5-(1-hydroxy-1-methylethyl)-3-thienylmethyl, 5-(2,2,2-trifluoro-1-hydroxy-1-trifluoromethylethyl)-3-thienylmethyl, 5-(1-carboxy-1-methylethyl)-3-thienylmethyl, 5-methoxycarbonyl-3-thienylmethyl, 4-thiazolylmethyl, 2-cyano-4-thiazolylmethyl, 2-carboxy-4-thiazolylmethyl, 2-methyl-4-thiazolylmethyl, 2-ethyl-4-thiazolylmethyl, 2-propyl-4-thiazolylmethyl, 2-isopropyl-4-thiazolylmethyl, 2-trifluoromethyl-4-thiazolylmethyl, 2-(1-hydroxy-1-methylethyl)-4-thiazolylmethyl, 2-(2,2,2-trifluoro-1-hydroxy-1-trifluoromethylethyl)-4-thiazolylmethyl, 2-(1-carboxy-1-methylethyl)-4-thiazolylmethyl, 2-methoxycarbonyl-4-thiazolylmethyl, 5-thiazolylmethyl, 2-cyano-5-thiazolylmethyl, 2-carboxy-5-thiazolylmethyl, 2-methyl-5-thiazolylmethyl, 2-ethyl-5-thiazolylmethyl, 2-trifluoromethyl-5-thiazolylmethyl, 2-(1-hydroxy-1-methylethyl)-5-thiazolylmethyl, 2-(2,2,2-trifluoro-1-hydroxy-1-trifluoromethylethyl)-5-thiazolylmethyl, 2-(1-carboxy-1-methylethyl)-5-thiazolyl, 2-methoxycarbonyl-5-thiazolylmethyl, 4-pyrazolylmethyl, 6-cyano-2-pyridylmethyl, 6-carboxy-2-pyridylmethyl, 6-trifluoromethyl-2-pyridylmethyl, 6-methoxy-2-pyridylmethyl, 6-ethoxy-2-pyridylmethyl, 6-methoxycarbonyl-2-pyridylmethyl, 6-ethoxycarbonyl-2-pyridylmethyl, 6-(1-hydroxy-1-methylethyl)-2-pyridylmethyl, 6-(2,2,2-trifluoro-1-hydroxy-1-trifluoromethylethyl)-2-pyridylmethyl, 6-(1-carboxy-1-methylethyl)-2-pyridylmethyl, 6-cyano-3-pyridylmethyl, 6-carboxy-3-pyridylmethyl, 6-trifluoromethyl-3-pyridylmethyl, 6-methoxy-3-pyridylmethyl, 6-ethoxy-3-pyridylmethyl, 6-methoxycarbonyl-3-pyridylmethyl, 6-ethoxycarbonyl-3-pyridylmethyl, 6-(1-hydroxy-1-methylethyl)-3-pyridylmethyl, 6-(2,2,2-trifluoro-1-hydroxy-1-trifluoromethylethyl)-3-pyridylmethyl, 6-(1-carboxy-1-methylethyl)-3-pyridylmethyl, 2-cyano-3-pyridylmethyl, 2-carboxy-3-pyridylmethyl, 2-trifluoromethyl-3-pyridylmethyl, 2-methoxy-3-pyridylmethyl, 2-ethoxy-3-pyridylmethyl, 2-propoxy-3-pyridylmethyl, 2-methoxycarbonyl-3-pyridylmethyl, 2-ethoxycarbonyl-3-pyridylmethyl, 2-propoxycarbonyl-3-pyridylmethyl, 2-(1-hydroxy-1-methylethyl)-3-pyridylmethyl, 2-(2,2,2-trifluoro-1-hydroxy-1-trifluoromethylethyl)-3-pyridylmethyl, 2-(1-carboxy-1-methylethyl)-3-pyridylmethyl, 2-cyano-4-pyridylmethyl, 2-carboxy-4-pyridylmethyl, 2-trifluoromethyl-4-pyridylmethyl, 2-methoxy-4-pyridylmethyl, 2-ethoxy-4-pyridylmethyl, 2-propoxy-4-pyridylmethyl, 2-methoxycarbonyl-4-pyridylmethyl, 2-ethoxycarbonyl-4-pyridylmethyl, 2-(1-hydroxy-1-methylethyl)-4-pyridylmethyl, 2-(2,2,2-trifluoro-1-hydroxy-1-trifluoromethylethyl)-4-pyridylmethyl, 2-(1-carboxy-1-methylethyl)-4-pyridylmethyl, phenethyl, 2-fluorophenethyl, 3-fluorophenethyl, 4-fluorophenethyl, 3-chlorophenethyl, 3-cyanophenethyl, 3-carboxyphenethyl, 3-methoxyphenethyl, 2-(2-thienyl)ethyl, 2-(3-thienyl)ethyl, 2-(4-thiazolyl)ethyl, 2-(5-thiazolyl)ethyl, 2-(4-pyrazolyl)ethyl, 2-(6-cyano-2-pyridyl)ethyl, 2-(6-carboxy-2-pyridyl)ethyl, 2-(6-methoxy-2-pyridyl)ethyl, 2-(6-cyano-3-pyridyl)ethyl, 2-(6-carboxy-3-pyridyl)ethyl, 2-(6-methoxy-3-pyridyl)ethyl, 2-(2-cyano-3-pyridyl)ethyl, 2-(2-carboxy-3-pyridyl)ethyl, 2-(2-methoxy-3-pyridyl)ethyl, hydroxylphenylmethyl, (2-fluorophenyl)hydroxymethyl, (3-fluorophenyl)hydroxymethyl, (4-fluorophenyl)hydroxymethyl, (3-chlorophenyl)hydroxymethyl, (3,4-difluorophenyl)hydroxymethyl, (2,4-difluorophenyl)hydroxymethyl, (3-cyanophenyl)hydroxymethyl, hydroxy(3-trifluoromethylphenyl)methyl or hydroxy(2-thienyl)methyl group, more preferably a benzyl, 2-fluorobenzyl, 3-fluorobenzyl, 4-fluorobenzyl, 2,4-difluorobenzyl, 3,4-difluorobenzyl, 2-chlorobenzyl, 3-chlorobenzyl, 4-chlorobenzyl, 2,4-dichlorobenzyl, 3,4-dichlorobenzyl, 2-cyanobenzyl, 3-cyanobenzyl, 4-cyanobenzyl, 3-nitrobenzyl, 3-carboxybenzyl, 4-carboxybenzyl, 3-trifluoromethylbenzyl, 4-trifluoromethylbenzyl, 3-(1-hydroxy-1-methylethyl)benzyl, 4-(1-hydroxy-1-methylethyl)benzyl, 3-(2,2,2-trifluoro-1-hydroxy-1-trifluoromethylethyl)benzyl, 4-(2,2,2-trifluoro-1-hydroxy-1-trifluoromethylethyl)benzyl, 4-(1-carboxy-1-methylethyl)benzyl, 3-methoxybenzyl, 4-methoxybenzyl, 3-methoxycarbonylbenzyl, 4-methoxycarbonylbenzyl, 2-thienylmethyl, 5-cyano-2-thienylmethyl, 5-carboxy-2-thienylmethyl, 5-methyl-2-thienylmethyl, 5-trifluoromethyl-2-thienylmethyl, 5-(1-hydroxy-1-methylethyl)-2-thienylmethyl, 5-(2,2,2-trifluoro-1-hydroxy-1-trifluoromethylethyl)-2-thienylmethyl, 4-(1-carboxy-1-methylethyl)-2-thienylmethyl, 3-thienylmethyl, 5-cyano-3-thienylmethyl, 5-carboxy-3-thienylmethyl, 5-methyl-3-thienylmethyl, 5-trifluoromethyl-3-thienylmethyl, 5-(1-hydroxy-1-methylethyl)-3-thienylmethyl, 5-(2,2,2-trifluoro-1-hydroxy-1-trifluoromethylethyl)-3-thienylmethyl, 4-thiazolylmethyl, 2-cyano-4-thiazolylmethyl, 2-carboxy-4-thiazolylmethyl, 2-methyl-4-thiazolylmethyl, 2-trifluoromethyl-4-thiazolylmethyl, 2-(1-hydroxy-1-methylethyl)-4-thiazolylmethyl, 2-(2,2,2-trifluoro-1-hydroxy-1-trifluoromethylethyl)-4-thiazolylmethyl, 5-thiazolylmethyl, 2-cyano-5-thiazolylmethyl, 2-carboxy-5-thiazolylmethyl, 2-methyl-5-thiazolylmethyl, 2-trifluoromethyl-5-thiazolylmethyl, 2-(1-hydroxy-1-methylethyl)-5-thiazolylmethyl, 2-(2,2,2-trifluoro-1-hydroxy-1-trifluoromethylethyl)-5-thiazolylmethyl, 4-pyrazolylmethyl, 6-cyano-2-pyridylmethyl, 6-carboxy-2-pyridylmethyl, 6-trifluoromethyl-2-pyridylmethyl, 6-methoxy-2-pyridylmethyl, 6-(1-hydroxy-1-methylethyl)-2-pyridylmethyl, 6-(2,2,2-trifluoro-1-hydroxy-1-trifluoromethylethyl)-2-pyridylmethyl, 6-cyano-3-pyridylmethyl, 6-carboxy-3-pyridylmethyl, 6-trifluoromethyl-3-pyridylmethyl, 6-methoxy-3-pyridylmethyl, 6-(1-hydroxy-1-methylethyl)-3-pyridylmethyl, 6-(2,2,2-trifluoro-1-hydroxy-1-trifluoromethylethyl)-3-pyridylmethyl, 2-cyano-3-pyridylmethyl, 2-carboxy-3-pyridylmethyl, 2-trifluoromethyl-3-pyridylmethyl, 2-methoxy-3-pyridylmethyl, 2-(1-hydroxy-1-methylethyl)-3-pyridylmethyl, 2-(2,2,2-trifluoro-1-hydroxy-1-trifluoromethylethyl)-3-pyridylmethyl, 2-cyano-4-pyridylmethyl, 2-carboxy-4-pyridylmethyl, 2-trifluoromethyl-4-pyridylmethyl, 2-methoxy-4-pyridylmethyl, 2-(1-hydroxy-1-methylethyl)-4-pyridylmethyl, 2-(2,2,2-trifluoro-1-hydroxy-1-trifluoromethylethyl)-4-pyridylmethyl, phenethyl, 2-fluorophenethyl, 3-fluorophenethyl, 4-fluorophenethyl, 3-chlorophenethyl, 3-cyanophenethyl, 3-carboxyphenethyl, 3-methoxyphenethyl, 2-(2-thienyl)ethyl, 2-(3-thienyl)ethyl, 2-(6-cyano-2-pyridyl)ethyl, 2-(6-methoxy-2-pyridyl)ethyl, 2-(6-cyano-3-pyridyl)ethyl, 2-(6-methoxy-3-pyridyl)ethyl, 2-(2-cyano-3-pyridyl)ethyl, 2-(2-methoxy-3-pyridyl)ethyl, hydroxyphenylmethyl, (2-fluorophenyl)hydroxymethyl, (3-fluorophenyl)hydroxymethyl, (4-fluorophenyl)hydroxymethyl, (3,4-difluorophenyl)hydroxymethyl or hydroxy(2-thienyl)methyl group,
particularly preferably a benzyl, 2-fluorobenzyl, 3-fluorobenzyl, 4-fluorobenzyl, 2,4-difluorobenzyl, 3,4-difluorobenzyl, 2-chlorobenzyl, 3-chlorobenzyl, 2-cyanobenzyl, 3-cyanobenzyl, 3-carboxybenzyl, 4-carboxybenzyl, 3-trifluoromethylbenzyl, 4-methoxybenzyl, 3-methoxycarbonylbenzyl, 2-thienylmethyl, 5-cyano-2-thienylmethyl, 5-carboxy-2-thienylmethyl, 5-trifluoromethyl-2-thienylmethyl, 3-thienylmethyl, 5-cyano-3-thienylmethyl, 5-carboxy-3-thienylmethyl, 5-trifluoromethyl-3-thienylmethyl, 4-thiazolylmethyl, 2-cyano-4-thiazolylmethyl, 2-carboxy-4-thiazolylmethyl, 2-(1-hydroxy-1-methylethyl)-4-thiazolylmethyl, 2-(2,2,2-trifluoro-1-hydroxy-1-trifluoromethylethyl)-4-thiazolylmethyl, 2-cyano-5-thiazolylmethyl, 2-carboxy-5-thiazolylmethyl, 2-(1-hydroxy-1-methylethyl)-5-thiazolylmethyl, 2-(2,2,2-trifluoro-1-hydroxy-1-trifluoromethylethyl)-5-thiazolylmethyl, 6-cyano-2-pyridylmethyl, 6-carboxy-2-pyridylmethyl, 6-methoxy-2-pyridylmethyl, 6-(1-hydroxy-1-methylethyl)-2-pyridylmethyl, 6-(2,2,2-trifluoro-1-hydroxy-1-trifluoromethylethyl)-2-pyridylmethyl, 6-cyano-3-pyridylmethyl, 6-carboxy-3-pyridylmethyl, 6-methoxy-3-pyridylmethyl, 6-(1-hydroxy-1-methylethyl)-3-pyridylmethyl, 6-(2,2,2-trifluoro-1-hydroxy-1-trifluoromethylethyl)-3-pyridylmethyl, 2-cyano-3-pyridylmethyl, 2-carboxy-3-pyridylmethyl, 2-methoxy-3-pyridylmethyl, 2-(1-hydroxy-1-methylethyl)-3-pyridylmethyl, 2-(2,2,2-trifluoro-1-hydroxy-1-trifluoromethylethyl)-3-pyridylmethyl, 2-cyano-4-pyridylmethyl, 2-carboxy-4-pyridylmethyl, 2-methoxy-4-pyridylmethyl, 2-(1-hydroxy-1-methylethyl)-4-pyridylmethyl, 2-(2,2,2-trifluoro-1-hydroxy-1-trifluoromethylethyl)-4-pyridylmethyl, phenethyl, 2-fluorophenethyl, 3-fluorophenethyl, 4-fluorophenethyl, 3-cyanophenethyl, 2-(2-thienyl)ethyl, 2-(6-cyano-2-pyridyl)ethyl, 2-(6-cyano-3-pyridyl)ethyl, 2-(2-cyano-3-pyridyl)ethyl, hydroxyphenylmethyl, (3-fluorophenyl)hydroxymethyl, (4-fluorophenyl)hydroxymethyl or hydroxy(2-thienyl)methyl group.

As $R^4$, there may be preferably mentioned a hydrogen atom, chlorine atom, bromine atom, iodine atom, methyl, ethyl, propyl, isopropyl, butyl, isobutyl, pentyl, isopentyl, neopentyl, 2-methylbutyl, hexyl, 2-methylpentyl, 3-methylpentyl, 4-methylpentyl, 2-ethylbutyl, 2,2-dimethylbutyl, 3,3-dimethylbutyl, 2,3-dimethylbutyl, heptyl, 2-methylhexyl, 3-methylhexyl, 4-methylhexyl, 5-methylhexyl, 2,3-dimethylpentyl, 2,4-dimethylpentyl, 3,4-dimethylpentyl, 2,2-dimethylpentyl, 3,3-dimethylpentyl, 4,4-dimethylpentyl, octyl, 2-methylheptyl, 3-methylheptyl, 4-methylheptyl, 5-methylheptyl, 6-methylheptyl, 2-ethylhexyl, 3-ethylhexyl, 4-ethylhexyl, 2,3-dimethylhexyl, 2,4-dimethylhexyl, 2,5-dimethylhexyl, 3,4-dimethylhexyl, 3,5-dimethylhexyl, 2,2-dimethylhexyl, 3,3-dimethylhexyl, 4,4-dimethylhexyl, 5,5-dimethylhexyl, 2-methyl-3-ethylpentyl, 2-propylpentyl, 2,2,3,3-tetramethylbutyl, trifluoromethyl, 2,2,2-trifluoroethyl, 3,3,3-trifluoropropyl, 2-chloroethyl, hydroxymethyl, 1-hydroxyethyl, 2-hydroxyethyl, 1-hydroxypropyl, 3-hydroxypropyl, 1-hydroxybutyl, 4-hydroxybutyl, 1-hydroxypentyl, 5-hydroxypentyl, 1-hydroxyhexyl, 6-hydroxyhexyl, 1-hydroxy-2-methylpropyl, 2-hydroxy-2-methylpropyl, 1-hydroxy-3-methylbutyl, 3-hydroxy-3-methylbutyl, 1-hydroxy-4-methylpentyl, 4-hydroxy-4-methylpentyl, 2-ethyl-2-hydroxybutyl, cyanomethyl, 2-cyanoethyl, 3-cyanopropyl, 4-cyanobutyl, 5-cyanopentyl, 6-cyanohexyl, 2-cyano-2-methylpropyl, 3-cyano-3-methylbutyl, 4-cyano-4-methylpentyl, 2-cyano-2-ethylbutyl, carboxymethyl, 2-carboxyethyl, 3-carboxypropyl, 4-carboxybutyl, 5-carboxypentyl, 6-carboxyhexyl, 2-carboxy-2-methylpropyl, 3-carboxy-3-methylbutyl, 4-carboxy-4-methylpentyl, 2-carboxy-2-ethylbutyl, methoxymethyl, 2-methoxyethyl, 2-methoxypropyl, 3-methoxypropyl, 4-methoxybutyl, 5-methoxypentyl, 6-methoxyhexyl, 2-methoxy-2-methylpropyl, 3-methoxy-3-methylbutyl, 4-methoxy-4-methylpentyl, 2-ethyl-2-methoxybutyl, ethoxymethyl, 2-ethoxyethyl, 2-ethoxypropyl, 3-ethoxypropyl, 4-ethoxybutyl, 5-ethoxypentyl, 6-ethoxyhexyl, 2-ethoxy-2-methylpropyl, 3-ethoxy-3-methylbutyl, 4-ethoxy-4-methylpentyl, 2-ethoxy-2-ethylbutyl, propoxymethyl, 2-propoxyethyl, 3-propoxypropyl, 4-propoxybutyl, 5-propoxypentyl, 6-propoxyhexyl, 2-methyl-2-propoxypropyl, 3-methyl-3-propoxybutyl, 4-methyl-4-propoxypentyl, 2-ethyl-2-propoxybutyl, butoxymethyl, 2-butoxyethyl, 3-butoxypropyl, 4-butoxybutyl, 5-butoxypentyl, 6-butoxyhexyl, 2-butoxy-2-methylpropyl, 3-butoxy-3-methylbutyl, 4-butoxy-4-methylpentyl, 2-butoxy-2-ethylbutyl, isopropoxymethyl, 2-isopropoxyethyl, 3-isopropoxypropyl, 4-isopropoxybutyl, 5-isopropoxypentyl, 6-isopropoxyhexyl, 2-isopropoxy-2-methylpropyl, 3-isopropoxy-3-methylbutyl, 4-isopropoxy-4-methylpentyl, 2-ethyl-2-isopropoxybutyl, isobutoxymethyl, 2-isobutoxyethyl, sec-butoxymethyl, 2-(sec-butoxy)ethyl, tert-butoxymethyl, 2-(tert-butoxy)ethyl, 1-ethylpropoxymethyl, 2-(1-ethylpropoxy)ethyl, 2-fluoroethoxymethyl, 2-(2-fluoroethoxy)ethyl, 2-(2-fluoroethoxy)propyl, 3-(2-fluoroethoxy)propyl, 4-(2-fluoroethoxy)butyl, 5-(2-fluoroethoxy)pentyl, 6-(2-fluoroethoxy)hexyl, 2-(2-fluoroethoxy)-2-methylpropyl, 3-(2-fluoroethoxy)-3-methylbutyl, 4-(2-fluoroethoxy)-4-methylpentyl, 2-ethyl-2-(2-fluoroethoxy)butyl, (2,2,2-trifluoroethoxy)methyl, 2-(2,2,2-trifluoroethoxy)ethyl, 2-(2,2,2-trifluoroethoxy)propyl, 3-(2,2,2-trifluoroethoxy)propyl, 4-(2,2,2-trifluoroethoxy)butyl, 5-(2,2,2-trifluoroethoxy)pentyl, 6-(2,2,2-trifluoroethoxy)hexyl, 2-(2,2,2-trifluoroethoxy)-2-methylpropyl, 3-(2,2,2-trifluoroethoxy)-3-methylbutyl, 4-(2,2,2-trifluoroethoxy)-4-methylpentyl, 2-ethyl-2-(2,2,2-trifluoroethoxy)butyl, cyclopropoxymethyl, 2-cyclopropoxyethyl, 2-cyclopropoxypropyl, 3-cyclopropoxypropyl, 4-cyclopropoxybutyl, 5-cyclopropoxypentyl, 6-cyclopropoxyhexyl, 2-cyclopropoxy-2-methylpropyl, 3-cyclopropoxy-3-methylbutyl, 4-cyclopropoxy-4-methylpentyl, 2-cyclopropoxy-2-ethylbutyl, cyclobutoxymethyl, 2-cyclobutoxyethyl, 2-cyclobutoxypropyl, 3-cyclobutoxypropyl, 4-cyclobutoxybutyl, 5-cyclobutoxypentyl, 6-cyclobutoxyhexyl, 2-cyclobutoxy-2-methylpropyl, 3-cyclobutoxy-3-methylbutyl, 4-cyclobutoxy-4-methylpentyl, 2-cyclobutoxy-2-ethylbutyl, cyclopropylmethoxymethyl, 2-cyclopropylmethoxyethyl, 2-cyclopropylmethoxypropyl, 3-cyclopropylmethoxypropyl, 4-cyclopropylmethoxybutyl, 5-cyclopropylmethoxypentyl, 6-cyclopropylmethoxyhexyl, 2-cyclopropylmethoxy-2-methylpropyl, 3-cyclopropylmethoxy-3-methylbutyl, 4-cyclopropylmethoxy-4-methylpentyl, 2-cyclopropylmethoxy-2-ethylbutyl, cyclobutylmethoxymethyl, 2-cyclobutylmethoxyethyl, 2-cyclobutylmethoxypropyl, 3-cyclobutylmethoxypropyl, 4-cyclobutylmethoxybutyl, 5-cyclobutylmethoxypentyl, 6-cyclobutylmethoxyhexyl, 2-cyclobutylmethoxy-2-methylpropyl, 3-cyclobutylmethoxy-3-methylbutyl, 4-cyclobutylmethoxy-4-methylpentyl, 2-cyclobutylmethoxy-2-ethylbutyl, methoxycarbonylmethyl, 2-methoxycarbonylethyl, 3-methoxycarbonylpropyl, 4-methoxycarbonylbutyl, 5-methoxycarbonylpentyl, 6-methoxycarbonylhexyl, 2-methoxycarbonyl-2-methylpropyl, 3-methoxycarbonyl-3-methylbutyl, 4-methoxycarbonyl-4-methylpentyl, 2-ethyl-2-methoxycarbonylbutyl, ethoxycarbonylmethyl, 2-ethoxycarbonylethyl, 3-ethoxycarbonylpropyl, 4-ethoxycarbonylbutyl, 5-ethoxycarbonylpentyl, 6-ethoxycarbonylhexyl, 2-ethoxycarbonyl-2-methylpropyl, 3-ethoxycarbonyl-3-methylbutyl, 4-ethoxycarbonyl-4-methylpentyl, 2-ethoxycarbonyl-2-ethylbutyl, propoxycarbonylmethyl, 2-propoxycarbonylethyl, 3-propoxycarbonylpropyl, 4-propoxycarbonylbutyl, 5-propoxycarbonylpentyl, 6-propoxycarbonylhexyl, 2-methyl-2-propoxycarbonylpropyl, 3-methyl-3-propoxycarbonylbutyl, 4-methyl-4-propoxycarbonylpentyl, 2-ethyl-2-propoxycarbonylbutyl, butoxycarbonylmethyl, 2-butoxycarbonylethyl, 3-butoxycarbonylpropyl, 4-butoxycarbonylbutyl, 5-butoxycarbonylpentyl, 6-butoxycarbonylhexyl, 2-butoxycarbonyl-2-methylpropyl, 3-butoxycarbonyl-3-methylbutyl, 4-butoxycarbonyl-4-methylpentyl, 2-butoxycarbonyl-2-ethylbutyl, isopropoxycarbonylmethyl, 2-isopropoxycarbonylethyl, 3-isopropoxycarbonylpropyl, 4-isopropoxycarbonylbutyl, 5-isopropoxycarbonylpentyl, 6-isopropoxycarbonylhexyl, 2-isopropoxycarbonyl-2-methylpropyl, 3-isopropoxycarbonyl-3-methylbutyl, 4-isopropoxycarbonyl-4-methylpentyl, 2-ethyl-2-isopropoxycarbonylbutyl, isobutoxycarbonylmethyl, 2-isobutoxycarbonylethyl, 3-isobutoxycarbonylpropyl, 4-isobutoxycarbonylbutyl, 5-isobutoxycarbonylpentyl, 6-isobutoxycarbonylhexyl, 2-isobutoxycarbonyl-2-methylpropyl, 3-isobutoxycarbonyl-3-methylbutyl, 4-isobutoxycarbonyl-4-methylpentyl, 2-ethyl-2-isobutoxycarbonylbutyl, acetyloxymethyl, 2-acetyloxyethyl, 3-acetyloxypropyl, 4-acetyloxybutyl, 5-acetyloxypentyl, 6-acetyloxyhexyl, 2-acetyloxy-2-methylpropyl, 3-acetyloxy-3-methylbutyl, 4-acetyloxy-4-methylpentyl, 2-acetyloxy-2-ethylbutyl, propionyloxymethyl, 2-propionyloxyethyl, 3-propionyloxypropyl, 4-propionyloxybutyl, 5-propionyloxypentyl, 6-propionyloxyhexyl, 2-methyl-2-propionyloxypropyl, 3-methyl-3-propionyloxybutyl, 4-methyl-4-propionyloxypentyl, 2-ethyl-2-propionyloxybutyl, butyryloxymethyl, 2-butyryloxyethyl, 3-butyryloxypropyl, 4-butyryloxybutyl, 5-butyryloxypentyl, 6-butyryloxyhexyl, 2-butyryloxy-2-methylpropyl, 3-butyryloxy-3-methylbutyl, 4-butyryloxy-4-methylpentyl, 2-butyryloxy-2-ethylbutyl, acetylmethyl, 2-acetylethyl, 3-acetylpropyl, 4-acetylbutyl, 5-acetylpentyl, 6-acetylhexyl, 2-acetyl-2-methylpropyl, 3-acetyl-3-methylbutyl, 4-acetyl-4-methylpentyl, 2-acetyl-2-ethylbutyl, propionylmethyl, 2-propionylethyl, 3-propionylpropyl, 4-propionylbutyl, 5-propionylpentyl, 6-propionylhexyl, 3-propionyl-3-methylbutyl, 4-propionyl-4-methylpentyl, 2-ethyl-2-propionylbutyl, butyrylmethyl, 2-butyrylethyl, 3-butyrylpropyl, 4-butyrylbutyl, 5-butyrylpentyl, 6-butyrylhexyl, 2-butyryl-2-methylpropyl, 3-butyryl-3-methylbutyl, 4-butyryl-4-methylpentyl, 2-butyryl-2-ethylbutyl, dimethylaminomethyl, 2-dimethylaminoethyl, 3-dimethylaminopropyl, 4-dimethylaminobutyl, diethylaminomethyl, 2-diethylaminoethyl, 3-diethylaminopropyl, 4-diethylaminobutyl, dipropylaminomethyl, 2-dipropylaminoethyl, 3-dipropylaminopropyl, 4-dipropylaminobutyl, dibutylaminomethyl, 2-dibutylaminoethyl, 3-dibutylaminopropyl, 4-dibutylaminobutyl, diisopropylaminomethyl, 2-diisopropylaminoethyl, 3-diisopropylaminopropyl, 4-diisopropylaminobutyl, cyclopropyl, 1-hydroxycyclopropyl, cyclobutyl, 1-hydroxycyclobutyl, cyclopropylmethyl, (1-hydroxycyclopropyl)methyl, cyclobutylmethyl, (1-hydroxycyclobutyl)methyl, cyclopropylhydroxymethyl, hydroxy(1-hydroxycyclopropyl)methyl, cyclobutylhydroxymethyl, hydroxy(1-hydroxycyclobutyl)methyl, 2-cyclopropylethyl, 2-(1-hydroxycyclopropyl)ethyl, 2-cyclobutylethyl, 2-(1-hydroxycyclobutyl)ethyl, 3-cyclopropylpropyl, 3-(1-hydroxycyclopropyl)propyl, 3-cyclobutylpropyl, 3-(1-hydroxycyclobutyl)propyl, 2-cyclopropyl-2-hydroxyethyl, 2-hydroxy-2-(1-hydroxycyclopropyl)ethyl, 2-cyclobutyl-2-hydroxyethyl, 2-hydroxy-2-(1-hydroxycyclobutyl)ethyl, 3-cyclopropyl-3-hydroxypropyl, 3-hydroxy-3-(1-hydroxycyclopropyl)propyl, 3-cyclobutyl-3-hydroxypropyl, 3-hydroxy-3-(1-hydroxycyclobutyl)propyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, 2-methyl-2-butenyl, 3-methyl-2-butenyl, 2-methyl-3-butenyl, 3-methyl-3-butenyl, 2-methyl-2-pentenyl, 3-methyl-2-pentenyl, 4-methyl-2-pentenyl, 2-methyl-3-pentenyl, 3-methyl-3-pentenyl, 4-methyl-3-pentenyl, 2-methyl-4-pentenyl, 3-methyl-4-pentenyl, 4-methyl-4-pentenyl, 2,3-dimethyl-2-butenyl, ethynyl, 2-propynyl, 2-butynyl, 3-butynyl, 2-pentynyl, 3-pentynyl, 4-pentynyl, 2-methyl-3-butynyl, 2-hexynyl, 3-hexynyl, 4-hexynyl, 5-hexynyl, 4-methyl-2-pentynyl, 2-methyl-3-pentynyl, 2-methyl-4-pentynyl, 3-methyl-4-pentynyl, 2,2-dimethyl-3-butynyl, 1-hydroxy-2-propenyl, 1-hydroxy-2-butenyl, 2-hydroxy-3-butenyl, 1-hydroxy-2-pentenyl, 2-hydroxy-3-pentenyl, 3-hydroxy-4-pentenyl, 1-hydroxy-2-hexenyl, 2-hydroxy-3-hexenyl, 3-hydroxy-4-hexenyl, 4-hydroxy-5-hexenyl, 1-hydroxy-2-propynyl, 1-hydroxy-2-butynyl, 2-hydroxy-3-butynyl, 1-hydroxy-2-pentynyl, 2-hydroxy-3-pentynyl, 3-hydroxy-4-pentynyl, 1-hydroxy-2-hexynyl, 2-hydroxy-3-hexynyl, 3-hydroxy-4-hexynyl, 4-hydroxy-5-hexynyl, phenyl, 2-fluorophenyl, 3-fluorophenyl, 4-fluorophenyl, 2,4-difluorophenyl, 2,6-difluorophenyl, 3,4-difluorophenyl, 2,4,6-trifluorophenyl, 2-chlorophenyl, 3-chlorophenyl, 4-chlorophenyl, 2,4-dichlorophenyl, 2,6-dichlorophenyl, 3,4-dichlorophenyl, 2,4,6-trichlorophenyl, 3-hydroxyphenyl, 4-hydroxyphenyl, 3-cyanophenyl, 4-cyanophenyl, 3-nitrophenyl, 4-nitrophenyl, 3-carboxyphenyl, 4-carboxyphenyl, 3-methylphenyl, 4-methylphenyl, 3-trifluoromethylphenyl, 4-trifluoromethylphenyl, 3-ethylphenyl, 4-ethylphenyl, 3-propylphenyl, 4-propylphenyl, 3-isopropylphenyl, 4-isopropylphenyl, 3-(1-hydroxy-1-methylethyl)phenyl, 4-(1-hydroxy-1-methylethyl)phenyl, 3-(2,2,2-trifluoro-1-hydroxy-1-trifluoromethylethyl)phenyl, 4-(2,2,2-trifluoro-1-hydroxy-1-trifluoromethylethyl)phenyl, 3-(1-carboxy-1-methylethyl)phenyl, 4-(1-carboxy-1-methylethyl)phenyl, 3-methoxyphenyl, 4-methoxyphenyl, 3-ethoxyphenyl, 4-ethoxyphenyl, 3-propoxyphenyl, 4-propoxyphenyl, 3-butoxyphenyl, 4-butoxyphenyl, 3-isopropoxyphenyl, 4-isopropoxyphenyl, 3-methoxycarbonylphenyl, 4-methoxycarbonylphenyl, 3-ethoxycarbonylphenyl, 4-ethoxycarbonylphenyl, 3-acetoxyphenyl, 4-acetoxyphenyl, 3-dimethylaminophenyl, 4-dimethylaminophenyl, 3-diethylaminophenyl, 4-diethylaminophenyl, 3-dipropylaminophenyl, 4-dipropylaminophenyl, 2-thienyl, 4-cyano-2-thienyl, 5-cyano-2-thienyl, 4-carboxy-2-thienyl, 5-carboxy-2-thienyl, 4-methyl-2-thienyl, 5-methyl-2-thienyl, 4-trifluoromethyl-2-thienyl, 5-trifluoromethyl-2-thienyl, 4-ethyl-2-thienyl, 5-ethyl-2-thienyl, 4-propyl-2-thienyl, 5-propyl-2-thienyl, 4-isopropyl-2-thienyl, 5-isopropyl-2-thienyl, 4-(1-hydroxy-1-methylethyl)-2-thienyl, 5-(1-hydroxy-1-methylethyl)-2-thienyl, 4-(2,2,2-trifluoro-1-hydroxy-1-trifluoromethylethyl)-2-thienyl, 5-(2,2,2-trifluoro-1-hydroxy-1-trifluoromethylethyl)-2-thienyl, 4-(1-carboxy-1-methylethyl)-2-thienyl, 5-(1-carboxy-1-methylethyl)-2-thienyl, 4-methoxycarbonyl-2-thienyl, 5-methoxycarbonyl-2-thienyl, 4-ethoxycarbonyl-2-thienyl, 5-ethoxycarbonyl-2-thienyl, 4-propoxycarbonyl-2-thienyl, 5-propoxycarbonyl-2-thienyl, 4-butoxycarbonyl-2-thienyl, 5-butoxycarbonyl-2-thienyl, 4-isopropoxycarbonyl-2-thienyl, 5-isopropoxycarbonyl-2-thienyl, 3-thienyl, 4-cyano-3- thienyl, 5-cyano-3-thienyl, 4-carboxy-3-thienyl, 5-carboxy-3-thienyl, 4-methyl-3-thienyl, 5-methyl-3-thienyl, 4-trifluoromethyl-3-thienyl, 5-trifluoromethyl-3-thienyl, 5-ethyl-3-thienyl, 5-propyl-3-thienyl, 5-isopropyl-3-thienyl, 5-(1-hydroxy-1-methylethyl)-3-thienyl, 5-(2,2,2-trifluoro-1-hydroxy-1-trifluoromethylethyl)-3-thienyl, 5-(1-carboxy-1-methylethyl)-3-thienyl, 5-methoxycarbonyl-3-thienyl, 5-ethoxycarbonyl-3-thienyl, 4-thiazolyl, 2-cyano-4-thiazolyl, 2-carboxy-4-thiazolyl, 2-methyl-4-thiazolyl, 2-ethyl-4-thiazolyl, 2-propyl-4-thiazolyl, 2-isopropyl-4-thiazolyl, 2-trifluoromethyl-4-thiazolyl, 2-(1-hydroxy-1-methylethyl)-4-thiazolyl, 2-(2,2,2-trifluoro-1-hydroxy-1-trifluoromethylethyl)-4-thiazolyl, 2-(1-carboxy-1-methylethyl)-4-thiazolyl, 2-methoxycarbonyl-4-thiazolyl, 2-ethoxycarbonyl-4-thiazolyl, 5-thiazolyl, 2-cyano-5-thiazolyl, 2-carboxy-5-thiazolyl, 2-methyl-5-thiazolyl, 2-ethyl-5-thiazolyl, 2-propyl-5-thiazolyl, 2-isopropyl-5-thiazolyl, 2-trifluoromethyl-5-thiazolyl, 2-(1-hydroxy-1-methylethyl)-5-thiazolyl, 2-(2,2,2-trifluoro-1-hydroxy-1-trifluoromethylethyl)-5-thiazolyl, 2-(1-carboxy-1-methylethyl)-5-thiazolyl, 2-methoxycarbonyl-5-thiazolyl, 2-ethoxycarbonyl-5-thiazolyl, 2-propoxycarbonyl-5-thiazolyl, 2-isopropoxycarbonyl-5-thiazolyl, 4-pyrazolyl, 1-methyl-4-pyrazolyl, 1-ethyl-4-pyrazolyl, 3-pyrazolyl, 1-methyl-3-pyrazolyl, 1-ethyl-3-pyrazolyl, 6-cyano-2-pyridyl, 6-carboxy-2-pyridyl, 6-trifluoromethyl-2-pyridyl, 6-methoxy-2-pyridyl, 6-ethoxy-2-pyridyl, 6-methoxycarbonyl-2-pyridyl, 6-ethoxycarbonyl-2-pyridyl, 6-(1-hydroxy-1-methylethyl)-2-pyridyl, 6-(2,2,2-trifluoro-1-hydroxy-1-trifluoromethylethyl)-2-pyridyl, 6-(1-carboxy-1-methylethyl)-2-pyridyl, 6-cyano-3-pyridyl, 6-carboxy-3-pyridyl, 6-trifluoromethyl-3-pyridyl, 6-methoxy-3-pyridyl, 6-ethoxy-3-pyridyl, 6-methoxycarbonyl-3-pyridyl, 6-ethoxycarbonyl-3-pyridyl, 6-(1-hydroxy-1-methylethyl)-3-pyridyl, 6-(2,2,2-trifluoro-1-hydroxy-1-trifluoromethylethyl)-3-pyridyl, 6-(1-carboxy-1-methylethyl)-3-pyridyl, 2-cyano-3-pyridyl, 2-carboxy-3-pyridyl, 2-trifluoromethyl-3-pyridyl, 2-methoxy-3-pyridyl, 2-ethoxy-3-pyridyl, 2-propoxy-3-pyridyl, 2-methoxycarbonyl-3-pyridyl, 2-ethoxycarbonyl-3-pyridyl, 2-propoxycarbonyl-3-pyridyl, 2-(1-hydroxy-1-methylethyl)-3-pyridyl, 2-(2,2,2-trifluoro-1-hydroxy-1-trifluoromethylethyl)-3-pyridyl, 2-(1-carboxy-1-methylethyl)-3-pyridyl, 2-cyano-4-pyridyl, 2-carboxy-4-pyridyl, 2-trifluoromethyl-4-pyridyl, 2-methoxy-4-pyridyl, 2-ethoxy-4-pyridyl, 2-propoxy-4-pyridyl, 2-methoxycarbonyl-4-pyridyl, 2-ethoxycarbonyl-4-pyridyl, 2-(1-hydroxy-1-methylethyl)-4-pyridyl, 2-(2,2,2-trifluoro-1-hydroxy-1-trifluoromethylethyl)-4-pyridyl, 2-(1-carboxy-1-methylethyl)-4-pyridyl, benzyl, 2-fluorobenzyl, 3-fluorobenzyl, 4-fluorobenzyl, 2,4-difluorobenzyl, 2,6-difluorobenzyl, 3,4-difluorobenzyl, 2-chlorobenzyl, 3-chlorobenzyl, 4-chlorobenzyl, 2,4-dichlorobenzyl, 2,6-dichlorobenzyl, 3,4-dichlorobenzyl, 2-cyanobenzyl, 3-cyanobenzyl, 4-cyanobenzyl, 3-nitrobenzyl, 4-nitrobenzyl, 3-carboxybenzyl, 4-carboxybenzyl, 3-trifluoromethylbenzyl, 4-trifluoromethylbenzyl, 3-(1-hydroxy-1-methylethyl)benzyl, 4-(1-hydroxy-1-methylethyl)benzyl, 3-(2,2,2-trifluoro-1-hydroxy-1-trifluoromethylethyl)benzyl, 4-(2,2,2-trifluoro-1-hydroxy-1-trifluoromethylethyl)benzyl, 3-(1-carboxy-1-methylethyl)benzyl, 4-(1-carboxy-1-methylethyl)benzyl, 3-methoxybenzyl, 4-methoxybenzyl, 3-ethoxybenzyl, 4-ethoxybenzyl, 3-methoxycarbonylbenzyl, 4-methoxycarbonylbenzyl, 3-ethoxycarbonylbenzyl, 4-ethoxycarbonylbenzyl, 2-thienylmethyl, 4-cyano-2-thienylmethyl, 5-cyano-2-thienylmethyl, 4-carboxy-2-thienylmethyl, 5-carboxy-2-thienylmethyl, 4-methyl-2-thienylmethyl, 5-methyl-2-thienylmethyl, 4-trifluoromethyl-2-thienylmethyl, 5-trifluoromethyl-2-thienylmethyl, 4-(1-hydroxy-1-methylethyl)-2-thienylmethyl, 5-(1-hydroxy-1-methylethyl)-2-thienylmethyl, 4-(2,2,2-trifluoro-1-hydroxy-1-trifluoromethylethyl)-2-thienylmethyl, 5-(2,2,2-trifluoro-1-hydroxy-1-trifluoromethylethyl)-2-thienylmethyl, 4-(1-carboxy-1-methylethyl)-2-thienylmethyl, 5-(1-carboxy-1-methylethyl)-2-thienylmethyl, 3-thienylmethyl, 4-cyano-3-thienylmethyl, 5-cyano-3-thienylmethyl, 4-carboxy-3-thienylmethyl, 5-carboxy-3-thienylmethyl, 4-methyl-3-thienylmethyl, 5-methyl-3-thienylmethyl, 4-trifluoromethyl-3-thienylmethyl, 5-trifluoromethyl-3-thienylmethyl, 5-ethyl-3-thienylmethyl, 5-(1-hydroxy-1-methylethyl)-3-thienylmethyl, 5-(2,2,2-trifluoro-1-hydroxy-1-trifluoromethylethyl)-3-thienylmethyl, 5-(1-carboxy-1-methylethyl)-3-thienylmethyl, 5-methoxycarbonyl-3-thienylmethyl, 4-thiazolylmethyl, 2-cyano-4-thiazolylmethyl, 2-carboxy-4-thiazolylmethyl, 2-methyl-4-thiazolylmethyl, 2-ethyl-4-thiazolylmethyl, 2-propyl-4-thiazolylmethyl, 2-isopropyl-4-thiazolylmethyl, 2-trifluoromethyl-4-thiazolylmethyl, 2-(1-hydroxy-1-methylethyl)-4-thiazolylmethyl, 2-(2,2,2-trifluoro-1-hydroxy-1-trifluoromethylethyl)-4-thiazolylmethyl, 2-(1-carboxy-1-methylethyl)-4-thiazolylmethyl, 2-methoxycarbonyl-4-thiazolylmethyl, 5-thiazolylmethyl, 2-cyano-5-thiazolylmethyl, 2-carboxy-5-thiazolylmethyl, 2-methyl-5-thiazolylmethyl, 2-ethyl-5-thiazolylmethyl, 2-trifluoromethyl-5-thiazolylmethyl, 2-(1-hydroxy-1-methylethyl)-5-thiazolylmethyl, 2-(2,2,2-trifluoro-1-hydroxy-1-trifluoromethylethyl)-5-thiazolylmethyl, 2-(1-carboxy-1-methylethyl)-5-thiazolylmethyl, 2-methoxycarbonyl-5-thiazolylmethyl, 4-pyrazolylmethyl, 6-cyano-2-pyridylmethyl, 6-carboxy-2-pyridylmethyl, 6-trifluoromethyl-2-pyridylmethyl, 6-methoxy-2-pyridylmethyl, 6-ethoxy-2-pyridylmethyl, 6-methoxycarbonyl-2-pyridylmethyl, 6-ethoxycarbonyl-2-pyridylmethyl, 6-(1-hydroxy-1-methylethyl)-2-pyridylmethyl, 6-(2,2,2-trifluoro-1-hydroxy-1-trifluoromethylethyl)-2-pyridylmethyl, 6-(1-carboxy-1-methylethyl)-2-pyridylmethyl, 6-cyano-3-pyridylmethyl, 6-carboxy-3-pyridylmethyl, 6-trifluoromethyl-3-pyridylmethyl, 6-methoxy-3-pyridylmethyl, 6-ethoxy-3-pyridylmethyl, 6-methoxycarbonyl-3-pyridylmethyl, 6-ethoxycarbonyl-3-pyridylmethyl, 6-(1-hydroxy-1-methylethyl)-3-pyridylmethyl, 6-(2,2,2-trifluoro-1-hydroxy-1-trifluoromethylethyl)-3-pyridylmethyl, 6-(1-carboxy-1-methylethyl)-3-pyridylmethyl, 2-cyano-3-pyridylmethyl, 2-carboxy-3-pyridylmethyl, 2-trifluoromethyl-3-pyridylmethyl, 2-methoxy-3-pyridylmethyl, 2-ethoxy-3-pyridylmethyl, 2-propoxy-3-pyridylmethyl, 2-methoxycarbonyl-3-pyridylmethyl, 2-ethoxycarbonyl-3-pyridylmethyl, 2-propoxycarbonyl-3-pyridylmethyl, 2-(1-hydroxy-1-methylethyl)-3-pyridylmethyl, 2-(2,2,2-trifluoro-1-hydroxy-1-trifluoromethylethyl)-3-pyridylmethyl, 2-(1-carboxy-1-methylethyl)-3-pyridylmethyl, 2-cyano-4-pyridylmethyl, 2-carboxy-4-pyridylmethyl, 2-trifluoromethyl-4-pyridylmethyl, 2-methoxy-4-pyridylmethyl, 2-ethoxy-4-pyridylmethyl, 2-propoxy-4-pyridylmethyl, 2-methoxycarbonyl-4-pyridylmethyl, 2-ethoxycarbonyl-4-pyridylmethyl, 2-(1-hydroxy-1-methylethyl)-4-pyridyl, 2-(2,2,2-trifluoro-1-hydroxy-1-trifluoromethylethyl)-4-pyridylmethyl, 2-(1-carboxy-1-methylethyl)-4-pyridylmethyl, phenethyl, 2-fluorophenethyl, 3-fluorophenethyl, 4-fluorophenethyl, 3-chlorophenethyl, 3-cyanophenethyl, 3-carboxyphenethyl, 3-methoxyphenethyl, 2-(2-thienyl)ethyl, 2-(3-thienyl)ethyl, 2-(4-thiazolyl)ethyl, 2-(5-thiazolyl)ethyl, 2-(4-pyrazolyl)ethyl, 2-(6-cyano-2-pyridyl)ethyl, 2-(6-carboxy-2-pyridyl)ethyl, 2-(6-methoxy-2-pyridyl)ethyl, 2-(6-cyano-3-pyridyl)ethyl, 2-(6-carboxy-3-pyridyl)ethyl, 2-(6- methoxy-3-pyridyl)ethyl, 2-(2-cyano-3-pyridyl)ethyl, 2-(2-carboxy-3-pyridyl)ethyl, 2-(2-methoxy-3-pyridyl)ethyl, hydroxyphenylmethyl, (2-fluorophenyl)hydroxymethyl, (3-fluorophenyl)hydroxymethyl, (4-fluorophenyl)hydroxymethyl, (3-chlorophenyl)hydroxymethyl, (3,4-difluorophenyl)hydroxymethyl, (2,4-difluorophenyl)hydroxymethyl, (3-cyanophenyl)hydroxymethyl, hydroxy(3-trifluoromethylphenyl)methyl or hydroxy(2-thienyl)methyl group, more preferably a hydrogen atom, chlorine atom, bromine atom, methyl, ethyl, propyl, isopropyl, butyl, isobutyl, pentyl, isopentyl, neopentyl, hexyl, 2-ethylbutyl, 2,2-dimethylbutyl, 3,3-dimethylbutyl, heptyl, 2,2-dimethylpentyl, 3,3-dimethylpentyl, 4,4-dimethylpentyl, octyl, 4-ethylhexyl, 2,2-dimethylhexyl, 3,3-dimethylhexyl, 4,4-dimethylhexyl, 5,5-dimethylhexyl, 2-propylpentyl, 2,2,3,3-tetramethylbutyl, 2,2,2-trifluoroethyl, 3,3,3-trifluoropropyl, 2-chloroethyl, hydroxyethyl, 2-hydroxyethyl, 3-hydroxypropyl, 4-hydroxybutyl, 5-hydroxypentyl, 6-hydroxyhexyl, 2-hydroxy-2-methylpropyl, 3-hydroxy-3-methylbutyl, 4-hydroxy-4-methylpentyl, 2-ethyl-2-hydroxybutyl, 2-cyano-2-methylpropyl, 3-cyano-3-methylbutyl, 4-cyano-4-methylpentyl, 2-cyano-2-ethylbutyl, 2-carboxy-2-methylpropyl, 3-carboxy-3-methylbutyl, 4-carboxy-4-methylpentyl, 2-carboxy-2-ethylbutyl, methoxymethyl, 2-methoxyethyl, 3-methoxypropyl, 4-methoxybutyl, 5-methoxypentyl, 6-methoxyhexyl, 2-methoxy-2-methylpropyl, 3-methoxy-3-methylbutyl, 4-methoxy-4-methylpentyl, 2-ethyl-2-methoxybutyl, ethoxymethyl, 2-ethoxyethyl, 3-ethoxypropyl, 4-ethoxybutyl, 5-ethoxypentyl, 6-ethoxyhexyl, 2-ethoxy-2-methylpropyl, 3-ethoxy-3-methylbutyl, 4-ethoxy-4-methylpentyl, 2-ethoxy-2-ethylbutyl, propoxymethyl, 2-propoxyethyl, 3-propoxypropyl, 4-propoxybutyl, 2-methyl-2-propoxypropyl, 3-methyl-3-propoxybutyl, 4-methyl-4-propoxypentyl, 2-ethyl-2-propoxybutyl, butoxymethyl, 2-butoxyethyl, 3-butoxypropyl, 4-butoxybutyl, 2-butoxy-2-methylpropyl, 3-butoxy-3-methylbutyl, 4-butoxy-4-methylpentyl, 2-butoxy-2-ethylbutyl, isopropoxymethyl, 2-isopropoxyethyl, 3-isopropoxypropyl, 4-isopropoxybutyl, isobutoxymethyl, sec-butoxymethyl, tert-butoxymethyl, 1-ethylpropoxymethyl, 2-fluoroethoxymethyl, 2-(2-fluoroethoxy)ethyl, 3-(2-fluoroethoxy)propyl, 4-(2-fluoroethoxy)butyl, 5-(2-fluoroethoxy)pentyl, 6-(2-fluoroethoxy)hexyl, 2-(2-fluoroethoxy)-2-methylpropyl, 3-(2-fluoroethoxy)-3-methylbutyl, 4-(2-fluoroethoxy)-4-methylpentyl, 2-ethyl-2-(2-fluoroethoxy)butyl, (2,2,2-trifluoroethoxy)methyl, cyclopropoxymethyl, cyclobutoxymethyl, 2-cyclobutoxyethyl, 3-cyclobutoxypropyl, 4-cyclobutoxybutyl, 5-cyclobutoxypentyl, 6-cyclobutoxyhexyl, 2-cyclobutoxy-2-methylpropyl, 3-cyclobutoxy-3-methylbutyl, 4-cyclobutoxy-4-methylpentyl, 2-cyclobutoxy-2-ethylbutyl, cyclopropylmethoxymethyl, 2-cyclopropylmethoxyethyl, 3-cyclopropylmethoxypropyl, 4-cyclopropylmethoxybutyl, 5-cyclopropylmethoxypentyl, 6-cyclopropylmethoxyhexyl, 2-cyclopropylmethoxy-2-methylpropyl, 3-cyclopropylmethoxy-3-methylbutyl, 4-cyclopropylmethoxy-4-methylpentyl, 2-cyclopropylmethoxy-2-ethylbutyl, cyclobutylmethoxymethyl, methoxycarbonylmethyl, 2-methoxycarbonylethyl, 3-methoxycarbonylpropyl, 4-methoxycarbonylbutyl, 2-methoxycarbonyl-2-methylpropyl, 3-methoxycarbonyl-3-methylbutyl, 4-methoxycarbonyl-4-methylpentyl, 2-ethyl-2-methoxycarbonylbutyl, ethoxycarbonylmethyl, 2-ethoxycarbonylethyl, 3-ethoxycarbonylpropyl, 4-ethoxycarbonylbutyl, 2-ethoxycarbonyl-2-methylpropyl, 3-ethoxycarbonyl-3-methylbutyl, 4-ethoxycarbonyl-4-methylpentyl, 2-ethoxycarbonyl-2-ethylbutyl, propoxycarbonylmethyl, 2-propoxycarbonylethyl, 3-propoxycarbonylpropyl, 4-propoxycarbonylbutyl, 2-methyl-2-propoxycarbonylpropyl, 3-methyl-3-propoxycarbonylbutyl, 4-methyl-4-propoxycarbonylpentyl, 2-ethyl-2-propoxycarbonylbutyl, butoxycarbonylmethyl, 2-butoxycarbonylethyl, 3-butoxycarbonylpropyl, 4-butoxycarbonylbutyl, 2-butoxycarbonyl-2-methylpropyl, 3-butoxycarbonyl-3-methylbutyl, 4-butoxycarbonyl-4-methylpentyl, 2-butoxycarbonyl-2-ethylbutyl, isopropoxycarbonylmethyl, 2-isopropoxycarbonylethyl, 3-isopropoxycarbonylpropyl, 4-isopropoxycarbonylbutyl, 2-isopropoxycarbonyl-2-methylpropyl, 3-isopropoxycarbonyl-3-methylbutyl, 4-isopropoxycarbonyl-4-methylpentyl, 2-ethyl-2-isopropoxycarbonylbutyl, isobutoxycarbonylmethyl, 2-isobutoxycarbonylethyl, 3-isobutoxycarbonylpropyl, 4-isobutoxycarbonylbutyl, acetyloxymethyl, 2-acetyloxyethyl, 3-acetyloxypropyl, 4-acetyloxybutyl, 5-acetyloxypentyl, 6-acetyloxyhexyl, 2-acetyloxy-2-methylpropyl, 3-acetyloxy-3-methylbutyl, 4-acetyloxy-4-methylpentyl, 2-acetyloxy-2-ethylbutyl, propionyloxymethyl, 2-propionyloxyethyl, 3-propionyloxypropyl, 4-propionyloxybutyl, 5-propionyloxypentyl, acetylmethyl, 2-acetylethyl, 3-acetylpropyl, 4-acetylbutyl, 5-acetylpentyl, 6-acetylhexyl, 2-acetyl-2-methylpropyl, 3-acetyl-3-methylbutyl, 4-acetyl-4-methylpentyl, 2-acetyl-2-ethylbutyl, propionylmethyl, 2-propionylethyl, 3-propionylpropyl, 4-propionylbutyl, 5-propionylpentyl, dimethylaminomethyl, 2-dimethylaminoethyl, diethylaminomethyl, 2-diethylaminoethyl, dipropylaminomethyl, 2-dipropylaminoethyl, 2-dibutylaminomethyl, 3-dibutylaminoethyl, diisopropylaminomethyl, 2-diisopropylaminoethyl, cyclopropyl, 1-hydroxycyclopropyl, cyclobutyl, 1-hydroxycyclobutyl, cyclopropylmethyl, (1-hydroxycyclopropyl)methyl, cyclobutylmethyl, (1-hydroxycyclobutyl)methyl, cyclopropylhydroxymethyl, hydroxy(1-hydroxycyclopropyl)methyl, cyclobutylhydroxymethyl, hydroxy(1-hydroxycyclobutyl)methyl, 2-cyclopropylethyl, 2-(1-hydroxycyclopropyl)ethyl, 2-cyclobutylethyl, 2-(1-hydroxycyclobutyl)ethyl, 2-propenyl, 2-butenyl, 2-pentenyl, 2-hexenyl, 2-methyl-2-propenyl, 2-methyl-2-butenyl, 3-methyl-2-butenyl, 2-methyl-2-pentenyl, 3-methyl-2-pentenyl, 4-methyl-2-pentenyl, 2,3-dimethyl-2-butenyl, ethynyl, 2-propynyl, 2-butynyl, 2-pentynyl, 2-hexynyl, 4-methyl-2-pentynyl, 1-hydroxy-2-propenyl, 1-hydroxy-2-butenyl, 1-hydroxy-2-pentenyl, 1-hydroxy-2-hexenyl, 1-hydroxy-2-propynyl, 1-hydroxy-2-butynyl, 1-hydroxy-2-pentynyl, 1-hydroxy-2-hexynyl, phenyl, 2-fluorophenyl, 3-fluorophenyl, 4-fluorophenyl, 2,4-difluorophenyl, 2,6-difluorophenyl, 3,4-difluorophenyl, 2-chlorophenyl, 3-chlorophenyl, 4-chlorophenyl, 2,4-dichlorophenyl, 2,6-dichlorophenyl, 3,4-dichlorophenyl, 3-cyanophenyl, 4-cyanophenyl, 3-nitrophenyl, 4-nitrophenyl, 3-carboxyphenyl, 4-carboxyphenyl, 3-trifluoromethylphenyl, 4-trifluoromethylphenyl, 3-(1-hydroxy-1-methylethyl)phenyl, 4-(1-hydroxy-1-methylethyl)phenyl, 3-(2,2,2-trifluoro-1-hydroxy-1-trifluoromethylethyl)phenyl, 4-(2,2,2-trifluoro-1-hydroxy-1-trifluoromethylethyl)phenyl, 3-(1-carboxy-1-methylethyl)phenyl, 4-(1-carboxy-1-methylethyl)phenyl, 3-methoxyphenyl, 4-methoxyphenyl, 3-ethoxyphenyl, 4-ethoxyphenyl, 3-methoxycarbonylphenyl, 4-methoxycarbonylphenyl, 3-ethoxycarbonylphenyl, 4-ethoxycarbonylphenyl, 2-thienyl, 4-cyano-2-thienyl, 5-cyano-2-thienyl, 4-carboxy-2-thienyl, 5-carboxy-2-thienyl, 4-methyl-2-thienyl, 5-methyl-2-thienyl, 4-trifluoromethyl-2-thienyl, 5-trifluoromethyl-2-thienyl, 4-(1-hydroxy-1-methylethyl)-2-thienyl, 5-(1-hydroxy-1-methylethyl)-2-thienyl, 4-(2,2,2-trifluoro-1-hydroxy-1-trifluoromethylethyl)-2-thienyl, 5-(2,2,2-trifluoro-1-hydroxy-1-trifluoromethylethyl)-2-thienyl, 4-(1-carboxy-1-methylethyl)-2-thienyl, 5-(1-carboxy-1-methylethyl)-2-thienyl, 3-thienyl, 4-cyano-3-thienyl, 5-cyano-3-thienyl, 4-carboxy-3-thienyl, 5-carboxy-3-thienyl, 4-methyl-3-thienyl, 5-methyl-3-thienyl, 4-trifluoromethyl-3-thienyl, 5-trifluoromethyl-3-thienyl, 5-ethyl-3-thienyl, 5-(1-hydroxy-1-methylethyl)-3-thienyl, 5-(2,2,2-trifluoro-1-hydroxy-1-trifluoromethylethyl)-3-thienyl, 5-(1-carboxy-1-methylethyl)-3-thienyl, 5-methoxycarbonyl-3-thienyl, 4-thiazolyl, 2-cyano-4-thiazolyl, 2-carboxy-4-thiazolyl, 2-methyl-4-thiazolyl, 2-ethyl-4-thiazolyl, 2-propyl-4-thiazolyl, 2-isopropyl-4-thiazolyl, 2-trifluoromethyl-4-thiazolyl, 2-(1-hydroxy-1-methylethyl)-4-thiazolyl, 2-(2,2,2-trifluoro-1-hydroxy-1-trifluoromethylethyl)-4-thiazolyl, 2-(1-carboxy-1-methylethyl)-4-thiazolyl, 2-methoxycarbonyl-4-thiazolyl, 5-thiazolyl, 2-cyano-5-thiazolyl, 2-carboxy-5-thiazolyl, 2-methyl-5-thiazolyl, 2-ethyl-5-thiazolyl, 2-trifluoromethyl-5-thiazolyl, 2-(1-hydroxy-1-methylethyl)-5-thiazolyl, 2-(2,2,2-trifluoro-1-hydroxy-1-trifluoromethylethyl)-5-thiazolyl, 2-(1-carboxy-1-methylethyl)-5-thiazolyl, 2-methoxycarbonyl-5-thiazolyl, 2-ethoxycarbonyl-5-thiazolyl, 2-propoxycarbonyl-5-thiazolyl, 2-isopropoxycarbonyl-5-thiazolyl, 4-pyrazolyl, 6-cyano-2-pyridyl, 6-carboxy-2-pyridyl, 6-trifluoromethyl-2-pyridyl, 6-methoxy-2-pyridyl, 6-ethoxy-2-pyridyl, 6-methoxycarbonyl-2-pyridyl, 6-ethoxycarbonyl-2-pyridyl, 6-(1-hydroxy-1-methylethyl)-2-pyridyl, 6-(2,2,2-trifluoro-1-hydroxy-1-trifluoromethylethyl)-2-pyridyl, 6-(1-carboxy-1-methylethyl)-2-pyridyl, 6-cyano-3-pyridyl, 6-carboxy-3-pyridyl, 6-trifluoromethyl-3-pyridyl, 6-methoxy-3-pyridyl, 6-ethoxy-3-pyridyl, 6-methoxycarbonyl-3-pyridyl, 6-ethoxycarbonyl-3-pyridyl, 6-(1-hydroxy-1-methylethyl)-3-pyridyl, 6-(2,2,2-trifluoro-1-hydroxy-1-trifluoromethylethyl)-3-pyridyl, 6-(1-carboxy-1-methylethyl)-3-pyridyl, 2-cyano-3-pyridyl, 2-carboxy-3-pyridyl, 2-trifluoromethyl-3-pyridyl, 2-methoxy-3-pyridyl, 2-ethoxy-3-pyridyl, 2-propoxy-3-pyridyl, 2-methoxycarbonyl-3-pyridyl, 2-ethoxycarbonyl-3-pyridyl, 2-propoxycarbonyl-3-pyridyl, 2-(1-hydroxy-1-methylethyl)-3-pyridyl, 2-(2,2,2-trifluoro-1-hydroxy-1-trifluoromethylethyl)-3-pyridyl, 2-(1-carboxy-1-methylethyl)-3-pyridyl, 2-cyano-4-pyridyl, 2-carboxy-4-pyridyl, 2-trifluoromethyl-4-pyridyl, 2-methoxy-4-pyridyl, 2-ethoxy-4-pyridyl, 2-propoxy-4-pyridyl, 2-methoxycarbonyl-4-pyridyl, 2-ethoxycarbonyl-4-pyridyl, 2-(1-hydroxy-1-methylethyl)-4-pyridyl, 2-(2,2,2-trifluoro-1-hydroxy-1-trifluoromethylethyl)-4-pyridyl, 2-(1-carboxy-1-methylethyl)-4-pyridyl, benzyl, 2-fluorobenzyl, 3-fluorobenzyl, 4-fluorobenzyl, 2,4-difluorobenzyl, 3,4-difluorobenzyl, 2-chlorobenzyl, 3-chlorobenzyl, 4-chlorobenzyl, 2,4-dichlorobenzyl, 3,4-dichlorobenzyl, 2-cyanobenzyl, 3-cyanobenzyl, 4-cyanobenzyl, 3-nitrobenzyl, 3-carboxybenzyl, 4-carboxybenzyl, 3-trifluoromethylbenzyl, 4-trifluoromethylbenzyl, 3-(1-hydroxy-1-methylethyl)benzyl, 4-(1-hydroxy-1-methylethyl)benzyl, 3-(2,2,2-trifluoro-1-hydroxy-1-trifluoromethylethyl)benzyl, 4-(2,2,2-trifluoro-1-hydroxy-1-trifluoromethylethyl)benzyl, 4-(1-carboxy-1-methylethyl)benzyl, 3-methoxybenzyl, 4-methoxybenzyl, 3-methoxycarbonylbenzyl, 4-methoxycarbonylbenzyl,
2-thienylmethyl, 5-cyano-2-thienylmethyl, 5-carboxy-2-thienylmethyl, 5-methyl-2-thienylmethyl, 5-trifluoromethyl-2-thienylmethyl, 5-(1-hydroxy-1-methylethyl)-2-thienylmethyl, 5-(2,2,2-trifluoro-1-hydroxy-1-trifluoromethylethyl)-2-thienylmethyl, 4-(1-carboxy-1-methylethyl)-2-thienylmethyl, 3-thienylmethyl, 5-cyano-3-thienylmethyl, 5-carboxy-3-thienylmethyl, 5-methyl-3-thienylmethyl, 5-trifluoromethyl-3-thienylmethyl, 5-(1-hydroxy-1-methylethyl)-3-thienylmethyl, 5-(2,2,2-trifluoro-1-hydroxy-1-trifluoromethylethyl)-3-thienylmethyl, 4-thiazolylmethyl, 2-cyano-4-thiazolylmethyl, 2-carboxy-4-thiazolylmethyl, 2-methyl-4-thiazolylmethyl, 2-trifluoromethyl-4-thiazolylmethyl, 2-(1-hydroxy-1-methylethyl)-4-thiazolylmethyl, 2-(2,2,2-trifluoro-1-hydroxy-1-trifluoromethylethyl)-4-thiazolylmethyl, 5-thiazolylmethyl, 2-cyano-5-thiazolylmethyl, 2-carboxy-5-thiazolylmethyl, 2-methyl-5-thiazolylmethyl, 2-trifluoromethyl-5-thiazolylmethyl, 2-(1-hydroxy-1-methylethyl)-5-thiazolylmethyl, 2-(2,2,2-trifluoro-1-hydroxy-1-trifluoromethylethyl)-5-thiazolylmethyl, 4-pyrazolylmethyl, 6-cyano-2-pyridylmethyl, 6-carboxy-2-pyridylmethyl, 6-trifluoromethyl-2-pyridylmethyl, 6-methoxy-2-pyridylmethyl, 6-(1-hydroxy-1-methylethyl)-2-pyridylmethyl, 6-(2,2,2-trifluoro-1-hydroxy-1-trifluoromethylethyl)-2-pyridylmethyl, 6-cyano-3-pyridylmethyl, 6-carboxy-3-pyridylmethyl, 6-trifluoromethyl-3-pyridylmethyl, 6-methoxy-3-pyridylmethyl, 6-(1-hydroxy-1-methylethyl)-3-pyridylmethyl, 6-(2,2,2-trifluoro-1-hydroxy-1-trifluoromethylethyl)-3-pyridylmethyl, 2-cyano-3-pyridylmethyl, 2-carboxy-3-pyridylmethyl, 2-trifluoromethyl-3-pyridylmethyl, 2-methoxy-3-pyridylmethyl, 2-(1-hydroxy-1-methylethyl)-3-pyridylmethyl, 2-(2,2,2-trifluoro-1-hydroxy-1-trifluoromethylethyl)-3-pyridylmethyl, 2-cyano-4-pyridylmethyl, 2-carboxy-4-pyridylmethyl, 2-trifluoromethyl-4-pyridylmethyl, 2-methoxy-4-pyridylmethyl, 2-(1-hydroxy-1-methylethyl)-4-pyridyl, 2-(2,2,2-trifluoro-1-hydroxy-1-trifluoromethylethyl)-4-pyridylmethyl, phenethyl, 2-fluorophenethyl, 3-fluorophenethyl, 4-fluorophenethyl, 3-chlorophenethyl, 3-cyanophenethyl, 3-carboxyphenethyl, 3-methoxyphenethyl, 2-(2-thienyl)ethyl, 2-(3-thienyl)ethyl, 2-(6-cyano-2-pyridyl)ethyl, 2-(6-methoxy-2-pyridyl)ethyl, 2-(6-cyano-3-pyridyl)ethyl, 2-(6-methoxy-3-pyridyl)ethyl, 2-(2-cyano-3-pyridyl)ethyl, 2-(2-methoxy-3-pyridyl)ethyl, hydroxyphenylmethyl, (2-fluorophenyl)hydroxymethyl, (3-fluorophenyl)hydroxymethyl, (4-fluorophenyl)hydroxymethyl, (3,4-difluorophenyl)hydroxymethyl or hydroxy(2-thienyl)methyl group,
more preferably a hydrogen atom, chlorine atom, bromine atom, methyl, ethyl, propyl, isopropyl, butyl, isobutyl, pentyl, isopentyl, neopentyl, hexyl, 2-ethylbutyl, 2,2-dimethylbutyl, 3,3-dimethylbutyl, 2,2,2-trifluoroethyl, 3,3,3-trifluoropropyl, 2-chloroethyl, hydroxymethyl, 2-hydroxy-2-methylpropyl, 3-hydroxy-3-methylbutyl, 4-hydroxy-4-methylpentyl, 2-ethyl-2-hydroxybutyl, 2-cyano-2-methylpropyl, 3-cyano-3-methylbutyl, 2-carboxy-2-methylpropyl, 3-carboxy-3-methylbutyl, 4-carboxy-4-methylpentyl, methoxymethyl, ethoxymethyl, isopropoxymethyl, 2-methoxyethyl, 2-ethoxyethyl, 2-isopropoxyethyl, isobutoxymethyl, sec-butoxymethyl, tert-butoxymethyl, 1-ethylpropoxymethyl, 2-fluoroethoxymethyl, cyclobutoxymethyl, cyclopropylmethoxymethyl, dimethylaminomethyl, cyclopropyl, 1-hydroxycyclopropyl, cyclobutyl, 1-hydroxycyclobutyl, cyclopropylmethyl, (1-hydroxycyclopropyl)methyl, cyclobutylmethyl, (1-hydroxycyclobutyl)methyl, cyclopropylhydroxymethyl, hydroxy(1-hydroxycyclopropyl)methyl, cyclobutylhydroxymethyl, hydroxy(1-hydroxycyclobutyl)methyl, 2-cyclopropylethyl, 2-(1-hydroxycyclopropyl)ethyl, 2-cyclobutylethyl, 2-(1-hydroxycyclobutyl)ethyl, 2-propenyl, 2-butenyl, 2-methyl-2-propenyl, 2-methyl-2-butenyl, 3-methyl-2-butenyl, 2,3-dimethyl-2-butenyl, ethynyl, 2-propynyl, 2-butynyl, 4-methyl-2-pentynyl, 1-hydroxy-2-propenyl, 1-hydroxy-2-butenyl, 1-hydroxy-2-propynyl, 1-hydroxy-2-butynyl,
phenyl, 2-fluorophenyl, 4-fluorophenyl, 2,4-difluorophenyl, 2-chlorophenyl, 4-chlorophenyl, 4-cyanophenyl, 4-nitrophenyl, 4-carboxyphenyl, 4-trifluoromethylphenyl, 3-methoxyphenyl, 4-methoxyphenyl, 4-methoxycarbonylphenyl, 2-thienyl, 5-cyano-2-thienyl, 5-carboxy-2-thienyl, 5-methyl- 2-thienyl, 5-trifluoromethyl-2-thienyl, 3-thienyl, 5-cyano-3-thienyl, 5-carboxy-3-thienyl, 5-methyl-3-thienyl, 5-trifluoromethyl-3-thienyl, 4-thiazolyl, 2-cyano-4-thiazolyl, 2-carboxy-4-thiazolyl, 2-methyl-4-thiazolyl, 2-trifluoromethyl-4-thiazolyl, 2-(1-hydroxy-1-methylethyl)-4-thiazolyl, 2-(2,2,2-trifluoro-1-hydroxy-1-trifluoromethylethyl)-4-thiazolyl, 5-thiazolyl, 2-cyano-5-thiazolyl, 2-carboxy-5-thiazolyl, 2-methyl-5-thiazolyl, 2-trifluoromethyl-5-thiazolyl, 2-(1-hydroxy-1-methylethyl)-5-thiazolyl, 2-(2,2,2-trifluoro-1-hydroxy-1-trifluoromethylethyl)-5-thiazolyl, 4-pyrazolyl, 6-cyano-2-pyridyl, 6-carboxy-2-pyridyl, 6-trifluoromethyl-2-pyridyl, 6-methoxy-2-pyridyl, 6-(1-hydroxy-1-methylethyl)-2-pyridyl, 6-(2,2,2-trifluoro-1-hydroxy-1-trifluoromethylethyl)-2-pyridyl, 6-cyano-3-pyridyl, 6-carboxy-3-pyridyl, 6-trifluoromethyl-3-pyridyl, 6-methoxy-3-pyridyl, 6-(1-hydroxy-1-methylethyl)-3-pyridyl, 6-(2,2,2-trifluoro-1-hydroxy-1-trifluoromethylethyl)-3-pyridyl, 2-cyano-4-pyridyl, 2-carboxy-4-pyridyl, 2-trifluoromethyl-4-pyridyl, 2-methoxy-4-pyridyl, 2-(1-hydroxy-1-methylethyl)-4-pyridyl, 2-(2,2,2-trifluoro-1-hydroxy-1-trifluoromethylethyl)-4-pyridyl, benzyl, 2-fluorobenzyl, 3-fluorobenzyl, 4-fluorobenzyl, 2,4-difluorobenzyl, 3,4-difluorobenzyl, 2-chlorobenzyl, 3-chlorobenzyl, 2-cyanobenzyl, 3-cyanobenzyl, 3-carboxybenzyl, 4-carboxybenzyl, 3-trifluoromethylbenzyl, 4-methoxybenzyl, 3-methoxycarbonylbenzyl, 2-thienylmethyl, 5-cyano-2-thienylmethyl, 5-carboxy-2-thienylmethyl, 5-trifluoromethyl-2-thienylmethyl, 3-thienylmethyl, 5-cyano-3-thienylmethyl, 5-carboxy-3-thienylmethyl, S-trifluoromethyl-3-thienylmethyl, 4-thiazolylmethyl, 2-cyano-4-thiazolylmethyl, 2-carboxy-4-thiazolylmethyl, 2-(1-hydroxy-1-methylethyl)-4-thiazolylmethyl, 2-(2,2,2-trifluoro-1-hydroxy-1-trifluoromethylethyl)-4-thiazolylmethyl, 2-cyano-5-thiazolylmethyl, 2-carboxy-5-thiazolylmethyl, 2-(1-hydroxy-1-methylethyl)-5-thiazolylmethyl, 2-(2,2,2-trifluoro-1-hydroxy-1-trifluoromethylethyl)-5-thiazolylmethyl, 6-cyano-2-pyridylmethyl, 6-carboxy-2-pyridylmethyl, 6-methoxy-2-pyridylmethyl, 6-(1-hydroxy-1-methylethyl)-2-pyridylmethyl, 6-(2,2,2-trifluoro-1-hydroxy-1-trifluoromethylethyl)-2-pyridylmethyl, 6-cyano-3-pyridylmethyl, 6-carboxy-3-pyridylmethyl, 6-methoxy-3-pyridylmethyl, 6-(1-hydroxy-1-methylethyl)-3-pyridylmethyl, 6-(2,2,2-trifluoro-1-hydroxy-1-trifluoromethylethyl)-3-pyridylmethyl, 2-cyano-3-pyridylmethyl, 2-carboxy-3-pyridylmethyl, 2-methoxy-3-pyridylmethyl, 2-(1-hydroxy-1-methylethyl)-3-pyridylmethyl, 2-(2,2,2-trifluoro-1-hydroxy-1-trifluoromethylethyl)-3-pyridylmethyl, 2-cyano-4-pyridylmethyl, 2-carboxy-4-pyridylmethyl, 2-methoxy-4-pyridylmethyl, 2-(1-hydroxy-1-methylethyl)-4-pyridyl, 2-(2,2,2-trifluoro-1-hydroxy-1-trifluoromethylethyl)-4-pyridylmethyl, phenethyl, 2-fluorophenethyl, 3-fluorophenethyl, 4-fluorophenethyl, 3-cyanophenethyl, 2-(2-thienyl)ethyl, 2-(6-cyano-2-pyridyl)ethyl, 2-(6-cyano-3-pyridyl)ethyl, 2-(2-cyano-3-pyridyl)ethyl, hydroxyphenylmethyl, (3-fluorophenyl)hydroxymethyl, (4-fluorophenyl)hydroxymethyl or hydroxy(2-thienyl)methyl group, further more preferably a hydrogen atom, chlorine atom, bromine atom, methyl, ethyl, propyl, isopropyl, butyl, isobutyl, pentyl, isopentyl, neopentyl, hexyl, 2-ethylbutyl, 2,2,2-trifluoroethyl, 3,3,3-trifluoropropyl, 2-chloroethyl, hydroxymethyl, methoxymethyl, ethoxymethyl, isopropoxymethyl, 2-methoxyethyl, 2-ethoxyethyl, 2-isopropoxyethyl, isobutoxymethyl, sec-butoxymethyl, tert-butoxymethyl, 1-ethylpropoxymethyl, 2-fluoroethoxymethyl, cyclobutoxymethyl, cyclopropylmethoxymethyl, dimethylaminomethyl, cyclopropyl, cyclobutyl, cyclopropylmethyl, cyclobutylmethyl, cyclopropylhydroxymethyl, cyclobutylhydroxymethyl, 2-cyclopropylethyl, 2-cyclobutylethyl, 2-propenyl, 2-butenyl, 2-methyl-2-propenyl, 2-methyl-2-butenyl, 3-methyl-2-butenyl, 2,3-dimethyl-2-butenyl, ethynyl, 2-propynyl, 2-butynyl, 4-methyl-2-pentynyl, 1-hydroxy-2-propenyl, phenyl, 2-fluorophenyl, 4-fluorophenyl, 2,4-difluorophenyl, 2-chlorophenyl, 4-chlorophenyl, 4-cyanophenyl, 2-thienyl, 3-thienyl, 4-thiazolyl, 5-thiazolyl, 4-pyrazolyl, 6-methoxy-2-pyridyl, 6-methoxy-3-pyridyl, benzyl, 2-fluorobenzyl, 3-fluorobenzyl, 4-fluorobenzyl, 2,4-difluorobenzyl, 3,4-difluorobenzyl, 2-chlorobenzyl, 3-chlorobenzyl, 2-cyanobenzyl, 3-cyanobenzyl, 3-carboxybenzyl, 4-carboxybenzyl, 2-thienylmethyl, 5-cyano-2-thienylmethyl, 5-carboxy-2-thienylmethyl, 3-thienylmethyl, 5-cyano-3-thienylmethyl, 5-carboxy-3-thienylmethyl, 2-carboxy-4-thiazolylmethyl, 6-cyano-2-pyridylmethyl, 6-carboxy-2-pyridylmethyl, 6-methoxy-2-pyridylmethyl, 6-cyano-3-pyridylmethyl, 6-carboxy-3-pyridylmethyl, 6-methoxy-3-pyridylmethyl, 2-cyano-3-pyridylmethyl, 2-carboxy-3-pyridylmethyl, 2-cyano-4-pyridylmethyl, 2-carboxy-4-pyridylmethyl, phenethyl, 2-fluorophenethyl, 3-fluorophenethyl, 4-fluorophenethyl, 3-cyanophenethyl, 2-(2-thienyl)ethyl, 2-(6-cyano-2-pyridyl)ethyl, 2-(6-cyano-3-pyridyl)ethyl, 2-(2-cyano-3-pyridyl)ethyl, hydroxyphenylmethyl, (2-fluorophenyl)hydroxymethyl, (3-fluorophenyl) hydroxymethyl or (4-fluorophenyl)hydroxymethyl group, particularly preferably a hydrogen atom, chlorine atom, bromine atom, methyl, ethyl, propyl, isopropyl, butyl, isobutyl, pentyl, isopentyl, hexyl, 2-ethylbutyl, 2,2,2-trifluoroethyl, 3,3,3-trifluoropropyl, 2-chloroethyl, hydroxymethyl, methoxymethyl, ethoxymethyl, isopropoxymethyl, 2-methoxyethyl, 2-ethoxyethyl, 2-isopropoxyethyl, isobutoxymethyl, sec-butoxymethyl, tert-butoxymethyl, 1-ethylpropoxymethyl, 2-fluoroethoxymethyl, cyclobutoxymethyl, cyclopropylmethoxymethyl, dimethylaminomethyl, cyclopropyl, cyclopropylmethyl, cyclopropylhydroxymethyl, 2-cyclopropylethyl, 2-propenyl, 2-butenyl, 2-methyl-2-propenyl, 2-methyl-2-butenyl, 3-methyl-2-butenyl, 2,3-dimethyl-2-butenyl, ethynyl, 2-propynyl, 2-butynyl, 4-methyl-2-pentynyl, 1-hydroxy-2-propenyl, phenyl, 2-thienyl, 3-thienyl, 4-pyrazolyl, benzyl, 2-fluorobenzyl, 3-fluorobenzyl, 4-fluorobenzyl, 2,4-difluorobenzyl, 3,4-difluorobenzyl, 2-chlorobenzyl, 3-chlorobenzyl, 2-cyanobenzyl, 3-cyanobenzyl, 3-carboxybenzyl, 2-thienylmethyl, 3-thienylmethyl, 6-methoxy-2-pyridylmethyl, 6-methoxy-3-pyridylmethyl, phenethyl, hydroxyphenylmethyl, (2-fluorophenyl)hydroxymethyl, (3-fluorophenyl)hydroxymethyl or (4-fluorophenyl)hydroxymethyl group, most preferably a hydrogen atom, chlorine atom, bromine atom, methyl, ethyl, propyl, isopropyl, butyl, isobutyl, pentyl, isopentyl, hexyl, hydroxymethyl, methoxymethyl, ethoxymethyl, isopropoxymethyl, 2-methoxyethyl, 2-ethoxyethyl, isobutoxymethyl, sec-butoxymethyl, tert-butoxymethyl, 1-ethylpropoxymethyl, 2-fluoroethoxymethyl, cyclobutoxymethyl, cyclopropylmethoxymethyl, dimethylaminomethyl, cyclopropyl, cyclopropylmethyl, 2-cyclopropylethyl, 2-propenyl, ethynyl, 2-propynyl, 2-butynyl, 4-methyl-2-pentynyl, 1-hydroxy-2-propenyl, phenyl, 4-pyrazolyl, benzyl, 2-fluorobenzyl, 3-fluorobenzyl, 4-fluorobenzyl, 2-cyanobenzyl, 3-cyanobenzyl, 3-carboxybenzyl, 6-methoxy-2-pyridylmethyl, 6-methoxy-3-pyridylmethyl, phenethyl or hydroxyphenylmethyl group.

In the substituent(s) referred to in the present invention, respective atoms or respective rings are also included.

When geometric isomers or optical isomers exist in the pyrrolopyridazinone compound represented by the formula (1) of the present invention, these isomers are included in the scope of the present invention, and also, when proton tautomers exist, these tautomers are included in the scope of the present invention.

The pyrrolopyridazinone compound of the present invention can exist as a hydrate or a solvate, or a HCl adduct, and these are included in the present invention.

In the pyrrolopyridazinone compound represented by the formula (1) of the present invention, preferred are (1) a compound wherein $R^1$ is a methyl or difluoromethyl group,
(2) a compound wherein $R^1$ is a difluoromethyl group,
(3) a compound wherein $R^2$ is a cyclopropyl, cyclobutyl, cyclopentyl, cyclopropylmethyl, cyclobutylmethyl, ethyl or isopropyl group,
(4) a compound wherein $R^2$ is a cyclopropyl, cyclobutyl, cyclopentyl, cyclopropylmethyl or isopropyl group,
(5) a compound wherein $R^2$ is a cyclopropyl or cyclopropylmethyl group,
(6) a compound wherein $R^3$ is a hydrogen atom or a substituted oxygen-containing hetero ring formed in combination with the group —O—$R^2$ (a 2,2-(1,2-ethylene)-tetrahydrofuran ring, 2,2-(1,3-propylene)-tetrahydrofuran ring, 2,2-(1,4-butylene)-tetrahydrofuran ring, 2-cyclopropyl-tetrahydrofuran ring, 2-cyclobutyl-tetrahydrofuran ring, 2,2-dimethyl-tetrahydrofuran ring, 6,6-(1,2-ethylene)-3,6-dihydro-2H-pyran ring, 6,6-(1,3-propylene)-3,6-dihydro-2H-pyran ring, 6,6-(1,4-butylene)-3,6-dihydro-2H-pyran ring, 6-cyclopropyl-3,6-dihydro-2H-pyran ring, 6-cyclobutyl-3,6-dihydro-2H-pyran ring or 6,6-dimethyl-3,6-dihydro-2H-pyran ring),
(7) a compound wherein $R^3$ is a hydrogen atom or a substituted oxygen-containing hetero ring formed in combination with the group —O—$R^2$ (a 2,2-(1,4-butylene)-tetrahydrofuran ring, 6,6-(1,3-propylene)-3,6-dihydro-2H-pyran ring, 6,6-(1,4-butylene)-3,6-dihydro-2H-pyran ring, 6-cyclopropyl-3,6-dihydro-2H-pyran ring or 6,6-dimethyl-3,6-dihydro-2H-pyran ring),
(8) a compound wherein $R^4$ is a hydrogen atom, chlorine atom, bromine atom, iodine atom, methyl, ethyl, propyl, isopropyl, butyl, isobutyl, pentyl, isopentyl, neopentyl, 2-methylbutyl, hexyl, 2-methylpentyl, 3-methylpentyl, 4-methylpentyl, 2-ethylbutyl, 2,2-dimethylbutyl, 3,3-dimethylbutyl, 2,3-dimethylbutyl, heptyl, 2-methylhexyl, 3-methylhexyl, 4-methylhexyl, 5-methylhexyl, 2,3-dimethylpentyl, 2,4-dimethylpentyl, 3,4-dimethylpentyl, 2,2-dimethylpentyl, 3,3-dimethylpentyl, 4,4-dimethylpentyl, octyl, 2-methylheptyl, 3-methylheptyl, 4-methylheptyl, 5-methylheptyl, 6-methylheptyl, 2-ethylhexyl, 3-ethylhexyl, 4-ethylhexyl, 2,3-dimethylhexyl, 2,4-dimethylhexyl, 2,5-dimethylhexyl, 3,4-dimethylhexyl, 3,5-dimethylhexyl, 2,2-dimethylhexyl, 3,3-dimethylhexyl, 4,4-dimethylhexyl, 5,5-dimethylhexyl, 2-methyl-3-ethylpentyl, 2-propylpentyl, 2,2,3,3-tetramethylbutyl, trifluoromethyl, 2,2,2-trifluoroethyl, 3,3,3-trifluoropropyl, 2-chloroethyl, hydroxymethyl, 1-hydroxyethyl, 2-hydroxyethyl, 1-hydroxypropyl, 3-hydroxypropyl, 1-hydroxybutyl, 4-hydroxybutyl, 1-hydroxypentyl, 5-hydroxypentyl, 1-hydroxyhexyl, 6-hydroxyhexyl, 1-hydroxy-2-methylpropyl, 2-hydroxy-2-methylpropyl, 1-hydroxy-3-methylbutyl, 3-hydroxy-3-methylbutyl, 1-hydroxy-4-methylpentyl, 4-hydroxy-4-methylpentyl, 2-ethyl-2-hydroxybutyl, cyanomethyl, 2-cyanoethyl, 3-cyanopropyl, 4-cyanobutyl, 5-cyanopentyl, 6-cyanohexyl, 2-cyano-2-methylpropyl, 3-cyano-3-methylbutyl, 4-cyano-4-methylpentyl, 2-cyano-2-ethylbutyl, carboxymethyl, 2-carboxyethyl, 3-carboxypropyl, 4-carboxybutyl, 5-carboxypentyl, 6-carboxyhexyl, 2-carboxy-2-methylpropyl, 3-carboxy-3-methylbutyl, 4-carboxy-4-methylpentyl, 2-carboxy-2-ethylbutyl, methoxymethyl, 2-methoxyethyl, 2-methoxypropyl, 3-methoxypropyl, 4-methoxybutyl, 5-methoxypentyl, 6-methoxyhexyl, 2-methoxy-2-methylpropyl, 3-methoxy-3-methylbutyl, 4-methoxy-4-methylpentyl, 2-ethyl-2-methoxybutyl, ethoxymethyl, 2-ethoxyethyl, 2-ethoxypropyl, 3-ethoxypropyl, 4-ethoxybutyl, 5-ethoxypentyl, 6-ethoxyhexyl, 2-ethoxy-2-methylpropyl, 3-ethoxy-3-methylbutyl, 4-ethoxy-4-methylpentyl, 2-ethoxy-2-ethylbutyl, propoxymethyl, 2-propoxyethyl, 3-propoxypropyl, 4-propoxybutyl, 5-propoxypentyl, 6-propoxyhexyl, 2-methyl-2-propoxypropyl, 3-methyl-3-propoxybutyl, 4-methyl-4-propoxypentyl, 2-ethyl-2-propoxybutyl, butoxymethyl, 2-butoxyethyl, 3-butoxypropyl, 4-butoxybutyl, 5-butoxypentyl, 6-butoxyhexyl, 2-butoxy-2-methylpropyl, 3-butoxy-3-methylbutyl, 4-butoxy-4-methylpentyl, 2-butoxy-2-ethylbutyl, isopropoxymethyl, 2-isopropoxyethyl, 3-isopropoxypropyl, 4-isopropoxybutyl, 5-isopropoxypentyl, 6-isopropoxyhexyl, 2-isopropoxy-2-methylpropyl, 3-isopropoxy-3-methylbutyl, 4-isopropoxy-4-methylpentyl, 2-ethyl-2-isopropoxybutyl, 2-fluoroethoxymethyl, 2-(2-fluoroethoxy)ethyl, isobutoxymethyl, 2-isobutoxyethyl, sec-butoxymethyl, 2-(sec-butoxy)ethyl, tert-butoxymethyl, 2-(tert-butoxy)ethyl, 1-ethylpropoxymethyl, 2-(1-ethylpropoxy)ethyl, 2-(2-fluoroethoxy)propyl, 3-(2-fluoroethoxy)propyl, 4-(2-fluoroethoxy)butyl, 5-(2-fluoroethoxy)pentyl, 6-(2-fluoroethoxy)hexyl, 2-(2-fluoroethoxy)-2-methylpropyl, 3-(2-fluoroethoxy)-3-methylbutyl, 4-(2-fluoroethoxy)-4-methylpentyl, 2-ethyl-2-(2-fluoroethoxy)butyl, (2,2,2-trifluoroethoxy)methyl, 2-(2,2,2-trifluoroethoxy)ethyl, 2-(2,2,2-trifluoroethoxy)propyl, 3-(2,2,2-trifluoroethoxy)propyl, 4-(2,2,2-trifluoroethoxy)butyl, 5-(2,2,2-trifluoroethoxy)pentyl, 6-(2,2,2-trifluoroethoxy)hexyl, 2-(2,2,2-trifluoroethoxy)-2-methylpropyl, 3-(2,2,2-trifluoroethoxy)-3-methylbutyl, 4-(2,2,2-trifluoroethoxy)-4-methylpentyl, 2-ethyl-2-(2,2,2-trifluoroethoxy)butyl, cyclopropoxymethyl, 2-cyclopropoxyethyl, 2-cyclopropoxypropyl, 3-cyclopropoxypropyl, 4-cyclopropoxybutyl, 5-cyclopropoxypentyl, 6-cyclopropoxyhexyl, 2-cyclopropoxy-2-methylpropyl, 3-cyclopropoxy-3-methylbutyl, 4-cyclopropoxy-4-methylpentyl, 2-cyclopropoxy-2-ethylbutyl, cyclobutoxymethyl, 2-cyclobutoxyethyl, 2-cyclobutoxypropyl, 3-cyclobutoxypropyl, 4-cyclobutoxybutyl, 5-cyclobutoxypentyl, 6-cyclobutoxyhexyl, 2-cyclobutoxy-2-methylpropyl, 3-cyclobutoxy-3-methylbutyl, 4-cyclobutoxy-4-methylpentyl, 2-cyclobutoxy-2-ethylbutyl, cyclopropylmethoxymethyl, 2-cyclopropylmethoxyethyl, 2-cyclopropylmethoxypropyl, 3-cyclopropylmethoxypropyl, 4-cyclopropylmethoxybutyl, 5-cyclopropylmethoxypentyl, 6-cyclopropylmethoxyhexyl, 2-cyclopropylmethoxy-2-methylpropyl, 3-cyclopropylmethoxy-3-methylbutyl, 4-cyclopropylmethoxy-4-methylpentyl, 2-cyclopropylmethoxy-2-ethylbutyl, cyclobutylmethoxymethyl, 2-cyclobutylmethoxyethyl, 2-cyclobutylmethoxypropyl, 3-cyclobutylmethoxypropyl, 4-cyclobutylmethoxybutyl, 5-cyclobutylmethoxypentyl, 6-cyclobutylmethoxyhexyl, 2-cyclobutylmethoxy-2-methylpropyl, 3-cyclobutylmethoxy-3-methylbutyl, 4-cyclobutylmethoxy-4-methylpentyl, 2-cyclobutylmethoxy-2-ethylbutyl, methoxycarbonylmethyl, 2-methoxycarbonylethyl, 3-methoxycarbonylpropyl, 4-methoxycarbonylbutyl, 5-methoxycarbonylpentyl, 6-methoxycarbonylhexyl, 2-methoxycarbonyl-2-methylpropyl, 3-methoxycarbonyl-3-methylbutyl, 4-methoxycarbonyl-4-methylpentyl, 2-ethyl-2-methoxycarbonylbutyl, ethoxycarbonylmethyl, 2-ethoxycarbonylethyl, 3-ethoxycarbonylpropyl, 4-ethoxycarbonylbutyl, 5-ethoxycarbonylpentyl, 6-ethoxycarbonylhexyl, 2-ethoxycarbonyl-2-methylpropyl, 3-ethoxycarbonyl-3-methylbutyl, 4-ethoxycarbonyl-4-methylpentyl, 2-ethoxycarbonyl-2-ethylbutyl, propoxycarbonylmethyl, 2-propoxycarbonylethyl, 3-propoxycarbonylpropyl, 4-propoxycarbonylbutyl, 5-propoxycarbonylpentyl, 6-propoxycarbonylhexyl, 2-methyl-2-propoxycarbonylpropyl, 3-methyl-3-propoxycarbonylbutyl, 4-methyl-4-propoxycarbonylpentyl, 2-ethyl-2-propoxycarbonylbutyl, butoxycarbonylmethyl, 2-butoxycarbonylethyl, 3-butoxycarbonylpropyl, 4-butoxycarbonylbutyl, 5-butoxycarbonylpentyl, 6-butoxycarbonylhexyl, 2-butoxycarbonyl-2-methylpropyl, 3-butoxycarbonyl-3-methylbutyl, 4-butoxycarbonyl-4-methylpentyl, 2-butoxycarbonyl-2-ethylbutyl, isopropoxycarbonylmethyl, 2-isopropoxycarbonylethyl, 3-isopropoxycarbonylpropyl, 4-isopropoxycarbonylbutyl, 5-isopropoxycarbonylpentyl, 6-isopropoxycarbonylhexyl, 2-isopropoxycarbonyl-2-methylpropyl, 3-isopropoxycarbonyl-3-methylbutyl, 4-isopropoxycarbonyl-4-methylpentyl, 2-ethyl-2-isopropoxycarbonylbutyl, isobutoxycarbonylmethyl, 2-isobutoxycarbonylethyl, 3-isobutoxycarbonylpropyl, 4-isobutoxycarbonylbutyl, 5-isobutoxycarbonylpentyl, 6-isobutoxycarbonylhexyl, 2-isobutoxycarbonyl-2-methylpropyl, 3-isobutoxycarbonyl-3-methylbutyl, 4-isobutoxycarbonyl-4-methylpentyl, 2-ethyl-2-isobutoxycarbonylbutyl, acetyloxymethyl, 2-acetyloxyethyl, 3-acetyloxypropyl, 4-acetyloxybutyl, 5-acetyloxypentyl, 6-acetyloxyhexyl, 2-acetyloxy-2-methylpropyl, 3-acetyloxy-3-methylbutyl, 4-acetyloxy-4-methylpentyl, 2-acetyloxy-2-ethylbutyl, propionyloxymethyl, 2-propionyloxyethyl, 3-propionyloxypropyl, 4-propionyloxybutyl, 5-propionyloxypentyl, 6-propionyloxyhexyl, 2-methyl-2-propionyloxypropyl, 3-methyl-3-propionyloxybutyl, 4-methyl-4-propionyloxypentyl, 2-ethyl-2-propionyloxybutyl, butyryloxymethyl, 2-butyryloxyethyl, 3-butyryloxypropyl, 4-butyryloxybutyl, 5-butyryloxypentyl, 6-butyryloxyhexyl, 2-butyryloxy-2-methylpropyl, 3-butyryloxy-3-methylbutyl, 4-butyryloxy-4-methylpentyl, 2-butyryloxy-2-ethylbutyl, acetylmethyl, 2-acetylethyl, 3-acetylpropyl, 4-acetylbutyl, 5-acetylpentyl, 6-acetylhexyl, 2-acetyl-2-methylpropyl, 3-acetyl-3-methylbutyl, 4-acetyl-4-methylpentyl, 2-acetyl-2-ethylbutyl, propionylmethyl, 2-propionylethyl, 3-propionylpropyl, 4-propionylbutyl, 5-propionylpentyl, 6-propionylhexyl, 3-propionyl-3-methylbutyl, 4-propionyl-4-methylpentyl, 2-ethyl-2-propionylbutyl, butyrylmethyl, 2-butyrylethyl, 3-butyrylpropyl, 4-butyrylbutyl, 5-butyrylpentyl, 6-butyrylhexyl, 2-butyryl-2-methylpropyl, 3-butyryl-3-methylbutyl, 4-butyryl-4-methylpentyl, 2-butyryl-2-ethylbutyl, dimethylaminomethyl, 2-dimethylaminoethyl, 3-dimethylaminopropyl, 4-dimethylaminobutyl, diethylaminomethyl, 2-diethylaminoethyl, 3-diethylaminopropyl, 4-diethylaminobutyl, dipropylaminomethyl, 2-dipropylaminoethyl, 3-dipropylaminopropyl, 4-dipropylaminobutyl, dibutylaminomethyl, 2-dibutylaminoethyl, 3-dibutylaminopropyl, 4-dibutylaminobutyl, diisopropylaminomethyl, 2-diisopropylaminoethyl, 3-diisopropylaminopropyl, 4-diisopropylaminobutyl, cyclopropyl, 1-hydroxycyclopropyl, cyclobutyl, 1-hydroxycyclobutyl, cyclopropylmethyl, (1-hydroxycyclopropyl)methyl, cyclobutylmethyl, (1-hydroxycyclobutyl)methyl, cyclopropylhydroxymethyl, hydroxy(1-hydroxycyclopropyl)methyl, cyclobutylhydroxymethyl, hydroxy(1-hydroxycyclobutyl)methyl, 2-cyclopropylethyl, 2-(1-hydroxycyclopropyl)ethyl, 2-cyclobutylethyl, 2-(1-hydroxycyclobutyl)ethyl, 3-cyclopropylpropyl, 3-(1-hydroxycyclopropyl)propyl, 3-cyclobutylpropyl, 3-(1-hydroxycyclobutyl)propyl, 2-cyclopropyl-2-hydroxyethyl, 2-hydroxy-2-(1-hydroxycyclopropyl)ethyl, 2-cyclobutyl-2-hydroxyethyl, 2-hydroxy-2-(1-hydroxycyclobutyl)ethyl, 3-cyclopropyl-3-hydroxypropyl, 3-hydroxy-3-(1-hydroxycyclopropyl)propyl, 3-cyclobutyl-3-hydroxypropyl, 3-hydroxy-3-(1-hydroxycyclobutyl)propyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, 2-methyl-2-butenyl, 3-methyl-2-butenyl, 2-methyl-3-butenyl, 3-methyl-3-butenyl, 2-methyl-2-pentenyl, 3-methyl-2-pentenyl, 4-methyl-2-pentenyl, 2-methyl-3-pentenyl, 3-methyl-3-pentenyl, 4-methyl-3-pentenyl, 2-methyl-4-pentenyl, 3-methyl-4-pentenyl, 4-methyl-4-pentenyl, 2,3-dimethyl-2-butenyl, ethynyl, 2-propynyl, 2-butynyl, 3-butynyl, 2-pentynyl, 3-pentynyl, 4-pentynyl, 2-methyl-3-butynyl, 2-hexynyl, 3-hexynyl, 4-hexynyl, 5-hexynyl, 4-methyl-2-pentynyl, 2-methyl-3-pentynyl, 2-methyl-4-pentynyl, 3-methyl-4-pentynyl, 2,2-dimethyl-3-butynyl, 1-hydroxy-2-propenyl, 1-hydroxy-2-butenyl, 2-hydroxy-3-butenyl, 1-hydroxy-2-pentenyl, 2-hydroxy-3-pentenyl, 3-hydroxy-4-pentenyl, 1-hydroxy-2-hexenyl, 2-hydroxy-3-hexenyl, 3-hydroxy-4-hexenyl, 4-hydroxy-5-hexenyl, 1-hydroxy-2-propynyl, 1-hydroxy-2-butynyl, 2-hydroxy-3-butynyl, 1-hydroxy-2-pentynyl, 2-hydroxy-3-pentynyl, 3-hydroxy-4-pentynyl, 1-hydroxy-2-hexynyl, 2-hydroxy-3-hexynyl, 3-hydroxy-4-hexynyl, 4-hydroxy-5-hexynyl, phenyl, 2-fluorophenyl, 3-fluorophenyl, 4-fluorophenyl, 2,4-difluorophenyl, 2,6-difluorophenyl, 3,4-difluorophenyl, 2,4,6-trifluorophenyl, 2-chlorophenyl, 3-chlorophenyl, 4-chlorophenyl, 2,4-dichlorophenyl, 2,6-dichlorophenyl, 3,4-dichlorophenyl, 2,4,6-trichlorophenyl, 3-hydroxyphenyl, 4-hydroxyphenyl, 3-cyanophenyl, 4-cyanophenyl, 3-nitrophenyl, 4-nitrophenyl, 3-carboxyphenyl, 4-carboxyphenyl, 3-methylphenyl, 4-methylphenyl, 3-trifluoromethylphenyl, 4-trifluoromethylphenyl, 3-ethylphenyl, 4-ethylphenyl, 3-propylphenyl, 4-propylphenyl, 3-isopropylphenyl, 4-isopropylphenyl, 3-(1-hydroxy-1-methylethyl)phenyl, 4-(1-hydroxy-1-methylethyl)phenyl, 3-(2,2,2-trifluoro-1-hydroxy-1-trifluoromethylethyl)phenyl, 4-(2,2,2-trifluoro-1-hydroxy-1-trifluoromethylethyl)phenyl, 3-(1-carboxy-1-methylethyl)phenyl, 4-(1-carboxy-1-methylethyl)phenyl, 3-methoxyphenyl, 4-methoxyphenyl, 3-ethoxyphenyl, 4-ethoxyphenyl, 3-propoxyphenyl, 4-propoxyphenyl, 3-butoxyphenyl, 4-butoxyphenyl, 3-isopropoxyphenyl, 4-isopropoxyphenyl, 3-methoxycarbonylphenyl, 4-methoxycarbonylphenyl, 3-ethoxycarbonylphenyl, 4-ethoxycarbonylphenyl, 3-acetoxyphenyl, 4-acetoxyphenyl, 3-dimethylaminophenyl, 4-dimethylaminophenyl, 3-diethylaminophenyl, 4-diethylaminophenyl, 3-dipropylaminophenyl, 4-dipropylaminophenyl, 2-thienyl, 4-cyano-2-thienyl, 5-cyano-2-thienyl, 4-carboxy-2-thienyl, 5-carboxy-2-thienyl, 4-methyl-2-thienyl, 5-methyl-2-thienyl, 4-trifluoromethyl-2-thienyl, 5-trifluoromethyl-2-thienyl, 4-ethyl-2-thienyl, 5-ethyl-2-thienyl, 4-propyl-2-thienyl, 5-propyl-2-thienyl, 4-isopropyl-2-thienyl, 5-isopropyl-2-thienyl, 4-(1-hydroxy-1-methylethyl)-2-thienyl, 5-(1-hydroxy-1-methylethyl)-2-thienyl, 4-(2,2,2-trifluoro-1-hydroxy-1-trifluoromethylethyl)-2-thienyl, 5-(2,2,2-trifluoro-1-hydroxy-1-trifluoromethylethyl)-2-thienyl, 4-(1-carboxy-1-methylethyl)-2-thienyl, 5-(1-carboxy-1-methylethyl)-2-thienyl, 4-methoxycarbonyl-2-thienyl, 5-methoxycarbonyl-2-thienyl, 4-ethoxycarbonyl-2-thienyl, 5-ethoxycarbonyl-2-thienyl, 4-propoxycarbonyl-2-thienyl, 5-propoxycarbonyl-2-thienyl, 4-butoxycarbonyl-2-thienyl, 5-butoxycarbonyl-2-thienyl, 4-isopropoxycarbonyl-2-thienyl, 5-isopropoxycarbonyl-2-thienyl, 3-thienyl, 4-cyano-3-thienyl, 5-cyano-3-thienyl, 4-carboxy-3-thienyl, 5-carboxy-3-thienyl, 4-methyl-3-thienyl, 5-methyl-3-thienyl, 4-trifluoromethyl-3-thienyl, 5-trifluoromethyl-3-thienyl, 4-ethyl-3-thienyl, 5-ethyl-3-thienyl, 4-propyl-3-thienyl, 5-propyl-3-thienyl, 4-isopropyl-3-thienyl, 5-(1-hydroxy-1-methylethyl)-3-thienyl, 5-(2,2,2-trifluoro-1-hydroxy-1-trifluoromethylethyl)-3-thienyl, 5-(1-carboxy-1-methylethyl)-3-thienyl, 5-methoxycarbonyl-3-thienyl, 5-ethoxycarbonyl-3-thienyl, 4-thiazolyl, 2-cyano-4-thiazolyl, 2-carboxy-4-thiazolyl, 2-methyl-4-thiazolyl, 2-ethyl-4-thiazolyl, 2-propyl-4-thiazolyl, 2-isopropyl-4-thiazolyl, 2-trifluoromethyl-4-thiazolyl, 2-(1-hydroxy-1-methylethyl)-4-thiazolyl, 2-(2,2,2-trifluoro-1-hydroxy-1-trifluoromethylethyl)-4-thiazolyl, 2-(1-carboxy-1-methylethyl)-4-thiazolyl, 2-methoxycarbonyl-4-thiazolyl, 2-ethoxycarbonyl-4-thiazolyl, 5-thiazolyl, 2-cyano-5-thiazolyl, 2-carboxy-5-thiazolyl, 2-methyl-5-thiazolyl, 2-ethyl-5-thiazolyl, 2-propyl-5-thiazolyl, 2-isopropyl-5-thiazolyl, 2-trifluoromethyl-5-thiazolyl, 2-(1-hydroxy-1-methylethyl)-5-thiazolyl, 2-(2,2,2-trifluoro-1-hydroxy-1-trifluoromethylethyl)-5-thiazolyl, 2-(1-carboxy-1-methylethyl)-5-thiazolyl, 2-methoxycarbonyl-5-thiazolyl, 2-ethoxycarbonyl-5-thiazolyl, 2-propoxycarbonyl-5-thiazolyl, 2-isopropoxycarbonyl-5-thiazolyl, 4-pyrazolyl, 1-methyl-4-pyrazolyl, 1-ethyl-4-pyrazolyl, 3-pyrazolyl, 1-methyl-3-pyrazolyl, 1-ethyl-3-pyrazolyl, 6-cyano-2-pyridyl, 6-carboxy-2-pyridyl, 6-trifluoromethyl-2-pyridyl, 6-methoxy-2-pyridyl, 6-ethoxy-2-pyridyl, 6-methoxycarbonyl-2-pyridyl, 6-ethoxycarbonyl-2-pyridyl, 6-(1-hydroxy-1-methylethyl)-2-pyridyl, 6-(2,2,2-trifluoro-1-hydroxy-1-trifluoromethylethyl)-2-pyridyl, 6-(1-carboxy-1-methylethyl)-2-pyridyl, 6-cyano-3-pyridyl, 6-carboxy-3-pyridyl, 6-trifluoromethyl-3-pyridyl, 6-methoxy-3-pyridyl, 6-ethoxy-3-pyridyl, 6-methoxycarbonyl-3-pyridyl, 6-ethoxycarbonyl-3-pyridyl, 6-(1-hydroxy-1-methylethyl)-3-pyridyl, 6-(2,2,2-trifluoro-1-hydroxy-1-trifluoromethylethyl)-3-pyridyl, 6-(1-carboxy-1-methylethyl)-3-pyridyl, 2-cyano-3-pyridyl, 2-carboxy-3-pyridyl, 2-trifluoromethyl-3-pyridyl, 2-methoxy-3-pyridyl, 2-ethoxy-3-pyridyl, 2-propoxy-3-pyridyl, 2-methoxycarbonyl-3-pyridyl, 2-ethoxycarbonyl-3-pyridyl, 2-propoxycarbonyl-3-pyridyl, 2-(1-hydroxy-1-methylethyl)-3-pyridyl, 2-(2,2,2-trifluoro-1-hydroxy-1-trifluoromethylethyl)-3-pyridyl, 2-(1-carboxy-1-methylethyl)-3-pyridyl, 2-cyano-4-pyridyl, 2-carboxy-4-pyridyl, 2-trifluoromethyl-4-pyridyl, 2-methoxy-4-pyridyl, 2-ethoxy-4-pyridyl, 2-propoxy-4-pyridyl, 2-methoxycarbonyl-4-pyridyl, 2-ethoxycarbonyl-4-pyridyl, 2-(1-hydroxy-1-methylethyl)-4-pyridyl, 2-(2,2,2-trifluoro-1-hydroxy-1-trifluoromethylethyl)-4-pyridyl, 2-(1-carboxy-1-methylethyl)-4-pyridyl, benzyl, 2-fluorobenzyl, 3-fluorobenzyl, 4-fluorobenzyl, 2,4-difluorobenzyl, 2,6-difluorobenzyl, 3,4-difluorobenzyl, 2-chlorobenzyl, 3-chlorobenzyl, 4-chlorobenzyl, 2,4-dichlorobenzyl, 2,6-dichlorobenzyl, 3,4-dichlorobenzyl, 2-cyanobenzyl, 3-cyanobenzyl, 4-cyanobenzyl, 3-nitrobenzyl, 4-nitrobenzyl, 3-carboxybenzyl, 4-carboxybenzyl, 3-trifluoromethylbenzyl, 4-trifluoromethylbenzyl, 3-(1-hydroxy-1-methylethyl)benzyl, 4-(1-hydroxy-1-methylethyl)benzyl, 3-(2,2,2-trifluoro-1-hydroxy-1-trifluoromethylethyl)benzyl, 4-(2,2,2-trifluoro-1-hydroxy-1-trifluoromethylethyl)benzyl, 3-(1-carboxy-1-methylethyl)benzyl, 4-(1-carboxy-1-methylethyl)benzyl, 3-methoxybenzyl, 4-methoxybenzyl, 3-ethoxybenzyl, 4-ethoxybenzyl, 3-methoxycarbonylbenzyl, 4-methoxycarbonylbenzyl, 3-ethoxycarbonylbenzyl, 4-ethoxycarbonylbenzyl, 2-thienylmethyl, 4-cyano-2-thienylmethyl, 5-cyano-2-thienylmethyl, 4-carboxy-2-thienylmethyl, 5-carboxy-2-thienylmethyl, 4-methyl-2-thienylmethyl, 5-methyl-2-thienylmethyl, 4-trifluoromethyl-2-thienylmethyl, 5-trifluoromethyl-2-thienylmethyl, 4-(1-hydroxy-1-methylethyl)-2-thienylmethyl, 5-(1-hydroxy-1-methylethyl)-2-thienylmethyl, 4-(2,2,2-trifluoro-1-hydroxy-1-trifluoromethylethyl)-2-thienylmethyl, 5-(2,2,2-trifluoro-1-hydroxy-1-trifluoromethylethyl)-2-thienylmethyl, 4-(1-carboxy-1-methylethyl)-2-thienylmethyl, 5-(1-carboxy-1-methylethyl)-2-thienylmethyl, 3-thienylmethyl, 4-cyano-3-thienylmethyl, 5-cyano-3-thienylmethyl, 4-carboxy-3-thienylmethyl, 5-carboxy-3-thienylmethyl, 4-methyl-3-thienylmethyl, 5-methyl-3-thienylmethyl, 4-trifluoromethyl-3-thienylmethyl, 5-trifluoromethyl-3-thienylmethyl, 5-ethyl-3-thienylmethyl, 5-(1-hydroxy-1-methylethyl)-3-thienylmethyl, 5-(2,2,2-trifluoro-1-hydroxy-1-trifluoromethylethyl)-3-thienylmethyl, 5-(1-carboxy-1-methylethyl)-3-thienylmethyl, 5-methoxycarbonyl-3-thienylmethyl, 4-thiazolylmethyl, 2-cyano-4-thiazolylmethyl, 2-carboxy-4-thiazolylmethyl, 2-methyl-4-thiazolylmethyl, 2-ethyl-4-thiazolylmethyl, 2-propyl-4-thiazolylmethyl, 2-isopropyl-4-thiazolylmethyl, 2-trifluoromethyl-4-thiazolylmethyl, 2-(1-hydroxy-1-methylethyl)-4-thiazolylmethyl, 2-(2,2,2-trifluoro-1-hydroxy-1-trifluoromethylethyl)-4-thiazolylmethyl, 2-(1-carboxy-1-methylethyl)-4-thiazolylmethyl, 2-methoxycarbonyl-4-thiazolylmethyl, 5-thiazolylmethyl, 2-cyano-5-thiazolylmethyl, 2-carboxy-5-thiazolylmethyl, 2-methyl-5-thiazolylmethyl, 2-ethyl-5-thiazolylmethyl, 2-trifluoromethyl-5-thiazolylmethyl, 2-(1-hydroxy-1-methylethyl)-5-thiazolylmethyl, 2-(2,2,2-trifluoro-1-hydroxy-1-trifluoromethylethyl)-5-thiazolylmethyl, 2-(1-carboxy-1-methylethyl)-5-thiazolylmethyl, 2-methoxycarbonyl-5-thiazolylmethyl, 4-pyrazolylmethyl, 6-cyano-2-pyridylmethyl, 6-carboxy-2-pyridylmethyl, 6-trifluoromethyl-2-pyridylmethyl, 6-methoxy-2-pyridylmethyl, 6-ethoxy-2-pyridylmethyl, 6-methoxycarbonyl-2-pyridylmethyl, 6-ethoxycarbonyl-2-pyridylmethyl, 6-(1-hydroxy-1-methylethyl)-2-pyridylmethyl, 6-(2,2,2-trifluoro-1-hydroxy-1-trifluoromethylethyl)-2-pyridylmethyl, 6-(1-carboxy-1-methylethyl)-2-pyridylmethyl, 6-cyano-3-pyridylmethyl, 6-carboxy-3-pyridylmethyl, 6-trifluoromethyl-3-pyridylmethyl, 6-methoxy-3-pyridylmethyl, 6-ethoxy-3-pyridylmethyl, 6-methoxycarbonyl-3-pyridylmethyl, 6-ethoxycarbonyl-3-pyridylmethyl, 6-(1-hydroxy-1-methylethyl)-3-pyridylmethyl, 6-(2,2,2-trifluoro-1-hydroxy-1-trifluoromethylethyl)-3-pyridylmethyl, 6-(1-carboxy-1-methylethyl)-3-pyridylmethyl, 2-cyano-3-pyridylmethyl, 2-carboxy-3-pyridylmethyl, 2-trifluoromethyl-3-pyridylmethyl, 2-methoxy-3-pyridylmethyl, 2-ethoxy-3-pyridylmethyl, 2-propoxy-3-pyridylmethyl, 2-methoxycarbonyl-3-pyridylmethyl, 2-ethoxycarbonyl-3-pyridylmethyl, 2-propoxycarbonyl-3-pyridylmethyl, 2-(1-hydroxy-1-methylethyl)-3-pyridylmethyl, 2-(2,2,2-trifluoro-1-hydroxy-1-trifluoromethylethyl)-3-pyridylmethyl, 2-(1-carboxy-1-methylethyl)-3-pyridylmethyl, 2-cyano-4-pyridylmethyl, 2-carboxy-4-pyridylmethyl, 2-trifluoromethyl-4-pyridylmethyl, 2-methoxy-4-pyridylmethyl, 2-ethoxy-4-pyridylmethyl, 2-propoxy-4-pyridylmethyl, 2-methoxycarbonyl-4-pyridylmethyl, 2-ethoxycarbonyl-4-pyridylmethyl, 2-(1-hydroxy-1-methylethyl)-4-pyridyl, 2-(2,2,2-trifluoro-1-hydroxy-1-trifluoromethylethyl)-4-pyridylmethyl, 2-(1-carboxy-1-methylethyl)-4-pyridylmethyl, phenethyl, 2-fluorophenethyl, 3-fluorophenethyl, 4-fluorophenethyl, 3-chlorophenethyl, 3-cyanophenethyl, 3-carboxyphenethyl, 3-methoxyphenethyl, 2-(2-thienyl)ethyl, 2-(3-thienyl)ethyl, 2-(4-thiazolyl)ethyl, 2-(5-thiazolyl)ethyl, 2-(4-pyrazolyl)ethyl, 2-(6-cyano-2-pyridyl)ethyl, 2-(6-carboxy-2-pyridyl)ethyl, 2-(6-methoxy-2-pyridyl)ethyl, 2-(6-cyano-3-pyridyl)ethyl, 2-(6-carboxy-3-pyridyl)ethyl, 2-(6-methoxy-3-pyridyl)ethyl, 2-(2-cyano-3-pyridyl)ethyl, 2-(2-carboxy-3-pyridyl)ethyl, 2-(2-methoxy-3-pyridyl)ethyl, hydroxyphenylmethyl, (2-fluorophenyl)hydroxymethyl, (3-fluorophenyl)hydroxymethyl, (4-fluorophenyl)hydroxymethyl, (3-chlorophenyl)hydroxymethyl, (3,4-difluorophenyl)hydroxymethyl, (2,4-difluorophenyl)hydroxymethyl, (3-cyanophenyl)hydroxymethyl, hydroxy(3-trifluoromethylphenyl)methyl or hydroxy(2-thienyl)methyl group,
(9) a compound wherein $R^4$ is a hydrogen atom, chlorine atom, bromine atom, methyl, ethyl, propyl, isopropyl, butyl, isobutyl, pentyl, isopentyl, neopentyl, hexyl, 2-ethylbutyl, 2,2-dimethylbutyl, 3,3-dimethylbutyl, heptyl, 2,2-dimethylpentyl, 3,3-dimethylpentyl, 4,4-dimethylpentyl, octyl, 4-ethylhexyl, 2,2-dimethylhexyl, 3,3-dimethylhexyl, 4,4-dimethylhexyl, 5,5-dimethylhexyl, 2-propylpentyl, 2,2,3,3-tetramethylbutyl, 2,2,2-trifluoroethyl, 3,3,3-trifluoropropyl, 2-chloroethyl, hydroxyethyl, 2-hydroxyethyl, 3-hydroxypropyl, 4-hydroxybutyl, 5-hydroxypentyl, 6-hydroxyhexyl, 2-hydroxy-2-methylpropyl, 3-hydroxy-3-methylbutyl, 4-hydroxy-4-methylpentyl, 2-ethyl-2-hydroxybutyl, 2-cyano-2-methylpropyl, 3-cyano-3-methylbutyl, 4-cyano-4-methylpentyl, 2-cyano-2-ethylbutyl, 2-carboxy-2-methylpropyl, 3-carboxy-3-methylbutyl, 4-carboxy-4-methylpentyl, 2-carboxy-2-ethylbutyl, methoxymethyl, 2-methoxyethyl, 3-methoxypropyl, 4-methoxybutyl, 5-methoxypentyl, 6-methoxyhexyl, 2-methoxy-2-methylpropyl, 3-methoxy-3-methylbutyl, 4-methoxy-4-methylpentyl, 2-ethyl-2-methoxybutyl, ethoxymethyl, 2-ethoxyethyl, 3-ethoxypropyl, 4-ethoxybutyl, 5-ethoxypentyl, 6-ethoxyhexyl, 2-ethoxy-2-methylpropyl, 3-ethoxy-3-methylbutyl, 4-ethoxy-4-methylpentyl, 2-ethoxy-2-ethylbutyl, propoxymethyl, 2-propoxyethyl, 3-propoxypropyl, 4-propoxybutyl, 2-methyl-2-propoxypropyl, 3-methyl-3-propoxybutyl, 4-methyl-4-propoxypentyl, 2-ethyl-2-propoxybutyl, butoxymethyl, 2-butoxyethyl, 3-butoxypropyl, 4-butoxybutyl, 2-butoxy-2-methylpropyl, 3-butoxy-3-methylbutyl, 4-butoxy-4-methylpentyl, 2-butoxy-2-ethylbutyl, isopropoxymethyl, 2-isopropoxyethyl, 3-isopropoxypropyl, 4-isopropoxybutyl, isobutoxymethyl, sec-butoxymethyl, tert-butoxymethyl, 1-ethylpropoxymethyl, 2-fluoroethoxymethyl, 2-(2-fluoroethoxy)ethyl, 3-(2-fluoroethoxy)propyl, 4-(2-fluoroethoxy)butyl, 5-(2-fluoroethoxy)pentyl, 6-(2-fluoroethoxy)hexyl, 2-(2-fluoroethoxy)-2-methylpropyl, 3-(2-fluoroethoxy)-3-methylbutyl, 4-(2-fluoroethoxy)-4-methylpentyl, 2-ethyl-2-(2-fluoroethoxy)butyl, (2,2,2-trifluoroethoxy)methyl, cyclopropoxymethyl, cyclobutoxymethyl, 2-cyclobutoxyethyl, 3-cyclobutoxypropyl, 4-cyclobutoxybutyl, 5-cyclobutoxypentyl, 6-cyclobutoxyhexyl, 2-cyclobutoxy-2-methylpropyl, 3-cyclobutoxy-3-methylbutyl, 4-cyclobutoxy-4-methylpentyl, 2-cyclobutoxy-2-ethylbutyl, cyclopropylmethoxymethyl, 2-cyclopropylmethoxyethyl, 3-cyclopropylmethoxypropyl, 4-cyclopropylmethoxybutyl, 5-cyclopropylmethoxypentyl, 6-cyclopropylmethoxyhexyl, 2-cyclopropylmethoxy-2-methylpropyl, 3-cyclopropylmethoxy-3-methylbutyl, 4-cyclopropylmethoxy-4-methylpentyl, 2-cyclopropylmethoxy-2-ethylbutyl, cyclobutylmethoxymethyl, methoxycarbonylmethyl, 2-methoxycarbonylethyl, 3-methoxycarbonylpropyl, 4-methoxycarbonylbutyl, 2-methoxycarbonyl-2-methylpropyl, 3-methoxycarbonyl-3-methylbutyl, 4-methoxycarbonyl-4-methylpentyl, 2-ethyl-2-methoxycarbonylbutyl, ethoxycarbonylmethyl, 2-ethoxycarbonylethyl, 3-ethoxycarbonylpropyl, 4-ethoxycarbonylbutyl, 2-ethoxycarbonyl-2-methylpropyl, 3-ethoxycarbonyl-3-methylbutyl, 4-ethoxycarbonyl-4-methylpentyl, 2-ethoxycarbonyl-2-ethylbutyl, propoxycarbonylmethyl, 2-propoxycarbonylethyl, 3-propoxycarbonylpropyl, 4-propoxycarbonylbutyl, 2-methyl-2-propoxycarbonylpropyl, 3-methyl-3-propoxycarbonylbutyl, 4-methyl-4-propoxycarbonylpentyl, 2-ethyl-2-propoxycarbonylbutyl, butoxycarbonylmethyl, 2-butoxycarbonylethyl, 3-butoxycarbonylpropyl, 4-butoxycarbonylbutyl, 2-butoxycarbonyl-2-methylpropyl, 3-butoxycarbonyl-3-methylbutyl, 4-butoxycarbonyl-4-methylpentyl, 2-butoxycarbonyl-2-ethylbutyl, isopropoxycarbonylmethyl, 2-isopropoxycarbonylethyl, 3-isopropoxycarbonylpropyl, 4-isopropoxycarbonylbutyl, 2-isopropoxycarbonyl-2-methylpropyl, 3-isopropoxycarbonyl-3-methylbutyl, 4-isopropoxycarbonyl-4-methylpentyl, 2-ethyl-2-isopropoxycarbonylbutyl, isobutoxycarbonylmethyl, 2-isobutoxycarbonylethyl, 3-isobutoxycarbonylpropyl, 4-isobutoxycarbonylbutyl, acetyloxymethyl, 2-acetyloxyethyl, 3-acetyloxypropyl, 4-acetyloxybutyl, 5-acetyloxypentyl, 6-acetyloxyhexyl, 2-acetyloxy-2-methylpropyl, 3-acetyloxy-3-methylbutyl, 4-acetyloxy-4-methylpentyl, 2-acetyloxy-2-ethylbutyl, propionyloxymethyl, 2-propionyloxyethyl, 3-propionyloxypropyl, 4-propionyloxybutyl, 5-propionyloxypentyl, acetylmethyl, 2-acetylethyl, 3-acetylpropyl, 4-acetylbutyl, 5-acetylpentyl, 6-acetylhexyl, 2-acetyl-2-methylpropyl, 3-acetyl-3-methylbutyl, 4-acetyl-4-methylpentyl, 2-acetyl-2-ethylbutyl, propionylmethyl, 2-propionylethyl, 3-propionylpropyl, 4-propionylbutyl, 5-propionylpentyl, dimethylaminomethyl, 2-dimethylaminoethyl, diethylaminomethyl, 2-diethylaminoethyl, dipropylaminomethyl, 2-dipropylaminoethyl, 2-dibutylaminomethyl, 3-dibutylaminoethyl, diisopropylaminomethyl, 2-diisopropylaminoethyl, cyclopropyl, 1-hydroxycyclopropyl, cyclobutyl, 1-hydroxycyclobutyl, cyclopropylmethyl, (1-hydroxycyclopropyl)methyl, cyclobutylmethyl, (1-hydroxycyclobutyl)methyl, cyclopropylhydroxymethyl, hydroxy(1-hydroxycyclopropyl)methyl, cyclobutylhydroxymethyl, hydroxy(1-hydroxycyclobutyl)methyl, 2-cyclopropylethyl, 2-(1-hydroxycyclopropyl)ethyl, 2-cyclobutylethyl, 2-(1-hydroxycyclobutyl)ethyl, 2-propenyl, 2-butenyl, 2-pentenyl, 2-hexenyl, 2-methyl-2-propenyl, 2-methyl-2-butenyl, 3-methyl-2-butenyl, 2-methyl-2-pentenyl, 3-methyl-2-pentenyl, 4-methyl-2-pentenyl, 2,3-dimethyl-2-butenyl, ethynyl, 2-propynyl, 2-butynyl, 2-pentynyl, 2-hexynyl, 4-methyl-2-pentynyl, 1-hydroxy-2-propenyl, 1-hydroxy-2-butenyl, 1-hydroxy-2-pentenyl, 1-hydroxy-2-hexenyl, 1-hydroxy-2-propynyl, 1-hydroxy-2-butynyl, 1-hydroxy-2-pentynyl, 1-hydroxy-2-hexynyl, phenyl, 2-fluorophenyl, 3-fluorophenyl, 4-fluorophenyl, 2,4-difluorophenyl, 2,6-difluorophenyl, 3,4-difluorophenyl, 2-chlorophenyl, 3-chlorophenyl, 4-chlorophenyl, 2,4-dichlorophenyl, 2,6-dichlorophenyl, 3,4-dichlorophenyl, 3-cyanophenyl, 4-cyanophenyl, 3-nitrophenyl, 4-nitrophenyl, 3-carboxyphenyl, 4-carboxyphenyl, 3-trifluoromethylphenyl, 4-trifluoromethylphenyl, 3-(1-hydroxy-1-methylethyl)phenyl, 4-(1-hydroxy-1-methylethyl)phenyl, 3-(2,2,2-trifluoro-1-hydroxy-1-trifluoromethylethyl)phenyl, 4-(2,2,2-trifluoro-1-hydroxy-1-trifluoromethylethyl)phenyl, 3-(1-carboxy-1-methylethyl)phenyl, 4-(1-carboxy-1-methylethyl)phenyl, 3-methoxyphenyl, 4-methoxyphenyl, 3-ethoxyphenyl, 4-ethoxyphenyl, 3-methoxycarbonylphenyl, 4-methoxycarbonylphenyl, 3-ethoxycarbonylphenyl, 4-ethoxycarbonylphenyl, 2-thienyl, 4-cyano-2-thienyl, 5-cyano-2-thienyl, 4-carboxy-2-thienyl, 5-carboxy-2-thienyl, 4-methyl-2-thienyl, 5-methyl-2-thienyl, 4-trifluoromethyl-2-thienyl, 5-trifluoromethyl-2-thienyl, 4-(1-hydroxy-1-methylethyl)-2-thienyl, 5-(1-hydroxy-1-methylethyl)-2-thienyl, 4-(2,2,2-trifluoro-1-hydroxy-1-trifluoromethylethyl)-2-thienyl, 5-(2,2,2-trifluoro-1-hydroxy-1-trifluoromethylethyl)-2-thienyl, 4-(1-carboxy-1-methylethyl)-2-thienyl, 5-(1-carboxy-1-methylethyl)-2-thienyl, 3-thienyl, 4-cyano-3-thienyl, 5-cyano-3-thienyl, 4-carboxy-3-thienyl, 5-carboxy-3-thienyl, 4-methyl-3-thienyl, 5-methyl-3-thienyl, 4-trifluoromethyl-3-thienyl, 5-trifluoromethyl-3-thienyl, 5-ethyl-3-thienyl, 5-(1-hydroxy-1-methylethyl)-3-thienyl, 5-(2,2,2-trifluoro-1-hydroxy-1-trifluoromethylethyl)-3-thienyl, 5-(1-carboxy-1-methylethyl)-3-thienyl, 5-methoxycarbonyl-3-thienyl, 4-thiazolyl, 2-cyano-4-thiazolyl, 2-carboxy-4-thiazolyl, 2-methyl-4-thiazolyl, 2-ethyl-4-thiazolyl, 2-propyl-4-thiazolyl, 2-isopropyl-4-thiazolyl, 2-trifluoromethyl-4-thiazolyl,
2-(1-hydroxy-1-methylethyl)-4-thiazolyl, 2-(2,2,2-trifluoro-1-hydroxy-1-trifluoromethylethyl)-4-thiazolyl, 2-(1-carboxy-1-methylethyl)-4-thiazolyl, 2-methoxycarbonyl-4-thiazolyl, 5-thiazolyl, 2-cyano-5-thiazolyl, 2-carboxy-5-thiazolyl, 2-methyl-5-thiazolyl, 2-ethyl-5-thiazolyl, 2-trifluoromethyl-5-thiazolyl, 2-(1-hydroxy-1-methylethyl)-5-thiazolyl, 2-(2,2,2-trifluoro-1-hydroxy-1-trifluoromethylethyl)-5-thiazolyl, 2-(1-carboxy-1-methylethyl)-5-thiazolyl, 2-methoxycarbonyl-5-thiazolyl, 2-ethoxycarbonyl-5-thiazolyl, 2-propoxycarbonyl-5-thiazolyl, 2-isopropoxycarbonyl-5-thiazolyl, 4-pyrazolyl, 6-cyano-2-pyridyl, 6-carboxy-2-pyridyl, 6-trifluoromethyl-2-pyridyl, 6-methoxy-2-pyridyl, 6-ethoxy-2-pyridyl, 6-methoxycarbonyl-2-pyridyl, 6-ethoxycarbonyl-2-pyridyl, 6-(1-hydroxy-1-methylethyl)-2-pyridyl, 6-(2,2,2-trifluoro-1-hydroxy-1-trifluoromethylethyl)-2-pyridyl, 6-(1-carboxy-1-methylethyl)-2-pyridyl, 6-cyano-3-pyridyl, 6-carboxy-3-pyridyl, 6-trifluoromethyl-3-pyridyl, 6-methoxy-3-pyridyl, 6-ethoxy-3-pyridyl, 6-methoxycarbonyl-3-pyridyl, 6-ethoxycarbonyl-3-pyridyl, 6-(1-hydroxy-1-methylethyl)-3-pyridyl, 6-(2,2,2-trifluoro-1-hydroxy-1-trifluoromethylethyl)-3-pyridyl, 6-(1-carboxy-1-methylethyl)-3-pyridyl, 2-cyano-3-pyridyl, 2-carboxy-3-pyridyl, 2-trifluoromethyl-3-pyridyl, 2-methoxy-3-pyridyl, 2-ethoxy-3-pyridyl, 2-propoxy-3-pyridyl, 2-methoxycarbonyl-3-pyridyl, 2-ethoxycarbonyl-3-pyridyl, 2-propoxycarbonyl-3-pyridyl, 2-(1-hydroxy-1-methylethyl)-3-pyridyl, 2-(2,2,2-trifluoro-1-hydroxy-1-trifluoromethylethyl)-3-pyridyl, 2-(1-carboxy-1-methylethyl)-3-pyridyl, 2-cyano-4-pyridyl, 2-carboxy-4-pyridyl, 2-trifluoromethyl-4-pyridyl, 2-methoxy-4-pyridyl, 2-ethoxy-4-pyridyl, 2-propoxy-4-pyridyl, 2-methoxycarbonyl-4-pyridyl, 2-ethoxycarbonyl-4-pyridyl, 2-(1-hydroxy-1-methylethyl)-4-pyridyl, 2-(2,2,2-trifluoro-1-hydroxy-1-trifluoromethylethyl)-4-pyridyl, 2-(1-carboxy-1-methylethyl)-4-pyridyl,
benzyl, 2-fluorobenzyl, 3-fluorobenzyl, 4-fluorobenzyl, 2,4-difluorobenzyl, 3,4-difluorobenzyl, 2-chlorobenzyl, 3-chlorobenzyl, 4-chlorobenzyl, 2,4-dichlorobenzyl, 3,4-dichlorobenzyl, 2-cyanobenzyl, 3-cyanobenzyl, 4-cyanobenzyl, 3-nitrobenzyl, 3-carboxybenzyl, 4-carboxybenzyl, 3-trifluoromethylbenzyl, 4-trifluoromethylbenzyl, 3-(1-hydroxy-1-methylethyl)benzyl, 4-(1-hydroxy-1-methylethyl)benzyl, 3-(2,2,2-trifluoro-1-hydroxy-1-trifluoromethylethyl)benzyl, 4-(2,2,2-trifluoro-1-hydroxy-1-trifluoromethylethyl)benzyl, 4-(1-carboxy-1-methylethyl)benzyl, 3-methoxybenzyl, 4-methoxybenzyl, 3-methoxycarbonylbenzyl, 4-methoxycarbonylbenzyl, 2-thienylmethyl, 5-cyano-2-thienylmethyl, 5-carboxy-2-thienylmethyl, 5-methyl-2-thienylmethyl, 5-trifluoromethyl-2-thienylmethyl, 5-(1-hydroxy-1-methylethyl)-2-thienylmethyl, 5-(2,2,2-trifluoro-1-hydroxy-1-trifluoromethylethyl)-2-thienylmethyl, 4-(1-carboxy-1-methylethyl)-2-thienylmethyl, 3-thienylmethyl, 5-cyano-3-thienylmethyl, 5-carboxy-3-thienylmethyl, 5-methyl-3-thienylmethyl, 5-trifluoromethyl-3-thienylmethyl, 5-(1-hydroxy-1-methylethyl)-3-thienylmethyl, 5-(2,2,2-trifluoro-1-hydroxy-1-trifluoromethylethyl)-3-thienylmethyl, 4-thiazolylmethyl, 2-cyano-4-thiazolylmethyl, 2-carboxy-4-thiazolylmethyl, 2-methyl-4-thiazolylmethyl, 2-trifluoromethyl-4-thiazolylmethyl, 2-(1-hydroxy-1-methylethyl)-4-thiazolylmethyl, 2-(2,2,2-trifluoro-1-trifluoromethylethyl)-4-thiazolylmethyl, 5-thiazolylmethyl, 2-cyano-5-thiazolylmethyl, 2-carboxy-5-thiazolylmethyl, 2-methyl-5-thiazolylmethyl, 2-trifluoromethyl-5-thiazolylmethyl, 2-(1-hydroxy-1-methylethyl)-5-thiazolylmethyl, 2-(2,2,2-trifluoro-1-hydroxy-1-trifluoromethylethyl)-5-thiazolylmethyl, 4-pyrazolylmethyl, 6-cyano-2-pyridylmethyl, 6-carboxy-2-pyridylmethyl, 6-trifluoromethyl-2-pyridylmethyl, 6-methoxy-2-pyridylmethyl, 6-(1-hydroxy-1-methylethyl)-2-pyridylmethyl, 6-(2,2,2-trifluoro-1-hydroxy-1-trifluoromethylethyl)-2-pyridylmethyl, 6-cyano-3-pyridylmethyl, 6-carboxy-3-pyridylmethyl, 6-trifluoromethyl-3-pyridylmethyl, 6-methoxy-3-pyridylmethyl, 6-(1-hydroxy-1-methylethyl)-3-pyridylmethyl, 6-(2,2,2-trifluoro-1-hydroxy-1-trifluoromethylethyl)-3-pyridylmethyl, 2-cyano-3-pyridylmethyl, 2-carboxy-3-pyridylmethyl, 2-trifluoromethyl-3-pyridylmethyl, 2-methoxy-3-pyridylmethyl, 2-(1-hydroxy-1-methylethyl)-3-pyridylmethyl, 2-(2,2,2-trifluoro-1-hydroxy-1-trifluoromethylethyl)-3-pyridylmethyl, 2-cyano-4-pyridylmethyl, 2-carboxy-4-pyridylmethyl, 2-trifluoromethyl-4-pyridylmethyl, 2-methoxy-4-pyridylmethyl, 2-(1-hydroxy-1-methylethyl)-4-pyridyl, 2-(2,2,2-trifluoro-1-hydroxy-1-trifluoromethylethyl)-4-pyridylmethyl, phenethyl, 2-fluorophenethyl, 3-fluorophenethyl, 4-fluorophenethyl, 3-chlorophenethyl, 3-cyanophenethyl, 3-carboxyphenethyl, 3-methoxyphenethyl, 2-(2-thienyl)ethyl, 2-(3-thienyl)ethyl, 2-(6-cyano-2-pyridyl)ethyl, 2-(6-methoxy-2-pyridyl)ethyl, 2-(6-cyano-3-pyridyl)ethyl, 2-(6-methoxy-3-pyridyl)ethyl, 2-(2-cyano-3-pyridyl)ethyl, 2-(2-methoxy-3-pyridyl)ethyl, hydroxyphenylmethyl, (2-fluorophenyl)hydroxymethyl, (3-fluorophenyl)hydroxymethyl, (4-fluorophenyl)hydroxymethyl, (3,4-difluorophenyl)hydroxymethyl or hydroxy(2-thienyl)methyl group,

(10) a compound wherein $R^4$ is a hydrogen atom, chlorine atom, bromine atom, methyl, ethyl, propyl, isopropyl, butyl, isobutyl, pentyl, isopentyl, neopentyl, hexyl, 2-ethylbutyl, 2,2-dimethylbutyl, 3,3-dimethylbutyl, 2,2,2-trifluoroethyl, 3,3,3-trifluoropropyl, 2-chloroethyl, hydroxymethyl, 2-hydroxy-2-methylpropyl, 3-hydroxy-3-methylbutyl, 4-hydroxy-4-methylpentyl, 2-ethyl-2-hydroxybutyl, 2-cyano-2-methylpropyl, 3-cyano-3-methylbutyl, 2-carboxy-2-methylpropyl, 3-carboxy-3-methylbutyl, 4-carboxy-4-methylpentyl, methoxymethyl, ethoxymethyl, isopropoxymethyl, 2-methoxyethyl, 2-ethoxyethyl, 2-isopropoxyethyl, isobutoxymethyl, sec-butoxymethyl, tert-butoxymethyl, 1-ethylpropoxymethyl, 2-fluoroethoxymethyl, cyclobutoxymethyl, cyclopropylmethoxymethyl, dimethylaminomethyl, cyclopropyl, 1-hydroxycyclopropyl, cyclobutyl, 1-hydroxycyclobutyl, cyclopropylmethyl, (1-hydroxycyclopropyl)methyl, cyclobutylmethyl, (1-hydroxycyclobutyl) methyl, cyclopropylhydroxymethyl, hydroxy(1-hydroxycyclopropyl)methyl, cyclobutylhydroxymethyl, hydroxy(1-hydroxycyclobutyl)methyl, 2-cyclopropylethyl, 2-(1-hydroxycyclopropyl)ethyl, 2-cyclobutylethyl, 2-(1-hydroxycyclobutyl)ethyl, 2-propenyl, 2-butenyl, 2-methyl-2-propenyl, 2-methyl-2-butenyl, 3-methyl-2-butenyl, 2,3-dimethyl-2-butenyl, ethynyl, 2-propynyl, 2-butynyl, 4-methyl-2-pentynyl, 1-hydroxy-2-propenyl, 1-hydroxy-2-butenyl, 1-hydroxy-2-propynyl, 1-hydroxy-2-butynyl, phenyl, 2-fluorophenyl, 4-fluorophenyl, 2,4-difluorophenyl, 2-chlorophenyl, 4-chlorophenyl, 4-cyanophenyl, 4-nitrophenyl, 4-carboxyphenyl, 4-trifluoromethylphenyl, 3-methoxyphenyl, 4-methoxyphenyl, 4-methoxycarbonylphenyl, 2-thienyl, 5-cyano-2-thienyl, 5-carboxy-2-thienyl, 5-methyl-2-thienyl, 5-trifluoromethyl-2-thienyl, 3-thienyl, 5-cyano-3-thienyl, 5-carboxy-3-thienyl, 5-methyl-3-thienyl, 5-trifluoromethyl-3-thienyl, 4-thiazolyl, 2-cyano-4-thiazolyl, 2-carboxy-4-thiazolyl, 2-methyl-4-thiazolyl, 2-trifluoromethyl-4-thiazolyl, 2-(1-hydroxy-1-methylethyl)-4-thiazolyl, 2-(2,2,2-trifluoro-1-hydroxy-1-trifluoromethylethyl)-4-thiazolyl, 5-thiazolyl, 2-cyano-5-thiazolyl, 2-carboxy-5-thiazolyl, 2-methyl-5-thiazolyl, 2-trifluoromethyl-5-thiazolyl, 2-(1-hydroxy-1-methylethyl)-5-thiazolyl, 2-(2,2,2-trifluoro-1-hydroxy-1-trifluoromethylethyl)-5-thiazolyl, 4-pyrazolyl, 6-cyano-2-pyridyl, 6-carboxy-2-pyridyl, 6-trifluoromethyl-2-pyridyl, 6-methoxy-2-pyridyl, 6-(1-hydroxy-1-methylethyl)-2-pyridyl, 6-(2,2,2-trifluoro-1-hydroxy-1-trifluoromethylethyl)-2-pyridyl, 6-cyano-3-pyridyl, 6-carboxy-3-pyridyl, 6-trifluoromethyl-3-pyridyl, 6-methoxy-3-pyridyl, 6-(1-hydroxy-1-methylethyl)-3-pyridyl, 6-(2,2,2-trifluoro-1-hydroxy-1-trifluoromethylethyl)-3-pyridyl, 2-cyano-4-pyridyl, 2-carboxy-4-pyridyl, 2-trifluoromethyl-4-pyridyl, 2-methoxy-4-pyridyl, 2-(1-hydroxy-1-methylethyl)-4-pyridyl, 2-(2,2,2-trifluoro-1-hydroxy-1-trifluoromethylethyl)-4-pyridyl, benzyl, 2-fluorobenzyl, 3-fluorobenzyl, 4-fluorobenzyl, 2,4-difluorobenzyl, 3,4-difluorobenzyl, 2-chlorobenzyl, 3-chlorobenzyl, 2-cyanobenzyl, 3-cyanobenzyl, 3-carboxybenzyl, 4-carboxybenzyl, 3-trifluoromethylbenzyl, 4-methoxybenzyl, 3-methoxycarbonylbenzyl, 2-thienylmethyl, 5-cyano-2-thienylmethyl, 5-carboxy-2-thienylmethyl, 5-trifluoromethyl-2-thienylmethyl, 3-thienylmethyl, 5-cyano-3-thienylmethyl, 5-carboxy-3-thienylmethyl, 5-trifluoromethyl-3-thienylmethyl, 4-thiazolylmethyl, 2-cyano-4-thiazolylmethyl, 2-carboxy-4-thiazolylmethyl, 2-(1-hydroxy-1-methylethyl)-4-thiazolylmethyl, 2-(2,2,2-trifluoro-1-hydroxy-1-trifluoromethylethyl)-4-thiazolylmethyl, 2-cyano-5-thiazolylmethyl, 2-carboxy-5-thiazolylmethyl, 2-(1-hydroxy-1-methylethyl)-5-thiazolylmethyl, 2-(2,2,2-trifluoro-1-hydroxy-1-trifluoromethylethyl)-5-thiazolylmethyl, 6-cyano-2-pyridylmethyl, 6-carboxy-2-pyridylmethyl, 6-methoxy-2-pyridylmethyl, 6-(1-hydroxy-1-methylethyl)-2-pyridylmethyl, 6-(2,2,2-trifluoro-1-hydroxy-1-trifluoromethylethyl)-2-pyridylmethyl, 6-cyano-3-pyridylmethyl, 6-carboxy-3-pyridylmethyl, 6-methoxy-3-pyridylmethyl, 6-(1-hydroxy-1-methylethyl)-3-pyridylmethyl, 6-(2,2,2-trifluoro-1-hydroxy-1-trifluoromethylethyl)-3-pyridylmethyl, 2-cyano-3-pyridylmethyl, 2-carboxy-3-pyridylmethyl, 2-methoxy-3-pyridylmethyl, 2-(1-hydroxy-1-methylethyl)-3-pyridylmethyl, 2-(2,2,2-trifluoro-1-hydroxy-1-trifluoromethylethyl)-3-pyridylmethyl, 2-cyano-4-pyridylmethyl, 2-carboxy-4-pyridylmethyl, 2-methoxy-4-pyridylmethyl, 2-(1-hydroxy-1-methylethyl)-4-pyridyl, 2-(2,2,2-trifluoro-1-hydroxy-1-trifluoromethylethyl)-4-pyridylmethyl, phenethyl, 2-fluorophenethyl, 3-fluorophenethyl, 4-fluorophenethyl, 3-cyanophenethyl, 2-(2-thienyl)ethyl, 2-(6-cyano-2-pyridyl)ethyl, 2-(6-cyano-3-pyridyl)ethyl, 2-(2-cyano-3-pyridyl)ethyl, hydroxyphenylmethyl, (3-fluorophenyl)hydroxymethyl, (4-fluorophenyl)hydroxymethyl or hydroxy(2-thienyl)methyl group,

(11) a compound wherein $R^4$ is a hydrogen atom, chlorine atom, bromine atom, methyl, ethyl, propyl, isopropyl, butyl, isobutyl, pentyl, isopentyl, neopentyl, hexyl, 2-ethylbutyl, 2,2,2-trifluoroethyl, 3,3,3-trifluoropropyl, 2-chloroethyl, hydroxymethyl, methoxymethyl, ethoxymethyl, isopropoxymethyl, 2-methoxyethyl, 2-ethoxyethyl, 2-isopropoxyethyl, isobutoxymethyl, sec-butoxymethyl, tert-butoxymethyl, 1-ethylpropoxymethyl, 2-fluoroethoxymethyl, cyclobutoxymethyl, cyclopropylmethoxymethyl, dimethylaminomethyl, cyclopropyl, cyclobutyl, cyclopropylmethyl, cyclobutylmethyl, cyclopropylhydroxymethyl, cyclobutylhydroxymethyl, 2-cyclopropylethyl, 2-cyclobutylethyl, 2-propenyl, 2-butenyl, 2-methyl-2-propenyl, 2-methyl-2-butenyl, 3-methyl-2-butenyl, 2,3-dimethyl-2-butenyl, ethynyl, 2-propynyl, 2-butynyl, 4-methyl-2-pentynyl, 1-hydroxy-2-propenyl, phenyl, 2-fluorophenyl, 4-fluorophenyl, 2,4-difluorophenyl, 2-chlorophenyl, 4-chlorophenyl, 4-cyanophenyl, 2-thienyl, 3-thienyl, 4-thiazolyl, 5-thiazolyl, 4-pyrazolyl, 6-methoxy-2-pyridyl, 6-methoxy-3-pyridyl, benzyl, 2-fluorobenzyl, 3-fluorobenzyl, 4-fluorobenzyl, 2,4-difluorobenzyl, 3,4-difluorobenzyl, 2-chlorobenzyl, 3-chlorobenzyl, 2-cyanobenzyl, 3-cyanobenzyl, 3-carboxybenzyl, 4-carboxybenzyl, 2-thienylmethyl, 5-cyano-2-thienylmethyl, 5-carboxy-2-thienylmethyl, 3-thienylmethyl, 5-cyano-3-thienylmethyl, 5-carboxy-3-thienylmethyl, 2-carboxy-4-thiazolylmethyl, 6-cyano-2-pyridylmethyl, 6-carboxy-2-pyridylmethyl, 6-methoxy-2-pyridylmethyl, 6-cyano-3-pyridylmethyl, 6-carboxy-3-pyridylmethyl, 6-methoxy-3-pyridylmethyl, 2-cyano-3-pyridylmethyl, 2-carboxy-3-pyridylmethyl, 2-cyano-4-pyridylmethyl, 2-carboxy-4-pyridylmethyl, phenethyl, 2-fluorophenethyl, 3-fluorophenethyl, 4-fluorophenethyl, 3-cyanophenethyl, 2-(2-thienyl)ethyl, 2-(6-cyano-2-pyridyl)ethyl, 2-(6-cyano-3-pyridyl)ethyl, 2-(2-cyano-3-pyridyl)ethyl, hydroxyphenylmethyl, (2-fluorophenyl)hydroxymethyl, (3-fluorophenyl)hydroxymethyl or (4-fluorophenyl)hydroxymethyl group,

(12) a compound wherein $R^4$ is a hydrogen atom, chlorine atom, bromine atom, methyl, ethyl, propyl, isopropyl, butyl, isobutyl, pentyl, isopentyl, hexyl, 2-ethylbutyl, 2,2,2-trifluoroethyl, 3,3,3-trifluoropropyl, 2-chloroethyl, hydroxymethyl, methoxymethyl, ethoxymethyl, isopropoxymethyl, 2-methoxyethyl, 2-ethoxyethyl, 2-isopropoxyethyl, isobutoxymethyl, sec-butoxymethyl, tert-butoxymethyl, 1-ethylpropoxymethyl, 2-fluoroethoxymethyl, cyclobutoxymethyl, cyclopropylmethoxymethyl, dimethylaminomethyl, cyclopropyl, cyclopropylmethyl, cyclopropylhydroxymethyl, 2-cyclopropylethyl, 2-propenyl, 2-butenyl, 2-methyl-2-propenyl, 2-methyl-2-butenyl, 3-methyl-2-butenyl, 2,3-dimethyl-2-butenyl, ethynyl, 2-propynyl, 2-butynyl, 4-methyl-2-pentynyl, 1-hydroxy-2-propenyl, phenyl, 2-thienyl, 3-thienyl, 4-pyrazolyl, benzyl, 2-fluorobenzyl, 3-fluorobenzyl, 4-fluorobenzyl, 2,4-difluorobenzyl, 3,4-difluorobenzyl, 2-chlorobenzyl, 3-chlorobenzyl, 2-cyanobenzyl, 3-cyanobenzyl, 3-carboxybenzyl, 2-thienylmethyl, 3-thienylmethyl, 6-methoxy-2-pyridylmethyl, 6-methoxy-3-pyridylmethyl, phenethyl, hydroxyphenylmethyl, (2-fluorophenyl)hydroxymethyl, (3-fluorophenyl)hydroxymethyl or (4-fluorophenyl)hydroxymethyl group,

(13) a compound wherein $R^4$ is a hydrogen atom, chlorine atom, bromine atom, methyl, ethyl, propyl, isopropyl, butyl, isobutyl, pentyl, isopentyl, hexyl, hydroxymethyl, methoxymethyl, ethoxymethyl, isopropoxymethyl, 2-methoxyethyl, 2-ethoxyethyl, isobutoxymethyl, sec-butoxymethyl, tert-butoxymethyl, 1-ethylpropoxymethyl, 2-fluoroethoxymethyl, cyclobutoxymethyl, cyclopropylmethoxymethyl, dimethylaminomethyl, cyclopropyl, cyclopropylmethyl, 2-cyclopropylethyl, 2-propenyl, ethynyl, 2-propynyl, 2-butynyl, 4-methyl-2-pentynyl, 1-hydroxy-2-propenyl, phenyl, 4-pyrazolyl, benzyl, 2-fluorobenzyl, 3-fluorobenzyl, 4-fluorobenzyl, 2-cyanobenzyl, 3-cyanobenzyl, 3-carboxybenzyl, 6-methoxy-2-pyridylmethyl, 6-methoxy-3-pyridylmethyl, phenethyl or hydroxyphenylmethyl group.

Also, in the above-mentioned groups of (1)-(2), (3)(5), (6)-(7), and (8)-(13), a larger number shows a preferred compound, and a compound obtained by optionally selecting $R^1$ from the groups (1)-(2), $R^2$ from the groups (3)-(5), $R^3$ from the groups (6)-(7), and $R^4$ from the groups (8)-(13), and also, these are optionally combined is a preferred compound.

Such a compound may be mentioned
(14) a compound wherein $R^1$ is a methyl or difluoromethyl group, R² represents a cyclopropyl, cyclobutyl, cyclopentyl, cyclopropylmethyl, cyclobutylmethyl, ethyl or isopropyl group, R³ represents a hydrogen atom, and R⁴ represents a hydrogen atom, chlorine atom, bromine atom, methyl, ethyl, propyl, isopropyl, butyl, isobutyl, pentyl, isopentyl, neopentyl, hexyl, 2-ethylbutyl, 2,2,2-trifluoroethyl, 3,3,3-trifluoropropyl, 2-chloroethyl, hydroxymethyl, methoxymethyl, ethoxymethyl, isopropoxymethyl, 2-methoxyethyl, 2-ethoxyethyl, 2-isopropoxyethyl, isobutoxymethyl, sec-butoxymethyl, tert-butoxymethyl, 1-ethylpropoxymethyl, 2-fluoroethoxymethyl, cyclobutoxymethyl, cyclopropylmethoxymethyl, dimethylaminomethyl, cyclopropyl, cyclobutyl, cyclopropylmethyl, cyclobutylmethyl, cyclopropylhydroxymethyl, cyclobutylhydroxymethyl, 2-cyclopropylethyl, 2-cyclobutylethyl, 2-propenyl, 2-butenyl, 2-methyl-2-propenyl, 2-methyl-2-butenyl, 3-methyl-2-butenyl, 2,3-dimethyl-2-butenyl, ethynyl, 2-propynyl, 2-butynyl, 4-methyl-2-pentynyl, 1-hydroxy-2-propenyl, phenyl, 2-fluorophenyl, 4-fluorophenyl, 2,4-difluorophenyl, 2-chlorophenyl, 4-chlorophenyl, 4-cyanophenyl, 2-thienyl, 3-thienyl, 4-thiazolyl, 5-thiazolyl, 4-pyrazolyl, 6-methoxy-2-pyridyl, 6-methoxy-3-pyridyl, benzyl, 2-fluorobenzyl, 3-fluorobenzyl, 4-fluorobenzyl, 2,4-difluorobenzyl, 3,4-difluorobenzyl, 2-chlorobenzyl, 3-chlorobenzyl, 2-cyanobenzyl, 3-cyanobenzyl, 3-carboxybenzyl, 4-carboxybenzyl, 2-thienylmethyl, 5-cyano-2-thienylmethyl, 5-carboxy-2-thienylmethyl, 3-thienylmethyl, 5-cyano-3-thienylmethyl, 5-carboxy-3-thienylmethyl, 2-carboxy-4-thiazolylmethyl, 6-cyano-2-pyridylmethyl, 6-carboxy-2-pyridylmethyl, 6-methoxy-2-pyridylmethyl, 6-cyano-3-pyridylmethyl, 6-carboxy-3-pyridylmethyl, 2-cyano-3-pyridylmethyl, 6-methoxy-3-pyridylmethyl, 2-carboxy-3-pyridylmethyl, 2-cyano-4-pyridylmethyl, 2-carboxy-4-pyridylmethyl, phenethyl, 2-fluorophenethyl, 3-fluorophenethyl, 4-fluorophenethyl, 3-cyanophenethyl, 2-(2-thienyl)ethyl, 2-(6-cyano-2-pyridyl)ethyl, 2-(6-cyano-3-pyridyl)ethyl, 2-(2-cyano-3-pyridyl)ethyl, hydroxyphenylmethyl, (2-fluorophenyl)hydroxymethyl, (3-fluorophenyl)hydroxymethyl or (4-fluorophenyl)hydroxymethyl group,

(15) a compound wherein R¹ represents a methyl or difluoromethyl group,

R² represents a cyclopropyl, cyclobutyl, cyclopentyl, cyclopropylmethyl or isopropyl group, R³ represents a hydrogen atom, and R⁴ represents a hydrogen atom, chlorine atom, bromine atom, methyl, ethyl, propyl, isopropyl, butyl, isobutyl, pentyl, isopentyl, neopentyl, hexyl, 2-ethylbutyl, 2,2,2-trifluoroethyl, 3,3,3-trifluoropropyl, 2-chloroethyl, hydroxymethyl, methoxymethyl, ethoxymethyl, isopropoxymethyl, 2-methoxyethyl, 2-ethoxyethyl, 2-isopropoxyethyl, isobutoxymethyl, sec-butoxymethyl, tert-butoxymethyl, 1-ethylpropoxymethyl, 2-fluoroethoxymethyl, cyclobutoxymethyl, cyclopropylmethoxymethyl, dimethylaminomethyl, cyclopropyl, cyclobutyl, cyclopropylmethyl, cyclobutylmethyl, cyclopropylhydroxymethyl, cyclobutylhydroxymethyl, 2-cyclopropylethyl, 2-cyclobutylethyl, 2-propenyl, 2-butenyl, 2-methyl-2-propenyl, 2-methyl-2-butenyl, 3-methyl-2-butenyl, 2,3-dimethyl-2-butenyl, ethynyl, 2-propynyl, 2-butynyl, 4-methyl-2-pentynyl, 1-hydroxy-2-propenyl, phenyl, 2-fluorophenyl, 4-fluorophenyl, 2,4-difluorophenyl, 2-chlorophenyl, 4-chlorophenyl, 4-cyanophenyl, 2-thienyl, 3-thienyl, 4-thiazolyl, 5-thiazolyl, 4-pyrazolyl, 6-methoxy-2-pyridyl, 6-methoxy-3-pyridyl, benzyl, 2-fluorobenzyl, 3-fluorobenzyl, 4-fluorobenzyl, 2,4-difluorobenzyl, 3,4-difluorobenzyl, 2-chlorobenzyl, 3-chlorobenzyl, 2-cyanobenzyl, 3-cyanobenzyl, 3-carboxybenzyl, 4-carboxybenzyl, 2-thienylmethyl, 5-cyano-2-thienylmethyl, 5-carboxy-2-thienylmethyl, 3-thienylmethyl, 5-cyano-3-thienylmethyl, 5-carboxy-3-thienylmethyl, 2-carboxy-4-thiazolylmethyl, 6-cyano-2-pyridylmethyl, 6-carboxy-2-pyridylmethyl, 6-methoxy-2-pyridylmethyl, 6-cyano-3-pyridylmethyl, 6-carboxy-3-pyridylmethyl, 6-methoxy-3-pyridylmethyl, 2-cyano-3-pyridylmethyl, 2-carboxy-3-pyridylmethyl, 2-cyano-4-pyridylmethyl, 2-carboxy-4-pyridylmethyl, phenethyl, 2-fluorophenethyl, 3-fluorophenethyl, 4-fluorophenethyl, 3-cyanophenethyl, 2-(2-thienyl)ethyl, 2-(6-cyano-2-pyridyl)ethyl, 2-(6-cyano-3-pyridyl)ethyl, 2-(2-cyano-3-pyridyl)ethyl, hydroxyphenylmethyl, (2-fluorophenyl)hydroxymethyl, (3-fluorophenyl)hydroxymethyl or (4-fluorophenyl)hydroxymethyl group,

(16) a compound wherein R¹ represents a difluoromethyl group,

R² represents a cyclopropyl or cyclopropylmethyl group,

R³ represents a hydrogen atom, and

R⁴ represents a hydrogen atom, chlorine atom, bromine atom, methyl, ethyl, propyl, isopropyl, butyl, isobutyl, pentyl, isopentyl, hexyl, 2-ethylbutyl, 2,2,2-trifluoroethyl, 3,3,3-trifluoropropyl, 2-chloroethyl, hydroxymethyl, methoxymethyl, ethoxymethyl, isopropoxymethyl, 2-methoxyethyl, 2-ethoxyethyl, 2-isopropoxyethyl, isobutoxymethyl, sec-butoxymethyl, tert-butoxymethyl, 1-ethylpropoxymethyl, 2-fluoroethoxymethyl, cyclobutoxymethyl, cyclopropylmethoxymethyl, dimethylaminomethyl, cyclopropyl, cyclopropylmethyl, cyclopropylhydroxymethyl, 2-cyclopropylethyl, 2-propenyl, 2-butenyl, 2-methyl-2-propenyl, 2-methyl-2-butenyl, 3-methyl-2-butenyl, 2,3-dimethyl-2-butenyl, ethynyl, 2-propynyl, 2-butynyl, 4-methyl-2-pentynyl, 1-hydroxy-2-propenyl, phenyl, 2-thienyl, 3-thienyl, 4-pyrazolyl, benzyl, 2-fluorobenzyl, 3-fluorobenzyl, 4-fluorobenzyl, 2,4-difluorobenzyl, 3,4-difluorobenzyl, 2-chlorobenzyl, 3-chlorobenzyl, 2-cyanobenzyl, 3-cyanobenzyl, 3-carboxybenzyl, 2-thienylmethyl, 3-thienylmethyl, 6-methoxy-2-pyridylmethyl, 6-methoxy-3-pyridylmethyl, phenethyl, hydroxyphenylmethyl, (2-fluorophenyl)hydroxylmethyl, (3-fluorophenyl)hydroxymethyl or (4-fluorophenyl)hydroxymethyl group,

(17) a compound wherein R¹ represents a difluoromethyl group,

R² represents a cyclopropyl or cyclopropylmethyl group,

R³ represents a hydrogen atom, and

R⁴ represents a hydrogen atom, chlorine atom, bromine atom, methyl, ethyl, propyl, isopropyl, butyl, isobutyl, pentyl, isopentyl, hexyl, hydroxymethyl, methoxymethyl, ethoxymethyl, isopropoxymethyl, 2-methoxyethyl, 2-ethoxyethyl, isobutoxymethyl, sec-butoxymethyl, tert-butoxymethyl, 1-ethylpropoxymethyl, 2-fluoroethoxymethyl, cyclobutoxymethyl, cyclopropylmethoxymethyl, dimethylaminomethyl, cyclopropyl, cyclopropylmethyl, 2-cyclopropylethyl, 2-propenyl, ethynyl, 2-propynyl, 2-butynyl, 4-methyl-2-pentynyl, 1-hydroxy-2-propenyl, phenyl, 4-pyrazolyl, benzyl, 2-fluorobenzyl, 3-fluorobenzyl, 4-fluorobenzyl, 2-cyanobenzyl, 3-cyanobenzyl, 3-carboxybenzyl, 6-methoxy-2-pyridylmethyl, 6-methoxy-3-pyridylmethyl, phenethyl or hydroxyphenylmethyl group,

(18) the pyrrolopyridazinone compound is a compound of
2-(3-cyclopropoxy-4-difluoromethoxyphenyl)-1,5-dihydropyrrolo[2,3-d]pyridazin-4-one,
3-chloro-2-(3-cyclopropoxy-4-difluoromethoxyphenyl)-1,5-dihydropyrrolo[2,3-d]pyridazin-4-one,
3-bromo-2-(3-cyclopropoxy-4-difluoromethoxyphenyl)-1,5-dihydropyrrolo[2,3-d]pyridazin-4-one,
2-(3-cyclopropoxy-4-difluoromethoxyphenyl)-3-methyl-1,5-dihydropyrrolo[2,3-d]pyridazin-4-one, 2-(3-cyclopropoxy-4-difluoromethoxyphenyl)-3-ethyl-1,5-dihydropyrrolo[2,3-d]pyridazin-4-one,
2-(3-cyclopropoxy-4-difluoromethoxyphenyl)-3-propyl-1,5-dihydropyrrolo[2,3-d]pyridazin-4-one,
2-(3-cyclopropoxy-4-difluoromethoxyphenyl)-3-isopropyl-1,5-dihydropyrrolo[2,3-d]pyridazin-4-one,
3-butyl-2-(3-cyclopropoxy-4-difluoromethoxyphenyl)-1,5-dihydropyrrolo[2,3-d]pyridazin-4-one,
2-(3-cyclopropoxy-4-difluoromethoxyphenyl)-3-isobutyl-1,5-dihydropyrrolo[2,3-d]pyridazin-4-one,
2-(3-cyclopropoxy-4-difluoromethoxyphenyl)-3-pentyl-1,5-dihydropyrrolo[2,3-d]pyridazin-4-one,
2-(3-cyclopropoxy-4-difluoromethoxyphenyl)-3-hexyl-1,5-dihydropyrrolo[2,3-d]pyridazin-4-one,
2-(3-cyclopropoxy-4-difluoromethoxyphenyl)-3-hydroxymethyl-1,5-dihydropyrrolo[2,3-d]pyridazin-4-one,
2-(3-cyclopropoxy-4-difluoromethoxyphenyl)-3-methoxymethyl-1,5-dihydropyrrolo[2,3-d]pyridazin-4-one,
2-(3-cyclopropoxy-4-difluoromethoxyphenyl)-3-(2-methoxyethyl)-1,5-dihydropyrrolo[2,3-d]pyridazin-4-one,
2-(3-cyclopropoxy-4-difluoromethoxyphenyl)-3-ethoxymethyl-1,5-dihydropyrrolo[2,3-d]pyridazin-4-one,
2-(3-cyclopropoxy-4-difluoromethoxyphenyl)-3-(2-ethoxyethyl)-1,5-dihydropyrrolo[2,3-d]pyridazin-4-one,
2-(3-cyclopropoxy-4-difluoromethoxyphenyl)-3-isopropoxymethyl-1,5-dihydropyrrolo[2,3-d]pyridazin-4-one,
2-(3-cyclopropoxy-4-difluoromethoxyphenyl)-3-(2-fluoroethoxymethyl)-1,5-dihydropyrrolo[2,3-d]pyridazin-4-one,
3-cyclobutoxymethyl-2-(3-cyclopropoxy-4-difluoromethoxyphenyl)-1,5-dihydropyrrolo[2,3-d]pyridazin-4-one,
2-(3-cyclopropoxy-4-difluoromethoxyphenyl)-3-cyclopropylmethoxymethyl-1,5-dihydropyrrolo[2,3-d]pyridazin-4-one,
2-(3-cyclopropoxy-4-difluoromethoxyphenyl)-3-dimethylaminomethyl-1,5-dihydropyrrolo[2,3-d]pyridazin-4-one,
2-(3-cyclopropoxy-4-difluoromethoxyphenyl)-3-cyclopropyl-1,5-dihydropyrrolo[2,3-d]pyridazin-4-one,
2-(3-cyclopropoxy-4-difluoromethoxyphenyl)-3-cyclopropylmethyl-1,5-dihydropyrrolo[2,3-d]pyridazin-4-one,
2-(3-cyclopropoxy-4-difluoromethoxyphenyl)-3-(2-cyclopropylethyl)-1,5-dihydropyrrolo[2,3-d]pyridazin-4-one,
2-(3-cyclopropoxy-4-difluoromethoxyphenyl)-3-(2-propenyl)-1,5-dihydropyrrolo[2,3-d]pyridazin-4-one,
2-(3-cyclopropoxy-4-difluoromethoxyphenyl)-3-ethynyl-1,5-dihydropyrrolo[2,3-d]pyridazin-4-one,
2-(3-cyclopropoxy-4-difluoromethoxyphenyl)-3-(2-propynyl)-1,5-dihydropyrrolo[2,3-d]pyridazin-4-one,
3-(2-butynyl)-2-(3-cyclopropoxy-4-difluoromethoxyphenyl)-1,5-dihydropyrrolo[2,3-d]pyridazin-4-one,
2-(3-cyclopropoxy-4-difluoromethoxyphenyl)-3-(4-methyl-2-pentynyl)-1,5-dihydropyrrolo[2,3-d]pyridazin-4-one,
2-(3-cyclopropoxy-4-difluoromethoxyphenyl)-3-(1-hydroxy-2-propenyl)-1,5-dihydropyrrolo[2,3-d]pyridazin-4-one,
2-(3-cyclopropoxy-4-difluoromethoxyphenyl)-3-phenyl-1,5-dihydropyrrolo[2,3-d]pyridazin-4-one,
2-(3-cyclopropoxy-4-difluoromethoxyphenyl)-3-(4-pyrazolyl)-1,5-dihydropyrrolo[2,3-d]pyridazin-4-one,
3-benzyl-2-(3-cyclopropoxy-4-difluoromethoxyphenyl)-1,5-dihydropyrrolo[2,3-d]pyridazin-4-one,
2-(3-cyclopropoxy-4-difluoromethoxyphenyl)-3-(2-fluorobenzyl)-1,5-dihydropyrrolo[2,3-d]pyridazin-4-one,
2-(3-cyclopropoxy-4-difluoromethoxyphenyl)-3-(3-fluorobenzyl)-1,5-dihydropyrrolo[2,3-d]pyridazin-4-one,
2-(3-cyclopropoxy-4-difluoromethoxyphenyl)-3-(4-fluorobenzyl)-1,5-dihydropyrrolo[2,3-d]pyridazin-4-one,
3-(2-cyanobenzyl)-2-(3-cyclopropoxy-4-difluoromethoxyphenyl)-1,5-dihydropyrrolo[2,3-d]pyridazin-4-one,
3-(3-cyanobenzyl)-2-(3-cyclopropoxy-4-difluoromethoxyphenyl)-1,5-dihydropyrrolo[2,3-d]pyridazin-4-one,
3-(3-carboxybenzyl)-2-(3-cyclopropoxy-4-difluoromethoxyphenyl)-1,5-dihydropyrrolo[2,3-d]pyridazin-4-one,
2-(3-cyclopropoxy-4-difluoromethoxyphenyl)-3-(6-methoxy-2-pyridylmethyl)-1,5-dihydropyrrolo[2,3-d]pyridazin-4-one,
2-(3-cyclopropoxy-4-difluoromethoxyphenyl)-3-(6-methoxy-3-pyridylmethyl)-1,5-dihydropyrrolo[2,3-d]pyridazin-4-one,
2-(3-cyclopropoxy-4-difluoromethoxyphenyl)-3-phenethyl-1,5-dihydropyrrolo[2,3-d]pyridazin-4-one,
2-(3-cyclopropoxy-4-difluoromethoxyphenyl)-3-hydroxyphenylmethyl-1,5-dihydropyrrolo[2,3-d]pyridazin-4-one,
2-(3-cyclopropylmethoxy-4-difluoromethoxyphenyl)-1,5-dihydropyrrolo[2,3-d]pyridazin-4-one,
3-chloro-2-(3-cyclopropylmethoxy-4-difluoromethoxyphenyl)-1,5-dihydropyrrolo[2,3-d]pyridazin-4-one,
2-(3-cyclopropylmethoxy-4-difluoromethoxyphenyl)-3-ethyl-1,5-dihydropyrrolo[2,3-d]pyridazin-4-one,
2-(3-cyclopropylmethoxy-4-difluoromethoxyphenyl)-3-phenyl-1,5-dihydropyrrolo[2,3-d]pyridazin-4-one,
2-(4-difluoromethoxy-3-isopropoxyphenyl)-1,5-dihydropyrrolo[2,3-d]pyridazin-4-one,
3-chloro-2-(4-difluoromethoxy-3-isopropoxyphenyl)-1,5-dihydropyrrolo[2,3-d]pyridazin-4-one,
3-bromo-2-(4-difluoromethoxy-3-isopropoxyphenyl)-1,5-dihydropyrrolo[2,3-d]pyridazin-4-one,
2-(3-cyclobutoxy-4-difluoromethoxyphenyl)-1,5-dihydropyrrolo[2,3-d]pyridazin-4-one,
3-chloro-2-(3-cyclobutoxy-4-difluoromethoxyphenyl)-1,5-dihydropyrrolo[2,3-d]pyridazin-4-one,
3-bromo-2-(3-cyclobutoxy-4-difluoromethoxyphenyl)-1,5-dihydropyrrolo[2,3-d]pyridazin-4-one,
2-(3-cyclobutoxy-4-difluoromethoxyphenyl)-3-phenyl-1,5-dihydropyrrolo[2,3-d]pyridazin-4-one,
3-chloro-2-(3-cyclopropoxy-4-methoxyphenyl)-1,5-dihydropyrrolo[2,3-d]pyridazin-4-one,
3-bromo-2-(3-cyclopropoxy-4-methoxyphenyl)-1,5-dihydropyrrolo[2,3-d]pyridazin-4-one,
3-butyl-2-(3-cyclopropoxy-4-methoxyphenyl)-1,5-dihydropyrrolo[2,3-d]pyridazin-4-one,
3-chloro-2-(3-cyclopropylmethoxy-4-methoxyphenyl)-1,5-dihydropyrrolo[2,3-d]pyridazin-4-one,
3-chloro-2-(3-isopropoxy-4-methoxyphenyl)-1,5-dihydropyrrolo[2,3-d]pyridazin-4-one,
3-chloro-2-(3-cyclobutoxy-4-methoxyphenyl)-1,5-dihydropyrrolo[2,3-d]pyridazin-4-one,
2-(3-cyclopentoxy-4-methoxyphenyl)-1,5-dihydropyrrolo[2,3-d]pyridazin-4-one,
2-(3-cyclopropoxy-4-difluoromethoxyphenyl)-3-isobutoxymethyl-1,5-dihydropyrrolo[2,3-d]pyridazin-4-one,
3-(sec-butoxymethyl)-2-(3-cyclopropoxy-4-difluoromethoxyphenyl)-1,5-dihydropyrrolo[2,3-d]pyridazin-4-one,
3-(tert-butoxymethyl)-2-(3-cyclopropoxy-4-difluoromethoxyphenyl)-1,5-dihydropyrrolo[2,3-d]pyridazin-4-one, or
2-(3-cyclopropoxy-4-difluoromethoxyphenyl)-3-(1-ethylpropoxymethyl)-1,5-dihydropyrrolo[2,3-d]pyridazin-4-one,

(19) a compound wherein $R^1$ represents a methyl or difluoromethyl group, the substituted oxygen-containing hetero ring formed by $R^3$ in combination with the group —O—$R^2$ represents a 2,2-(1,4-butylene)-tetrahydrofuran ring, 6,6-(1,3-propylene)-3,6-dihydro-2H-pyran ring, 6,6-(1,4-butylene)-3,6-dihydro-2H-pyran ring, 6-cyclopropyl-3,6-dihydro-2H-pyran ring or 6,6-dimethyl-3,6-dihydro-2H-pyran ring, and $R^4$ represents a hydrogen atom, chlorine atom, bromine atom, methyl, ethyl, propyl, isopropyl, butyl, isobutyl, pentyl, isopentyl, neopentyl, hexyl, 2-ethylbutyl, 2,2,2-trifluoroethyl, 3,3,3-trifluoropropyl, 2-chloroethyl, hydroxymethyl, methoxymethyl, ethoxymethyl, isopropoxymethyl, 2-methoxyethyl, 2-ethoxyethyl, 2-isopropoxyethyl, isobutoxymethyl, sec-butoxymethyl, tert-butoxymethyl, 1-ethylpropoxymethyl, 2-fluoroethoxymethyl, cyclobutoxymethyl, cyclopropylmethoxymethyl, dimethylaminomethyl, cyclopropyl, cyclobutyl, cyclopropylmethyl, cyclobutylmethyl, cyclopropylhydroxymethyl, cyclobutylhydroxymethyl, 2-cyclopropylethyl, 2-cyclobutylethyl, 2-propenyl, 2-butenyl, 2-methyl-2-propenyl, 2-methyl-2-butenyl, 3-methyl-2-butenyl, 2,3-dimethyl-2-butenyl, ethynyl, 2-propynyl, 2-butynyl, 4-methyl-2-pentynyl, 1-hydroxy-2-propenyl, phenyl, 2-fluorophenyl, 4-fluorophenyl, 2,4-difluorophenyl, 2-chlorophenyl, 4-chlorophenyl, 4-cyanophenyl, 2-thienyl, 3-thienyl, 4-thiazolyl, 5-thiazolyl, 4-pyrazolyl, 6-methoxy-2-pyridyl, 6-methoxy-3-pyridyl, benzyl, 2-fluorobenzyl, 3-fluorobenzyl, 4-fluorobenzyl, 2,4-difluorobenzyl, 3,4-difluorobenzyl, 2-chlorobenzyl, 3-chlorobenzyl, 2-cyanobenzyl, 3-cyanobenzyl, 3-carboxybenzyl, 4-carboxybenzyl, 2-thienylmethyl, 5-cyano-2-thienylmethyl, 5-carboxy-2-thienylmethyl, 3-thienylmethyl, 5-cyano-3-thienylmethyl, 5-carboxy-3-thienylmethyl, 2-carboxy-4-thiazolylmethyl, 6-cyano-2-pyridylmethyl, 6-carboxy-2-pyridylmethyl, 6-methoxy-2-pyridylmethyl, 6-cyano-3-pyridylmethyl, 6-carboxy-3-pyridylmethyl, 6-methoxy-3-pyridylmethyl, 2-cyano-3-pyridylmethyl, 2-carboxy-3-pyridylmethyl, 2-cyano-4-pyridylmethyl, 2-carboxy-4-pyridylmethyl, phenethyl, 2-fluorophenethyl, 3-fluorophenethyl, 4-fluorophenethyl, 3-cyanophenethyl, 2-(2-thienyl)ethyl, 2-(6-cyano-2-pyridyl)ethyl, 2-(6-cyano-3-pyridyl)ethyl, 2-(2-cyano-3-pyridyl)ethyl, hydroxyphenylmethyl, (2-fluorophenyl)hydroxymethyl, (3-fluorophenyl)hydroxymethyl or (4-fluorophenyl)hydroxymethyl group,

(20) a compound wherein $R^1$ represents a methyl or difluoromethyl group, the substituted oxygen-containing hetero ring formed by $R^3$ in combination with the group —O—$R^2$ represents a 2,2-(1,4-butylene)-tetrahydrofuran ring, 6,6-(1,3-propylene)-3,6-dihydro-2H-pyran ring, 6,6-(1,4-butylene)-3,6-dihydro-2H-pyran ring, 6-cyclopropyl-3,6-dihydro-2H-pyran ring or 6,6-dimethyl-3,6-dihydro-2H-pyran ring, and $R^4$ represents a hydrogen-atom, chlorine atom, bromine atom, methyl, ethyl, propyl, isopropyl, butyl, isobutyl, pentyl, isopentyl, hexyl, 2-ethylbutyl, 2,2,2-trifluoroethyl, 3,3,3-trifluoropropyl, 2-chloroethyl, hydroxymethyl, methoxymethyl, ethoxymethyl, isopropoxymethyl, 2-methoxyethyl, 2-ethoxyethyl, 2-isopropoxyethyl, isobutoxymethyl, sec-butoxymethyl, tert-butoxymethyl, 1-ethylpropoxymethyl, 2-fluoroethoxymethyl, cyclobutoxymethyl, cyclopropylmethoxymethyl, dimethylaminomethyl, cyclopropyl, cyclopropylmethyl, cyclopropylhydroxymethyl, 2-cyclopropylethyl, 2-propenyl, 2-butenyl, 2-methyl-2-propenyl, 2-methyl-2-butenyl, 3-methyl-2-butenyl, 2,3-dimethyl-2-butenyl, ethynyl, 2-propynyl, 2-butynyl, 4-methyl-2-pentynyl, 1-hydroxy-2-propenyl, phenyl, 2-thienyl, 3-thienyl, 4-pyrazolyl, benzyl, 2-fluorobenzyl, 3-fluorobenzyl, 4-fluorobenzyl, 2,4-difluorobenzyl, 3,4-difluorobenzyl, 2-chlorobenzyl, 3-chlorobenzyl, 2-cyanobenzyl, 3-cyanobenzyl, 3-carboxybenzyl, 2-thienylmethyl, 3-thienylmethyl, 6-methoxy-2-pyridylmethyl, 6-methoxy-3-pyridylmethyl, phenethyl, hydroxyphenylmethyl, (2-fluorophenyl)hydroxymethyl, (3-fluorophenyl)hydroxymethyl or (4-fluorophenyl)hydroxymethyl group,

(21) a compound wherein $R^1$ represents a difluoromethyl group, the substituted oxygen-containing hetero ring formed by $R^3$ in combination with the group —O—$R^2$ represents a 2,2-(1,4-butylene)-tetrahydrofuran ring, 6,6-(1,3-propylene)-3,6-dihydro-2H-pyran ring, 6,6-(1,4-butylene)-3,6-dihydro-2H-pyran ring, 6-cyclopropyl-3,6-dihydro-2H-pyran ring or 6,6-dimethyl-3,6-dihydro-2H-pyran ring, and $R^4$ represents a hydrogen atom, chlorine atom, bromine atom, methyl, ethyl, propyl, isopropyl, butyl, isobutyl, pentyl, isopentyl, hexyl, 2-ethylbutyl, 2,2,2-trifluoroethyl, 3,3,3-trifluoropropyl, 2-chloroethyl, hydroxymethyl, methoxymethyl, ethoxymethyl, isopropoxymethyl, 2-methoxyethyl, 2-ethoxyethyl, 2-isopropoxyethyl, isobutoxymethyl, sec-butoxymethyl, tert-butoxymethyl, 1-ethylpropoxymethyl, 2-fluoroethoxymethyl, cyclobutoxymethyl, cyclopropylmethoxymethyl, dimethylaminomethyl, cyclopropyl, cyclopropylmethyl, cyclopropylhydroxymethyl, 2-cyclopropylethyl, 2-propenyl, 2-butenyl, 2-methyl-2-propenyl, 2-methyl-2-butenyl, 3-methyl-2-butenyl, 2,3-dimethyl-2-butenyl, ethynyl, 2-propynyl, 2-butynyl, 4-methyl-2-pentynyl, 1-hydroxy-2-propenyl, phenyl, 2-thienyl, 3-thienyl, 4-pyrazolyl, benzyl, 2-fluorobenzyl, 3-fluorobenzyl, 4-fluorobenzyl, 2,4-difluorobenzyl, 3,4-difluorobenzyl, 2-chlorobenzyl, 3-chlorobenzyl, 2-cyanobenzyl, 3-cyanobenzyl, 3-carboxybenzyl, 2-thienylmethyl, 3-thienylmethyl, 6-methoxy-2-pyridylmethyl, 6-methoxy-3-pyridylmethyl, phenethyl, hydroxyphenylmethyl, (2-fluorophenyl)hydroxymethyl, (3-fluorophenyl)hydroxymethyl or (4-fluorophenyl)hydroxymethyl group,

(22) a compound wherein $R^1$ represents a difluoromethyl group, the substituted oxygen-containing hetero ring formed by $R^3$ in combination with the group —O—$R^2$ represents a 2,2-(1,4-butylene)-tetrahydrofuran ring, 6,6-(1,3-propylene)-3,6-dihydro-2H-pyran ring, 6,6-(1,4-butylene)-3,6-dihydro-2H-pyran ring, 6-cyclopropyl-3,6-dihydro-2H-pyran ring or 6,6-dimethyl-3,6-dihydro-2H-pyran ring, and $R^4$ represents a hydrogen atom, chlorine atom, bromine atom, methyl, ethyl, propyl, isopropyl, butyl, isobutyl, pentyl, isopentyl, hexyl, hydroxymethyl, methoxymethyl, ethoxymethyl, isopropoxymethyl, 2-methoxyethyl, 2-ethoxyethyl, isobutoxymethyl, sec-butoxymethyl, tert-butoxymethyl, 1-ethylpropoxymethyl, 2-fluoroethoxymethyl, cyclobutoxymethyl, cyclopropylmethoxymethyl, dimethylaminomethyl, cyclopropyl, cyclopropylmethyl, 2-cyclopropylethyl, 2-propenyl, ethynyl, 2-propynyl, 2-butynyl, 4-methyl-2-pentynyl, 1-hydroxy-2-propenyl, phenyl, 4-pyrazolyl, benzyl, 2-fluorobenzyl, 3-fluorobenzyl, 4-fluorobenzyl, 2-cyanobenzyl, 3-cyanobenzyl, 3-carboxybenzyl, 6-methoxy-2-pyridylmethyl, 6-methoxy-3-pyridylmethyl, phenethyl or hydroxyphenylmethyl group,

(23) a compound wherein the pyrrolopyridazinone compound is a compound of 3-chloro-2-(8-difluoromethoxy-2,2-dimethyl-2H-chromen-5-yl)-1,5-dihydropyrrolo[2,3-d]pyridazin-4-one, 2-(8-difluoromethoxy-2,2-dimethyl-2H-chromen-5-yl)-3-methyl-1,5-dihydropyrrolo[2,3-d]pyridazin-4-one, 2-(8-difluoromethoxy-2,2-dimethyl-2H-chromen-5-yl)-3-ethyl-1,5-dihydropyrrolo[2,3-d]pyridazin-4-one, 3-cyclopropyl-2-(8-difluoromethoxy-2,2-dimethyl-2H-chromen-5-yl)-1,5-dihydropyrrolo[2,3-d]pyridazin-4-one, 2-(2-cyclopropyl-8-difluoromethoxy-2H-chromen-5-yl)-1,5-dihydropyrrolo[2,3-d]pyridazin-4-one, 3-chloro-2-(8-difluoromethoxy-2H-chromen-2-spiro-1'-cyclobutan-5-yl)-1,5-dihydropyrrolo[2,3-d]pyridazin-4-one, 3-chloro-2-(8-difluoromethoxy-2H-chromen-2-spiro-1'-cyclopentan-5-yl)-1,5-dihydropyrrolo[2,3-d]pyridazin-4-one, 2-(7-difluoromethoxy-2,3-dihydrobenzofuran-2-spiro-1'-cyclopentan-4-yl)-1,5-dihydropyrrolo[2,3-d]pyridazin-4-one, 2-(2,3-dihydro-7-methoxybenzofuran-2-spiro-1'-cyclopentan-4-yl)-1,5-dihydropyrrolo[2,3-d]pyridazin-4-one, or 3-chloro-2-(2,3-dihydro-7-methoxybenzofuran-2-spiro-1'-cyclopentan-4-yl)-1,5-dihydropyrrolo[2,3-d]pyridazin-4-one, etc.

Incidentally, the present invention also provides

(24) a pharmaceutical composition which contains a compound represented by the above-mentioned formula (1), a pyrrolopyridazinone compound or a pharmaceutically acceptable salt thereof as described in any one of (1) to (17) as an effective ingredient, and

(25) a pharmaceutical composition as described in (24), wherein the pharmaceutical composition is a composition for prevention or treatment of a respiratory disease and/or an inflammatory disease.

As preferred compounds having the formula (1) in the present invention, those compounds of Table 1 to Table 5 can be specifically exemplified. Incidentally, the compound described in Table 1 has a structure represented by the formula (1a), the compound described in Table 2 has a structure represented by the formula (1b), the compound described in Table 3 has a structure represented by the formula (1c), the compound described in Table 4 has a structure represented by the formula (1d), and the compound described in Table 5 has a structure represented by the formula (1e).

TABLE 1

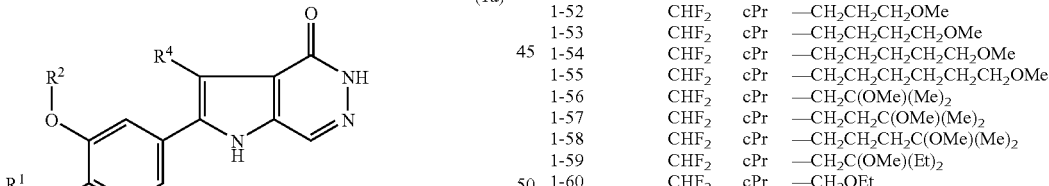

(1a)

| Compound No. | $R^1$ | $R^2$ | $R^4$ |
|---|---|---|---|
| 1-1 | $CHF_2$ | cPr | H |
| 1-2 | $CHF_2$ | cPr | Cl |
| 1-3 | $CHF_2$ | cPr | Br |
| 1-4 | $CHF_2$ | cPr | Me |
| 1-5 | $CHF_2$ | cPr | Et |
| 1-6 | $CHF_2$ | cPr | Pr |
| 1-7 | $CHF_2$ | cPr | iPr |
| 1-8 | $CHF_2$ | cPr | Bu |
| 1-9 | $CHF_2$ | cPr | iBu |
| 1-10 | $CHF_2$ | cPr | Pent |
| 1-11 | $CHF_2$ | cPr | —$CH_2CH_2CH(Me)_2$ |
| 1-12 | $CHF_2$ | cPr | —$CH_2CH_2CH_2CH_2CH_2CH_3$ |
| 1-13 | $CHF_2$ | cPr | —$CH_2CH(Et)_2$ |
| 1-14 | $CHF_2$ | cPr | —$CH_2C(Me)_2CH_2CH_3$ |
| 1-15 | $CHF_2$ | cPr | —$CH_2C(Me)_3$ |

TABLE 1-continued

| Compound No. | $R^1$ | $R^2$ | $R^4$ |
|---|---|---|---|
| 1-16 | $CHF_2$ | cPr | —$CH_2CH_2C(Me)_3$ |
| 1-17 | $CHF_2$ | cPr | —$CH_2CH_2CH_2CH_2CH_2CH_3$ |
| 1-18 | $CHF_2$ | cPr | —$CH_2C(Me)_2CH_2CH_2CH_3$ |
| 1-19 | $CHF_2$ | cPr | —$CH_2C(Me)_2CH_2CH_3$ |
| 1-20 | $CHF_2$ | cPr | —$CH_2CH_2CH_2C(Me)_3$ |
| 1-21 | $CHF_2$ | cPr | —$CH_2CH_2CH_2CH_2CH_2CH_2CH_3$ |
| 1-22 | $CHF_2$ | cPr | —$CH_2CH_2CH_2CH(Et)_2$ |
| 1-23 | $CHF_2$ | cPr | —$CH_2C(Me)_2CH_2CH_2CH_2CH_3$ |
| 1-24 | $CHF_2$ | cPr | —$CH_2CH_2C(Me)_2CH_2CH_2CH_3$ |
| 1-25 | $CHF_2$ | cPr | —$CH_2CH_2C(Me)_2CH_2CH_3$ |
| 1-26 | $CHF_2$ | cPr | —$CH_2CH_2CH_2CH_2C(Me)_3$ |
| 1-27 | $CHF_2$ | cPr | —$CH_2CH(Pr)_2$ |
| 1-28 | $CHF_2$ | cPr | —$CH_2C(Me)_2C(Me)_3$ |
| 1-29 | $CHF_2$ | cPr | —$CH_2CF_3$ |
| 1-30 | $CHF_2$ | cPr | —$CH_2CH_2CF_3$ |
| 1-31 | $CHF_2$ | cPr | —$CH_2CH_2Cl$ |
| 1-32 | $CHF_2$ | cPr | —$CH_2OH$ |
| 1-33 | $CHF_2$ | cPr | —$CH_2CH_2OH$ |
| 1-34 | $CHF_2$ | cPr | —$CH_2CH_2CH_2OH$ |
| 1-35 | $CHF_2$ | cPr | —$CH_2CH_2CH_2CH_2OH$ |
| 1-36 | $CHF_2$ | cPr | —$CH_2CH_2CH_2CH_2CH_2OH$ |
| 1-37 | $CHF_2$ | cPr | —$CH_2CH_2CH_2CH_2CH_2CH_2OH$ |
| 1-38 | $CHF_2$ | cPr | —$CH_2C(OH)(Me)_2$ |
| 1-39 | $CHF_2$ | cPr | —$CH_2CH_2C(OH)(Me)_2$ |
| 1-40 | $CHF_2$ | cPr | —$CH_2CH_2CH_2C(OH)(Me)_2$ |
| 1-41 | $CHF_2$ | cPr | —$CH_2C(OH)(Et)_2$ |
| 1-42 | $CHF_2$ | cPr | —$CH_2C(CN)(Me)_2$ |
| 1-43 | $CHF_2$ | cPr | —$CH_2CH_2C(CN)(Me)_2$ |
| 1-44 | $CHF_2$ | cPr | —$CH_2CH_2CH_2C(CN)(Me)_2$ |
| 1-45 | $CHF_2$ | cPr | —$CH_2C(CN)(Et)_2$ |
| 1-46 | $CHF_2$ | cPr | —$CH_2C(COOH)(Me)_2$ |
| 1-47 | $CHF_2$ | cPr | —$CH_2CH_2C(COOH)(Me)_2$ |
| 1-48 | $CHF_2$ | cPr | —$CH_2CH_2CH_2C(COOH)(Me)_2$ |
| 1-49 | $CHF_2$ | cPr | —$CH_2C(COOH)(Et)_2$ |
| 1-50 | $CHF_2$ | cPr | —$CH_2OMe$ |
| 1-51 | $CHF_2$ | cPr | —$CH_2CH_2OMe$ |
| 1-52 | $CHF_2$ | cPr | —$CH_2CH_2CH_2OMe$ |
| 1-53 | $CHF_2$ | cPr | —$CH_2CH_2CH_2CH_2OMe$ |
| 1-54 | $CHF_2$ | cPr | —$CH_2CH_2CH_2CH_2CH_2OMe$ |
| 1-55 | $CHF_2$ | cPr | —$CH_2CH_2CH_2CH_2CH_2CH_2OMe$ |
| 1-56 | $CHF_2$ | cPr | —$CH_2C(OMe)(Me)_2$ |
| 1-57 | $CHF_2$ | cPr | —$CH_2CH_2C(OMe)(Me)_2$ |
| 1-58 | $CHF_2$ | cPr | —$CH_2CH_2CH_2C(OMe)(Me)_2$ |
| 1-59 | $CHF_2$ | cPr | —$CH_2C(OMe)(Et)_2$ |
| 1-60 | $CHF_2$ | cPr | —$CH_2OEt$ |
| 1-61 | $CHF_2$ | cPr | —$CH_2CH_2OEt$ |
| 1-62 | $CHF_2$ | cPr | —$CH_2CH_2CH_2OEt$ |
| 1-63 | $CHF_2$ | cPr | —$CH_2CH_2CH_2CH_2OEt$ |
| 1-64 | $CHF_2$ | cPr | —$CH_2CH_2CH_2CH_2CH_2OEt$ |
| 1-65 | $CHF_2$ | cPr | —$CH_2CH_2CH_2CH_2CH_2CH_2OEt$ |
| 1-66 | $CHF_2$ | cPr | —$CH_2C(OEt)(Me)_2$ |
| 1-67 | $CHF_2$ | cPr | —$CH_2CH_2C(OEt)(Me)_2$ |
| 1-68 | $CHF_2$ | cPr | —$CH_2CH_2CH_2C(OEt)(Me)_2$ |
| 1-69 | $CHF_2$ | cPr | —$CH_2C(OEt)(Et)_2$ |
| 1-70 | $CHF_2$ | cPr | —$CH_2OPr$ |
| 1-71 | $CHF_2$ | cPr | —$CH_2CH_2OPr$ |
| 1-72 | $CHF_2$ | cPr | —$CH_2CH_2CH_2OPr$ |
| 1-73 | $CHF_2$ | cPr | —$CH_2CH_2CH_2CH_2OPr$ |
| 1-74 | $CHF_2$ | cPr | —$CH_2C(OPr)(Me)_2$ |
| 1-75 | $CHF_2$ | cPr | —$CH_2CH_2C(OPr)(Me)_2$ |
| 1-76 | $CHF_2$ | cPr | —$CH_2CH_2CH_2C(OPr)(Me)_2$ |
| 1-77 | $CHF_2$ | cPr | —$CH_2C(OPr)(Et)_2$ |
| 1-78 | $CHF_2$ | cPr | —$CH_2OBu$ |
| 1-79 | $CHF_2$ | cPr | —$CH_2CH_2OBu$ |
| 1-80 | $CHF_2$ | cPr | —$CH_2CH_2CH_2OBu$ |

TABLE 1-continued

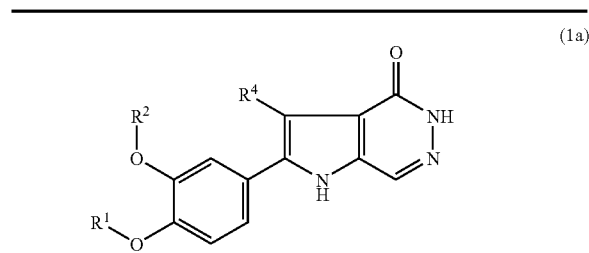

(1a)

| Compound No. | $R^1$ | $R^2$ | $R^4$ |
|---|---|---|---|
| 1-81 | $CHF_2$ | cPr | —$CH_2CH_2CH_2CH_2OBu$ |
| 1-82 | $CHF_2$ | cPr | —$CH_2C(OBu)(Me)_2$ |
| 1-83 | $CHF_2$ | cPr | —$CH_2CH_2C(OBu)(Me)_2$ |
| 1-84 | $CHF_2$ | cPr | —$CH_2CH_2CH_2C(OBu)(Me)_2$ |
| 1-85 | $CHF_2$ | cPr | —$CH_2C(OBu)(Et)_2$ |
| 1-86 | $CHF_2$ | cPr | —$CH_2OiPr$ |
| 1-87 | $CHF_2$ | cPr | —$CH_2CH_2OiPr$ |
| 1-88 | $CHF_2$ | cPr | —$CH_2CH_2CH_2OiPr$ |
| 1-89 | $CHF_2$ | cPr | —$CH_2CH_2CH_2CH_2OiPr$ |
| 1-90 | $CHF_2$ | cPr | —$CH_2OCH_2CH_2F$ |
| 1-91 | $CHF_2$ | cPr | —$CH_2CH_2OCH_2CH_2F$ |
| 1-92 | $CHF_2$ | cPr | —$CH_2CH_2CH_2OCH_2CH_2F$ |
| 1-93 | $CHF_2$ | cPr | —$CH_2CH_2CH_2CH_2OCH_2CH_2F$ |
| 1-94 | $CHF_2$ | cPr | —$CH_2CH_2CH_2CH_2CH_2OCH_2CH_2F$ |
| 1-95 | $CHF_2$ | cPr | —$CH_2CH_2CH_2CH_2CH_2CH_2OCH_2CH_2F$ |
| 1-96 | $CHF_2$ | cPr | —$CH_2C(Me)_2OCH_2CH_2F$ |
| 1-97 | $CHF_2$ | cPr | —$CH_2CH_2C(Me)_2OCH_2CH_2F$ |
| 1-98 | $CHF_2$ | cPr | —$CH_2CH_2CH_2C(Me)_2OCH_2CH_2F$ |
| 1-99 | $CHF_2$ | cPr | —$CH_2C(Et)_2OCH_2CH_2F$ |
| 1-100 | $CHF_2$ | cPr | —$CH_2OCH_2CF_3$ |
| 1-101 | $CHF_2$ | cPr | —$CH_2OcPr$ |
| 1-102 | $CHF_2$ | cPr | —$CH_2OcBu$ |
| 1-103 | $CHF_2$ | cPr | —$CH_2CH_2OcBu$ |
| 1-104 | $CHF_2$ | cPr | —$CH_2CH_2CH_2OcBu$ |
| 1-105 | $CHF_2$ | cPr | —$CH_2CH_2CH_2CH_2OcBu$ |
| 1-106 | $CHF_2$ | cPr | —$CH_2CH_2CH_2CH_2CH_2OcBu$ |
| 1-107 | $CHF_2$ | cPr | —$CH_2CH_2CH_2CH_2CH_2CH_2OcBu$ |
| 1-108 | $CHF_2$ | cPr | —$CH_2C(Me)_2OcBu$ |
| 1-109 | $CHF_2$ | cPr | —$CH_2CH_2C(Me)_2OcBu$ |
| 1-110 | $CHF_2$ | cPr | —$CH_2CH_2CH_2C(Me)_2OcBu$ |
| 1-111 | $CHF_2$ | cPr | —$CH_2C(Et)_2OcBu$ |
| 1-112 | $CHF_2$ | cPr | —$CH_2OCH_2cPr$ |
| 1-113 | $CHF_2$ | cPr | —$CH_2CH_2OCH_2cPr$ |
| 1-114 | $CHF_2$ | cPr | —$CH_2CH_2CH_2OCH_2cPr$ |
| 1-115 | $CHF_2$ | cPr | —$CH_2CH_2CH_2CH_2OCH_2cPr$ |
| 1-116 | $CHF_2$ | cPr | —$CH_2CH_2CH_2CH_2CH_2OCH_2cPr$ |
| 1-117 | $CHF_2$ | cPr | —$CH_2CH_2CH_2CH_2CH_2CH_2OCH_2cPr$ |
| 1-118 | $CHF_2$ | cPr | —$CH_2C(Me)_2OCH_2cPr$ |
| 1-119 | $CHF_2$ | cPr | —$CH_2CH_2C(Me)_2OCH_2cPr$ |
| 1-120 | $CHF_2$ | cPr | —$CH_2CH_2CH_2C(Me)_2OCH_2cPr$ |
| 1-121 | $CHF_2$ | cPr | —$CH_2C(Et)_2OCH_2cPr$ |
| 1-122 | $CHF_2$ | cPr | —$CH_2OCH_2cBu$ |
| 1-123 | $CHF_2$ | cPr | —$CH_2COOMe$ |
| 1-124 | $CHF_2$ | cPr | —$CH_2CH_2COOMe$ |
| 1-125 | $CHF_2$ | cPr | —$CH_2CH_2CH_2COOMe$ |
| 1-126 | $CHF_2$ | cPr | —$CH_2CH_2CH_2CH_2COOMe$ |
| 1-127 | $CHF_2$ | cPr | —$CH_2C(COOMe)(Me)_2$ |
| 1-128 | $CHF_2$ | cPr | —$CH_2CH_2C(COOMe)(Me)_2$ |
| 1-129 | $CHF_2$ | cPr | —$CH_2CH_2CH_2C(COOMe)(Me)_2$ |
| 1-130 | $CHF_2$ | cPr | —$CH_2C(COOMe)(Et)_2$ |
| 1-131 | $CHF_2$ | cPr | —$CH_2COOEt$ |
| 1-132 | $CHF_2$ | cPr | —$CH_2CH_2COOEt$ |
| 1-133 | $CHF_2$ | cPr | —$CH_2CH_2CH_2COOEt$ |
| 1-134 | $CHF_2$ | cPr | —$CH_2CH_2CH_2CH_2COOEt$ |
| 1-135 | $CHF_2$ | cPr | —$CH_2C(COOEt)(Me)_2$ |
| 1-136 | $CHF_2$ | cPr | —$CH_2CH_2C(COOEt)(Me)_2$ |
| 1-137 | $CHF_2$ | cPr | —$CH_2CH_2CH_2C(COOEt)(Me)_2$ |
| 1-138 | $CHF_2$ | cPr | —$CH_2C(COOEt)(Et)_2$ |
| 1-139 | $CHF_2$ | cPr | —$CH_2COOPr$ |
| 1-140 | $CHF_2$ | cPr | —$CH_2CH_2COOPr$ |
| 1-141 | $CHF_2$ | cPr | —$CH_2CH_2CH_2COOPr$ |
| 1-142 | $CHF_2$ | cPr | —$CH_2CH_2CH_2CH_2COOPr$ |
| 1-143 | $CHF_2$ | cPr | —$CH_2C(COOPr)(Me)_2$ |
| 1-144 | $CHF_2$ | cPr | —$CH_2CH_2C(COOPr)(Me)_2$ |
| 1-145 | $CHF_2$ | cPr | —$CH_2CH_2CH_2C(COOPr)(Me)_2$ |
| 1-146 | $CHF_2$ | cPr | —$CH_2C(COOPr)(Et)_2$ |
| 1-147 | $CHF_2$ | cPr | —$CH_2COOBu$ |
| 1-148 | $CHF_2$ | cPr | —$CH_2CH_2COOBu$ |
| 1-149 | $CHF_2$ | cPr | —$CH_2CH_2CH_2COOBu$ |
| 1-150 | $CHF_2$ | cPr | —$CH_2CH_2CH_2CH_2COOBu$ |
| 1-151 | $CHF_2$ | cPr | —$CH_2C(COOBu)(Me)_2$ |
| 1-152 | $CHF_2$ | cPr | —$CH_2CH_2C(COOBu)(Me)_2$ |
| 1-153 | $CHF_2$ | cPr | —$CH_2CH_2CH_2C(COOBu)(Me)_2$ |
| 1-154 | $CHF_2$ | cPr | —$CH_2C(COOBu)(Et)_2$ |
| 1-155 | $CHF_2$ | cPr | —$CH_2COOiPr$ |
| 1-156 | $CHF_2$ | cPr | —$CH_2CH_2COOiPr$ |
| 1-157 | $CHF_2$ | cPr | —$CH_2CH_2CH_2COOiPr$ |
| 1-158 | $CHF_2$ | cPr | —$CH_2CH_2CH_2CH_2COOiPr$ |
| 1-159 | $CHF_2$ | cPr | —$CH_2C(COOiPr)(Me)_2$ |
| 1-160 | $CHF_2$ | cPr | —$CH_2CH_2C(COOiPr)(Me)_2$ |
| 1-161 | $CHF_2$ | cPr | —$CH_2CH_2CH_2C(COOiPr)(Me)_2$ |
| 1-162 | $CHF_2$ | cPr | —$CH_2C(COOiPr)(Et)_2$ |
| 1-163 | $CHF_2$ | cPr | —$CH_2COOiBu$ |
| 1-164 | $CHF_2$ | cPr | —$CH_2CH_2COOiBu$ |
| 1-165 | $CHF_2$ | cPr | —$CH_2CH_2CH_2COOiBu$ |
| 1-166 | $CHF_2$ | cPr | —$CH_2CH_2CH_2CH_2COOiBu$ |
| 1-167 | $CHF_2$ | cPr | —$CH_2OAc$ |
| 1-168 | $CHF_2$ | cPr | —$CH_2CH_2OAc$ |
| 1-169 | $CHF_2$ | cPr | —$CH_2CH_2CH_2OAc$ |
| 1-170 | $CHF_2$ | cPr | —$CH_2CH_2CH_2CH_2OAc$ |
| 1-171 | $CHF_2$ | cPr | —$CH_2CH_2CH_2CH_2CH_2OAc$ |
| 1-172 | $CHF_2$ | cPr | —$CH_2CH_2CH_2CH_2CH_2CH_2OAc$ |
| 1-173 | $CHF_2$ | cPr | —$CH_2C(OAc)(Me)_2$ |
| 1-174 | $CHF_2$ | cPr | —$CH_2CH_2C(OAc)(Me)_2$ |
| 1-175 | $CHF_2$ | cPr | —$CH_2CH_2CH_2C(OAc)(Me)_2$ |
| 1-176 | $CHF_2$ | cPr | —$CH_2C(OAc)(Et)_2$ |
| 1-177 | $CHF_2$ | cPr | —$CH_2OCOEt$ |
| 1-178 | $CHF_2$ | cPr | —$CH_2CH_2OCOEt$ |
| 1-179 | $CHF_2$ | cPr | —$CH_2CH_2CH_2OCOEt$ |
| 1-180 | $CHF_2$ | cPr | —$CH_2CH_2CH_2CH_2OCOEt$ |
| 1-181 | $CHF_2$ | cPr | —$CH_2CH_2CH_2CH_2CH_2OCOEt$ |
| 1-182 | $CHF_2$ | cPr | —$CH_2Ac$ |
| 1-183 | $CHF_2$ | cPr | —$CH_2CH_2Ac$ |
| 1-184 | $CHF_2$ | cPr | —$CH_2CH_2CH_2Ac$ |
| 1-185 | $CHF_2$ | cPr | —$CH_2CH_2CH_2CH_2Ac$ |
| 1-186 | $CHF_2$ | cPr | —$CH_2CH_2CH_2CH_2CH_2Ac$ |
| 1-187 | $CHF_2$ | cPr | —$CH_2CH_2CH_2CH_2CH_2CH_2Ac$ |
| 1-188 | $CHF_2$ | cPr | —$CH_2C(Ac)(Me)_2$ |
| 1-189 | $CHF_2$ | cPr | —$CH_2CH_2C(Ac)(Me)_2$ |
| 1-190 | $CHF_2$ | cPr | —$CH_2CH_2CH_2C(Ac)(Me)_2$ |
| 1-191 | $CHF_2$ | cPr | —$CH_2C(Ac)(Et)_2$ |
| 1-192 | $CHF_2$ | cPr | —$CH_2COEt$ |
| 1-193 | $CHF_2$ | cPr | —$CH_2CH_2COEt$ |
| 1-194 | $CHF_2$ | cPr | —$CH_2CH_2CH_2COEt$ |
| 1-195 | $CHF_2$ | cPr | —$CH_2CH_2CH_2CH_2COEt$ |
| 1-196 | $CHF_2$ | cPr | —$CH_2CH_2CH_2CH_2CH_2COEt$ |
| 1-197 | $CHF_2$ | cPr | —$CH_2N(Me)_2$ |
| 1-198 | $CHF_2$ | cPr | —$CH_2CH_2N(Me)_2$ |
| 1-199 | $CHF_2$ | cPr | —$CH_2N(Et)_2$ |
| 1-200 | $CHF_2$ | cPr | —$CH_2CH_2N(Et)_2$ |
| 1-201 | $CHF_2$ | cPr | —$CH_2N(Pr)_2$ |
| 1-202 | $CHF_2$ | cPr | —$CH_2CH_2N(Pr)_2$ |
| 1-203 | $CHF_2$ | cPr | —$CH_2N(Bu)_2$ |
| 1-204 | $CHF_2$ | cPr | —$CH_2CH_2N(Bu)_2$ |
| 1-205 | $CHF_2$ | cPr | —$CH_2N(iPr)_2$ |
| 1-206 | $CHF_2$ | cPr | —$CH_2CH_2N(iPr)_2$ |
| 1-207 | $CHF_2$ | cPr | cPr |
| 1-208 | $CHF_2$ | cPr | —$CH_2cPr$ |
| 1-209 | $CHF_2$ | cPr | —$CH_2cPr(1-OH)$ |
| 1-210 | $CHF_2$ | cPr | —$CH_2cBu$ |

TABLE 1-continued (1a)

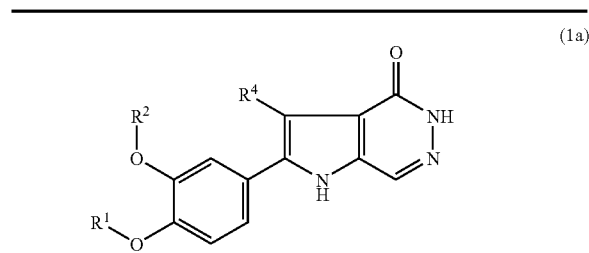

| Compound No. | R¹ | R² | R⁴ |
|---|---|---|---|
| 1-211 | CHF₂ | cPr | —CH₂cBu(1-OH) |
| 1-212 | CHF₂ | cPr | —CH(OH)cPr |
| 1-213 | CHF₂ | cPr | —CH(OH)cPr(1-OH) |
| 1-214 | CHF₂ | cPr | —CH(OH)cBu |
| 1-215 | CHF₂ | cPr | —CH(OH)cBu(1-OH) |
| 1-216 | CHF₂ | cPr | —CH₂CH₂cPr |
| 1-217 | CHF₂ | cPr | —CH₂CH₂cPr(1-OH) |
| 1-218 | CHF₂ | cPr | —CH₂CH₂cBu |
| 1-219 | CHF₂ | cPr | —CH₂CH₂cBu(1-OH) |
| 1-220 | CHF₂ | cPr | —CH₂CH=CH₂ |
| 1-221 | CHF₂ | cPr | —CH₂CH=CHMe |
| 1-222 | CHF₂ | cPr | —CH₂CH=CHEt |
| 1-223 | CHF₂ | cPr | —CH₂CH=CHPr |
| 1-224 | CHF₂ | cPr | —CH₂C(Me)=CH₂ |
| 1-225 | CHF₂ | cPr | —CH₂C(Me)=CHMe |
| 1-226 | CHF₂ | cPr | —CH₂CH=C(Me)₂ |
| 1-227 | CHF₂ | cPr | —CH₂C(Me)=CHEt |
| 1-228 | CHF₂ | cPr | —CH₂CH=C(Me)Et |
| 1-229 | CHF₂ | cPr | —CH₂CH=CHCH(Me)₂ |
| 1-230 | CHF₂ | cPr | —CH₂C(Me)=C(Me)₂ |
| 1-231 | CHF₂ | cPr | —C≡CH |
| 1-232 | CHF₂ | cPr | —CH₂C≡CH |
| 1-233 | CHF₂ | cPr | —CH₂C≡CMe |
| 1-234 | CHF₂ | cPr | —CH₂C≡CEt |
| 1-235 | CHF₂ | cPr | —CH₂C≡CPr |
| 1-236 | CHF₂ | cPr | —CH₂C≡CCH(Me)₂ |
| 1-237 | CHF₂ | cPr | —CH(OH)CH=CH₂ |
| 1-238 | CHF₂ | cPr | —CH(OH)CH=CHMe |
| 1-239 | CHF₂ | cPr | —CH(OH)CH=CHEt |
| 1-240 | CHF₂ | cPr | —CH(OH)CH=CHPr |
| 1-241 | CHF₂ | cPr | —CH(OH)C≡CH |
| 1-242 | CHF₂ | cPr | —CH(OH)C≡CMe |
| 1-243 | CHF₂ | cPr | —CH(OH)C≡CEt |
| 1-244 | CHF₂ | cPr | —CH(OH)C≡CPr |
| 1-245 | CHF₂ | cPr | Ph |
| 1-246 | CHF₂ | cPr | 2-F-Ph |
| 1-247 | CHF₂ | cPr | 3-F-Ph |
| 1-248 | CHF₂ | cPr | 4-F-Ph |
| 1-249 | CHF₂ | cPr | 2,4-diF-Ph |
| 1-250 | CHF₂ | cPr | 2,6-diF-Ph |
| 1-251 | CHF₂ | cPr | 3,4-diF-Ph |
| 1-252 | CHF₂ | cPr | 2-Cl-Ph |
| 1-253 | CHF₂ | cPr | 3-Cl-Ph |
| 1-254 | CHF₂ | cPr | 4-Cl-Ph |
| 1-255 | CHF₂ | cPr | 2,4-diCl-Ph |
| 1-256 | CHF₂ | cPr | 2,6-diCl-Ph |
| 1-257 | CHF₂ | cPr | 3,4-diCl-Ph |
| 1-258 | CHF₂ | cPr | 3-CN-Ph |
| 1-259 | CHF₂ | cPr | 4-CN-Ph |
| 1-260 | CHF₂ | cPr | 3-NO₂-Ph |
| 1-261 | CHF₂ | cPr | 4-NO₂-Ph |
| 1-262 | CHF₂ | cPr | 3-COOH-Ph |
| 1-263 | CHF₂ | cPr | 4-COOH-Ph |
| 1-264 | CHF₂ | cPr | 3-CF₃-Ph |
| 1-265 | CHF₂ | cPr | 4-CF₃-Ph |
| 1-266 | CHF₂ | cPr | 3-C(OH)(Me)₂-Ph |
| 1-267 | CHF₂ | cPr | 4-C(OH)(Me)₂-Ph |
| 1-268 | CHF₂ | cPr | 3-C(OH)(CF₃)₂-Ph |
| 1-269 | CHF₂ | cPr | 4-C(OH)(CF₃)₂-Ph |
| 1-270 | CHF₂ | cPr | 3-C(COOH)(Me)₂-Ph |
| 1-271 | CHF₂ | cPr | 4-C(COOH)(Me)₂-Ph |
| 1-272 | CHF₂ | cPr | 3-OMe-Ph |
| 1-273 | CHF₂ | cPr | 4-OMe-Ph |
| 1-274 | CHF₂ | cPr | 3-OEt-Ph |
| 1-275 | CHF₂ | cPr | 4-OEt-Ph |
| 1-276 | CHF₂ | cPr | 3-COOMe-Ph |
| 1-277 | CHF₂ | cPr | 4-COOMe-Ph |
| 1-278 | CHF₂ | cPr | 3-COOEt-Ph |
| 1-279 | CHF₂ | cPr | 4-COOEt-Ph |
| 1-280 | CHF₂ | cPr | Th-2-yl |
| 1-281 | CHF₂ | cPr | 4-CN—Th-2-yl |
| 1-282 | CHF₂ | cPr | 5-CN—Th-2-yl |
| 1-283 | CHF₂ | cPr | 4-COOH—Th-2-yl |
| 1-284 | CHF₂ | cPr | 5-COOH—Th-2-yl |
| 1-285 | CHF₂ | cPr | 4-Me—Th-2-yl |
| 1-286 | CHF₂ | cPr | 5-Me—Th-2-yl |
| 1-287 | CHF₂ | cPr | 4-CF₃—Th-2-yl |
| 1-288 | CHF₂ | cPr | 5-CF₃—Th-2-yl |
| 1-289 | CHF₂ | cPr | 4-C(OH)(Me)₂—Th-2-yl |
| 1-290 | CHF₂ | cPr | 5-C(OH)(Me)₂—Th-2-yl |
| 1-291 | CHF₂ | cPr | 4-C(OH)(CF₃)₂—Th-2-yl |
| 1-292 | CHF₂ | cPr | 5-C(OH)(CF₃)₂—Th-2-yl |
| 1-293 | CHF₂ | cPr | 4-C(COOH)(Me)₂—Th-2-yl |
| 1-294 | CHF₂ | cPr | 5-C(COOH)(Me)₂—Th-2-yl |
| 1-295 | CHF₂ | cPr | Th-3-yl |
| 1-296 | CHF₂ | cPr | 4-CN—Th-3-yl |
| 1-297 | CHF₂ | cPr | 5-CN—Th-3-yl |
| 1-298 | CHF₂ | cPr | 4-COOH—Th-3-yl |
| 1-299 | CHF₂ | cPr | 5-COOH—Th-3-yl |
| 1-300 | CHF₂ | cPr | 4-Me—Th-3-yl |
| 1-301 | CHF₂ | cPr | 5-Me—Th-3-yl |
| 1-302 | CHF₂ | cPr | 4-CF₃—Th-3-yl |
| 1-303 | CHF₂ | cPr | 5-CF₃—Th-3-yl |
| 1-304 | CHF₂ | cPr | 5-Et—Th-3-yl |
| 1-305 | CHF₂ | cPr | 5-C(OH)(Me)₂—Th-3-yl |
| 1-306 | CHF₂ | cPr | 5-C(OH)(CF₃)₂—Th-3-yl |
| 1-307 | CHF₂ | cPr | 5-C(COCH)(Me)₂—Th-3-yl |
| 1-308 | CHF₂ | cPr | 5-COOMe—Th-3-yl |
| 1-309 | CHF₂ | cPr | Thz-4-yl |
| 1-310 | CHF₂ | cPr | 2-CN-Thz-4-yl |
| 1-311 | CHF₂ | cPr | 2-COOH-Thz-4-yl |
| 1-312 | CHF₂ | cPr | 2-Me-Thz-4-yl |
| 1-313 | CHF₂ | cPr | 2-Et-Thz-4-yl |
| 1-314 | CHF₂ | cPr | 2-Pr-Thz-4-yl |
| 1-315 | CHF₂ | cPr | 2-iPr-Thz-4-yl |
| 1-316 | CHF₂ | cPr | 2-CF₃-Thz-4-yl |
| 1-317 | CHF₂ | cPr | 2-C(OH)(Me)₂-Thz-4-yl |
| 1-318 | CHF₂ | cPr | 2-C(OH)(CF₃)₂-Thz-4-yl |
| 1-319 | CHF₂ | cPr | 2-C(COOH)(Me)₂-Thz-4-yl |
| 1-320 | CHF₂ | cPr | 2-COOMe-Thz-4-yl |
| 1-321 | CHF₂ | cPr | Thz-5-yl |
| 1-322 | CHF₂ | cPr | 2-CN-Thz-5-yl |
| 1-323 | CHF₂ | cPr | 2-COOH-Thz-5-yl |
| 1-324 | CHF₂ | cPr | 2-Me-Thz-5-yl |
| 1-325 | CHF₂ | cPr | 2-Et-Thz-5-yl |
| 1-326 | CHF₂ | cPr | 2-CF₃-Thz-5-yl |
| 1-327 | CHF₂ | cPr | 2-C(OH)(Me)₂-Thz-5-yl |
| 1-328 | CHF₂ | cPr | 2-C(OH)(CF₃)₂-Thz-5-yl |
| 1-329 | CHF₂ | cPr | 2-C(COOH)(Me)₂-Thz-5-yl |
| 1-330 | CHF₂ | cPr | 2-COOMe-Thz-5-yl |
| 1-331 | CHF₂ | cPr | 2-COOEt-Thz-5-yl |
| 1-332 | CHF₂ | cPr | 2-COOPr-Thz-5-yl |
| 1-333 | CHF₂ | cPr | 2-COOiPr-Thz-5-yl |
| 1-334 | CHF₂ | cPr | Pyz-4-yl |
| 1-335 | CHF₂ | cPr | 6-CN-Py-2-yl |
| 1-336 | CHF₂ | cPr | 6-COOH-Py-2-yl |
| 1-337 | CHF₂ | cPr | 6-CF₃-Py-2-yl |
| 1-338 | CHF₂ | cPr | 6-OMe-Py-2-yl |
| 1-339 | CHF₂ | cPr | 6-OEt-Py-2-yl |
| 1-340 | CHF₂ | cPr | 6-COOMe-Py-2-yl |

TABLE 1-continued (1a)

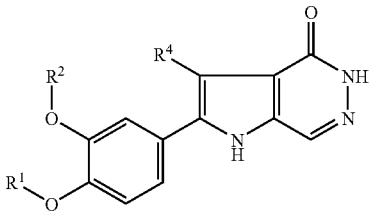

| Compound No. | R¹ | R² | R⁴ |
|---|---|---|---|
| 1-341 | $CHF_2$ | cPr | 6-COOEt-Py-2-yl |
| 1-342 | $CHF_2$ | cPr | 6-C(OH)(Me)₂-Py-2-yl |
| 1-343 | $CHF_2$ | cPr | 6-C(OH)(CF₃)₂-Py-2-yl |
| 1-344 | $CHF_2$ | cPr | 6-C(COOH)(Me)₂-Py-2-yl |
| 1-345 | $CHF_2$ | cPr | 6-CN-Py-3-yl |
| 1-346 | $CHF_2$ | cPr | 6-COOH-Py-3-yl |
| 1-347 | $CHF_2$ | cPr | 6-CF₃-Py-3-yl |
| 1-348 | $CHF_2$ | cPr | 6-OMe-Py-3-yl |
| 1-349 | $CHF_2$ | cPr | 6-OEt-Py-3-yl |
| 1-350 | $CHF_2$ | cPr | 6-COOMe-Py-3-yl |
| 1-351 | $CHF_2$ | cPr | 6-COOEt-Py-3-yl |
| 1-352 | $CHF_2$ | cPr | 6-C(OH)(Me)₂-Py-3-yl |
| 1-353 | $CHF_2$ | cPr | 6-C(OH)(CF₃)₂-Py-3-yl |
| 1-354 | $CHF_2$ | cPr | 6-C(COOH)(Me)₂-Py-3-yl |
| 1-355 | $CHF_2$ | cPr | 2-CN-Py-3-yl |
| 1-356 | $CHF_2$ | cPr | 2-COOH-Py-3-yl |
| 1-357 | $CHF_2$ | cPr | 2-CF₃-Py-3-yl |
| 1-358 | $CHF_2$ | cPr | 2-OMe-Py-3-yl |
| 1-359 | $CHF_2$ | cPr | 2-OEt-Py-3-yl |
| 1-360 | $CHF_2$ | cPr | 2-OPr-Py-3-yl |
| 1-361 | $CHF_2$ | cPr | 2-COOMe-Py-3-yl |
| 1-362 | $CHF_2$ | cPr | 2-COOEt-Py-3-yl |
| 1-363 | $CHF_2$ | cPr | 2-COOPr-Py-3-yl |
| 1-364 | $CHF_2$ | cPr | 2-C(OH)(Me)₂-Py-3-y1 |
| 1-365 | $CHF_2$ | cPr | 2-C(OH)(CF₃)₂-Py-3-yl |
| 1-366 | $CHF_2$ | cPr | 2-C(COOH)(Me)₂-Py-3-yl |
| 1-367 | $CHF_2$ | cPr | 2-CN-Py-4-yl |
| 1-368 | $CHF_2$ | cPr | 2-COOH-Py-4-yl |
| 1-369 | $CHF_2$ | cPr | 2-CF₃-Py-4-yl |
| 1-370 | $CHF_2$ | cPr | 2-OMe-Py-4-y1 |
| 1-371 | $CHF_2$ | cPr | 2-OEt-Py-4-yl |
| 1-372 | $CHF_2$ | cPr | 2-OPr-Py-4-yl |
| 1-373 | $CHF_2$ | cPr | 2-COOMe-Py-4-yl |
| 1-374 | $CHF_2$ | cPr | 2-COOEt-Py-4-yl |
| 1-375 | $CHF_2$ | cPr | 2-C(OH)(Me)₂-Py-4-yl |
| 1-376 | $CHF_2$ | cPr | 2-C(OH)(CF₃)₂-Py-4-yl |
| 1-377 | $CHF_2$ | cPr | 2-C(COOH)(Me)₂-Py-4-yl |
| 1-378 | $CHF_2$ | cPr | Bn |
| 1-379 | $CHF_2$ | cPr | 2-F-Bn |
| 1-380 | $CHF_2$ | cPr | 3-F-Bn |
| 1-381 | $CHF_2$ | cPr | 4-F-Bn |
| 1-382 | $CHF_2$ | cPr | 2,4-diF-Bn |
| 1-383 | $CHF_2$ | cPr | 3,4-diF-Bn |
| 1-384 | $CHF_2$ | cPr | 2-Cl-Bn |
| 1-385 | $CHF_2$ | cPr | 3-Cl-Bn |
| 1-386 | $CHF_2$ | cPr | 4-Cl-Bn |
| 1-387 | $CHF_2$ | cPr | 2,4-diCl-Bn |
| 1-388 | $CHF_2$ | cPr | 3,4-diCl-Bn |
| 1-389 | $CHF_2$ | cPr | 2-CN-Bn |
| 1-390 | $CHF_2$ | cPr | 3-CN-Bn |
| 1-391 | $CHF_2$ | cPr | 4-CN-Bn |
| 1-392 | $CHF_2$ | cPr | 3-NO₂-Bn |
| 1-393 | $CHF_2$ | cPr | 3-COOH-Bn |
| 1-394 | $CHF_2$ | cPr | 4-COOH-Bn |
| 1-395 | $CHF_2$ | cPr | 3-CF₃-Bn |
| 1-396 | $CHF_2$ | cPr | 4-CF₃-Bn |
| 1-397 | $CHF_2$ | cPr | 3-C(OH)(Me)₂-Bn |
| 1-398 | $CHF_2$ | cPr | 4-C(OH)(Me)₂-Bn |
| 1-399 | $CHF_2$ | cPr | 3-C(OH)(CF₃)₂-Bn |
| 1-400 | $CHF_2$ | cPr | 4-C(OH)(CF₃)₂-Bn |
| 1-401 | $CHF_2$ | cPr | 4-C(COOH)(Me)₂-Bn |
| 1-402 | $CHF_2$ | cPr | 3-OMe-Bn |
| 1-403 | $CHF_2$ | cPr | 4-OMe-Bn |
| 1-404 | $CHF_2$ | cPr | 3-COOMe-Bn |
| 1-405 | $CHF_2$ | cPr | 4-COOMe-Bn |

TABLE 1-continued (1a)

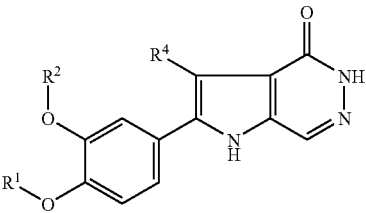

| Compound No. | R¹ | R² | R⁴ |
|---|---|---|---|
| 1-406 | $CHF_2$ | cPr | —CH₂(Th-2-yl) |
| 1-407 | $CHF_2$ | cPr | —CH₂(5-CN—Th-2-yl) |
| 1-408 | $CHF_2$ | cPr | —CH₂(5-COOH—Th-2-yl) |
| 1-409 | $CHF_2$ | cPr | —CH₂(5-Me—Th-2-yl) |
| 1-410 | $CHF_2$ | cPr | —CH₂(5-CF₃—Th-2-yl) |
| 1-411 | $CHF_2$ | cPr | —CH₂(5-C(OH)(Me)₂—Th-2-yl) |
| 1-412 | $CHF_2$ | cPr | —CH₂(5-C(OH)(CF₃)₂—Th-2-yl) |
| 1-413 | $CHF_2$ | cPr | —CH₂(4-C(COOH)(Me)₂—Th-2-yl) |
| 1-414 | $CHF_2$ | cPr | —CH₂(Th-3-yl) |
| 1-415 | $CHF_2$ | cPr | —CH₂(5-CN—Th-3-yl) |
| 1-416 | $CHF_2$ | cPr | —CH₂(5-COOH—Th-3-yl) |
| 1-417 | $CHF_2$ | cPr | —CH₂(5-Me—Th-3-yl) |
| 1-418 | $CHF_2$ | cPr | —CH₂(5-CF₃—Th-3-yl) |
| 1-419 | $CHF_2$ | cPr | —CH₂(5-C(OH)(Me)₂—Th-3-yl) |
| 1-420 | $CHF_2$ | cPr | —CH₂(5-C(OH)(CF₃)₂—Th-3-yl) |
| 1-421 | $CHF_2$ | cPr | —CH₂(Thz-4-yl) |
| 1-422 | $CHF_2$ | cPr | —CH₂(2-CN-Thz-4-yl) |
| 1-423 | $CHF_2$ | cPr | —CH₂(2-COOH-Thz-4-yl) |
| 1-424 | $CHF_2$ | cPr | —CH₂(2-Me-Thz-4-yl) |
| 1-425 | $CHF_2$ | cPr | —CH₂(2-CF₃-Thz-4-yl) |
| 1-426 | $CHF_2$ | cPr | —CH₂(2-C(OH)(Me)₂-Thz-4-yl) |
| 1-427 | $CHF_2$ | cPr | —CH₂(2-C(OH)(CF₃)₂-Thz-4-yl) |
| 1-428 | $CHF_2$ | cPr | —CH₂(Thz-5-yl) |
| 1-429 | $CHF_2$ | cPr | —CH₂(2-CN-Thz-5-yl) |
| 1-430 | $CHF_2$ | cPr | —CH₂(2-COOH-Thz-5-yl) |
| 1-431 | $CHF_2$ | cPr | —CH₂(2-Me-Thz-5-yl) |
| 1-432 | $CHF_2$ | cPr | —CH₂(2-CF₃-Thz-5-yl) |
| 1-433 | $CHF_2$ | cPr | —CH₂(2-C(OH)(Me)₂-Thz-5-yl) |
| 1-434 | $CHF_2$ | cPr | —CH₂(2-C(OH)(CF₃)₂-Thz-5-yl) |
| 1-435 | $CHF_2$ | cPr | —CH₂(Pyz-4-yl) |
| 1-436 | $CHF_2$ | cPr | —CH₂(6-CN-Py-2-yl) |
| 1-437 | $CHF_2$ | cPr | —CH₂(6-COOH-Py-2-yl) |
| 1-438 | $CHF_2$ | cPr | —CH₂(6-CF₃-Py-2-yl) |
| 1-439 | $CHF_2$ | cPr | —CH₂(6-OMe-Py-2-yl) |
| 1-440 | $CHF_2$ | cPr | —CH₂(6-C(OH)(Me)₂-Py-2-yl) |
| 1-441 | $CHF_2$ | cPr | —CH₂(6-C(OH)(CF₃)₂-Py-2-yl) |
| 1-442 | $CHF_2$ | cPr | —CH₂(6-CN-Py-3-yl) |
| 1-443 | $CHF_2$ | cPr | —CH₂(6-COOH-Py-3-yl) |
| 1-444 | $CHF_2$ | cPr | —CH₂(6-CF₃-Py-3-yl) |
| 1-445 | $CHF_2$ | cPr | —CH₂(6-OMe-Py-3-yl) |
| 1-446 | $CHF_2$ | cPr | —CH₂(6-C(OH)(Me)₂-Py-3-yl) |
| 1-447 | $CHF_2$ | cPr | —CH₂(6-C(OH)(CF₃)₂-Py-3-yl) |
| 1-448 | $CHF_2$ | cPr | —CH₂(2-CN-Py-3-yl) |
| 1-449 | $CHF_2$ | cPr | —CH₂(2-COOH-Py-3-yl) |
| 1-450 | $CHF_2$ | cPr | —CH₂(2-CF₃-Py-3-yl) |
| 1-451 | $CHF_2$ | cPr | —CH₂(2-OMe-Py-3-yl) |
| 1-452 | $CHF_2$ | cPr | —CH₂(2-C(OH)(Me)₂-Py-3-yl) |
| 1-453 | $CHF_2$ | cPr | —CH₂(2-C(OH)(CF₃)₂-Py-3-yl) |
| 1-454 | $CHF_2$ | cPr | —CH₂(2-CN-Py-4-yl) |
| 1-455 | $CHF_2$ | cPr | —CH₂(2-COOH-Py-4-yl) |
| 1-456 | $CHF_2$ | cPr | —CH₂(2-CF₃-Py-4-yl) |
| 1-457 | $CHF_2$ | cPr | —CH₂(2-OMe-Py-4-yl) |
| 1-458 | $CHF_2$ | cPr | —CH₂(2-C(OH)(Me)₂-Py-4-yl) |
| 1-459 | $CHF_2$ | cPr | —CH₂(2-C(OH)(CF₃)₂-Py-4-yl) |
| 1-460 | $CHF_2$ | cPr | —CH₂CH₂Ph |
| 1-461 | $CHF_2$ | cPr | —CH₂CH₂(2-F-Ph) |
| 1-462 | $CHF_2$ | cPr | —CH₂CH₂(3-F-Ph) |
| 1-463 | $CHF_2$ | cPr | —CH₂CH₂(4-F-Ph) |
| 1-464 | $CHF_2$ | cPr | —CH₂CH₂(3-Cl-Ph) |
| 1-465 | $CHF_2$ | cPr | —CH₂CH₂(3-CN-Ph) |
| 1-466 | $CHF_2$ | cPr | —CH₂CH₂(3-COOH-Ph) |
| 1-467 | $CHF_2$ | cPr | —CH₂CH₂(3-OMe-Ph) |
| 1-468 | $CHF_2$ | cPr | —CH₂CH₂(Th-2-yl) |
| 1-469 | $CHF_2$ | cPr | —CH₂CH₂(Th-3-yl) |
| 1-470 | $CHF_2$ | cPr | —CH₂CH₂(6-CN-Py-2-yl) |

TABLE 1-continued

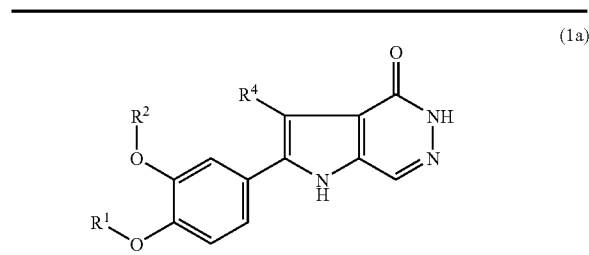

(1a)

| Compound No. | R¹ | R² | R⁴ |
|---|---|---|---|
| 1-471 | CHF₂ | cPr | —CH₂CH₂(6-OMe-Py-2-yl) |
| 1-472 | CHF₂ | cPr | —CH₂CH₂(6-CN-Py-3-yl) |
| 1-473 | CHF₂ | cPr | —CH₂CH₂(6-OMe-Py-3-yl) |
| 1-474 | CHF₂ | cPr | —CH₂CH₂(2-CN-Py-3-yl) |
| 1-475 | CHF₂ | cPr | —CH₂CH₂(2-OMe-Py-3-yl) |
| 1-476 | CHF₂ | cPr | —CH(OH)Ph |
| 1-477 | CHF₂ | cPr | —CH(OH)(2-F-Ph) |
| 1-478 | CHF₂ | cPr | —CH(OH)(3-F-Ph) |
| 1-479 | CHF₂ | cPr | —CH(OH)(4-F-Ph) |
| 1-480 | CHF₂ | cPr | —CH(OH)(3,4-diF-Ph) |
| 1-481 | CHF₂ | cPr | —CH(OH)(Th-2-yl) |
| 1-482 | CHF₂ | CH₂cPr | H |
| 1-483 | CHF₂ | CH₂cPr | Cl |
| 1-484 | CHF₂ | CH₂cPr | Br |
| 1-485 | CHF₂ | CH₂cPr | Me |
| 1-486 | CHF₂ | CH₂cPr | Et |
| 1-487 | CHF₂ | CH₂cPr | Pr |
| 1-488 | CHF₂ | CH₂cPr | iPr |
| 1-489 | CHF₂ | CH₂cPr | Bu |
| 1-490 | CHF₂ | CH₂cPr | iBu |
| 1-491 | CHF₂ | CH₂cPr | Pent |
| 1-492 | CHF₂ | CH₂cPr | —CH₂CH₂CH(Me)₂ |
| 1-493 | CHF₂ | CH₂cPr | —CH₂CH₂CH₂CH₂CH₂CH₃ |
| 1-494 | CHF₂ | CH₂cPr | —CH₂C(Me)₂CH₂CH₃ |
| 1-495 | CHF₂ | CH₂cPr | —CH₂CH₂C(Me)₃ |
| 1-496 | CHF₂ | CH₂cPr | —CH₂CF₃ |
| 1-497 | CHF₂ | CH₂cPr | —CH₂CH₂CF₃ |
| 1-498 | CHF₂ | CH₂cPr | —CH₂CH₂Cl |
| 1-499 | CHF₂ | CH₂cPr | —CH₂OH |
| 1-500 | CHF₂ | CH₂cPr | —CH₂C(OH)(Me)₂ |
| 1-501 | CHF₂ | CH₂cPr | —CH₂CH₂C(OH)(Me)₂ |
| 1-502 | CHF₂ | CH₂cPr | —CH₂CH₂CH₂C(OH)(Me)₂ |
| 1-503 | CHF₂ | CH₂cPr | —CH₂C(OH)(Et)₂ |
| 1-504 | CHF₂ | CH₂cPr | —CH₂C(CN)(Me)₂ |
| 1-505 | CHF₂ | CH₂cPr | —CH₂CH₂C(CN)(Me)₂ |
| 1-506 | CHF₂ | CH₂cPr | —CH₂C(COOH)(Me)₂ |
| 1-507 | CHF₂ | CH₂cPr | —CH₂CH₂C(COOH)(Me)₂ |
| 1-508 | CHF₂ | CH₂cPr | —CH₂CH₂CH₂C(COOH)(Me)₂ |
| 1-509 | CHF₂ | CH₂cPr | —CH₂OMe |
| 1-510 | CHF₂ | CH₂cPr | —CH₂CH₂OMe |
| 1-511 | CHF₂ | CH₂cPr | —CH₂OEt |
| 1-512 | CHF₂ | CH₂cPr | —CH₂CH₂OEt |
| 1-513 | CHF₂ | CH₂cPr | —CH₂OiPr |
| 1-514 | CHF₂ | CH₂cPr | —CH₂CH₂OiPr |
| 1-515 | CHF₂ | CH₂cPr | —CH₂OCH₂CH₂F |
| 1-516 | CHF₂ | CH₂cPr | —CH₂OcBu |
| 1-517 | CHF₂ | CH₂cPr | —CH₂OCH₂cPr |
| 1-518 | CHF₂ | CH₂cPr | —CH₂N(Me)₂ |
| 1-519 | CHF₂ | CH₂cPr | cPr |
| 1-520 | CHF₂ | CH₂cPr | —CH₂cPr |
| 1-521 | CHF₂ | CH₂cPr | —CH₂cPr(1-OH) |
| 1-522 | CHF₂ | CH₂cPr | —CH₂cBu |
| 1-523 | CHF₂ | CH₂cPr | —CH₂cBu(1-OH) |
| 1-524 | CHF₂ | CH₂cPr | —CH(OH)cPr |
| 1-525 | CHF₂ | CH₂cPr | —CH(OH)cPr(1-OH) |
| 1-526 | CHF₂ | CH₂cPr | —CH(OH)cBu |
| 1-527 | CHF₂ | CH₂cPr | —CH(OH)cBu(1-OH) |
| 1-528 | CHF₂ | CH₂cPr | —CH₂CH₂cPr |
| 1-529 | CHF₂ | CH₂cPr | —CH₂CH₂cPr(1-OH) |
| 1-530 | CHF₂ | CH₂cPr | —CH₂CH₂cBu |
| 1-531 | CHF₂ | CH₂cPr | —CH₂CH₂cBu(1-OH) |
| 1-532 | CHF₂ | CH₂cPr | —CH₂CH=CH₂ |
| 1-533 | CHF₂ | CH₂cPr | —CH₂CH=CHMe |
| 1-534 | CHF₂ | CH₂cPr | —CH₂C(Me)=CH₂ |
| 1-535 | CHF₂ | CH₂cPr | —CH₂C(Me)=CHMe |
| 1-536 | CHF₂ | CH₂cPr | —CH₂CH=C(Me)₂ |
| 1-537 | CHF₂ | CH₂cPr | —CH₂C(Me)=C(Me)₂ |
| 1-538 | CHF₂ | CH₂cPr | —C≡CH |
| 1-539 | CHF₂ | CH₂cPr | —CH₂C≡CH |
| 1-540 | CHF₂ | CH₂cPr | —CH₂C≡CMe |
| 1-541 | CHF₂ | CH₂cPr | —CH(OH)CH=CH₂ |
| 1-542 | CHF₂ | CH₂cPr | —CH(OH)CH=CHMe |
| 1-543 | CHF₂ | CH₂cPr | —CH(OH)C≡CH |
| 1-544 | CHF₂ | CH₂cPr | —CH(OH)C≡CMe |
| 1-545 | CHF₂ | CH₂cPr | Ph |
| 1-546 | CHF₂ | CH₂cPr | 2-F-Ph |
| 1-547 | CHF₂ | CH₂cPr | 4-F-Ph |
| 1-548 | CHF₂ | CH₂cPr | 2,4-diF-Ph |
| 1-549 | CHF₂ | CH₂cPr | 2-Cl-Ph |
| 1-550 | CHF₂ | CH₂cPr | 4-Cl-Ph |
| 1-551 | CHF₂ | CH₂cPr | 4-CN-Ph |
| 1-552 | CHF₂ | CH₂cPr | 4-NO₂-Ph |
| 1-553 | CHF₂ | CH₂cPr | 4-COOH-Ph |
| 1-554 | CHF₂ | CH₂cPr | 4-CF₃-Ph |
| 1-555 | CHF₂ | CH₂cPr | 3-OMe-Ph |
| 1-556 | CHF₂ | CH₂cPr | 4-OMe-Ph |
| 1-557 | CHF₂ | CH₂cPr | 4-COOMe-Ph |
| 1-558 | CHF₂ | CH₂cPr | Th-2-yl |
| 1-559 | CHF₂ | CH₂cPr | 5-CN-Th-2-yl |
| 1-560 | CHF₂ | CH₂cPr | 5-COOH-Th-2-yl |
| 1-561 | CHF₂ | CH₂cPr | 5-Me-Th-2-yl |
| 1-562 | CHF₂ | CH₂cPr | 5-CF₃-Th-2-yl |
| 1-563 | CHF₂ | CH₂cPr | Th-3-yl |
| 1-564 | CHF₂ | CH₂cPr | 5-CN-Th-3-yl |
| 1-565 | CHF₂ | CH₂cPr | 5-COOH-Th-3-yl |
| 1-566 | CHF₂ | CH₂cPr | 5-Me-Th-3-yl |
| 1-567 | CHF₂ | CH₂cPr | 5-CF₃-Th-3-yl |
| 1-568 | CHF₂ | CH₂cPr | Thz-4-yl |
| 1-569 | CHF₂ | CH₂cPr | 2-CN-Thz-4-yl |
| 1-570 | CHF₂ | CH₂cPr | 2-COOH-Thz-4-yl |
| 1-571 | CHF₂ | CH₂cPr | 2-Me-Thz-4-yl |
| 1-572 | CHF₂ | CH₂cPr | 2-CF₃-Thz-4-y1 |
| 1-573 | CHF₂ | CH₂cPr | 2-C(OH)(Me)₂-Thz-4-yl |
| 1-574 | CHF₂ | CH₂cPr | 2-C(OH)(CF₃)₂-Thz-4-yl |
| 1-575 | CHF₂ | CH₂cPr | Thz-5-yl |
| 1-576 | CHF₂ | CH₂cPr | 2-CN-Thz-5-yl |
| 1-577 | CHF₂ | CH₂cPr | 2-COOH-Thz-5-yl |
| 1-578 | CHF₂ | CH₂cPr | 2-Me-Thz-5-yl |
| 1-579 | CHF₂ | CH₂cPr | 2-CF₃-Thz-5-yl |
| 1-580 | CHF₂ | CH₂cPr | 2-C(OH)(Me)₂-Thz-5-yl |
| 1-581 | CHF₂ | CH₂cPr | 2-C(OH)(CF₃)₂-Thz-5-yl |
| 1-582 | CHF₂ | CH₂cPr | Pyz-4-yl |
| 1-583 | CHF₂ | CH₂cPr | 6-CN-Py-2-yl |
| 1-584 | CHF₂ | CH₂cPr | 6-COOH-Py-2-yl |
| 1-585 | CHF₂ | CH₂cPr | 6-CF₃-Py-2-yl |
| 1-586 | CHF₂ | CH₂cPr | 6-OMe-Py-2-yl |
| 1-587 | CHF₂ | CH₂cPr | 6-C(OH)(Me)₂-Py-2-yl |
| 1-588 | CHF₂ | CH₂cPr | 6-C(OH)(CF₃)₂-Py-2-yl |
| 1-589 | CHF₂ | CH₂cPr | 6-CN-Py-3-yl |
| 1-590 | CHF₂ | CH₂cPr | 6-COOH-Py-3-yl |
| 1-591 | CHF₂ | CH₂cPr | 6-CF₃-Py-3-yl |
| 1-592 | CHF₂ | CH₂cPr | 6-OMe-Py-3-yl |
| 1-593 | CHF₂ | CH₂cPr | 6-C(OH)(Me)₂-Py-3-yl |
| 1-594 | CHF₂ | CH₂cPr | 6-C(OH)(CF₃)₂-Py-3-yl |
| 1-595 | CHF₂ | CH₂cPr | 2-CN-Py-4-yl |
| 1-596 | CHF₂ | CH₂cPr | 2-COOH-Py-4-yl |
| 1-597 | CHF₂ | CH₂cPr | 2-CF₃-Py-4-yl |
| 1-598 | CHF₂ | CH₂cPr | 2-OMe-Py-4-yl |
| 1-599 | CHF₂ | CH₂cPr | 2-C(OH)(Me)₂-Py-4-yl |
| 1-600 | CHF₂ | CH₂cPr | 2-C(OH)(CF₃)₂-Py-4-yl |

TABLE 1-continued

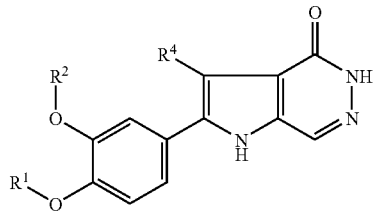

(1a)

| Compound No. | R¹ | R² | R⁴ |
|---|---|---|---|
| 1-601 | CHF₂ | CH₂cPr | Bn |
| 1-602 | CHF₂ | CH₂cPr | 2-F-Bn |
| 1-603 | CHF₂ | CH₂cPr | 3-F-Bn |
| 1-604 | CHF₂ | CH₂cPr | 4-F-Bn |
| 1-605 | CHF₂ | CH₂cPr | 2,4-diF-Bn |
| 1-606 | CHF₂ | CH₂cPr | 3,4-diF-Bn |
| 1-607 | CHF₂ | CH₂cPr | 2-Cl-Bn |
| 1-608 | CHF₂ | CH₂cPr | 3-Cl-Bn |
| 1-609 | CHF₂ | CH₂cPr | 2-CN-Bn |
| 1-610 | CHF₂ | CH₂cPr | 3-CN-Bn |
| 1-611 | CHF₂ | CH₂cPr | 3-COOH-Bn |
| 1-612 | CHF₂ | CH₂cPr | 4-COOH-Bn |
| 1-613 | CHF₂ | CH₂cPr | 3-CF₃-Bn |
| 1-614 | CHF₂ | CH₂cPr | 4-OMe-Bn |
| 1-615 | CHF₂ | CH₂cPr | 3-COOMe-Bn |
| 1-616 | CHF₂ | CH₂cPr | —CH₂(Th-2-yl) |
| 1-617 | CHF₂ | CH₂cPr | —CH₂(5-CN—Th-2-yl) |
| 1-618 | CHF₂ | CH₂cPr | —CH₂(5-COOH—Th-2-yl) |
| 1-619 | CHF₂ | CH₂cPr | —CH₂(5-CF₃—Th-2-yl) |
| 1-620 | CHF₂ | CH₂cPr | —CH₂(Th-3-yl) |
| 1-621 | CHF₂ | CH₂cPr | —CH₂(5-CN—Th-3-yl) |
| 1-622 | CHF₂ | CH₂cPr | —CH₂(5-COOH—Th-3-yl) |
| 1-623 | CHF₂ | CH₂cPr | —CH₂(5-CF₃—Th-3-yl) |
| 1-624 | CHF₂ | CH₂cPr | —CH₂(Thz-4-yl) |
| 1-625 | CHF₂ | CH₂cPr | —CH₂(2-CN-Thz-4-yl) |
| 1-626 | CHF₂ | CH₂cPr | —CH₂(2-COOH-Thz-4-yl) |
| 1-627 | CHF₂ | CH₂cPr | —CH₂(2-C(OH)(Me)₂-Thz-4-yl) |
| 1-628 | CHF₂ | CH₂cPr | —CH₂(2-C(OH)(CF₃)₂-Thz-4-yl) |
| 1-629 | CHF₂ | CH₂cPr | —CH₂(2-CN-Thz-5-yl) |
| 1-630 | CHF₂ | CH₂cPr | —CH₂(2-COOH-Thz-5-yl) |
| 1-631 | CHF₂ | CH₂cPr | —CH₂(2-C(OH)(Me)₂-Thz-5-yl) |
| 1-632 | CHF₂ | CH₂cPr | —CH₂(2-C(OH)(CF₃)₂-Thz-5-yl) |
| 1-633 | CHF₂ | CH₂cPr | —CH₂(6-CN-Py-2-yl) |
| 1-634 | CHF₂ | CH₂cPr | —CH₂(6-COOH-Py-2-yl) |
| 1-635 | CHF₂ | CH₂cPr | —CH₂(6-OMe-Py-2-yl) |
| 1-636 | CHF₂ | CH₂cPr | —CH₂(6-C(OH)(Me)₂-Py-2-yl) |
| 1-637 | CHF₂ | CH₂cPr | —CH₂(6-C(OH)(CF₃)₂-Py-2-yl) |
| 1-638 | CHF₂ | CH₂cPr | —CH₂(6-CN-Py-3-yl) |
| 1-639 | CHF₂ | CH₂cPr | —CH₂(6-COOH-Py-3-yl) |
| 1-640 | CHF₂ | CH₂cPr | —CH₂(6-OMe-Py-3-yl) |
| 1-641 | CHF₂ | CH₂cPr | —CH₂(6-C(OH)(Me)₂-Py-3-yl) |
| 1-642 | CHF₂ | CH₂cPr | —CH₂(6-C(OH)(CF₃)₂-Py-3-yl) |
| 1-643 | CHF₂ | CH₂cPr | —CH₂(2-CN-Py-3-yl) |
| 1-644 | CHF₂ | CH₂cPr | —CH₂(2-COOH-Py-3-yl) |
| 1-645 | CHF₂ | CH₂cPr | —CH₂(2-OMe-Py-3-yl) |
| 1-646 | CHF₂ | CH₂cPr | —CH₂(2-C(OH)(Me)₂-Py-3-yl) |
| 1-647 | CHF₂ | CH₂cPr | —CH₂(2-C(OH)(CF₃)₂-Py-3-yl) |
| 1-648 | CHF₂ | CH₂cPr | —CH₂(2-CN-Py-4-yl) |
| 1-649 | CHF₂ | CH₂cPr | —CH₂(2-COOH-Py-4-yl) |
| 1-650 | CHF₂ | CH₂cPr | —CH₂(2-OMe-Py-4-yl) |
| 1-651 | CHF₂ | CH₂cPr | —CH₂(2-C(OH)(Me)₂-Py-4-yl) |
| 1-652 | CHF₂ | CH₂cPr | —CH₂(2-C(OH)(CF₃)₂-Py-4-yl) |
| 1-653 | CHF₂ | CH₂cPr | —CH₂CH₂Ph |
| 1-654 | CHF₂ | CH₂cPr | —CH₂CH₂(2-F-Ph) |
| 1-655 | CHF₂ | CH₂cPr | —CH₂CH₂(3-F-Ph) |
| 1-656 | CHF₂ | CH₂cPr | —CH₂CH₂(4-F-Ph) |
| 1-657 | CHF₂ | CH₂cPr | —CH₂CH₂(3-CN-Ph) |
| 1-658 | CHF₂ | CH₂cPr | —CH₂CH₂(Th-2-yl) |
| 1-659 | CHF₂ | CH₂cPr | —CH₂CH₂(6-CN-Py-2-yl) |
| 1-660 | CHF₂ | CH₂cPr | —CH₂CH₂(6-CN-Py-3-yl) |
| 1-661 | CHF₂ | CH₂cPr | —CH₂CH₂(2-CN-Py-3-yl) |
| 1-662 | CHF₂ | CH₂cPr | —CH(OH)Ph |
| 1-663 | CHF₂ | CH₂cPr | —CH(OH)(3-F-Ph) |
| 1-664 | CHF₂ | CH₂cPr | —CH(OH)(4-F-Ph) |
| 1-665 | CHF₂ | CH₂cPr | —CH(OH)(Th-2-yl) |

TABLE 1-continued

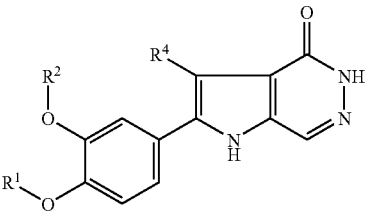

(1a)

| Compound No. | R¹ | R² | R⁴ |
|---|---|---|---|
| 1-666 | CHF₂ | iPr | H |
| 1-667 | CHF₂ | iPr | Cl |
| 1-668 | CHF₂ | iPr | Br |
| 1-669 | CHF₂ | iPr | Me |
| 1-670 | CHF₂ | iPr | Et |
| 1-671 | CHF₂ | iPr | Pr |
| 1-672 | CHF₂ | iPr | iPr |
| 1-673 | CHF₂ | iPr | Bu |
| 1-674 | CHF₂ | iPr | iBu |
| 1-675 | CHF₂ | iPr | Pent |
| 1-676 | CHF₂ | iPr | —CH₂CH₂CH(Me)₂ |
| 1-677 | CHF₂ | iPr | —CH₂CH₂CH₂CH₂CH₂CH₃ |
| 1-678 | CHF₂ | iPr | —CH₂C(Me)₂CH₂CH₃ |
| 1-679 | CHF₂ | iPr | —CH₂CH₂C(Me)₃ |
| 1-680 | CHF₂ | iPr | —CH₂CF₃ |
| 1-681 | CHF₂ | iPr | —CH₂CH₂CF₃ |
| 1-682 | CHF₂ | iPr | —CH₂CH₂Cl |
| 1-683 | CHF₂ | iPr | —CH₂OH |
| 1-684 | CHF₂ | iPr | —CH₂C(OH)(Me)₂ |
| 1-685 | CHF₂ | iPr | —CH₂CH₂C(OH)(Me)₂ |
| 1-686 | CHF₂ | iPr | —CH₂CH₂CH₂C(OH)(Me)₂ |
| 1-687 | CHF₂ | iPr | —CH₂C(OH)(Et)₂ |
| 1-688 | CHF₂ | iPr | —CH₂C(CN)(Me)₂ |
| 1-689 | CHF₂ | iPr | —CH₂CH₂C(CN)(Me)₂ |
| 1-690 | CHF₂ | iPr | —CH₂C(COOH)(Me)₂ |
| 1-691 | CHF₂ | iPr | —CH₂CH₂C(COOH)(Me)₂ |
| 1-692 | CHF₂ | iPr | —CH₂CH₂CH₂C(COOH)(Me)₂ |
| 1-693 | CHF₂ | iPr | —CH₂OMe |
| 1-694 | CHF₂ | iPr | —CH₂CH₂OMe |
| 1-695 | CHF₂ | iPr | —CH₂OEt |
| 1-696 | CHF₂ | iPr | —CH₂CH₂OEt |
| 1-697 | CHF₂ | iPr | —CH₂OiPr |
| 1-698 | CHF₂ | iPr | —CH₂CH₂OiPr |
| 1-699 | CHF₂ | iPr | —CH₂OCH₂CH₂F |
| 1-700 | CHF₂ | iPr | —CH₂OcBu |
| 1-701 | CHF₂ | iPr | —CH₂OCH₂cPr |
| 1-702 | CHF₂ | iPr | —CH₂N(Me)₂ |
| 1-703 | CHF₂ | iPr | cPr |
| 1-704 | CHF₂ | iPr | —CH₂cPr |
| 1-705 | CHF₂ | iPr | —CH₂cPr(1-OH) |
| 1-706 | CHF₂ | iPr | —CH₂cBu |
| 1-707 | CHF₂ | iPr | —CH₂cBu(1-OH) |
| 1-708 | CHF₂ | iPr | —CH(OH)cPr |
| 1-709 | CHF₂ | iPr | —CH(OH)cPr(1-OH) |
| 1-710 | CHF₂ | iPr | —CH(OH)cBu |
| 1-711 | CHF₂ | iPr | —CH(OH)cBu(1-OH) |
| 1-712 | CHF₂ | iPr | —CH₂CH₂cPr |
| 1-713 | CHF₂ | iPr | —CH₂CH₂cPr(1-OH) |
| 1-714 | CHF₂ | iPr | —CH₂CH₂cBu |
| 1-715 | CHF₂ | iPr | —CH₂CH₂cBu(1-OH) |
| 1-716 | CHF₂ | iPr | —CH₂CH=CH₂ |
| 1-717 | CHF₂ | iPr | —CH₂CH=CHMe |
| 1-718 | CHF₂ | iPr | —CH₂C(Me)=CH₂ |
| 1-719 | CHF₂ | iPr | —CH₂C(Me)=CHMe |
| 1-720 | CHF₂ | iPr | —CH₂CH=C(Me)₂ |
| 1-721 | CHF₂ | iPr | —CH₂C(Me)=C(Me)₂ |
| 1-722 | CHF₂ | iPr | —C≡CH |
| 1-723 | CHF₂ | iPr | —CH₂C≡CH |
| 1-724 | CHF₂ | iPr | —CH₂C≡CMe |
| 1-725 | CHF₂ | iPr | —CH(OH)CH=CH₂ |
| 1-726 | CHF₂ | iPr | —CH(OH)CH=CHMe |
| 1-727 | CHF₂ | iPr | —CH(OH)C≡CH |
| 1-728 | CHF₂ | iPr | —CH(OH)C≡CMe |
| 1-729 | CHF₂ | iPr | Ph |
| 1-730 | CHF₂ | iPr | 2-F-Ph |

TABLE 1-continued (1a)

| Compound No. | R¹ | R² | R⁴ |
|---|---|---|---|
| 1-731 | CHF₂ | iPr | 4-F-Ph |
| 1-732 | CHF₂ | iPr | 2,4-diF-Ph |
| 1-733 | CHF₂ | iPr | 2-Cl-Ph |
| 1-734 | CHF₂ | iPr | 4-Cl-Ph |
| 1-735 | CHF₂ | iPr | 4-CN-Ph |
| 1-736 | CHF₂ | iPr | 4-NO₂-Ph |
| 1-737 | CHF₂ | iPr | 4-COOH-Ph |
| 1-738 | CHF₂ | iPr | 4-CF₃-Ph |
| 1-739 | CHF₂ | iPr | 3-OMe-Ph |
| 1-740 | CHF₂ | iPr | 4-OMe-Ph |
| 1-741 | CHF₂ | iPr | 4-COOMe-Ph |
| 1-742 | CHF₂ | iPr | Th-2-yl |
| 1-743 | CHF₂ | iPr | 5-CN—Th-2-yl |
| 1-744 | CHF₂ | iPr | 5-COOH—Th-2-yl |
| 1-745 | CHF₂ | iPr | 5-Me—Th-2-yl |
| 1-746 | CHF₂ | iPr | 5-CF₃—Th-2-yl |
| 1-747 | CHF₂ | iPr | Th-3-yl |
| 1-748 | CHF₂ | iPr | 5-CN—Th-3-yl |
| 1-749 | CHF₂ | iPr | 5-COOH—Th-3-yl |
| 1-750 | CHF₂ | iPr | 5-Me—Th-3-yl |
| 1-751 | CHF₂ | iPr | 5-CF₃—Th-3-yl |
| 1-752 | CHF₂ | iPr | Thz-4-yl |
| 1-753 | CHF₂ | iPr | 2-CN-Thz-4-yl |
| 1-754 | CHF₂ | iPr | 2-COOH-Thz-4-yl |
| 1-755 | CHF₂ | iPr | 2-Me-Thz-4-yl |
| 1-756 | CHF₂ | iPr | 3-CF₃-Thz-4-yl |
| 1-757 | CHF₂ | iPr | 2-C(OH)(Me)₂-Thz-4-yl |
| 1-758 | CHF₂ | iPr | 2-C(OH)(CF₃)₂-Thz-4-yl |
| 1-759 | CHF₂ | iPr | Thz-5-yl |
| 1-760 | CHF₂ | iPr | 2-CN-Thz-5-yl |
| 1-761 | CHF₂ | iPr | 2-COOH-Thz-5-yl |
| 1-762 | CHF₂ | iPr | 2-Me-Thz-5-yl |
| 1-763 | CHF₂ | iPr | 2-CF₃-Thz-5-yl |
| 1-764 | CHF₂ | iPr | 2-C(OH)(Me)₂-Thz-5-yl |
| 1-765 | CHF₂ | iPr | 2-C(OH)(CF₃)₂-Thz-5-yl |
| 1-766 | CHF₂ | iPr | Pyz-4-yl |
| 1-767 | CHF₂ | iPr | 6-CN-Py-2-yl |
| 1-768 | CHF₂ | iPr | 6-COOH-Py-2-yl |
| 1-769 | CHF₂ | iPr | 6-CF₃-Py-2-yl |
| 1-770 | CHF₂ | iPr | 6-OMe-Py-2-yl |
| 1-771 | CHF₂ | iPr | 6-C(OH)(Me)₂-Py-2-yl |
| 1-772 | CHF₂ | iPr | 6-C(OH)(CF₃)₂-Py-2-yl |
| 1-773 | CHF₂ | iPr | 6-CN-Py-3-yl |
| 1-774 | CHF₂ | iPr | 6-COOH-Py-3-yl |
| 1-775 | CHF₂ | iPr | 6-CF₃-Py-3-yl |
| 1-776 | CHF₂ | iPr | 6-OMe-Py-3-yl |
| 1-777 | CHF₂ | iPr | 6-C(OH)(Me)₂-Py-3-yl |
| 1-778 | CHF₂ | iPr | 6-C(OH)(CF₃)₂-Py-3-yl |
| 1-779 | CHF₂ | iPr | 2-CN-Py-4-yl |
| 1-780 | CHF₂ | iPr | 2-COOH-Py-4-yl |
| 1-781 | CHF₂ | iPr | 2-CF₃-Py-4-yl |
| 1-782 | CHF₂ | iPr | 2-OMe-Py-4-yl |
| 1-783 | CHF₂ | iPr | 2-C(OH)(Me)₂-Py-4-yl |
| 1-784 | CHF₂ | iPr | 2-C(OH)(CF₃)₂-Py-4-yl |
| 1-785 | CHF₂ | iPr | Bn |
| 1-786 | CHF₂ | iPr | 2-F-Bn |
| 1-787 | CHF₂ | iPr | 3-F-Bn |
| 1-788 | CHF₂ | iPr | 4-F-Bn |
| 1-789 | CHF₂ | iPr | 2,4-diF-Bn |
| 1-790 | CHF₂ | iPr | 3,4-diF-Bn |
| 1-791 | CHF₂ | iPr | 2-Cl-Bn |
| 1-792 | CHF₂ | iPr | 3-Cl-Bn |
| 1-793 | CHF₂ | iPr | 2-CN-Bn |
| 1-794 | CHF₂ | iPr | 3-CN-Bn |
| 1-795 | CHF₂ | iPr | 3-COOH-Bn |
| 1-796 | CHF₂ | iPr | 4-COOH-Bn |
| 1-797 | CHF₂ | iPr | 3-CF₃-Bn |
| 1-798 | CHF₂ | iPr | 4-OMe-Bn |
| 1-799 | CHF₂ | iPr | 3-COOMe-Bn |
| 1-800 | CHF₂ | iPr | —CH₂(Th-2-yl) |
| 1-801 | CHF₂ | iPr | —CH₂(5-CN—Th-2-yl) |
| 1-802 | CHF₂ | iPr | —CH₂(5-COOH—Th-2-yl) |
| 1-803 | CHF₂ | iPr | —CH₂(5-CF₃—Th-2-yl) |
| 1-804 | CHF₂ | iPr | —CH₂(Th-3-yl) |
| 1-805 | CHF₂ | iPr | —CH₂(5-CN—Th-3-yl) |
| 1-806 | CHF₂ | iPr | —CH₂(5-COOH—Th-3-yl) |
| 1-807 | CHF₂ | iPr | —CH₂(5-CF₃—Th-3-yl) |
| 1-808 | CHF₂ | iPr | —CH₂(Thz-4-yl) |
| 1-809 | CHF₂ | iPr | —CH₂(2-CN-Thz-4-yl) |
| 1-810 | CHF₂ | iPr | —CH₂(2-COOH-Thz-4-yl) |
| 1-811 | CHF₂ | iPr | —CH₂(2-C(OH)(Me)₂-Thz-4-yl) |
| 1-812 | CHF₂ | iPr | —CH₂(2-C(OH)(CF₃)₂-Thz-4-yl) |
| 1-813 | CHF₂ | iPr | —CH₂(2-CN-Thz-5-yl) |
| 1-814 | CHF₂ | iPr | —CH₂(2-COOH-Thz-5-yl) |
| 1-815 | CHF₂ | iPr | —CH₂(2-C(OH)(Me)₂-Thz-5-yl) |
| 1-816 | CHF₂ | iPr | —CH₂(2-C(OH)(CF₃)₂-Thz-5-yl) |
| 1-817 | CHF₂ | iPr | —CH₂(6-CN-Py-2-yl) |
| 1-818 | CHF₂ | iPr | —CH₂(6-COOH-Py-2-yl) |
| 1-819 | CHF₂ | iPr | —CH₂(6-OMe-Py-2-yl) |
| 1-820 | CHF₂ | iPr | —CH₂(6-C(OH)(Me)₂-Py-2-yl) |
| 1-821 | CHF₂ | iPr | —CH₂(6-C(OH)(CF₃)₂-Py-2-yl) |
| 1-822 | CHF₂ | iPr | —CH₂(6-CN-Py-3-yl) |
| 1-823 | CHF₂ | iPr | —CH₂(6-COOH-Py-3-yl) |
| 1-824 | CHF₂ | iPr | —CH₂(6-OMe-Py-3-yl) |
| 1-825 | CHF₂ | iPr | —CH₂(6-C(OH)(Me)₂-Py-3-yl) |
| 1-826 | CHF₂ | iPr | —CH₂(6-C(OH)(CF₃)₂-Py-3-yl) |
| 1-827 | CHF₂ | iPr | —CH₂(2-CN-Py-3-yl) |
| 1-828 | CHF₂ | iPr | —CH₂(2-COOH-Py-3-yl) |
| 1-829 | CHF₂ | iPr | —CH₂(2-OMe-Py-3-yl) |
| 1-830 | CHF₂ | iPr | —CH₂(2-C(OH)(Me)₂-Py-3-yl) |
| 1-831 | CHF₂ | iPr | —CH₂(2-C(OH)(CF₃)₂-Py-3-yl) |
| 1-832 | CHF₂ | iPr | —CH₂(2-CN-Py-4-yl) |
| 1-833 | CHF₂ | iPr | —CH₂(2-COOH-Py-4-yl) |
| 1-834 | CHF₂ | iPr | —CH₂(2-OMe-Py-4-yl) |
| 1-835 | CHF₂ | iPr | —CH₂(2-C(OH)(Me)₂-Py-4-yl) |
| 1-836 | CHF₂ | iPr | —CH₂(2-C(OH)(CF₃)₂-Py-4-yl) |
| 1-837 | CHF₂ | iPr | —CH₂CH₂Ph |
| 1-838 | CHF₂ | iPr | —CH₂CH₂(2-F-Ph) |
| 1-839 | CHF₂ | iPr | —CH₂CH₂(3-F-Ph) |
| 1-840 | CHF₂ | iPr | —CH₂CH₂(4-F-Ph) |
| 1-841 | CHF₂ | iPr | —CH₂CH₂(3-CN-Ph) |
| 1-842 | CHF₂ | iPr | —CH₂CH₂(Th-2-yl) |
| 1-843 | CHF₂ | iPr | —CH₂CH₂(6-CN-Py-2-yl) |
| 1-844 | CHF₂ | iPr | —CH₂CH₂(6-CN-Py-3-yl) |
| 1-845 | CHF₂ | iPr | —CH₂CH₂(2-CN-Py-3-yl) |
| 1-846 | CHF₂ | iPr | —CH(OH)Ph |
| 1-847 | CHF₂ | iPr | —CH(OH)(3-F-Ph) |
| 1-848 | CHF₂ | iPr | —CH(OH)(4-F-Ph) |
| 1-849 | CHF₂ | iPr | —CH(OH)(Th-2-yl) |
| 1-850 | CHF₂ | cBu | H |
| 1-851 | CHF₂ | cBu | Cl |
| 1-852 | CHF₂ | cBu | Br |
| 1-853 | CHF₂ | cBu | Me |
| 1-854 | CHF₂ | cBu | Et |
| 1-855 | CHF₂ | cBu | Pr |
| 1-856 | CHF₂ | cBu | iPr |
| 1-857 | CHF₂ | cBu | Bu |
| 1-858 | CHF₂ | cBu | iBu |
| 1-859 | CHF₂ | cBu | —CH₂OH |
| 1-860 | CHF₂ | cBu | —CH₂OMe |

TABLE 1-continued

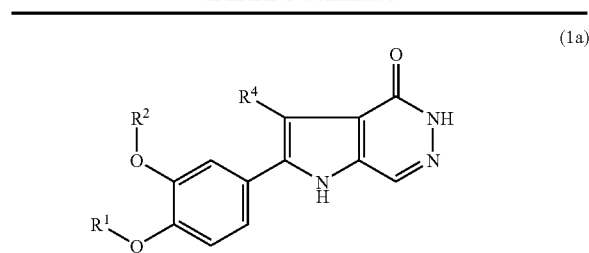

(1a)

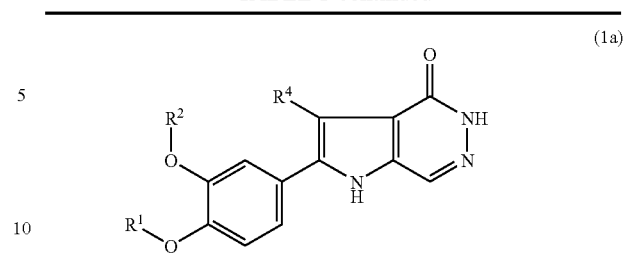

(1a)

| Compound No. | R¹ | R² | R⁴ |
|---|---|---|---|
| 1-861 | CHF₂ | cBu | —CH₂OEt |
| 1-862 | CHF₂ | cBu | —CH₂OiPr |
| 1-863 | CHF₂ | cBu | —CH₂OCH₂CH₂F |
| 1-864 | CHF₂ | cBu | —CH₂OcBu |
| 1-865 | CHF₂ | cBu | —CH₂OCH₂cPr |
| 1-866 | CHF₂ | cBu | —CH₂N(Me)₂ |
| 1-867 | CHF₂ | cBu | cPr |
| 1-868 | CHF₂ | cBu | —CH₂cPr |
| 1-869 | CHF₂ | cBu | —C≡CH |
| 1-870 | CHF₂ | cBu | Ph |
| 1-871 | CHF₂ | cBu | Pyz-4-yl |
| 1-872 | CHF₂ | cBu | Bn |
| 1-873 | CHF₂ | cBu | 2-F-Bn |
| 1-874 | CHF₂ | cBu | 3-F-Bn |
| 1-875 | CHF₂ | cBu | 4-F-Bn |
| 1-876 | CHF₂ | cBu | 2-CN-Bn |
| 1-877 | CHF₂ | cBu | 3-CN-Bn |
| 1-878 | CHF₂ | cBu | 3-COOH-Bn |
| 1-879 | CHF₂ | cBu | —CH₂(6-OMe-Py-2-yl) |
| 1-880 | CHF₂ | cBu | —CH₂(6-OMe-Py-3-yl) |
| 1-881 | CHF₂ | cBu | —CH₂CH₂Ph |
| 1-882 | CHF₂ | cBu | —CH(OH)Ph |
| 1-883 | CHF₂ | cPent | H |
| 1-884 | CHF₂ | cPent | Cl |
| 1-885 | CHF₂ | cPent | Br |
| 1-886 | CHF₂ | cPent | Me |
| 1-887 | CHF₂ | cPent | Et |
| 1-888 | CHF₂ | cPent | Pr |
| 1-889 | CHF₂ | cPent | iPr |
| 1-890 | CHF₂ | cPent | Bu |
| 1-891 | CHF₂ | cPent | iBu |
| 1-892 | CHF₂ | cPent | —CH₂OH |
| 1-893 | CHF₂ | cPent | —CH₂OMe |
| 1-894 | CHF₂ | cPent | —CH₂OEt |
| 1-895 | CHF₂ | cPent | —CH₂OiPr |
| 1-896 | CHF₂ | cPent | —CH₂OCH₂CH₂F |
| 1-897 | CHF₂ | cPent | —CH₂OcBu |
| 1-898 | CHF₂ | cPent | —CH₂OCH₂cPr |
| 1-899 | CHF₂ | cPent | —CH₂N(Me)₂ |
| 1-900 | CHF₂ | cPent | cPr |
| 1-901 | CHF₂ | cPent | —CH₂cPr |
| 1-902 | CHF₂ | cPent | —C≡CH |
| 1-903 | CHF₂ | cPent | Ph |
| 1-904 | CHF₂ | cPent | Pyz-4-yl |
| 1-905 | CHF₂ | cPent | Bn |
| 1-906 | CHF₂ | cPent | 2-F-Bn |
| 1-907 | CHF₂ | cPent | 3-F-Bn |
| 1-908 | CHF₂ | cPent | 4-F-Bn |
| 1-909 | CHF₂ | cPent | 2-CN-Bn |
| 1-910 | CHF₂ | cPent | 3-CN-Bn |
| 1-911 | CHF₂ | cPent | 3-COOH-Bn |
| 1-912 | CHF₂ | cPent | —CH₂(6-OMe-Py-2-yl) |
| 1-913 | CHF₂ | cPent | —CH₂(6-OMe-Py-3-yl) |
| 1-914 | CHF₂ | cPent | —CH₂CH₂Ph |
| 1-915 | CHF₂ | cPent | —CH(OH)Ph |
| 1-916 | CH₃ | cPr | H |
| 1-917 | CH₃ | cPr | Cl |
| 1-918 | CH₃ | cPr | Br |
| 1-919 | CH₃ | cPr | Me |
| 1-920 | CH₃ | cPr | Et |
| 1-921 | CH₃ | cPr | Pr |
| 1-922 | CH₃ | cPr | iPr |
| 1-923 | CH₃ | cPr | Bu |
| 1-924 | CH₃ | cPr | iBu |
| 1-925 | CH₃ | cPr | Pent |
| 1-926 | CH₃ | cPr | —CH₂CH₂CH(Me)₂ |
| 1-927 | CH₃ | cPr | —CH₂CH₂CH₂CH₂CH₃ |
| 1-928 | CH₃ | cPr | —CH₂C(Me)₂CH₂CH₃ |
| 1-929 | CH₃ | cPr | —CH₂CH₂C(Me)₃ |
| 1-930 | CH₃ | cPr | —CH₂CF₃ |
| 1-931 | CH₃ | cPr | —CH₂CH₂CF₃ |
| 1-932 | CH₃ | cPr | —CH₂CH₂Cl |
| 1-933 | CH₃ | cPr | —CH₂OH |
| 1-934 | CH₃ | cPr | —CH₂C(OH)(Me)₂ |
| 1-935 | CH₃ | cPr | —CH₂CH₂C(OH)(Me)₂ |
| 1-936 | CH₃ | cPr | —CH₂CH₂CH₂C(OH)(Me)₂ |
| 1-937 | CH₃ | cPr | —CH₂C(OH)(Et)₂ |
| 1-938 | CH₃ | cPr | —CH₂C(CN)(Me)₂ |
| 1-939 | CH₃ | cPr | —CH₂CH₂C(CN)(Me)₂ |
| 1-940 | CH₃ | cPr | —CH₂C(COOH)(Me)₂ |
| 1-941 | CH₃ | cPr | —CH₂CH₂C(COOH)(Me)₂ |
| 1-942 | CH₃ | cPr | —CH₂CH₂CH₂C(COOH)(Me)₂ |
| 1-943 | CH₃ | cPr | —CH₂OMe |
| 1-944 | CH₃ | cPr | —CH₂CH₂OMe |
| 1-945 | CH₃ | cPr | —CH₂OEt |
| 1-946 | CH₃ | cPr | —CH₂CH₂OEt |
| 1-947 | CH₃ | cPr | —CH₂OiPr |
| 1-948 | CH₃ | cPr | —CH₂CH₂OiPr |
| 1-949 | CH₃ | cPr | —CH₂OCH₂CH₂F |
| 1-950 | CH₃ | cPr | —CH₂OcBu |
| 1-951 | CH₃ | cPr | —CH₂OCH₂cPr |
| 1-952 | CH₃ | cPr | —CH₂N(Me)₂ |
| 1-953 | CH₃ | cPr | cPr |
| 1-954 | CH₃ | cPr | —CH₂cPr |
| 1-955 | CH₃ | cPr | —CH₂cPr(1-OH) |
| 1-956 | CH₃ | cPr | —CH₂cBu |
| 1-957 | CH₃ | cPr | —CH₂cBu(1-OH) |
| 1-958 | CH₃ | cPr | —CH(OH)cPr |
| 1-959 | CH₃ | cPr | —CH(OH)cPr(1-OH) |
| 1-960 | CH₃ | cPr | —CH(OH)cBu |
| 1-961 | CH₃ | cPr | —CH(OH)cBu(1-OH) |
| 1-962 | CH₃ | cPr | —CH₂CH₂cPr |
| 1-963 | CH₃ | cPr | —CH₂CH₂cPr(1-OH) |
| 1-964 | CH₃ | cPr | —CH₂CH₂cBu |
| 1-965 | CH₃ | cPr | —CH₂CH₂cBu(1-OH) |
| 1-966 | CH₃ | cPr | —CH₂CH=CH₂ |
| 1-967 | CH₃ | cPr | —CH₂CH=CHMe |
| 1-968 | CH₃ | cPr | —CH₂C(Me)=CH₂ |
| 1-969 | CH₃ | cPr | —CH₂C(Me)=CHMe |
| 1-970 | CH₃ | cPr | —CH₂CH=C(Me)₂ |
| 1-971 | CH₃ | cPr | —CH₂C(Me)=C(Me)₂ |
| 1-972 | CH₃ | cPr | —C≡CH |
| 1-973 | CH₃ | cPr | —CH₂C≡CH |
| 1-974 | CH₃ | cPr | —CH₂C≡CMe |
| 1-975 | CH₃ | cPr | —CH(OH)CH=CH₂ |
| 1-976 | CH₃ | cPr | —CH(OH)CH=CHMe |
| 1-977 | CH₃ | cPr | —CH(OH)C≡CH |
| 1-978 | CH₃ | cPr | —CH(OH)C≡CMe |
| 1-979 | CH₃ | cPr | Ph |
| 1-980 | CH₃ | cPr | 2-F-Ph |
| 1-981 | CH₃ | cPr | 4-F-Ph |
| 1-982 | CH₃ | cPr | 2,4-diF-Ph |
| 1-983 | CH₃ | cPr | 2-Cl-Ph |
| 1-984 | CH₃ | cPr | 4-Cl-Ph |
| 1-985 | CH₃ | cPr | 4-CN-Ph |
| 1-986 | CH₃ | cPr | 4-NO₂-Ph |
| 1-987 | CH₃ | cPr | 4-COOH-Ph |
| 1-988 | CH₃ | cPr | 4-CF₃-Ph |
| 1-989 | CH₃ | cPr | 3-OMe-Ph |
| 1-990 | CH₃ | cPr | 4-OMe-Ph |

TABLE 1-continued (1a)

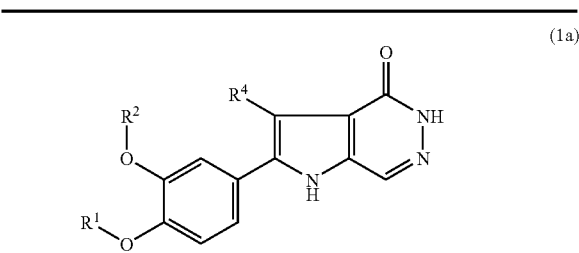

| Compound No. | R¹ | R² | R⁴ |
|---|---|---|---|
| 1-991 | CH₃ | cPr | 4-COOMe-Ph |
| 1-992 | CH₃ | cPr | Th-2-yl |
| 1-993 | CH₃ | cPr | 5-CN-Th-2-yl |
| 1-994 | CH₃ | cPr | 5-COOH-Th-2-yl |
| 1-995 | CH₃ | cPr | 5-Me-Th-2-yl |
| 1-996 | CH₃ | cPr | 5-CF₃-Th-2-yl |
| 1-997 | CH₃ | cPr | Th-3-yl |
| 1-998 | CH₃ | cPr | 5-CN-Th-3-yl |
| 1-999 | CH₃ | cPr | 5-COOH-Th-3-yl |
| 1-1000 | CH₃ | cPr | 5-Me-Th-3-yl |
| 1-1001 | CH₃ | cPr | 5-CF₃-Th-3-yl |
| 1-1002 | CH₃ | cPr | Thz-4-yl |
| 1-1003 | CH₃ | cPr | 2-CN-Thz-4-yl |
| 1-1004 | CH₃ | cPr | 2-COOH-Thz-4-yl |
| 1-1005 | CH₃ | cPr | 2-Me-Thz-4-yl |
| 1-1006 | CH₃ | cPr | 2-CF₃-Thz-4-yl |
| 1-1007 | CH₃ | cPr | 2-C(OH)(Me)₂-Thz-4-yl |
| 1-1008 | CH₃ | cPr | 2-C(OH)(CF₃)₂-Thz-4-yl |
| 1-1009 | CH₃ | cPr | Thz-5-yl |
| 1-1010 | CH₃ | cPr | 2-CN-Thz-5-yl |
| 1-1011 | CH₃ | cPr | 2-COOH-Thz-5-yl |
| 1-1012 | CH₃ | cPr | 2-Me-Thz-5-yl |
| 1-1013 | CH₃ | cPr | 2-CF₃-Thz-5-yl |
| 1-1014 | CH₃ | cPr | 2-C(OH)(Me)₂-Thz-5-yl |
| 1-1015 | CH₃ | cPr | 2-C(OH)(CF₃)₂-Thz-5-yl |
| 1-1016 | CH₃ | cPr | Pyz-4-yl |
| 1-1017 | CH₃ | cPr | 6-CN-Py-2-yl |
| 1-1018 | CH₃ | cPr | 6-COOH-Py-2-yl |
| 1-1019 | CH₃ | cPr | 6-CF₃-Py-2-yl |
| 1-1020 | CH₃ | cPr | 6-OMe-Py-2-yl |
| 1-1021 | CH₃ | cPr | 6-C(OH)(Me)₂-Py-2-yl |
| 1-1022 | CH₃ | cPr | 6-C(OH)(CF₃)₂-Py-2-yl |
| 1-1023 | CH₃ | cPr | 6-CN-Py-3-yl |
| 1-1024 | CH₃ | cPr | 6-COOH-Py-3-yl |
| 1-1025 | CH₃ | cPr | 6-CF₃-Py-3-yl |
| 1-1026 | CH₃ | cPr | 6-OMe-Py-3-yl |
| 1-1027 | CH₃ | cPr | 6-C(OH)(Me)₂-Py-3-yl |
| 1-1028 | CH₃ | cPr | 6-C(OH)(CF₃)₂-Py-3-yl |
| 1-1029 | CH₃ | cPr | 2-CN-Py-4-yl |
| 1-1030 | CH₃ | cPr | 2-COOH-Py-4-yl |
| 1-1031 | CH₃ | cPr | 2-CF₃-Py-4-yl |
| 1-1032 | CH₃ | cPr | 2-OMe-Py-4-yl |
| 1-1033 | CH₃ | cPr | 2-C(OH)(Me)₂-Py-4-yl |
| 1-1034 | CH₃ | cPr | 2-C(OH)(CF₃)₂-Py-4-yl |
| 1-1035 | CH₃ | cPr | Bn |
| 1-1036 | CH₃ | cPr | 2-F-Bn |
| 1-1037 | CH₃ | cPr | 3-F-Bn |
| 1-1038 | CH₃ | cPr | 4-F-Bn |
| 1-1039 | CH₃ | cPr | 2,4-diF-Bn |
| 1-1040 | CH₃ | cPr | 3,4-diF-Bn |
| 1-1041 | CH₃ | cPr | 2-Cl-Bn |
| 1-1042 | CH₃ | cPr | 3-Cl-Bn |
| 1-1043 | CH₃ | cPr | 2-CN-Bn |
| 1-1044 | CH₃ | cPr | 3-CN-Bn |
| 1-1045 | CH₃ | cPr | 3-COOH-Bn |
| 1-1046 | CH₃ | cPr | 4-COOH-Bn |
| 1-1047 | CH₃ | cPr | 3-CF₃-Bn |
| 1-1048 | CH₃ | cPr | 4-OMe-Bn |
| 1-1049 | CH₃ | cPr | 3-COOMe-Bn |
| 1-1050 | CH₃ | cPr | —CH₂(Th-2-yl) |
| 1-1051 | CH₃ | cPr | —CH₂(5-CN—Th-2-yl) |
| 1-1052 | CH₃ | cPr | —CH₂(5-COOH—Th-2-yl) |
| 1-1053 | CH₃ | cPr | —CH₂(5-CF₃—Th-2-yl) |
| 1-1054 | CH₃ | cPr | —CH₂(Th-3-yl) |
| 1-1055 | CH₃ | cPr | —CH₂(5-CN—Th-3-yl) |
| 1-1056 | CH₃ | cPr | —CH₂(5-COOH—Th-3-yl) |
| 1-1057 | CH₃ | cPr | —CH₂(5-CF₃—Th-3-yl) |
| 1-1058 | CH₃ | cPr | —CH₂(Thz-4-yl) |
| 1-1059 | CH₃ | cPr | —CH₂(2-CN-Thz-4-yl) |
| 1-1060 | CH₃ | cPr | —CH₂(2-COOH-Thz-4-yl) |
| 1-1061 | CH₃ | cPr | —CH₂(2-C(OH)(Me)₂-Thz-4-yl) |
| 1-1062 | CH₃ | cPr | —CH₂(2-C(OH)(CF₃)₂-Thz-4-yl) |
| 1-1063 | CH₃ | cPr | —CH₂(2-CN-Thz-5-yl) |
| 1-1064 | CH₃ | cPr | —CH₂(2-COOH-Thz-5-yl) |
| 1-1065 | CH₃ | cPr | —CH₂(2-C(OH)(Me)₂-Thz-5-yl) |
| 1-1066 | CH₃ | cPr | —CH₂(2-C(OH)(CF₃)₂-Thz-5-yl) |
| 1-1067 | CH₃ | cPr | —CH₂(6-CN-Py-2-yl) |
| 1-1068 | CH₃ | cPr | —CH₂(6-COOH-Py-2-yl) |
| 1-1069 | CH₃ | cPr | —CH₂(6-OMe-Py-2-yl) |
| 1-1070 | CH₃ | cPr | —CH₂(6-C(OH)(Me)₂-Py-2-yl) |
| 1-1071 | CH₃ | cPr | —CH₂(6-C(OH)(CF₃)₂-Py-2-yl) |
| 1-1072 | CH₃ | cPr | —CH₂(6-CN-Py-3-yl) |
| 1-1073 | CH₃ | cPr | —CH₂(6-COOH-Py-3-yl) |
| 1-1074 | CH₃ | cPr | —CH₂(6-OMe-Py-3-yl) |
| 1-1075 | CH₃ | cPr | —CH₂(6-C(OH)(Me)₂-Py-3-yl) |
| 1-1076 | CH₃ | cPr | —CH₂(6-C(OH)(CF₃)₂-Py-3-yl) |
| 1-1077 | CH₃ | cPr | —CH₂(2-CN-Py-3-yl) |
| 1-1078 | CH₃ | cPr | —CH₂(2-COOH-Py-3-yl) |
| 1-1079 | CH₃ | cPr | —CH₂(2-OMe-Py-3-yl) |
| 1-1080 | CH₃ | cPr | —CH₂(2-C(OH)(Me)₂-Py-3-yl) |
| 1-1081 | CH₃ | cPr | —CH₂(2-C(OH)(CF₃)₂-Py-3-yl) |
| 1-1082 | CH₃ | cPr | —CH₂(2-CN-Py-4-yl) |
| 1-1083 | CH₃ | cPr | —CH₂(2-COOH-Py-4-yl) |
| 1-1084 | CH₃ | cPr | —CH₂(2-OMe-Py-4-yl) |
| 1-1085 | CH₃ | cPr | —CH₂(2-C(OH)(Me)₂-Py-4-yl) |
| 1-1086 | CH₃ | cPr | —CH₂(2-C(OH)(CF₃)₂-Py-4-yl) |
| 1-1087 | CH₃ | cPr | —CH₂CH₂Ph |
| 1-1088 | CH₃ | cPr | —CH₂CH₂(2-F-Ph) |
| 1-1089 | CH₃ | cPr | —CH₂CH₂(3-F-Ph) |
| 1-1090 | CH₃ | cPr | —CH₂CH₂(4-F-Ph) |
| 1-1091 | CH₃ | cPr | —CH₂CH₂(3-CN-Ph) |
| 1-1092 | CH₃ | cPr | —CH₂CH₂(Th-2-yl) |
| 1-1093 | CH₃ | cPr | —CH₂CH₂(6-CN-Py-2-yl) |
| 1-1094 | CH₃ | cPr | —CH₂CH₂(6-CN-Py-3-yl) |
| 1-1095 | CH₃ | cPr | —CH₂CH₂(2-CN-Py-3-yl) |
| 1-1096 | CH₃ | cPr | —CH(OH)Ph |
| 1-1097 | CH₃ | cPr | —CH(OH)(3-F-Ph) |
| 1-1098 | CH₃ | cPr | —CH(OH)(4-F-Ph) |
| 1-1099 | CH₃ | cPr | —CH(OH)(Th-2-yl) |
| 1-1100 | CH₃ | CH₂cPr | H |
| 1-1101 | CH₃ | CH₂cPr | Cl |
| 1-1102 | CH₃ | CH₂cPr | Br |
| 1-1103 | CH₃ | CH₂cPr | Me |
| 1-1104 | CH₃ | CH₂cPr | Et |
| 1-1105 | CH₃ | CH₂cPr | Pr |
| 1-1106 | CH₃ | CH₂cPr | iPr |
| 1-1107 | CH₃ | CH₂cPr | Bu |
| 1-1108 | CH₃ | CH₂cPr | iBu |
| 1-1109 | CH₃ | CH₂cPr | Pent |
| 1-1110 | CH₃ | CH₂cPr | —CH₂CH₂CH(Me)₂ |
| 1-1111 | CH₃ | CH₂cPr | —CH₂CH₂CH₂CH₂CH₃ |
| 1-1112 | CH₃ | CH₂cPr | —CH₂CH₂C(Me)₃ |
| 1-1113 | CH₃ | CH₂cPr | —CH₂CF₃ |
| 1-1114 | CH₃ | CH₂cPr | —CH₂CH₂Cl |
| 1-1115 | CH₃ | CH₂cPr | —CH₂OH |
| 1-1116 | CH₃ | CH₂cPr | —CH₂C(OH)(Me)₂ |
| 1-1117 | CH₃ | CH₂cPr | —CH₂C(OH)(Et)₂ |
| 1-1118 | CH₃ | CH₂cPr | —CH₂C(CN)(Me)₂ |
| 1-1119 | CH₃ | CH₂cPr | —CH₂C(COOH)(Me)₂ |
| 1-1120 | CH₃ | CH₂cPr | —CH₂OMe |

TABLE 1-continued

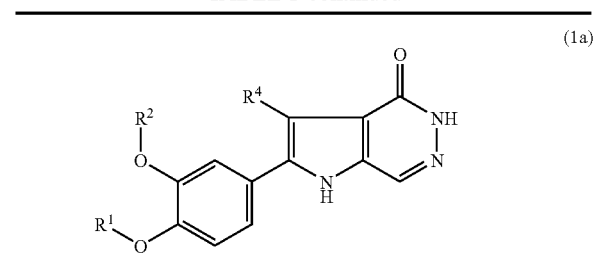

(1a)

| Compound No. | R¹ | R² | R⁴ |
|---|---|---|---|
| 1-1121 | CH₃ | CH₂cPr | —CH₂CH₂OMe |
| 1-1122 | CH₃ | CH₂cPr | —CH₂OEt |
| 1-1123 | CH₃ | CH₂cPr | —CH₂CH₂OEt |
| 1-1124 | CH₃ | CH₂cPr | —CH₂OiPr |
| 1-1125 | CH₃ | CH₂cPr | —CH₂CH₂OiPr |
| 1-1126 | CH₃ | CH₂cPr | —CH₂OCH₂CH₂F |
| 1-1127 | CH₃ | CH₂cPr | —CH₂OcBu |
| 1-1128 | CH₃ | CH₂cPr | —CH₂OCH₂cPr |
| 1-1129 | CH₃ | CH₂cPr | —CH₂N(Me)₂ |
| 1-1130 | CH₃ | CH₂cPr | cPr |
| 1-1131 | CH₃ | CH₂cPr | —CH₂cPr |
| 1-1132 | CH₃ | CH₂cPr | —CH₂cPr(1-OH) |
| 1-1133 | CH₃ | CH₂cPr | —CH₂cBu |
| 1-1134 | CH₃ | CH₂cPr | —CH(OH)cPr |
| 1-1135 | CH₃ | CH₂cPr | —CH₂CH₂cPr |
| 1-1136 | CH₃ | CH₂cPr | —CH₂CH₂cPr(1-OH) |
| 1-1137 | CH₃ | CH₂cPr | —CH₂CH=CH₂ |
| 1-1138 | CH₃ | CH₂cPr | —CH₂C(Me)=CH₂ |
| 1-1139 | CH₃ | CH₂cPr | —CH₂CH=C(Me)₂ |
| 1-1140 | CH₃ | CH₂cPr | —CH₂C(Me)=C(Me)₂ |
| 1-1141 | CH₃ | CH₂cPr | —C≡CH |
| 1-1142 | CH₃ | CH₂cPr | —CH₂C≡CH |
| 1-1143 | CH₃ | CH₂cPr | —CH₂C≡CMe |
| 1-1144 | CH₃ | CH₂cPr | Ph |
| 1-1145 | CH₃ | CH₂cPr | 2-F-Ph |
| 1-1146 | CH₃ | CH₂cPr | 4-F-Ph |
| 1-1147 | CH₃ | CH₂cPr | 4-CN-Ph |
| 1-1148 | CH₃ | CH₂cPr | 4-COOH-Ph |
| 1-1149 | CH₃ | CH₂cPr | 4-CF₃-Ph |
| 1-1150 | CH₃ | CH₂cPr | 3-OMe-Ph |
| 1-1151 | CH₃ | CH₂cPr | 4-OMe-Ph |
| 1-1152 | CH₃ | CH₂cPr | Th-2-yl |
| 1-1153 | CH₃ | CH₂cPr | Th-3-yl |
| 1-1154 | CH₃ | CH₂cPr | Thz-4-yl |
| 1-1155 | CH₃ | CH₂cPr | Thz-5-yl |
| 1-1156 | CH₃ | CH₂cPr | Pyz-4-yl |
| 1-1157 | CH₃ | CH₂cPr | 6-OMe-Py-2-yl |
| 1-1158 | CH₃ | CH₂cPr | 6-OMe-Py-3-yl |
| 1-1159 | CH₃ | CH₂cPr | 2-OMe-Py-4-yl |
| 1-1160 | CH₃ | CH₂cPr | Bn |
| 1-1161 | CH₃ | CH₂cPr | 2-F-Bn |
| 1-1162 | CH₃ | CH₂cPr | 3-F-Bn |
| 1-1163 | CH₃ | CH₂cPr | 4-F-Bn |
| 1-1164 | CH₃ | CH₂cPr | 2,4-diF-Bn |
| 1-1165 | CH₃ | CH₂cPr | 2-Cl-Bn |
| 1-1166 | CH₃ | CH₂cPr | 2-CN-Bn |
| 1-1167 | CH₃ | CH₂cPr | 3-CN-Bn |
| 1-1168 | CH₃ | CH₂cPr | 3-COOH-Bn |
| 1-1169 | CH₃ | CH₂cPr | 4-OMe-Bn |
| 1-1170 | CH₃ | CH₂cPr | —CH₂(Th-2-yl) |
| 1-1171 | CH₃ | CH₂cPr | —CH₂(Th-3-yl) |
| 1-1172 | CH₃ | CH₂cPr | —CH₂(Thz-4-yl) |
| 1-1173 | CH₃ | CH₂cPr | —CH₂(2-CN-Thz-4-yl) |
| 1-1174 | CH₃ | CH₂cPr | —CH₂(2-C(OH)(Me)₂-Th-4-yl) |
| 1-1175 | CH₃ | CH₂cPr | —CH₂(2-C(OH)(CF₃)₂-Th-4-yl) |
| 1-1176 | CH₃ | CH₂cPr | —CH₂(2-C(OH)(Me)₂-Th-5-yl) |
| 1-1177 | CH₃ | CH₂cPr | —CH₂(2-C(OH)(CF₃)₂-Th-5-yl) |
| 1-1178 | CH₃ | CH₂cPr | —CH₂(6-OMe-Py-2-yl) |
| 1-1179 | CH₃ | CH₂cPr | —CH₂(6-OMe-Py-3-yl) |
| 1-1180 | CH₃ | CH₂cPr | —CH₂(2-OMe-Py-3-yl) |
| 1-1181 | CH₃ | CH₂cPr | —CH₂(2-OMe-Py-4-yl) |
| 1-1182 | CH₃ | CH₂cPr | —CH₂CH₂Ph |
| 1-1183 | CH₃ | CH₂cPr | —CH₂CH₂(2-F-Ph) |
| 1-1184 | CH₃ | CH₂cPr | —CH₂CH₂(3-F-Ph) |
| 1-1185 | CH₃ | CH₂cPr | —CH₂CH₂(4-F-Ph) |
| 1-1186 | CH₃ | CH₂cPr | —CH₂CH₂(Th-2-yl) |
| 1-1187 | CH₃ | CH₂cPr | —CH(OH)Ph |
| 1-1188 | CH₃ | CH₂cPr | —CH(OH)(3-F-Ph) |
| 1-1189 | CH₃ | CH₂cPr | —CH(OH)(4-F-Ph) |
| 1-1190 | CH₃ | iPr | H |
| 1-1191 | CH₃ | iPr | Cl |
| 1-1192 | CH₃ | iPr | Br |
| 1-1193 | CH₃ | iPr | Me |
| 1-1194 | CH₃ | iPr | Et |
| 1-1195 | CH₃ | iPr | Pr |
| 1-1196 | CH₃ | iPr | iPr |
| 1-1197 | CH₃ | iPr | Bu |
| 1-1198 | CH₃ | iPr | iBu |
| 1-1199 | CH₃ | iPr | —CH₂OH |
| 1-1200 | CH₃ | iPr | —CH₂OMe |
| 1-1201 | CH₃ | iPr | —CH₂OEt |
| 1-1202 | CH₃ | iPr | —CH₂OiPr |
| 1-1203 | CH₃ | iPr | —CH₂OCH₂CH₂F |
| 1-1204 | CH₃ | iPr | —CH₂OcBu |
| 1-1205 | CH₃ | iPr | —CH₂OCH₂cPr |
| 1-1206 | CH₃ | iPr | —CH₂N(Me)₂ |
| 1-1207 | CH₃ | iPr | cPr |
| 1-1208 | CH₃ | iPr | —CH₂cPr |
| 1-1209 | CH₃ | iPr | —C≡CH |
| 1-1210 | CH₃ | iPr | Ph |
| 1-1211 | CH₃ | iPr | Pyz-4-yl |
| 1-1212 | CH₃ | iPr | Bn |
| 1-1213 | CH₃ | iPr | 2-F-Bn |
| 1-1214 | CH₃ | iPr | 3-F-Bn |
| 1-1215 | CH₃ | iPr | 4-F-Bn |
| 1-1216 | CH₃ | iPr | 2-CN-Bn |
| 1-1217 | CH₃ | iPr | 3-CN-Bn |
| 1-1218 | CH₃ | iPr | 3-COOH-Bn |
| 1-1219 | CH₃ | iPr | —CH₂(6-OMe-Py-2-yl) |
| 1-1220 | CH₃ | iPr | —CH₂(6-OMe-Py-3-yl) |
| 1-1221 | CH₃ | iPr | —CH₂CH₂Ph |
| 1-1222 | CH₃ | iPr | —CH(OH)Ph |
| 1-1223 | CH₃ | cBu | H |
| 1-1224 | CH₃ | cBu | Cl |
| 1-1225 | CH₃ | cBu | Br |
| 1-1226 | CH₃ | cBu | Me |
| 1-1227 | CH₃ | cBu | Et |
| 1-1228 | CH₃ | cBu | Pr |
| 1-1229 | CH₃ | cBu | iPr |
| 1-1230 | CH₃ | cBu | Bu |
| 1-1231 | CH₃ | cBu | iBu |
| 1-1232 | CH₃ | cBu | —CH₂OH |
| 1-1233 | CH₃ | cBu | —CH₂OMe |
| 1-1234 | CH₃ | cBu | —CH₂OEt |
| 1-1235 | CH₃ | cBu | —CH₂OiPr |
| 1-1236 | CH₃ | cBu | —CH₂OCH₂CH₂F |
| 1-1237 | CH₃ | cBu | —CH₂OcBu |
| 1-1238 | CH₃ | cBu | —CH₂OCH₂cPr |
| 1-1239 | CH₃ | cBu | —CH₂N(Me)₂ |
| 1-1240 | CH₃ | cBu | cPr |
| 1-1241 | CH₃ | cBu | —CH₂cPr |
| 1-1242 | CH₃ | cBu | —C≡CH |
| 1-1243 | CH₃ | cBu | Ph |
| 1-1244 | CH₃ | cBu | Pyz-4-yl |
| 1-1245 | CH₃ | cBu | Bn |
| 1-1246 | CH₃ | cBu | 2-F-Bn |
| 1-1247 | CH₃ | cBu | 3-F-Bn |
| 1-1248 | CH₃ | cBu | 4-F-Bn |
| 1-1249 | CH₃ | cBu | 2-CN-Bn |
| 1-1250 | CH₃ | cBu | 3-CN-Bn |

TABLE 1-continued

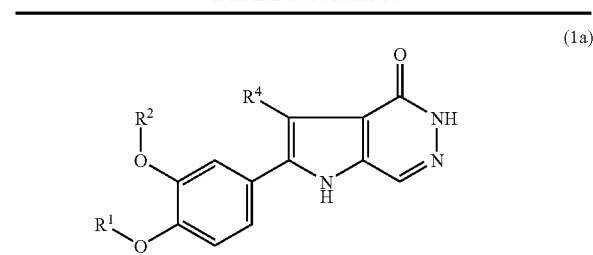
(1a)

| Compound No. | R¹ | R² | R⁴ |
|---|---|---|---|
| 1-1251 | CH₃ | cBu | 3-COOH-Bn |
| 1-1252 | CH₃ | cBu | —CH₂(6-OMe-Py-2-yl) |
| 1-1253 | CH₃ | cBu | —CH₂(6-OMe-Py-3-yl) |
| 1-1254 | CH₃ | cBu | —CH₂CH₂Ph |
| 1-1255 | CH₃ | cBu | —CH(OH)Ph |
| 1-1256 | CH₃ | cPent | H |
| 1-1257 | CH₃ | cPent | Cl |
| 1-1258 | CH₃ | cPent | Br |
| 1-1259 | CH₃ | cPent | Me |
| 1-1260 | CH₃ | cPent | Et |
| 1-1261 | CH₃ | cPent | Pr |
| 1-1262 | CH₃ | cPent | iPr |
| 1-1263 | CH₃ | cPent | Bu |
| 1-1264 | CH₃ | cPent | iBu |
| 1-1265 | CH₃ | cPent | —CH₂OH |
| 1-1266 | CH₃ | cPent | —CH₂OMe |
| 1-1267 | CH₃ | cPent | —CH₂OEt |
| 1-1268 | CH₃ | cPent | —CH₂OiPr |
| 1-1269 | CH₃ | cPent | —CH₂OCH₂F |
| 1-1270 | CH₃ | cPent | —CH₂OcBu |
| 1-1271 | CH₃ | cPent | —CH₂OCH₂cPr |
| 1-1272 | CH₃ | cPent | —CH₂N(Me)₂ |
| 1-1273 | CH₃ | cPent | cPr |
| 1-1274 | CH₃ | cPent | —CH₂cPr |
| 1-1275 | CH₃ | cPent | —C≡CH |
| 1-1276 | CH₃ | cPent | Ph |
| 1-1277 | CH₃ | cPent | Pyz-4-yl |
| 1-1278 | CH₃ | cPent | Bn |
| 1-1279 | CH₃ | cPent | 2-F-Bn |
| 1-1280 | CH₃ | cPent | 3-F-Bn |
| 1-1281 | CH₃ | cPent | 4-F-Bn |
| 1-1282 | CH₃ | cPent | 2-CN-Bn |
| 1-1283 | CH₃ | cPent | 3-CN-Bn |
| 1-1284 | CH₃ | cPent | 3-COOH-Bn |
| 1-1285 | CH₃ | cPent | —CH₂(6-OMe-Py-2-yl) |
| 1-1286 | CH₃ | cPent | —CH₂(6-OMe-Py-3-yl) |
| 1-1287 | CH₃ | cPent | —CH₂CH₂Ph |
| 1-1288 | CH₃ | cPent | —CH(OH) |
| 1-1289 | CHF₂ | cPr | —CH₂OiBu |
| 1-1290 | CHF₂ | CH₂cPr | —CH₂OiBu |
| 1-1291 | CHF₂ | iPr | —CH₂OiBu |
| 1-1292 | CHF₂ | cBu | —CH₂OiBu |
| 1-1293 | CHF₂ | cPent | —CH₂OiBu |
| 1-1294 | CH₃ | cPr | —CH₂OiBu |
| 1-1295 | CH₃ | CH₂cPr | —CH₂OiBu |
| 1-1296 | CH₃ | iPr | —CH₂OiBu |
| 1-1297 | CH₃ | cBu | —CH₂OiBu |
| 1-1298 | CH₃ | cPent | —CH₂OiBu |
| 1-1299 | CHF₂ | cPr | —CH₂OsBu |
| 1-1300 | CHF₂ | CH₂cPr | —CH₂OsBu |
| 1-1301 | CHF₂ | iPr | —CH₂OsBu |
| 1-1302 | CHF₂ | cBu | —CH₂OsBu |
| 1-1303 | CHF₂ | cPent | —CH₂OsBu |
| 1-1304 | CH₃ | cPr | —CH₂OsBu |
| 1-1305 | CH₃ | CH₂cPr | —CH₂OsBu |
| 1-1306 | CH₃ | iPr | —CH₂OsBu |
| 1-1307 | CH₃ | cBu | —CH₂OsBu |
| 1-1308 | CH₃ | cPent | —CH₂OsBu |
| 1-1309 | CHF₂ | cPr | —CH₂OtBu |
| 1-1310 | CHF₂ | CH₂cPr | —CH₂OtBu |
| 1-1311 | CHF₂ | iPr | —CH₂OtBu |
| 1-1312 | CHF₂ | cBu | —CH₂OtBu |
| 1-1313 | CHF₂ | cPent | —CH₂OtBu |
| 1-1314 | CH₃ | cPr | —CH₂OtBu |
| 1-1315 | CH₃ | CH₂cPr | —CH₂OtBu |

TABLE 1-continued

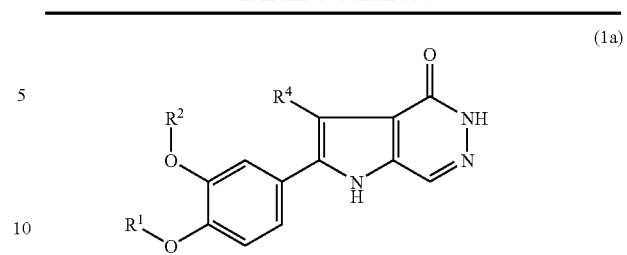
(1a)

| Compound No. | R¹ | R² | R⁴ |
|---|---|---|---|
| 1-1316 | CH₃ | iPr | —CH₂OtBu |
| 1-1317 | CH₃ | cBu | —CH₂OtBu |
| 1-1318 | CH₃ | cPent | —CH₂OtBu |
| 1-1319 | CHF₂ | cPr | —CH₂OCH(CH₂CH₃)₂ |
| 1-1320 | CHF₂ | CH₂cPr | —CH₂OCH(CH₂CH₃)₂ |
| 1-1321 | CHF₂ | iPr | —CH₂OCH(CH₂CH₃)₂ |
| 1-1322 | CHF₂ | cBu | —CH₂OCH(CH₂CH₃)₂ |
| 1-1323 | CHF₂ | cPent | —CH₂OCH(CH₂CH₃)₂ |
| 1-1324 | CH₃ | cPr | —CH₂OCH(CH₂CH₃)₂ |
| 1-1325 | CH₃ | CH₂cPr | —CH₂OCH(CH₂CH₃)₂ |
| 1-1326 | CH₃ | iPr | —CH₂OCH(CH₂CH₃)₂ |
| 1-1327 | CH₃ | cBu | —CH₂OCH(CH₂CH₃)₂ |
| 1-1328 | CH₃ | cPent | —CH₂OCH(CH₂CH₃)₂ |

TABLE 2

(1b)

| Compound No. | R¹ | R⁴ |
|---|---|---|
| 2-1 | CHF₂ | H |
| 2-2 | CHF₂ | Cl |
| 2-3 | CHF₂ | Br |
| 2-4 | CHF₂ | Me |
| 2-5 | CHF₂ | Et |
| 2-6 | CHF₂ | Pr |
| 2-7 | CHF₂ | iPr |
| 2-8 | CHF₂ | Bu |
| 2-9 | CHF₂ | iBu |
| 2-10 | CHF₂ | Pent |
| 2-11 | CHF₂ | —CH₂CH₂CH(Me)₂ |
| 2-12 | CHF₂ | —CH₂CH₂CH₂CH₂CH₂CH₃ |
| 2-13 | CHF₂ | —CH₂C(Me)₂CH₂CH₃ |
| 2-14 | CHF₂ | —CH₂CH₂C(Me)₃ |
| 2-15 | CHF₂ | —CH₂CF₃ |
| 2-16 | CHF₂ | —CH₂CH₂CF₃ |
| 2-17 | CHF₂ | —CH₂CH₂Cl |
| 2-18 | CHF₂ | —CH₂OH |
| 2-19 | CHF₂ | —CH₂C(OH)(Me)₂ |
| 2-20 | CHF₂ | —CH₂CH₂C(OH)(Me)₂ |
| 2-21 | CHF₂ | —CH₂CH₂CH₂C(OH)(Me)₂ |
| 2-22 | CHF₂ | —CH₂C(OH)(Et)₂ |
| 2-23 | CHF₂ | —CH₂C(CN)(Me)₂ |
| 2-24 | CHF₂ | —CH₂CH₂C(CN)(Me)₂ |
| 2-25 | CHF₂ | —CH₂C(COOH)(Me)₂ |
| 2-26 | CHF₂ | —CH₂CH₂C(COOH)(Me)₂ |
| 2-27 | CHF₂ | —CH₂CH₂CH₂C(COOH)(Me)₂ |
| 2-28 | CHF₂ | —CH₂OMe |
| 2-29 | CHF₂ | —CH₂CH₂OMe |
| 2-30 | CHF₂ | —CH₂OEt |
| 2-31 | CHF₂ | —CH₂CH₂OEt |
| 2-32 | CHF₂ | —CH₂OiPr |

TABLE 2-continued (1b)

| Compound No. | R¹ | R⁴ |
|---|---|---|
| 2-33 | CHF₂ | —CH₂CH₂OiPr |
| 2-34 | CHF₂ | —CH₂OCH₂CH₂F |
| 2-35 | CHF₂ | —CH₂OcBu |
| 2-36 | CHF₂ | —CH₂OCH₂cPr |
| 2-37 | CHF₂ | —CH₂N(Me)₂ |
| 2-38 | CHF₂ | cPr |
| 2-39 | CHF₂ | —CH₂cPr |
| 2-40 | CHF₂ | —CH₂cPr(1-OH) |
| 2-41 | CHF₂ | —CH₂cBu |
| 2-42 | CHF₂ | —CH₂cBu(1-OH) |
| 2-43 | CHF₂ | —CH(OH)cPr |
| 2-44 | CHF₂ | —CH(OH)cPr(1-OH) |
| 2-45 | CHF₂ | —CH(OH)cBu |
| 2-46 | CHF₂ | —CH(OH)cBu(1-OH) |
| 2-47 | CHF₂ | —CH₂CH₂cPr |
| 2-48 | CHF₂ | —CH₂CH₂cPr(1-OH) |
| 2-49 | CHF₂ | —CH₂CH₂cBu |
| 2-50 | CHF₂ | —CH₂CH₂cBu(1-OH) |
| 2-51 | CHF₂ | —CH₂CH=CH₂ |
| 2-52 | CHF₂ | —CH₂CH=CHMe |
| 2-53 | CHF₂ | —CH₂C(Me)=CH₂ |
| 2-54 | CHF₂ | —CH₂C(Me)=CHMe |
| 2-55 | CHF₂ | —CH₂CH=C(Me)₂ |
| 2-56 | CHF₂ | —CH₂C(Me)=C(Me)₂ |
| 2-57 | CHF₂ | —C≡CH |
| 2-58 | CHF₂ | —CH₂C≡CH |
| 2-59 | CHF₂ | —CH₂C≡CMe |
| 2-60 | CHF₂ | —CH(OH)CH=CH₂ |
| 2-61 | CHF₂ | —CH(OH)CH=CHMe |
| 2-62 | CHF₂ | —CH(OH)C≡CH |
| 2-63 | CHF₂ | —CH(OH)C≡CMe |
| 2-64 | CHF₂ | Ph |
| 2-65 | CHF₂ | 2-F-Ph |
| 2-66 | CHF₂ | 4-F-Ph |
| 2-67 | CHF₂ | 2,4-diF-Ph |
| 2-68 | CHF₂ | 2-Cl-Ph |
| 2-69 | CHF₂ | 4-Cl-Ph |
| 2-70 | CHF₂ | 4-CN-Ph |
| 2-71 | CHF₂ | 4-NO₂-Ph |
| 2-72 | CHF₂ | 4-COOH-Ph |
| 2-73 | CHF₂ | 4-CF₃-Ph |
| 2-74 | CHF₂ | 3-OMe-Ph |
| 2-75 | CHF₂ | 4-OMe-Ph |
| 2-76 | CHF₂ | 4-COOMe-Ph |
| 2-77 | CHF₂ | Th-2-yl |
| 2-78 | CHF₂ | 5-CN—Th-2-yl |
| 2-79 | CHF₂ | 5-COOH—Th-2-yl |
| 2-80 | CHF₂ | 5-Me—Th-2-yl |
| 2-81 | CHF₂ | 5-CF₃—Th-2-yl |
| 2-82 | CHF₂ | Th-3-yl |
| 2-83 | CHF₂ | 5-CN—Th-3-yl |
| 2-84 | CHF₂ | 5-COOH—Th-3-yl |
| 2-85 | CHF₂ | 5-Me—Th-3-yl |
| 2-86 | CHF₂ | 5-CF₃—Th-3-yl |
| 2-87 | CHF₂ | Thz-4-yl |
| 2-88 | CHF₂ | 2-CN—Thz-4-yl |
| 2-89 | CHF₂ | 2-COOH-Thz-4-yl |
| 2-90 | CHF₂ | 2-Me-Thz-4-yl |
| 2-91 | CHF₂ | 2-CF₃-Thz-4-yl |
| 2-92 | CHF₂ | 2-C(OH)(Me)₂-Thz-4-yl |
| 2-93 | CHF₂ | 2-C(OH)(CF₃)₂-Thz-4-yl |
| 2-94 | CHF₂ | Thz-5-yl |
| 2-95 | CHF₂ | 2-CN-Thz-5-yl |
| 2-96 | CHF₂ | 2-COOH-Thz-5-yl |
| 2-97 | CHF₂ | 2-Me-Thz-5-yl |
| 2-98 | CHF₂ | 2-CF₃-Thz-5-yl |
| 2-99 | CHF₂ | 2-C(OH)(Me)₂-Thz-5-yl |
| 2-100 | CHF₂ | 2-C(OH)(CF₃)₂-Thz-5-yl |
| 2-101 | CHF₂ | Pyz-4-yl |
| 2-102 | CHF₂ | 6-CN-Py-2-yl |
| 2-103 | CHF₂ | 6-COOH-Py-2-yl |
| 2-104 | CHF₂ | 6-CF₃-Py-2-yl |
| 2-105 | CHF₂ | 6-OMe-Py-2-yl |
| 2-106 | CHF₂ | 6-C(OH)(Me)₂-Py-2-yl |
| 2-107 | CHF₂ | 6-C(OH)(CF₃)₂-Py-2-yl |
| 2-108 | CHF₂ | 6-CN-Py-3-yl |
| 2-109 | CHF₂ | 6-COOH-Py-3-yl |
| 2-110 | CHF₂ | 6-CF₃-Py-3-yl |
| 2-111 | CHF₂ | 6-OMe-Py-3-yl |
| 2-112 | CHF₂ | 6-C(OH)(Me)₂-Py-3-yl |
| 2-113 | CHF₂ | 6-C(OH)(CF₃)₂-Py-3-yl |
| 2-114 | CHF₂ | 2-CN-Py-4-yl |
| 2-115 | CHF₂ | 2-COOH-Py-4-yl |
| 2-116 | CHF₂ | 2-CF₃-Py-4-yl |
| 2-117 | CHF₂ | 2-OMe-Py-4-yl |
| 2-118 | CHF₂ | 2-C(OH)(Me)₂-Py-4-yl |
| 2-119 | CHF₂ | 2-C(OH)(CF₃)₂-Py-4-yl |
| 2-120 | CHF₂ | Bn |
| 2-121 | CHF₂ | 2-F-Bn |
| 2-122 | CHF₂ | 3-F-Bn |
| 2-123 | CHF₂ | 4-F-Bn |
| 2-124 | CHF₂ | 2,4-diF-Bn |
| 2-125 | CHF₂ | 3,4-diF-Bn |
| 2-126 | CHF₂ | 2-Cl-Bn |
| 2-127 | CHF₂ | 3-Cl-Bn |
| 2-128 | CHF₂ | 2-CN-Bn |
| 2-129 | CHF₂ | 3-CN-Bn |
| 2-130 | CHF₂ | 3-COOH-Bn |
| 2-131 | CHF₂ | 4-COOH-Bn |
| 2-132 | CHF₂ | 3-CF₃-Bn |
| 2-133 | CHF₂ | 4-OMe-Bn |
| 2-134 | CHF₂ | 3-COOMe-Bn |
| 2-135 | CHF₂ | —CH₂(Th-2-yl) |
| 2-136 | CHF₂ | —CH₂(5-CN—Th-2-yl) |
| 2-137 | CHF₂ | —CH₂(5-COOH—Th-2-yl) |
| 2-138 | CHF₂ | —CH₂(5-CF₃—Th-2-yl) |
| 2-139 | CHF₂ | —CH₂(Th-3-yl) |
| 2-140 | CHF₂ | —CH₂(5-CN—Th-3-yl) |
| 2-141 | CHF₂ | —CH₂(5-COOH—Th-3-yl) |
| 2-142 | CHF₂ | —CH₂(5-CF₃—Th-3-yl) |
| 2-143 | CHF₂ | —CH₂(Thz—4-yl) |
| 2-144 | CHF₂ | —CH₂(2-CN-Thz-4-yl) |
| 2-145 | CHF₂ | —CH₂(2-COOH-Thz-4-yl) |
| 2-146 | CHF₂ | —CH₂(2-C(OH)(Me)₂-Thz-4-yl) |
| 2-147 | CHF₂ | —CH₂(2-C(OH)(CF₃)₂-Thz-4-yl) |
| 2-148 | CHF₂ | —CH₂(2-CN-Thz-5-yl) |
| 2-149 | CHF₂ | —CH₂(2-COOH-Thz-5-yl) |
| 2-150 | CHF₂ | —CH₂(2-C(OH)(Me)₂-Thz-5-yl) |
| 2-151 | CHF₂ | —CH₂(2-C(OH)(CF₃)₂-Thz-5-yl) |
| 2-152 | CHF₂ | —CH₂(6-CN-Py-2-yl) |
| 2-153 | CHF₂ | —CH₂(6-COOH-Py-2-yl) |
| 2-154 | CHF₂ | —CH₂(6-OMe-Py-2-yl) |
| 2-155 | CHF₂ | —CH₂(6-C(OH)(Me)₂-Py-2-yl) |
| 2-156 | CHF₂ | —CH₂(6-C(OH)(CF₃)₂-Py-2-yl) |
| 2-157 | CHF₂ | —CH₂(6-CN-Py-3-yl) |
| 2-158 | CHF₂ | —CH₂(6-COOH-Py-3-yl) |
| 2-159 | CHF₂ | —CH₂(6-OMe-Py-3-yl) |
| 2-160 | CHF₂ | —CH₂(6-C(OH)(Me)₂-Py-3-yl) |
| 2-161 | CHF₂ | —CH₂(6-C(OH)(CF₃)₂-Py-3-yl) |
| 2-162 | CHF₂ | —CH₂(2-CN-Py-3-yl) |
| 2-163 | CHF₂ | —CH₂(2-COOH-Py-3-yl) |
| 2-164 | CHF₂ | —CH₂(2-OMe-Py-3-yl) |

TABLE 2-continued (1b)

| Compound No. | R¹ | R⁴ |
|---|---|---|
| 2-165 | CHF₂ | —CH₂(2-C(OH)(Me)₂-Py-3-yl) |
| 2-166 | CHF₂ | —CH₂(2-C(OH)(CF₃)₂-Py-3-yl) |
| 2-167 | CHF₂ | —CH₂(2-CN-Py-4-yl) |
| 2-168 | CHF₂ | —CH₂(2-COOH-Py-4-yl) |
| 2-169 | CHF₂ | —CH₂(2-OMe-Py-4-yl) |
| 2-170 | CHF₂ | —CH₂(2-C(OH)(Me)₂-Py-4-yl) |
| 2-171 | CHF₂ | —CH₂(2-C(OH)(CF₃)₂-Py-4-yl) |
| 2-172 | CHF₂ | —CH₂CH₂Ph |
| 2-173 | CHF₂ | —CH₂CH₂(2-F-Ph) |
| 2-174 | CHF₂ | —CH₂CH₂(3-F-Ph) |
| 2-175 | CHF₂ | —CH₂CH₂(4-F-Ph) |
| 2-176 | CHF₂ | —CH₂CH₂(3-CN-Ph) |
| 2-177 | CHF₂ | —CH₂CH₂(Th-2-yl) |
| 2-178 | CHF₂ | —CH₂CH₂(6-CN-Py-2-yl) |
| 2-179 | CHF₂ | —CH₂CH₂(6-CN-Py-3-yl) |
| 2-180 | CHF₂ | —CH₂CH₂(2-CN-Py-3-yl) |
| 2-181 | CHF₂ | —CH(OH)Ph |
| 2-182 | CHF₂ | —CH(OH)(3-F-Ph) |
| 2-183 | CHF₂ | —CH(OH)(4-F-Ph) |
| 2-184 | CHF₂ | —CH(OH)(Th-2-yl) |
| 2-185 | CH₃ | H |
| 2-186 | CH₃ | Cl |
| 2-187 | CH₃ | Br |
| 2-188 | CH₃ | Me |
| 2-189 | CH₃ | Et |
| 2-190 | CH₃ | Pr |
| 2-191 | CH₃ | iPr |
| 2-192 | CH₃ | Bu |
| 2-193 | CH₃ | iBu |
| 2-194 | CH₃ | Pent |
| 2-195 | CH₃ | —CH₂CH₂CH(Me)₂ |
| 2-196 | CH₃ | —CH₂CH₂CH₂CH₂CH₃ |
| 2-197 | CH₃ | —CH₂CH₂C(Me)₃ |
| 2-198 | CH₃ | —CH₂CF₃ |
| 2-199 | CH₃ | —CH₂CH₂Cl |
| 2-200 | CH₃ | —CH₂OH |
| 2-201 | CH₃ | —CH₂C(OH)(Me)₂ |
| 2-202 | CH₃ | —CH₂C(OH)(Et)₂ |
| 2-203 | CH₃ | —CH₂C(CN)(Me)₂ |
| 2-204 | CH₃ | —CH₂C(COOH)(Me)₂ |
| 2-205 | CH₃ | —CH₂OMe |
| 2-206 | CH₃ | —CH₂CH₂OMe |
| 2-207 | CH₃ | —CH₂OEt |
| 2-208 | CH₃ | —CH₂CH₂OEt |
| 2-209 | CH₃ | —CH₂OiPr |
| 2-210 | CH₃ | —CH₂CH₂OiPr |
| 2-211 | CH₃ | —CH₂OCH₂CH₂F |
| 2-212 | CH₃ | —CH₂OcBu |
| 2-213 | CH₃ | —CH₂OCH₂cPr |
| 2-214 | CH₃ | —CH₂N(Me)₂ |
| 2-215 | CH₃ | cPr |
| 2-216 | CH₃ | —CH₂cPr |
| 2-217 | CH₃ | —CH₂cPr(1-OH) |
| 2-218 | CH₃ | —CH₂cBu |
| 2-219 | CH₃ | —CH(OH)cPr |
| 2-220 | CH₃ | —CH₂CH₂cPr |
| 2-221 | CH₃ | —CH₂CH₂cPr(1-OH) |
| 2-222 | CH₃ | —CH₂CH=CH₂ |
| 2-223 | CH₃ | —CH₂C(Me)=CH₂ |
| 2-224 | CH₃ | —CH₂CH=C(Me)₂ |
| 2-225 | CH₃ | —CH₂C(Me)=C(Me)₂ |
| 2-226 | CH₃ | —C≡CH |
| 2-227 | CH₃ | —CH₂C≡CH |
| 2-228 | CH₃ | —CH₂C≡CMe |
| 2-229 | CH₃ | Ph |
| 2-230 | CH₃ | 2-F-Ph |

TABLE 2-continued (1b)

| Compound No. | R¹ | R⁴ |
|---|---|---|
| 2-231 | CH₃ | 4-F-Ph |
| 2-232 | CH₃ | 4-CN-Ph |
| 2-233 | CH₃ | 4-COOH-Ph |
| 2-234 | CH₃ | 4-CF₃-Ph |
| 2-235 | CH₃ | 3-OMe-Ph |
| 2-236 | CH₃ | 4-OMe-Ph |
| 2-237 | CH₃ | Th-2-yl |
| 2-238 | CH₃ | Th-3-yl |
| 2-239 | CH₃ | Thz-4-yl |
| 2-240 | CH₃ | Thz-5-yl |
| 2-241 | CH₃ | Pyz-4-yl |
| 2-242 | CH₃ | 6-OMe-Py-2-yl |
| 2-243 | CH₃ | 6-OMe-Py-3-yl |
| 2-244 | CH₃ | 2-OMe-Py-4-yl |
| 2-245 | CH₃ | Bn |
| 2-246 | CH₃ | 2-F-Bn |
| 2-247 | CH₃ | 3-F-Bn |
| 2-248 | CH₃ | 4-F-Bn |
| 2-249 | CH₃ | 2,4-diF-Bn |
| 2-250 | CH₃ | 2-Cl-Bn |
| 2-251 | CH₃ | 2-CN-Bn |
| 2-252 | CH₃ | 3-CN-Bn |
| 2-253 | CH₃ | 3-COOH-Bn |
| 2-254 | CH₃ | 4-OMe-Bn |
| 2-255 | CH₃ | —CH₂(Th-2-yl) |
| 2-256 | CH₃ | —CH₂(Th-3-yl) |
| 2-257 | CH₃ | —CH₂(Thz-4-yl) |
| 2-258 | CH₃ | —CH₂(2-CN-Thz-4-yl) |
| 2-259 | CH₃ | —CH₂(2-C(OH)(Me)₂—Th-4-yl) |
| 2-260 | CH₃ | —CH₂(2-C(OH)(CF₃)₂—Th-4-yl) |
| 2-261 | CH₃ | —CH₂(2-C(OH)(Me)₂-Th-5-yl) |
| 2-262 | CH₃ | —CH₂(2-C(OH)(CF₃)₂-Th-5-yl) |
| 2-263 | CH₃ | —CH₂(6-OMe-Py-2-yl) |
| 2-264 | CH₃ | —CH₂(6-OMe-Py-3-yl) |
| 2-265 | CH₃ | —CH₂(2-OMe-Py-3-yl) |
| 2-266 | CH₃ | —CH₂(2-OMe-Py-4-yl) |
| 2-267 | CH₃ | —CH₂CH₂Ph |
| 2-268 | CH₃ | —CH₂CH₂(2-F-Ph) |
| 2-269 | CH₃ | —CH₂CH₂(3-F-Ph) |
| 2-270 | CH₃ | —CH₂CH₂(4-F-Ph) |
| 2-271 | CH₃ | —CH₂CH₂(Th-2-yl) |
| 2-272 | CH₃ | —CH(OH)Ph |
| 2-273 | CH₃ | —CH(OH)(3-F-Ph) |
| 2-274 | CH₃ | —CH(OH)(4-F-Ph) |

TABLE 3

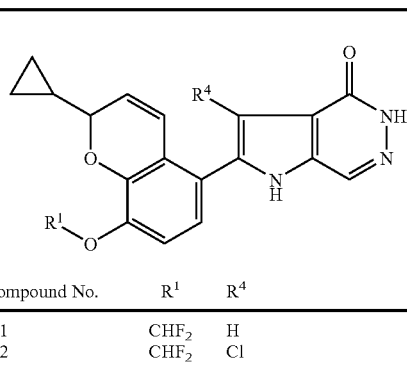

(1c)

| Compound No. | R¹ | R⁴ |
|---|---|---|
| 3-1 | CHF₂ | H |
| 3-2 | CHF₂ | Cl |

TABLE 3-continued (1c)

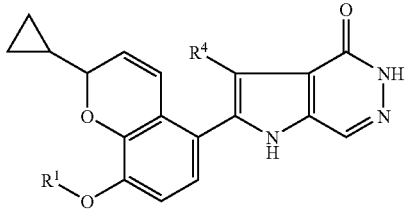

| Compound No. | R¹ | R⁴ |
|---|---|---|
| 3-3 | CHF₂ | Br |
| 3-4 | CHF₂ | Me |
| 3-5 | CHF₂ | Et |
| 3-6 | CHF₂ | Pr |
| 3-7 | CHF₂ | iPr |
| 3-8 | CHF₂ | Bu |
| 3-9 | CHF₂ | iBu |
| 3-10 | CHF₂ | Pent |
| 3-11 | CHF₂ | —CH₂CH₂CH(Me)₂ |
| 3-12 | CHF₂ | —CH₂CH₂CH₂CH₂CH₂CH₃ |
| 3-13 | CHF₂ | —CH₂C(Me)₂CH₂CH₃ |
| 3-14 | CHF₂ | —CH₂CH₂C(Me)₃ |
| 3-15 | CHF₂ | —CH₂CF₃ |
| 3-16 | CHF₂ | —CH₂CH₂CF₃ |
| 3-17 | CHF₂ | —CH₂CH₂Cl |
| 3-18 | CHF₂ | —CH₂OH |
| 3-19 | CHF₂ | —CH₂C(OH)(Me)₂ |
| 3-20 | CHF₂ | —CH₂CH₂C(OH)(Me)₂ |
| 3-21 | CHF₂ | —CH₂CH₂CH₂C(OH)(Me)₂ |
| 3-22 | CHF₂ | —CH₂C(OH)(Et)₂ |
| 3-23 | CHF₂ | —CH₂C(CN)(Me)₂ |
| 3-24 | CHF₂ | —CH₂CH₂C(CN)(Me)₂ |
| 3-25 | CHF₂ | —CH₂C(COOH)(Me)₂ |
| 3-26 | CHF₂ | —CH₂CH₂C(COOH)(Me)₂ |
| 3-27 | CHF₂ | —CH₂CH₂CH₂C(COOH)(Me)₂ |
| 3-28 | CHF₂ | —CH₂OMe |
| 3-29 | CHF₂ | —CH₂CH₂OMe |
| 3-30 | CHF₂ | —CH₂OEt |
| 3-31 | CHF₂ | —CH₂CH₂OEt |
| 3-32 | CHF₂ | —CH₂OiPr |
| 3-33 | CHF₂ | —CH₂CH₂OiPr |
| 3-34 | CHF₂ | —CH₂OCH₂CH₂F |
| 3-35 | CHF₂ | —CH₂OcBu |
| 3-36 | CHF₂ | —CH₂OCH₂cPr |
| 3-37 | CHF₂ | —CH₂N(Me)₂ |
| 3-38 | CHF₂ | cPr |
| 3-39 | CHF₂ | —CH₂cPr |
| 3-40 | CHF₂ | —CH₂cPr(1-OH) |
| 3-41 | CHF₂ | —CH₂cBu |
| 3-42 | CHF₂ | —CH₂cBu(1-OH) |
| 3-43 | CHF₂ | —CH(OH)cPr |
| 3-44 | CHF₂ | —CH(OH)cPr(1-OH) |
| 3-45 | CHF₂ | —CH(OH)cBu |
| 3-46 | CHF₂ | —CH(OH)cBu(1-OH) |
| 3-47 | CHF₂ | —CH₂CH₂cPr |
| 3-48 | CHF₂ | —CH₂CH₂cPr(1-OH) |
| 3-49 | CHF₂ | —CH₂CH₂cBu |
| 3-50 | CHF₂ | —CH₂CH₂cBu(1-OH) |
| 3-51 | CHF₂ | —CH₂CH=CH₂ |
| 3-52 | CHF₂ | —CH₂CH=CHMe |
| 3-53 | CHF₂ | —CH₂C(Me)=CH₂ |
| 3-54 | CHF₂ | —CH₂C(Me)=CHMe |
| 3-55 | CHF₂ | —CH₂CH=C(Me)₂ |
| 3-56 | CHF₂ | —CH₂C(Me)=C(Me)₂ |
| 3-57 | CHF₂ | —C≡CH |
| 3-58 | CHF₂ | —CH₂C≡CH |
| 3-59 | CHF₂ | —CH₂C≡CMe |
| 3-60 | CHF₂ | —CH(OH)CH=CH₂ |
| 3-61 | CHF₂ | —CH(OH)CH=CHMe |
| 3-62 | CHF₂ | —CH(OH)C≡CH |
| 3-63 | CHF₂ | —CH(OH)C≡CMe |
| 3-64 | CHF₂ | Ph |
| 3-65 | CHF₂ | 2-F-Ph |
| 3-66 | CHF₂ | 4-F-Ph |
| 3-67 | CHF₂ | 2,4-diF-Ph |
| 3-68 | CHF₂ | 2-Cl-Ph |

TABLE 3-continued (1c)

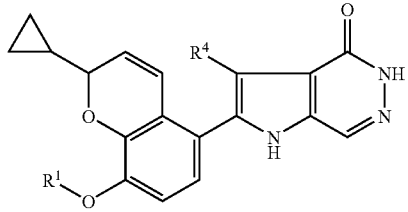

| Compound No. | R¹ | R⁴ |
|---|---|---|
| 3-69 | CHF₂ | 4-Cl-Ph |
| 3-70 | CHF₂ | 4-CN-Ph |
| 3-71 | CHF₂ | 4-NO₂-Ph |
| 3-72 | CHF₂ | 4-COOH-Ph |
| 3-73 | CHF₂ | 4-CF₃-Ph |
| 3-74 | CHF₂ | 3-OMe-Ph |
| 3-75 | CHF₂ | 4-OMe-Ph |
| 3-76 | CHF₂ | 4-COOMe-Ph |
| 3-77 | CHF₂ | Th-2-yl |
| 3-78 | CHF₂ | 5-CN—Th-2-yl |
| 3-79 | CHF₂ | 5-COOH—Th-2-yl |
| 3-80 | CHF₂ | 5-Me-Th-2-yl |
| 3-81 | CHF₂ | 5-CF₃-Th-2-yl |
| 3-82 | CHF₂ | Th-3-yl |
| 3-83 | CHF₂ | 5-CN—Th-3-yl |
| 3-84 | CHF₂ | 5-COOH—Th-3-yl |
| 3-85 | CHF₂ | 5-Me-Th-3-yl |
| 3-86 | CHF₂ | 5-CF₃-Th-3-yl |
| 3-87 | CHF₂ | Thz-4-yl |
| 3-88 | CHF₂ | 2-CN-Thz-4-yl |
| 3-89 | CHF₂ | 2-COOH-Thz-4-yl |
| 3-90 | CHF₂ | 2-Me-Thz-4-yl |
| 3-91 | CHF₂ | 2-CF₃-Thz-4-yl |
| 3-92 | CHF₂ | 2-C(OH)(Me)₂-Thz-4-yl |
| 3-93 | CHF₂ | 2-C(OH)(CF₃)₂-Thz-4-yl |
| 3-94 | CHF₂ | Thz-5-yl |
| 3-95 | CHF₂ | 2-CN-Thz-5-yl |
| 3-96 | CHF₂ | 2-COOH-Thz-5-yl |
| 3-97 | CHF₂ | 2-Me-Thz-5-yl |
| 3-98 | CHF₂ | 2-CF₃-Thz-5-yl |
| 3-99 | CHF₂ | 2-C(OH)(Me)₂-Thz-5-yl |
| 3-100 | CHF₂ | 2-C(OH)(CF₃)₂-Thz-5-yl |
| 3-101 | CHF₂ | Pyz-4-yl |
| 3-102 | CHF₂ | 6-CN-Py-2-yl |
| 3-103 | CHF₂ | 6-COOH-Py-2-yl |
| 3-104 | CHF₂ | 6-CF₃-Py-2-yl |
| 3-105 | CHF₂ | 6-OMe-Py-2-yl |
| 3-106 | CHF₂ | 6-C(OH)(Me)₂-Py-2-yl |
| 3-107 | CHF₂ | 6-C(OH)(CF₃)₂-Py-2-yl |
| 3-108 | CHF₂ | 6-CN-Py-3-yl |
| 3-109 | CHF₂ | 6-COOH-Py-3-yl |
| 3-110 | CHF₂ | 6-CF₃-Py-3-yl |
| 3-111 | CHF₂ | 6-OMe-Py-3-yl |
| 3-112 | CHF₂ | 6-C(OH)(Me)₂-Py-3-yl |
| 3-113 | CHF₂ | 6-C(OH)(CF₃)₂-Py-3-yl |
| 3-114 | CHF₂ | 2-CN-Py-4-yl |
| 3-115 | CHF₂ | 2-COOH-Py-4-yl |
| 3-116 | CHF₂ | 2-CF₃-Py-4-yl |
| 3-117 | CHF₂ | 2-OMe-Py-4-yl |
| 3-118 | CHF₂ | 2-C(OH)(Me)₂-Py-4-yl |
| 3-119 | CHF₂ | 2-C(OH)(CF₃)₂-Py-4-yl |
| 3-120 | CHF₂ | Bn |
| 3-121 | CHF₂ | 2-F-Bn |
| 3-122 | CHF₂ | 3-F-Bn |
| 3-123 | CHF₂ | 4-F-Bn |
| 3-124 | CHF₂ | 2,4-diF-Bn |
| 3-125 | CHF₂ | 3,4-diF-Bn |
| 3-126 | CHF₂ | 2-Cl-Bn |
| 3-127 | CHF₂ | 3-Cl-Bn |
| 3-128 | CHF₂ | 2-CN-Bn |
| 3-129 | CHF₂ | 3-CN-Bn |
| 3-130 | CHF₂ | 3-COOH-Bn |
| 3-131 | CHF₂ | 4-COOH-Bn |
| 3-132 | CHF₂ | 3-CF₃-Bn |
| 3-133 | CHF₂ | 4-OMe-Bn |
| 3-134 | CHF₂ | 3-COOMe-Bn |

TABLE 3-continued

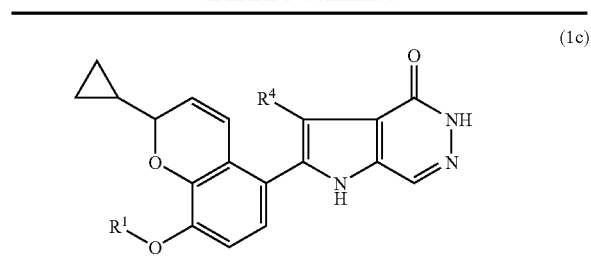

(1c)

| Compound No. | R¹ | R⁴ |
|---|---|---|
| 3-135 | CHF₂ | —CH₂(Th-2-yl) |
| 3-136 | CHF₂ | —CH₂(5-CN—Th-2-yl) |
| 3-137 | CHF₂ | —CH₂(5-COOH—Th-2-yl) |
| 3-138 | CHF₂ | —CH₂(5-CF₃—Th-2-yl) |
| 3-139 | CHF₂ | —CH₂(Th-3-yl) |
| 3-140 | CHF₂ | —CH₂(5-CN—Th-3-yl) |
| 3-141 | CHF₂ | —CH₂(5-COOH—Th-3-yl) |
| 3-142 | CHF₂ | —CH₂(5-CF₃—Th-3-yl) |
| 3-143 | CHF₂ | —CH₂(Thz-4-yl) |
| 3-144 | CHF₂ | —CH₂(2-CN-Thz-4-yl) |
| 3-145 | CHF₂ | —CH₂(2-COOH-Thz-4-yl) |
| 3-146 | CHF₂ | —CH₂(2-C(OH)(Me)₂-Thz-4-yl) |
| 3-147 | CHF₂ | —CH₂(2-C(OH)(CF₃)₂-Thz-4-yl) |
| 3-148 | CHF₂ | —CH₂(2-CN-Thz-5-yl) |
| 3-149 | CHF₂ | —CH₂(2-COOH-Thz-5-yl) |
| 3-150 | CHF₂ | —CH₂(2-C(OH)(Me)₂-Thz-5-yl) |
| 3-151 | CHF₂ | —CH₂(2-C(OH)(CF₃)₂-Thz-5-yl) |
| 3-152 | CHF₂ | —CH₂(6-CN-Py-2-yl) |
| 3-153 | CHF₂ | —CH₂(6-COOH-Py-2-yl) |
| 3-154 | CHF₂ | —CH₂(6-OMe-Py-2-yl) |
| 3-155 | CHF₂ | —CH₂(6-C(OH)(Me)₂-Py-2-yl) |
| 3-156 | CHF₂ | —CH₂(6-C(OH)(CF₃)₂-Py-2-yl) |
| 3-157 | CHF₂ | —CH₂(6-CN-Py-3-yl) |
| 3-158 | CHF₂ | —CH₂(6-COOH-Py-3-yl) |
| 3-159 | CHF₂ | —CH₂(6-OMe-Py-3-yl) |
| 3-160 | CHF₂ | —CH₂(6-C(OH)(Me)₂-Py-3-yl) |
| 3-161 | CHF₂ | —CH₂(6-C(OH)(CF₃)₂-Py-3-yl) |
| 3-162 | CHF₂ | —CH₂(2-CN-Py-3-yl) |
| 3-163 | CHF₂ | —CH₂(2-COOH-Py-3-yl) |
| 3-164 | CHF₂ | —CH₂(2-OMe-Py-3-yl) |
| 3-165 | CHF₂ | —CH₂(2-C(OH)(Me)₂-Py-3-yl) |
| 3-166 | CHF₂ | —CH₂(2-C(OH)(CF₃)₂-Py-3-yl) |
| 3-167 | CHF₂ | —CH₂(2-CN-Py-4-yl) |
| 3-168 | CHF₂ | —CH₂(2-COOH-Py-4-yl) |
| 3-169 | CHF₂ | —CH₂(2-OMe-Py-4-yl) |
| 3-170 | CHF₂ | —CH₂(2-C(OH)(Me)₂-Py-4-yl) |
| 3-171 | CHF₂ | —CH₂(2-C(OH)(CF₃)₂-Py-4-yl) |
| 3-172 | CHF₂ | —CH₂CH₂Ph |
| 3-173 | CHF₂ | —CH₂CH₂(2-F-Ph) |
| 3-174 | CHF₂ | —CH₂CH₂(3-F-Ph) |
| 3-175 | CHF₂ | —CH₂CH₂(4-F-Ph) |
| 3-176 | CHF₂ | —CH₂CH₂(3-CN-Ph) |
| 3-177 | CHF₂ | —CH₂CH₂(Th-2-yl) |
| 3-178 | CHF₂ | —CH₂CH₂(6-CN-Py-2-yl) |
| 3-179 | CHF₂ | —CH₂CH₂(6-CN-Py-3-yl) |
| 3-180 | CHF₂ | —CH₂CH₂(2-CN-Py-3-yl) |
| 3-181 | CHF₂ | —CH(OH)Ph |
| 3-182 | CHF₂ | —CH(OH)(3-F-Ph) |
| 3-183 | CHF₂ | —CH(OH)(4-F-Ph) |
| 3-184 | CHF₂ | —CH(OH)(Th-2-yl) |
| 3-185 | CH₃ | H |
| 3-186 | CH₃ | Cl |
| 3-187 | CH₃ | Br |
| 3-188 | CH₃ | Me |
| 3-189 | CH₃ | Et |
| 3-190 | CH₃ | Pr |
| 3-191 | CH₃ | iPr |
| 3-192 | CH₃ | Bu |
| 3-193 | CH₃ | iBu |
| 3-194 | CH₃ | Pent |
| 3-195 | CH₃ | —CH₂CH(Me)₂ |
| 3-196 | CH₃ | —CH₂CH₂CH₂CH₂CH₃ |
| 3-197 | CH₃ | —CH₂CH₂C(Me)₃ |
| 3-198 | CH₃ | —CH₂CF₃ |
| 3-199 | CH₃ | —CH₂CH₂Cl |
| 3-200 | CH₃ | —CH₂OH |
| 3-201 | CH₃ | —CH₂C(OH)(Me)₂ |
| 3-202 | CH₃ | —CH₂C(OH)(Et)₂ |
| 3-203 | CH₃ | —CH₂C(CN)(Me)₂ |
| 3-204 | CH₃ | —CH₂C(COOH)(Me)₂ |
| 3-205 | CH₃ | —CH₂OMe |
| 3-206 | CH₃ | —CH₂CH₂OMe |
| 3-207 | CH₃ | —CH₂OEt |
| 3-208 | CH₃ | —CH₂CH₂OEt |
| 3-209 | CH₃ | —CH₂OiPr |
| 3-210 | CH₃ | —CH₂CH₂OiPr |
| 3-211 | CH₃ | —CH₂OCH₂CH₂F |
| 3-212 | CH₃ | —CH₂OcBu |
| 3-213 | CH₃ | —CH₂OCH₂cPr |
| 3-214 | CH₃ | —CH₂N(Me)₂ |
| 3-215 | CH₃ | cPr |
| 3-216 | CH₃ | —CH₂cPr |
| 3-217 | CH₃ | —CH₂cPr(1-OH) |
| 3-218 | CH₃ | —CH₂cBu |
| 3-219 | CH₃ | —CH(OH)cPr |
| 3-220 | CH₃ | —CH₂cPr |
| 3-221 | CH₃ | —CH₂CH₂cPr(1-OH) |
| 3-222 | CH₃ | —CH₂CH=CH₂ |
| 3-223 | CH₃ | —CH₂C(Me)=CH₂ |
| 3-224 | CH₃ | —CH₂CH=C(Me)₂ |
| 3-225 | CH₃ | —CH₂C(Me)=C(Me)₂ |
| 3-226 | CH₃ | —C≡CH |
| 3-227 | CH₃ | —CH₂C≡CH |
| 3-228 | CH₃ | —CH₂C≡CMe |
| 3-229 | CH₃ | Ph |
| 3-230 | CH₃ | 2-F-Ph |
| 3-231 | CH₃ | 4-F-Ph |
| 3-232 | CH₃ | 4-CN-Ph |
| 3-233 | CH₃ | 4-COOH-Ph |
| 3-234 | CH₃ | 4-CF₃-Ph |
| 3-235 | CH₃ | 3-OMe-Ph |
| 3-236 | CH₃ | 4-OMe-Ph |
| 3-237 | CH₃ | Th-2-yl |
| 3-238 | CH₃ | Th-3-yl |
| 3-239 | CH₃ | Thz-4-yl |
| 3-240 | CH₃ | Thz-5-yl |
| 3-241 | CH₃ | Pyz-4-yl |
| 3-242 | CH₃ | 6-OMe-Py-2-yl |
| 3-243 | CH₃ | 6-OMe-Py-3-yl |
| 3-244 | CH₃ | 2-OMe-Py-4-yl |
| 3-245 | CH₃ | Bn |
| 3-246 | CH₃ | 2-F-Bn |
| 3-247 | CH₃ | 3-F-Bn |
| 3-248 | CH₃ | 4-F-Bn |
| 3-249 | CH₃ | 2,4-diF-Bn |
| 3-250 | CH₃ | 2-Cl-Bn |
| 3-251 | CH₃ | 2-CN-Bn |
| 3-252 | CH₃ | 3-CN-Bn |
| 3-253 | CH₃ | 3-COOH-Bn |
| 3-254 | CH₃ | 4-OMe-Bn |
| 3-255 | CH₃ | —CH₂(Th-2-yl) |
| 3-256 | CH₃ | —CH₃(Th-3-yl) |
| 3-257 | CH₃ | —CH₂(Thz-4-yl) |
| 3-258 | CH₃ | —CH₂(2-CN-Thz-4-yl) |
| 3-259 | CH₃ | —CH₂(2-C(OH)(Me)₂-Th-4-yl) |
| 3-260 | CH₃ | —CH₂(2-C(OH)(CF₃)₂—Th-4-yl) |
| 3-261 | CH₃ | —CH₂(2-C(OH)(Me)₂-Th-5-yl) |
| 3-262 | CH₃ | —CH₂(2-C(OH)(CF₃)₂—Th-5-yl) |
| 3-263 | CH₃ | —CH₂(6-OMe-Py-2-yl) |
| 3-264 | CH₃ | —CH₂(6-OMe-Py-3-yl) |
| 3-265 | CH₃ | —CH₂(2-OMe-Py-3-yl) |
| 3-266 | CH₃ | —CH₂(2-OMe-Py-4-yl) |

TABLE 3-continued (1c)

| Compound No. | R¹ | R⁴ |
| --- | --- | --- |
| 3-267 | CH₃ | —CH₂CH₂Ph |
| 3-268 | CH₃ | —CH₂CH₂(2-F-Ph) |
| 3-269 | CH₃ | —CH₂CH₂(3-F-Ph) |
| 3-270 | CH₃ | —CH₂CH₂(4-F-Ph) |
| 3-271 | CH₃ | —CH₂CH₂(Th-2-yl) |
| 3-272 | CH₃ | —CH(OH)Ph |
| 3-273 | CH₃ | —CH(OH)(3-F-Ph) |
| 3-274 | CH₃ | —CH(OH)(4-F-Ph) |

TABLE 4

(1d)

| Compound No. | n | R¹ | R⁴ |
| --- | --- | --- | --- |
| 4-1 | 1 | CHF₂ | H |
| 4-2 | 1 | CHF₂ | Cl |
| 4-3 | 1 | CHF₂ | Br |
| 4-4 | 1 | CHF₂ | Me |
| 4-5 | 1 | CHF₂ | Et |
| 4-6 | 1 | CHF₂ | Pr |
| 4-7 | 1 | CHF₂ | iPr |
| 4-8 | 1 | CHF₂ | Bu |
| 4-9 | 1 | CHF₂ | iBu |
| 4-10 | 1 | CHF₂ | —CH₂OH |
| 4-11 | 1 | CHF₂ | —CH₂OMe |
| 4-12 | 1 | CHF₂ | —CH₂OEt |
| 4-13 | 1 | CHF₂ | —CH₂OiPr |
| 4-14 | 1 | CHF₂ | —CH₂OCH₂CH₂F |
| 4-15 | 1 | CHF₂ | —CH₂OcBu |
| 4-16 | 1 | CHF₂ | —CH₂OCH₂cPr |
| 4-17 | 1 | CHF₂ | —CH₂N(Me)₂ |
| 4-18 | 1 | CHF₂ | cPr |
| 4-19 | 1 | CHF₂ | —CH₂cPr |
| 4-20 | 1 | CHF₂ | —C≡CH |
| 4-21 | 1 | CHF₂ | Ph |
| 4-22 | 1 | CHF₂ | Pyz-4-yl |
| 4-23 | 1 | CHF₂ | Bn |
| 4-24 | 1 | CHF₂ | 2-F-Bn |
| 4-25 | 1 | CHF₂ | 3-F-Bn |
| 4-26 | 1 | CHF₂ | 4-F-Bn |
| 4-27 | 1 | CHF₂ | 2-CN-Bn |
| 4-28 | 1 | CHF₂ | 3-CN-Bn |
| 4-29 | 1 | CHF₂ | 3-COOH-Bn |
| 4-30 | 1 | CHF₂ | —CH₂(6-OMe-Py-2-yl) |
| 4-31 | 1 | CHF₂ | —CH₂(6-OMe-Py-3-yl) |
| 4-32 | 1 | CHF₂ | —CH₂CH₂Ph |
| 4-33 | 1 | CHF₂ | —CH(OH)Ph |
| 4-34 | 2 | CHF₂ | H |
| 4-35 | 2 | CHF₂ | Cl |
| 4-36 | 2 | CHF₂ | Br |
| 4-37 | 2 | CHF₂ | Me |
| 4-38 | 2 | CHF₂ | Et |

TABLE 4-continued (1d)

| Compound No. | n | R¹ | R⁴ |
| --- | --- | --- | --- |
| 4-39 | 2 | CHF₂ | Pr |
| 4-40 | 2 | CHF₂ | iPr |
| 4-41 | 2 | CHF₂ | Bu |
| 4-42 | 2 | CHF₂ | iBu |
| 4-43 | 2 | CHF₂ | —CH₂OH |
| 4-44 | 2 | CHF₂ | —CH₂OMe |
| 4-45 | 2 | CHF₂ | —CH₂OEt |
| 4-46 | 2 | CHF₂ | —CH₂OiPr |
| 4-47 | 2 | CHF₂ | —CH₂OCH₂CH₂F |
| 4-48 | 2 | CHF₂ | —CH₂OcBu |
| 4-49 | 2 | CHF₂ | —CH₂OCH₂cPr |
| 4-50 | 2 | CHF₂ | —CH₂N(Me)₂ |
| 4-51 | 2 | CHF₂ | cPr |
| 4-52 | 2 | CHF₂ | —CH₂cPr |
| 4-53 | 2 | CHF₂ | —C≡CH |
| 4-54 | 2 | CHF₂ | Ph |
| 4-55 | 2 | CHF₂ | Pyz-4-yl |
| 4-56 | 2 | CHF₂ | Bn |
| 4-57 | 2 | CHF₂ | 2-F-Bn |
| 4-58 | 2 | CHF₂ | 3-F-Bn |
| 4-59 | 2 | CHF₂ | 4-F-Bn |
| 4-60 | 2 | CHF₂ | 2-CN-Bn |
| 4-61 | 2 | CHF₂ | 3-CN-Bn |
| 4-62 | 2 | CHF₂ | 3-COOH-Bn |
| 4-63 | 2 | CHF₂ | —CH₂(6-OMe-Py-2-yl) |
| 4-64 | 2 | CHF₂ | —CH₂(6-OMe-Py-3-yl) |
| 4-65 | 2 | CHF₂ | —CH₂CH₂Ph |
| 4-66 | 2 | CHF₂ | —CH(OH)Ph |
| 4-67 | 3 | CHF₂ | H |
| 4-68 | 3 | CHF₂ | Cl |
| 4-69 | 3 | CHF₂ | Br |
| 4-70 | 3 | CHF₂ | Me |
| 4-71 | 3 | CHF₂ | Et |
| 4-72 | 3 | CHF₂ | Pr |
| 4-73 | 3 | CHF₂ | iPr |
| 4-74 | 3 | CHF₂ | Bu |
| 4-75 | 3 | CHF₂ | iBu |
| 4-76 | 3 | CHF₂ | —CH₂OH |
| 4-77 | 3 | CHF₂ | —CH₂OMe |
| 4-78 | 3 | CHF₂ | —CH₂OEt |
| 4-79 | 3 | CHF₂ | —CH₂OiPr |
| 4-80 | 3 | CHF₂ | —CH₂OCH₂CH₂F |
| 4-81 | 3 | CHF₂ | —CH₂OcBu |
| 4-82 | 3 | CHF₂ | —CH₂OCH₂cPr |
| 4-83 | 3 | CHF₂ | —CH₂N(Me)₂ |
| 4-84 | 3 | CHF₂ | cPr |
| 4-85 | 3 | CHF₂ | —CH₂cPr |
| 4-86 | 3 | CHF₂ | —C≡CH |
| 4-87 | 3 | CHF₂ | Ph |
| 4-88 | 3 | CHF₂ | Pyz-4-yl |
| 4-89 | 3 | CHF₂ | Bn |
| 4-90 | 3 | CHF₂ | 2-F-Bn |
| 4-91 | 3 | CHF₂ | 3-F-Bn |
| 4-92 | 3 | CHF₂ | 4-F-Bn |
| 4-93 | 3 | CHF₂ | 2-CN-Bn |
| 4-94 | 3 | CHF₂ | 3-CN-Bn |
| 4-95 | 3 | CHF₂ | 3-COOH-Bn |
| 4-96 | 3 | CHF₂ | —CH₂(6-OMe-Py-2-yl) |
| 4-97 | 3 | CHF₂ | —CH₂(6-OMe-Py-3-yl) |
| 4-98 | 3 | CHF₂ | —CH₂CH₂Ph |
| 4-99 | 3 | CHF₂ | —CH(OH)Ph |
| 4-100 | 1 | CH₃ | H |
| 4-101 | 1 | CH₃ | Cl |
| 4-102 | 1 | CH₃ | Br |
| 4-103 | 1 | CH₃ | Me |
| 4-104 | 1 | CH₃ | Et |

TABLE 4-continued (1d)

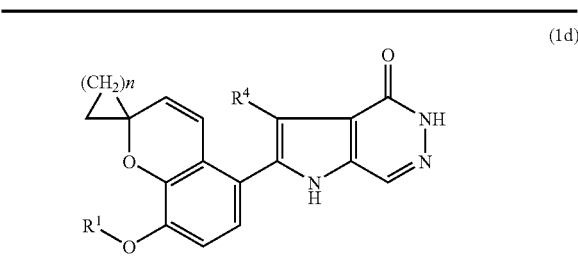

| Compound No. | n | R¹ | R⁴ |
|---|---|---|---|
| 4-105 | 1 | CH₃ | Pr |
| 4-106 | 1 | CH₃ | iPr |
| 4-107 | 1 | CH₃ | Bu |
| 4-108 | 1 | CH₃ | iBu |
| 4-109 | 1 | CH₃ | —CH₂OH |
| 4-110 | 1 | CH₃ | —CH₂OMe |
| 4-111 | 1 | CH₃ | —CH₂OEt |
| 4-112 | 1 | CH₃ | —CH₂OiPr |
| 4-113 | 1 | CH₃ | —CH₂OCH₂CH₂F |
| 4-114 | 1 | CH₃ | —CH₂OcBu |
| 4-115 | 1 | CH₃ | —CH₂OCH₂cPr |
| 4-116 | 1 | CH₃ | —CH₂N(Me)₂ |
| 4-117 | 1 | CH₃ | cPr |
| 4-118 | 1 | CH₃ | —CH₂cPr |
| 4-119 | 1 | CH₃ | —C≡CH |
| 4-120 | 1 | CH₃ | Ph |
| 4-121 | 1 | CH₃ | Pyz-4-yl |
| 4-122 | 1 | CH₃ | Bn |
| 4-123 | 1 | CH₃ | 2-F-Bn |
| 4-124 | 1 | CH₃ | 3-F-Bn |
| 4-125 | 1 | CH₃ | 4-F-Bn |
| 4-126 | 1 | CH₃ | 2-CN-Bn |
| 4-127 | 1 | CH₃ | 3-CN-Bn |
| 4-128 | 1 | CH₃ | 3-COOH-Bn |
| 4-129 | 1 | CH₃ | —CH₂(6-OMe-Py-2-yl) |
| 4-130 | 1 | CH₃ | —CH₂(6-OMe-Py-3-yl) |
| 4-131 | 1 | CH₃ | —CH₂CH₂Ph |
| 4-132 | 1 | CH₃ | —CH(OH)Ph |
| 4-133 | 2 | CH₃ | H |
| 4-134 | 2 | CH₃ | Cl |
| 4-135 | 2 | CH₃ | Br |
| 4-136 | 2 | CH₃ | Me |
| 4-137 | 2 | CH₃ | Et |
| 4-138 | 2 | CH₃ | Pr |
| 4-139 | 2 | CH₃ | iPr |
| 4-140 | 2 | CH₃ | Bu |
| 4-141 | 2 | CH₃ | iBu |
| 4-142 | 2 | CH₃ | —CH₂OH |
| 4-143 | 2 | CH₃ | —CH₂OMe |
| 4-144 | 2 | CH₃ | —CH₂OEt |
| 4-145 | 2 | CH₃ | —CH₂OiPr |
| 4-146 | 2 | CH₃ | —CH₂OCH₂CH₂F |
| 4-147 | 2 | CH₃ | —CH₂OcBu |
| 4-148 | 2 | CH₃ | —CH₂OCH₂cPr |
| 4-149 | 2 | CH₃ | —CH₂N(Me)₂ |
| 4-150 | 2 | CH₃ | cPr |
| 4-151 | 2 | CH₃ | —CH₂cPr |
| 4-152 | 2 | CH₃ | —C≡CH |
| 4-153 | 2 | CH₃ | Ph |
| 4-154 | 2 | CH₃ | Pyz-4-yl |
| 4-155 | 2 | CH₃ | Bn |
| 4-156 | 2 | CH₃ | 2-F-Bn |
| 4-157 | 2 | CH₃ | 3-F-Bn |
| 4-158 | 2 | CH₃ | 4-F-Bn |
| 4-159 | 2 | CH₃ | 2-CN-Bn |
| 4-160 | 2 | CH₃ | 3-CN-Bn |
| 4-161 | 2 | CH₃ | 3-COOH-Bn |
| 4-162 | 2 | CH₃ | —CH₂(6-OMe-Py-2-yl) |
| 4-163 | 2 | CH₃ | —CH₂(6-OMe-Py-3-yl) |
| 4-164 | 2 | CH₃ | —CH₂CH₂Ph |
| 4-165 | 2 | CH₃ | —CH(OH)Ph |
| 4-166 | 3 | CH₃ | H |
| 4-167 | 3 | CH₃ | Cl |
| 4-168 | 3 | CH₃ | Br |
| 4-169 | 3 | CH₃ | Me |
| 4-170 | 3 | CH₃ | Et |

TABLE 4-continued (1d)

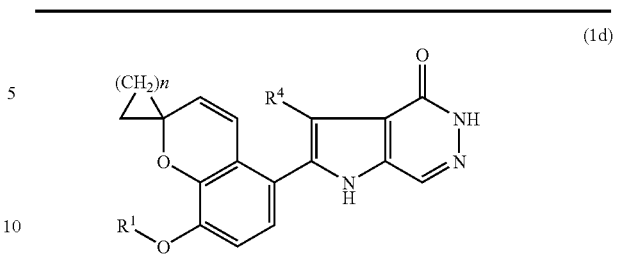

| Compound No. | n | R¹ | R⁴ |
|---|---|---|---|
| 4-171 | 3 | CH₃ | Pr |
| 4-172 | 3 | CH₃ | iPr |
| 4-173 | 3 | CH₃ | Bu |
| 4-174 | 3 | CH₃ | iBu |
| 4-175 | 3 | CH₃ | —CH₂OH |
| 4-176 | 3 | CH₃ | —CH₂OMe |
| 4-177 | 3 | CH₃ | —CH₂OEt |
| 4-178 | 3 | CH₃ | —CH₂OiPr |
| 4-179 | 3 | CH₃ | —CH₂OCH₂CH₂F |
| 4-180 | 3 | CH₃ | —CH₂OcBu |
| 4-181 | 3 | CH₃ | —CH₂OCH₂cPr |
| 4-182 | 3 | CH₃ | —CH₂N(Me)₂ |
| 4-183 | 3 | CH₃ | cPr |
| 4-184 | 3 | CH₃ | —CH₂cPr |
| 4-185 | 3 | CH₃ | —C≡CH |
| 4-186 | 3 | CH₃ | Ph |
| 4-187 | 3 | CH₃ | Pyz-4-yl |
| 4-188 | 3 | CH₃ | Bn |
| 4-189 | 3 | CH₃ | 2-F-Bn |
| 4-190 | 3 | CH₃ | 3-F-Bn |
| 4-191 | 3 | CH₃ | 4-F-Bn |
| 4-192 | 3 | CH₃ | 2-CN-Bn |
| 4-193 | 3 | CH₃ | 3-CN-Bn |
| 4-194 | 3 | CH₃ | 3-COOH-Bn |
| 4-195 | 3 | CH₃ | —CH₂(6-OMe-Py-2-yl) |
| 4-196 | 3 | CH₃ | —CH₂(6-OMe-Py-3-yl) |
| 4-197 | 3 | CH₃ | —CH₂CH₂Ph |
| 4-198 | 3 | CH₃ | —CH(OH) |

TABLE 5

(1e)

| Compound No. | n | R¹ | R⁴ |
|---|---|---|---|
| 5-1 | 1 | CHF₂ | H |
| 5-2 | 1 | CHF₂ | Cl |
| 5-3 | 1 | CHF₂ | Br |
| 5-4 | 1 | CHF₂ | Me |
| 5-5 | 1 | CHF₂ | Et |
| 5-6 | 1 | CHF₂ | Pr |
| 5-7 | 1 | CHF₂ | iPr |
| 5-8 | 1 | CHF₂ | Bu |
| 5-9 | 1 | CHF₂ | iBu |
| 5-10 | 1 | CHF₂ | —CH₂OH |
| 5-11 | 1 | CHF₂ | —CH₂OMe |
| 5-12 | 1 | CHF₂ | —CH₂OEt |
| 5-13 | 1 | CHF₂ | —CH₂OiPr |
| 5-14 | 1 | CHF₂ | —CH₂OCH₂CH₂F |
| 5-15 | 1 | CHF₂ | —CH₂OcBu |
| 5-16 | 1 | CHF₂ | —CH₂OCH₂cPr |
| 5-17 | 1 | CHF₂ | —CH₂N(Me)₂ |
| 5-18 | 1 | CHF₂ | cPr |

TABLE 5-continued

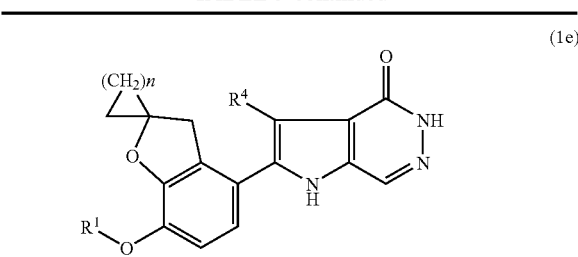

(1e)

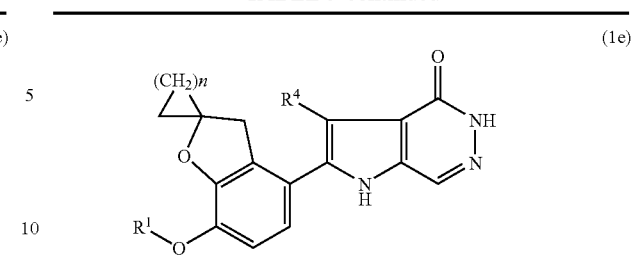

(1e)

| Compound No. | n | R¹ | R⁴ | | Compound No. | n | R¹ | R⁴ |
|---|---|---|---|---|---|---|---|---|
| 5-19 | 1 | CHF₂ | —CH₂cPr | | 5-85 | 3 | CHF₂ | —CH₂cPr |
| 5-20 | 1 | CHF₂ | —C≡CH | | 5-86 | 3 | CHF₂ | —C≡CH |
| 5-21 | 1 | CHF₂ | Ph | | 5-87 | 3 | CHF₂ | Ph |
| 5-22 | 1 | CHF₂ | Pyz-4-yl | | 5-88 | 3 | CHF₂ | Pyz-4-yl |
| 5-23 | 1 | CHF₂ | Bn | | 5-89 | 3 | CHF₂ | Bn |
| 5-24 | 1 | CHF₂ | 2-F-Bn | | 5-90 | 3 | CHF₂ | 2-F-Bn |
| 5-25 | 1 | CHF₂ | 3-F-Bn | | 5-91 | 3 | CHF₂ | 3-F-Bn |
| 5-26 | 1 | CHF₂ | 4-F-Bn | | 5-92 | 3 | CHF₂ | 4-F-Bn |
| 5-27 | 1 | CHF₂ | 2-CN-Bn | | 5-93 | 3 | CHF₂ | 2-CN-Bn |
| 5-28 | 1 | CHF₂ | 3-CN-Bn | | 5-94 | 3 | CHF₂ | 3-CN-Bn |
| 5-29 | 1 | CHF₂ | 3-COOH-Bn | | 5-95 | 3 | CHF₂ | 3-COOH-Bn |
| 5-30 | 1 | CHF₂ | —CH₂(6-OMe-Py-2-yl) | | 5-96 | 3 | CHF₂ | —CH₂(6-OMe-Py-2-yl) |
| 5-31 | 1 | CHF₂ | —CH₂(6-OMe-Py-3-yl) | | 5-97 | 3 | CHF₂ | —CH₂(6-OMe-Py-3-yl) |
| 5-32 | 1 | CHF₂ | —CH₂CH₂Ph | | 5-98 | 3 | CHF₂ | —CH₂CH₂Ph |
| 5-33 | 1 | CHF₂ | —CH(OH)Ph | | 5-99 | 3 | CHF₂ | —CH(OH)Ph |
| 5-34 | 2 | CHF₂ | H | | 5-100 | 1 | CH₃ | H |
| 5-35 | 2 | CHF₂ | Cl | | 5-101 | 1 | CH₃ | Cl |
| 5-36 | 2 | CHF₂ | Br | | 5-102 | 1 | CH₃ | Br |
| 5-37 | 2 | CHF₂ | Me | | 5-103 | 1 | CH₃ | Me |
| 5-38 | 2 | CHF₂ | Et | | 5-104 | 1 | CH₃ | Et |
| 5-39 | 2 | CHF₂ | Pr | | 5-105 | 1 | CH₃ | Pr |
| 5-40 | 2 | CHF₂ | iPr | | 5-106 | 1 | CH₃ | iPr |
| 5-41 | 2 | CHF₂ | Bu | | 5-107 | 1 | CH₃ | Bu |
| 5-42 | 2 | CHF₂ | iBu | | 5-108 | 1 | CH₃ | iBu |
| 5-43 | 2 | CHF₂ | —CH₂OH | | 5-109 | 1 | CH₃ | —CH₂OH |
| 5-44 | 2 | CHF₂ | —CH₂OMe | | 5-110 | 1 | CH₃ | —CH₂OMe |
| 5-45 | 2 | CHF₂ | —CH₂OEt | | 5-111 | 1 | CH₃ | —CH₂OEt |
| 5-46 | 2 | CHF₂ | —CH₂OiPr | | 5-112 | 1 | CH₃ | —CH₂OiPr |
| 5-47 | 2 | CHF₂ | —CH₂OCH₂CH₂F | | 5-113 | 1 | CH₃ | —CH₂OCH₂CH₂F |
| 5-48 | 2 | CHF₂ | —CH₂OcBu | | 5-114 | 1 | CH₃ | —CH₂OcBu |
| 5-49 | 2 | CHF₂ | —CH₂OCH₂cPr | | 5-115 | 1 | CH₃ | —CH₂OCH₂cPr |
| 5-50 | 2 | CHF₂ | —CH₂N(Me)₂ | | 5-116 | 1 | CH₃ | —CH₂N(Me)₂ |
| 5-51 | 2 | CHF₂ | cPr | | 5-117 | 1 | CH₃ | cPr |
| 5-52 | 2 | CHF₂ | —CH₂cPr | | 5-118 | 1 | CH₃ | —CH₂cPr |
| 5-53 | 2 | CHF₂ | —C≡CH | | 5-119 | 1 | CH₃ | —C≡CH |
| 5-54 | 2 | CHF₂ | Ph | | 5-120 | 1 | CH₃ | Ph |
| 5-55 | 2 | CHF₂ | Pyz-4-yl | | 5-121 | 1 | CH₃ | Pyz-4-yl |
| 5-56 | 2 | CHF₂ | Bn | | 5-122 | 1 | CH₃ | Bn |
| 5-57 | 2 | CHF₂ | 2-F-Bn | | 5-123 | 1 | CH₃ | 2-F-Bn |
| 5-58 | 2 | CHF₂ | 3-F-Bn | | 5-124 | 1 | CH₃ | 3-F-Bn |
| 5-59 | 2 | CHF₂ | 4-F-Bn | | 5-125 | 1 | CH₃ | 4-F-Bn |
| 5-60 | 2 | CHF₂ | 2-CN-Bn | | 5-126 | 1 | CH₃ | 2-CN-Bn |
| 5-61 | 2 | CHF₂ | 3-CN-Bn | | 5-127 | 1 | CH₃ | 3-CN-Bn |
| 5-62 | 2 | CHF₂ | 3-COOH-Bn | | 5-128 | 1 | CH₃ | 3-COOH-Bn |
| 5-63 | 2 | CHF₂ | —CH₂(6-OMe-Py-2-yl) | | 5-129 | 1 | CH₃ | —CH₂(6-OMe-Py-2-yl) |
| 5-64 | 2 | CHF₂ | CH₂(6-OMe-Py-3-yl) | | 5-130 | 1 | CH₃ | —CH₂(6-OMe-Py-3-yl) |
| 5-65 | 2 | CHF₂ | —CH₂CH₂Ph | | 5-131 | 1 | CH₃ | —CH₂CH₂Ph |
| 5-66 | 2 | CHF₂ | —CH(OH)Ph | | 5-132 | 1 | CH₃ | —CH(OH)Ph |
| 5-67 | 3 | CHF₂ | H | | 5-133 | 2 | CH₃ | H |
| 5-68 | 3 | CHF₂ | Cl | | 5-134 | 2 | CH₃ | Cl |
| 5-69 | 3 | CHF₂ | Br | | 5-135 | 2 | CH₃ | Br |
| 5-70 | 3 | CHF₂ | Me | | 5-136 | 2 | CH₃ | Me |
| 5-71 | 3 | CHF₂ | Et | | 5-137 | 2 | CH₃ | Et |
| 5-72 | 3 | CHF₂ | Pr | | 5-138 | 2 | CH₃ | Pr |
| 5-73 | 3 | CHF₂ | iPr | | 5-139 | 2 | CH₃ | iPr |
| 5-74 | 3 | CHF₂ | Bu | | 5-140 | 2 | CH₃ | Bu |
| 5-75 | 3 | CHF₂ | iBu | | 5-141 | 2 | CH₃ | iBu |
| 5-76 | 3 | CHF₂ | —CH₂OH | | 5-142 | 2 | CH₃ | —CH₂OH |
| 5-77 | 3 | CHF₂ | —CH₂OMe | | 5-143 | 2 | CH₃ | —CH₂OMe |
| 5-78 | 3 | CHF₂ | —CH₂OEt | | 5-144 | 2 | CH₃ | —CH₂OEt |
| 5-79 | 3 | CHF₂ | —CH₂OiPr | | 5-145 | 2 | CH₃ | —CH₂OiPr |
| 5-80 | 3 | CHF₂ | —CH₂CCH₂CH₂F | | 5-146 | 2 | CH₃ | —CH₂OCH₂CH₂F |
| 5-81 | 3 | CHF₂ | —CH₂OcBu | | 5-147 | 2 | CH₃ | —CH₂OcBu |
| 5-82 | 3 | CHF₂ | —CH₂OCH₂cPr | | 5-148 | 2 | CH₃ | —CH₂OCH₂cPr |
| 5-83 | 3 | CHF₂ | —CH₂N(Me)₂ | | 5-149 | 2 | CH₃ | —CH₂N(Me)₂ |
| 5-84 | 3 | CHF₂ | cPr | | 5-150 | 2 | CH₃ | cPr |

TABLE 5-continued

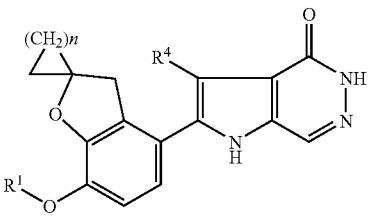

(1e)

| Compound No. | n | R¹ | R⁴ |
|---|---|---|---|
| 5-151 | 2 | CH₃ | —CH₂cPr |
| 5-152 | 2 | CH₃ | —C≡CH |
| 5-153 | 2 | CH₃ | Ph |
| 5-154 | 2 | CH₃ | Pyz-4-yl |
| 5-155 | 2 | CH₃ | Bn |
| 5-156 | 2 | CH₃ | 2-F-Bn |
| 5-157 | 2 | CH₃ | 3-F-Bn |
| 5-158 | 2 | CH₃ | 4-F-Bn |
| 5-159 | 2 | CH₃ | 2-CN-Bn |
| 5-160 | 2 | CH₃ | 3-CN-Bn |
| 5-161 | 2 | CH₃ | 3-COOH-Bn |
| 5-162 | 2 | CH₃ | —CH₂(6-OMe-Py-2-yl) |
| 5-163 | 2 | CH₃ | —CH₂(6-OMe-Py-3-yl) |
| 5-164 | 2 | CH₃ | —CH₂CH₂Ph |
| 5-165 | 2 | CH₃ | —CH(OH)Ph |
| 5-166 | 3 | CH₃ | H |
| 5-167 | 3 | CH₃ | Cl |
| 5-168 | 3 | CH₃ | Br |
| 5-169 | 3 | CH₃ | Me |
| 5-170 | 3 | CH₃ | Et |
| 5-171 | 3 | CH₃ | Pr |
| 5-172 | 3 | CH₃ | iPr |
| 5-173 | 3 | CH₃ | Bu |
| 5-174 | 3 | CH₃ | iBu |
| 5-175 | 3 | CH₃ | —CH₂OH |
| 5-176 | 3 | CH₃ | —CH₂OMe |
| 5-177 | 3 | CH₃ | —CH₂OEt |
| 5-178 | 3 | CH₃ | —CH₂OiPr |
| 5-179 | 3 | CH₃ | —CH₂OCH₂CH₂F |
| 5-180 | 3 | CH₃ | —CH₂OcBu |
| 5-181 | 3 | CH₃ | —CH₂OCH₂cPr |
| 5-182 | 3 | CH₃ | —CH₂N(Me)₂ |
| 5-183 | 3 | CH₃ | cPr |
| 5-184 | 3 | CH₃ | —CH₂cPr |
| 5-185 | 3 | CH₃ | —C≡CH |
| 5-186 | 3 | CH₃ | Ph |
| 5-187 | 3 | CH₃ | Pyz-4-yl |
| 5-188 | 3 | CH₃ | Bn |
| 5-189 | 3 | CH₃ | 2-F-Bn |
| 5-190 | 3 | CH₃ | 3-F-Bn |
| 5-191 | 3 | CH₃ | 4-F-Bn |
| 5-192 | 3 | CH₃ | 2-CN-Bn |
| 5-193 | 3 | CH₃ | 3-CN-Bn |
| 5-194 | 3 | CH₃ | 3-COOH-Bn |
| 5-195 | 3 | CH₃ | —CH₂(6-OMe-Py-2-yl) |
| 5-196 | 3 | CH₃ | —CH₂(6-OMe-Py-3-yl) |
| 5-197 | 3 | CH₃ | —CH₂CH₂Ph |
| 5-198 | 3 | CH₃ | —CH(OH)Ph |

Incidentally, the abbreviations in the above-mentioned respective Tables mean the following groups.
Me: methyl group,
Et: ethyl group,
Pr: propyl group,
Bu: butyl group,
Pent: pentyl group,
iPr: isopropyl group,
iBu: isobutyl group,
sBu: sec-butyl group,
tBu: tert-butyl group,
cPr: cyclopropyl group,
cBu: cyclobutyl group,
cPent: cyclopentyl group,
Ac: acetyl group,
cPr(1-OH): 1-hydroxycyclopropyl group,
cBu(1-OH): 1-hydroxycyclobutyl group,
Ph: phenyl group,
2-F-Ph: 2-fluorophenyl group,
3-F-Ph: 3-fluorophenyl group,
4-F-Ph: 4-fluorophenyl group,
2,4-diF-Ph: 2,4-difluorophenyl group,
2,6-diF-Ph: 2,6-difluorophenyl group,
3,4-diF-Ph: 3,4-difluorophenyl group,
2-Cl-Ph: 2-chlorophenyl group,
3-Cl-Ph: 3-chlorophenyl group,
4-Cl-Ph: 4-chlorophenyl group,
2,4-diCl-Ph: 2,4-dichlorophenyl group,
2,6-diCl-Ph: 2,6-dichlorophenyl group,
3,4-diCl-Ph: 3,4-dichlorophenyl group,
3-CN-Ph: 3-cyanophenyl group,
4-CN-Ph: 4-cyanophenyl group,
3-NO₂-Ph: 3-nitrophenyl group,
4-NO₂-Ph: 4-nitrophenyl group,
3-COOH-Ph: 3-carboxyphenyl group,
4-COOH-Ph: 4-carboxyphenyl group,
3-CF₃-Ph: 3-trifluoromethylphenyl group,
4-CF₃-Ph: 4-trifluoromethylphenyl group,
3-C(OH) (Me)₂-Ph: 3-(1-hydroxy-1-methylethyl)phenyl group,
4-C(OH) (Me)₂-Ph: 4-(1-hydroxy-1-methylethyl)phenyl group,
3-C(OH) (CF₃)₂-Ph: 3-(2,2,2-trifluoro-1-hydroxy-1-trifluoromethylethyl)phenyl group,
4-C(OH) (CF₃)₂-Ph: 4-(2,2,2-trifluoro-1-hydroxy-1-trifluoromethylethyl)phenyl group,
3-C(COOH)(Me)₂-Ph: 3-(1-carboxy-1-methylethyl)phenyl group,
4-C(COOH) (Me)₂-Ph: 4-(1-carboxy-1-methylethyl)phenyl group,
3-OMe-Ph: 3-methoxyphenyl group,
4-OMe-Ph: 4-methoxyphenyl group,
3-OEt-Ph: 3-ethoxyphenyl group,
4-OEt-Ph: 4-ethoxyphenyl group,
3-COOMe-Ph: 3-methoxycarbonylphenyl group,
4-COOMe-Ph: 4-methoxycarbonylphenyl group,
3-COOEt-Ph: 3-ethoxycarbonylphenyl group,
4-COOEt-Ph: 4-ethoxycarbonylphenyl group,
Th-2-yl: 2-thienyl group,
4-CN—Th-2-yl: 4-cyano-2-thienyl group,
5-CN—Th-2-yl: 5-cyano-2-thienyl group,
4-COOH—Th-2-yl: 4-carboxy-2-thienyl group,
5-COOH—Th-2-yl: 5-carboxy-2-thienyl group,
4-Me-Th-2-yl: 4-methyl-2-thienyl group,
5-Me-Th-2-yl: 5-methyl-2-thienyl group,
4-CF₃—Th-2-yl: 4-trifluoromethyl-2-thienyl group,
5-CF₃—Th-2-yl: 5-trifluoromethyl-2-thienyl group,
4-C(OH)(Me)₂-Th-2-yl: 4-(1-hydroxy-1-methylethyl)-2-thienyl group,
5-C(OH)(Me)₂-Th-2-yl: 5-(1-hydroxy-1-methylethyl)-2-thienyl group,
4-C(OH)(CF₃)₂—Th-2-yl: 4-(2,2,2-trifluoro-1-hydroxy-1-trifluoromethylethyl)-2-thienyl group,
5-C(OH)(CF₃)₂—Th-2-yl: 5-(2,2,2-trifluoro-1-hydroxy-1-trifluoromethylethyl)-2-thienyl group,
4-C(COOH)(Me)₂-Th-2-yl: 4-(1-carboxy-1-methylethyl)-2-thienyl group,
5-C(COOH)(Me)₂-Th-2-yl: 5-(1-carboxy-1-methylethyl)-2-thienyl group,
Th-3-yl: 3-thienyl group,
4-CN—Th-3-yl: 4-cyano-3-thienyl group, 5-CN—Th-3-yl: 5-cyano-3-thienyl group,
4-COOH—Th-3-yl: 4-carboxy-3-thienyl group,
5-COOH—Th-3-yl: 5-carboxy-3-thienyl group,
4-Me-Th-3-yl: 4-methyl-3-thienyl group,
5-Me-Th-3-yl: 5-methyl-3-thienyl group,
4-CF$_3$—Th-3-yl: 4-trifluoromethyl-3-thienyl group,
5-CF$_3$—Th-3-yl: 5-trifluoromethyl-3-thienyl group,
5-Et-Th-3-yl: 5-ethyl-3-thienyl group,
5-C(OH)(Me)$_2$-Th-3-yl: 5-(1-hydroxy-1-methylethyl)-3-thienyl group,
5-C(OH)(CF$_3$)$_2$—Th-3-yl: 5-(2,2,2-trifluoro-1-hydroxy-1-trifluoromethylethyl)-3-thienyl group,
5-C(COOH)(Me)$_2$-Th-3-yl: 5-(1-carboxy-1-methylethyl)-3-thienyl group,
5-COOMe-Th-3-yl: 5-methoxycarbonyl-3-thienyl group,
Thz-4-yl: 4-thiazolyl group,
2-CN-Thz-4-yl: 2-cyano-4-thiazolyl group,
2-COOH-Thz-4-yl: 2-carboxy-4-thiazolyl group,
2-Me-Thz-4-yl: 2-methyl-4-thiazolyl group,
2-Et-Thz-4-yl: 2-ethyl-4-thiazolyl group,
2-Pr-Thz-4-yl: 2-propyl-4-thiazolyl group,
2-iPr-Thz-4-yl: 2-isopropyl-4-thiazolyl group,
2-CF$_3$-Thz-4-yl: 2-trifluoromethyl-4-thiazolyl group,
2-C(OH)(Me)$_2$-Thz-4-yl: 2-(1-hydroxy-1-methylethyl)-4-thiazolyl group,
2-C(OH)(CF$_3$)$_2$-Thz-4-yl: 2-(2,2,2-trifluoro-1-hydroxy-1-trifluoromethylethyl)-4-thiazolyl group,
2-C(COOH)(Me)$_2$-Thz-4-yl: 2-(1-carboxy-1-methylethyl)-4-thiazolyl group,
2-COOMe-Thz-4-yl: 2-methoxycarbonyl-4-thiazolyl group,
Thz-5-yl: 5-thiazolyl group,
2-CN-Thz-5-yl: 2-cyano-5-thiazolyl group,
2-COOH-Thz-5-yl: 2-carboxy-5-thiazolyl group,
2-Me-Thz-5-yl: 2-methyl-5-thiazolyl group,
2-Et-Thz-5-yl: 2-ethyl-5-thiazolyl group,
2-CF$_3$-Thz-5-yl: 2-trifluoromethyl-5-thiazolyl group,
2-C(OH)(Me)$_2$-Thz-5-yl: 2-(1-hydroxy-1-methylethyl)-5-thiazolyl group,
2-C(OH)(CF$_3$)$_2$-Thz-5-yl: 2-(2,2,2-trifluoro-1-hydroxy-1-trifluoromethylethyl)-5-thiazolyl group,
2-C(COOH)(Me)$_2$-Thz-5-yl: 2-(1-carboxy-1-methylethyl)-5-thiazolyl group,
2-COOMe-Thz-5-yl: 2-methoxycarbonyl-5-thiazolyl group,
2-COOEt-Thz-5-yl: 2-ethoxycarbonyl-5-thiazolyl group,
2-COOPr-Thz-5-yl: 2-propoxycarbonyl-5-thiazolyl group,
2-COOiPr-Thz-5-yl: 2-isopropoxycarbonyl-5-thiazolyl group,
Pyz-4-yl: 4-pyrazolyl group,
6-CN-Py-2-yl: 6-cyano-2-pyridyl group,
6-COOH-Py-2-yl: 6-carboxy-2-pyridyl group,
6-CF$_3$-Py-2-yl: 6-trifluoromethyl-2-pyridyl group,
6-OMe-Py-2-yl: 6-methoxy-2-pyridyl group,
6-OEt-Py-2-yl: 6-ethoxy-2-pyridyl group,
6-COOMe-Py-2-yl: 6-methoxycarbonyl-2-pyridyl group,
6-COOEt-Py-2-yl: 6-ethoxycarbonyl-2-pyridyl group,
6-C(OH)(Me)$_2$-Py-2-yl: 6-(1-hydroxy-1-methylethyl)-2-pyridyl group,
6-C(OH)(CF$_3$)$_2$-Py-2-yl: 6-(2,2,2-trifluoro-1-hydroxy-1-trifluoromethylethyl)-2-pyridyl group,
6-C(COOH)(Me)$_2$-Py-2-yl: 6-(1-carboxy-1-methylethyl)-2-pyridyl group,
6-CN-Py-3-yl: 6-cyano-3-pyridyl group,
6-COOH-Py-3-yl: 6-carboxy-3-pyridyl group,
6-CF$_3$-Py-3-yl: 6-trifluoromethyl-3-pyridyl group,
6-OMe-Py-3-yl: 6-methoxy-3-pyridyl group,
6-OEt-Py-3-yl: 6-ethoxy-3-pyridyl group,
6-COOMe-Py-3-yl: 6-methoxycarbonyl-3-pyridyl group,
6-COOEt-Py-3-yl: 6-ethoxycarbonyl-3-pyridyl group,
6-C(OH)(Me)$_2$-Py-3-yl: 6-(1-hydroxy-1-methylethyl)-3-pyridyl group,
6-C(OH)(CF$_3$)$_2$-Py-3-yl: 6-(2,2,2-trifluoro-1-hydroxy-1-trifluoromethylethyl)-3-pyridyl group,
6-C(COOH)(Me)$_2$-Py-3-yl: 6-(1-carboxy-1-methylethyl)-3-pyridyl group,
2-CN-Py-3-yl: 2-cyano-3-pyridyl group,
2-COOH-Py-3-yl: 2-carboxy-3-pyridyl group,
2-CF$_3$-Py-3-yl: 2-trifluoromethyl-3-pyridyl group,
2-OMe-Py-3-yl: 2-methoxy-3-pyridyl group,
2-OEt-Py-3-yl: 2-ethoxy-3-pyridyl group,
2-OPr-Py-3-yl: 2-propoxy-3-pyridyl group,
2-COOMe-Py-3-yl: 2-methoxycarbonyl-3-pyridyl group,
2-COOEt-Py-3-yl: 2-ethoxycarbonyl-3-pyridyl group,
2-COOPr-Py-3-yl: 2-propoxycarbonyl-3-pyridyl group,
2-C(OH)(Me)$_2$-Py-3-yl: 2-(1-hydroxy-1-methylethyl)-3-pyridyl group,
2-C(OH)(CF$_3$)$_2$-Py-3-yl: 2-(2,2,2-trifluoro-1-hydroxy-1-trifluoromethylethyl)-3-pyridyl group,
2-C(COOH)(Me)$_2$-Py-3-yl: 2-(1-carboxy-1-methylethyl)-3-pyridyl group,
2-CN-Py-4-yl: 2-cyano-4-pyridyl group,
2-COOH-Py-4-yl: 2-carboxy-4-pyridyl group,
2-CF$_3$-Py-4-yl: 2-trifluoromethyl-4-pyridyl group,
2-OMe-Py-4-yl: 2-methoxy-4-pyridyl group,
2-OEt-Py-4-yl: 2-ethoxy-4-pyridyl group,
2-OPr-Py-4-yl: 2-propoxy-4-pyridyl group,
2-COOMe-Py-4-yl: 2-methoxycarbonyl-4-pyridyl group,
2-COOEt-Py-4-yl: 2-ethoxycarbonyl-4-pyridyl group,
2-C(OH)(Me)$_2$-Py-4-yl: 2-(1-hydroxy-1-methylethyl)-4-pyridyl group,
2-C(OH)(CF$_3$)$_2$-Py-4-yl: 2-(2,2,2-trifluoro-1-hydroxy-1-trifluoromethylethyl)-4-pyridyl group,
2-C(COOH)(Me)$_2$-Py-4-yl: 2-(1-carboxy-1-methylethyl)-4-pyridyl group,
Bn: benzyl group,
2-F-Bn: 2-fluorobenzyl group,
3-F-Bn: 3-fluorobenzyl group,
4-F-Bn: 4-fluorobenzyl group,
2,4-diF-Bn: 2,4-difluorobenzyl group,
3,4-diF-Bn: 3,4-difluorobenzyl group,
2—Cl-Bn: 2-chlorobenzyl group,
3—Cl-Bn: 3-chlorobenzyl group,
4—Cl-Bn: 4-chlorobenzyl group,
2,4-diCl-Bn: 2,4-dichlorobenzyl group,
3,4-diCl-Bn: 3,4-dichlorobenzyl group,
2-CN-Bn: 2-cyanobenzyl group,
3-CN-Bn: 3-cyanobenzyl group,
4-CN-Bn: 4-cyanobenzyl group,
3-NO$_2$-Bn: 3-nitrobenzyl group,
3-COOH-Bn: 3-carboxybenzyl group,
4-COOH-Bn: 4-carboxybenzyl group,
3-CF$_3$-Bn: 3-trifluoromethylbenzyl group,
4-CF$_3$-Bn: 4-trifluoromethylbenzyl group,
3-C(OH)(Me)$_2$-Bn: 3-(1-hydroxy-1-methylethyl)benzyl group,
4-C(OH)(Me)$_2$-Bn: 4-(1-hydroxy-1-methylethyl)benzyl group,
3-C(OH)(CF$_3$)$_2$-Bn: 3-(2,2,2-trifluoro-1-hydroxy-1-trifluoromethylethyl)benzyl group,
4-C(OH)(CF$_3$)$_2$-Bn: 4-(2,2,2-trifluoro-1-hydroxy-1-trifluoromethylethyl)benzyl group,
4-C(COOH)(Me)$_2$-Bn: 4-(1-carboxy-1-methylethyl)benzyl group,
3-OMe-Bn: 3-methoxybenzyl group,
4-OMe-Bn: 4-methoxybenzyl group, 3-COOMe-Bn: 3-methoxycarbonylbenzyl group, or
4-COOMe-Bn: 4-methoxycarbonylbenzyl group.

In the above-mentioned Tables, more preferred are compounds of Compounds Nos. 1-1, 1-2, 1-3, 1-4, 1-5, 1-6, 1-7, 1-8, 1-9, 1-10, 1-11, 1-12, 1-14, 1-15, 1-16, 1-29, 1-30, 1-31, 1-32, 1-33, 1-34, 1-38, 1-39, 1-40, 1-41, 1-42, 1-43, 1-46, 1-47, 1-48, 1-50, 1-51, 1-52, 1-56, 1-60, 1-61, 1-66, 1-70, 1-71, 1-78, 1-79, 1-86, 1-87, 1-90, 1-102, 1-112, 1-123, 1-124, 1-131, 1-132, 1-139, 1-140, 1-147, 1-155, 1-156, 1-163, 1-164, 1-167, 1-168, 1-177, 1-178, 1-182, 1-183, 1-192, 1-193, 1-197, 1-207, 1-208, 1-209, 1-210, 1-211, 1-212, 1-213, 1-214, 1-215, 1-216, 1-217, 1-218, 1-219, 1-220, 1-221, 1-224, 1-225, 1-226, 1-230, 1-231, 1-232, 1-233, 1-236, 1-237, 1-238, 1-241, 1-242, 1-245, 1-246, 1-247, 1-248, 1-249, 1-252, 1-254, 1-259, 1-261, 1-263, 1-265, 1-268, 1-269, 1-272, 1-273, 1-275, 1-280, 1-282, 1-284, 1-286, 1-288, 1-295, 1-297, 1-299, 1-301, 1-303, 1-309, 1-310, 1-311, 1-312, 1-316, 1-317, 1-318, 1-321, 1-322, 1-323, 1-324, 1-326, 1-327, 1-328, 1-334, 1-335, 1-336, 1-337, 1-338, 1-342, 1-343, 1-345, 1-346, 1-347, 1-348, 1-352, 1-353, 1-355, 1-356, 1-357, 1-358, 1-364, 1-365, 1-367, 1-378, 1-379, 1-380, 1-381, 1-382, 1-383, 1-384, 1-385, 1-386, 1-387, 1-388, 1-389, 1-390, 1-391, 1-392, 1-393, 1-394, 1-395, 1-396, 1-403, 1-404, 1-406, 1-407, 1-408, 1-410, 1-414, 1-415, 1-416, 1-418, 1-421, 1-422, 1-423, 1-426, 1-427, 1-429, 1-430, 1-433, 1-434, 1-436, 1-437, 1-439, 1-440, 1-441, 1-442, 1-443, 1-445, 1-446, 1-447, 1-448, 1-449, 1-451, 1-452, 1-453, 1-454, 1-455, 1-457, 1-458, 1-459, 1-460, 1-461, 1-462, 1-463, 1-464, 1-465, 1-468, 1-470, 1-472, 1-474, 1-476, 1-477, 1-479, 1-481, 1-482, 1-483, 1-484, 1-485, 1-486, 1-487, 1-488, 1-489, 1-490, 1-491, 1-492, 1-493, 1-495, 1-496, 1-498, 1-499, 1-500, 1-503, 1-504, 1-506, 1-509, 1-510, 1-511, 1-512, 1-513, 1-514, 1-515, 1-516, 1-517, 1-518, 1-519, 1-520, 1-521, 1-522, 1-524, 1-528, 1-529, 1-532, 1-534, 1-536, 1-537, 1-538, 1-539, 1-540, 1-545, 1-546, 1-547, 1-551, 1-553, 1-554, 1-555, 1-556, 1-558, 1-563, 1-568, 1-575, 1-582, 1-586, 1-592, 1-598, 1-601, 1-602, 1-603, 1-604, 1-605, 1-607, 1-609, 1-610, 1-611, 1-614, 1-616, 1-620, 1-624, 1-625, 1-627, 1-628, 1-631, 1-632, 1-635, 1-640, 1-645, 1-650, 1-653, 1-654, 1-655, 1-656, 1-658, 1-662, 1-663, 1-664, 1-666, 1-667, 1-668, 1-669, 1-670, 1-671, 1-672, 1-673, 1-674, 1-675, 1-676, 1-677, 1-679, 1-680, 1-682, 1-683, 1-684, 1-687, 1-688, 1-690, 1-693, 1-694, 1-695, 1-696, 1-697, 1-698, 1-699, 1-700, 1-701, 1-702, 1-703, 1-704, 1-705, 1-706, 1-707, 1-712, 1-713, 1-716, 1-718, 1-720, 1-721, 1-722, 1-723, 1-724, 1-729, 1-730, 1-731, 1-735, 1-737, 1-738, 1-739, 1-740, 1-742, 1-747, 1-752, 1-759, 1-766, 1-770, 1-776, 1-782, 1-785, 1-786, 1-787, 1-788, 1-789, 1-791, 1-793., 1-794, 1-795, 1-798, 1-800, 1-804, 1-808, 1-809, 1-811, 1-812, 1-815, 1-816, 1-819, 1-824, 1-829, 1-834, 1-837, 1-838, 1-839, 1-840, 1-842, 1-846, 1-847, 1-848, 1-850, 1-851, 1-852, 1-854, 1-856, 1-857, 1-862, 1-863, 1-864, 1-865, 1-868, 1-870, 1-873, 1-880, 1-883, 1-887, 1-890, 1-894, 1-895, 1-896, 1-897, 1-898, 1-901, 1-906, 1-907, 1-913, 1-915, 1-916, 1-917, 1-918, 1-919, 1-920, 1-921, 1-922, 1-923, 1-924, 1-925, 1-926, 1-927, 1-929, 1-930, 1-932, 1-933, 1-934, 1-937, 1-938, 1-940, 1-943, 1-944, 1-945, 1-946, 1-947, 1-948, 1-949, 1-950, 1-951, 1-952, 1-953, 1-954, 1-955, 1-956, 1-957, 1-962, 1-963, 1-966, 1-968, 1-970, 1-971, 1-972, 1-973, 1-974, 1-979, 1-980, 1-981, 1-985, 1-987, 1-988, 1-989, 1-990, 1-992, 1-997, 1-1002, 1-1009, 1-1016, 1-1020, 1-1026, 1-1032, 1-1035, 1-1036, 1-1037, 1-1038, 1-1039, 1-1041, 1-1043, 1-1044, 1-1045, 1-1048, 1-1050, 1-1054, 1-1058, 1-1059, 1-1061, 1-1062, 1-1065, 1-1066, 1-1069, 1-1074, 1-1079, 1-1084, 1-1087, 1-1088, 1-1089, 1-1090, 1-1092, 1-1096, 1-1097, 1-1098, 1-1100, 1-1101, 1-1102, 1-1103, 1-1104, 1-1105, 1-1106, 1-1107, 1-1108, 1-1115, 1-1120, 1-1122, 1-1124, 1-1126, 1-1127, 1-1128, 1-1129, 1-1130, 1-1131, 1-1141, 1-1144, 1-1156, 1-1160, 1-1161, 1-1162, 1-1163, 1-1166, 1-1167, 1-1168, 1-1178, 1-1179, 1-1182, 1-1187, 1-1191, 1-1193, 1-1197, 1-1198, 1-1202, 1-1203, 1-1204, 1-1205, 1-1208, 1-1212, 1-1213, 1-1224, 1-1227, 1-1230, 1-1231, 1-1234, 1-1236, 1-1237, 1-1238, 1-1241, 1-1245, 1-1246, 1-1256, 1-1260, 1-1263, 1-1264, 1-1267, 1-1269, 1-1270, 1-1271, 1-1274, 1-1278, 1-1279, 1-1289, 1-1299, 1-1309, 1-1319, 2-1, 2-2, 2-3, 2-4, 2-5, 2-6, 2-7, 2-8, 2-9, 2-10, 2-11, 2-12, 2-14, 2-15, 2-17, 2-18, 2-19, 2-22, 2-23, 2-25, 2-28, 2-29, 2-30, 2-31, 2-32, 2-33, 2-34, 2-35, 2-36, 2-37, 2-38, 2-39, 2-40, 2-41, 2-43, 2-47, 2-48, 2-51, 2-53, 2-55, 2-56, 2-57, 2-58, 2-59, 2-64, 2-65, 2-66, 2-70, 2-72, 2-73, 2-74, 2-75, 2-77, 2-82, 2-87, 2-94, 2-101, 2-105, 2-111, 2-117, 2-120, 2-121, 2-122, 2-123, 2-124, 2-126, 2-128, 2-129, 2-130, 2-133, 2-135, 2-139, 2-143, 2-144, 2-146, 2-147, 2-150, 2-151, 2-155, 2-159, 2-164, 2-169, 2-172, 2-173, 2-174, 2-175, 2-177, 2-181, 2-182, 2-183, 2-185, 2-186, 2-187, 2-188, 2-189, 2-190, 2-191, 2-192, 2-193, 2-198, 2-200, 2-205, 2-207, 2-209, 2-211, 2-212, 2-213, 2-214, 2-215, 2-216, 2-226, 2-229, 2-241, 2-245, 2-246, 2-247, 2-248, 2-251, 2-252, 2-253, 2-263, 2-264, 2-267, 2-272, 3-1, 3-2, 3-3,3-4, 3-5, 3-6, 3-7, 3-8, 3-9, 3-10, 3-11, 3-12, 3-14, 3-15, 3-17, 3-18, 3-19, 3-22, 3-23, 3-25, 3-28, 3-29, 3-30, 3-31, 3-32, 3-33, 3-34, 3-35, 3-36, 3-37, 3-38, 3-39, 3-40, 3-41, 3-42, 3-47, 3-48, 3-51, 3-53, 3-55, 3-56, 3-57, 3-58, 3-59, 3-64, 3-65, 3-66, 3-70, 3-72, 3-73, 3-74, 3-75, 3-77, 3-82, 3-87, 3-94, 3-101, 3-105, 3-111, 3-117, 3-120, 3-121, 3-122, 3-123, 3-124, 3-126, 3-128, 3-129, 3-130, 3-133, 3-135, 3-139, 3-143, 3-144, 3-146, 3-147, 3-150, 3-151, 3-154, 3-159, 3-164, 3-169, 3-172, 3-173, 3-174, 3-175, 3-177, 3-181, 3-182, 3-183, 3-185, 3-186, 3-187, 3-188, 3-189, 3-190, 3-191, 3-192, 3-193, 3-198, 3-200, 3-205, 3-207, 3-209, 3-211, 3-212, 3-213, 3-214, 3-215, 3-216, 3-226, 3-229, 3-241, 3-245, 3-246, 3-247, 3-248, 3-251, 3-252, 3-253, 3-263, 3-264, 3-267, 3-272, 4-1, 4-2, 4-8, 4-12, 4-13, 4-14, 4-15, 4-16, 4-19, 4-23, 4-24, 4-31, 4-33, 4-34, 4-35, 4-41, 4-45, 4-46, 4-47, 4-48, 4-49, 4-52, 4-56, 4-57, 4-64, 4-66, 4-67, 4-68, 4-74, 4-78, 4-79, 4-80, 4-81, 4-82, 4-85, 4-89, 4-90, 4-97, 4-99, 4-107, 4-108, 4-110, 4-111, 4-113, 4-114, 4-115, 4-118, 4-122, 4-123, 4-130, 4-140, 4-141, 4-144, 4-146, 4-147, 4-148, 4-151, 4-155, 4-156, 4-163, 4-173, 4-174, 4-176, 4-177, 4-178, 4-179, 4-180, 4-181, 4-184, 4-189, 4-196, 5-1, 5-2, 5-8, 5-11, 5-12, 5-13, 5-14, 5-15, 5-16, 5-19, 5-23, 5-24, 5-31, 5-33, 5-34, 5-35, 5-41, 5-45, 5-46, 5-47, 5-48, 5-49, 5-52, 5-56, 5-57, 5-64, 5-66, 5-67, 5-68, 5-74, 5-78, 5-79, 5-80, 5-81, 5-82, 5-85, 5-89, 5-90, 5-97, 5-99, 5-107, 5-108, 5-110, 5-111, 5-113, 5-114, 5-115, 5-118, 5-122, 5-123, 5-130, 5-140, 5-141, 5-144, 5-146, 5-147, 5-148, 5-151, 5-155, 5-156, 5-163, 5-166, 5-167, 5-173, 5-174, 5-176, 5-177, 5-178, 5-179, 5-180, 5-181, 5-184, 5-188, 5-189 and 5-196, further more preferably compounds of Compounds Nos. 1-1, 1-2, 1-3, 1-4, 1-5, 1-6, 1-7, 1-8, 1-9, 1-10, 1-12, 1-29, 1-30, 1-32, 1-33, 1-38, 1-50, 1-51, 1-60, 1-61, 1-70, 1-78, 1-86, 1-87, 1-90, 1-102, 1-112, 1-139, 1-155, 1-163, 1-167, 1-177, 1-182, 1-192, 1-197, 1-207, 1-208, 1-210, 1-216, 1-226, 1-230, 1-231, 1-232, 1-233, 1-236, 1-237, 1-245, 1-0.246, 1-247, 1-248, 1-252, 1-254, 1-259, 1-265, 1-268, 1-269, 1-273, 1-280, 1-286, 1-295, 1-301, 1-309, 1-312, 1-321, 1-324, 1-334, 1-335, 1-345, 1-355, 1-367, 1-378, 1-379, 1-380, 1-381, 1-389, 1-390, 1-393, 1-394, 1-403, 1-406, 1-414, 1-421, 1-429, 1-436, 1-439, 1-442, 1-445, 1-448, 1-451, 1-454, 1-460, 1-461, 1-462, 1-463, 1-464, 1-468, 1-476, 1-477, 1-481, 1-482, 1-483, 1-484, 1-485, 1-486, 1-487, 1-488, 1-489, 1-490, 1-496, 1-499, 1-509, 1-511, 1-513, 1-515, 1-516, 1-517, 1-519, 1-520, 1-522, 1-528, 1-538, 1-545, 1-546, 1-558, 1-563, 1-568, 1-575, 1-582, 1-586, 1-592, 1-602, 1-603, 1-616, 1-620, 1-635, 1-640, 1-645, 1-653, 1-654, 1-662, 1-666, 1-667, 1-668, 1-669, 1-670, 1-671, 1-672, 1-673, 1-674, 1-683, 1-695, 1-699, 1-700, 1-701, 1-703, 1-704, 1-729, 1-730, 1-731, 1-785, 1-786, 1-787, 1-788, 1-819, 1-824, 1-829, 1-837, 1-850, 1-851, 1-852, 1-856, 1-857, 1-862, 1-863, 1-864, 1-865, 1-868, 1-870, 1-873, 1-883, 1-890, 1-895, 1-896, 1-897, 1-898, 1-901, 1-906, 1-916, 1-917, 1-918, 1-923, 1-930, 1-933, 1-943, 1-945, 1-947, 1-949, 1-950, 1-951, 1-953, 1-954, 1-956, 1-972, 1-979, 1-992, 1-997, 1-1016, 1-1026, 1-1032, 1-1036, 1-1037, 1-1038, 1-1069, 1-1074, 1-1079, 1-1087, 1-1088, 1-1101, 1-1103, 1-1107, 1-1108, 1-1115, 1-1120, 1-1122, 1-1124, 1-1126, 1-1127, 1-1128, 1-1131, 1-1141, 1-1144, 1-1156, 1-1160, 1-1161, 1-1182, 1-1191, 1-1193, 1-1197, 1-1198, 1-1202, 1-1203, 1-1204, 1-1205, 1-1208, 1-1212, 1-1213, 1-1224, 1-1227, 1-1230, 1-1231, 1-1234, 1-1236, 1-1237, 1-1238, 1-1241, 1-1246, 1-1256, 1-1263, 1-1264, 1-1269, 1-1270, 1-1271, 1-1274, 1-1279, 1-1289, 1-1299, 1-1309, 1-1319, 2-1, 2-2, 2-3, 2-4, 2-5, 2-6, 2-7, 2-8, 2-9, 2-15, 2-18, 2-28, 2-30, 2-32, 2-34, 2-35, 2-36, 2-38, 2-39, 2-41, 2-47, 2-57, 2-64, 2-65, 2-66, 2-77, 2-82, 2-87, 2-94, 2-101, 2-105, 2-111, 2-121, 2-122, 2-135, 2-139, 2-155, 2-159, 2-164, 2-172, 2-173, 2-181, 2-185, 2-186, 2-187, 2-188, 2-189, 2-192, 2-193, 2-198, 2-200, 2-205, 2-207, 2-209, 2-211, 2-212, 2-213, 2-215, 2-216, 2-226, 2-245, 2-246, 2-247, 2-251, 2-252, 2-263, 2-264, 2-267, 3-1, 3-2, 3-3, 3-8, 3-9, 3-15, 3-18, 3-28, 3-30, 3-32, 3-34, 3-35, 3-36, 3-38, 3-39, 3-41, 3-47, 3-57, 3-64, 3-65, 3-66, 3-77, 3-82, 3-87, 3-94, 3-101, 3-105, 3-111, 3-120, 3-121, 3-122, 3-135, 3-139, 3-143, 3-154, 3-159, 3-164, 3-169, 3-172, 3-177, 3-185, 3-188, 3-189, 3-192, 3-193, 3-198, 3-200, 3-205, 3-207, 3-209, 3-211, 3-212, 3-213, 3-215, 3-216, 3-226, 3-229, 3-245, 3-246, 3-247, 3-267, 4-1, 4-8, 4-14, 4-15, 4-16, 4-24, 4-35, 4-41, 4-45, 4-46, 4-47, 4-48, 4-49, 4-56, 4-57, 4-64, 4-68, 4-78, 4-80, 4-81, 4-82, 4-89, 4-99, 4-107, 4-108, 4-113, 4-114, 4-115, 4-122, 4-140, 4-141, 4-144, 4-146, 4-147, 4-148, 4-151, 4-176, 4-179, 4-180, 4-181, 4-184, 4-189, 5-1, 5-8, 5-14, 5-15, 5-16, 5-24, 5-35, 5-41, 5-45, 5-46, 5-47, 5-48, 5-49, 5-56, 5-57, 5-64, 5-67, 5-68, 5-78, 5-80, 5-81, 5-82, 5-89, 5-99, 5-107, 5-108, 5-113, 5-114, 5-115, 5-122, 5-140, 5-141, 5-144, 5-146, 5-147, 5-148, 5-151, 5-166, 5-167, 5-176, 5-179, 5-180, 5-181, 5-184 and 5-189, particularly preferably Compound No. 1-1: 2-(3-cyclopropoxy-4-difluoromethoxyphenyl)-1,5-dihydropyrrolo[2,3-d]pyridazin-4-one, Compound No. 1-2: 3-chloro-2-(3-cyclopropoxy-4-difluoromethoxyphenyl)-1,5-dihydropyrrolo[2,3-d]pyridazin-4-one, Compound No. 1-3: 3-bromo-2-(3-cyclopropoxy-4-difluoromethoxyphenyl)-1,5-dihydropyrrolo[2,3-d]pyridazin-4-one, Compound No. 1-4: 2-(3-cyclopropoxy-4-difluoromethoxyphenyl)-3-methyl-1,5-dihydropyrrolo[2,3-d]pyridazin-4-one, Compound No. 1-5: 2-(3-cyclopropoxy-4-difluoromethoxyphenyl)-3-ethyl-1,5-dihydropyrrolo[2,3-d]pyridazin-4-one, Compound No. 1-6: 2-(3-cyclopropoxy-4-difluoromethoxyphenyl)-3-propyl-1,5-dihydropyrrolo[2,3-d]pyridazin-4-one, Compound No. 1-7: 2-(3-cyclopropoxy-4-difluoromethoxyphenyl)-3-isopropyl-1,5-dihydropyrrolo[2,3-d]pyridazin-4-one, Compound No. 1-8: 3-butyl-2-(3-cyclopropoxy-4-difluoromethoxyphenyl)-1,5-dihydropyrrolo[2,3-d]pyridazin-4-one, Compound No. 1-9: 2-(3-cyclopropoxy-4-difluoromethoxyphenyl)-3-isobutyl-1,5-dihydropyrrolo[2,3-d]pyridazin-4-one, Compound No. 1-10: 2-(3-cyclopropoxy-4-difluoromethoxyphenyl)-3-pentyl-1,5-dihydropyrrolo[2,3-d]pyridazin-4-one, Compound No. 1-12: 2-(3-cyclopropoxy-4-difluoromethoxyphenyl)-3-hexyl-1,5-dihydropyrrolo[2,3-d]pyridazin-4-one, Compound No. 1-32: 2-(3-cyclopropoxy-4-difluoromethoxyphenyl)-3-hydroxymethyl-1,5-dihydropyrrolo[2,3-d]pyridazin-4-one, Compound No. 1-50: 2-(3-cyclopropoxy-4-difluoromethoxyphenyl)-3-methoxymethyl-1,5-dihydropyrrolo[2,3-d]pyridazin-4-one, Compound No. 1-51: 2-(3-cyclopropoxy-4-difluoromethoxyphenyl)-3-(2-methoxyethyl)-1,5-dihydropyrrolo[2,3-d]pyridazin-4-one, Compound No. 1-60: 2-(3-cyclopropoxy-4-difluoromethoxyphenyl)-3-ethoxymethyl-1,5-dihydropyrrolo[2,3-d]pyridazin-4-one, Compound No. 1-61: 2-(3-cyclopropoxy-4-difluoromethoxyphenyl)-3-(2-ethoxyethyl)-1,5-dihydropyrrolo[2,3-d]pyridazin-4-one, Compound No. 1-86: 2-(3-cyclopropoxy-4-difluoromethoxyphenyl)-3-isopropoxymethyl-1,5-dihydropyrrolo[2,3-d]pyridazin-4-one, Compound No. 1-90: 2-(3-cyclopropoxy-4-difluoromethoxyphenyl)-3-(2-fluoroethoxymethyl)-1,5-dihydropyrrolo[2,3-d]-pyridazin-4-one, Compound No. 1-102: 3-cyclobutoxymethyl-2-(3-cyclopropoxy-4-difluoromethoxyphenyl)-1,5-dihydropyrrolo[2,3-d]pyridazin-4-one, Compound No. 1-112: 2-(3-cyclopropoxy-4-difluoromethoxyphenyl)-3-cyclopropylmethoxymethyl-1,5-dihydropyrrolo[2,3-d]pyridazin-4-one, Compound No. 1-197: 2-(3-cyclopropoxy-4-difluoromethoxyphenyl)-3-dimethylaminomethyl-1,5-dihydropyrrolo[2,3-d]-pyridazin-4-one, Compound No. 1-207: 2-(3-cyclopropoxy-4-difluoromethoxyphenyl)-3-cyclopropyl-1,5-dihydropyrrolo[2,3-d]pyridazin-4-one, Compound No. 1-208: 2-(3-cyclopropoxy-4-difluoromethoxyphenyl)-3-cyclopropylmethyl-1,5-dihydropyrrolo[2,3-d]pyridazin-4-one, Compound No. 1-216: 2-(3-cyclopropoxy-4-difluoromethoxyphenyl)-3-(2-cyclopropylethyl)-1,5-dihydropyrrolo[2,3-d]-pyridazin-4-one, Compound No. 1-220: 2-(3-cyclopropoxy-4-difluoromethoxyphenyl)-3-(2-propenyl)-1,5-dihydropyrrolo[2,3-d]pyridazin-4-one, Compound No. 1-231: 2-(3-cyclopropoxy-4-difluoromethoxyphenyl)-3-ethynyl-1,5-dihydropyrrolo[2,3-d]pyridazin-4-one, Compound No. 1-232: 2-(3-cyclopropoxy-4-difluoromethoxyphenyl)-3-(2-propynyl)-1,5-dihydropyrrolo[2,3-d]pyridazin-4-one, Compound No. 1-233: 3-(2-butynyl)-2-(3-cyclopropoxy-4-difluoromethoxyphenyl)-1,5-dihydropyrrolo[2,3-d]pyridazin-4-one, Compound No. 1-236: 2-(3-cyclopropoxy-4-difluoromethoxyphenyl)-3-(4-methyl-2-pentynyl)-1,5-dihydropyrrolo[2,3-d]-pyridazin-4-one,
Compound No. 1-237: 2-(3-cyclopropoxy-4-difluoromethoxyphenyl)-3-(1-hydroxy-2-propenyl)-1,5-dihydropyrrolo[2,3-d]-pyridazin-4-one,
Compound No. 1-245: 2-(3-cyclopropoxy-4-difluoromethoxyphenyl)-3-phenyl-1,5-dihydropyrrolo[2,3-d]pyridazin-4-one,
Compound No. 1-334: 2-(3-cyclopropoxy-4-difluoromethoxyphenyl)-3-(4-pyrazolyl)-1,5-dihydropyrrolo[2,3-d]pyridazin-4-one,
Compound No. 1-378: 3-benzyl-2-(3-cyclopropoxy-4-difluoromethoxyphenyl)-1,5-dihydropyrrolo[2,3-d]pyridazin-4-one,
Compound No. 1-379: 2-(3-cyclopropoxy-4-difluoromethoxyphenyl)-3-(2-fluorobenzyl)-1,5-dihydropyrrolo[2,3-d]pyridazin-4-one,
Compound No. 1-380: 2-(3-cyclopropoxy-4-difluoromethoxyphenyl)-3-(3-fluorobenzyl)-1,5-dihydropyrrolo[2,3-d]pyridazin-4-one,
Compound No. 1-381: 2-(3-cyclopropoxy-4-difluoromethoxyphenyl)-3-(4-fluorobenzyl)-1,5-dihydropyrrolo[2,3-d]pyridazin-4-one,
Compound No. 1-389: 3-(2-cyanobenzyl)-2-(3-cyclopropoxy-4-difluoromethoxyphenyl)-1,5-dihydropyrrolo[2,3-d]pyridazin-4-one,
Compound No. 1-390: 3-(3-cyanobenzyl)-2-(3-cyclopropoxy-4-difluoromethoxyphenyl)-1,5-dihydropyrrolo[2,3-d]pyridazin-4-one,
Compound No. 1-393: 3-(3-carboxybenzyl)-2-(3-cyclopropoxy-4-difluoromethoxyphenyl)-1,5-dihydropyrrolo[2,3-d]pyridazin-4-one,
Compound No. 1-439: 2-(3-cyclopropoxy-4-difluoromethoxyphenyl)-3-(6-methoxy-2-pyridylmethyl)-1,5-dihydropyrrolo-[2,3-d]pyridazin-4-one,
Compound No. 1-445: 2-(3-cyclopropoxy-4-difluoromethoxyphenyl)-3-(6-methoxy-3-pyridylmethyl)-1,5-dihydropyrrolo-[2,3-d]pyridazin-4-one,
Compound No. 1-460: 2-(3-cyclopropoxy-4-difluoromethoxyphenyl)-3-phenethyl-1,5-dihydropyrrolo[2,3-d]pyridazin-4-one,
Compound No. 1-476: 2-(3-cyclopropoxy-4-difluoromethoxyphenyl)-3-hydroxyphenylmethyl-1,5-dihydropyrrolo[2,3-d]-pyridazin-4-one,
Compound No. 1-482: 2-(3-cyclopropylmethoxy-4-difluoromethoxyphenyl)-1,5-dihydropyrrolo[2,3-d]pyridazin-4-one,
Compound No. 1-483: 3-chloro-2-(3-cyclopropylmethoxy-4-difluoromethoxyphenyl)-1,5-dihydropyrrolo[2,3-d]pyridazin-4-one,
Compound No. 1-486: 2-(3-cyclopropylmethoxy-4-difluoromethoxyphenyl)-3-ethyl-1,5-dihydropyrrolo[2,3-d]pyridazin-4-one,
Compound No. 1-545: 2-(3-cyclopropylmethoxy-4-difluoromethoxyphenyl)-3-phenyl-1,5-dihydropyrrolo[2,3-d]pyridazin-4-one,
Compound No. 1-666: 2-(4-difluoromethoxy-3-isopropoxyphenyl)-1,5-dihydropyrrolo[2,3-d]pyridazin-4-one,
Compound No. 1-667: 3-chloro-2-(4-difluoromethoxy-3-isopropoxyphenyl)-1,5-dihydropyrrolo[2,3-d]pyridazin-4-one,
Compound No. 1-668: 3-bromo-2-(4-difluoromethoxy-3-isopropoxyphenyl)-1,5-dihydropyrrolo[2,3-d]pyridazin-4-one,
Compound No. 1-850: 2-(3-cyclobutoxy-4-difluoromethoxyphenyl)-1,5-dihydropyrrolo[2,3-d]pyridazin-4-one,
Compound No. 1-851: 3-chloro-2-(3-cyclobutoxy-4-difluoromethoxyphenyl)-1,5-dihydropyrrolo[2,3-d]pyridazin-4-one,
Compound No. 1-852: 3-bromo-2-(3-cyclobutoxy-4-difluoromethoxyphenyl)-1,5-dihydropyrrolo[2,3-d]pyridazin-4-one,
Compound No. 1-870: 2-(3-cyclobutoxy-4-difluoromethoxyphenyl)-3-phenyl-1,5-dihydropyrrolo[2,3-d]pyridazin-4-one,
Compound No. 1-917: 3-chloro-2-(3-cyclopropoxy-4-methoxyphenyl)-1,5-dihydropyrrolo[2,3-d]pyridazin-4-one,
Compound No. 1-918: 3-bromo-2-(3-cyclopropoxy-4-methoxyphenyl)-1,5-dihydropyrrolo[2,3-d]pyridazin-4-one,
Compound No. 1-923: 3-butyl-2-(3-cyclopropoxy-4-methoxyphenyl)-1,5-dihydropyrrolo[2,3-d]pyridazin-4-one,
Compound No. 1-1101: 3-chloro-2-(3-cyclopropylmethoxy-4-methoxyphenyl)-1,5-dihydropyrrolo[2,3-d]pyridazin-4-one,
Compound No. 1-1191: 3-chloro-2-(3-isopropoxy-4-methoxyphenyl)-1,5-dihydropyrrolo[2,3-d]pyridazin-4-one,
Compound No. 1-1224: 3-chloro-2-(3-cyclobutoxy-4-methoxyphenyl)-1,5-dihydropyrrolo[2,3-d]pyridazin-4-one,
Compound No. 1-1256: 2-(3-cyclopentoxy-4-methoxyphenyl)-1,5-dihydropyrrolo[2,3-d]pyridazin-4-one,
Compound No. 1-1289: 2-(3-cyclopropoxy-4-difluoromethoxyphenyl)-3-isobutoxymethyl-1,5-dihydropyrrolo[2,3-d]pyridazin-4-one,
Compound No. 1-1299: 3-(sec-butoxymethyl)-2-(3-cyclopropoxy-4-difluoromethoxyphenyl)-1,5-dihydropyrrolo[2,3-d]-pyridazin-4-one,
Compound No. 1-1309: 3-(tert-butoxymethyl)-2-(3-cyclopropoxy-4-difluoromethoxyphenyl)-1,5-dihydropyrrolo[2,3-d]-pyridazin-4-one,
Compound No. 1-1319: 2-(3-cyclopropoxy-4-difluoromethoxyphenyl)-3-(1-ethylpropoxymethyl)-1,5-dihydropyrrolo[2,3-d]-pyridazin-4-one,
Compound No. 2-2: 3-chloro-2-(8-difluoromethoxy-2,2-dimethyl-2H-chromen-5-yl)-1,5-dihydropyrrolo[2,3-d]pyridazin-4-one,
Compound No. 2-4: 2-(8-difluoromethoxy-2,2-dimethyl-2H-chromen-5-yl)-3-methyl-1,5-dihydropyrrolo[2,3-d]pyridazin-4-one,
Compound No. 2-5: 2-(8-difluoromethoxy-2,2-dimethyl-2H-chromen-5-yl)-3-ethyl-1,5-dihydropyrrolo[2,3-d]pyridazin-4-one,
Compound No. 2-38: 3-cyclopropyl-2-(8-difluoromethoxy-2,2-dimethyl-2H-chromen-5-yl)-1,5-dihydropyrrolo[2,3-d]pyridazin-4-one,
Compound No. 3-1: 2-(2-cyclopropyl-8-difluoromethoxy-2H-chromen-5-yl)-1,5-dihydropyrrolo[2,3-d]pyridazin-4-one,
Compound No. 4-35: 3-chloro-2-(8-difluoromethoxy-2H-chromen-2-spiro-1'-cyclobutan-5-yl)-1,5-dihydropyrrolo[2,3-d]pyridazin-4-one,
Compound No. 4-68: 3-chloro-2-(8-difluoromethoxy-2H-chromen-2-spiro-1'-cyclopentan-5-yl)-1,5-dihydropyrrolo-[2,3-d]pyridazin-4-one,
Compound No. 5-67: 2-(7-difluoromethoxy-2,3-dihydrobenzofuran-2-spiro-1'-cyclopentan-4-yl)-1,5-dihydropyrrolo[2,3-d]pyridazin-4-one,
Compound No. 5-166: 2-(2,3-dihydro-7-methoxybenzofuran-2-spiro-1'-cyclopentan-4-yl)-1,5-dihydropyrrolo[2,3-d]pyridazin-4-one, and
Compound No. 5-167: 3-chloro-2-(2,3-dihydro-7-methoxybenzofuran-2-spiro-1'-cyclopentan-4-yl)-1,5-dihydropyrrolo[2,3-d]pyridazin-4-one.

EFFECTS OF THE INVENTION

The pyrrolopyridazinone compound represented by the formula (1) or a pharmaceutically acceptable salt thereof of the present invention has excellent properties in the points of solubility, oral absorbability, concentration in blood, metabolic stability, tissue transferability, bioavailability (BA), in vitro activity, in vivo activity, rapidness of showing medical effects, continuity of medical effects, physical stability, medicaments interaction, toxicity, etc., also shows excellent PDE4 inhibiting activity, and less occurrence of side effects such as emesis, etc., whereby according to the present invention, it is useful as a prophylaxis or treatment agent of a respiratory disease to which PDE4 participates (for example, bronchitic asthma (including atopic asthma), COPD, chronic bronchitis, pneumonial disease, adult respiratory distress syndrome (ARDS), etc.) (particularly expected to be a prophylaxis or treatment agent of bronchitic asthma and COPD.).

Moreover, Compound (1) of the present invention is useful as a prevention and treatment agent for other diseases which have been known to be participated by PDE4, for example, diseases to which cytokine (IL-1, IL-4, IL-6 and TNF (tumor necrosis factor)), etc., pertains (for example, chronic rheumatism, ulcerative colitis, Crohn's disease, sepsis, septic shock, endotoxin shock, Gram-negative bacterial sepsis, toxic shock syndrome, nephritis, hepatitis, infection (bacteria and virus), circulatory failure (cardiac insufficiency, arteriosclerosis, cardiac infarction, cerebral apoplexy), etc.), and the like.

The pyrrolopyridazinone compound of the present invention can be prepared by the following methods.

[Preparation Method 1]

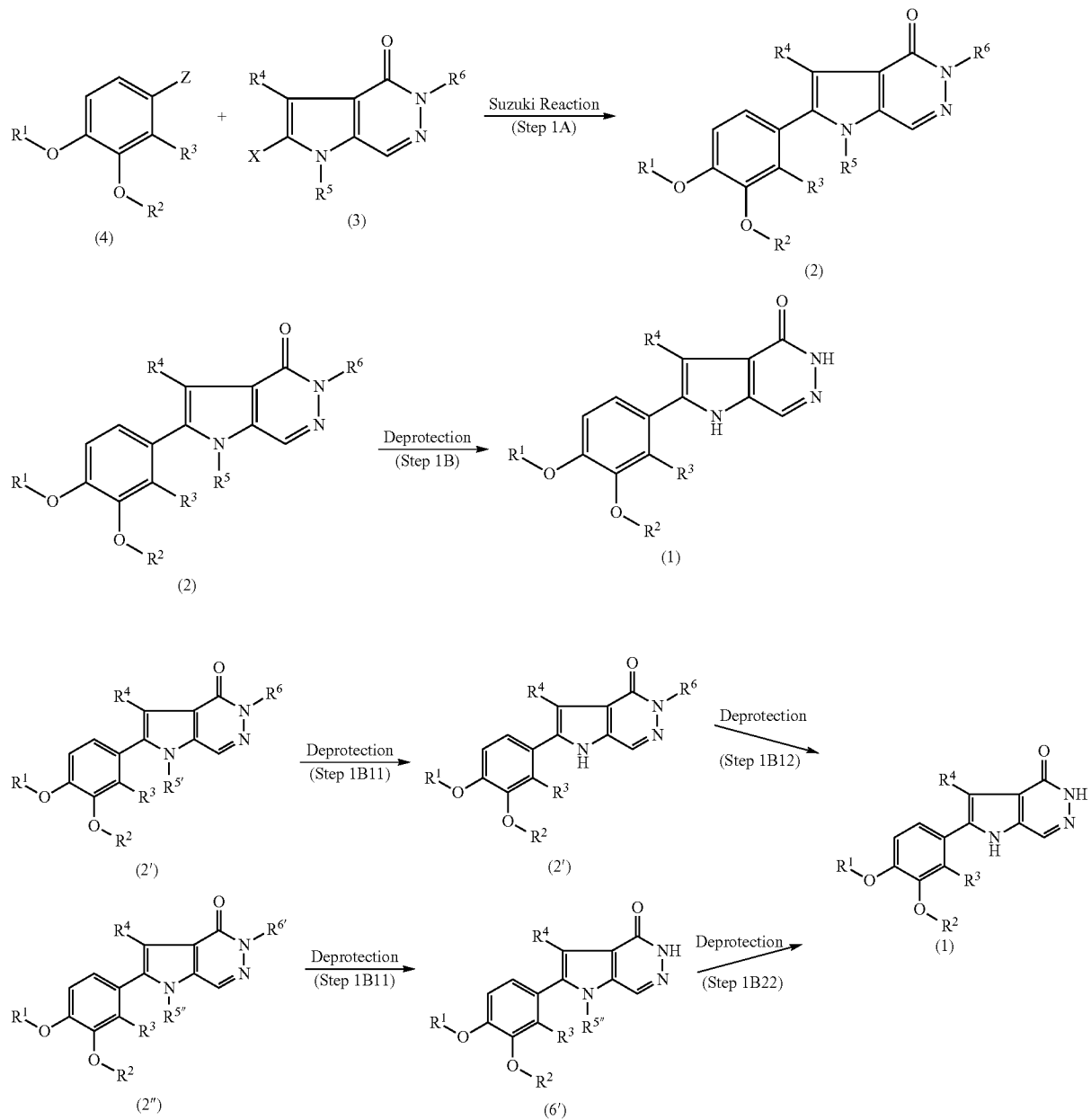

wherein $R^1$, $R^2$, $R^3$ and $R^4$ have the same meanings as defined above, $R^5$ represents a 4-methoxybenzyl group, methoxymethyl (hereinafter abbreviated to as MOM) group, methoxyethoxymethyl (hereinafter abbreviated to as MEM) group, benzyloxymethyl (hereinafter abbreviated to as BOM) group, 2-trimethylsilylethoxymethyl (hereinafter abbreviated to as SEM) group, tert-butoxycarbonyl (hereinafter abbreviated to as BOC) group or tetrahydropyranyl (hereinafter abbreviated to as THP) group, $R^6$ represents a benzyl group, 4-methoxybenzyl group, MOM group, MEM group, BOM group, SEM group, BOC group or THP group, $R^{5'}$ represents a SEM group or BOM group (provided that when $R^{5'}$ is a BOM group, $R^6$ is not a BOM group), $R^{5''}$ represents a BOM group, $R^{6'}$ represents a MOM group, MEM group, BOM group, SEM group, BOC group or THP group, X represents a chlorine, bromine or iodine atom, Z represents a dihydroxyboryl group or a boronic acid ester group such as a 4,4,5,5-tetramethyl[1,3,2]dioxaborolanyl group, etc.

Preparation method 1 is a method of preparing Compound (1) of the present invention by reacting a pyrrolopyridazinone compound (3) with a boronic acid compound (4) to prepare an intermediate compound (2), and then, removing two protective groups simultaneously or stepwise.

[Step 1A]

Step 1A is a so-called Suzuki reaction, and is a step of preparing Compound (2) by reacting Compound (3) with Compound (4) in an inert solvent and in an inert gas atmosphere, in the presence of either a base or a fluoride (provided that $R^5$ is a SEM group, a base is preferred.), and in the presence of a palladium catalyst.

As the palladium catalyst to be used, there may be mentioned, for example, a metal palladium such as palladium-active carbon or palladium black, etc.; an organopalladium complex such as tetrakis(triphenylphosphine)palladium, bis(triphenylphosphine)palladium chloride, 1,1'-bis(diphenylphosphino)ferrocene palladium chloride or tris(dibenzylideneacetone)dipalladium, etc.; or a palladium salt such as palladium chloride or palladium acetate, etc. and the like, preferably tetrakis(triphenylphosphine)palladium or palladium acetate. An amount of palladium to be used as a catalyst is generally 0.0001 to 1-fold mol amount, preferably 0.005 to 0.3-fold mol amount based on 1 mol of Compound (3).

Incidentally, when tris(dibenzylideneacetone) dipalladium, palladium chloride or palladium acetate is used as a catalyst, it is particularly preferred to copresent an organophosphine compound.

As the organophosphine compound to be used, there may be mentioned, for example, tributylphosphine, tri(tertbutyl) phosphine, tricyclohexylphosphine, butyl-di-1-adamantylphosphine, triphenylphosphine, tri(o-tolyl)phosphine, 2-dicyclohexylphosphino-2',6'-dimethoxybiphenyl, 1,1'-bis(diphenylphosphino)ferrocene or 1,2,3,4,5-pentaphenyl-1'-(di-t-butylphosphino)ferrocene, etc., preferably tricyclohexylphosphine, butyl-di-1-adamantylphosphine, triphenylphosphine or 2-dicyclohexylphosphino-2',6'-dimethoxybiphenyl. An amount of the organophosphine compound to be used is generally 1 to 3-fold mol amount, preferably 1.5 to 2.5-fold mol amount based on 1 mol of palladium.

As the base or fluoride to be used, there may be mentioned, for example, an alkali metal acetate such as sodium acetate or potassium acetate, etc.; an alkali metal carbonate such as sodium carbonate, potassium carbonate or cesium carbonate, etc.; an alkali metal phosphate such as sodium phosphate or potassium phosphate, etc.; an alkali metal hydroxide such as lithium hydroxide, sodium hydroxide or potassium hydroxide, etc.; a quaternary ammonium hydroxide such as tetramethylammonium hydroxide, tetraethylammonium hydroxide or tetrabutylammonium hydroxide, etc.; or a fluoride such as cesium fluoride, tetramethylammonium fluoride, tetraethylammonium fluoride or tetrabutylammonium fluoride, etc., preferably sodium carbonate or potassium phosphate. An amount of the base or fluoride to be used is generally 1 to 10-fold mol amount, preferably 2 to 5-fold mol amount based on 1 mol of Compound (3).

As the inert gas to be used, there may be mentioned, for example, a nitrogen, helium or argon gas, etc.

As the inert solvent to be used, it is not specifically limited so long as it does not inhibit the reaction and dissolves the starting materials, a catalyst and a base (or a fluoride) with a certain extent, and there may be mentioned, for example, an aromatic hydrocarbon such as benzene or toluene, etc.; an ether such as tetrahydrofuran, 1,2-dimethoxyethane or 1,4-dioxane, etc.; an alcohol such as methanol, ethanol, propanol or isopropanol, etc.; an ester such as methyl acetate or ethyl acetate, etc.; an amide such as N,N-dimethylformamide, N,N-dimethylacetamide or N-methylpyrrolidone, etc.; a sulfoxides such as dimethylsulfoxide, etc.; a nitrile such as acetonitrile or propionitrile, etc.; water; or a mixed solvent of an optional combination of the above, etc., preferably toluene, toluene-ethanol-water mixed solvent or toluene-water mixed solvent.

An amount of Compound (4) to be used is generally 1 to 3-fold mol amount, preferably 1 to 1.5-fold mol amount based on 1 mol of Compound (3).

A reaction temperature may vary depending on a kind, an amount to be used of starting materials, solvent(s), etc., and is generally in the range of 0° C. to 200° C., preferably 50° C. to 150° C.

A reaction time may vary depending on a reaction temperature, etc., and is generally for 10 minutes to 240 hours, preferably 1 hour to 48 hours.

Step 1B, (Step 1B11-Step 1B12) and (Step 1B21-Step 1B22) are all, steps for preparing Compound (1) of the present invention by removing a protective group from Compound (2).

(A) Step 1B is a step of preparing Compound (1) of the present invention by removing $R^5$ and $R^6$ which are protective groups from Compound (2) simultaneously.

(B) (Step 1B11-Step 1B12) and (Step 1B21-Step 1B22) are steps of preparing Compound (1) of the present invention by removing each of $R^{5'}$ and $R^{6'}$, as well as $R^{6''}$ and $R^{5'''}$ which are protective groups stepwise.

[Step 1B]

In Step 1B, to remove $R^5$ and $R^6$ simultaneously, it is necessary to select optional combination of $R^5$ and $R^6$, and with respective combinations, it is carried out by a treatment under acidic conditions, a treatment under hydrogenation decomposition conditions or a treatment under fluoride treatment conditions with specific conditions.

As a combination of $R^5$ and $R^6$ to remove them under acidic conditions, a combination in which both of $R^5$ and $R^6$ are 4-methoxybenzyl group, MOM group, MEM group, BOM group, SEM group, BOC group or THP group is suitable.

As a combination of $R^5$ and $R^6$ to remove them under hydrogenation decomposition conditions, a combination in which $R^5$ is a BOM group, and $R^6$ is a benzyl group or BOM group is suitable.

To remove them under fluoride treatment conditions with specific conditions, a combination in which both of $R^5$ and $R^6$ are SEM groups is suitable, and, for example, it is necessary to carry out the reaction under specific conditions that it is carried out in an inert solvent, and a reaction temperature of 80° C. or higher.

When Step 1B is carried out under acidic conditions, it is carried out in an inert solvent by treating with an acid or a Lewis acid.

As the inert solvent to be used, it is not specifically limited so long as it does not inhibit the reaction and dissolves the starting materials with a certain extent, and there may be mentioned, for example, an alcohol such as methanol, ethanol, propanol or isopropanol, etc.; an ether such as tetrahydrofuran, 1,4-dioxane or 1,2-dimethoxyethane, etc.; a halogenated aliphatic hydrocarbon such as dichloromethane, chloroform or 1,2-dichloroethane, etc.; an organic acid such as formic acid, acetic acid, propionic acid or trifluoroacetic acid, etc.; water; or a mixed solvent of an optional combination of the above, etc., preferably methanol, ethanol or 1,4-dioxane.

As the acid or Lewis acid to be used, there may be mentioned, for example, a hydrogen chloride gas, hydrochloric acid, hydrobromic acid, hydroiodic acid, sulfuric acid, phosphoric acid, p-toluenesulfonic acid, methanesulfonic acid, trifluoroacetic acid or boron trifluoride diethyl ether complex, etc., preferably a hydrogen chloride gas or hydrochloric acid.

An amount of the acid to be used is generally 10 to 2000-fold mol amount, preferably 30 to 300-fold mol amount based on 1 mol of Compound (2).

A reaction temperature may vary depending on a kind, an amount to be used of starting materials, solvent(s), etc., and is generally in the range of 0° C. to 200° C., preferably 15° C. to 150° C.

A reaction time may vary depending on a reaction temperature, etc., and is generally for 10 minutes to 240 hours, preferably 1 to 48 hours.

When Step 1B is carried out under hydrogenation decomposition conditions (the case where $R^5$ of a compound is a BOM group, and $R^6$ is a benzyl group or BOM group), it is carried out in an inert solvent in the presence of a catalyst.

As the inert solvent to be used, it is not specifically limited so long as it does not inhibit the reaction and dissolves the starting materials with a certain extent, and there may be mentioned, for example, an alcohol such as methanol, ethanol, propanol or isopropanol, etc.; an ether such as tetrahydrofuran, 1,4-dioxane or 1,2-dimethoxyethane, etc.; a halogenated aliphatic hydrocarbon such as dichloromethane, chloroform or 1,2-dichloroethane, etc.; an ester such as methyl formate, ethyl formate, methyl acetate or ethyl acetate, etc.; an organic acid such as formic acid, acetic acid, propionic acid or trifluoroacetic acid, etc.; an aromatic hydrocarbon such as benzene or toluene, etc.; water; or a mixed solvent of an optional combination of the above, etc., preferably methanol or ethanol.

The catalyst to be used may be mentioned, for example, palladium-active carbon, platinum-active carbon, platinum black, rhodium-active carbon or Raney nickel, etc., preferably palladium-active carbon or Raney nickel. An amount of the catalyst to be used is generally 0.0005 to 1-fold mol amount, preferably 0.01 to 0.1-fold mol amount based on 1 mol of Compound (2).

Incidentally, an acid may be added as an additive to promote the reaction.

As the acid to be used, there may be mentioned, for example, a hydrogen chloride gas, hydrochloric acid, hydrobromic acid, hydroiodic acid, p-toluenesulfonic acid, methanesulfonic acid or trifluoroacetic acid, etc., preferably hydrochloric acid, hydrobromic acid, p-toluenesulfonic acid, methanesulfonic acid or trifluoroacetic acid. An amount of the acid to be used is generally 0.5 to 10-fold mol amount, preferably 1 to 3-fold mol amount based on 1 mol of Compound (2).

A hydrogen partial pressure in the hydrogenation decomposition reaction is generally 1 atm to 10 atm, preferably 1 atm to 5 atm.

A reaction temperature may vary depending on a kind, an amount to be used of starting materials, solvent(s), etc., and is generally in the range of 0° C. to 100° C., preferably 15° C. to 80° C.

A reaction time may vary depending on a reaction temperature, etc., and is usually 15 minutes to 72 hours, preferably 30 minutes to 48 hours.

When Step 1B is carried out under fluoride treatment conditions, specific reaction conditions of (the case where $R^5$ and $R^6$ of a compound are both SEM groups) are as follows.

As the inert solvent to be used, it is not specifically limited so long as it does not inhibit the reaction and dissolves the starting materials with a certain extent, and there may be mentioned, for example, an amide such as N,N-dimethylformamide, N-methylpyrrolidone or N,N-dimethylacetamide, etc.; an ether such as 1,4-dioxane or 1,2-dimethoxyethane, etc.; an aromatic hydrocarbon such as benzene or toluene, etc.; or a sulfoxide such as dimethylsulfoxide, etc., preferably N,N-dimethylformamide, N-methylpyrrolidone or N,N-dimethylacetamide.

As the fluoride to be used, there may be mentioned, for example, tetraethylammonium fluoride or tetrabutylammonium fluoride, etc. An amount of the fluoride to be used is generally 1 to 100-fold mol amount, preferably 5 to 15-fold mol amount based on 1 mol of Compound (2). To promote the reaction, an amine, for example, ammonia, methylamine, ethylamine, propylamine or ethylenediamine, etc. may be added. An amount of the amine to be used is generally 1 to 100-fold mol amount, preferably 1 to 15-fold mol amount based on 1 mol of Compound (2).

A reaction temperature may vary depending on a kind, an amount to be used of starting materials, solvent(s), etc., and is generally in the range of 80° C. to 150° C., preferably 80° C. to 100° C.

A reaction time may vary depending on a reaction temperature, etc., and is usually 15 minutes to 72 hours, preferably 30 minutes to 48 hours.

(Step 1B11-Step 1B12) are steps of removing protective groups in the order of firstly $R^{5'}$, and then $R^6$.

In (Step 1B11-Step 1B12), to prepare Compound (1) of the present invention from Compound (2'), it is necessary to select suitable reaction conditions under a suitable combination of $R^{5'}$ and $R^6$.

[Step 1B11]

In Step 1B11, as a treatment method of removing $R^{5'}$,
(Treatment 1) a treatment with a fluoride in the case that $R^{5'}$ is a SEM group, or
(Treatment 2) a treatment under hydrogenation decomposition conditions wherein $R^{5'}$ is a BOM group, and $R^6$ is a group other than the BOM group is suitable.

(Treatment 1)

A step of preparing Compound (5) from Compound (2') (the case where $R^{5'}$ is a SEM group) of Step 1B11 is carried out in the presence of an inert solvent by treating with a fluoride.

As the inert solvent to be used, it is not specifically limited so long as it does not inhibit the reaction and dissolves the starting materials with a certain extent, and there may be mentioned, for example, an alcohol such as methanol, ethanol, propanol or isopropanol, etc.; an ether such as tetrahydrofuran, 1,4-dioxane or 1,2-dimethoxyethane, etc.; an ester such as methyl formate, ethyl formate, methyl acetate or ethyl acetate, etc.; a nitrile such as acetonitrile or propionitrile, etc.;

water; or a mixed solvent of an optional combination of the above, etc., preferably tetrahydrofuran, 1,4-dioxane or 1,2-dimethoxyethane.

As the fluoride to be used, there may be mentioned, tetraethylammonium fluoride or tetrabutylammonium fluoride, etc. An amount of the fluoride to be used is generally 1 to 100-fold mol amount, preferably 5 to 15-fold mol amount based on 1 mol of Compound (2').

To promote the reaction, an amine derivative such as ammonia, methylamine, ethylamine, propylamine or ethylenediamine, etc. may be added.

An amount of the amine derivative to be used is generally 1 to 100-fold mol amount, preferably 5 to 15-fold mol amount based on 1 mol of Compound (2').

A reaction temperature may vary depending on a kind, an amount to be used of starting materials, solvent(s), etc., and is generally in the range of 0° C. to 100° C., preferably 15° C. to 80° C.

A reaction time may vary depending on a reaction temperature, etc., and is generally for 10 minutes to 240 hours, preferably 1 to 24 hours.

(Treatment 2)

A step of preparing Compound (5) from Compound (2') (the case where $R^5$ is a BOM group, and $R^6$ is a group other than the BOM group) of Step 1B11 is carried out in the same manner as in the treatment under hydrogenation decomposition conditions of the above-mentioned "Step 1B".

[Step 1B12]

In Step 1B12, as a treatment method of removing $R^6$, (Treatment 3) a treatment under acidic conditions wherein $R^6$ is a 4-methoxybenzyl group, MOM group, MEM group, BOM group, SEM group, BOC group or THP group, (Treatment 4) a treatment under strong hydrogenation decomposition conditions wherein $R^6$ is a benzyl group, or (Treatment 5) a treatment by a fluoride wherein $R^6$ is a SEM group is suitable.

(Treatment 3)

The step of preparing Compound (1) of the present invention from Compound (5) of Step 1B12 can be carried out in the same treatment under acidic conditions of the above-mentioned "Step 1B".

(Treatment 4)

In the step of preparing Compound (1) of the present invention from Compound (5) of Step 1B12, the strong hydrogenation decomposition conditions when $R^6$ of Compound (5) is a benzyl group refer to the same treatment conditions of the hydrogenation decomposition conditions of the above-mentioned "Step 1B" except that acetic acid is used as an inert solvent, a reaction temperature is preferably in the range of 80° C. to 110° C., a reaction time may vary depending on a reaction temperature, etc., preferably 6 to 48 hours.

(Treatment 5)

A step of preparing Compound (1) of the present invention from Compound (5) where $R^6$ is a SEM group of Step 1B12 can be carried out in the same manner as in the above-mentioned (Treatment 1) of the above-mentioned "Step 1B11". To promote the reaction, lithium bromide may be added.

An amount of the lithium bromide to be used is generally 1 to 20-fold mol amount, preferably 1 to 5-fold mol amount based on 1 mol of Compound (5).

(Step 1B21-Step 1B22) are steps of removing protective groups in the order of firstly $R^{6'}$, and then $R^{5''}$.

In (Step 1B21-Step 1B22), to prepare Compound (1) of the present invention from Compound (2"), it is necessary to select suitable reaction conditions in the respective steps with a suitable combination of $R^{5''}$ and $R^{6''}$.

[Step 1B21]

In Step 1B21, as a treatment method of removing $R^{6'}$, (Treatment 6) a treatment under relatively weak acidic conditions when $R^{5''}$ is a BOM group, and $R^{6'}$ is a MOM group, MEM group, BOM group, SEM group, BOC group or THP group, is suitable.

(Treatment 6)

The step of preparing Compound (6') from Compound (2") of Step 1B21 can be carried out in the same manner as in the treatment under acidic conditions of the above-mentioned "Step 1B" except for a reaction temperature and a reaction time.

A reaction temperature is preferably in the range of 0° C. to 100° C., more preferably 15° C. to 60° C.

A reaction time may vary depending on a reaction temperature, etc., and is generally for 10 minutes to 10 hours, preferably 30 minutes to 5 hours.

[Step 1B22]

In Step 1B22, as a treatment method of removing $R^{5''}$, (Treatment 7) in Step 1B, a treatment under stronger acidic conditions than the conditions for removing $R^6$ is suitable.

(Treatment 7)

In the step of preparing Compound (1) of the present invention from Compound (6') of Step 1B22, treatment conditions under stronger acidic conditions than the conditions for removing $R^6$ in "Step 1B" are the same treatment conditions as in the treatment conditions under acidic conditions of the above-mentioned "Step 1B" except for a reaction temperature and a reaction time.

A reaction temperature is preferably in the range of 50° C. to 150° C., more preferably 80° C. to 120° C.

A reaction time may vary depending on a reaction temperature, etc., and is preferably 1 hour to 48 hours, more preferably 5 hours to 24 hours.

[Preparation Method 2]

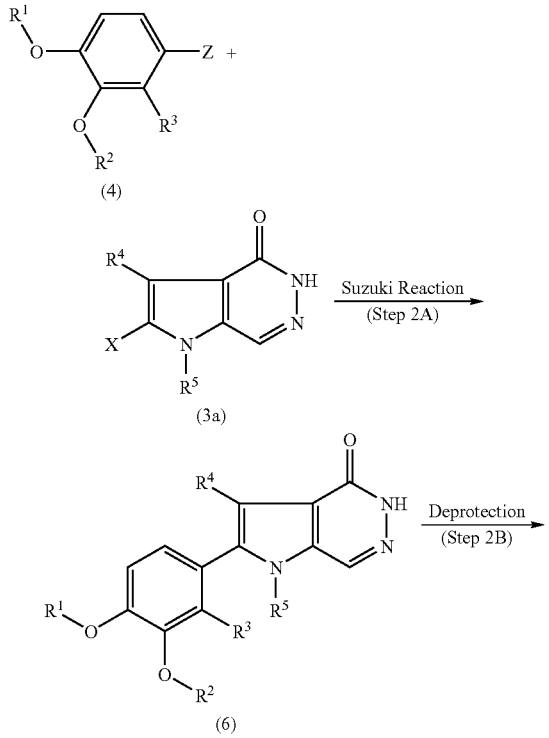

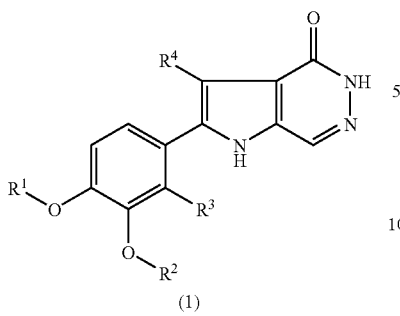

(1)

wherein $R^1$, $R^2$, $R^3$, $R^4$, $R^5$, X and Z have the same meanings as defined above.

Preparation method 2 is another method of preparing Compound (1) of the present invention.

Step 2A is a step of preparing Compound (6) by Suzuki Reaction of boric acid Compound (4) and Compound (3a). This step is carried out in the same manner as in the above-mentioned "Step 1A" except for using Compound (3a) in place of Compound (3), and using tetrakis(triphenylphosphine)palladium as a catalyst.

Step 2B is a step of preparing Compound (1) of the present invention by removing a protective group $R^5$ from Compound (6). This step is carried out in the same manner as in the above-mentioned "Step 1B" except for using Compound (6) in place of Compound (2).

Incidentally, a compound in which $R^1$ is a difluoromethyl group in Compound (3) or Compound (4) which is used as a starting substance in "Preparation method 1" and "Preparation method 2", and Compound (2), Compound (5) or Compound (6) which is an intermediate substance are novel compounds, and can be prepared by any one of Preparation methods shown as Preparation methods 4 to 31, or 43 to 47 mentioned below.

Also, a compound in which $R^1$ in Compound (4) is a methyl group is conventionally known, or can be prepared from a conventionally known compound by a conventionally known method (for example, see Synthesis, 18, 2805 (2003)).

[Preparation Method 3]

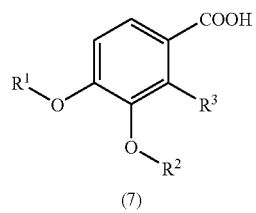

(7)

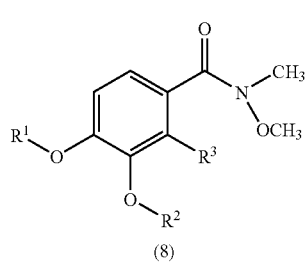

(8)

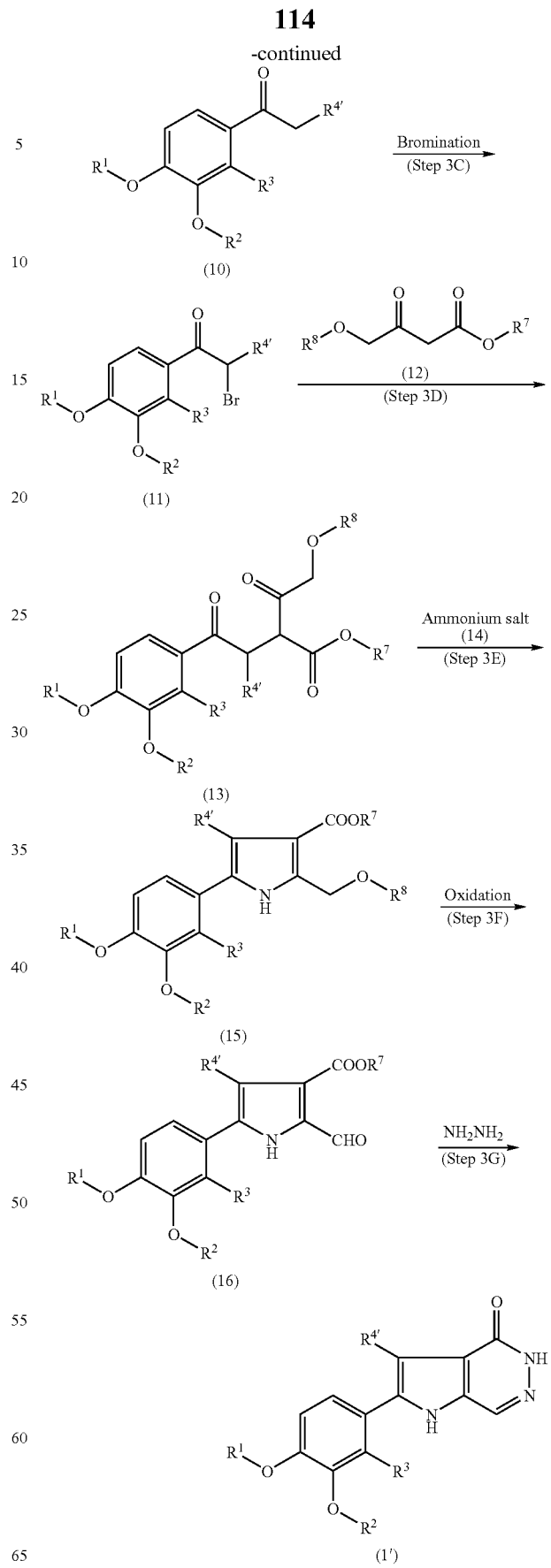

wherein $R^1$, $R^2$ and $R^3$ have the same meanings as defined above, $R^{4'}$ represents a hydrogen atom, a $C_7$-$C_8$ aralkyl group, an aromatic ring group, a heteroaromatic ring group or a $C_1$-$C_8$ alkyl group defined in $R^4$, (the $C_7$-$C_8$ aralkyl group may be mentioned, for example, a benzyl or phenethyl group, the aromatic ring group may be mentioned, for example, a phenyl or naphthyl group, preferably a phenyl group, and the heteroaromatic ring group may be mentioned, for example, a thienyl, oxazolyl, isoxazolyl, thiazolyl, isothiazolyl, imidazolyl, pyrazolyl, pyridyl, pyridazinyl, pyrimidinyl or pyrazinyl group, etc., preferably a thienyl, thiazolyl, pyrazolyl or pyridyl group.), $R^7$ and $R^8$ may be the same or different from each other, and each represents a $C_1$-$C_4$ alkyl group or a "$C_7$-$C_8$ aralkyl group which may be substituted by a $C_1$-$C_2$ alkoxy group", (the $C_1$-$C_4$ alkyl group may be mentioned, for example, a methyl, ethyl, propyl, isopropyl, butyl, isobutyl, sec-butyl or tert-butyl group, preferably a methyl or ethyl group, the "$C_7$-$C_8$ aralkyl group which may be substituted by a $C_1$-$C_2$ alkoxy group" may be mentioned, for example, benzyl, 4-methoxybenzyl, 3-methoxybenzyl, 2-methoxybenzyl, 4-ethoxybenzyl, 3-ethoxybenzyl, 2-ethoxybenzyl, phenethyl, 4-methoxyphenethyl, 3-methoxyphenethyl, 2-methoxyphenethyl, 4-ethoxyphenethyl, 3-ethoxyphenethyl or 2-ethoxyphenethyl group, etc., preferably benzyl or 4-methoxybenzyl group.), M represents a counter metal such as MgCl, MgBr or Li, etc. which form an organometallic compound such as a Grignard reagent and an organolithium reagent, etc.

Preparation method 3 is a method for preparing Compound (1') of the present invention by using a benzoic acid compound (7) as a starting substance and constructing a pyrrolopyridazinone skeleton stepwise.

Step 3A is a step of preparing an amide compound (8) by reacting Compound (7) with a halogenating agent in an inert solvent to lead to an acid halide compound, then, reacting the compound with a N,O-dimethylhydroxylamine in the presence of a base. Compound (7) is a compound which is conventionally known, or can be prepared by the below mentioned "Preparation method 41".

As the inert solvent to be used, it is not specifically limited so long as it does not inhibit the reaction and dissolves the starting materials with a certain extent, and there may be mentioned, for example, a halogenated aliphatic hydrocarbon such as chloroform, dichloromethane or 1,2-dichloroethane, etc.; an ether such as 1,4-dioxane, tetrahydrofuran, diethyl ether or 1,2-dimethoxyethane, etc.; an amide such as N,N-dimethylformamide, N,N-dimethylacetamide or N-methylpyrrolidone, etc.; or a mixed solvent of an optional combination of the above, etc., preferably dichloromethane, 1,2-dichloroethane, N,N-dimethylformamide or a mixed solvent thereof.

As the halogenating agent to be used, there may be mentioned, for example, thionyl chloride, phosphorus trichloride, phosphorus tribromide, phosphorus oxychloride or phosphorus pentachloride, etc., preferably thionyl chloride. An amount of the halogenating agent to be used is generally 1 to 10-fold mol amount, preferably 1 to 3-fold mol amount based on 1 mol of Compound (7).

An amount of the N,O-dimethylhydroxylamine to be used is generally 1 to 10-fold mol amount, preferably 4.5 to 5.5-fold mol amount based on 1 mol of Compound (7).

As the base to be used, there may be mentioned, for example, an organic base such as triethylamine or N,N-diisopropylethylamine, etc.; or an inorganic base such as sodium carbonate or potassium carbonate, etc., preferably triethylamine or N,N-diisopropylethylamine. An amount of the base to be used is generally 1 to 100-fold mol amount, preferably 1 to 20-fold mol amount based on 1 mol of Compound (7).

A reaction temperature may vary depending on a kind, an amount to be used of starting materials, solvent(s), etc., and is generally in the range of $-20°$ C. to $100°$ C., preferably $-5°$ C. to $50°$ C.

A reaction time may vary depending on a reaction temperature, etc., and is generally for 10 minutes to 24 hours, preferably 1 hour to 6 hours.

Step 3B is a step of preparing a carbonyl compound (10) by reacting Compound (8) with an organometallic compound (9) such as an organolithium compound or a Grignard compound, etc., in an inert solvent.

As the inert solvent to be used, it is not specifically limited so long as it does not inhibit the reaction and dissolves the starting materials with a certain extent, and there may be mentioned, for example, an ether such as 1,4-dioxane, tetrahydrofuran, diethyl ether or 1,2-dimethoxyethane, etc. or a mixed solvent of an optional combination of the above, preferably tetrahydrofuran, diethyl ether or a mixed solvent thereof.

As the organometallic compound (9) to be used, there may be mentioned, for example, an organolithium reagent such as methyl lithium, butyl lithium, phenyl lithium, etc.; or an organomagnesium reagent (Grignard reagent) such as methyl magnesium bromide, ethyl magnesium bromide, propyl magnesium bromide, butyl magnesium bromide, phenyl magnesium bromide, benzyl magnesium bromide, phenethyl magnesium bromide, etc., preferably methyl magnesium bromide, ethyl magnesium bromide, propyl magnesium bromide, butyl magnesium bromide, phenyl magnesium bromide, benzyl magnesium bromide or phenethyl magnesium bromide. An amount of the organometallic compound (9) to be used is generally 1 to 10-fold mol amount, preferably 1 to 3-fold mol amount based on 1 mol of Compound (8).

A reaction temperature may vary depending on a kind, an amount to be used of starting materials, solvent(s), etc., and is generally in the range of $-20°$ C. to $100°$ C., preferably $-5°$ C. to $50°$ C.

A reaction time may vary depending on a reaction temperature, etc., and is generally for 10 minutes to 240 hours, preferably 1 hour to 24 hours.

Step 3C is a step of preparing a brominated compound (11) by using a brominating agent in an inert solvent.

As the inert solvent to be used, it is not specifically limited so long as it does not inhibit the reaction and dissolves the starting materials with a certain extent, and there may be mentioned, for example, an alcohol such as methanol, ethanol, propanol or isopropanol, etc.; an ether such as diethyl ether, 1,2-dimethoxyethane, 1,4-dioxane or tetrahydrofuran, etc.; a halogenated aliphatic hydrocarbon such as dichloromethane, chloroform or 1,2-dichloroethane, etc.; an ester such as methyl acetate or ethyl acetate, etc.; an organic acid such as acetic acid, propionic acid or trifluoroacetic acid, etc.; or a mixed solvent of an optional combination of the above, preferably methanol, isopropanol or tetrahydrofuran.

As the brominating agent to be used, there may be mentioned, for example, bromine, benzyltrimethylammonium tribromide, trimethylphenylammonium tribromide, tetramethylammonium tribromide, tetraethylammonium tribromide, tetrabutylammonium tribromide or pyridinium hydrobromide perbromide, etc., preferably bromine or trimethylphenylammonium tribromide. An amount of the brominating agent to be used is generally 1 to 50-fold mol amount, preferably 1 to 10-fold mol amount based on 1 mol of Compound (10).

A reaction temperature may vary depending on a kind, an amount to be used of starting materials, solvent(s), etc., and is generally in the range of −20° C. to 100° C., preferably −5° C. to 50° C.

A reaction time may vary depending on a reaction temperature, etc., and is generally for 10 minutes to 240 hours, preferably 1 hour to 48 hours.

Step 3D is a step of preparing a diketone compound (13) by the reaction of Compound (11) and an acetoacetic acid ester derivative (12) in an inert solvent in the presence of a base.

As the inert solvent to be used, it is not specifically limited so long as it does not inhibit the reaction and dissolves the starting materials with a certain extent, and there may be mentioned, for example, an alcohol such as methanol, ethanol, propanol or isopropanol, etc.; an ether such as diethyl ether, 1,4-dioxane or tetrahydrofuran, etc.; a halogenated aliphatic hydrocarbon such as dichloromethane, chloroform or 1,2-dichloroethane, etc.; an ester such as methyl acetate or ethyl acetate, etc.; an amide such as N,N-dimethylformamide, N,N-dimethylacetamide or N-methylpyrrolidone, etc.; a nitrile such as acetonitrile or propionitrile, etc.; or a mixed solvent of an optional combination of the above, preferably methanol or ethanol.

As the acetoacetic acid ester derivative (12) to be used, there may be mentioned, for example, methyl 4-benzyloxy-3-oxobutyrate, ethyl 4-benzyloxy-3-oxobutyrate, propyl 4-benzyloxy-3-oxobutyrate, isopropyl 4-benzyloxy-3-oxobutyrate, methyl 4-methoxy-3-oxobutyrate, ethyl 4-methoxy-3-oxobutyrate, propyl 4-methoxy-3-oxobutyrate, isopropyl 4-methoxy-3-oxobutyrate, methyl 4-ethoxy-3-oxobutyrate, ethyl 4-ethoxy-3-oxobutyrate, propyl 4-ethoxy-3-oxobutyrate, isopropyl 4-ethoxy-3-oxobutyrate, methyl 3-oxo-4-propoxybutyrate, ethyl 3-oxo-4-propoxybutyrate, propyl 3-oxo-4-propoxybutyrate, isopropyl 3-oxo-4-propoxybutyrate, methyl 4-(4-methoxybenzyloxy)-3-oxobutyrate, ethyl 4-(4-methoxybenzyloxy)-3-oxobutyrate, propyl 4-(4-methoxybenzyloxy)-3-oxobutyrate or isopropyl 4-(4-methoxybenzyloxy)-3-oxobutyrate, etc., preferably methyl 4-benzyloxy-3-oxobutyrate, ethyl 4-benzyloxy-3-oxobutyrate, methyl 4-methoxy-3-oxobutyrate, ethyl 4-methoxy-3-oxobutyrate, methyl 4-ethoxy-3-oxobutyrate, ethyl 4-ethoxy-3-oxobutyrate, methyl 4-(4-methoxybenzyloxy)-3-oxobutyrate or ethyl 4-(4-methoxybenzyloxy)-3-oxobutyrate. An amount of the acetoacetic acid ester derivative (12) to be used is generally 1 to 10-fold mol amount, preferably 1 to 2-fold mol amount based on 1 mol of Compound (11).

As the base to be used, there may be mentioned, for example, sodium methoxide, sodium ethoxide, potassium methoxide, potassium ethoxide, sodium tert-butoxide or potassium tert-butoxide, etc., preferably sodium methoxide or sodium ethoxide. An amount of the base to be used is generally 1 to 10-fold mol amount, preferably 1 to 2-fold mol amount based on 1 mol of Compound (11).

A reaction temperature may vary depending on a kind, an amount to be used of starting materials, solvent(s), etc., and is generally in the range of −20° C. to 100° C., preferably −5° C. to 50° C.

A reaction time may vary depending on a reaction temperature, etc., and is generally for 10 minutes to 240 hours, preferably 30 minutes to 48 hours.

Step 3E is a step of preparing a pyrrole compound (15) by the reaction of Compound (13) and an ammonium salt (14) in an inert solvent.

As the inert solvent to be used, it is not specifically limited so long as it does not inhibit the reaction and dissolves the starting materials with a certain extent, and there may be mentioned, for example, an alcohol such as methanol, ethanol, propanol or isopropanol, etc.; an ether such as diethyl ether, 1,4-dioxane or tetrahydrofuran, etc.; a halogenated aliphatic hydrocarbon such as dichloromethane, chloroform or 1,2-dichloroethane, etc.; an ester such as methyl acetate or ethyl acetate, etc.; an amide such as N,N-dimethylformamide, N,N-dimethylacetamide or N-methylpyrrolidone, etc.; a nitrile such as acetonitrile or propionitrile, etc.; or a mixed solvent of an optional combination of the above, etc., preferably methanol or ethanol.

As the ammonium salt (14) to be used, there may be mentioned, for example, ammonium formate, ammonium acetate or ammonium propionate, etc., preferably ammonium acetate. An amount of the ammonium salt (14) is generally 1 to 50-fold mol amount, preferably 1 to 10-fold mol amount based on 1 mol of Compound (13).

A reaction temperature may vary depending on a kind, an amount to be used of starting materials, solvent(s), etc., and is generally in the range of 0° C. to 200° C., preferably 15° C. to 100° C.

A reaction time may vary depending on a reaction temperature, etc., and is generally for 10 minutes to 240 hours, preferably 30 minutes to 48 hours.

Step 3F is a step of preparing a pyrrole compound (16) by treating Compound (15) with an oxidizing agent in an inert solvent.

As the inert solvent to be used, it is not specifically limited so long as it does not inhibit the reaction and dissolves the starting materials with a certain extent, and there may be mentioned, for example, an alcohol such as methanol, ethanol, propanol or isopropanol, etc.; an ether such as diethyl ether, 1,4-dioxane or tetrahydrofuran, etc.; a halogenated aliphatic hydrocarbon such as dichloromethane, chloroform or 1,2-dichloroethane, etc.; an ester such as methyl acetate or ethyl acetate, etc.; an amide such as N,N-dimethylformamide, N,N-dimethylacetamide or N-methylpyrrolidone, etc.; a nitrile such as acetonitrile or propionitrile, etc.; water; or a mixed solvent of an optional combination of the above, etc., preferably a mixed solvent of dichloromethane and water.

As the oxidizing agent to be used, there may be mentioned, for example, 2,3-dichloro-5,6-dicyano-1,4-benzoquinone or ammonium cerium(IV) nitrate, etc., preferably 2,3-dichloro-5,6-dicyano-1,4-benzoquinone. An amount of the oxidizing agent to be used is generally 1 to 50-fold mol amount, preferably 1 to 3-fold mol amount based on 1 mol of Compound (15).

A reaction temperature may vary depending on a kind, an amount to be used of starting materials, solvent(s), etc., and is generally in the range of −20° C. to 100° C., preferably −5° C. to 50° C.

A reaction time may vary depending on a reaction temperature, etc., and is generally for 10 minutes to 240 hours, preferably 30 minutes to 48 hours.

Step 3G is a step of preparing Compound (1') of the present invention having a pyrrolopyridazinone skeleton by reacting Compound (16) with a hydrazine monohydrate in an inert solvent.

As the inert solvent to be used, it is not specifically limited so long as it does not inhibit the reaction and dissolves the starting materials with a certain extent, and there may be mentioned, for example, an alcohol such as methanol, ethanol, propanol, isopropanol, ethylene glycol or diethylene glycol, etc.; a nitrile such as acetonitrile or propionitrile, etc.; an ether such as 1,2-dimethoxyethane, 1,4-dioxane or tetrahydrofuran, etc.; an amide such as N,N-dimethylformamide, N,N-dimethylacetamide or N-methylpyrrolidone, etc.; water;

or a mixed solvent of an optional combination of the above, etc., preferably ethylene glycol or diethylene glycol.

An amount of the hydrazine monohydrate to be used is generally 1 to 100-fold mol amount, preferably 1 to 10-fold mol amount based on 1 mol of Compound (16).

A reaction temperature may vary depending on a kind, an amount to be used of starting materials, solvent(s), etc., and is generally in the range of 0° C. to 300° C., preferably 50° C. to 200° C.

A reaction time may vary depending on a reaction temperature, etc., and is generally for 10 minutes to 240 hours, preferably 1 hour to 72 hours.

[Preparation Method 4]

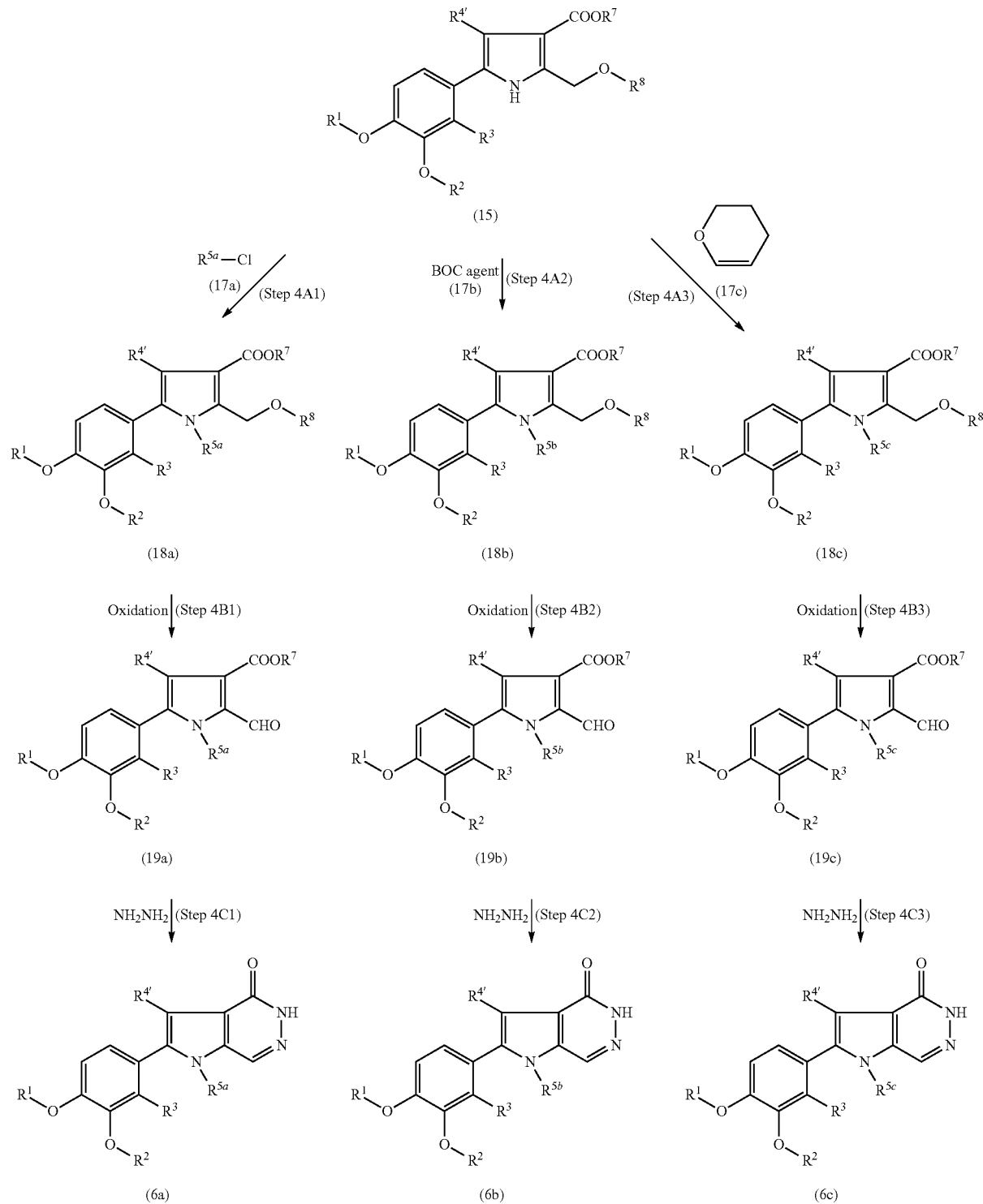

wherein $R^1$, $R^2$, $R^3$, $R^{4'}$, $R^7$ and $R^8$ have the same meanings as defined above, $R^{5a}$ represents a 4-methoxybenzyl group, MOM group, MEM group, BOM group, SEM group or THP group, $R^{5b}$ represents a BOC group, and $R^{5c}$ represents a THP group.

Preparation method 4 is a method for preparing intermediate compound (6a), (6b) or (6c) of Preparation method 1 from a pyrrole compound (15), and comprises the corresponding Step 4A (Step 4A1, 4A2, 4A3), Step 4B (Step 4B1, 4B2, 4B3) and Step 4C (Step 4C1, 4C2, 4C3), respectively.

Step 4A is a step of introducing $R^{5a}$, $R^{5b}$ or $R^{5c}$ which is a protective group corresponding to respective groups by reacting a pyrrole compound (15) with Compound (17a), (17b) or (17c), and a method or conditions for introduction can be referred to a written book (see W. Greene and P. G. H. Wuts "Protective Groups in Organic Synthesis" $3^{rd}$ Ed., John Wiley & Sons), etc., and it is not specifically limited by these conditions.

Step 4A1 is a step of preparing Compound (18a) in which $R^{5a}$ is introduced as a protective group into the NH group of the pyrrole ring of Compound (15) by reacting a pyrrole compound (15) with Compound (17a) in an inert solvent in the presence of a base. Compound (15) can be prepared by the above-mentioned "Step 3e".

As Compound (17a) to be used, there may be mentioned, for example, 4-methoxybenzyl chloride, methoxymethyl chloride, methoxyethoxymethyl chloride, benzyloxymethyl chloride, (2-trimethylsilylethoxy)methyl chloride or tetrahydropyranyl chloride, etc. An amount of Compound (17a) to be used is generally 1 to 3-fold mol amount, preferably 1 to 1.5-fold mol amount based on 1 mol of Compound (15).

As the inert solvent to be used, it is not specifically limited so long as it does not inhibit the reaction and dissolves the starting materials with a certain extent, and there may be mentioned, for example, an ether such as tetrahydrofuran, 1,4-dioxane or 1,2-dimethoxyethane, etc.; an ester such as methyl acetate or ethyl acetate, etc.; a nitrile such as acetonitrile or propionitrile, etc.; an amide such as N,N-dimethylformamide, N,N-dimethylacetamide or N-methylpyrrolidone, etc.; a sulfoxide such as dimethylsulfoxide, etc.; a halogenated aliphatic hydrocarbon such as dichloromethane, chloroform or 1,2-dichloroethane, etc.; or a mixed solvent of an optional combination of the above, etc., preferably N,N-dimethylformamide, dichloromethane or 1,2-dichloroethane.

Incidentally, when the inert solvent is an ester, a nitrile or a halogenated aliphatic hydrocarbon, an amine is preferred as a base.

As the base to be used, there may be mentioned, for example, an alkali metal such as metal sodium or metal potassium, etc.; an alkali metal hydride such as sodium hydride or potassium hydride, etc.; an alkali metal amide such as lithium amide, sodium amide, lithium diisopropyl amide or lithium bis(trimethylsilyl) amide, etc.; an alkali metal alkoxide such as sodium tert-butoxide or potassium tert-butoxide, etc.; or an amine such as triethylamine, tributylamine, N,N-diisopropylethylamine, pyridine, picoline, 2,6-lutidine or 4-dimethylaminopyridine, etc., and the like, preferably metal sodium, sodium hydride, triethylamine or N,N-diisopropylethylamine. An amount of the base to be used is generally 1 to 3-fold mol amount, preferably 1 to 1.5-fold mol amount based on 1 mol of Compound (15).

A reaction temperature may vary depending on a kind, an amount to be used of starting materials, solvent(s), etc., and is generally in the range of −80° C. to 100° C., preferably 0° C. to 60° C.

A reaction time may vary depending on a reaction temperature, etc., and is generally for 10 minutes to 240 hours, preferably 1 hour to 48 hours.

Step 4A2 is a step of preparing Compound (18b) in which $R^{5b}$ is introduced into the NH group of the pyrrole ring of Compound (15) as a protective group by reacting a pyrrole compound (15) with Compound (17b) in an inert solvent in the presence of a base.

As Compound (17b) to be used, there may be mentioned, for example, di(tert-butyl) dicarbonate, tert-butoxy carbonyl azide or tert-butyl phenyl carbonate, etc., preferably tert-butoxy carbonyl azide or tert-butyl phenyl carbonate. An amount of Compound (17b) to be used is generally 1 to 3-fold mol amount, preferably 1 to 1.5-fold mol amount based on 1 mol of Compound (15).

As the inert solvent to be used, it is not specifically limited so long as it does not inhibit the reaction and dissolves the starting materials with a certain extent, and there may be mentioned, for example, an ether such as tetrahydrofuran, 1,4-dioxane or 1,2-dimethoxyethane, etc.; an amide such as N,N-dimethylformamide, N,N-dimethylacetamide or N-methylpyrrolidone, etc.; a sulfoxide such as dimethylsulfoxide, etc.; or a mixed solvent of an optional combination of the above, etc., preferably N,N-dimethylformamide.

As the base to be used, there may be mentioned, for example, an alkali metal such as metal sodium or metal potassium, etc.; an alkali metal hydride such as sodium hydride or potassium hydride, etc.; an alkali metal amide such as lithium amide, sodium amide, lithium diisopropyl amide or lithium bistrimethylsilyl amide, etc.; or an alkali metal alkoxide such as sodium tert-butoxide or potassium tert-butoxide, etc., and the like, preferably sodium hydride. An amount of the base to be used is generally 1 to 3-fold mol amount, preferably 1 to 1.5-fold mol amount based on 1 mol of Compound (15).

A reaction temperature may vary depending on a kind, an amount to be used of starting materials, solvent(s), etc., and is generally in the range of −80° C. to 100° C., preferably 0° C. to 60° C.

A reaction time may vary depending on a reaction temperature, etc., and is generally for 10 minutes to 240 hours, preferably 1 hour to 48 hours.

Step 4A3 is a step of preparing Compound (18c) in which $R^{5c}$ is introduced into the NH group of the pyrrole ring of Compound (15) as a protective group by reacting a pyrrole compound (15) with Compound (17c) in an inert solvent in the presence of a chloride or an acid, which is another method for introducing a THP group.

An amount of Compound (17c) to be used is generally 1 to 5-fold mol amount, preferably 1 to 3-fold mol amount based on 1 mol of Compound (15).

As the inert solvent to be used, it is not specifically limited so long as it does not inhibit the reaction and dissolves the starting materials with a certain extent, and there may be mentioned, for example, an ether such as diethyl ether, tetrahydrofuran, 1,4-dioxane or 1,2-dimethoxyethane, etc.; an ester such as methyl acetate or ethyl acetate, etc.; a nitrile such as acetonitrile or propionitrile, etc.; a halogenated aliphatic hydrocarbon such as dichloromethane, chloroform or 1,2-dichloroethane, etc.; or a mixed solvent of an optional combination of the above, etc., preferably diethyl ether, tetrahydrofuran, acetonitrile, dichloromethane or 1,2-dichloroethane.

As the chloride or acid to be used, there may be mentioned, for example, a chloride which generates a hydrogen chloride gas in a system such as oxalyl chloride, thionyl chloride or acetyl chloride, etc.; an acid such as a hydrogen chloride gas, methanesulfonic acid or p-toluenesulfonic acid, etc., preferably a hydrogen chloride gas or p-toluenesulfonic acid. An amount of the chloride or the acid to be used is generally 0.05 to 3-fold mol amount, preferably 0.1 to 0.5-fold mol amount based on 1 mol of Compound (15).

A reaction temperature may vary depending on a kind, an amount to be used of starting materials, solvent(s), etc., and is generally in the range of −20° C. to 100° C., preferably 0° C. to 50° C.

A reaction time may vary depending on a reaction temperature, etc., and is generally for 10 minutes to 48 hours, preferably 1 hour to 24 hours.

Step 4B (Steps 4B1, 4B2 and 4B3) is a step of preparing a corresponding formyl compound (19a), (19b) or (19c) by treating each of Compound (18a), (18b) or (18c) with an oxidizing agent. This step is carried out in the same manner as in the above-mentioned "Step 3F" except for using Compound (18a), (18b) or (18c) in place of Compound (15).

Step 4C (Steps 4C1, 4C2 and 4C3) is a step of preparing Compound (6a), (6b) or (6c) each having a corresponding pyrrolopyridazinone skeleton by reacting Compound (19a), (19b) or (19c) with hydrazine monohydrate, respectively. This step is carried out in the same manner as in the above-mentioned "Step 3G" except for using Compound (19a), (19b) or (19c) in place of Compound (16).

[Preparation Method 5]

wherein $R^1$, $R^2$, $R^3$, $R^5$, $R^7$, X and Z have the same meanings as defined above, and $R^9$ represents "an aromatic ring group or heteroaromatic ring group each may be substituted by a substituent(s) selected from Substituent group (c)" having the same meaning as defined above.

Preparation method 5 is a method for preparing Compound (6d) in which $R^4$ of the above-mentioned intermediate compound (6) is a methyl group substituted by $R^9$.

Step 5A is a step of preparing Compound (19) by Suzuki reaction of a boronic acid compound (4) and a pyrrole compound (20). Compound (4) can be prepared by either method of the following mentioned "Preparation method 28", "Preparation method 29", "Preparation method 30" or "Preparation method 31". Compound (20) can be prepared by the following mentioned "Step 23D". This step is carried out in the same manner as in the above-mentioned "Step 1A" except for using Compound (20) in place of Compound (3).

Step 5B is a step of preparing Compound (6d) having a pyrrolopyridazinone skeleton by reacting Compound (19d) with hydrazine monohydrate. This step is carried out in the same manner as in the above-mentioned "Step 3G" except for using Compound (19d) in place of Compound (16).

[Preparation Method 6]

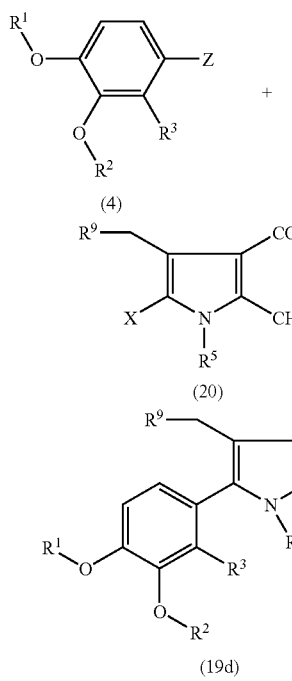

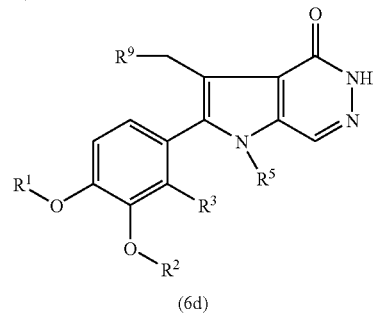

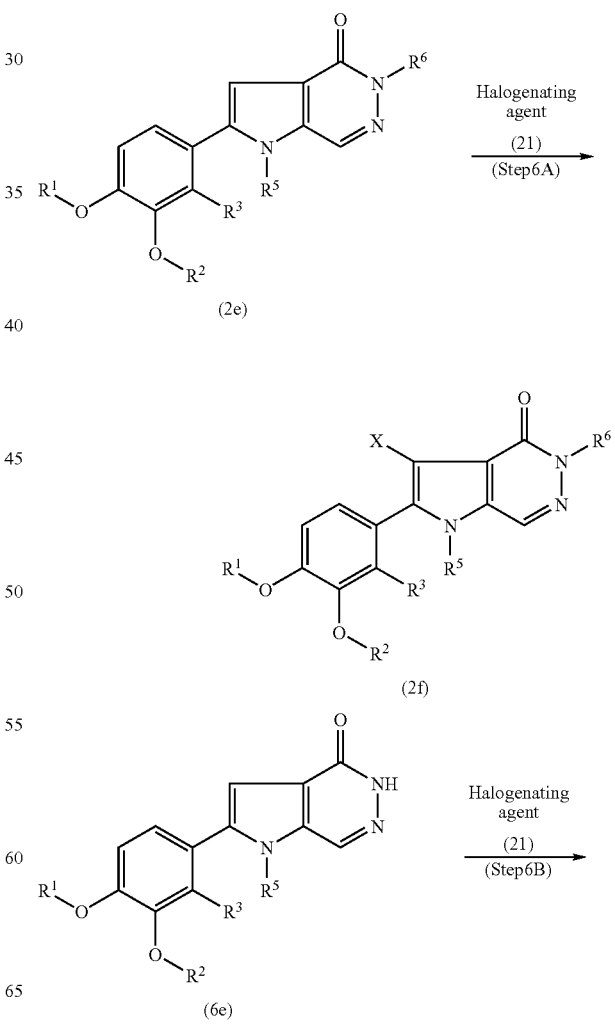

-continued

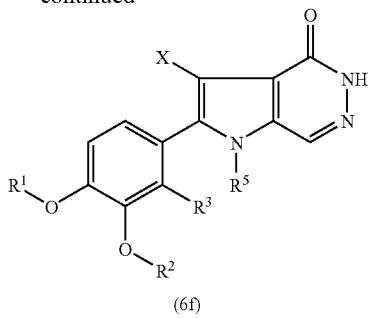

(6f)

wherein $R^1$, $R^2$, $R^3$, $R^5$, $R^6$ and X have the same meanings as defined above.

Preparation method 6 is a method for preparing a compound in which $R^4$ of the above-mentioned intermediate compound (2) or compound (6) is a chlorine, bromine or iodine atom, respectively. This preparation method comprises a step (Step 6A) for preparing Compound (2f) and a step (Step 6B) for preparing Compound (6f) each using a common halogenating agent (21).

Step 6A is a step of preparing a halogenated compound (2f) by reacting Compound (2e) with a halogenating agent (21) in an inert solvent.

Compound (2e) can be prepared, for example, by the above-mentioned "Step 1A".

As the halogenating agent (21) to be used, there may be mentioned, for example, a chlorinating agent such as chlorine, sulfuryl chloride or N-chlorosuccineimide, etc.; a brominating agent such as bromine, benzyltrimethylammonium tribromide, trimethylphenylammonium tribromide, tetramethylammonium tribromide, tetraethylammonium tribromide, tetrabutylammonium tribromide, pyridinium hydrobromide perbromide or N-bromosuccineimide, etc.; or an iodinating agent such as iodine chloride or N-iodosuccineimide, etc., and the like, preferably N-chlorosuccineimide, N-bromosuccineimide or iodine chloride.

An amount of the halogenating agent to be used is generally 1 to 10-fold mol amount, preferably 1 to 3-fold mol amount based on 1 mol of Compound (2e).

Incidentally, when iodine chloride is used, it is necessary to add magnesium sulfate, sodium hydrogencarbonate and ε-caprolactam as an additive.

In such a case, an amount of the magnesium sulfate generally 1 to 20-fold mol amount, preferably 1 to 5-fold mol amount based on 1 mol of Compound (2e).

An amount of the sodium hydrogencarbonate to be used is generally 1 to 20-fold mol amount, preferably 1 to 5-fold mol amount based on 1 mol of Compound (2e).

An amount of the ε-caprolactam to be used is generally 1 to 10-fold mol amount, preferably 1 to 3-fold mol amount based on 1 mol of Compound (2e).

As the inert solvent to be used, it is not specifically limited so long as it does not inhibit the reaction and dissolves the starting materials with a certain extent, and there may be mentioned, for example, an aromatic hydrocarbon such as benzene or toluene, etc.; an ether such as diethyl ether, tetrahydrofuran, 1,2-dimethoxyethane or 1,4-dioxane, etc.; an alcohol such as methanol, ethanol, propanol or isopropanol, etc.; a nitrile such as acetonitrile or propionitrile, etc.; a halogenated aliphatic hydrocarbon such as dichloromethane, chloroform or 1,2-dichloroethane, etc.; or a mixed solvent of an optional combination of the above, etc., preferably acetonitrile or 1,2-dichloroethane.

A reaction temperature may vary depending on a kind, an amount to be used of starting materials, solvent(s), etc., and is generally in the range of −20° C. to 100° C., preferably 0° C. to 50° C.

A reaction time may vary depending on a reaction temperature, etc., and is generally for 10 minutes to 48 hours, preferably 1 hour to 24 hours.

Step 6B is a step of preparing a halogenated compound (6f) by reacting Compound (6e) with a halogenating agent (21) in an inert solvent. Compound (6e) can be prepared, for example, by the above-mentioned "Step 1A". This step is carried out in the same manner as in the above-mentioned "Step 6A" except for using Compound (6e) in place of Compound (2e).

[Preparation Method 7]

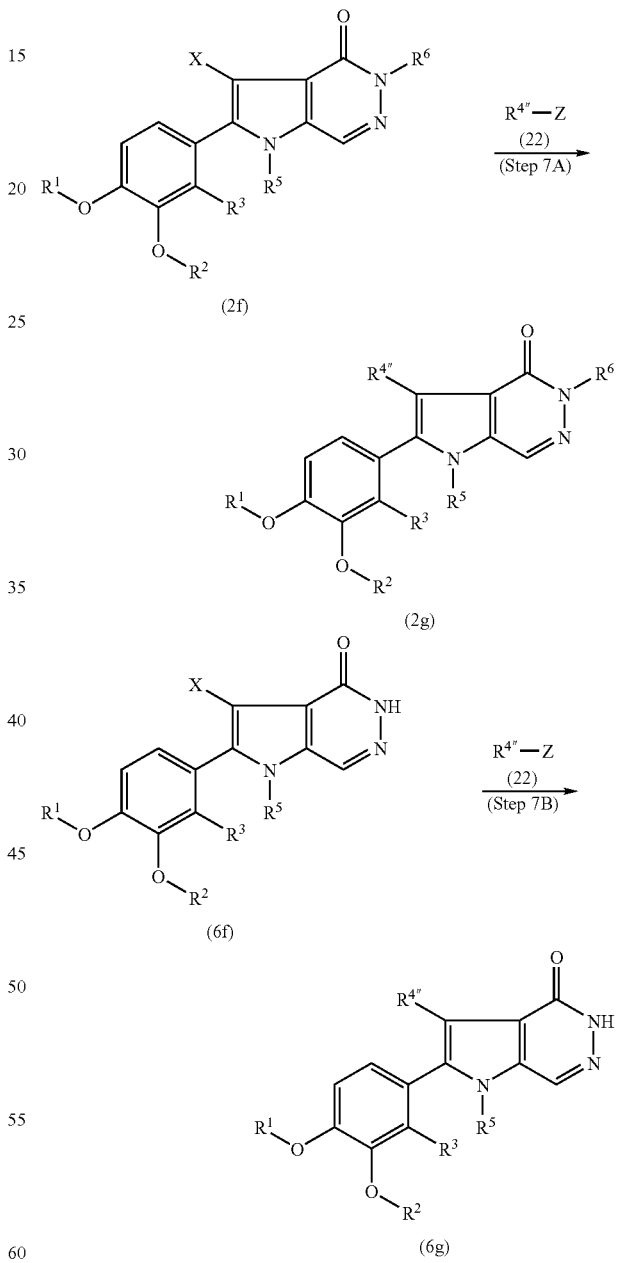

wherein $R^1$, $R^2$, $R^3$, $R^5$, $R^6$, X and Z have the same meanings as defined above, and $R^{4''}$ represents a $C_1$-$C_8$ alkyl group, a $C_2$-$C_6$ alkenyl group, "a $C_3$-$C_6$ cycloalkyl group which may be substituted by a substituent(s) selected from Substituent group (b)", "an aromatic ring group or heteroaromatic ring group each of which may be substituted by a substituent(s)

selected from Substituent group (c)" or "$C_1$-$C_2$ alkyl group which is substituted by an aromatic ring group or heteroaromatic ring group which may be substituted by a group selected from Substituent group (c), and may be substituted by a hydroxy group" (provided that the nitrogen atom of the heteroaromatic ring group may be protected by $R^5$.) which are defined in $R^4$.

Preparation method 7 is a method for preparing a compound in which $R^4$ of the above-mentioned intermediate compound (2) or compound (6) is both $R^4$. This preparation method comprises a step (Step 7A) for preparing Compound (2g) by applying Compound (2f) and a boronic acid compound (22) to Suzuki reaction, and a step (Step 7B) for preparing Compound (6g) by applying Compound (6f) and a boronic acid compound (22) to Suzuki reaction.

Step 7A is a step of preparing Compound (2g) by reacting Compound (2f) with Compound (22) in the presence or absence of an inert solvent (preferably in the presence) and in the presence of either a base or a fluoride (provided that $R^5$ is a SEM group, a base is preferred.) and a palladium catalyst.

Compound (2f) can be prepared by the above-mentioned "Step 6A".

As the boronic acid compound (22) to be used, there may be mentioned, for example, an alkylboronic acid such as methylboronic acid, ethylboronic acid, propylboronic acid, butylboronic acid, isobutylboronic acid, hexylboronic acid or octylboronic acid, etc.; an alkenylboronic acid such as cis-propenylboronic acid or trans-propenylboronic acid, etc.; a cycloalkylboronic acid such as cyclopropylboronic acid, etc.; a phenylboronic acid which may be substituted such as phenylboronic acid, 2-carboxyphenylboronic acid, 3-carboxyphenylboronic acid, 4-carboxyphenylboronic acid, 2-fluorophenylboronic acid, 3-fluorophenylboronic acid, 4-fluorophenylboronic acid, 2,3-difluorophenylboronic acid, 3,4-difluorophenylboronic acid, 2-chlorophenylboronic acid, 3-chlorophenylboronic acid, 4-chlorophenylboronic acid, 2,3-dichlorophenylboronic acid, 3,4-dichlorophenylboronic acid, 2-cyanophenylboronic acid, 3-hydroxyphenylboronic acid, 4-hydroxyphenylboronic acid, 3-methylphenylboronic acid, 4-methylphenylboronic acid, 3-isopropylphenylboronic acid, 4-isopropylphenylboronic acid, 3-methoxyphenylboronic acid, 4-methoxyphenylboronic acid, 3-cyanophenylboronic acid, 4-cyanophenylboronic acid, 3-trifluoromethylphenylboronic acid, 4-trifluoromethylphenylboronic acid, 2-methoxycarbonylphenylboronic acid or 3-nitrophenylboronic acid, etc.; an aralkylboronic acid such as phenethylboronic acid, etc.; a thienylboronic acid which may be substituted such as 2-thienylboronic acid, 3-thienylboronic acid, 5-cyano-2-thienylboronic acid or 5-methyl-2-thienylboronic acid, etc.; a pyrazolylboronic acid which may be substituted such as 1-(2-trimethylsilylethoxymethyl)-4-pyrazolylboronic acid, etc.: or a pinacol ester of the above-mentioned boronic acid, etc. An amount of Compound (22) to be used is generally 1 to 5-fold mol amount, preferably 1.5 to 3-fold mol amount based on 1 mol of Compound (2f).

This step is carried out in the same manner as in the above-mentioned "Step 1A" except for using Compound (2f) in place of Compound (3), and Compound (22) with the above-mentioned equivalent number in place of Compound (4).

Step 7B is a step of preparing Compound (6g) by reacting Compound (6f) with Compound (22) in the presence or absence of an inert solvent (preferably in the presence) and in the presence of either a base or a fluoride (provided that $R^5$ is a SEM group, a base is preferred.) and a palladium catalyst.

Compound (6f) can be prepared by the above-mentioned "Step 6B".

An amount of Compound (22) to be used is generally 1 to 5-fold mol amount, preferably 1.5 to 3-fold mol amount based on 1 mol of Compound (6f).

This step is carried out in the same manner as in the above-mentioned "Step 1A" except for using Compound (6f) in place of Compound (3), and Compound (22) with the above-mentioned equivalent number in place of Compound (4).

[Preparation Method 8]

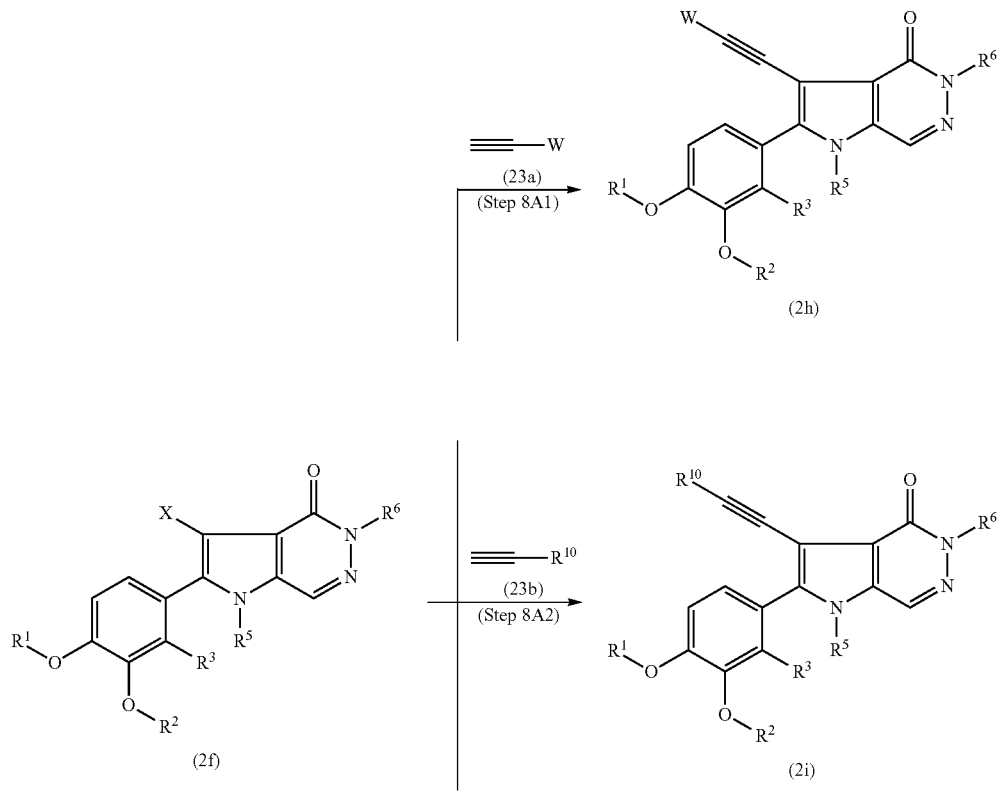

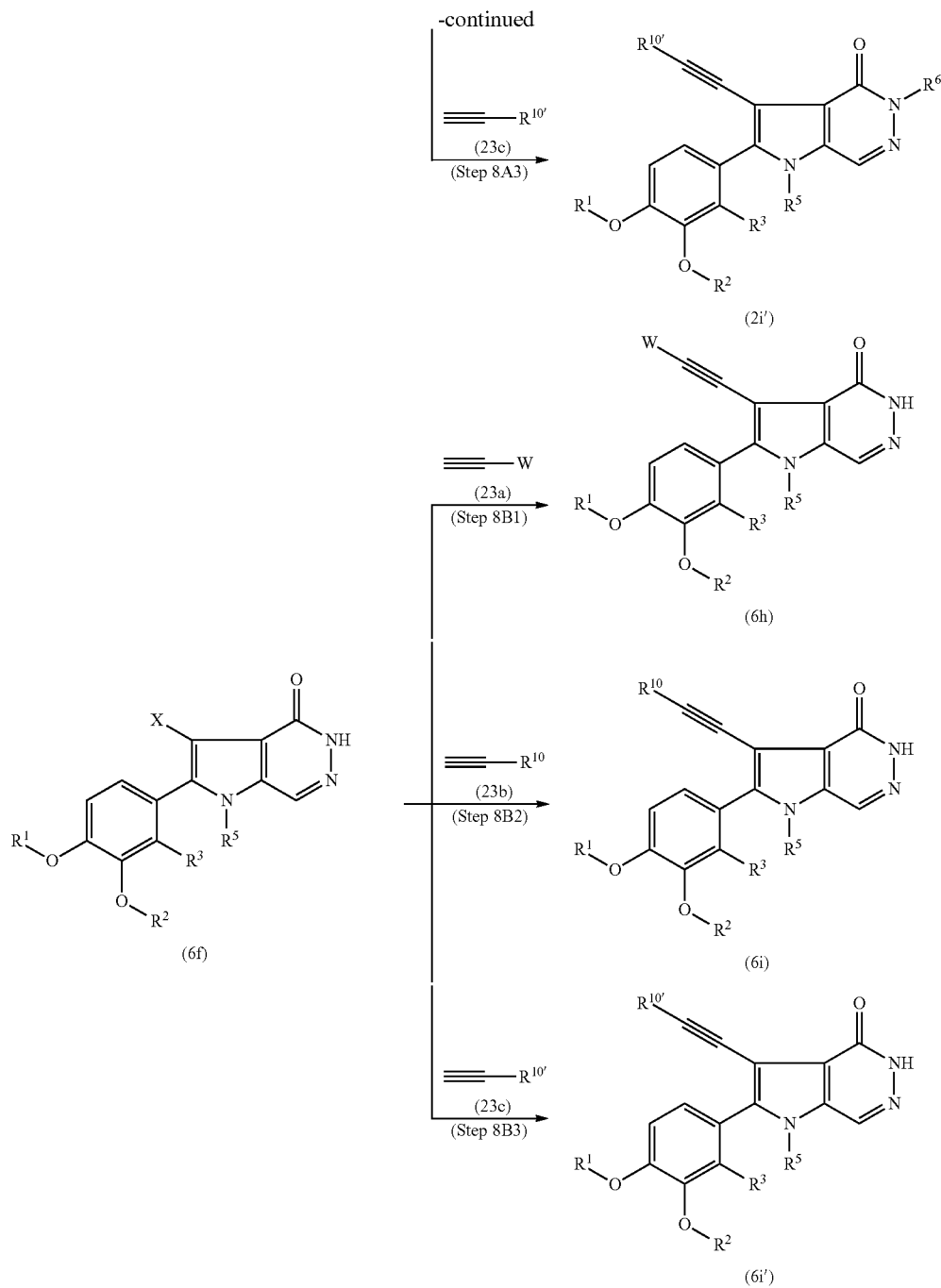

wherein $R^1$, $R^2$, $R^3$, $R^4$, $R^5$, $R^6$ and X have the same meanings as defined above, W represents a trimethylsilyl group or triethylsilyl group, $R^{10}$ represents "a $C_3$-$C_6$ cycloalkyl group which may be substituted by a substituent(s) selected from Substituent group (b)" or "a $C_1$-$C_6$ alkyl group" (the "$C_1$-$C_6$ alkyl group" has the same meaning as the unsubstituted "$C_1$-$C_6$ alkyl group" defined in $R^4$.) having the same meanings as defined above, and $R^{10'}$ represents a $C_1$-$C_4$ alkyl group having the same meaning as defined above.

Preparation method 8 is a method for preparing a compound in which an ethynyl group the terminal of which is substituted by W, $R^{10}$ or $R^{10'}$ is introduced at the 3-position of the pyrrolopyridazine ring.

This preparation method comprises (1) Step 8A1 for preparing Compound (2h) by reacting Compound (2f) with an acetylene-terminated compound (23a), (2) Step 8A2 for preparing Compound (2i) by reacting Compound (2f) with an acetylene-terminated compound (23b), (3) Step 8A3 for preparing Compound (2i') by reacting Compound (2f) with an acetylene-terminated compound (23c), (4) Step 8B1 for preparing Compound (6h) by reacting Compound (6f) with an acetylene-terminated compound (23a), (5) Step 8B2 for preparing Compound (6I) by reacting Compound (6f) with an acetylene-terminated compound (23b), and (6) Step 8B3 for preparing Compound (6i') by reacting Compound (6f) with an acetylene-terminated compound (23c).

These 6 Steps each can be carried out by the reaction of a halogen compound and an acetylene-terminated compound, which is the so-called Sonogashira reaction in the presence of a palladium catalyst, cuprous iodide and an amine.

Step 8A1 is a step of preparing Compound (2h) by reacting Compound (2f) with Compound (23a) in an inert gas atmosphere in the presence of a palladium catalyst, cuprous iodide and an amine and in the absence of a solvent or in an inert solvent.

Compound (2f) can be prepared by the above-mentioned "Step 6A".

As the inert gas to be used, there may be mentioned, for example, nitrogen, helium or argon gas, etc.

As the palladium catalyst to be used, the palladium catalyst mentioned in the above-mentioned "Step A1" can be used. Incidentally, when tris (dibenzylideneacetone)dipalladium, palladium chloride or palladium acetate is used as the catalyst, it is particularly preferred to coexist an organophosphine compound.

An amount of the palladium to be used as a catalyst in this case is generally 0.0001 to 1-fold mol amount, preferably 0.005 to 0.1-fold mol amount based on 1 mol of Compound (2f).

As the organophosphine compound to be used, triphenylphosphine or tri(o-tolyl)phosphine is preferred. An amount of the organophosphine compound to be used is generally 1 to 10-fold mol amount, preferably 2 to 5-fold mol amount based on 1 mol of the palladium.

An amount of the cuprous iodide to be used is generally 1 to 10-fold mol amount, preferably 1 to 5-fold mol amount based on 1 mol of the palladium.

As the amine to be used, there may be mentioned, for example, isopropylamine, butylamine, diethylamine, diisopropylamine, triethylamine or N,N-diisopropylethylamine, preferably diisopropylamine. An amount of the amine to be used is generally 1 to 10-fold mol amount, preferably 2 to 5-fold mol amount based on 1 mol of Compound (2f), and it may be used markedly excessively as a solvent.

As the inert solvent to be used, it is not specifically limited so long as it does not inhibit the reaction and dissolves the starting materials with a certain extent, and there may be mentioned, for example, an aromatic hydrocarbon such as benzene or toluene, etc.; an ether such as tetrahydrofuran, 1,2-dimethoxyethane or 1,4-dioxane, etc.; an ester such as methyl acetate or ethyl acetate, etc.; an amide such as N,N-dimethylformamide, N,N-dimethylacetamide or N-methylpyrrolidone, etc.; a sulfoxide such as dimethylsulfoxide, etc.; a nitrile such as acetonitrile or propionitrile, etc.; or a mixed solvent of an optional combination of the above, etc., preferably N,N-dimethylformamide, N,N-dimethylacetamide, N-methylpyrrolidone, dimethylsulfoxide or acetonitrile.

An amount of Compound (23a) to be used is generally 1 to 3-fold mol amount, preferably 1 to 1.5-fold mol amount based on 1 mol of Compound (2f).

A reaction temperature may vary depending on a kind, an amount to be used of starting materials, solvent(s), etc., and is generally in the range of 0° C. to 200° C., preferably 50° C. to 150° C.

A reaction time may vary depending on a reaction temperature, etc., and is generally for 10 minutes to 240 hours, preferably 1 hour to 48 hours.

Step 8A2 is carried out in the same manner as in the above-mentioned "Step 8A1" except for using Compound (23b) in place of Compound (23a).

Step 8A3 is carried out in the same manner as in the above-mentioned "Step 8A1" except for using Compound (23c) in place of Compound (23a).

Step 8B1 is carried out in the same manner as in the above-mentioned "Step 8A1" except for using Compound (6f) in place of Compound (2f). Compound (6f) can be prepared by the above-mentioned "Step 6B".

Step 8B2 is carried out in the same manner as in the above-mentioned "Step 8A1" except for using Compound (6f) in place of Compound (2f), and Compound (23b) in place of Compound (23a).

Step 8B3 is carried out in the same manner as in the above-mentioned "Step 8A1" except for using Compound (6f) in place of Compound (2f), and Compound (23c) in place of Compound (23a).

[Preparation Method 9]

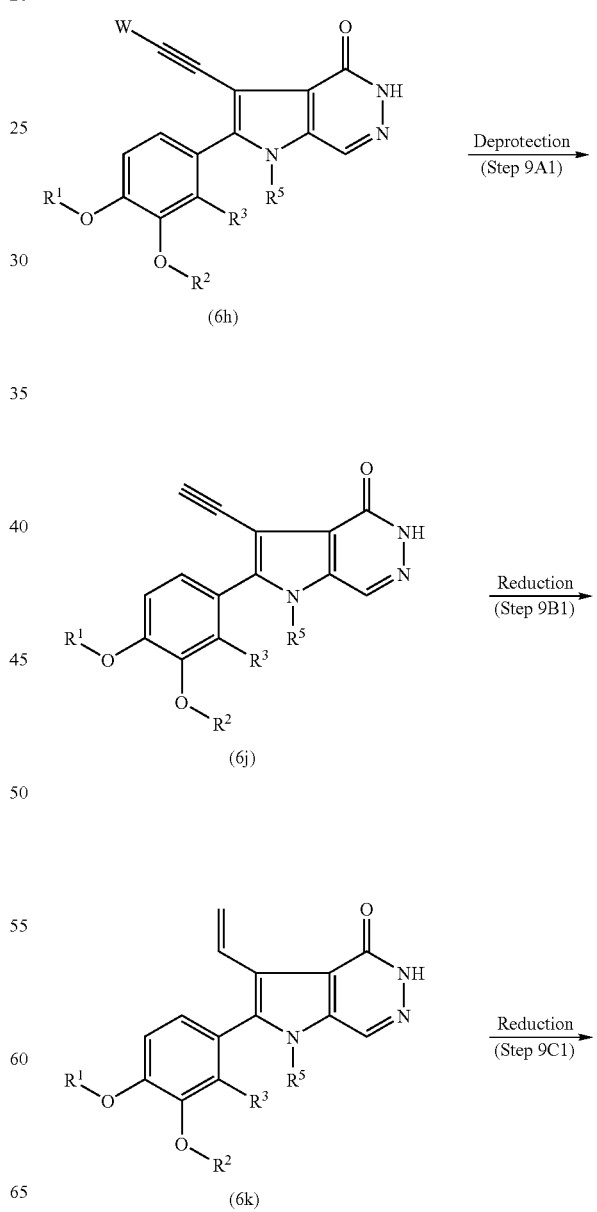

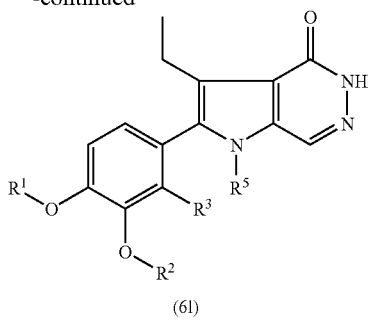

(6l)

wherein $R^1$, $R^2$, $R^3$, $R^5$, $R^6$ and W have the same meanings as defined above.

Preparation method 9 is a method for preparing Compound (2l) or Compound (6l) in which $R^4$ of the above-mentioned intermediate compound (2) or compound (6) is an ethyl group, respectively. This preparation method comprises steps (Step 9A1-Step 9B1-Step 9C1) for preparing Compound (6l) from Compound (6h), and steps (Step 9A2-Step 9B2-Step 9C2) for preparing Compound (2l) from Compound (2h).

Step 9A1 is a step of preparing Compound (6j) in which the protective group at the terminal ethynyl group is removed by treating Compound (6h) with a base in an inert solvent.

Compound (6h) can be prepared by the above-mentioned "Step 8B1".

As the inert solvent to be used, it is not specifically limited so long as it does not inhibit the reaction and dissolves the starting materials with a certain extent, and there may be mentioned, for example, an alcohol such as methanol, ethanol, propanol, isopropanol or tert-butanol, etc.; an ether such as diethyl ether, tetrahydrofuran, 1,2-dimethoxyethane or 1,4-dioxane, etc.; an amide such as N,N-dimethylformamide or N-methylpyrrolidone, etc.; a sulfoxide such as dimethylsulfoxide, etc.; a nitrile such as acetonitrile or propionitrile, etc.; water; or a mixed solvent of an optional combination of the above, etc., preferably methanol, ethanol, methanol-water or ethanol-water mixed solvent.

As the base to be used, there may be mentioned, for example, an alkali metal hydroxide such as lithium hydroxide, sodium hydroxide or potassium hydroxide, etc.; an alkali metal carbonate such as lithium carbonate, sodium carbonate or potassium carbonate, etc.; an alkali metal alkoxide such as sodium methoxide, sodium ethoxide or potassium tert-butoxide, etc.; or an organic base such as tetramethylguanidine, etc., and the like, preferably sodium hydroxide, potassium hydroxide, sodium carbonate or potassium carbonate. An amount of the base to be used is generally 0.1 to 100-fold mol amount, preferably 1 to 10-fold mol amount based on 1 mol of Compound (6h).

A reaction temperature may vary depending on a kind, an amount to be used of starting materials, solvent(s), etc., and is generally in the range of 0° C. to 200° C., preferably 10° C. to 100° C.

A reaction time may vary depending on a reaction temperature, etc., and is generally for 10 minutes to 24 hours, preferably 1 hour to 12 hours.

Step 9B1 is a step of preparing Compound (6k) in which $R^4$ is a vinyl group by subjecting Compound (6j) in which $R^4$ of Compound (6) is an ethynyl group to hydrogenation reduction by using a Lindlar catalyst.

An amount of the Lindlar catalyst to be used is generally 0.0005 to 1-fold mol amount, preferably 0.01 to 0.1-fold mol amount based on 1 mol of Compound (6j).

Step 9B1 can be carried out in the same manner as in the above-mentioned "treatment under hydrogenation decomposition conditions of Step 1B" except that a catalyst to be used is a Lindlar catalyst. Provided that it is necessary not to co-exist an acid.

Step 9C1 is a step of preparing Compound (6l) in which $R^4$ is an ethyl group by subjecting Compound (6k) in which $R^4$ of Compound (6) is a vinyl group to hydrogenation reduction in the presence of a catalyst. Step 9C1 can be carried out in the same manner as in the above-mentioned "treatment under hydrogenation decomposition conditions of Step 1B". Provided that in this case it is necessary not to co-exist an acid.

Step 9A2 is a step of preparing Compound (2j) in which the protective group at the terminal of the ethynyl group is removed by treating Compound (2h) with a base in an inert solvent. Compound (2h) can be prepared by the above-mentioned "Step 8A1". Step 9A2 can be carried out in the same manner as in the above-mentioned "Step 9A1" except for using Compound (2h) in place of Compound (6h).

Step 9B2 is a step of preparing Compound (2k) in which $R^4$ is a vinyl group by subjecting Compound (2j) in which $R^4$ of Compound (2) is an ethynyl group to hydrogenation reduction using a Lindlar catalyst. Step 9B2 can be carried out in the same manner as in the above-mentioned "Step 9B1" except for using Compound (2j) in place of Compound (6j).

Step 9C2 is a step of preparing Compound (2i) in which $R^4$ of Compound (2) is an ethyl group by subjecting Compound (2k) to hydrogenation reduction using a catalyst. Step 9C2 can be carried out in the same manner as in the above-mentioned "Step 9C1" except for using Compound (2k) in place of Compound (6k).

[Preparation Method 10]

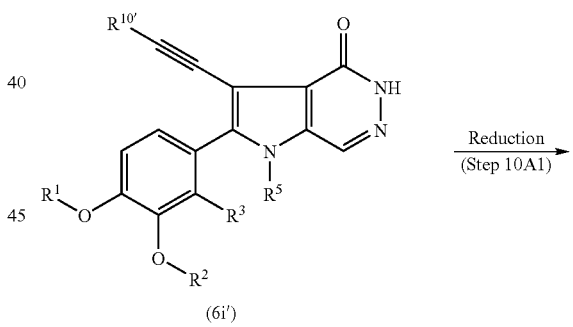

(6i')

Reduction
(Step 10A1)

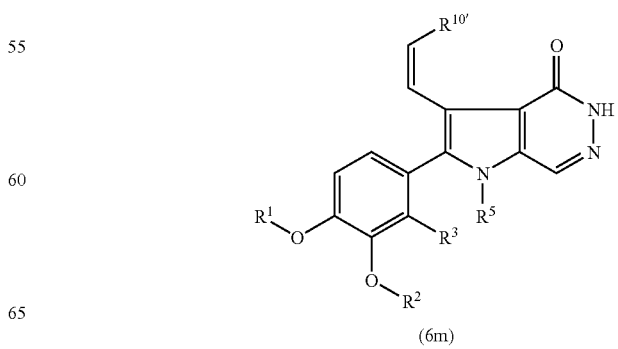

(6m)

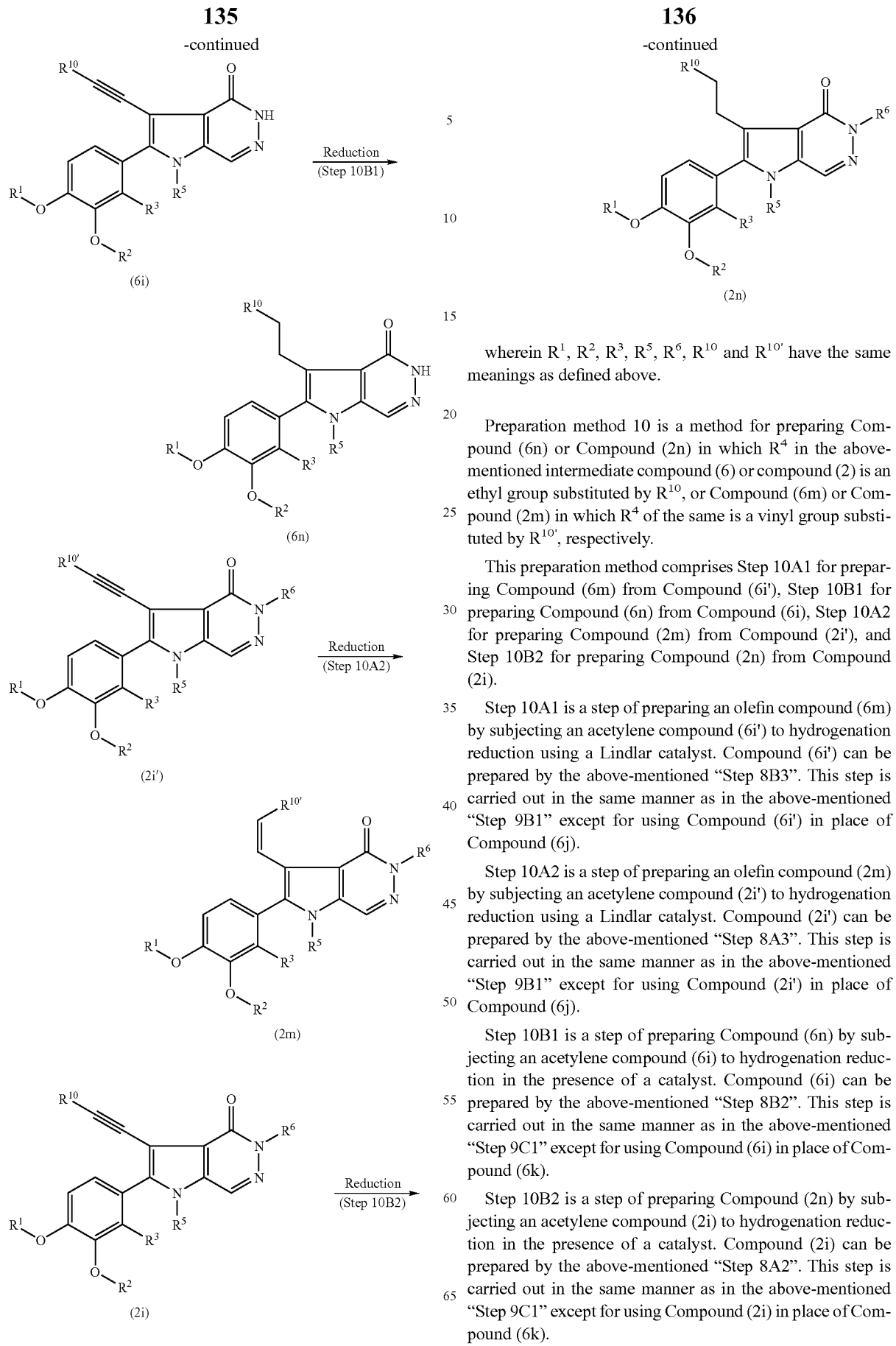

wherein $R^1$, $R^2$, $R^3$, $R^5$, $R^6$, $R^{10}$ and $R^{10'}$ have the same meanings as defined above.

Preparation method 10 is a method for preparing Compound (6n) or Compound (2n) in which $R^4$ in the above-mentioned intermediate compound (6) or compound (2) is an ethyl group substituted by $R^{10}$, or Compound (6m) or Compound (2m) in which $R^4$ of the same is a vinyl group substituted by $R^{10'}$, respectively.

This preparation method comprises Step 10A1 for preparing Compound (6m) from Compound (6i'), Step 10B1 for preparing Compound (6n) from Compound (6i), Step 10A2 for preparing Compound (2m) from Compound (2i'), and Step 10B2 for preparing Compound (2n) from Compound (2i).

Step 10A1 is a step of preparing an olefin compound (6m) by subjecting an acetylene compound (6i') to hydrogenation reduction using a Lindlar catalyst. Compound (6i') can be prepared by the above-mentioned "Step 8B3". This step is carried out in the same manner as in the above-mentioned "Step 9B1" except for using Compound (6i') in place of Compound (6j).

Step 10A2 is a step of preparing an olefin compound (2m) by subjecting an acetylene compound (2i') to hydrogenation reduction using a Lindlar catalyst. Compound (2i') can be prepared by the above-mentioned "Step 8A3". This step is carried out in the same manner as in the above-mentioned "Step 9B1" except for using Compound (2i') in place of Compound (6j).

Step 10B1 is a step of preparing Compound (6n) by subjecting an acetylene compound (6i) to hydrogenation reduction in the presence of a catalyst. Compound (6i) can be prepared by the above-mentioned "Step 8B2". This step is carried out in the same manner as in the above-mentioned "Step 9C1" except for using Compound (6i) in place of Compound (6k).

Step 10B2 is a step of preparing Compound (2n) by subjecting an acetylene compound (2i) to hydrogenation reduction in the presence of a catalyst. Compound (2i) can be prepared by the above-mentioned "Step 8A2". This step is carried out in the same manner as in the above-mentioned "Step 9C1" except for using Compound (2i) in place of Compound (6k).

[Preparation Method 11]

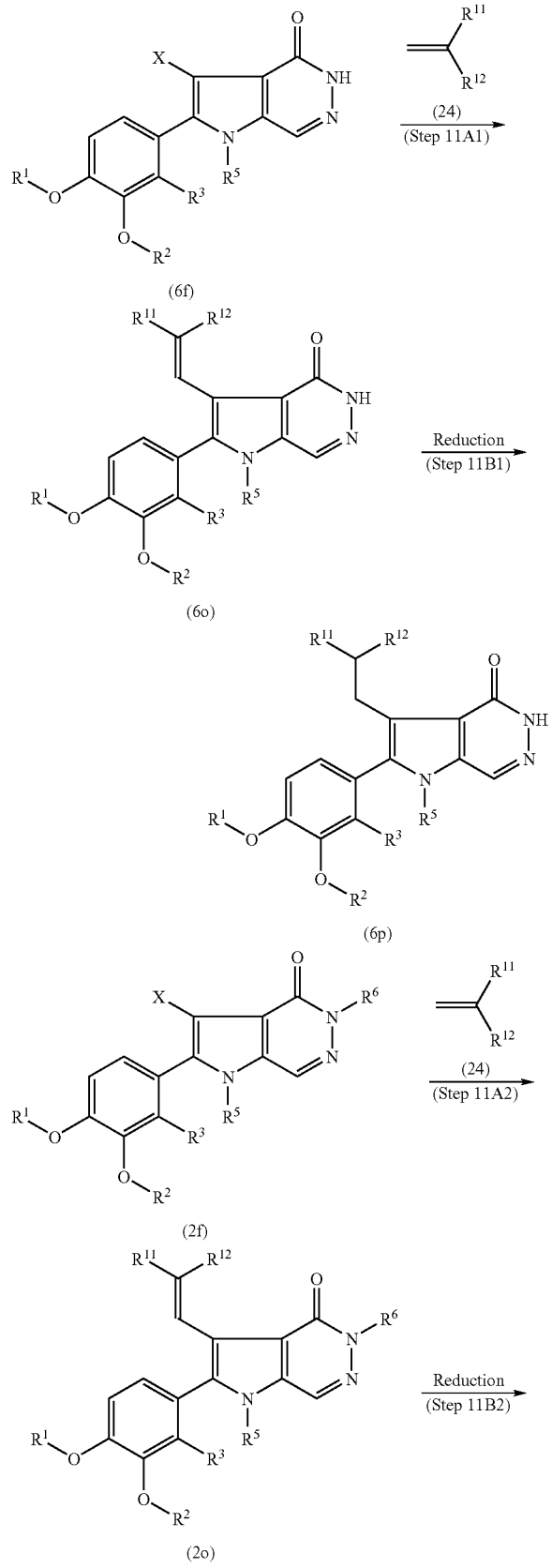

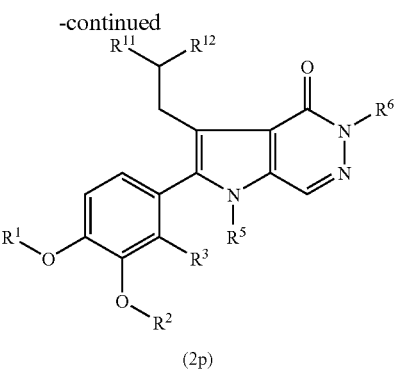

wherein $R^1$, $R^2$, $R^3$, $R^5$, $R^6$ and X have the same meanings as defined above, $R^{11}$ and $R^{12}$ may be the same or different from each other, and each represents a hydrogen atom, $C_1$-$C_4$ alkoxy group or $C_1$-$C_6$ alkyl group. (provided that $R^{11}$ and $R^{12}$ are both $C_1$-$C_6$ alkyl groups, a total carbon number of $R^{11}$ and $R^{12}$ is 6 or less.)

Preparation method 11 is a method for preparing compounds in which $R^4$ of the above-mentioned intermediate compound (2) or compound (6) is a vinyl group or ethyl group each substituted by $R^{11}$ or $R^{12}$, respectively. This preparation method comprises steps (Step 11A1-Step 11B1) for preparing Compound (6p) from Compound (6f), and steps (Step 11A2-Step 11B2) for preparing Compound (2p) from Compound (2f).

Step 11A1 is a step of preparing Compound (6o) by reacting Compound (6f) with Compound (24) in an inert gas atmosphere and in the presence of a palladium catalyst and a base in an inert solvent.

Compound (6f) can be prepared by the above-mentioned "Step 6B".

As the inert gas to be used, there may be mentioned, for example, nitrogen, helium or argon gas, etc.

As the palladium catalyst to be used, the palladium catalyst mentioned in the above-mentioned "Step A1" can be used, and co-presence of triphenylphosphine or tri(otolyl)phosphine is preferred.

An amount of the palladium catalyst to be used is generally 0.01 to 1-fold mol amount, preferably 0.01 to 0.3-fold mol amount based on 1 mol of Compound (6f). Compound (24) is a compound which is conventionally known, or can be prepared from a conventionally known compound by a conventionally known method. An amount of Compound (24) to be used is generally 1 to 3-fold mol amount, preferably 1 to 1.5-fold mol amount based on 1 mol of Compound (6f).

As the inert solvent to be used, it is not specifically limited so long as it does not inhibit the reaction and dissolves the starting materials with a certain extent, and there may be mentioned, for example, an amide such as N,N-dimethylformamide, N,N-dimethylacetamide or N-methylpyrrolidone, etc.; a sulfoxide such as dimethylsulfoxide, etc.; or a nitrile such as acetonitrile or propionitrile, etc., and the like, preferably N,N-dimethylformamide.

As the base to be used, there may be mentioned, for example, an amine such as triethylamine, tributylamine, N,N-diisopropylethylamine, pyridine, picoline, 2,6-lutidine or 4-dimethylaminopyridine, etc., preferably triethylamine. An amount of the base to be used is generally 1 to 10-fold mol amount, preferably 1 to 2-fold mol amount based on 1 mol of Compound (6f).

A reaction temperature may vary depending on a kind, an amount to be used of starting materials, solvent(s), etc., and is generally in the range of 0° C. to 200° C., preferably 50° C. to 150° C.

A reaction time may vary depending on a reaction temperature, etc., and is generally for 30 minutes to 48 hours, preferably 1 hour to 24 hours.

Step 11B1 is a step of preparing Compound (6p) by subjecting an olefin compound (6o) to hydrogenation reduction in the presence of a catalyst.

Step 11B1 is carried out in the same manner as in the above-mentioned "Step 9C1" except for using Compound (6o) in place of Compound (6k).

Step 11A2 is carried out in the same manner as in the above-mentioned "Step 11A1" except for using Compound (2f) in place of Compound (6f). Compound (2f) can be prepared by the above-mentioned "Step 6A".

Step 11B2 is carried out in the same manner as in the above-mentioned "Step 9C1" except for using Compound (2o) in place of Compound (6k).

[Preparation Method 12]

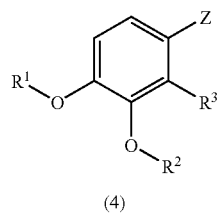

(4)

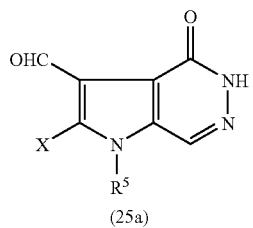

(25a)

Suzuki Reaction
(Step 12A1)

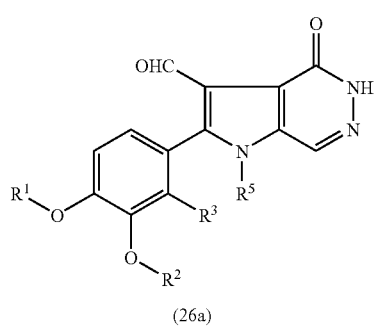

(26a)

R¹³—M
(27)
(Step 12B1)

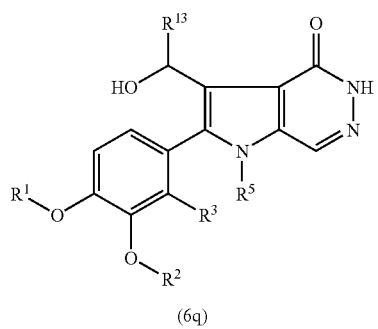

(6q)

Reduction
(Step 12C1)

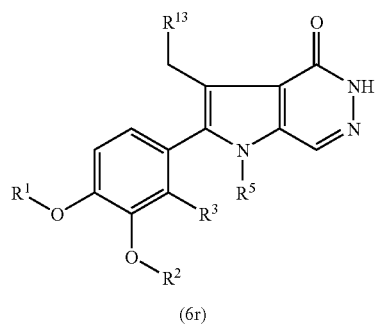

(6r)

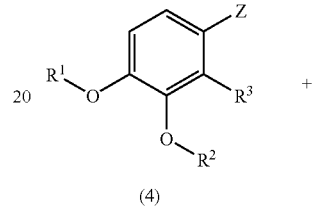

(4)

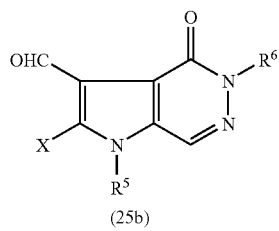

(25b)

Suzuki Reaction
(Step 12A2)

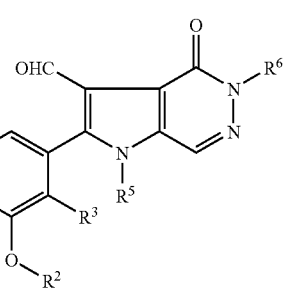

(26b)

R¹³—M
(27)
(Step 12B2)

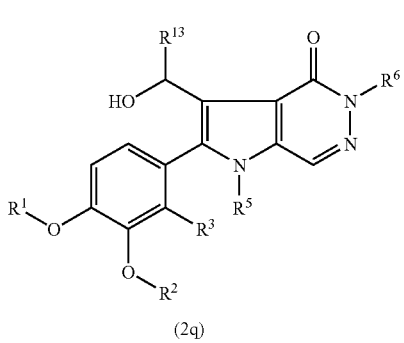

(2q)

Reduction
(Step 12C2)

-continued

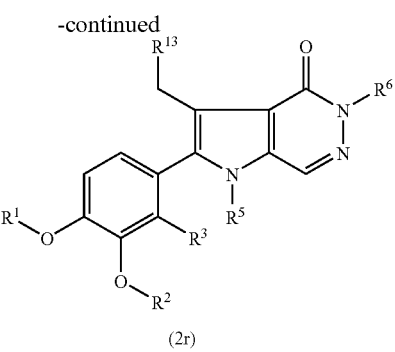

(2r)

wherein R¹, R², R³, R⁵, R⁶, M, X and Z have the same meanings as defined above, and R¹³ represents a C₁-C₇ alkyl group, a vinyl group or ethynyl group each of the terminal may be substituted by the above-mentioned "C₁-C₃ alkyl group", "a C₁-C₅ alkyl group substituted by a substituent(s) selected from Substituent group (a)", "a C₃-C₆ cycloalkyl group which may be substituted by a substituent(s) selected from Substituent group (b)" or "an aromatic ring group or heteroaromatic ring group each may be substituted by a substituent(s) selected from Substituent group (d)".

(As the C₁-C₇ alkyl group in R¹³, it represents, for example, a straight or branched alkyl chain such as a methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, 1-ethylpropyl, hexyl, 1-methylpentyl, 2-methylpentyl, 3-methylpentyl, 4-methylpentyl, 1-ethylbutyl, 2-ethylbutyl, 1,1-dimethylbutyl, 2,2-dimethylbutyl, 3,3-dimethylbutyl, 1,3-dimethylbutyl, 2,3-dimethylbutyl, heptyl, 1-methylhexyl, 2-methylhexyl, 3-methylhexyl, 4-methylhexyl, 5-methylhexyl, 1-ethylpentyl, 2-ethylpentyl, 3-ethylpentyl, 1,2-dimethylpentyl, 1,3-dimethylpentyl, 1,4-dimethylpentyl, 2,3-dimethylpentyl, 2,4-dimethylpentyl, 3,4-dimethylpentyl, 1,1-dimethylpentyl, 2,2-dimethylpentyl, 3,3-dimethylpentyl, 4,4-dimethylpentyl or 1-methyl-2-ethylbutyl group, etc., as the C₁-C₅ alkyl group in "a C₁-C₅ alkyl group substituted by a substituent(s) selected from Substituent group (a)", it represents, for example, a straight or branched alkyl chain such as a methyl, ethyl, propyl, isopropyl, butyl, isobutyl, sec-butyl, tert-butyl, pentyl, isopentyl, neopentyl, tert-pentyl, 1-methylbutyl, 2-methylbutyl and 1,2-dimethylpropyl group, etc., and Substituent group (d) in "an aromatic ring group or heteroaromatic ring group each may be substituted by a substituent(s) selected from Substituent group (d)" represents a C₁-C₄ alkyl group which may be substituted by a substituent (s) selected from the group consisting of (a halogen atom, a hydroxy group and a carboxy group), a halogen atom, a hydroxy group, a C₁-C₄ alkoxy group or a C₁-C₄ alkyl-substituted amino group.)

Preparation method 12 is a method for preparing a compound wherein R⁴ of the above-mentioned intermediate compound (2) or compound (6) is a methyl group substituted by R¹³ and a hydroxy group, or a compound wherein R⁴ of the same is a methyl group substituted by R¹³, respectively. This preparation method comprises steps (Step 12A1-Step 12B1-Step 12C1) for preparing Compound (6r) from Compound (4) and Compound (25a), and steps (Step 12A2-Step 12B2-Step 12C2) for preparing Compound (2r) from Compound (4) and Compound (25b).

Step 12A1 is a step of preparing Compound (26a) by reacting Compound (25a) with a boronic acid compound (4) in an inert gas atmosphere in an inert solvent and in the presence of a palladium catalyst and a base. Compound (4) can be prepared by either of the methods of the following mentioned "Preparation method 28", "Preparation method 29", "Preparation method 30" or "Preparation method 31". Compound (25a) can be prepared by the following mentioned "Step 26A2-Step 26B2" when X is a bromine atom, and by the following mentioned "Step 26A2-Step 26B2" when X is a chlorine atom or iodine atom, except for the case where a chlorinating agent or iodinating agent of the above-mentioned halogenating agent (21) is used. Step 12A1 is carried out in the same manner as in the above-mentioned "Step 1A" except for using Compound (25a) in place of Compound (3), and using tetrakis(triphenylphosphine)palladium as a catalyst.

Step 12B1 is a step of preparing Compound (6q) having a hydroxy group by reacting Compound (26a) having a formyl group with an organometallic compound (27) in an inert solvent.

As the organometallic compound (27) to be used, there may be mentioned, for example, an organolithium reagent such as methyl lithium, butyl lithium or phenyl lithium, etc.; or an organomagnesium reagent (Grignard reagent) such as methyl magnesium chloride, methyl magnesium bromide, ethyl magnesium chloride, ethyl magnesium bromide, propyl magnesium chloride, propyl magnesium bromide, butyl magnesium chloride, butyl magnesium bromide, vinyl magnesium bromide, ethynyl magnesium bromide, propynyl magnesium bromide, 3-methyl-1-butynyl magnesium bromide, cyclopropyl magnesium chloride, cyclopropyl magnesium bromide, phenyl magnesium chloride or phenyl magnesium bromide, etc.

Step 12B1 is carried out in the same manner as in the above-mentioned "Step 3B" except for using an organometallic compound (27) in place of the organometallic compound (9), and Compound (26a) (provided that an amount of the organometallic compound (27) to be used is generally 1 to 10-fold mol amount, preferably 2 to 4-fold mol amount based on 1 mol of Compound (26a)) in place of Compound (8), respectively.

Step 12C1 is a step of preparing Compound (6r) by reducing Compound (6q) having a hydroxy group with an organosilane compound or organotin compound in an inert solvent in the presence of an acid or a Lewis acid.

As the acid or Lewis acid to be used, there may be mentioned, for example, trifluoroacetic acid or boron trifluoride diethyl ether complex, etc., preferably trifluoroacetic acid. An amount of the acid or the Lewis acid to be used is generally 0.1 to 100-fold mol amount, preferably 1 to 10-fold mol amount based on 1 mol of Compound (6q), and it may be used markedly excessively as a solvent.

As the organosilane compound or organotin compound to be used, there may be mentioned, for example, an organosilane such as triethylsilane, etc., or an organotin such as tributyltin, etc., and the like, preferably triethylsilane. An amount of the organosilane compound or organotin compound to be used is generally 0.1 to 100-fold mol amount, preferably 1 to 10-fold mol amount based on 1 mol of Compound (6q).

As the inert solvent to be used, it is not specifically limited so long as it does not inhibit the reaction and dissolves the starting materials with a certain extent, and there may be mentioned, for example, a halogenated aliphatic hydrocarbon such as dichloromethane, chloroform or 1,2-dichloroethane, etc.; or an organic acid such as formic acid, acetic acid or propionic acid, etc., and the like, preferably dichloromethane or 1,2-dichloroethane.

A reaction temperature may vary depending on a kind, an amount to be used of starting materials, solvent(s), etc., and is generally in the range of −100° C. to 100° C., preferably 0° C. to 50° C.

A reaction time may vary depending on a reaction temperature, etc., and is generally for 10 minutes to 24 hours, preferably 1 hour to 12 hours.

Step 12A2 is carried out in the same manner as in the above-mentioned "Step 12A1" except for using Compound (25b) in place of Compound (25a). Compound (25b) is prepared by the following mentioned "Step 26A1-Step 26B1" when X is a bromine atom, and by the following mentioned "Step 26A1-Step 26B1" when X is a chlorine atom or iodine atom except for using a chlorinating agent or iodinating agent of the above-mentioned halogenating agent (21).

Step 12B2 is carried out in the same manner as in the above-mentioned "Step 12B1" except for using Compound (26b) in place of Compound (26a). Step 12C2 is carried out in the same manner as in the above-mentioned "Step 12C1" except for using Compound (2q) in place of Compound (6q).

[Preparation Method 13]

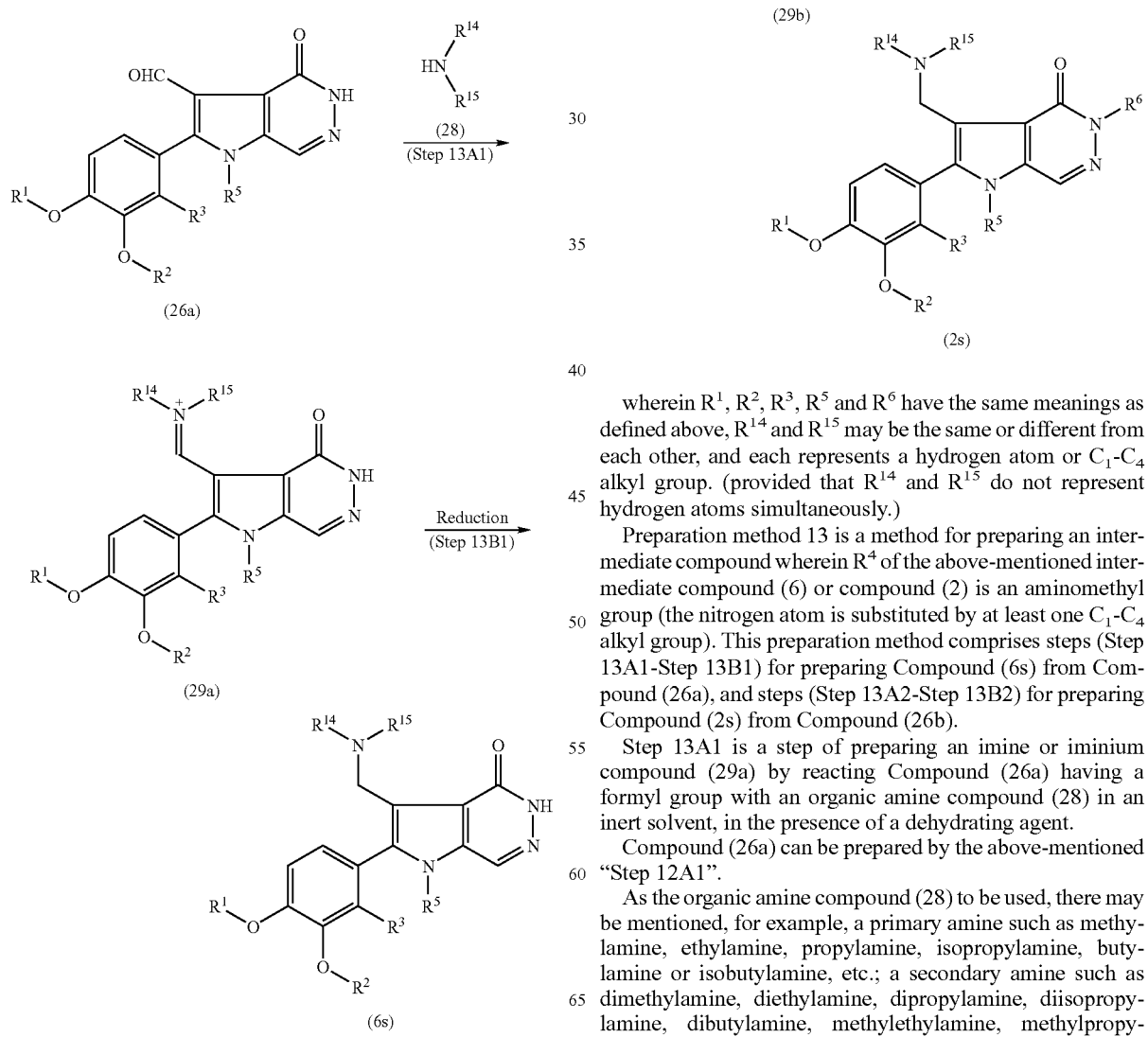

wherein $R^1$, $R^2$, $R^3$, $R^5$ and $R^6$ have the same meanings as defined above, $R^{14}$ and $R^{15}$ may be the same or different from each other, and each represents a hydrogen atom or $C_1$-$C_4$ alkyl group. (provided that $R^{14}$ and $R^{15}$ do not represent hydrogen atoms simultaneously.)

Preparation method 13 is a method for preparing an intermediate compound wherein $R^4$ of the above-mentioned intermediate compound (6) or compound (2) is an aminomethyl group (the nitrogen atom is substituted by at least one $C_1$-$C_4$ alkyl group). This preparation method comprises steps (Step 13A1-Step 13B1) for preparing Compound (6s) from Compound (26a), and steps (Step 13A2-Step 13B2) for preparing Compound (2s) from Compound (26b).

Step 13A1 is a step of preparing an imine or iminium compound (29a) by reacting Compound (26a) having a formyl group with an organic amine compound (28) in an inert solvent, in the presence of a dehydrating agent.

Compound (26a) can be prepared by the above-mentioned "Step 12A1".

As the organic amine compound (28) to be used, there may be mentioned, for example, a primary amine such as methylamine, ethylamine, propylamine, isopropylamine, butylamine or isobutylamine, etc.; a secondary amine such as dimethylamine, diethylamine, dipropylamine, diisopropylamine, dibutylamine, methylethylamine, methylpropylamine, butylmethylamine, ethylpropylamine or butylethylamine, etc.; a hydrochloride thereof; or a hydrobromide thereof, etc., preferably dimethylamine, diethylamine, dipropylamine, dimethylamine hydrochloride, diethylamine hydrochloride or dipropylamine hydrochloride.

When a salt is used, there may coexist, for example, a tertiary amine such as triethylamine or N,N-diisopropylethylamine, etc. An amount of the organic amine compound (28) to be used is generally 1 to 10-fold mol amount, preferably 1.5 to 3-fold mol amount based on 1 mol of Compound (26a).

When the organic amine compound is a salt, the above-mentioned tertiary amine can be presented with an equal mol amount.

As the dehydrating agent to be used, there may be mentioned, for example, Molecular Sieve or anhydrous magnesium sulfate, etc. An amount of the dehydrating agent to be used is generally 100 g to 2000 g, preferably 500 g to 1000 g based on 1 mol of Compound (26a).

As the inert solvent to be used, it is not specifically limited so long as it does not inhibit the reaction and dissolves the starting materials with a certain extent, and there may be mentioned, for example, a halogenated aliphatic saturated hydrocarbon such as dichloromethane, chloroform or 1,2-dichloroethane, etc.; or an aromatic hydrocarbon such as benzene or toluene, etc., and the like, preferably dichloromethane or 1,2-dichloroethane.

A reaction temperature may vary depending on a kind, an amount to be used of starting materials, solvent(s), etc., and is generally in the range of –100° C. to 100° C., preferably 0° C. to 50° C.

A reaction time may vary depending on a reaction temperature, etc., and is generally for 10 minutes to 24 hours, preferably 1 hour to 12 hours.

Incidentally, Compound (29a) obtained by the reaction is used in the next step without isolation.

Step 13B1 is a step of preparing Compound (6s) having a substituted aminomethyl group by reducing Compound (29a) using a borohydride compound.

As the borohydride compound to be used, there may be mentioned, for example, sodium borohydride, sodium cyanoborohydride or sodium triacetoxyborohydride, etc., preferably sodium triacetoxyborohydride. An amount of the borohydride compound to be used is generally 1 to 10-fold mol amount, preferably 1.5 to 3-fold mol amount based on 1 mol of Compound (29a).

As the inert solvent to be used, the similar inert solvent in the above-mentioned "Step 13A1" can be used.

A reaction temperature may vary depending on a kind, an amount to be used of starting materials, solvent(s), etc., and is generally in the range of –100° C. to 100° C., preferably 0° C. to 50° C.

A reaction time may vary depending on a reaction temperature, etc., and is generally for 10 minutes to 12 hours, preferably 1 hour to 6 hours.

Step 13A2 is carried out in the same manner as in the above-mentioned "Step 13A1" except for using Compound (26b) in place of Compound (26a). Compound (26b) can be prepared by the above-mentioned "Step 12A2". Step 13B2 is carried out in the same manner as in the above-mentioned "Step 13B1" except for using Compound (29b) in place of Compound (29a).

[Preparation Method 14]

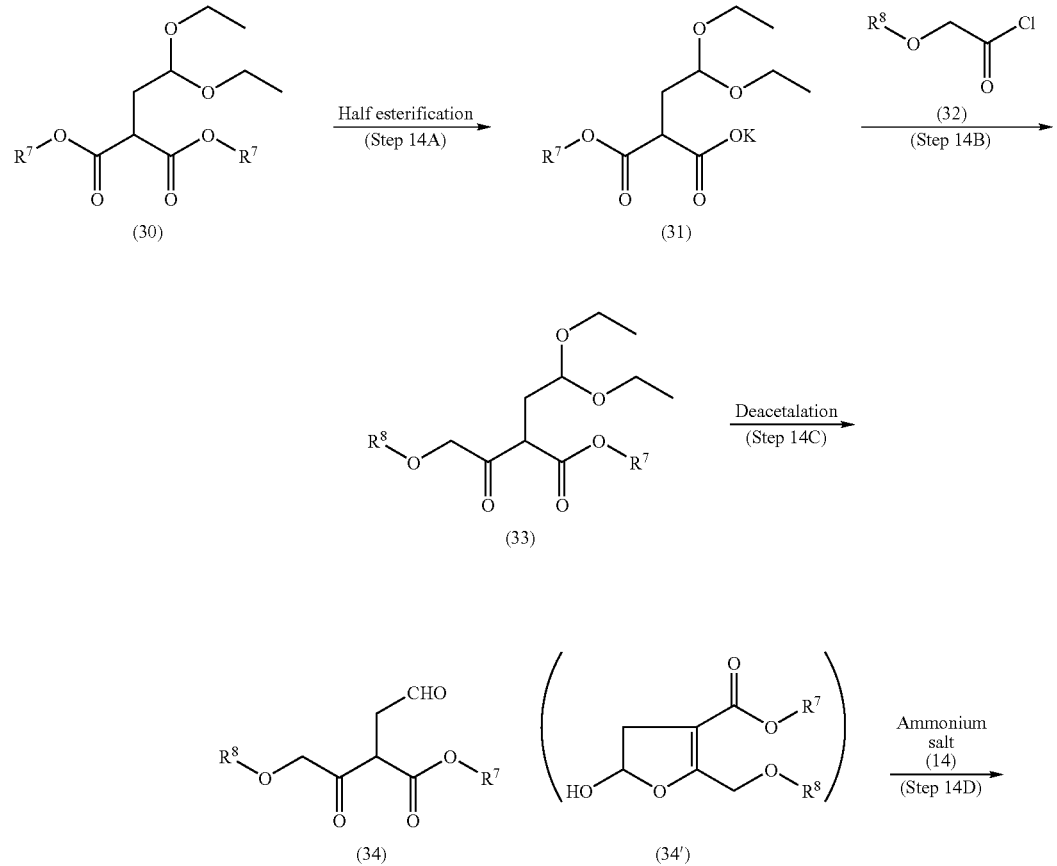

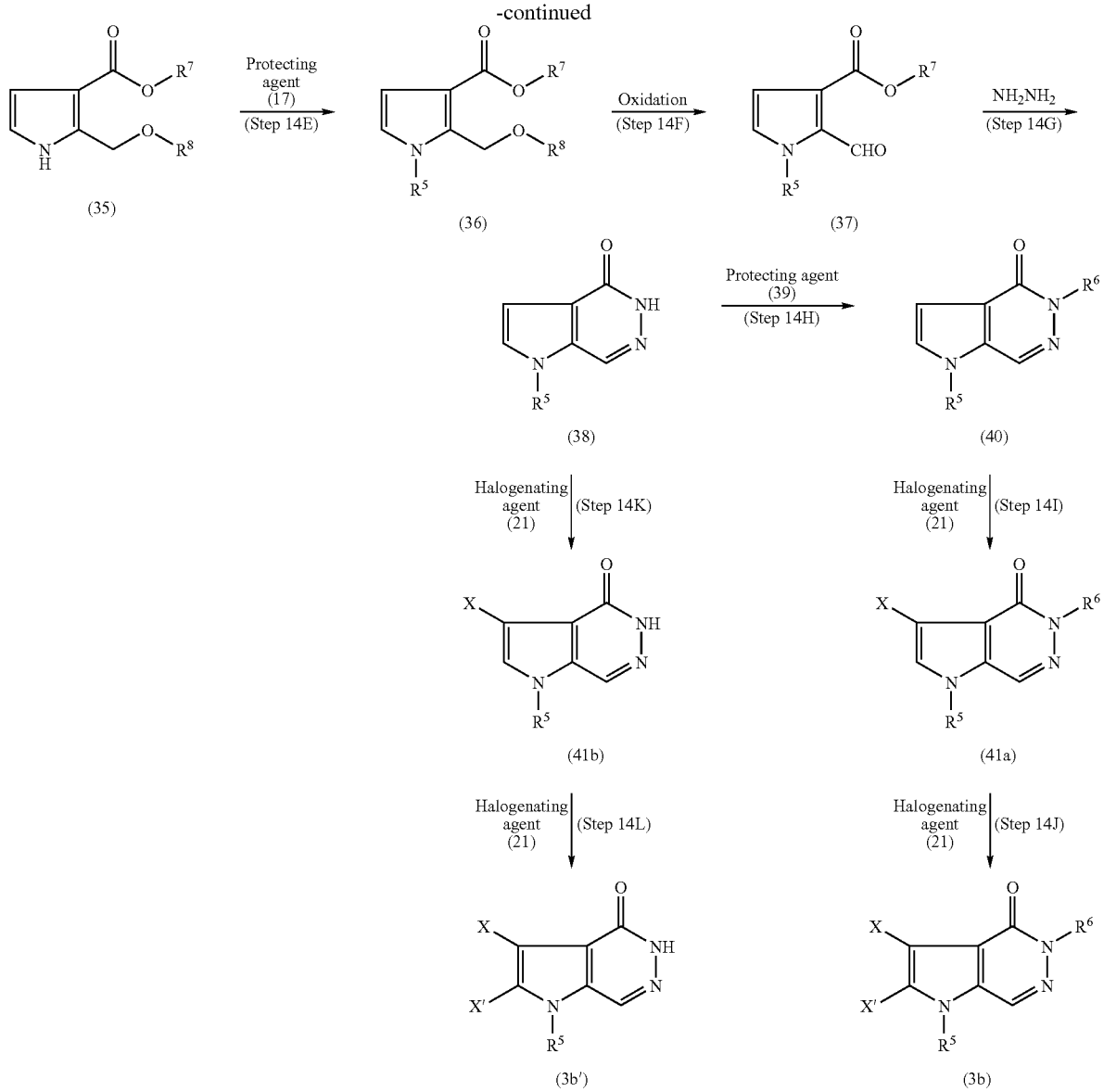

wherein $R^5$, $R^6$, $R^7$, $R^8$ and X have the same meanings as defined above, X' represents a chlorine, bromine or iodine atom, and X and X' may be the same or different from each other.

Preparation method 14 is a method for preparing Compound (3b) which is a compound in which $R^4$ of the above-mentioned compound (3) is a chlorine, bromine or iodine atom, or Compound (3b') which is a partially deprotected product of Compound (3b), respectively, by using Compound (30) as a starting compound.

Step 14A is a step of preparing a half ester compound (31) by treating a malonic acid compound (30) with an equivalent amount of potassium hydroxide in an inert solvent.

Compound (30) is a compound which has been known, or can be prepared from a conventionally known compound according to a conventionally known method.

As the inert solvent to be used, it is not specifically limited so long as it does not inhibit the reaction and dissolves the starting materials with a certain extent, and there may be mentioned, for example, an alcohol such as methanol, ethanol, propanol or isopropanol, etc., and the like, preferably ethanol.

A reaction temperature may vary depending on a kind, an amount to be used of starting materials, solvent(s), etc., and is generally in the range of −100° C. to 150° C., preferably 0° C. to 80° C.

A reaction time may vary depending on a reaction temperature, etc., and is generally for 10 minutes to 24 hours, preferably 1 hour to 12 hours.

Step 14B is a step of preparing Compound (33) by reacting Compound (31) with Compound (32) in an inert solvent in the presence of magnesium chloride and an organic base.

As the inert solvent to be used, it is not specifically limited so long as it does not inhibit the reaction and dissolves the starting materials with a certain extent, and there may be mentioned, for example, an ester such as methyl acetate or ethyl acetate, etc.; a nitrile such as acetonitrile or propionitrile, etc.; an aromatic hydrocarbon such as benzene or toluene, etc.; an ether such as tetrahydrofuran, 1,2-dimethoxyethane or 1,4-dioxane, etc.; or an amide such as N,N-dimethylformamide, N,N-dimethylacetamide or N-methylpyrrolidone, etc., and the like, preferably ethyl acetate or acetonitrile.

An amount of the magnesium chloride to be used is generally 0.5 to 5-fold mol amount, preferably 1 to 2-fold mol amount based on 1 mol of Compound (31).

As the organic base to be used, there may be mentioned, for example, triethylamine, N,N-diisopropylethylamine, 2,6-lutidine or 4-dimethylaminopyridine, etc., preferably triethylamine or N,N-diisopropylethylamine. An amount of the organic base to be used is generally 1 to 10-fold mol amount, preferably 2 to 3-fold mol amount based on 1 mol of Compound (31).

As Compound (32) to be used, there may be mentioned, for example, a conventionally known acid halide compound such as methoxyacetyl chloride, etc. An amount of Compound (32) to be used is generally 0.9 to 2-fold mol amount, preferably 1 to 1.5-fold mol amount based on 1 mol of Compound (31).

A reaction temperature may vary depending on a kind, an amount to be used of starting materials, solvent(s), etc., and is generally in the range of −100° C. to 100° C., preferably 0° C. to 60° C.

A reaction time may vary depending on a reaction temperature, etc., and is generally for 1 hour to 72 hours, preferably 12 hours to 24 hours.

Step 14C is a step of preparing a mixture of a 1,4-diketone compound (34) and a dihydrofuran compound (34') by subjecting Compound (33) to deacetalation under acidic conditions in an inert solvent.

As the inert solvent to be used, it is not specifically limited so long as it does not inhibit the reaction and dissolves the starting materials with a certain extent, and there may be mentioned, for example, an alcohol such as methanol, ethanol, propanol or isopropanol, etc.; an organic acid such as formic acid, acetic acid, propionic acid or trifluoroacetic acid, etc.; an aromatic hydrocarbon such as benzene or toluene, etc.; a halogenated aliphatic hydrocarbon such as dichloromethane, chloroform or 1,2-dichloroethane, etc.; water; or a mixed solvent of water and an optional combination of the above, etc., preferably water.

As the acid to be used, there may be mentioned, for example, hydrochloric acid, hydrobromic acid, hydroiodic acid, sulfuric acid, phosphoric acid or polyphosphoric acid, etc., preferably phosphoric acid. An amount of the acid to be used is generally 1 to 10-fold mol amount, preferably 3 to 6-fold mol amount based on 1 mol of Compound (33).

A reaction temperature may vary depending on a kind, an amount to be used of starting materials, solvent(s), etc., and is generally in the range of −100° C. to 50° C., preferably 0° C. to 20° C.

A reaction time may vary depending on a reaction temperature, etc., and is generally for 1 hour to 24 hours, preferably 2 hours to 12 hours.

Compound (34) and Compound (34') can be used in the next step without separation, and gives the same compound (35).

Step 14D is a step of preparing pyrrole compound (35) by reacting "a mixture of Compound (34) and Compound (34')" with an ammonium salt (14). This step is carried out in the same manner as in the above-mentioned "Step 3E" except for using "a mixture of Compound (34) and Compound (34')" in place of Compound (13).

Step 14E is a step of preparing Compound (36) by incorporating a $R^5$ group into the NH group of the pyrrole ring of Compound (35) as a protective group. This step is carried out in the same manner as in either of the above-mentioned "Step 4A1", "Step 4A2" or "Step 4A3" except for using Compound (35) in place of Compound (15).

Step 14F is a step of preparing Compound (37) having a formyl group by oxidizing Compound (36). This step is carried out in the same manner as in the above-mentioned "Step 3F" except for using Compound (36) in place of Compound (15).

Step 14G is a step of preparing pyrrolopyridazinone compound (38) by reacting Compound (37) with hydrazine monohydrate. This step is carried out in the same manner as in the above-mentioned "Step 3G" except for using Compound (37) in place of Compound (16).

Step 14H is a step of preparing pyrrolopyridazinone compound (40) by introducing a $R^6$ group into an amidic NH group of Compound (38) as a protective group.

As the protecting agent (39) to be used, there may be mentioned, for example, benzyl chloride, 4-methoxybenzyl chloride, methoxymethyl chloride, methoxyethoxymethyl chloride, benzyloxymethyl chloride, (2-trimethylsilylethoxy)methyl chloride, tetrahydropyranyl chloride or di(tert-butyl) dicarbonate, etc.

This step is carried out in the same manner as in either of the steps of the above-mentioned "Step 4A1", "Step 4A2" or "Step 4A3" except for using Compound (38) in place of Compound (15), and using Compound (39) in place of Compound (17a), (17b) or (17c), respectively.

Step 14I is a step of preparing Compound (41a) in which 3-position of the pyrrolopyridazinone ring is halogenated by reacting Compound (40) with a halogenating agent (21). This step is carried out in the same manner as in the above-mentioned "Step 6A" except for using Compound (40) in place of Compound (2e).

Step 14J is a step of preparing 2,3-dihalogeno compound (3b) by further reacting Compound (41a) with a halogenating agent (21). This step is carried out in the same manner as in the above-mentioned "Step 6A" except for using Compound (41a) in place of Compound (2e).

Step 14K is a step of preparing Compound (41b) in which 3-position of the pyrrolopyridazinone ring is halogenated by reacting Compound (38) with a halogenating agent (21). This step is carried out in the same manner as in the above-mentioned "Step 6A" except for using Compound (38) in place of Compound (2e).

Step 14L is a step of preparing 2,3-dihalogeno compound (3b') by further reacting Compound (41b) with a halogenating agent (21). This step is carried out in the same manner as in the above-mentioned "Step 6A" except for using Compound (41b) in place of Compound (2e).

[Preparation Method 15]

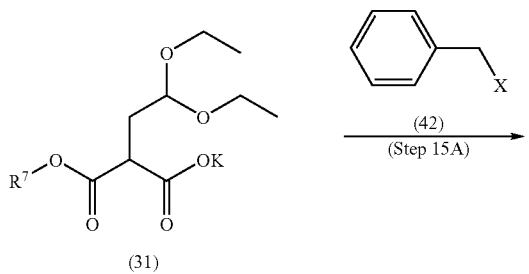

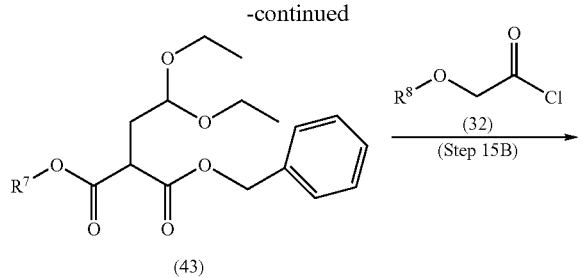

(43)

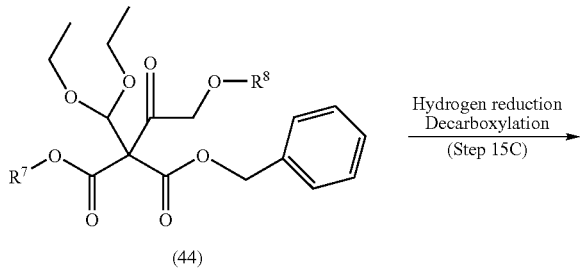

(44)

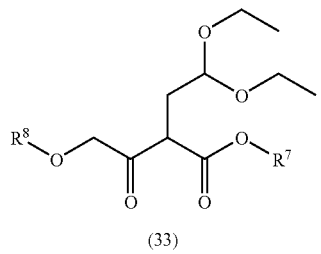

(33)

wherein $R^7$, $R^8$ and X have the same meanings as defined above.

Preparation method 15 is another method of preparing Compound (33) in the above-mentioned "Preparation method 14".

Step 15A is a step of preparing a benzyl ester compound (43) by reacting Compound (31) with a benzyl halide (42) in an inert solvent. Compound (31) can be prepared by the above-mentioned "Step 14A". As the benzyl halide (42) to be used, there may be mentioned, for example, a benzyl halide such as benzyl chloride and benzyl bromide, etc., preferably benzyl bromide. This step is carried out in the same manner as in the above-mentioned "Step 4A1" except for using a benzyl halide (42) in place of Compound (17a).

Step 15B is a step of preparing a triester compound (44) by reacting Compound (43) with Compound (32) in an inert solvent in the presence of a base.

An amount of Compound (32) to be used is generally 1 to 3-fold mol amount, preferably 1 to 1.5-fold mol amount based on 1 mol of Compound (43).

As the inert solvent to be used, it is not specifically limited so long as it does not inhibit the reaction and dissolves the starting materials with a certain extent, and there may be mentioned, for example, an ether such as tetrahydrofuran, 1,4-dioxane or 1,2-dimethoxyethane, etc.; an amide such as N,N-dimethylformamide, N,N-dimethylacetamide or N-methylpyrrolidone, etc.; or a sulfoxide such as dimethylsulfoxide, etc., preferably N,N-dimethylformamide.

As the base to be used, there may be mentioned, for example, an alkali metal such as metal sodium or metal potassium, etc.; an alkali metal hydride such as sodium hydride or potassium hydride, etc.; an alkali metal amide such as lithium amide, sodium amide, lithium diisopropyl amide or lithium bistrimethylsilyl amide, etc.; or an alkali metal alkoxide such as sodium tert-butoxide or potassium tert-butoxide, etc., and the like, preferably metal sodium or sodium hydride. An amount of the base to be used is generally 1 to 3-fold mol amount, preferably 1 to 1.5-fold mol amount based on 1 mol of Compound (43).

A reaction temperature may vary depending on a kind, an amount to be used of starting materials, solvent(s), etc., and is generally in the range of −20° C. to 100° C., preferably 0° C. to 50° C.

A reaction time may vary depending on a reaction temperature, etc., and is generally for 10 minutes to 24 hours, preferably 1 hour to 12 hours.

Step 15C is a step of preparing Compound (33) by subjecting Compound (44) to hydrogenation decomposition to carry out debenzylation and decarboxylation simultaneously. This step is carried out in the same manner as in "the treatment under hydrogenation decomposition conditions of Step 1B" except for using Compound (44) in place of Compound (2).

[Preparation Method 16]

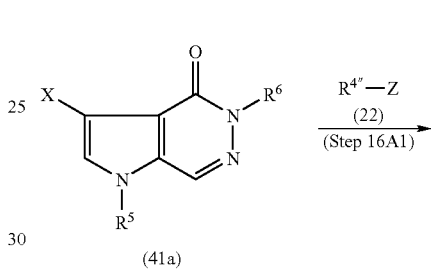

(41a)

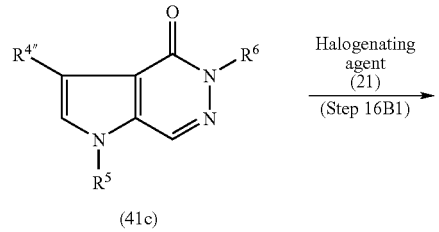

(41c)

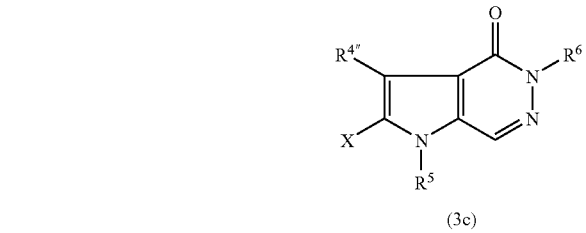

(3c)

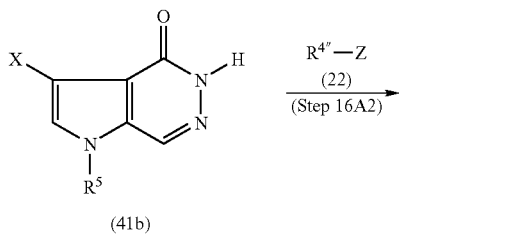

(41b)

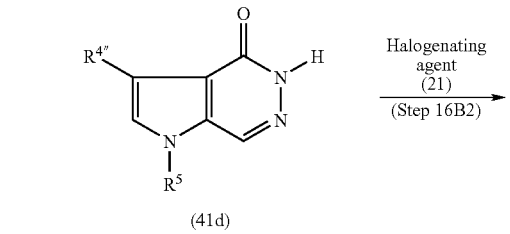

(41d)

-continued

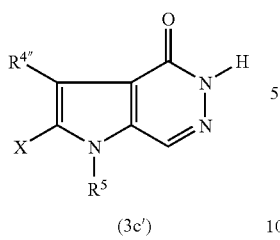

(3c′)

wherein $R^{4''}$, $R^5$, $R^6$, X and Z have the same meanings as defined above.

Preparation method 16 is a step of preparing Compound (3c) wherein $R^4$ of the above-mentioned compound (3) is $R^{4''}$, or Compound (3c′) which is a partially deprotected product of Compound (3c). This preparation method comprises steps (Step 16A1-Step 16B1) for preparing Compound (3c) from Compound (41a), and steps (Step 16A2-Step 16B2) for preparing Compound (3c′) from Compound (41b).

Step 16A1 is a step of preparing Compound (41c) by reacting a boronic acid compound (22) with Compound (41a) in an inert gas atmosphere in an inert solvent and in the presence of a palladium catalyst and a base. Compound (41a) can be prepared by the above-mentioned "Step 14I". Step 16A1 is carried out in the same manner as in the above-mentioned "Step 7A" except for using Compound (41a) in place of Compound (2f).

Step 16B1 is a step of preparing Compound (3c) by reacting Compound (41c) with a halogenating agent (21). Step 16B1 is carried out in the same manner as in the above-mentioned "Step 6A" except for using Compound (41c) in place of Compound (2e).

Step 16A2 is carried out in the same manner as in the above-mentioned "Step 7A" except for using Compound (41b) in place of Compound (2f). Compound (41b) can be prepared, for example, by reacting Compound (38) with a halogenating agent (21) in the same manner as in the above-mentioned "Step 14I". Step 16B2 is carried out in the same manner as in the above-mentioned "Step 6A" except for using Compound (41d) in place of Compound (2e).

[Preparation Method 17]

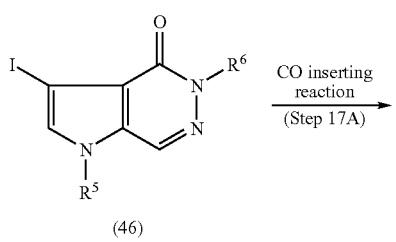

(46)

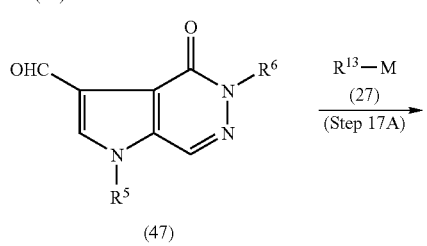

(47)

-continued

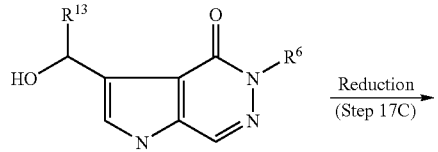

(48)

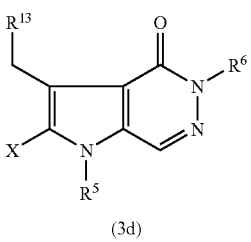

(49)

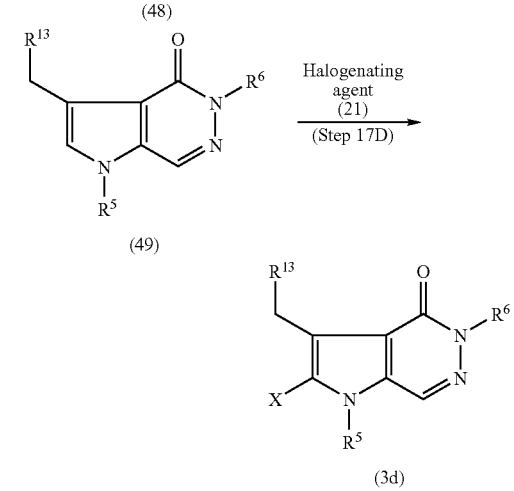

(3d)

wherein $R^5$, $R^6$, $R^{13}$, M and X have the same meanings as defined above.

Preparation method 17 is a method of preparing Compound (3d) wherein $R^4$ of the above-mentioned starting compound (3) is a methyl group substituted by $R^{13}$ by using Compound (46) as a starting compound.

Step 17A is a step of preparing a formyl compound (47) from Compound (46) in an inert solvent in the presence of a palladium catalyst, a base and a reducing agent under carbon monoxide atmosphere.

Compound (46) is a compound wherein X in the above-mentioned compound (41a) is an iodine atom, and can be prepared by the above-mentioned "Step 14I".

As the inert solvent to be used, it is not specifically limited so long as it does not inhibit the reaction and dissolves the starting materials with a certain extent, and there may be mentioned, for example, an amide such as N,N-dimethylformamide, N,N-dimethylacetamide or N-methylpyrrolidone, etc.; a sulfoxide such as dimethylsulfoxide, etc.; or a nitrile such as acetonitrile or propionitrile, etc., and the like, preferably N,N-dimethylformamide.

As the palladium catalyst to be used, there may be mentioned, for example, a metal palladium such as palladium-active carbon or palladium black, etc.; an organopalladium complex such as tetrakis(triphenylphosphine)palladium, bis(triphenylphosphine)palladium chloride, 1,1′-bis(diphenylphosphino)ferrocene palladium chloride or tris(dibenzylideneacetone)dipalladium, etc.; or a palladium salt such as palladium chloride or palladium acetate, etc., and the like, preferably palladium acetate. An amount of the palladium as a catalyst to be used is generally 0.0001 to 1-fold mol amount, preferably 0.005 to 0.1-fold mol amount based on 1 mol of Compound (46).

Incidentally, when tris(dibenzylideneacetone)dipalladium, palladium chloride or palladium acetate is used as a catalyst, it is particularly preferred to copresent an organophosphine compound.

As the organophosphine compound to be used, there may be mentioned, for example, tributylphosphine, tri(tertbutyl)phosphine, tricyclohexylphosphine, butyl-di-1-adamantylphosphine, triphenylphosphine, tri(o-tolyl)phosphine, 2-dicyclohexylphosphino-2',6'-dimethoxybiphenyl, 1,1'-bis(diphenylphosphino)ferrocene or 1,2,3,4,5-pentaphenyl-1'-(di-t-butylphosphino)ferrocene, etc., preferably 1,1'-bis(diphenylphosphino)ferrocene. An amount of the organophosphine compound to be used is generally 1 to 3-fold mol amount, preferably 1.5 to 2.5-fold mol amount based on 1 mol of palladium.

As the amine to be used, there may be mentioned, for example, an amine such as triethylamine, tributylamine, N,N-diisopropylethylamine, pyridine, picoline, 2,6-lutidine or 4-dimethylaminopyridine, etc., preferably triethylamine. An amount of the amine to be used is generally 1 to 10-fold mol amount, preferably 1 to 2-fold mol amount based on 1 mol of Compound (46).

As the reducing agent to be used, there may be mentioned, for example, an organosilane compound such as triethylsilane, etc.; or an organotin compound such as tributyltin, etc., and the like, preferably-triethylsilane. An amount of the reducing agent to be used is generally 1 to 5-fold mol amount, preferably 1.5 to 2.5-fold mol amount based on 1 mol of Compound (46).

A partial pressure of the carbon monoxide is generally 1 atm to 10 atm, preferably 1 atm to 5 atm.

A reaction temperature may vary depending on a kind, an amount to be used of starting materials, solvent(s), etc., and is generally in the range of 0° C. to 200° C., preferably 50° C. to 15° C.

A reaction time may vary depending on a reaction temperature, etc., and is generally for 30 minutes to 72 hours, preferably for 1 hour to 48 hours.

Step 17B is a step of preparing Compound (48) having a hydroxy group by reacting Compound (47) with an organometallic compound (27). This step is carried out in the same manner as in the above-mentioned "Step 3B" except for using an organometallic compound (27) in place of the organometallic compound (9), and using Compound (47) in place of Compound (8).

Step 17C is a step of preparing Compound (49) by reducing Compound (48) having a hydroxy group using an organosilane compound or organotin compound in an inert solvent in the presence of an acid or a Lewis acid. This step is carried out in the same manner as in the above-mentioned "Step 12C1" except for using Compound (48) in place of Compound (6q).

Step 17D is a step of preparing Compound (3d) by reacting Compound (49) with a halogenating agent (21). This step is carried out in the same manner as in the above-mentioned "Step 6A" except for using Compound (49) in place of Compound (2e).

[Preparation Method 18]

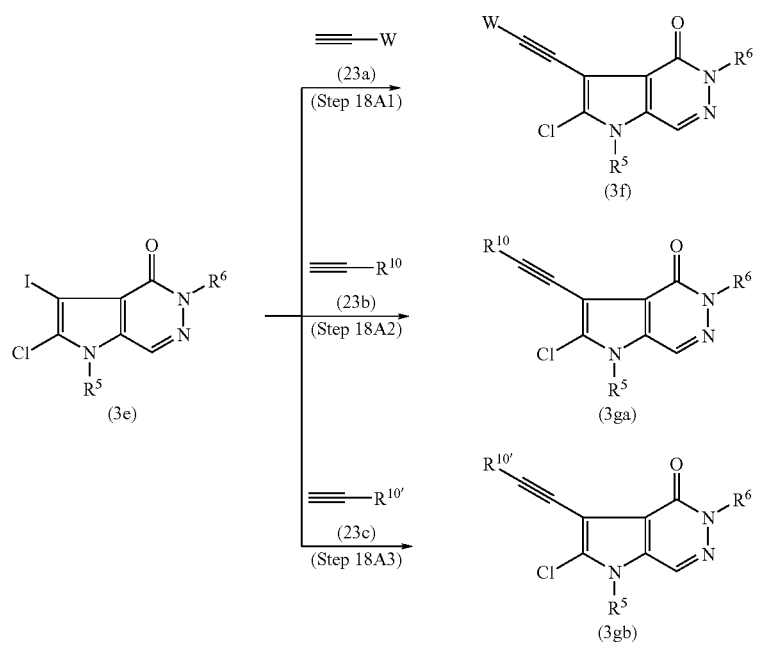

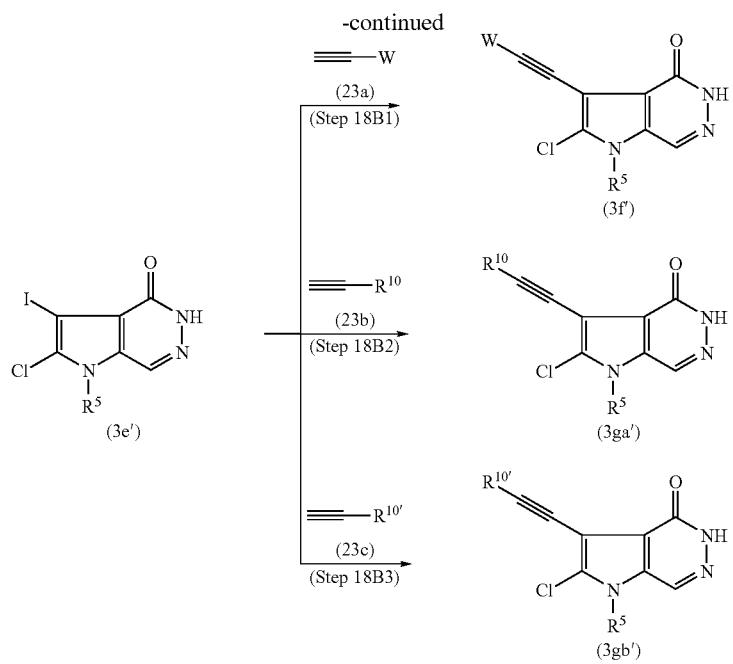

wherein $R^5$, $R^6$, $R^{10}$, $R^{10'}$ and W have the same meanings as defined above.

Preparation method 18 is a method for preparing a compound in which an ethynyl group the terminal of which is substituted by W, $R^{10}$ or $R^{10'}$ is introduced into the 3-position of the pyrrolopyridazine ring of the above-mentioned compound (3).

This preparation method comprises,
Step 18A1 for preparing Compound (3f) by reacting Compound (3e) with an acetylene-terminated compound (23a),
Step 18A2 for preparing Compound (3ga) by reacting Compound (3e) with an acetylene-terminated compound (23b),
Step 18A3 for preparing Compound (3gb) by reacting Compound (3e) with an acetylene-terminated compound (23c),
Step 18B1 for preparing Compound (3f') by reacting Compound (3e') with an acetylene-terminated compound (23a),
Step 18B2 for preparing Compound (3ga') by reacting Compound (3e') with an acetylene-terminated compound (23b), and
Step 18B3 for preparing Compound (3gb') by reacting Compound (3e') with an acetylene-terminated compound (23c).

These 6 Steps are all carried out by the reaction of a halogen compound and an acetylene-terminated compound in the presence of a palladium catalyst, cuprous iodide and an amine, which is so-called Sonogashira reaction.

Step 18A1 is carried out in the same manner as in the above-mentioned "Step 8A1" except for using Compound (3e) in place of Compound (2f). Compound (3e) is a compound wherein X of the above-mentioned compound (3b) is an iodine atom and X' is a chlorine atom, and can be prepared by the above-mentioned "Step 14J".

Step 18A2 is carried out in the same manner as in the above-mentioned "Step 8A1" except for using Compound (3e) in place of Compound (2f).

Step 18A3 is carried out in the same manner as in the above-mentioned "Step 8A1" except for using Compound (3e) in place of Compound (2f).

Step 18B1 is carried out in the same manner as in the above-mentioned "Step 8A1" except for using Compound (3e') in place of Compound (2f). Compound (3e') is a compound wherein X in the above-mentioned compound (3b') is an iodine atom, and X' is a chlorine atom, and can be prepared by the above-mentioned "Step 14L".

Step 18B2 is carried out in the same manner as in the above-mentioned "Step 8A1" except for using Compound (3e') in place of Compound (2f), and Compound (23b) in place of Compound (23a), respectively.

Step 18B3 is carried out in the same manner as in the above-mentioned "Step 8A1" except for using Compound (3e') in place of Compound (2f), and Compound (23c) in place of Compound (23a), respectively.

[Preparation Method 19]

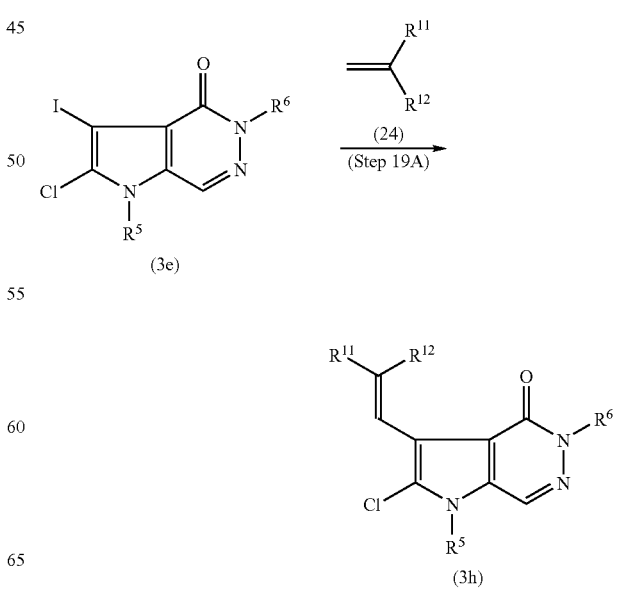

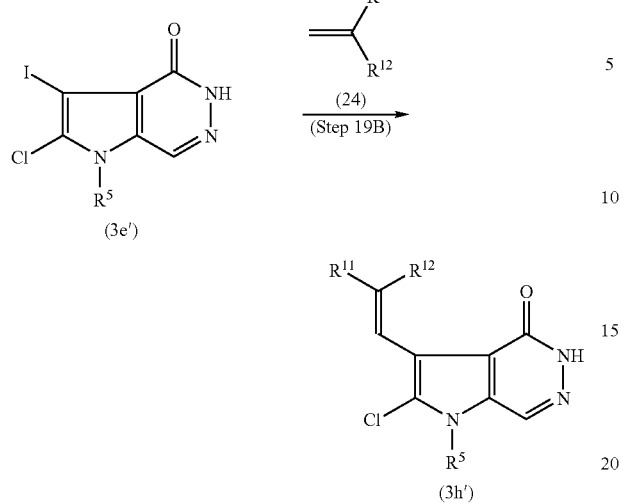

wherein $R^5$, $R^6$, $R^{11}$ and $R^{12}$ have the same meanings as defined above.

Preparation method 19 is a method for preparing Compound (3h) wherein $R^4$ of the above-mentioned compound (3) is a vinyl group substituted by $R^{11}$ and $R^{12}$, or Compound (3h') which is a partially deprotected product of Compound (3h), respectively.

Step 19A is a step for preparing Compound (3h) by applying Compound (3e) to Heck reaction with Compound (24). This step is carried out in the same manner as in the above-mentioned "Step 11A1" except for using Compound (3e) in place of Compound (6f).

Step 19B is a step for preparing Compound (3h') by applying Compound (3e') to Heck reaction with Compound (24). This step is carried out in the same manner as in the above-mentioned "Step 11A1" except for using Compound (3e') in place of Compound (6f).

[Preparation Method 20]

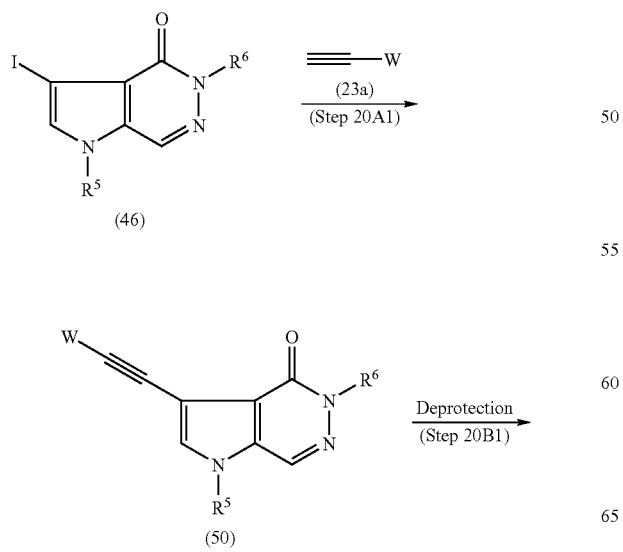

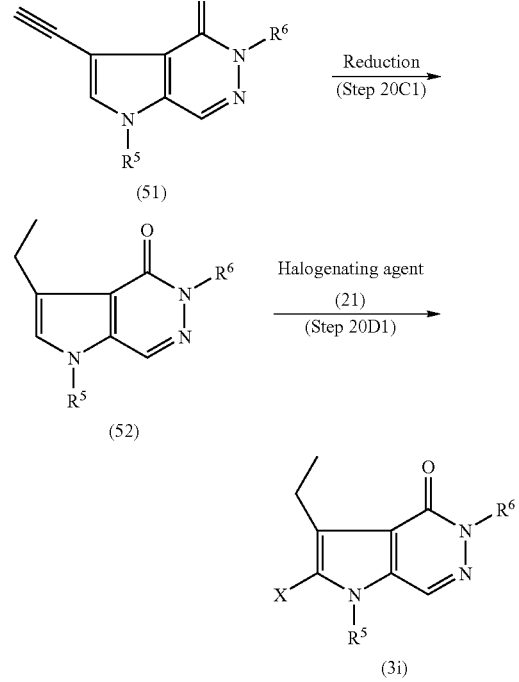

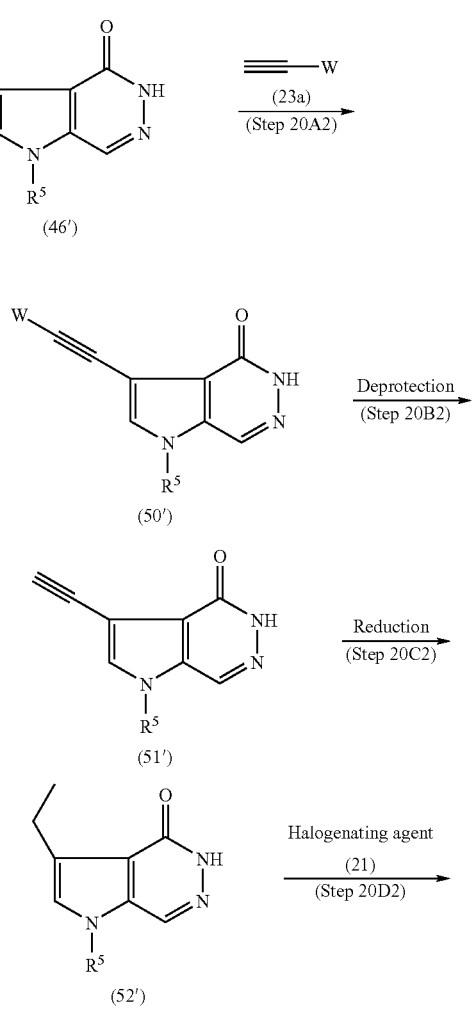

-continued

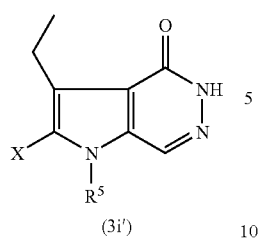

(3i')

wherein R⁵, R⁶, W and X have the same meanings as defined above.

Preparation method 20 is a method for preparing Compound (3i) wherein R⁴ of the above-mentioned compound (3) is an ethyl group, or Compound (3i') which is a partially deprotected product of Compound (3i), respectively. This preparation method comprises steps (Step 20A1-Step 20B1-Step 20C1-Step 20D1) for preparing Compound (3i) from Compound (46), and steps (Step 20A2-Step 20B2-Step 20C2-Step 20D2) for preparing Compound (3i') from Compound (46').

Step 20A1 is a step for preparing an acetylene compound (50) by reacting Compound (46) with an acetylene compound (23a) in an inert gas atmosphere in the absence of a solvent or in an inert solvent and in the presence of a palladium catalyst, cuprous iodide and an amine. This step is carried out in the same manner as in the above-mentioned "Step 8A1" except for using Compound (46) in place of Compound (2f).

Step 20B1 is a step for preparing Compound (51) in which the 3-position of the pyrrolopyridazine ring is an ethynyl group by removing the protective group W at the end of the ethynyl group of Compound (50). This step is carried out in the same manner as in the above-mentioned "Step 9A1" except for using Compound (50) in place of Compound (6h).

Step 20C1 is a step for preparing Compound (52) in which the 3-position is an ethyl group by applying Compound (51) to hydrogenation reduction. This step is carried out in the same manner as in the above-mentioned "Step 9C1" except for using Compound (51) in place of Compound (6k).

Step 20D1 is a step for preparing Compound (31) by reacting Compound (52) with a halogenating agent (21). This step is carried out in the same manner as in the above-mentioned "Step 6A" except for using Compound (52) in place of Compound (2e).

Step 20A2 is carried out in the same manner as in the above-mentioned "Step 8A1" except for using Compound (46') in place of Compound (2f). Compound (46') is a compound in which X of the above-mentioned compound (41b) is an iodine atom, and can be prepared by the above-mentioned "Step 14K".

Step 20B2 is carried out in the same manner as in the above-mentioned "Step 9A1" except for using Compound (50') in place of Compound (6h).

Step 20C2 is carried out in the same manner as in the above-mentioned "Step 9C1" except for using Compound (51') in place of Compound (6k).

Step 20D2 is carried out in the same manner as in the above-mentioned "Step 6A" except for using Compound (52') in place of Compound (2e).

[Preparation Method 21]

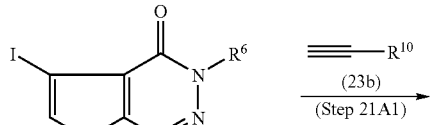

(46)

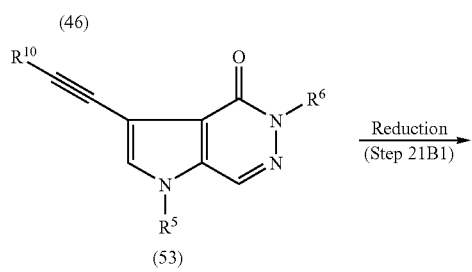

(53)

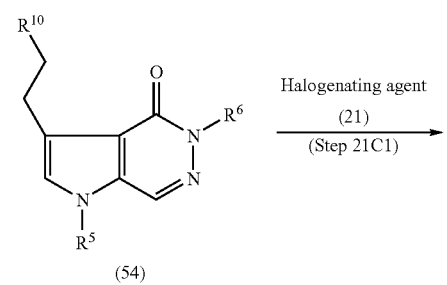

(54)

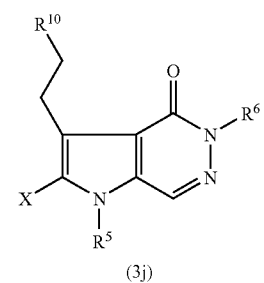

(3j)

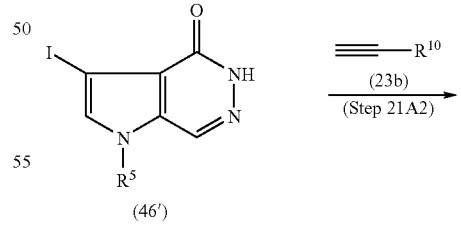

(46')

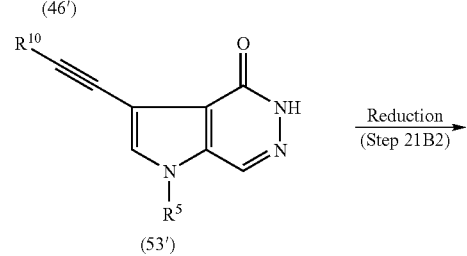

(53')

[Preparation Method 22]

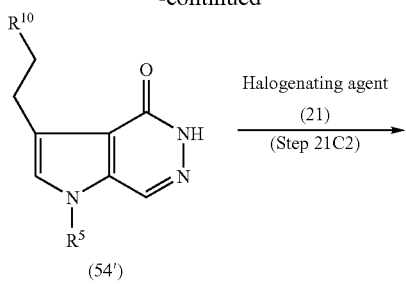

(54')

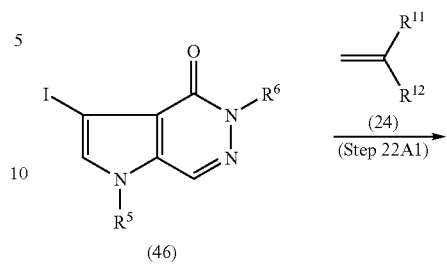

(46)

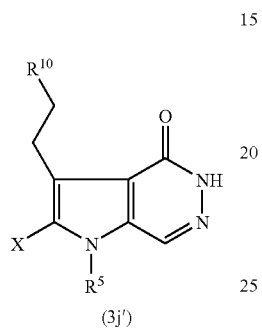

(3j')

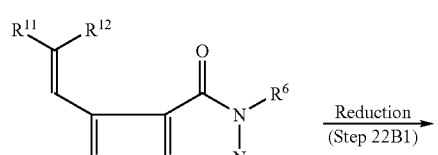

(55)

wherein $R^5$, $R^6$, $R^{10}$ and X have the same meanings as defined above.

Preparation method 21 is a method for preparing Compound (3j) wherein $R^4$ of the above-mentioned compound (3) is an ethyl group substituted by $R^{10}$, or Compound (3j') which is a partially deprotected product of Compound (3j), respectively. This preparation method comprises steps (Step 21A1-Step 21B1-Step 21C1) for preparing Compound (3j) from Compound (46), and steps (Step 21A2-Step 21B2-Step 21C2) for preparing Compound (3j') from Compound (46').

Step 21A1 is a step for preparing an acetylene compound (53) by reacting Compound (46) with an acetylene compound (23b) in an inert gas atmosphere in the absence of a solvent or in an inert solvent and in the presence of a palladium catalyst, cuprous iodide and an amine. This step is carried out in the same manner as in the above-mentioned "Step 8A2" except for using Compound (46) in place of Compound (2f).

Step 21B1 is a step for preparing Compound (54) by subjecting Compound (53) to hydrogenation reduction in the presence of a catalyst. This step is carried out in the same manner as in the above-mentioned "Step 9C1" except for using Compound (53) in place of Compound (6k).

Step 21C1 is a step for preparing Compound (3j) by reacting Compound (54) with a halogenating agent (21). This step is carried out in the same manner as in the above-mentioned "Step 6A" except for using Compound (54) in place of Compound (2e).

Step 21A2 is carried out in the same manner as in the above-mentioned "Step 8A2" except for using Compound (46') in place of Compound (2f).

Step 21B2 is carried out in the same manner as in the above-mentioned "Step 9C1" except for using Compound (53') in place of Compound (6k).

Step 21C2 is carried out in the same manner as in the above-mentioned "Step 6A" except for using Compound (54') in place of Compound (2e).

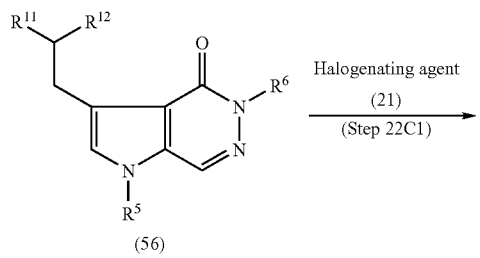

(56)

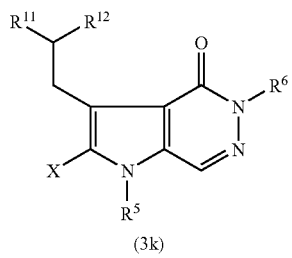

(3k)

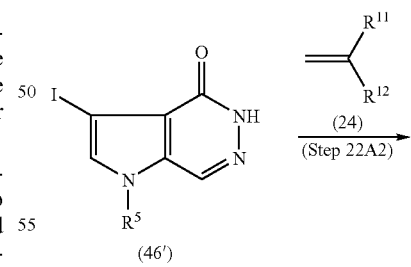

(46')

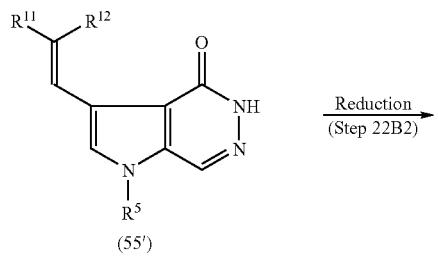

(55')

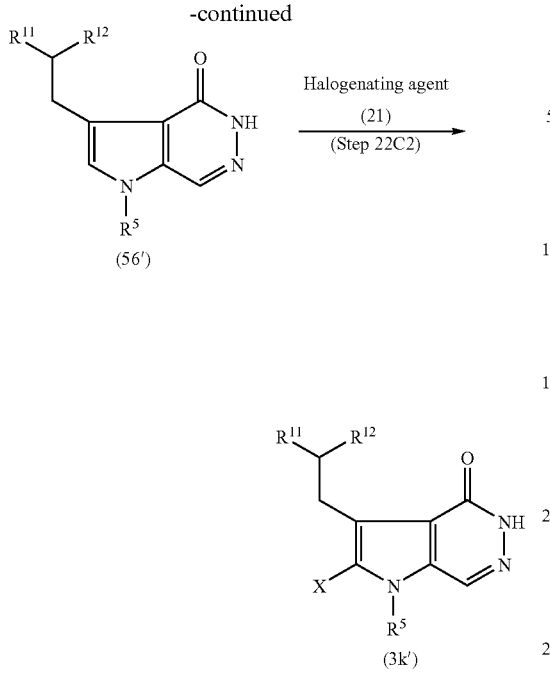

(56')

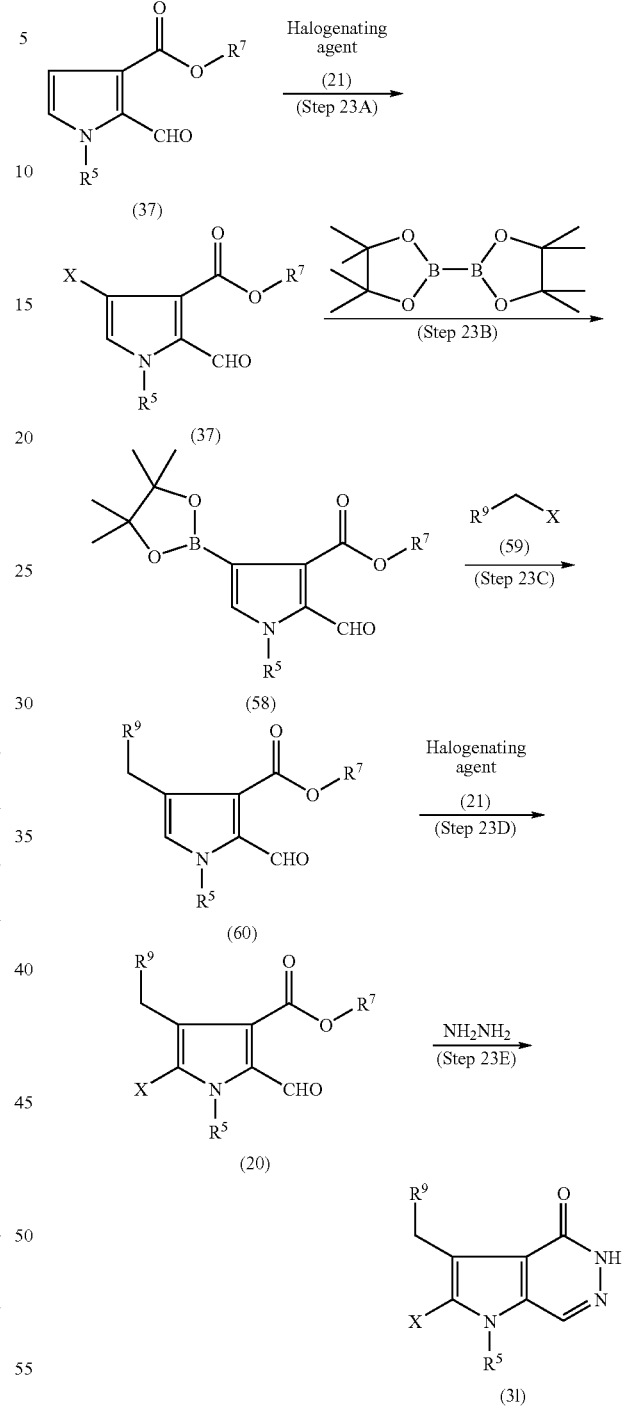

wherein $R^5$, $R^6$, $R^{11}$, $R^{12}$ and X have the same meanings as defined above.

Preparation method 22 is a method for preparing Compound (3k) wherein $R^4$ of the above-mentioned Compound (3) is an ethyl group substituted by $R^{11}$ and $R^{12}$, or Compound (3k') which is a partially deprotected product of Compound (3k), respectively. This preparation method comprises steps (Step 22A1-Step 22B1-Step 22C1) for preparing Compound (3k) from Compound (46), and steps (Step 22A2-Step 22B2-Step 22C2) for preparing Compound (3k') from Compound (46').

Step 22A1 is a step for preparing an olefin compound (55) by reacting Compound (46) with Compound (24) in an inert gas atmosphere in an inert solvent and in the presence of a palladium catalyst and a base. This step is carried out in the same manner as in the above-mentioned "Step 11A1" except for using Compound (46) in place of Compound (6f).

Step 22B1 is a step for preparing Compound (56) by subjecting Compound (55) to hydrogenation reduction in the presence of a catalyst. This step is carried out in the same manner as in the above-mentioned "Step 9C1" except for using Compound (55) in place of Compound (6k).

Step 22C1 is a step for preparing a halogenated compound (3k) by reacting Compound (56) with a halogenating agent (21). This step is carried out in the same manner as in the above-mentioned "Step 6A" except for using Compound (56) in place of Compound (2e).

Step 22A2 is carried out in the same manner as in the above-mentioned "Step 11A1" except for using Compound (46') in place of Compound (6f).

Step 22B2 is carried out in the same manner as in the above-mentioned "Step 9C1" except for using Compound (55') in place of Compound (6k).

Step 22C2 is carried out in the same manner as in the above-mentioned "Step 6A" except for using Compound (56') in place of Compound (2e).

[Preparation Method 23]

wherein $R^5$, $R^7$, $R^9$ and X have the same meanings as defined above.

Preparation method 23 is a method for preparing Compound (31) wherein $R^4$ of the above-mentioned compound (3) is a methyl group substituted by $R^9$ by using Compound (37) as a starting compound.

Step 23A is a step for preparing a halogenated pyrrole compound (57) by reacting a pyrrole compound (37) with a halogenating agent (21). Compound (37) can be prepared by the above-mentioned "Step 14F". This step is carried out in the same manner as in the above-mentioned "Step 6A" except for using Compound (37) in place of Compound (2e).

Step 23B is a step for preparing a boronic acid ester compound (58) by reacting Compound (57) with a bis(pinacolato) diboron in an inert solvent and in the presence of a palladium catalyst and a base. This step is carried out in the same manner as in the above-mentioned "Step 1A" except for selecting 1,4-dioxane as an inert solvent, 1,1'-bis(diphenylphosphino) ferrocene palladium chloride as a palladium catalyst, and potassium acetate as a base, respectively, and using Compound (57) in place of Compound (3), and using bis(pinacolato)diboron in place of Compound (4), respectively.

Step 23C is a step for preparing Compound (60) by reacting Compound (58) with Compound (59) in an inert solvent in an inert gas atmosphere and in the presence of a palladium catalyst and a base. This step is carried out in the same manner as in the above-mentioned "Step 1A" except for selecting a 1,2-dimethoxyethane-water mixed solvent as an inert solvent, tetrakis(triphenylphosphine)palladium as a palladium catalyst, and sodium carbonate as a base, respectively, and using Compound (59) in place of Compound (3), and using Compound (58) in place of Compound (4), respectively.

Step 23D is a step for preparing a halogenated pyrrole compound (20) by reacting Compound (60) with a halogenating agent (21). This step is carried out in the same manner as in the above-mentioned "Step 6A" except for using Compound (60) in place of Compound (2e).

Step 23E is a step for preparing a pyrrolopyridazinone compound (31) by reacting Compound (20) with a hydrazine monohydrate. This step is carried out in the same manner as in the above-mentioned "Step 3G" except for using Compound (20) in place of Compound (16).

[Preparation Method 24]

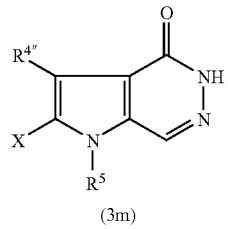

(3m)

wherein $R^{4''}$, $R^5$, $R^7$, X and Z have the same meanings as defined above.

Preparation method 24 is a method for preparing Compound (3m) wherein $R^4$ of the above-mentioned compound (3) is $R^{4''}$ and $R^6$ is deprotected by using a pyrrole compound (57) as a starting compound.

Step 24A is a step for preparing a pyrrole compound (61) by reacting Compound (57) with Compound (22) in an inert solvent in an inert gas atmosphere and in the presence of a palladium catalyst and a base. Compound (57) can be prepared by the above-mentioned "Step 23A". This step is carried out in the same manner as in the above-mentioned "Step 1A" except for using Compound (57) in place of Compound (3), and using Compound (22) in place of Compound (4), respectively.

Step 24B is a step for preparing a halogenated pyrrole compound (62) by reacting Compound (61) with a halogenating agent (21). This step is carried out in the same manner as in the above-mentioned "Step 6A" except for using Compound (61) in place of Compound (2e).

Step 24C is a step for preparing a pyrrolopyridazinone compound (3m) by reacting Compound (62) with a hydrazine monohydrate. This step is carried out in the same manner as in the above-mentioned "Step 3G" except for using Compound (62) in place of Compound (16).

[Preparation Method 25]

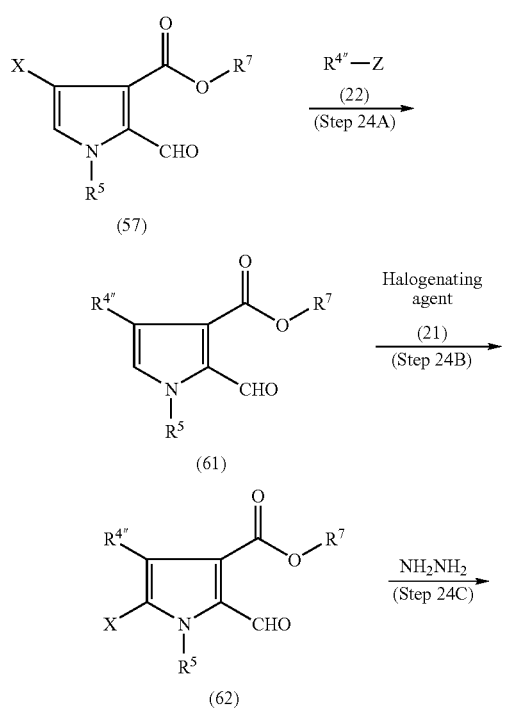

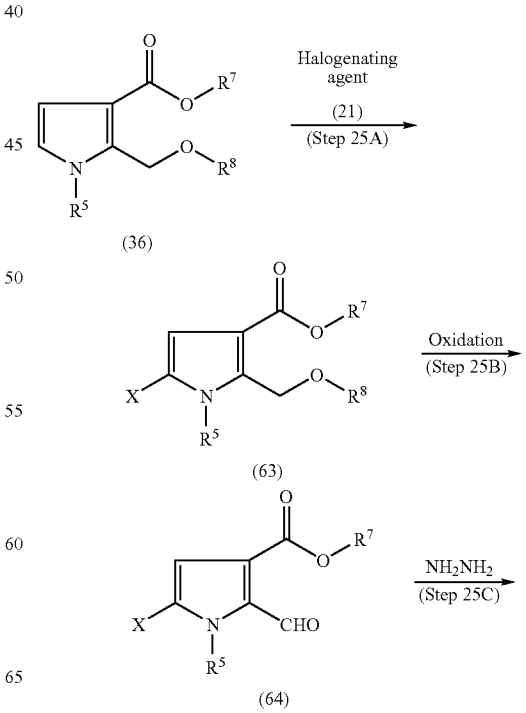

-continued

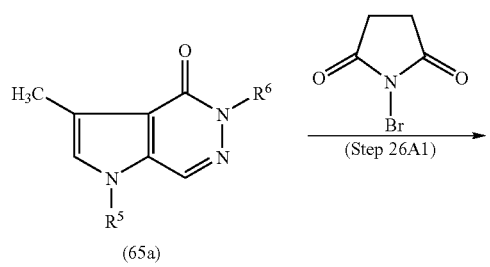

(3n)

Protecting agent
(39)
(Step 25D)

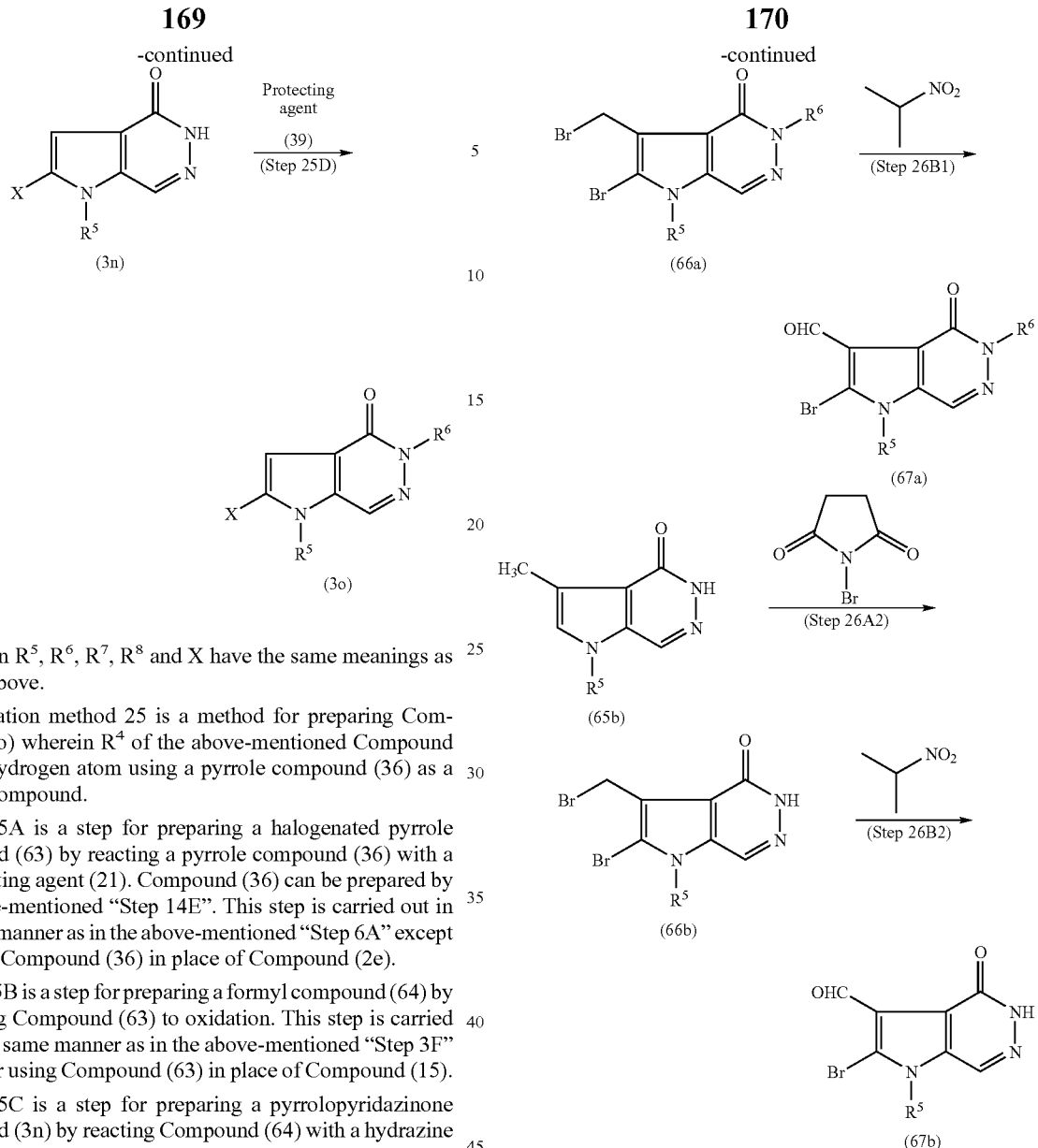

wherein $R^5$, $R^6$, $R^7$, $R^8$ and X have the same meanings as defined above.

Preparation method 25 is a method for preparing Compound (3o) wherein $R^4$ of the above-mentioned Compound (3) is a hydrogen atom using a pyrrole compound (36) as a starting compound.

Step 25A is a step for preparing a halogenated pyrrole compound (63) by reacting a pyrrole compound (36) with a halogenating agent (21). Compound (36) can be prepared by the above-mentioned "Step 14E". This step is carried out in the same manner as in the above-mentioned "Step 6A" except for using Compound (36) in place of Compound (2e).

Step 25B is a step for preparing a formyl compound (64) by subjecting Compound (63) to oxidation. This step is carried out in the same manner as in the above-mentioned "Step 3F" except for using Compound (63) in place of Compound (15).

Step 25C is a step for preparing a pyrrolopyridazinone compound (3n) by reacting Compound (64) with a hydrazine monohydrate. This step is carried out in the same manner as in the above-mentioned "Step 3G" except for using Compound (64) in place of Compound (16).

Step 25D is a step for preparing Compound (3o) by introducing $R^6$ as a protective group into amidic NH group of Compound (3n) This step is carried out in the same manner as in the above-mentioned "Step 14H" except for using Compound (3n) in place of Compound (38).

[Preparation Method 26]

wherein $R^5$ and $R^6$ have the same meanings as defined above.

Preparation method 26 is a method for preparing a formyl compound (67a) wherein X of Compound (25a) in the above-mentioned "Preparation method 12" is a bromine atom, or a formyl compound (67b) wherein X of Compound (25b) is a bromine atom, respectively. This preparation method comprises steps (Step 26A1-Step 26B1) for preparing Compound (67a) from Compound (65a), and steps (Step 26A2-Step 26B2) for preparing Compound (67b) from Compound (65b).

Step 26A1 is a step for preparing a bromomethyl compound (66a) by reacting Compound (65a) with N-bromosuccineimide as a brominating agent in an inert solvent in the presence of a radical initiator or under photoirradiation.

Compound (65a) is a compound wherein $R^4$ of Compound (41c) in the above-mentioned "Preparation method 16" is a methyl group, and can be prepared by the above-mentioned "Step 16A1".

As the inert solvent to be used, there may be mentioned, for example, a halogenated aliphatic hydrocarbon such as dichloromethane, chloroform or 1,2-dichloroethane, etc., and the like, preferably dichloromethane or 1,2-dichloroethane.

An amount of the N-bromosuccineimide to be used is generally 2 to 5-fold mol amount, preferably 2 to 3-fold mol amount based on 1 mol of Compound (65a).

As the radical initiator to be used, there may be mentioned, for example, a radical initiator such as azobisisobutyronitrile or benzoyl peroxide, etc. An amount of the radical initiator to be used is generally 0.001 to 0.1-fold mol amount, preferably 0.01 to 0.05-fold mol amount based on 1 mol of Compound (65a).

A reaction temperature may vary depending on a kind, an amount to be used of starting materials, solvent(s), etc., and is generally in the range of 0° C. to 100° C., preferably 30° C. to 80° C.

A reaction time may vary depending on a reaction temperature, etc., and is generally for 1 hour to 12 hours, preferably 3 hours to 8 hours.

When the reaction is carried out under photoirradiation, it is carried out in the same manner as in the case where the radical initiator is used except for irradiating light using a mercury lamp as a light source.

Step 26B1 is a step for preparing a formyl compound (67a) by reacting Compound (66a) with 2-nitropropane in an inert solvent in the presence of a base.

As the inert solvent to be used, it is not specifically limited so long as it does not inhibit the reaction and dissolves the starting materials with a certain extent, and there may be mentioned, for example, an alcohol such as methanol, ethanol, propanol or isopropanol, etc.; an amide such as N,N-dimethylformamide, N,N-dimethylacetamide or N-methylpyrrolidone, etc.; a sulfoxide such as dimethylsulfoxide, etc.; a nitrile such as acetonitrile or propionitrile, etc.; an ether such as tetrahydrofuran, 1,2-dimethoxyethane or 1,4-dioxane, etc.; or a mixed solvent of an optional combination of the above, etc., preferably ethanol.

As the base to be used, there may be mentioned, for example, an alkali metal such as lithium, sodium or potassium, etc.; an alkali metal hydride such as sodium hydride, etc.; or an alkali metal alkoxide such as sodium methoxide, sodium ethoxide, sodium butoxide or potassium tert-butoxide, etc., and the like, preferably sodium ethoxide. An amount of the base to be used is generally 1 to 20-fold mol amount, preferably 5 to 10-fold mol amount based on 1 mol of Compound (66a).

An amount of the 2-nitropropane to be used is generally 1 to 20-fold mol amount, preferably 5 to 10-fold mol amount based on 1 mol of Compound (66a).

A reaction temperature may vary depending on a kind, an amount to be used of starting materials, solvent(s), etc., and is generally in the range of –20° C. to 100° C., preferably 0° C. to 40° C.

A reaction time may vary depending on a reaction temperature, etc., and is generally for 1 hour to 12 hours, preferably 2 hours to 6 hours.

Step 26A2 is carried out in the same manner as in the above-mentioned "Step 26A1" except for using Compound (65b) in place of Compound (65a). Compound (65b) is a compound wherein $R^4$ of Compound (41d) in the above-mentioned "Preparation method 16" is a methyl group, and can be prepared by the above-mentioned "Step 16A2". Step 26B2 is carried out in the same manner as in the above-mentioned "Step 26B1" except for using Compound (66b) in place of Compound (66a).

[Preparation Method 27]

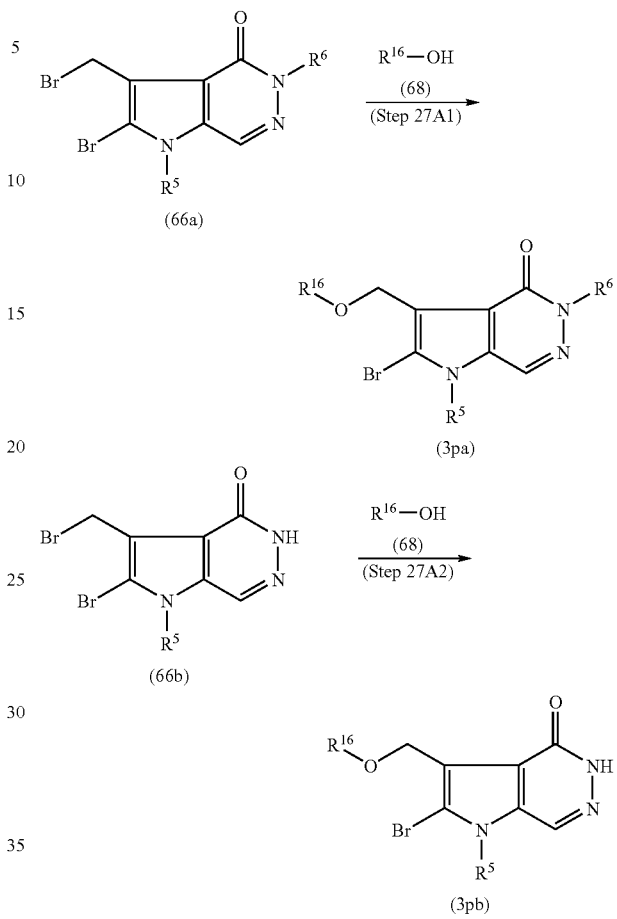

wherein $R^5$ and $R^6$ have the same meanings as defined above, and $R^{16}$ represents a $C_1$-$C_5$ alkyl group, halogeno $C_1$-$C_4$ alkyl group, $C_3$-$C_6$ cycloalkyl group or ($C_3$-$C_6$ cycloalkyl)$C_1$-$C_2$ alkyl group. (As the $C_1$-$C_5$ alkyl group, it represents a straight or branched alkyl chain, for example, a methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl or 1-ethylpropyl group, etc., the halogeno $C_1$-$C_4$ alkyl group has the same meaning as the "$C_1$-$C_4$ alkyl group substituted by a halogen atom" defined in Substituent group (c) of the above-mentioned $R^4$, the $C_3$-$C_6$ cycloalkyl group has the same meaning as the "$C_3$-$C_6$ cycloalkyl group which may be substituted by a substituent(s) selected from Substituent group (b)" of the above-mentioned $R^4$, and as the ($C_3$-$C_6$ cycloalkyl)$C_1$-$C_2$ alkyl group, there may be mentioned, for example, a cyclopropylmethyl, cyclobutylmethyl, cyclopentylmethyl, cyclohexylmethyl, 2-cyclopropylethyl, 2-cyclobutylethyl, 2-cyclopentylethyl or 2-cyclohexylethyl group, etc.)

Preparation method 27 is a method for preparing Compound (3pa) wherein $R^4$ of the above-mentioned compound (3) is an alkoxymethyl group, or Compound (3pb) which is a partially deprotected product of Compound (3pa), respectively.

Step 27A1 is a step for preparing an ether compound (3pa) by reacting a bromomethyl compound (66a) and an alcohol compound (68) in an inert solvent under basic conditions. Compound (66a) can be prepared by the above-mentioned "Step 26A1".

173

An amount of Compound (68) to be used is generally 1 to 50-fold mol amount, preferably 2 to 10-fold mol amount based on 1 mol of Compound (66a), and it may be used markedly excessively as a solvent.

As the inert solvent to be used, it is not specifically limited so long as it does not inhibit the reaction and dissolves the starting materials with a certain extent, and there may be mentioned, for example, an ether such as diethyl ether, tetrahydrofuran, 1,2-dimethoxyethane or 1,4-dioxane, etc.; an amide such as N,N-dimethylformamide, N,N-dimethylacetamide or N-methylpyrrolidone, etc.; or a mixed solvent thereof, etc., preferably tetrahydrofuran.

As the base to be used, there may be mentioned an alkali metal such as lithium, sodium or potassium, etc.; an alkali metal hydride such as sodium hydride or potassium hydride, etc.; or an alkali metal alkoxide such as sodium methoxide, sodium ethoxide, sodium butoxide, sodium tert-butoxide or potassium tert-butoxide, etc., and the like, preferably sodium hydride. An amount of the base to be used is generally 1 to 20-fold mol amount, preferably 1 to 10-fold mol amount based on 1 mol of Compound (66a).

A reaction temperature may vary depending on a kind, an amount to be used of starting materials, solvent(s), etc., and is generally in the range of 0° C. to 100° C., preferably 10° C. to 50° C.

A reaction time may vary depending on a reaction temperature, etc., and is generally for 10 minutes to 12 hours, preferably 1 hour to 6 hours.

Step 27A2 is carried out in the same manner as in the above-mentioned "Step 27A1" except for using Compound (66b) in place of Compound (66a), and a preferred amount of the base to be used is 2 to 10-fold mol amount based on 1 mol of Compound (66b). Compound (66b) can be prepared by the above-mentioned "Step 26A2".

[Preparation Method 28]

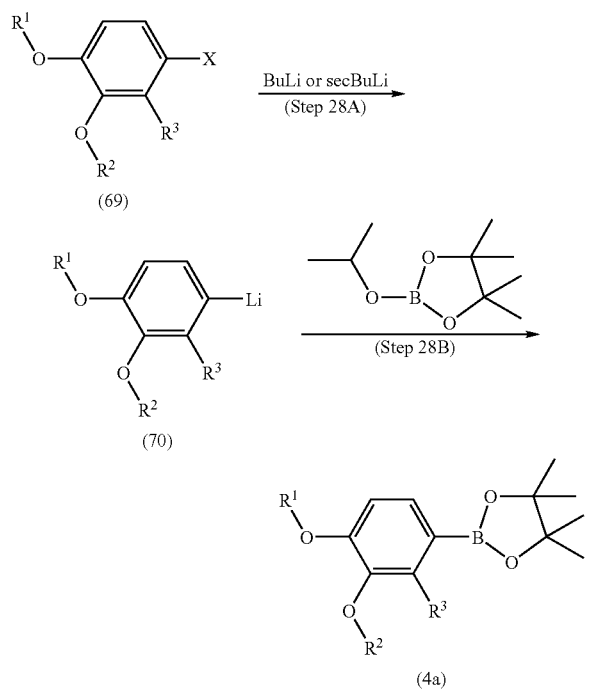

wherein $R^1$, $R^2$, $R^3$ and X have the same meanings as defined above.

174

Preparation method 28 is a method for preparing Compound (4a) wherein Z of the above-mentioned compound (4) is a 4,4,5,5-tetramethyl-[1,3,2]dioxaborolanyl group by using Compound (69) as a starting compound.

Step 28A is a step for preparing a lithiated compound (70) by reacting Compound (69) with an organolithium compound in an inert solvent. Compound (69) is a compound which is conventionally known, or can be prepared by either of the following mentioned "Preparation method 32", "Preparation method 36", "Preparation method 37", "Preparation method 38", "Preparation method 39" or "Preparation method 40".

As the inert solvent to be used, it is not specifically limited so long as it does not inhibit the reaction and dissolves the starting materials with a certain extent, and there may be mentioned, for example, an ether such as diethyl ether, tetrahydrofuran or 1,2-dimethoxyethane, etc.; an aliphatic saturated hydrocarbon such as pentane, hexane, cyclohexane or heptane, etc.; an aromatic hydrocarbon such as benzene or toluene, etc.; or a mixed solvent of an optional combination of the above, etc., preferably diethyl ether or tetrahydrofuran.

As the organolithium compound, there may be mentioned, for example, an organolithium compound such as butyl lithium or sec-butyl lithium, etc. An amount of the organolithium compound to be used is generally 0.9 to 1.5-fold mol amount, preferably 1 to 1.1-fold mol amount based on 1 mol of Compound (69).

A reaction temperature may vary depending on a kind, an amount to be used of starting materials, solvent(s), etc., and is generally in the range of −80° C. to 20° C., preferably −70° C. to 0° C.

A reaction time may vary depending on a reaction temperature, etc., and is generally for 10 minutes to 12 hours, preferably 30 minutes to 6 hours.

In this step, the lithiated compound (70) can be applied to the next Step 28B without isolation from the reaction mixture.

Step 28B is a step for preparing a boronic acid ester compound (4a) by reacting the lithiated compound (70) with 2-isopropoxy-4,4,5,5-tetramethyl[1,3,2]dioxaborolane in an inert solvent.

The inert solvent to be used in this step is the same solvents as those used in the above-mentioned "Step 28A".

An amount of the 2-isopropoxy-4,4,5,5-tetramethyl-[1,3,2]dioxaborolane to be used is generally 1 to 2-fold mol amount, preferably 1 to 1.5-fold mol amount based on 1 mol of Compound (69) or Compound (70).

A reaction temperature may vary depending on a kind, an amount to be used of starting materials, solvent(s), etc., and is generally in the range of −80° C. to 50° C., preferably −70° C. to 30° C.

A reaction time may vary depending on a reaction temperature, etc., and is generally for 30 minutes to 6 hours, preferably 30 minutes to 3 hours.

[Preparation Method 29]

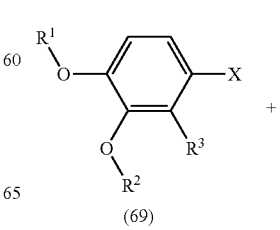

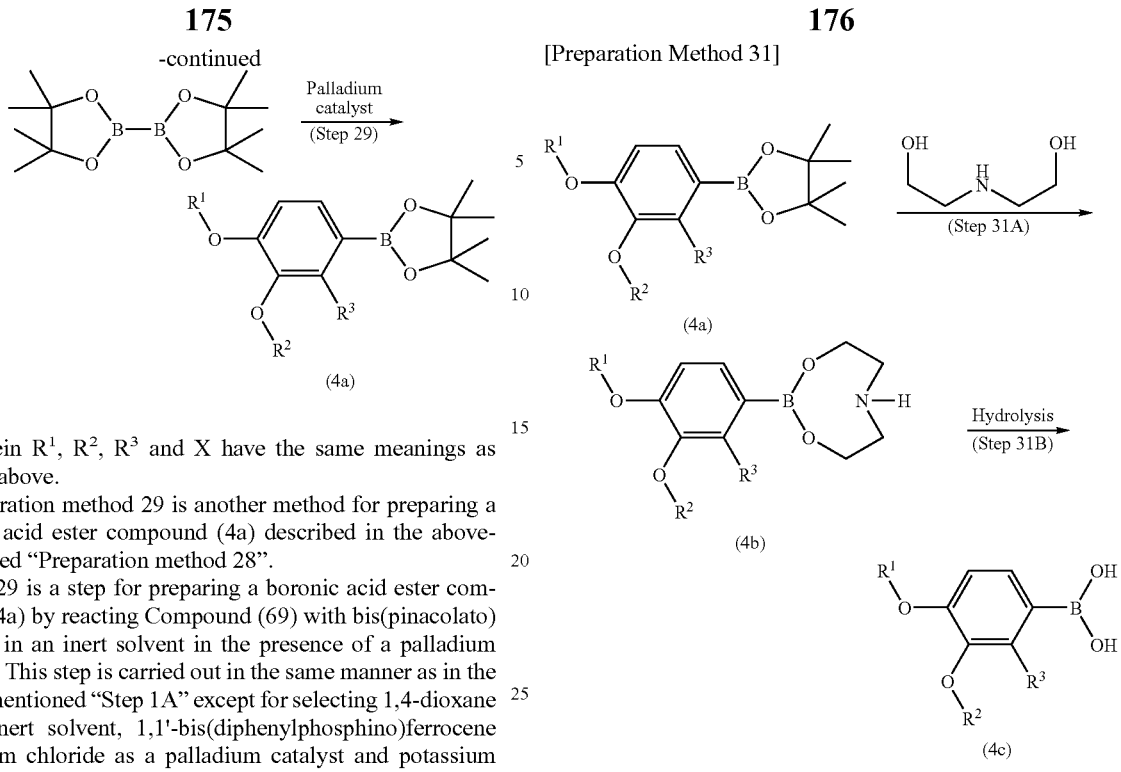

wherein $R^1$, $R^2$, $R^3$ and X have the same meanings as defined above.

Preparation method 29 is another method for preparing a boronic acid ester compound (4a) described in the above-mentioned "Preparation method 28".

Step 29 is a step for preparing a boronic acid ester compound (4a) by reacting Compound (69) with bis(pinacolato)diboron in an inert solvent in the presence of a palladium catalyst. This step is carried out in the same manner as in the above-mentioned "Step 1A" except for selecting 1,4-dioxane as an inert solvent, 1,1'-bis(diphenylphosphino)ferrocene palladium chloride as a palladium catalyst and potassium acetate as a base, respectively, and using Compound (69) in place of Compound (3), and bis(pinacolato)diboron in place of Compound (4), respectively.

[Preparation Method 30]

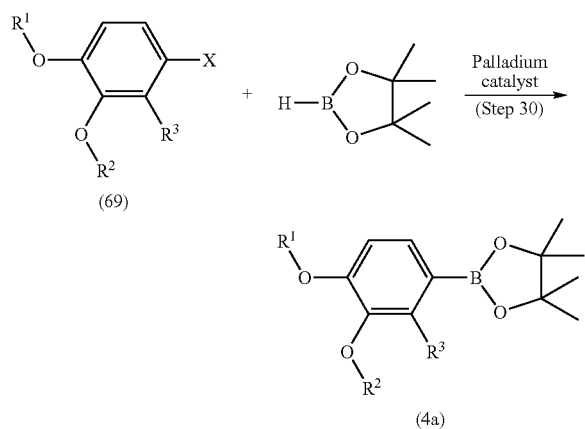

wherein $R^1$, $R^2$, $R^3$ and X have the same meanings as defined above.

Preparation method 30 is another method for preparing a boronic acid ester compound (4a) described in the above-mentioned "Preparation method 28".

Step 30 is a step for preparing a boronic acid ester compound (4a) by reacting Compound (69) with pinacol borane in an inert solvent in the presence of a palladium catalyst. This step is carried out in the same manner as in the above-mentioned "Step 1A" except for selecting 1,4-dioxane, 1,2-dimethoxyethane or toluene as an inert solvent, selecting 1,1'-bis(diphenylphosphino)ferrocene palladium chloride as a palladium catalyst and selecting triethylamine or N,N-diisopropylethylamine as a base, respectively, and using Compound (69) in place of Compound (3) and using pinacol borane in place of Compound (4).

[Preparation Method 31]

wherein $R^1$, $R^2$ and $R^3$ have the same meanings as defined above.

Preparation method 31 is a method for preparing Compound (4c) wherein Z in the above-mentioned boronic acid compound (4) is a dihydroxyboryl group and using a boronic acid ester compound (4a) as a starting compound.

Step 31A is a step for preparing a boronic acid amine complex compound (4b) by reacting Compound (4a) with diethanolamine in an inert solvent. Compound (4a) can be prepared by either method of the above-mentioned "Preparation method 28", "Preparation method 29" or "Preparation method 30".

As the inert solvent to be used, it is not specifically limited so long as it does not inhibit the reaction and dissolves the starting materials with a certain extent, and there may be mentioned, for example, an alcohol such as methanol, ethanol, propanol, isopropanol, butanol or tert-butanol, etc., and the like, preferably isopropanol.

An amount of diethanolamine to be used is generally 1 to 20-fold mol amount, preferably 3 to 10-fold mol amount based on 1 mol of Compound (4a).

A reaction temperature may vary depending on a kind, an amount to be used of starting materials, solvent(s), etc., and is generally in the range of −10° C. to 5° C., preferably 0° C. to 30° C.

A reaction time may vary depending on a reaction temperature, etc., and is generally for 30 minutes to 48 hours, preferably 1 hour to 24 hours.

Step 31B is a step for preparing a boronic acid compound (4c) by hydrolyzing Compound (4b) in an inert solvent under acidic conditions.

As the inert solvent to be used, it is not specifically limited so long as it does not inhibit the reaction and dissolves the starting materials with a certain extent, and there may be mentioned, for example, an ether such as tetrahydrofuran or 1,4-dioxane, etc.; an organic acid such as formic acid, acetic acid, propionic acid or trifluoroacetic acid, etc.; water; or a mixed solvent of an optional combination of the above, etc., preferably water.

As the acid to be used, there may be mentioned, for example, hydrochloric acid, hydrobromic acid, hydroiodic acid, sulfuric acid, phosphoric acid, p-toluenesulfonic acid, methanesulfonic acid or trifluoroacetic acid, etc., preferably hydrochloric acid. An amount of the acid to be used is generally 10 to 2000-fold mol amount, preferably 30 to 300-fold mol amount based on 1 mol of Compound (4b).

A reaction temperature may vary depending on a kind, an amount to be used of starting materials, solvent(s), etc., and is generally in the range of 0° C. to 100° C., preferably 15° C. to 50° C.

A reaction time may vary depending on a reaction temperature, etc., and is generally for 10 minutes to 48 hours, preferably 1 hour to 24 hours.

[Preparation Method 32]

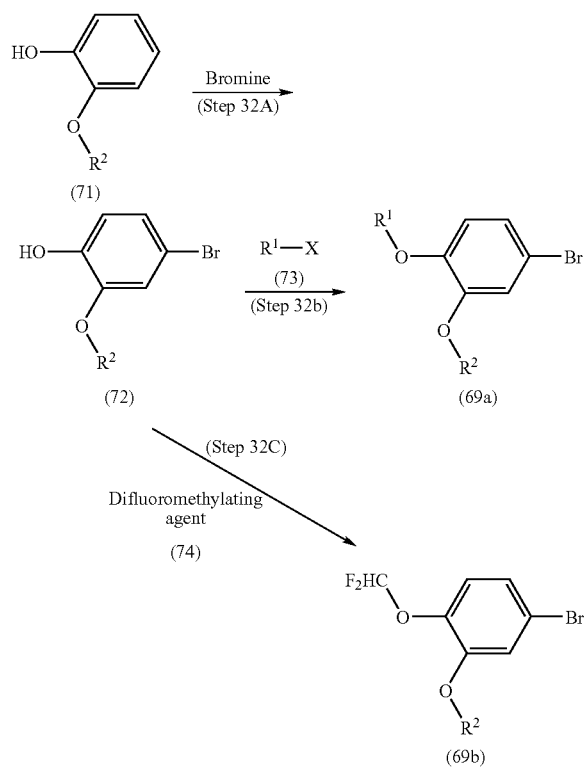

wherein $R^1$, $R^2$ and X have the same meanings as defined above.

Preparation method 32 is another method for preparing Compound (69a) wherein X in the above-mentioned compound (69) is a bromine atom, or Compound (69b) wherein X is a bromine atom, and $R^1$ is a difluoromethyl group, respectively.

Step 32A is a step for preparing Compound (72) by reacting Compound (71) with bromine in an inert solvent.

Compound (71) is conventionally known or can be prepared by the following mentioned "Preparation method 33".

As the inert solvent to be used, it is not specifically limited so long as it does not inhibit the reaction and dissolves the starting materials with a certain extent, and there may be mentioned, for example, an alcohol such as methanol, ethanol, propanol or isopropanol, etc.; a nitrile such as acetonitrile or propionitrile, etc.; an ether such as tetrahydrofuran, 1,2-dimethoxyethane or 1,4-dioxane, etc.; a halogenated aliphatic hydrocarbon such as dichloromethane, chloroform or 1,2-dichloroethane, etc.; or a mixed solvent of an optional combination of the above, etc., preferably dichloromethane or 1,4-dioxane.

An amount of bromine to be used is generally 1 to 1.5-fold mol amount, preferably 1 to 1.05-fold mol amount based on 1 mol of Compound (71).

A reaction temperature may vary depending on a kind, an amount to be used of starting materials, solvent(s), etc., and is generally in the range of −80° C. to 50° C., preferably −60° C. to 20° C.

A reaction time may vary depending on a reaction temperature, etc., and is generally for 10 minutes to 6 hours, preferably 30 minutes to 3 hours.

Step 32B is a step for preparing Compound (69a) by reacting Compound (72) with a halogen compound (73) in an inert solvent in the presence of a base.

As the inert solvent to be used, it is not specifically limited so long as it does not inhibit the reaction and dissolves the starting materials with a certain extent, and there may be mentioned, for example, a ketone such as acetone, methyl ethyl ketone or methyl isobutyl ketone, etc.; a nitrile such as acetonitrile or propionitrile, etc.; an amide such as N,N-dimethylformamide, N,N-dimethylacetamide or N-methylpyrrolidone, etc.; or a sulfoxide such as dimethylsulfoxide, etc., preferably acetone or N,N-dimethylformamide.

The halogen compound (73) is a known compound such as methyl iodide, etc., or a compound which can be prepared from a known compound according to a known method. An amount of the halogen compound (73) to be used is generally 1 to 5-fold mol amount, preferably 1 to 1.5-fold mol amount based on 1 mol of Compound (72).

As the base to be used, there may be mentioned, for example, an alkali metal carbonate such as sodium carbonate, potassium carbonate or cesium carbonate, etc.; an alkali metal alkoxide such as sodium methoxide, sodium ethoxide, sodium tert-butoxide or potassium tert-butoxide, etc.; or an alkali metal hydride such as sodium hydride, etc., preferably sodium carbonate or potassium carbonate. An amount of the base to be used is generally 1 to 5-fold mol amount, preferably 1 to 3-fold mol amount based on 1 mol of Compound (72).

A reaction temperature may vary depending on a kind, an amount to be used of starting materials, solvent(s), etc., and is generally in the range of 0° C. to 100° C., preferably 10° C. to 50° C.

A reaction time may vary depending on a reaction temperature, etc., and is generally for 10 minutes to 24 hours, preferably 1 hour to 12 hours.

Step 32C is a step for preparing Compound (69b) by reacting Compound (72) with a difluoromethylating agent (74) in an inert solvent in the presence of a base.

As the inert solvent to be used, it is not specifically limited so long as it does not inhibit the reaction and dissolves the starting materials with a certain extent, and there may be mentioned, for example, an alcohol such as methanol, ethanol, propanol or isopropanol, etc.; a nitrile such as acetonitrile or propionitrile, etc.; an amide such as N,N-dimethylformamide, N,N-dimethylacetamide or N-methylpyrrolidone, etc.; a sulfoxide such as dimethylsulfoxide, etc.; an ether such as tetrahydrofuran, 1,2-dimethoxyethane or 1,4-dioxane, etc.; a halogenated aliphatic hydrocarbon such as dichloromethane, chloroform or 1,2-dichloroethane, etc.; an aromatic hydrocarbon such as benzene or toluene, etc.; water; or a mixed solvent of an optional combination of the above, etc., preferably dichloromethane, 1,4-dioxane or toluene-water mixed solvent.

As the difluoromethylating agent (74) to be used, there may be mentioned, for example, chlorodifluoromethane, chlorodifluoroacetic acid, sodium chlorodifluoroacetate, methyl chlorodifluoroacetate or ethyl chlorodifluoroacetate, etc., preferably chlorodifluoromethane or sodium chlorodifluoroacetate. An amount of the difluoromethylating agent (74) to be used is generally 1 to 10-fold mol amount, preferably 1 to 3-fold mol amount based on 1 mol of Compound (72).

As the base to be used, there may be mentioned, for example, an alkali metal hydroxide such as lithium hydroxide, sodium hydroxide, potassium hydroxide, etc.; or an alkali metal carbonate such as sodium carbonate, potassium carbonate or cesium carbonate, etc., preferably sodium hydroxide or sodium carbonate. An amount of the base to be used is generally 1 to 10-fold mol amount, preferably 1 to 3-fold mol amount based on 1 mol of Compound (72).

Incidentally, when toluene-water mixed solvent is used as an inert solvent, a phase-transfer catalyst such as tetraethylammonium chloride or tetrabutylammonium bromide, etc. may be used.

An amount of the phase-transfer catalyst to be used is generally 0.05 to 10-fold mol amount, preferably 0.1 to 1-fold mol amount based on 1 mol of Compound (72).

A reaction temperature may vary depending on a kind, an amount to be used of starting materials, solvent(s), etc., and is generally in the range of 20° C. to 150° C., preferably 50° C. to 100° C.

A reaction time may vary depending on a reaction temperature, etc., and is generally for 10 minutes to 12 hours, preferably 1 hour to 6 hours.

[Preparation Method 33]

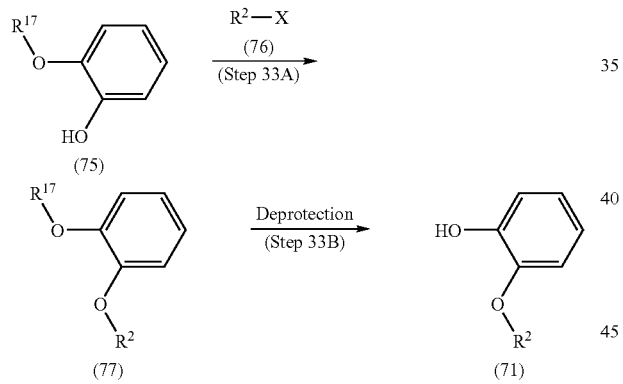

wherein $R^1$, $R^2$ and X have the same meanings as defined above, $R^{17}$ represents a methyl group, benzyl group, 4-methoxybenzyl group, cyclopropylmethyl group, MEM group, MOM group or BOM group.

Preparation method 33 is another method for preparing a starting compound (71) described in the above-mentioned "Preparation method 32".

Step 33A is a step for preparing Compound (77) by reacting Compound (75) with Compound (76). Compound (75) is a known compound such as 2-methoxyphenol or 2-benzyloxyphenol, etc., or a compound which can be prepared from a known compound according to a known method. Compound (76) is a known compound such as methyl iodide or cyclopropylmethyl bromide, etc., or a compound which can be prepared from a known compound according to a known method. This step is carried out in the same manner as in the above-mentioned "Step 32B" except for using Compound (75) in place of Compound (72), and using Compound (76) in place of Compound (73), respectively.

Step 33B is a step for preparing Compound (71) by removing $R^{17}$ which is a protective group of Compound (77). With regard to removal of the protective group, it can be carried out easily by referring to conventionally known literatures (W. Greene and P. G. H. Wuts "Protective Groups in Organic Synthesis" $3^{rd}$ Ed., John Wiley & Sons), etc. For example, when $R^{17}$ is a methyl group, it is carried out by a method using boron tribromide or sodium ethylthiolate; when $R^{17}$ is a 4-methoxybenzyl group, cyclopropylmethyl group, MEM group, MOM group or BOM group, by a method of applying acid treatment; or when $R^{17}$ is a benzyl group, 4-methoxybenzyl group or BOM group, by a method of hydrogenation decomposition using a palladium catalyst, respectively.

[Preparation Method 34]

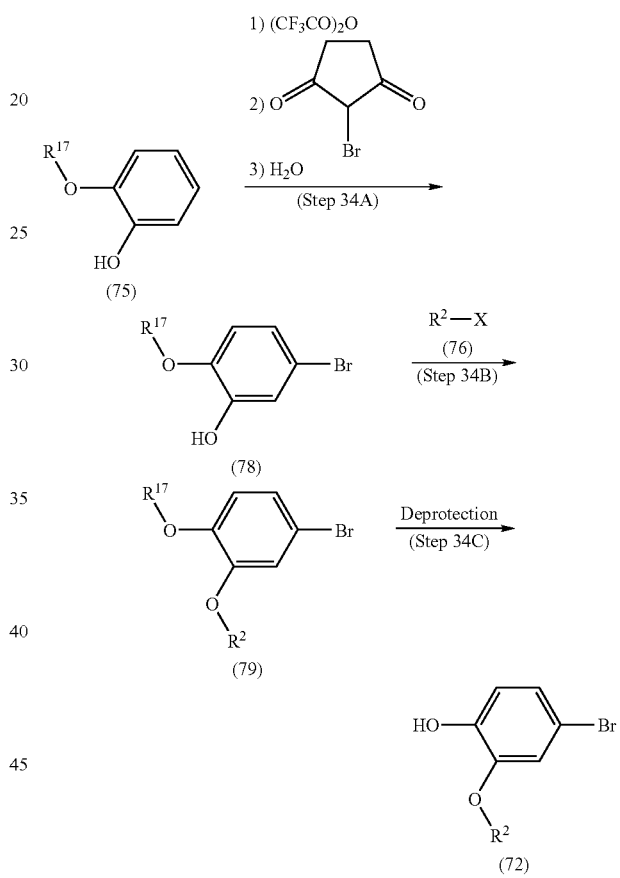

wherein $R^1$, $R^2$, $R^{17}$ and X have the same meanings as defined above.

Preparation method 34 is another method for preparing an intermediate compound (72) described in the above-mentioned "Preparation method 32".

Step 34A is a step for preparing Compound (78) by reacting Compound (75) with trifluoroacetic anhydride in an inert solvent in the presence of a base catalyst, then brominating the product using N-bromosuccineimide, and further treating the reaction mixture with water. This step is carried out according to the method described in WO 01/19785.

Step 34B is a step for preparing Compound (79) by reacting Compound (78) with Compound (76). This step is carried out in the same manner as in the above-mentioned "Step 32B" except for using Compound (78) in place of Compound (72), and using Compound (76) in place of Compound (73), respectively.

Step 34C is a step for preparing Compound (72) by removing $R^{17}$ which is a protective group of Compound (79). This step is carried out in the same manner as in the above-mentioned "Step 33B" except for using Compound (79) in place of Compound (77).

[Preparation Method 35]

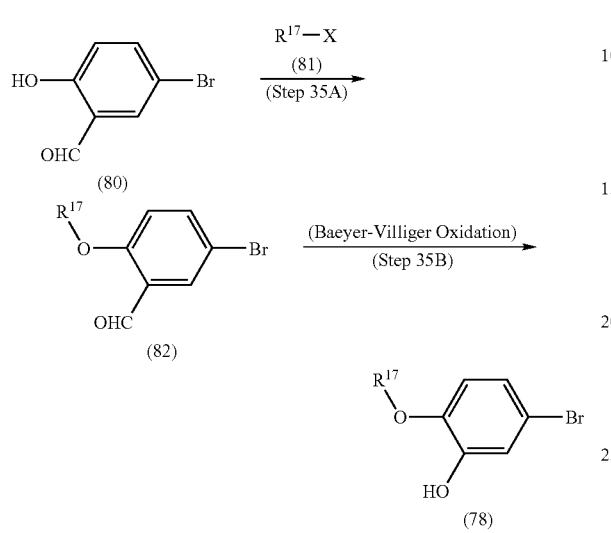

wherein $R^1$, $R^2$, $R^{17}$ and X have the same meanings as defined above.

Preparation method 35 is another method for preparing Compound (78) described in the above-mentioned "Preparation method 34" using the known compound (80) as a starting compound.

Step 35A is a step for preparing Compound (82) by reacting Compound (80) with Compound (81) in the presence of a base. As Compound (81), there may be mentioned, for example, known compounds such as methyl iodide, benzyl bromide, cyclopropylmethyl chloride, cyclopropylmethyl bromide, methoxymethyl chloride and methoxyethoxymethyl chloride, etc. This step is carried out in the same manner as in the above-mentioned "Step 32B" except for using Compound (80) in place of Compound (72), and using Compound (81) in place of Compound (73), respectively.

Step 35B is a step for preparing Compound (78) by applying Compound (82) to Baeyer-Villiger oxidation in an inert solvent.

As the inert solvent to be used, it is not specifically limited so long as it does not inhibit the reaction and dissolves the starting materials with a certain extent, and there may be mentioned, for example, a halogenated aliphatic hydrocarbon such as dichloromethane, chloroform or 1,2-dichloroethane, etc., and the like, preferably dichloromethane.

As the oxidizing agent to be used, there may be mentioned, for example, an oxidizing agent such as m-chloroperbenzoic acid and hydrogen peroxide, etc., preferably m-chloroperbenzoic acid. An amount of the oxidizing agent to be used is generally 1 to 10-fold mol amount, preferably 1 to 1.5-fold mol amount based on 1 mol of Compound (82).

A reaction temperature may vary depending on a kind, an amount to be used of starting materials, solvent(s), etc., and is generally in the range of 0° C. to 100° C., preferably 10° C. to 50° C.

A reaction time may vary depending on a reaction temperature, etc., and is generally for 1 day to 7 days, preferably 1 day to 3 days.

[Preparation Method 36]

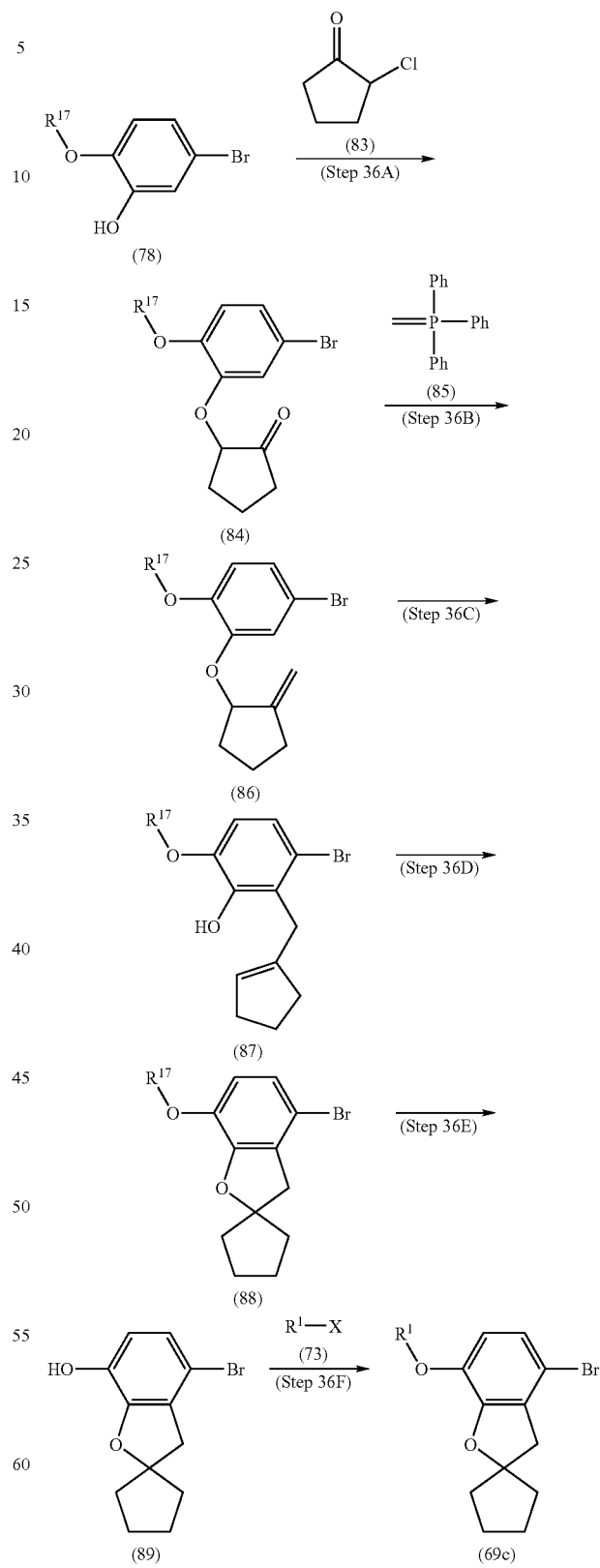

wherein $R^1$, $R^{17}$ and X have the same meanings as defined above.

Preparation method 36 is a method for preparing Compound (69c) wherein an oxygen-containing heterocyclic ring formed by ring fusion of $R^2$ and $R^3$ of the above-mentioned compound (69) is a 2,2-(1,4-butylene)-tetrahydrofuran ring by using Compound (78) as a starting compound.

Step 36A, Step 36B, Step 36C and Step 36D are carried out according to the method described in WO 96/03399. Compound (78) can be prepared, for example, by the above-mentioned "Preparation method 35".

Step 36E is a step for preparing a phenol compound (89) by removing $R^{17}$ which is a protective group of Compound (88). This step is carried out in the same manner as in the above-mentioned "Step 33B" except for using Compound (88) in place of Compound (77).

Step 36F is a step for preparing Compound (69c) by reacting Compound (89) with a halogen compound (73). This step is carried out in the same manner as in the above-mentioned "Step 32B" except for using Compound (89) in place of Compound (72).

[Preparation Method 37]

2-methyl-3-butyn-2-ol, 1-cyclopropyl-2-propyn-1-ol, 1-ethynylcyclopropanol, 1-ethynylcyclobutanol and 1-ethynylcyclopentanol, etc. This step is carried out in the same method as described in WO 97/43288.

Step 37B is a step for preparing Compound (921) by reacting Compound (90) with Compound (91'). As Compound (91'), there may be mentioned, for example, known compounds such as 4-trimethylsilyl-3-butyn-2-ol, 2-methyl-4-trimethylsilyl-3-butyn-2-ol, 1-cyclopropyl-3-trimethylsilyl-2-propyn-1-ol, 1-trimethylsilylethynylcyclopropanol, 1-trimethylsilylethynylcyclobutanol and 1-trimethylsilylethynylcyclopentanol, etc.

This step is carried out according to the method described in WO 97/43288 similarly as in the above-mentioned "Step 37A".

Step 37C is a step for preparing Compound (92) by removing a protective group at the end of the ethynyl group of Compound (92'). This step is carried out in the same manner as in the above-mentioned "Step 9A1" except for using Compound (92') in place of Compound (6h).

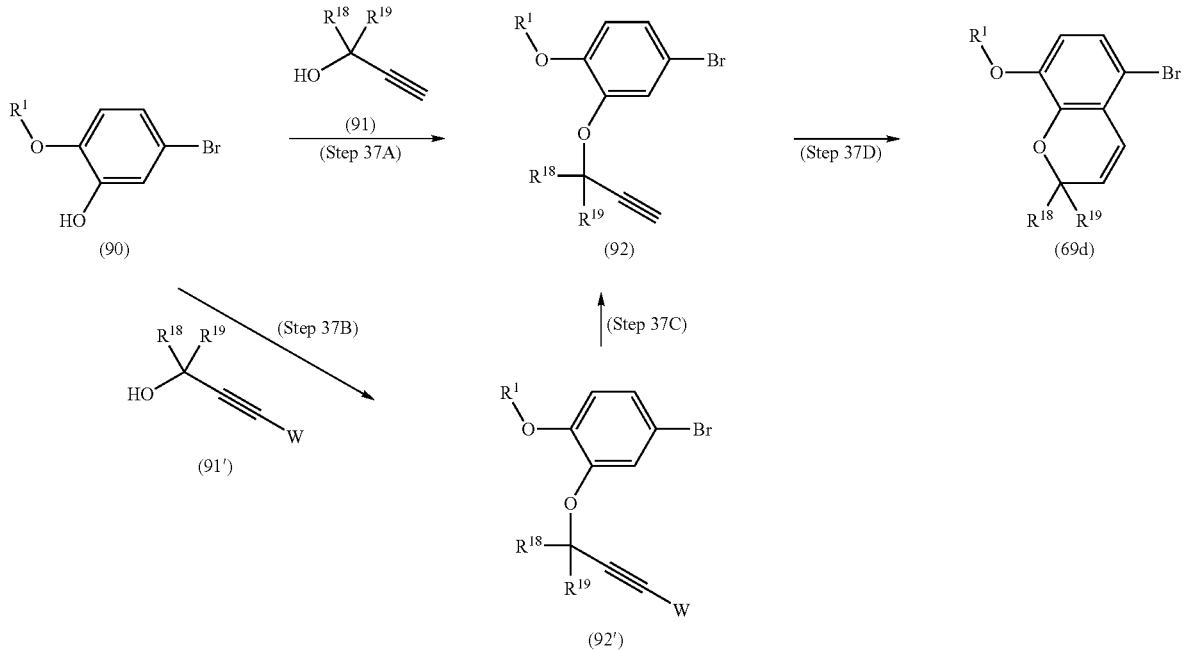

wherein $R^1$ and W have the same meanings as defined above, $R^{18}$ and $R^{19}$ each represents a hydrogen atom, methyl group or cyclopropyl group (provided that $R^{18}$ and $R^{19}$ do not represent hydrogen atoms or cyclopropyl groups simultaneously). Also, $R^{18}$ and $R^{19}$ may form a cyclic $C_2$-$C_4$ alkylene group in combination.

Preparation method 37 is a method for preparing Compound (69d) wherein an oxygen-containing heterocyclic ring formed by ring fusion of $R^2$ and $R^3$ of the above-mentioned compound (69) is a 3,6-dihydro-2H-pyran ring by using Compound (90) as a starting compound.

Step 37A is a step for preparing Compound (92) by reacting Compound (90) with Compound (91). Compound (90) can be prepared, for example, in the same manner as in the above-mentioned "Preparation method 35" except for using Compound (73) of the above-mentioned "Step 32B" in place of Compound (81). As Compound (91), there may be mentioned, for example, known compounds such as 3-butyn-2-ol, Step 37B is a step for preparing Compound (69d) by intramolecular cyclization of Compound (92). This step is carried out according to the method described in WO 97/43288 similarly as in the above-mentioned "Step 37A".

[Preparation Method 38]

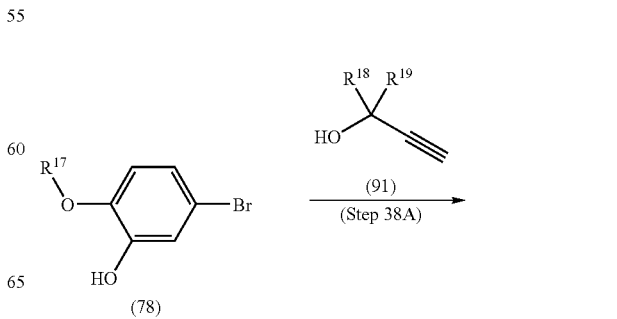

-continued

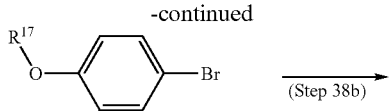
(93)

(Step 38b)

(94)

Deprotection
(Step 38C)

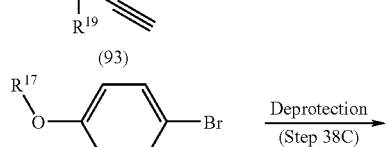
(94)

R¹—X
(73)
(Step 38D)

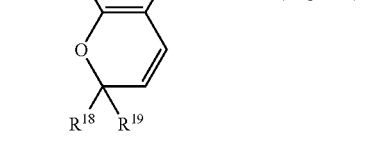
(69d)

wherein $R^1$, $R^{17}$, $R^{18}$ and $R^{19}$ have the same meanings as defined above.

Preparation method 38 is another method for preparing Compound (69d) wherein an oxygen-containing heterocyclic ring formed by ring fusion of $R^2$ and $R^3$ of the above-mentioned compound (69) is a 3,6-dihydro-2H-pyran ring by using Compound (78) as a starting compound.

Step 38A and Step 38B are carried out in the same method as described in WO 97/43288. Compound (78) can be prepared, for example, by the above-mentioned "Preparation method 35".

Step 38C is a step for preparing Compound (95) by removing $R^{17}$ which is a protective group of Compound (94). This step is carried out in the same manner as in the above-mentioned "Step 33B" except for using Compound (94) in place of Compound (77).

Step 38D is a step for preparing Compound (69d) by reacting Compound (95) with a halogen Compound (73). This step is carried out in the same manner as in the above-mentioned "Step 32B" except for using Compound (95) in place of Compound (72).

[Preparation Method 39]

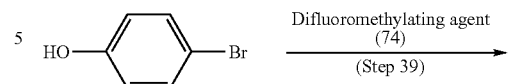

(95)

Difluoromethylating agent
(74)
(Step 39)

(69e)

wherein $R^{18}$ and $R^{19}$ have the same meanings as defined above.

Preparation method 39 is a method for preparing Compound (69e) wherein an oxygen-containing heterocyclic ring formed by ring fusion of $R^2$ and $R^3$ of the above-mentioned compound (69) is a 3,6-dihydro-2H-pyran ring and $R^1$ is a difluoromethyl group by using Compound (95) as a starting compound.

Step 39 is a step for preparing Compound (69e) by reacting Compound (95) with a difluoromethylating agent (74) in an inert solvent in the presence of a base.

Compound (95) can be prepared by the above-mentioned "Step 38C".

Step 39 is carried out in the same manner as in the above-mentioned "Step 32C" except for using Compound (95) in place of Compound (72).

[Preparation Method 40]

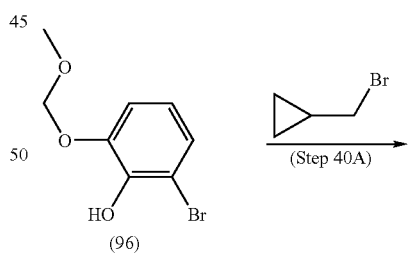
(96)

(Step 40A)

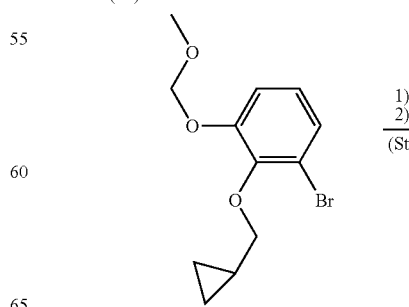
(97)

1) BuLi
2) Iodine
(Step 40B)

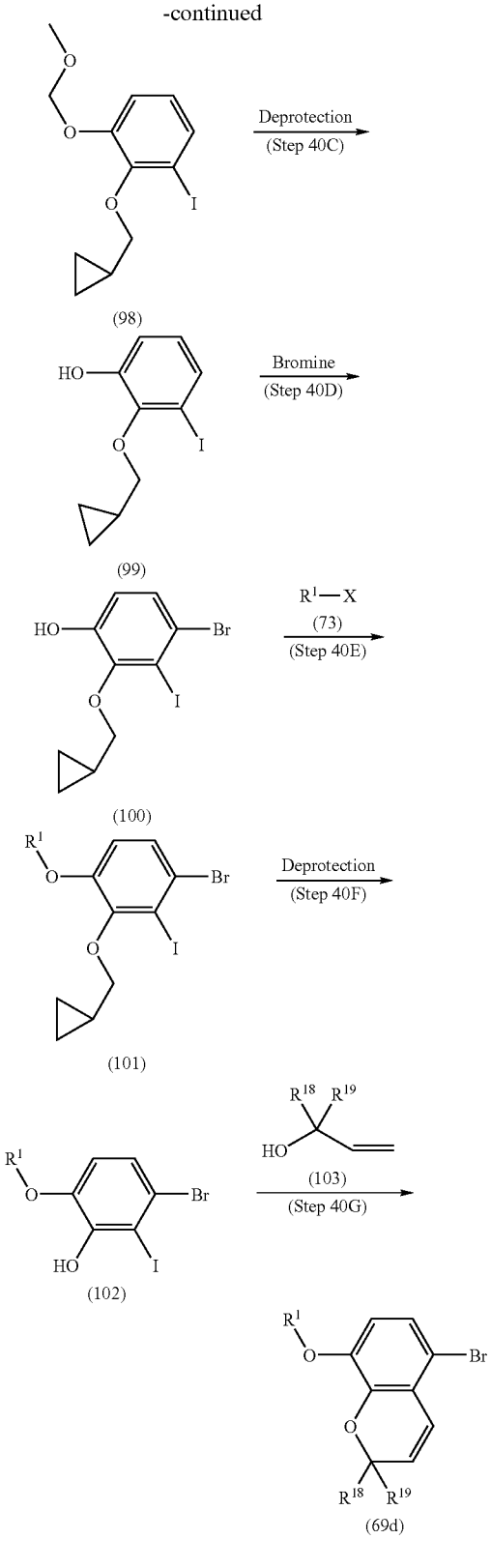

wherein $R^1$, $R^{18}$ and $R^{19}$ have the same meanings as defined above.

Preparation method 40 is a method for preparing Compound (69d) wherein an oxygen-containing heterocyclic ring formed by ring fusion of $R^2$ and $R^3$ of the above-mentioned compound (69) is a 3,6-dihydro-2H-pyran ring by using the known compound (96) as a starting compound.

Step 40A is a step for preparing Compound (97) by reacting the known compound (96) with cyclopropylmethyl bromide in an inert solvent in the presence of a base. This step is carried out in the same manner as in the above-mentioned "Step 32B" except for using Compound (96) in place of Compound (72), and using cyclopropylmethyl bromide in place of the halogen compound (73). In this case, it is particularly preferred that N,N-dimethylformamide is selected as an inert solvent, and potassium carbonate as a base, respectively, and amounts thereof are 1-fold mol amount based on 1 mol of Compound (96), a reaction temperature is 80° C., and a reaction time is 2 hours.

Step 40B is a step for preparing an iodized compound (98) after subjecting the bromine atom of Compound (97) to bromine atom-lithium metal exchange by using butyl lithium. This step is carried out in the same manner as in the above-mentioned "Preparation method 28" except for using Compound (97) in place of Compound (69), and using iodine in place of 2-isopropoxy-4,4,5,5-tetramethyl[1,3,2]dioxaborolane, respectively.

Step 40C is a step for preparing a phenol compound (99) by removing a MOM group which is a protective group of Compound (98). This step is carried out in the same manner as in the above-mentioned "Step 33B" except for using Compound (98) in place of Compound (77).

Step 40D is a step for preparing a brominated compound (100) by reacting Compound (99) with bromine. This step is carried out in the same manner as in the above-mentioned "Step 32A" except for using Compound (99) in place of Compound (71).

Step 40E is a step for preparing Compound (101) by reacting Compound (100) with a halogen compound (73). This step is carried out in the same manner as in the above-mentioned "Step 32B" except for using Compound (100) in place of Compound (72).

Step 40F is a step for preparing Compound (102) by removing a cyclopropylmethyl group which is a protective group of Compound (101). This step is carried out in the same manner as in the above-mentioned "Step 33B" except for using Compound (101) in place of Compound (77).

Step 40G is a step for preparing Compound (69d) by reacting Compound (102) with Compound (103) in the presence of a palladium catalyst. As Compound (103), there may be mentioned, for example, known compounds such as 3-buten-2-ol, 2-methyl-3-buten-2-ol, 1-cyclopropyl-2-propen-1-ol, 1-vinylcyclopropanol, 1-vinylcyclobutanol and 1-vinylcyclopentanol, etc. This step is carried out in the same method as described in WO 01/83476.

[Preparation Method 41]

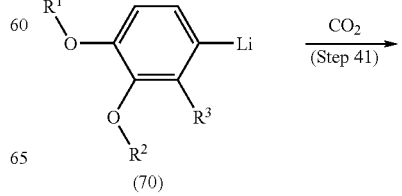

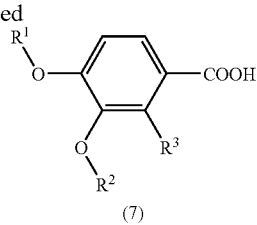

(7)

wherein $R^1$, $R^2$ and $R^3$ have the same meanings as defined above.

Preparation method 41 is a method for preparing Compound (7) in the above-mentioned "Preparation method 3".

Step 41 is a step for preparing Compound (7) to which a carboxy group is introduced by reacting a lithiated compound (70) with carbon dioxide. Compound (70) can be prepared by the above-mentioned "Step 28A". This step is carried out in the same manner as in the above-mentioned "Step 28B" except for using carbon dioxide in place of 2-isopropoxy-4,4,5,5-tetramethyl[1,3,2]dioxaborolane.

[Preparation Method 42]

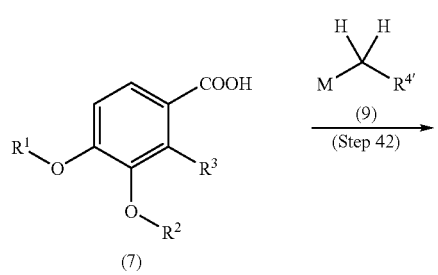
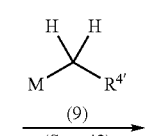

(9)
(Step 42)

(7)

(10)

wherein $R^1$, $R^2$, $R^3$, $R^{4'}$ and M have the same meanings as defined above.

Preparation method 42 is another method for preparing Compound (10) of the above-mentioned "Preparation method 3".

Step 42 is a step for preparing Compound (10) by reacting a benzoic acid compound (7) with an organometallic compound (9) in an inert solvent. Compound (7) can be prepared by, for example, the above-mentioned "Preparation method 41"; This step is carried out in the same manner as in the above-mentioned "Step 3B" except for using Compound (7) in place of Compound (8).

[Preparation Method 43]

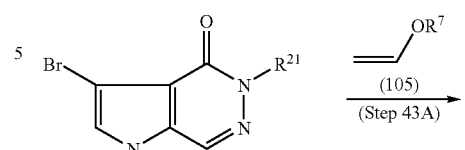

(105)
(Step 43A)

(104)

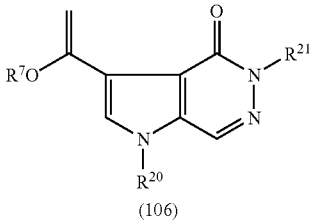

Acid hydrolysis
(Step 43B)

(106)

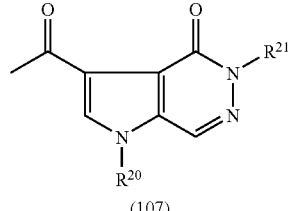

$R^{22}M$
(108)
(Step 43C)

(107)

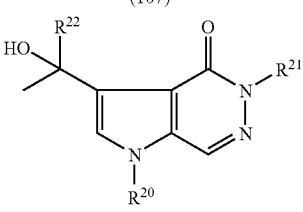

Reduction
(Step 43D)

(109)

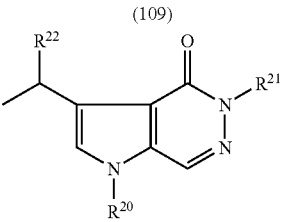

Halogenating agent
(21)
(Step 43E)

(110)

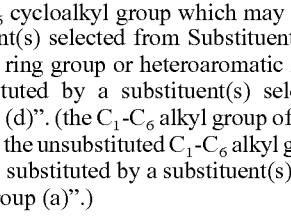

(111)

wherein $R^7$, X and M have the same meanings as defined above, $R^{20}$ represents a BOM group, 4-methoxybenzyl group or SEM group, $R^{21}$ represents a hydrogen atom, BOM group or SEM group, and $R^{22}$ represents a $C_1$-$C_6$ alkyl group, "a $C_3$-$C_6$ cycloalkyl group which may be substituted by a substituent(s) selected from Substituent group (b)" or "an aromatic ring group or heteroaromatic ring group each may be substituted by a substituent(s) selected from Substituent group (d)". (the $C_1$-$C_6$ alkyl group of $R^{22}$ has the same meaning as the unsubstituted $C_1$-$C_6$ alkyl group in the "$C_1$-$C_6$ alkyl group substituted by a substituent(s) selected from Substituent group (a)".)

Preparation method 43 is a method for preparing Compound (111) wherein $R^5$ and $R^6$ of the above-mentioned compound (3) are each a SEM group or BOM group, and $R^4$ is an ethyl group substituted by $R^{22}$, or $R^5$ of the above-mentioned compound (3a) is a SEM group or BOM group, and $R^4$ is an ethyl group substituted by $R^{22}$.

Step 43A is a step for preparing a vinyl ether compound (106) by reacting Compound (104) with Compound (105) in an inert gas atmosphere in an inert solvent and in the presence of a palladium catalyst and a base. Compound (104) is a compound wherein $R^5$ and $R^6$ of the above-mentioned compound (41a) are each a SEM group, 4-methoxybenzyl group or BOM group, and X is a bromine atom, or a compound wherein $R^5$ of the above-mentioned compound (41b) is a SEM group, 4-methoxybenzyl group or BOM group, and X is a bromine atom, and can be prepared by the above-mentioned "Step 14I" or "Step 14K". Compound (105) is a compound which is a known compound such as methylvinyl ether, ethylvinyl ether, propylvinyl ether, butylvinyl ether and tert-butylvinyl ether, etc., or can be prepared from a known compound according to the known method. This step is carried out in the same manner as in the above-mentioned "Step 11A1" except for using Compound (104) in place of Compound (6f) and using Compound (105) in place of Compound (24), respectively, using 1,3-bis(diphenylphosphino)propane in place of triphenylphosphine or tri(o-tolyl)phosphine as a phosphine derivative which is preferably co-present, using N,N-diisopropylethylamine as a preferred base, and using thallium acetate to control selectivity of the reaction. An amount of the thallium acetate to be used to control selectivity of the reaction is generally 0.5 to 3-fold mol amount, preferably 1 to 1.5-fold mol amount based on Compound (104).

Step 43B is a step for preparing Compound (107) having an acetyl group by hydrolyzing a vinyl ether compound (106) in an inert solvent in the presence of an acid catalyst.

As the inert solvent to be used, there may be mentioned, for example, an aliphatic hydrocarbon such as pentane, hexane or heptane, etc.; an aromatic hydrocarbon such as benzene or toluene, etc.; an ether such as tetrahydrofuran, 1,2-dimethoxyethane or 1,4-dioxane, etc.; an alcohol such as methanol, ethanol, propanol or isopropanol, etc.; an ester such as methyl acetate or ethyl acetate, etc.; an amide such as N,N-dimethylformamide, N,N-dimethylacetamide or N-methylpyrrolidone, etc.; a sulfoxide such as dimethylsulfoxide, etc.; a nitrile such as acetonitrile or propionitrile, etc.; water; or a mixed solvent of an optional combination of the above, etc., preferably a mixed solvent of hexane-ethyl acetate or methanol.

As the acid catalyst to be used, there may be mentioned a solid acid such as silica gel, etc.; an ion exchange resin such as Amberlite 15 (trade name), etc.; an inorganic acid such as hydrochloric acid, hydrobromic acid, sulfuric acid or phosphoric acid, etc.; an organic acid such as formic acid, acetic acid, propionic acid or trifluoroacetic acid, etc.; or a sulfonic acid such as methanesulfonic acid or p-toluenesulfonic acid, etc., preferably silica gel or hydrochloric acid. An amount of the acid catalyst to be used is generally 0.5 to 3-fold mol amount, preferably 1 to 1.5-fold mol amount based on 1 mol of Compound (106). Provided that in the case of the solid acid, it is generally 1 to 20 kg, preferably 5 to 15 kg based on 1 mol of Compound (106).

A reaction temperature may vary depending on a kind, an amount to be used of starting materials, solvent(s), etc., and is generally in the range of 0° C. to 200° C., preferably 10° C. to 50° C.

A reaction time may vary depending on a reaction temperature, etc., and is generally for 10 minutes to 72 hours, preferably 1 hour to 24 hours.

Step 43C is a step for preparing Compound (109) having a hydroxy group by reacting Compound (107) having an acetyl group with an organometallic compound (108) in an inert solvent. As the organometallic compound (108) to be used, there may be mentioned, for example, an organolithium reagent such as methyl lithium, butyl lithium or phenyl lithium, etc.; or an organomagnesium reagent (Grignard reagent) such as methyl magnesium chloride, methyl magnesium bromide, ethyl magnesium chloride, ethyl magnesium bromide, propyl magnesium chloride, propyl magnesium bromide, butyl magnesium chloride, butyl magnesium bromide, cyclopropyl magnesium chloride, cyclopropyl magnesium bromide, phenyl magnesium chloride or phenyl magnesium bromide, etc. Step 43C is carried out in the same manner as in the above-mentioned "Step 3B" except for using Compound (107) in place of Compound (8), and using an organometallic compound (108) in place of the organometallic compound (9), respectively.

Step 43D is a step for preparing Compound (110) by reducing Compound (109) having a hydroxy group using an organosilane compound or organotin compound in an inert solvent in the presence of an acid or a Lewis acid. Step 43D is carried out in the same manner as in the above-mentioned "Step 12C1" except for using Compound (109) in place of Compound (6q).

Step 43E is a step for preparing Compound (111) wherein the 2-position of the pyrrolopyridazinone ring is halogenated by reacting Compound (110) with a halogenating agent (21). This step is carried out in the same manner as in the above-mentioned "Step 6A" except for using Compound (110) in place of Compound (2e).

[Preparation Method 44]

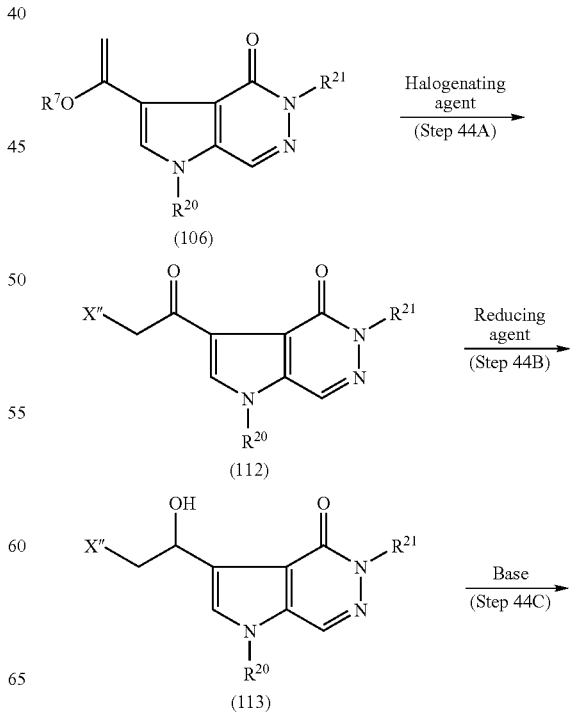

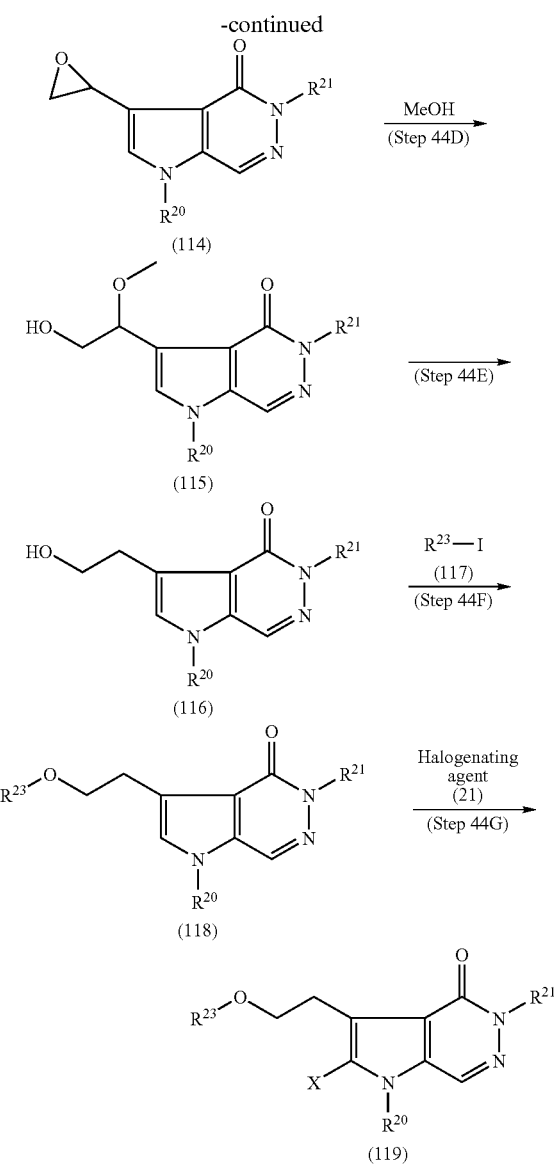

wherein $R^7$, $R^{20}$ and $R^{21}$ have the same meanings as defined above, $R^{23}$ represents a $C_1$-$C_4$ alkyl group having the same meaning as defined above or a ($C_3$-$C_6$ cycloalkyl)$C_1$-$C_2$ alkyl group having the same meaning as defined above, X represents a chlorine atom or bromine atom.

Preparation method 44 is a method for preparing Compound (119) wherein $R^4$ of the above-mentioned compound (3) is an ethyl group substituted by a group-$OR^{23}$.

Step 44A is a step for preparing a haloacetyl derivative (112) by reacting Compound (106) with a halogenating agent in an inert solvent.

Compound (106) can be prepared by the above-mentioned "Step 43A".

As the inert solvent to be used, it is not specifically limited so long as it does not inhibit the reaction and dissolves the starting materials with a certain extent, and there may be mentioned, for example, an aromatic hydrocarbon such as benzene or toluene, etc.; an ether such as diethyl ether, tetrahydrofuran, 1,2-dimethoxyethane or 1,4-dioxane, etc.; an alcohol such as methanol, ethanol, propanol or isopropanol, etc.; a nitrile such as acetonitrile or propionitrile, etc.; a halogenated aliphatic hydrocarbon such as dichloromethane, chloroform or 1,2-dichloroethane, etc.; water and a mixed solvent of the above with water, or a mixed solvent of an optional combination of the above, etc., preferably a mixed solvent of tetrahydrofuran-water.

As the halogenating agent to be used, there may be mentioned, for example, a chlorinating agent such as chlorine, sulfuryl chloride or N-chlorosuccineimide, etc.; a brominating agent such as bromine, benzyltrimethylammonium tribromide, trimethylphenylammonium tribromide, tetramethylammonium tribromide, tetraethylammonium tribromide, tetrabutylammonium tribromide, pyridinium hydrobromide perbromide or N-bromosuccineimide, etc., and the like, preferably N-chlorosuccineimide or N-bromosuccineimide. An amount of the halogenating agent to be used is generally 1 to 10-fold mol amount, preferably 1 to 3-fold mol amount based on 1 mol of Compound (106).

A reaction temperature may vary depending on a kind, an amount to be used of starting materials, solvent(s), etc., and is generally in the range of $-10°$ C. to $100°$ C., preferably $0°$ C. to $50°$ C.

A reaction time may vary depending on a reaction temperature, etc., and is generally for 10 minutes to 48 hours, preferably 1 hour to 24 hours.

Step 44B is a step for preparing a halohydrin compound (113) by treating a haloacetyl derivative (112) with a reducing agent in an inert solvent.

As the reducing agent to be used, there may be mentioned, for example, sodium borohydride, lithium borohydride, sodium cyanoborohydride, sodium trimethoxyborohydride and lithium aluminum hydride, etc., preferably sodium borohydride. An amount of the reducing agent to be used is generally 1 to 5-fold mol amount, preferably 1 to 2.5-fold mol amount based on 1 mol of Compound (112).

The solvent to be used may be mentioned, for example, an alcohol such as methanol, ethanol, propanol or butanol, etc.; an ether such as tetrahydrofuran, 1,4-dioxane or 1,2-dimethoxyethane, etc.; a nitrile such as acetonitrile or propionitrile, etc.; an amide such as N,N-dimethylformamide, N,N-dimethylacetamide or N-methylpyrrolidone, etc.; water or a mixed solvent of the above solvents, preferably tetrahydrofuran or a mixed solvent with tetrahydrofuran.

A reaction temperature may vary depending on a kind, an amount to be used of starting materials, solvent(s), etc., and is generally in the range of $-10°$ C. to $100°$ C., preferably $0°$ C. to $50°$ C.

A reaction time may vary depending on a reaction temperature, etc., and is generally for 10 minutes to 10 hours, preferably 30 minutes to 6 hours.

Step 44C is a step for preparing an epoxide derivative (114) by treating a halohydrin compound (113) with a base in an inert solvent.

As the inert solvent to be used, it is not specifically limited so long as it does not inhibit the reaction and dissolves the starting materials with a certain extent, and there may be mentioned, for example, an ether such as diethyl ether, tetrahydrofuran, 1,2-dimethoxyethane or 1,4-dioxane, etc.; an amide such as N,N-dimethylformamide, N,N-dimethylacetamide or N-methylpyrrolidone, etc.; or a mixed solvent of the above solvents, etc., preferably tetrahydrofuran.

As the base to be used, there may be mentioned an alkali metal such as lithium, sodium or potassium, etc.; an alkali metal hydride such as sodium hydride or potassium hydride, etc.; or an alkali metal alkoxide such as sodium methoxide, sodium ethoxide, sodium butoxide, sodium tert-butoxide or potassium tert-butoxide, etc., and the like, preferably potassium tert-butoxide. An amount of the base to be used is generally 1 to 5-fold mol amount, preferably 1 to 2-fold mol amount based on 1 mol of Compound (113).

A reaction temperature may vary depending on a kind, an amount to be used of starting materials, solvent(s), etc., and is generally in the range of −10° C. to 100° C., preferably 0° C. to 60° C.

A reaction time may vary depending on a reaction temperature, etc., and is generally for 10 minutes to 24 hours, preferably 1 hour to 12 hours.

Step 44D is a step for preparing Compound (115) by treating an epoxide derivative (114) with methanol.

A reaction temperature may vary depending on a kind, an amount to be used of starting materials, solvent(s), etc., and is generally in the range of −10° C. to 100° C., preferably 0° C. to 60° C.

A reaction time may vary depending on a reaction temperature, etc., and is generally for 10 minutes to 48 hours, preferably 1 hour to 24 hours.

Step 44E is a step for preparing Compound (116) by reducing Compound (115) under hydrogen atmosphere using a catalyst in an inert solvent.

As the inert solvent to be used, it is not specifically limited so long as it does not inhibit the reaction and dissolves the starting materials with a certain extent, and there may be mentioned, for example, an alcohol such as methanol, ethanol, propanol or isopropanol, etc.; an ether such as tetrahydrofuran, 1,4-dioxane or 1,2-dimethoxyethane, etc.; a halogenated aliphatic hydrocarbon such as dichloromethane, chloroform or 1,2-dichloroethane, etc.; an ester such as methyl formate, ethyl formate, methyl acetate or ethyl acetate, etc.; an organic acid such as formic acid, acetic acid, propionic acid or trifluoroacetic acid, etc.; an aromatic hydrocarbon such as benzene or toluene, etc.; water; or a mixed solvent of an optional combination of the above, etc., preferably acetic acid.

The catalyst to be used may be mentioned, for example, palladium-active carbon, platinum-active carbon, platinum black, rhodium-active carbon or Raney nickel, etc., preferably palladium-active carbon. An amount of the catalyst to be used is generally 0.0005 to 1-fold mol amount, preferably 0.01 to 0.1-fold mol amount based on 1 mol of Compound (115).

A hydrogen partial pressure in the reaction is generally 1 atm to 10 atm, preferably 1 atm to 5 atm.

A reaction temperature may vary depending on a kind, an amount to be used of starting materials, solvent(s), etc., and is generally in the range of 0° C. to 100° C., preferably 15° C. to 80° C.

A reaction time may vary depending on a reaction temperature, etc., and is generally for 15 minutes to 24 hours, preferably 30 minutes to 12 hours.

Step 44F is a step for preparing an alkoxyethyl derivative (118) by reacting Compound (116) with an alkylating agent (117) in an organic solvent in the presence of a base.

As the inert solvent to be used, it is not specifically limited so long as it does not inhibit the reaction and dissolves the starting materials with a certain extent, and there may be mentioned, for example, an aprotic polar solvent such as N,N-dimethylformamide, N-methylpyrrolidone, dimethylsulfoxide, N,N-dimethylacetamide or hexamethylphosphoric triamide, etc.; a halogenated hydrocarbon such as dichloromethane, chloroform or 1,2-dichloroethane, etc.; a ketone such as acetone, methyl ethyl ketone or methyl isobutyl ketone, etc.; a nitrile such as acetonitrile or propionitrile, etc.; an ester such as methyl formate, ethyl formate, methyl acetate or ethyl acetate, etc.; an ether such as diethyl ether, diisopropyl ether, tetrahydrofuran or 1,4-dioxane, etc.; or a mixed solvent of the above solvents, preferably an aprotic polar solvent, an ether or a mixed solvent thereof.

As the base to be used, there may be mentioned, for example, an alkali metal hydroxide such as sodium hydroxide or lithium hydroxide, etc.; an alkali metal hydride such as sodium hydride, etc.; an alkali metal amide such as sodium amide, etc.; an amine such as triethylamine, tributylamine, N,N-diisopropylethylamine, pyridine, picoline, lutidine or 4-dimethylaminopyridine, etc.; an alkali metal carbonate such as sodium carbonate, potassium carbonate or sodium hydrogencarbonate, etc.; or an alkali metal alkoxide such as sodium methoxide, sodium ethoxide, sodium butoxide, sodium tert-butoxide or potassium tert-butoxide, etc., and the like, preferably sodium tert-butoxide or potassium tert-butoxide. An amount of the base to be used is generally 1 to 10-fold mol amount, preferably 1 to 3-fold mol amount based on 1 mol of Compound (116).

Compound (117) is a compound which is conventionally known, or can be prepared from a conventionally known compound by a conventionally known method. An amount of Compound (117) to be used is generally 1 to 10-fold mol amount, preferably 1 to 5-fold mol amount based on 1 mol of Compound (116).

A reaction temperature may vary depending on a kind, an amount to be used of starting materials, solvent(s), etc., and is generally in the range of −50° C. to 150° C., preferably −10° C. to 100° C.

A reaction time may vary depending on a reaction temperature, etc., and is generally for 5 minutes to 10 hours, preferably 30 minutes to 5 hours.

Step 44G is a step for preparing a halogen compound (119) by reacting Compound (118) with a halogenating agent (21). This step is carried out in the same manner as in the above-mentioned "Step 6A" except for using Compound (118) in place of Compound (2e).

[Preparation Method 45]

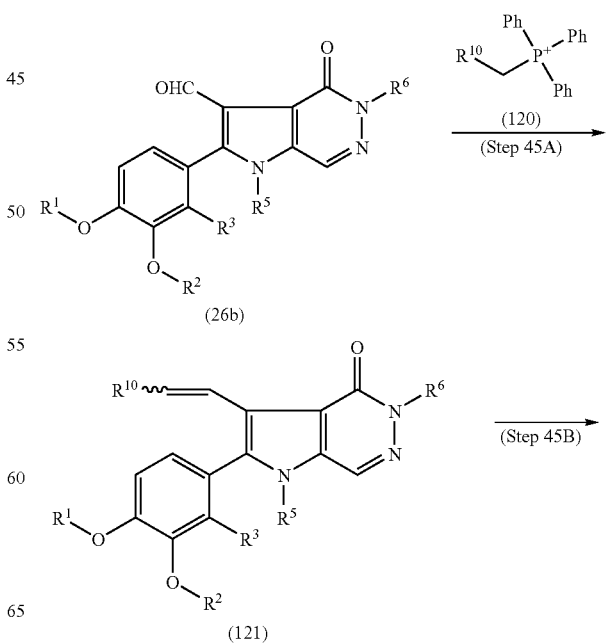

-continued

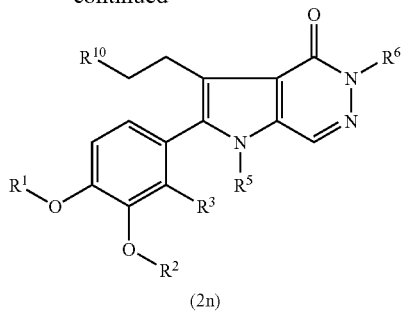

(2n)

wherein $R^1$, $R^2$, $R^3$, $R^5$, $R^6$, $R^{10}$ and X have the same meanings as defined above.

Preparation method 45 is a method for preparing Compound (2n) wherein $R^4$ of the above-mentioned compound (3) is an ethyl group substituted by $R^{10}$.

Step 45A is a step for preparing an olefin compound (121) by reacting Compound (26b) with Compound (120) in an inert solvent in the presence of a base. This step is a reaction which has been known as the so-called Wittig Reaction, and can be carried out by optionally selecting known conditions.

Compound (26b) can be prepared by the above-mentioned "Step 12A2".

As the inert solvent to be used, it is not specifically limited so long as it does not inhibit the reaction and dissolves the starting materials with a certain extent, and there may be mentioned, for example, a halogenated hydrocarbon such as dichloromethane, chloroform, 1,2-dichloroethane, etc.; an ether such as diethyl ether, tetrahydrofuran, 1,4-dioxane, 1,2-dimethoxyethane, etc.; an aromatic hydrocarbon such as benzene, toluene, xylene, etc.; an ester such as methyl acetate, ethyl acetate, etc.; a nitrile such as acetonitrile or propionitrile, etc.; an amide such as N,N-dimethylformamide, N,N-dimethylacetamide, N-methylpyrrolidone, etc.; dimethylsulfoxide; or a mixed solvent of the above.

The base to be used may be mentioned, for example, an alkali metal hydroxide such as lithium hydroxide, sodium hydroxide, potassium hydroxide, etc.; an alkali metal carbonate such as sodium carbonate, potassium carbonate, etc.; an alkali metal alkoxide such as sodium methoxide, sodium ethoxide, sodium tert-butoxide, potassium tert-butoxide, etc.; an alkali metal hydride such as sodium hydride, potassium hydride, etc.; an alkyl lithium such as methyl lithium, butyl lithium, etc.; a metal amide such as sodium amide, lithium diisopropyl amide, etc.; or an organic amine such as triethylamine, N,N-diisopropylethylamine, tripropylamine, 1,5-diazabicyclo[4.3.0]-5-nonene, etc. An amount of the base to be used is generally 1 to 5-fold mol amount, preferably 1 to 2-fold mol amount based on 1 mol of Compound (26b).

Compound (120) is a compound which is conventionally known, or can be prepared from a conventionally known compound by a conventionally known method. An amount of Compound (120) to be used is generally 1 to 10-fold mol amount, preferably 1 to 1.5-fold mol amount based on 1 mol of Compound (26b).

A reaction temperature may vary depending on a kind, an amount to be used of starting materials, solvent(s), etc., and is generally in the range of 0° C. to 150° C., preferably 15 to 80° C.

A reaction time may vary depending on a reaction temperature, etc., and is generally for 1 hour to 24 hours, preferably 1 hour to 6 hours.

Step 45B is a step for preparing Compound (2n) wherein $R^4$ of Compound (2) is an ethyl group substituted by $R^{10}$ group by subjecting Compound (121) to hydrogenation reduction in the presence of a catalyst. Step 45B is carried out in the same manner as in the above-mentioned "Step 9C1" except for using Compound (121) in place of Compound (6k).

[Preparation Method 46]

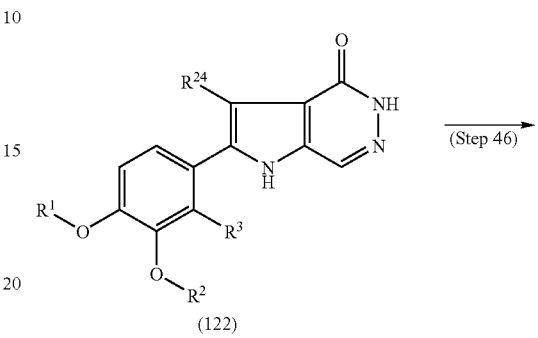

(122)

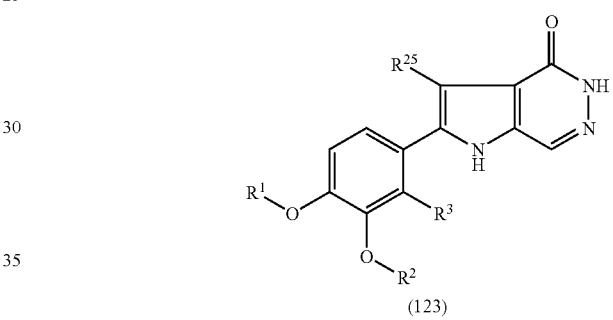

(123)

wherein $R^1$, $R^2$ and $R^3$ have the same meanings as defined above, $R^{24}$ represents a $C_2$-$C_6$ alkynyl group having the same meaning as defined above, and $R^{25}$ represents a $C_2$-$C_6$ alkenyl group having the same meaning as defined above.

Preparation method 46 is a step for preparing Compound (123) wherein $R^4$ of the above-mentioned compound (1) is a $C_2$-$C_6$ alkenyl group by subjecting Compound (122) wherein $R^4$ is a $C_2$-$C_6$ alkynyl group to hydrogenation reduction in the presence of a catalyst. This step is carried out in the same manner as in the above-mentioned "Step 9B1" except for using Compound (122) in place of Compound (6j).

[Preparation Method 47]

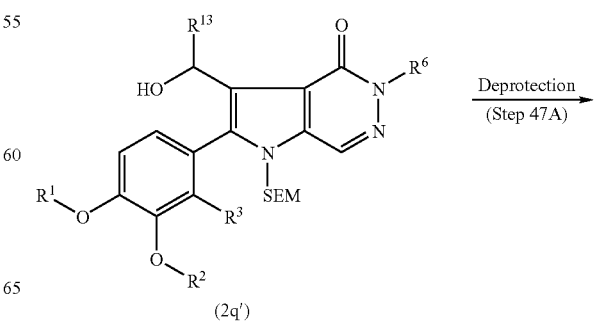

(2q')

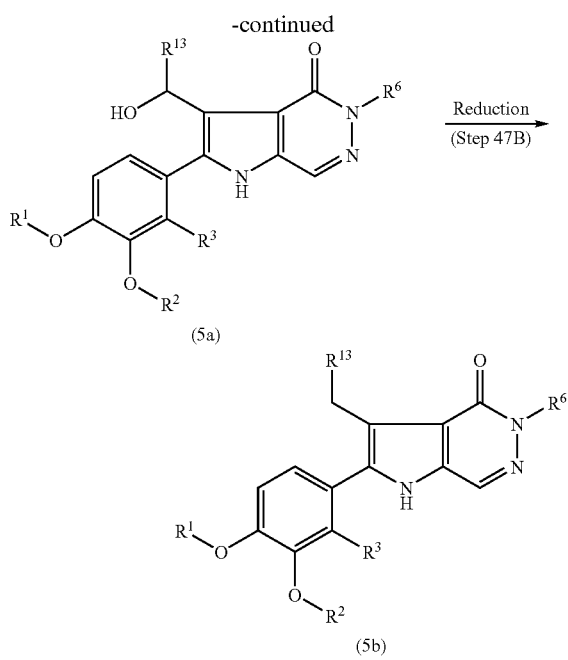

wherein $R^1$, $R^2$, $R^3$, $R^6$ and $R^{13}$ have the same meanings as defined above.

Preparation method 47 is a method for preparing Compound (5a) wherein $R^4$ of Compound (5) described in the above-mentioned "Preparation method 1" is a group —CH(OH)$R^{13}$, and Compound (5b) wherein $R^4$ of the same is a group —CH$_2$R$^{13}$.

Step 47A is a step for removing the SEM group as a protective group. Compound (2q') is a compound wherein $R^4$ of Compound (2) is a group —CH(OH)$R^{13}$ and $R^5$ of the same is a SEM group, and can be prepared, for example, by the above-mentioned "Step 12B". This step is carried out in the same manner as in the above-mentioned (Treatment 1) of "Step 1B11" except for using Compound (2q') in place of Compound (2').

Step 47B is a step for preparing Compound (5b) by reducing Compound (5a) having a hydroxy group using an organosilane compound or organotin compound in an inert solvent in the presence of an acid or a Lewis acid. This step is carried out in the same manner as in the above-mentioned "Step 12C1" except for using Compound (5a) in place of Compound (6q).

After completion of the above-mentioned respective reactions, the desired compound may be isolated from the reaction mixture according to the conventional manner. For example, it can be obtained by neutralizing the reaction mixture as needed, removing insoluble materials by filtration, if any one present, adding organic solvents which are not miscible with water such as ethyl acetate, washing with water, separating the organic layer containing the desired compound, drying it over anhydrous magnesium sulfate, etc., and then distillating off the solvent.

The obtained desired compound can be separated and purified, if necessary, by a conventional manner, for example, recrystallization; reprecipitation; or a method conventionally used for separation and purification of an organic compound in an optional combination by eluting with an appropriate eluent (for example, an adsorption column chromatography method using a carrier such as silica gel, alumina, etc.; ion exchange chromatography method; or a normal phase-reverse phase column chromatography method using silica gel or alkylated silica gel (suitably it is high performance liquid chromatography.)).

Compound (1) of the present invention can be converted into a pharmaceutically acceptable addition salt according to the conventional manner, if necessary, and it can be directly separated as an addition salt from the reaction mixture.

As the pharmaceutically acceptable addition salt, when Compound (1) of the present invention has a substituted amino group, there may be mentioned, for example, an inorganic acid addition salt such as hydrochloride, hydrobromide, hydroiodide, nitrate, sulfate or phosphate, etc.; or an organic acid addition salt such as acetate, benzoate, oxalate, malonate, succinate, maleate, fumarate, tartarate, citrate, methanesulfonate, ethanesulfonate, trifluoromethanesulfonate, benzenesulfonate, p-toluenesulfonate, glutamate or aspartate, etc. Also, when Compound (1) of the present invention has a carboxy group, there may be mentioned, for example, a metal salt such as a sodium salt, potassium salt, calcium salt or magnesium salt, etc.: or a salt with an organic base such as an ammonium salt, triethylamine salt or guanidine salt, etc., and the like.

When Compound (1) of the present invention or an addition salt thereof is used as a medicine, it can be administered as such (as a resulting powder as such), or as a preparation such as a tablet, capsule, granule, powder or syrup, etc., which are prepared by mixing with an optional pharmaceutically acceptable excipient, diluent, etc., orally, or non-orally (preferably orally) as a preparation such as an injection or suppository, etc., prepared in the same manner.

These preparations are prepared by the conventionally known method by using an additive such as an excipient, a lubricant, a binder, a disintegrator, an emulsifier, a stabilizer, a corrigent or a diluent, etc.

The excipient may be mentioned, for example, an organic excipient or an inorganic excipient. The organic excipient may be mentioned, for example, a sugar derivative such as lactose, sucrose, glucose, mannitol or sorbitol, etc.; a starch derivative such as corn starch, potato starch, α-starch or dextrin, etc.; a cellulose derivative such as crystalline cellulose, etc.; Gum Arabic; dextran; or pullulan, etc. The inorganic excipient may be mentioned, for example, light silicic acid anhydride; or a sulfate such as calcium sulfate, etc., and the like.

The lubricant may be mentioned, for example, stearic acid; a stearic acid metal salt such as calcium stearate or magnesium stearate, etc.; talc; colloidal silica; a wax such as beeds wax or spermaceti, etc.; boric acid; adipic acid; a sulfate such as sodium sulfate, etc.; glycol; fumaric acid; sodium benzoate; D,L-leucine; sodium lauryl sulfate; a silicic acid such as silicic anhydride or silicic acid hydrate, etc.; or the starch derivative in the above-mentioned excipient, etc.

The binder may be mentioned, for example, hydroxypropyl cellulose, hydroxypropylmethyl cellulose, polyvinylpyrrolidone, Macrogol or compounds shown in the above-mentioned excipient, etc.

The disintegrator may be mentioned, for example, a cellulose derivative such as low-substitution degree hydroxypropyl cellulose, carboxymethyl cellulose, calcium carboxymethyl cellulose or internally cross-linked calcium carboxymethyl cellulose, etc.; cross-linked polyvinylpyrrolidone; or chemically-modified starch or cellulose derivatives such as carboxymethyl starch or sodium carboxymethyl starch, etc.

The emulsifier may be mentioned, for example, a colloidal clay such as bentonite or bee gum, etc.; an anionic surfactant such as sodium lauryl sulfate, etc.; a cationic surfactant such as benzalkonium hydrochloride, etc.; or a nonionic surfactant such as polyoxyethylene alkyl ether, polyoxyethylene sorbitan aliphatic acid ester or sucrose aliphatic acid ester, etc., and the like.

The stabilizer may be mentioned, for example, a parahydroxybenzoic acid ester such as methylparaben or propylparaben, etc.; an alcohol such as chlorobutanol, benzylalcohol or phenylethylalcohol, etc.; benzalkonium hydrochloride; a phenol such as phenol or cresol, etc.; thimerosal; acetic anhydride; or sorbic acid.

The corrigent may be mentioned, for example, a sweetening agent such as sodium saccharin or Aspartame, etc.; a souring agent such as citric acid, malic acid or tartaric acid, etc.; or a flavoring agent such as menthol, lemon extract or orange extract, etc., and the like.

The diluent is a compound which is usually used as a diluent, and there may be mentioned, for example, lactose, mannitol, glucose, sucrose, calcium sulfate, hydroxypropyl cellulose, microcrystalline cellulose, water, ethanol, polyethylene glycol, propylene glycol, glycerol, starch, polyvinylpyrrolidone or a mixture thereof, etc.

A dose of the desired Compound (1) or an addition salt thereof of the present invention may vary depending on symptom, an age, a body weight, etc., of a patient, and in the case of an oral administration, each can be administered in a lower limit of 0.005 mg/Kg (preferably 0.02 mg/Kg) and an upper limit of 20 mg/Kg (preferably 10 mg/Kg) per one time, and in the case of a non-oral administration, each can be administered in a lower limit of 0.0005 mg/Kg (preferably 0.002 mg/Kg) and an upper limit of 20 mg/Kg (preferably 10 mg/Kg), with 1 to 6 times per day per an adult depending on symptom.

EXAMPLES

In the following, the present invention is explained in more detail by referring to Examples, Reference examples and Test examples, but the scope of the present invention is not limited by these.

Example 1

2-(3-Cyclopropoxy-4-difluoromethoxyphenyl)-1,5-dihydropyrrolo[2,3-d]pyridazin-4-one (Exemplary compound No. 1-1)

1-(a) 2-(3-Cyclopropoxy-4-difluoromethoxyphenyl)-1-(2-trimethylsilylethoxymethyl)-1,5-dihydropyrrolo[2,3-d]-pyridazin-4-one To a mixture of 1.01 g (2.93 mmol) of 2-bromo-1-(2-trimethylsilylethoxymethyl)-1,5-dihydropyrrolo[2,3-d]-pyridazin-4-one obtained in the following Reference example 15-(g) and 1.15 g (3.53 mmol) of 2-(3-cyclopropoxy-4-difluoromethoxyphenyl)-4,4,5,5-tetramethyl-[1,3,2]dioxaborolane obtained in the following Reference example 1-(a) were added 36 ml of toluene, 24 ml of ethanol and 6 ml of 2M aqueous sodium carbonate solution, and the mixture was degassed under reduced pressure and replaced with argon. Then, 702 mg (0.607 mmol) of tetrakis(triphenylphosphine) palladium was added to the mixture, and the mixture was refluxed for 26 hours. After completion of the reaction, water was added to the reaction mixture, and the mixture was extracted with ethyl acetate. The organic layer after separation was washed successively with water, and then with a saturated aqueous solution of sodium chloride, dried over anhydrous magnesium sulfate and then concentrated under reduced pressure. The obtained residue was applied to silica gel column chromatography (Eluent; hexane:ethyl acetate=1:1→1:4 (V/V)), and the fractions containing the desired compound were concentrated under reduced pressure to obtain 750 mg of the title compound as a yellowish solid. (Yield: 55%)

Mass Spectrum (CI, m/z): 464 ($M^+$+1).

$^1$H-NMR Spectrum (CDCl$_3$, δ ppm): −0.03 (s, 9H), 0.82-0.95 (m, 6H), 3.54-3.56 (m, 2H), 3.77-3.85 (m, 1H), 5.46 (s, 2H), 6.58 (t, J=74.7 Hz, 1H), 6.97 (d, J=0.7 Hz, 1H), 7.16 (dd, J=8.3, 2.0 Hz, 1H), 7.26 (d, J=8.3 Hz, 1H), 7.55 (d, J=2.0 Hz, 1H), 8.24 (d, J=0.7 Hz, 1H), 10.14 (brs, 1H)

IR Spectrum (KBr, cm$^{-1}$): 1661.

1-(b) 2-(3-Cyclopropoxy-4-difluoromethoxyphenyl)-1,5-dihydropyrrolo[2,3-d]pyridazin-4-one To 750 mg (1.62 mmol) of 2-(3-cyclopropoxy-4-difluoromethoxyphenyl)-1-(2-trimethylsilylethoxymethyl)-1,5-dihydropyrrolo[2,3-d]pyridazin-4-one obtained in Example 1-(a) were added 2.5 ml of tetrahydrofuran, 0.22 ml of ethylenediamine and 16.5 ml of tetrahydrofuran solution containing 1M tetrabutylammonium fluoride, and the mixture was refluxed for 48 hours. After completion of the reaction, water and hexane were added to the reaction mixture, precipitated solid was collected by filtration, and dried under reduced pressure. The obtained dried material was dissolved in ethanol, poured into water, and precipitated solid was collected by filtration. The obtained solid was washed with water, and dried under reduced pressure to obtain 459 mg of the title compound as a white solid. (Yield: 85%)

Melting point: 287-292° C.

Mass Spectrum (CI, m/z): 334($M^+$+1).

$^1$H-NMR Spectrum (DMSO-d$_6$, δ ppm): 0.72-0.79 (m, 2H), 0.85-0.94 (m, 2H), 4.03-4.11 (m, 1H), 7.07 (t, J=74.3 Hz, 1H), 7.19 (s, 1H), 7.27 (d, J=8.4 Hz, 1H), 7.49 (dd, J=8.4, 2.1 Hz, 1H), 7.88 (d, J=2.1 Hz, 1H), 8.17 (s, 1H), 12.28 (brs, 1H), 12.54 (brs, 1H).

IR Spectrum (KBr, cm$^{-1}$): 1648.

Example 2

3-Chloro-2-(3-cyclopropoxy-4-difluoromethoxyphenyl)-1,5-dihydropyrrolo[2,3-d]pyridazin-4-one (Exemplary compound No. 1-2)

2-(a) 3-Chloro-2-(3-cyclopropoxy-4-difluoromethoxyphenyl)-1-(2-trimethylsilylethoxymethyl)-1,5-dihydropyrrolo[2,3-d]-pyridazin-4-one Reaction and post treatment were carried out in the same manner as in Example 1-(a) except for using 0.25 g (0.66 mol) of 2-bromo-3-chloro-1-(2-trimethylsilylethoxymethyl)-1,5-dihydropyrrolo[2,3-d]pyridazin-4-one obtained in the following Reference example 16-(d) in place of 2-bromo-1-(2-trimethylsilylethoxymethyl)-1,5-dihydropyrrolo-[2,3-d] pyridazin-4-one, whereby 315 mg of the title compound was obtained as a pale yellowish foam. (Yield: 96%)

Mass Spectrum (CI, m/z): 498 ($M^+$+1)

$^1$H-NMR Spectrum (CDCl$_3$, δ ppm): −0.03 (s, 9H), 0.82-0.90 (m, 6H), 3.44-3.52 (m, 2H), 3.77-3.84 (m, 1H), 5.38 (s, 2H), 6.61 (t, J=74.6 Hz, 1H), 7.10 (dd, J=8.3, 2.1 Hz, 1H), 7.30 (d, J=8.3 Hz, 1H), 7.52 (d, J=2.1 Hz, 1H), 8.21 (s, 1H) 10.02 (brs, 1H).

2-(b) 3-Chloro-2-(3-cyclopropoxy-4-difluoromethoxyphenyl)-1,5-dihydropyrrolo[2,3-d]pyridazin-4-one To 311 mg (0.624 mmol) of 3-chloro-2-(3-cyclopropoxy-4-difluoromethoxyphenyl)-1-(2-trimethylsilylethoxymethyl)-1,5-dihydropyrrolo[2,3-d]pyridazin-4-one obtained in Example 2-(a) was added 15 ml of 1,4-dioxane solution containing 4N hydrogen chloride, and the mixture was stirred at 40° C. for 28 hours. After completion of the reaction, the reaction suspension was cooled by allowing to stand, and precipitated solid was collected by filtration and washed with diisopropyl ether. To the obtained solid were added 22 ml of methanol and 1.5 ml of 28% aqueous ammonia, and the mixture was stirred under room temperature for 3 hours. Then, the solution was concentrated under reduced pressure, diisopropyl ether and hexane were added to the obtained solid, a treatment with ultrasonic wave was carried out, and precipitated solid was collected by filtration. The obtained solid was washed with diisopropyl ether and dried under reduced pressure to obtain 177 mg of the title compound as a white solid. (Yield: 77%)

Melting point: 281-283° C.

Mass Spectrum (CI, m/z): 368 ($M^+$+1).

$^1$H-NMR Spectrum (DMSO-$d_6$, δ ppm): 0.74-0.91 (m, 4H), 3.96-4.03 (m, 1H), 7.12 (t, J=74.2 Hz, 1H), 7.35 (d, J=8.4 Hz, 1H), 7.43 (dd, J=8.4, 2.1 Hz, 1H), 7.89 (d, J=2.1 Hz, 1H), 8.15 (s, 1H), 12.37 (brs, 1H), 12.79 (brs, 1H).

IR Spectrum (KBr, $cm^{-1}$): 1639.

Example 3

3-Bromo-2-(3-cyclopropoxy-4-difluoromethoxyphenyl)-1,5-dihydropyrrolo[2,3-d]pyridazin-4-one (Exemplary compound No. 1-3)

3-(a) 1-Benzyloxymethyl-2-(3-cyclopropoxy-4-difluoromethoxyphenyl)-1,5-dihydropyrrolo[2,3-d]pyridazin-4-one Reaction was carried out in the same manner as in Example 1-(a) except for using 9.50 g (28.4 mmol) of 1-benzyloxymethyl-2-bromo-1,5-dihydropyrrolo[2,3-d]pyridazin-4-one obtained in the following Reference example 17-(d) in place of 2-bromo-1-(2-trimethylsilylethoxymethyl)-1,5-dihydropyrrolo[2,3-d]pyridazin-4-one. After completion of the reaction, water was added to the reaction mixture, and the mixture was extracted with ethyl acetate. The organic layer after separation was washed successively with water and then with a saturated aqueous solution of sodium chloride, dried over anhydrous magnesium sulfate and then concentrated under reduced pressure. The obtained crude solid was recrystallized from toluene to obtain 8.95 g of the title compound as a beige solid. (Yield: 69%)

Mass Spectrum (CI, m/z): 454 ($M^+$+1).

$^1$H-NMR Spectrum (CDCl$_3$, δ ppm): 0.67-0.83 (m, 4H), 3.69-3.75 (m, 1H), 4.55 (s, 2H), 5.52 (s, 2H), 6.58 (t, J=74.7 Hz, 1H), 6.97 (d, J=0.7 Hz, 1H), 7.14 (dd, J=8.2, 2.2 Hz, 1H), 7.20-7.36 (m, 6H), 7.56 (d, J=2.2 Hz, 1H), 8.12 (d, J=0.7 Hz, 1H), 9.99 (brs, 1H).

IR Spectrum (KBr, $cm^{-1}$): 1644.

3-(b) 1-Benzyloxymethyl-3-bromo-2-(3-cyclopropoxy-4-difluoromethoxyphenyl)-1,5-dihydropyrrolo[2,3-d]pyridazin-4-one To 460 mg (1.02 mmol) of 1-benzyloxymethyl-2-(3-cyclopropoxy-4-difluoromethoxyphenyl)-1,5-dihydropyrrolo[2,3-d]-pyridazin-4-one obtained in Example 3-(a) were added 10 ml of acetonitrile and 4 ml of dichloromethane, followed by addition of 214 mg (1.22 mmol) of N-bromosuccineimide, and the mixture was stirred under room temperature for 2.5 hours. After completion of the reaction, the reaction mixture was concentrated under reduced pressure, ethyl acetate and 5% aqueous sodium thiosulfate solution were added to the obtained solid, and the mixture was stirred under room temperature for 30 minutes. The organic layer after separation was washed successively with a saturated aqueous solution of sodium hydrogencarbonate and then with a saturated aqueous solution of sodium chloride, dried over anhydrous magnesium sulfate and then concentrated under reduced pressure. The obtained residue was applied to silica gel column chromatography (Eluent; toluene:ethyl acetate=1:0→1:1→0:1 (V/V)), and the fractions containing the desired compound were concentrated under reduced pressure to obtain 473 mg of the title compound as a beige solid. (Yield: 87%)

Mass Spectrum (CI, m/z): 532 ($M^+$+1).

$^1$H-NMR Spectrum (CDCl$_3$, δ ppm): 0.70-0.85 (m, 4H), 3.70-3.77 (m, 1H), 4.48 (s, 2H), 5.43 (s, 2H), 6.61 (t, J=74.6 Hz, 1H), 7.08 (dd, J=8.2, 2.1 Hz, 1H), 7.14-7.36 (m, 6H), 7.51 (d, J=2.1 Hz, 1H), 8.11 (s, 1H), 10.03 (brs, 1H).

IR Spectrum (KBr, $cm^{-1}$): 1650.

3-(c) 3-Bromo-2-(3-cyclopropoxy-4-difluoromethoxyphenyl)-1,5-dihydropyrrolo[2,3-d]pyridazin-4-one In an autoclave made of a glass were charged 463 mg (0.870 mmol) of 1-benzyloxymethyl-3-bromo-2-(3-cyclopropoxy-4-difluoromethoxyphenyl)-1,5-dihydropyrrolo[2,3-d]-pyridazin-4-one obtained in Example 3-(b), 25 ml of ethanol and 25 ml of conc. hydrochloric acid, and the mixture was stirred at 120° C. for 12 hours. After completion of the reaction, 50 ml of water was added to the reaction mixture, and precipitated solid was collected by filtration and washed with water. The obtained solid was purified by high performance liquid chromatography (column; Kromacil™ 100-5-C18 (20 mm×250 mm (manufactured by EKA CHEMICALS), Eluent; acetonitrile:water:trifluoroacetic acid=600:400:1 (V/V/V), Flow rate; 10 ml/min) to obtain 92 mg of the title compound as a white solid. (Yield: 26%)

Melting point: 267-270° C. (decomposed).

Mass Spectrum (CI, m/z): 412 ($M^+$+1).

$^1$H-NMR Spectrum (DMSO-$d_6$, δ ppm): 0.73-0.91 (m, 4H), 3.95-4.02 (m, 1H), 7.12 (t, J=74.2 Hz, 1H), 7.34 (d, J=8.4 Hz, 1H), 7.41 (dd, J=8.4, 2.0 Hz, 1H), 7.91 (d, J=2.0 Hz, 1H), 8.16 (s, 1H), 12.35 (brs, 1H).

IR Spectrum (KBr, $cm^{-1}$): 1634.

Example 4

2-(3-Cyclopropoxy-4-difluoromethoxyphenyl)-3-methyl-1,5-dihydropyrrolo[2,3-d]pyridazin-4-one (Exemplary compound No. 1-4)

4-(a) 2-(3-Cyclopropoxy-4-difluoromethoxyphenyl)-3-methyl-1,5-bis(2-trimethylsilylethoxymethyl)-1,5-dihydropyrrolo-[2,3-d]pyridazin-4-one To a mixture of 1.46 g (3.00 mmol) of 2-bromo-3-methyl-1,5-bis(2-trimethylsilylethoxymethyl)-1,5-dihydropyrrolo[2,3-d]pyridazin-4-one obtained in the following Reference example 18-(d) and 1.47 g (4.50 mmol) of 2-(3-cyclopropoxy-4-difluoromethoxyphenyl)-4,4,5,5-tetramethyl-[1,3,2]dioxaborolane obtained in the following Reference example 1-(a) were added 7 mg of palladium acetate, 22 mg of butyl-di-1-adamantylphosphine, 20 ml of toluene, 2.59 g of potassium phosphate and 1.2 ml of water, and the mixture was degassed under reduced pressure and replaced with argon. The reaction mixture was refluxed for 6 hours. After completion of the reaction, water was added to the reaction mixture, and the mixture was extracted with ethyl acetate. The organic layer after separation was washed with a saturated aqueous solution of sodium chloride, dried over anhydrous magnesium sulfate and then concentrated under reduced pressure. The obtained residue was applied to silica gel column chromatography (Eluent; hexane:ethyl acetate=1:0→2:3 (V/V)), and the fractions containing the desired compound were concentrated under reduced pressure to obtain 1.54 g of the title compound as a slightly yellowish oil. (Yield: 84%)

Mass Spectrum (CI, m/z): 608($M^+$+1).

$^1$H-NMR Spectrum (CDCl$_3$, δ ppm): −0.04 (s, 9H), 0.00 (s, 9H), 0.79-0.90 (m, 6H), 0.96-1.04 (m, 2H), 2.45 (s, 3H), 3.41-3.49 (m, 2H), 3.70-3.77 (m, 2H), 3.76-3.83 (m, 1H), 5.32 (s, 2H), 5.60 (s, 2H), 6.59 (t, J=74.7 Hz, 1H), 7.00 (dd, J=8.2, 2.1 Hz, 1H), 7.27 (d, J=8.2 Hz, 1H), 7.38 (d, J=2.0 Hz, 1H), 8.17 (s, 1H).

4-(b) 2-(3-Cyclopropoxy-4-difluoromethoxyphenyl)-3-methyl-5-(2-trimethylsilylethoxymethyl)-1,5-dihydropyrrolo[2,3-d]-pyridazin-4-one Reaction was carried out in the same manner as in Example 1-(b) except for using 1.54 g (2.53 mmol) of 2-(3-cyclopropoxy-4-difluoromethoxyphenyl)-3-methyl-1,5-bis(2-trimethylsilylethoxymethyl)-1,5-dihydropyrrolo[2,3-d]pyridazin-4-one obtained in Example 4-(a) in place of 2-(3-cyclopropoxy-4-difluoromethoxyphenyl)-1-(2-trimethylsilylethoxymethyl)-1,5-dihydropyrrolo[2,3-d]pyridazin-4-one. After completion of the reaction, water was added to the reaction mixture, and the mixture was extracted with ethyl acetate. The organic layer after separation was washed successively with water and then with a saturated aqueous solution of sodium chloride, dried over anhydrous magnesium sulfate, and then concentrated under reduced pressure. The obtained residue was applied to silica gel column chromatography (Eluent; hexane:ethyl acetate=19:1→1:1 (V/V)), and the fractions containing the desired compound were concentrated under reduced pressure to obtain 1.11 g of the title compound as a white solid. (Yield: 92%)

Mass Spectrum (CI, m/z): 478 ($M^+$+1).

$^1$H-NMR Spectrum (CDCl$_3$, δ ppm): −0.02 (s, 9H), 0.83-0.88 (m, 4H), 0.94-1.00 (m, 2H), 2.62 (s, 3H), 3.68-3.77 (m, 2H), 3.79-3.87 (m, 1H), 5.58 (s, 2H), 6.56 (t, J=74.7 Hz, 1H), 7.08 (dd, J=8.3, 2.1 Hz, 1H), 7.24 (d, J=8.3 Hz, 1H), 7.48 (d, J=2.1 Hz, 1H), 8.08 (s, 1H), 8.96 (brs, 1H)

4-(c) 2-(3-Cyclopropoxy-4-difluoromethoxyphenyl)-3-methyl-1,5-dihydropyrrolo[2,3-d]pyridazin-4-one To 1.10 g (2.30 mmol) of 2-(3-cyclopropoxy-4-difluoromethoxyphenyl)-3-methyl-5-(2-trimethylsilylethoxymethyl)-1,5-dihydropyrrolo[2,3-d]pyridazin-4-one obtained in Example 4-(b) were added 30 ml of dichloromethane and 6 ml of trifluoroacetic acid, and the mixture was stirred under room temperature for 2.5 hours. After completion of the reaction, the reaction mixture was concentrated under reduced pressure, 20 ml of methanol and 2 ml of 28% aqueous ammonia were added to the obtained solid, and the mixture was stirred under room temperature for 12 hours. Then, water was added to the solution, precipitated solid was collected by filtration, washed with water, and then, dried under reduced pressure.

To the obtained dried material was added ethyl acetate to dissolve therein, diisopropyl ether was added to the solution and precipitated solid was collected by filtration. The obtained solid was dried under reduced pressure to obtain 0.54 g of the title compound as a white solid. (Yield: 67%)

Melting point: 245-246° C.

Mass Spectrum (CI, m/z): 348 ($M^+$+1).

$^1$H-NMR Spectrum (DMSO-d$_6$, δ ppm): 0.73-0.90 (m, 4H), 2.56 (s, 3H), 3.97-4.05 (m, 1H), 7.09 (t, J=74.3 Hz, 1H), 7.24 (dd, J=8.4, 2.1 Hz, 1H), 7.31 (d, J=8.4 Hz, 1H), 7.64 (d, J=2.1 Hz, 1H), 8.09 (s, 1H), 12.14 (brs, 1H)

IR Spectrum (KBr, cm$^{-1}$): 1634.

Example 5

2-(3-Cyclopropoxy-4-difluoromethoxyphenyl)-3-ethyl-1,5-dihydropyrrolo[2,3-d]pyridazin-4-one (Exemplary compound No. 1-5)

5-(a) 2-(3-Cyclopropoxy-4-difluoromethoxyphenyl)-3-ethyl-1,5-bis(2-trimethylsilylethoxymethyl)-1,5-dihydropyrrolo-[2,3-d]pyridazin-4-one Reaction and post treatment were carried out in the same manner as in Example 1-(a) except for using 7.05 g (14.0 mmol) of 2-bromo-3-ethyl-1,5-bis(2-trimethylsilylethoxymethyl)-1,5-dihydropyrrolo[2,3-d]pyridazin-4-one obtained in the following Reference example 19-(d) in place of 2-bromo-1-(2-trimethylsilylethoxymethyl)-1,5-dihydropyrrolo[2,3-d]pyridazin-4-one, whereby 9.36 g of the title compound was obtained as a pale yellowish oil substantially quantitatively.

Mass Spectrum (CI, m/z): 622 ($M^+$+1).

$^1$H-NMR Spectrum (CDCl$_3$, δ ppm): −0.04 (s, 9H), 0.00 (s, 9H), 0.79-0.88 (m, 6H), 0.97-1.03 (m, 2H), 1.25 (t, J=7.4 Hz, 3H), 2.80 (q, J=7.4 Hz, 2H), 3.41-3.48 (m, 2H), 3.71-3.82 (m, 3H), 5.30 (s, 2H), 5.61 (s, 2H), 6.60 (t, J=74.7 Hz, 1H), 6.99 (dd, J=8.2, 2.0 Hz, 1H), 7.26 (d, J=8.2 Hz, 1H), 7.37 (d, J=2.0 Hz, 1H), 8.18 (s, 1H).

5-(b) 2-(3-Cyclopropoxy-4-difluoromethoxyphenyl)-3-ethyl-5-(2-trimethylsilylethoxymethyl)-1,5-dihydropyrrolo[2,3-d]-pyridazin-4-one Reaction and post treatment were carried out in the same manner as in Example 4-(b) except for using 9.35 g (containing an amount corresponding to 14.0 mmol) of 2-(3-cyclopropoxy-4-difluoromethoxyphenyl)-3-ethyl-1,5-bis(2-trimethylsilylethoxymethyl)-1,5-dihydropyrrolo[2,3-d]-pyridazin-4-one obtained in Example 5-(a) in place of 2-(3-cyclopropoxy-4-difluoromethoxyphenyl)-3-methyl-1,5-bis(2-trimethylsilylethoxymethyl)-1,5-dihydropyrrolo[2,3-d]-pyridazin-4-one, whereby 5.84 g of the title compound was obtained as a white solid. (Yield: 79%)

Mass Spectrum (CI, m/z): 492 ($M^+$+1).

$^1$H-NMR Spectrum (CDCl$_3$, δ ppm): −0.01 (s, 9H), 0.84-0.90 (m, 4H), 0.95-1.03 (m, 2H), 1.37 (t, J=7.4 Hz, 3H), 3.01 (q, J=7.4 Hz, 2H), 3.70-3.78 (m, 2H), 3.80-3.87 (m, 1H), 5.60 (s, 2H), 6.57 (t, J=74.8 Hz, 1H), 7.05 (dd, J=8.3, 2.1 Hz, 1H), 7.26 (d, J=8.3 Hz, 1H), 7.48 (d, J=2.1 Hz, 1H), 8.08 (s, 1H), 8.52 (brs, 1H).

IR Spectrum (KBr, cm$^{-1}$): 1636.

5-(c) 2-(3-Cyclopropoxy-4-difluoromethoxyphenyl)-3-ethyl-1,5-dihydropyrrolo[2,3-d]pyridazin-4-one Reaction and post treatment were carried out in the same manner as in Example 4-(c) except for using 5.84 g (11.9 mmol) of 2-(3-cyclopropoxy-4-difluoromethoxyphenyl)-3-ethyl-5-(2-trimethylsilylethoxymethyl)-1,5-dihydropyrrolo[2,3-d]pyridazin-4-one obtained in Example 5-(b) in place of 2-(3-cyclopropoxy-4-difluoromethoxyphenyl)-3-methyl-5-(2-trimethylsilylethoxymethyl)-1,5-dihydropyrrolo-[2,3-d]pyridazin-4-one, whereby 4.41 g of the title compound was obtained as a white solid substantially quantitatively.

Melting point: 223-225° C.
Mass Spectrum (CI, m/z): 362 ($M^+$+1).
$^1$H-NMR Spectrum (DMSO-$d_6$, δ ppm): 0.73-0.89 (m, 4H), 1.27 (t, J=7.3 Hz, 3H), 2.91 (q, J=7.3 Hz, 2H), 3.96-4.04 (m, 1H), 7.09 (t, J=74.3 Hz, 1H), 7.18 (dd, J=8.3, 2.0 Hz, 1H), 7.32 (d, J=8.3 Hz, 1H), 7.58 (d, J=2.0 Hz, 1H), 8.08 (s, 1H), 12.14 (brs, 1H), 12.16 (brs, 1H).
IR Spectrum (KBr, $cm^{-1}$): 1628.

Example 6

2-(3-Cyclopropoxy-4-difluoromethoxyphenyl)-3-propyl-1,5-dihydropyrrolo[2,3-d]pyridazin-4-one (Exemplary compound No. 1-6)

6-(a) 2-(3-Cyclopropoxy-4-difluoromethoxyphenyl)-3-propyl-1,5-bis(2-trimethylsilylethoxymethyl)-1,5-dihydropyrrolo-[2,3-d]pyridazin-4-one Reaction and post treatment were carried out in the same manner as in Example 4-(a) except for using 900 mg (1.74 mmol) of 2-bromo-3-propyl-1,5-bis(2-trimethylsilylethoxymethyl)-1,5-dihydropyrrolo[2,3-d]pyridazin-4-one obtained in the following Reference example 20-(c) in place of 2-bromo-3-methyl-1,5-bis(2-trimethylsilylethoxymethyl)-1,5-dihydropyrrolo[2,3-d]pyridazin-4-one, whereby 596 mg of the title compound was obtained as a pale yellowish oil. (Yield: 54%)

Mass Spectrum (CI, m/z): 636 ($M^+$+1).
$^1$H-NMR Spectrum (CDCl$_3$, δ ppm): −0.05 (s, 9H), 0.00 (s, 9H), 0.79-0.88 (m, 6H), 0.89 (t, J=7.8 Hz, 3H), 0.96-1.05 (m, 2H), 1.61-1.74 (m, 2H), 2.69-2.78 (m, 2H), 3.38-3.47 (m, 2H), 3.69-3.82 (m, 3H), 5.29 (s, 2H), 5.60 (s, 2H), 6.60 (t, J=74.7 Hz, 1H), 6.97 (dd, J=8.3, 2.0 Hz, 1H), 7.26 (d, J=8.3 Hz, 1H), 7.35 (d, J=2.0 Hz, 1H), 8.17 (s, 1H).

6-(b) 2-(3-Cyclopropoxy-4-difluoromethoxyphenyl)-3-propyl-5-(2-trimethylsilylethoxymethyl)-1,5-dihydropyrrolo[2,3-d]-pyridazin-4-one Reaction and post treatment were carried out in the same manner as in Example 4-(b) except for using 595 mg (0.936 mmol) of 2-(3-cyclopropoxy-4-difluoromethoxyphenyl)-3-propyl-1,5-bis(2-trimethylsilylethoxymethyl)-1,5-dihydropyrrolo[2,3-d]pyridazin-4-one obtained in Example 6-(a) in place of 2-(3-cyclopropoxy-4-difluoromethoxyphenyl)-3-methyl-1,5-bis(2-trimethylsilylethoxymethyl)-1,5-dihydropyrrolo[2,3-d]pyridazin-4-one, whereby 377 mg of the title compound was obtained as a white solid. (Yield: 80%)

Mass Spectrum (CI, m/z): 506 ($M^+$+1).
$^1$H-NMR Spectrum (DMSO-$d_6$, δ ppm): −0.04 (s, 9H), 0.74-0.90 (m, 6H), 0.92 (t, J=7.2 Hz, 3H), 1.60-1.74 (m, 2H), 2.84-2.94 (m, 2H), 3.64 (t, J=8.1 Hz, 2H), 3.93-4.06 (m, 1H), 5.42 (s, 2H), 7.10 (t, J=74.3 Hz, 1H), 7.18 (dd, J=8.4, 2.1 Hz, 1H), 7.33 (d, J=8.4 Hz, 1H), 7.58 (d, J=2.1 Hz, 1H), 8.14 (s, 1H), 12.25 (brs, 1H).
IR Spectrum (KBr, $cm^{-1}$): 1630.

6-(c) 2-(3-Cyclopropoxy-4-difluoromethoxyphenyl)-3-propyl-1,5-dihydropyrrolo[2,3-d]pyridazin-4-one To 431 mg (0.853 mmol) of 2-(3-cyclopropoxy-4-difluoromethoxyphenyl)-3-propyl-5-(2-trimethylsilylethoxymethyl)-1,5-dihydropyrrolo[2,3-d]pyridazin-4-one obtained in Example 6-(b) was added 6.7 ml of 1,4-dioxane solution containing 4N hydrogen chloride, and the mixture was stirred under room temperature for 24 hours. After completion of the reaction, the reaction mixture was concentrated under reduced pressure, 10 ml of methanol and 5 ml of 28% aqueous ammonia were added to the obtained solid, and the mixture was stirred under room temperature for 3 hours. Then, the solution was concentrated under reduced pressure, water was added to the obtained concentrate, and precipitated solid was collected by filtration. The obtained solid was washed with water and dried under reduced pressure to obtain 307 mg of the title compound as a white solid. (Yield: 96%)

Melting point: 208-210° C.
Mass Spectrum (CI, m/z): 376 ($M^+$+1).
$^1$H-NMR Spectrum (DMSO-$d_6$, δ ppm): 0.73-0.86 (m, 4H), 0.91 (t, J=7.3 Hz, 3H), 1.61-1.74 (m, 2H), 2.84-2.93 (m, 2H), 3.96-4.03 (m, 1H), 7.10 (t, J=74.3 Hz, 1H), 7.18 (dd, J=8.3, 2.0 Hz, 1H), 7.32 (d, J=8.3 Hz, 1H), 7.58 (d, J=2.0 Hz, 1H), 8.07 (s, 1H), 12.12 (brs, 1H), 12.16 (brs, 1H)
IR Spectrum (KBr, $cm^{-1}$): 1637.

Example 7

2-(3-Cyclopropoxy-4-difluoromethoxyphenyl)-3-isopropyl-1,5-dihydropyrrolo[2,3-d]pyridazin-4-one (Exemplary compound No. 1-7)

7-(a) 1-Benzyloxymethyl-2-(3-cyclopropoxy-4-difluoromethoxyphenyl)-3-isopropyl-5-(2-trimethylsilylethoxymethyl)-1,5-dihydropyrrolo[2,3-d]pyridazin-4-one Reaction and post treatment were carried out in the same manner as in Example 4-(a) except for using 414 mg (0.818 mmol) of 1-benzyloxymethyl-2-bromo-3-isopropyl-5-(2-trimethylsilylethoxymethyl)-1,5-dihydropyrrolo[2,3-d]pyridazin-4-one obtained in the following Reference example 21-(g) in place of 2-bromo-3-methyl-1,5-bis(2-trimethylsilylethoxymethyl)-1,5-dihydropyrrolo[2,3-d]pyridazin-4-one, whereby 369 mg of the title compound was obtained as a white solid. (Yield: 72%)

Mass Spectrum (CI, m/z): 626 ($M^+$+1).
$^1$H-NMR Spectrum (CDCl$_3$, δ ppm): 0.00 (s, 9H), 0.69-0.77 (m, 2H), 0.77-0.83 (m, 2H), 0.96-1.05 (m, 2H), 1.37 (d, J=7.1 Hz, 6H), 3.05-3.18 (m, 1H), 3.65-3.79 (m, 3H), 4.46 (s, 2H), 5.30 (s, 2H), 5.63 (s, 2H), 6.60 (t, J=74.7 Hz, 1H), 6.96 (dd, J=8.2, 2.1 Hz, 1H), 7.16-7.36 (m, 7H), 8.09 (s, 1H).

7-(b) 2-(3-Cyclopropoxy-4-difluoromethoxyphenyl)-3-isopropyl-5-(2-trimethylsilylethoxymethyl)-1,5-dihydropyrrolo-[2,3-d]pyridazin-4-one To 313 mg (0.500 mmol) of 1-benzyloxymethyl-2-(3-cyclopropoxy-4-difluoromethoxyphenyl)-3-isopropyl-5-(2-trimethylsilylethoxymethyl)-1,5-dihydropyrrolo[2,3-d]pyridazin-4-one obtained in Example 7-(a) were added 15 ml of ethanol, 1.6 ml of 28% aqueous ammonia and 39 mg of 5% palladium-active carbon, and the mixture was stirred under 1 atm hydrogen atmosphere at 30° C. for 7 days. After completion of the reaction, the reaction suspension was filtered, and the filtrate was concentrated under reduced pressure. The obtained residue was applied to silica gel column chromatography (Eluent; toluene:ethyl acetate=9:1→4:1 (V/V)), and the fractions containing the desired compound were concentrated under reduced pressure to obtain 152 mg of the title compound as a white foam. (Yield: 60%)

Mass Spectrum (CI, m/z): 506 (M$^+$+1).

$^1$H-NMR Spectrum (CDCl$_3$, δ ppm): −0.02 (s, 9H), 0.81-0.90 (m, 4H), 0.94-1.03 (m, 2H), 1.46 (d, J=6.8 Hz, 6H), 3.26-3.40 (m, 1H), 3.69-3.77 (m, 2H), 3.77-3.85 (m, 1H), 5.61 (s, 2H), 6.58 (t, J=74.8 Hz, 1H), 7.02 (dd, J=8.3, 2.1 Hz, 1H), 7.25 (d, J=8.3 Hz, 1H), 7.42 (d, J=2.1 Hz, 1H), 8.06 (s, 1H), 8.57 (brs, 1H).

7-(c) 2-(3-Cyclopropoxy-4-difluoromethoxyphenyl)-3-isopropyl-1,5-dihydropyrrolo[2,3-d]pyridazin-4-one Reaction and post treatment were carried out in the same manner as in Example 4-(c) except for using 152 mg (0.300 mmol) of 2-(3-cyclopropoxy-4-difluoromethoxyphenyl)-3-isopropyl-5-(2-trimethylsilylethoxymethyl)-1,5-dihydropyrrolo[2,3-d]pyridazin-4-one obtained in Example 7-(b) in place of 2-(3-cyclopropoxy-4-difluoromethoxyphenyl)-3-methyl-5-(2-trimethylsilylethoxymethyl)-1,5-dihydropyrrolo-[2,3-d]pyridazin-4-one, whereby 70 mg of the title compound was obtained as a white solid. (Yield: 62%)

Melting point: 265-267° C.

Mass Spectrum (CI, m/z): 376 (M$^+$+1).

$^1$H-NMR Spectrum (DMSO-d$_6$, δ ppm): 0.73-0.88 (m, 4H), 1.40 (d, J=6.8 Hz, 6H), 3.16-3.27 (m, 1H), 3.95-4.03 (m, 1H), 7.10 (t, J=74.3 Hz, 1H), 7.10 (dd, J=8.3, 2.1 Hz, 1H), 7.32 (d, J=8.3 Hz, 1H), 7.50 (d, J=2.1 Hz, 1H), 8.07 (s, 1H), 12.15 (brs, 2H).

IR Spectrum (KBr, cm$^{-1}$): 1646.

Example 8

3-Butyl-2-(3-cyclopropoxy-4-difluoromethoxyphenyl)-1,5-dihydropyrrolo[2,3-d]pyridazin-4-one (Exemplary compound No. 1-8)

8-(a) 3-Butyl-2-(3-cyclopropoxy-4-difluoromethoxyphenyl)-1,5-bis(2-trimethylsilylethoxymethyl)-1,5-dihydropyrrolo-[2,3-d]pyridazin-4-one Reaction and post treatment were carried out in the same manner as in Example 4-(a) except for using 4.86 g (9.15 mmol) of 2-bromo-3-butyl-1,5-bis(2-trimethylsilylethoxymethyl)-1,5-dihydropyrrolo[2,3-d]pyridazin-4-one obtained in the following Reference example 22-(b) in place of 2-bromo-3-methyl-1,5-bis(2-trimethylsilylethoxymethyl)-1,5-dihydropyrrolo[2,3-d]pyridazin-4-one, whereby 5.57 g of the title compound was obtained as a pale yellowish oil. (Yield: 94%)

Mass Spectrum (CI, m/z): 650 (M$^+$+1).

$^1$H-NMR Spectrum (CDCl$_3$, δ ppm): −0.05 (s, 9H), 0.00 (s, 9H), 0.79-0.88 (m, 9H), 0.96-1.04 (m, 2H), 1.23-1.36 (m, 2H), 1.56-1.68 (m, 2H), 2.73-2.81 (m, 2H), 3.38-3.47 (m, 2H), 3.70-3.81 (m, 3H), 5.29 (s, 2H), 5.61 (s, 2H), 6.60 (t, J=74.7 Hz, 1H), 6.97 (dd, J=8.3, 2.0 Hz, 1H), 7.26 (d, J=8.3 Hz, 1H), 7.35 (d, J=2.0 Hz, 1H), 8.17 (s, 1H)

IR Spectrum (neat, cm$^{-1}$): 1666.

8-(b) 3-Butyl-2-(3-cyclopropoxy-4-difluoromethoxyphenyl)-5-(2-trimethylsilylethoxymethyl)-1,5-dihydropyrrolo[2,3-d]-pyridazin-4-one Reaction and post treatment were carried out in the same manner as in Example 4-(b) except for using 5.57 g (8.57 mmol) of 3-butyl-2-(3-cyclopropoxy-4-difluoromethoxyphenyl)-1,5-bis(2-trimethylsilylethoxymethyl)-1,5-dihydropyrrolo[2,3-d]pyridazin-4-one obtained in Example 8-(a) in place of 2-(3-cyclopropoxy-4-difluoromethoxyphenyl)-3-methyl-1,5-bis(2-trimethylsilylethoxymethyl)-1,5-dihydropyrrolo[2,3-d]pyridazin-4-one, whereby 3.95 g of the title compound was obtained as a white solid. (Yield: 89%)

Mass Spectrum (CI, m/z): 520 (M$^+$+1).

$^1$H-NMR Spectrum (CDCl$_3$, δ ppm): −0.02 (s, 9H), 0.82-0.87 (m, 4H), 0.88 (t, J=7.3 Hz, 3H), 0.93-1.02 (m, 2H), 1.32-1.46 (m, 2H), 1.64-1.77 (m, 2H), 2.92-3.01 (m, 2H), 3.68-3.76 (m, 2H), 3.78-3.85 (m, 1H), 5.59 (s, 2H), 6.57 (t, J=74.7 Hz, 1H), 7.05 (dd, J=8.3, 2.1 Hz, 1H), 7.24 (d, J=8.3 Hz, 1H), 7.47 (d, J=2.1 Hz, 1H), 8.07 (s, 1H), 8.75 (brs, 1H).

IR Spectrum (KBr, cm$^{-1}$): 1630.

8-(c) 3-Butyl-2-(3-cyclopropoxy-4-difluoromethoxyphenyl)-1,5-dihydropyrrolo[2,3-d]pyridazin-4-one Reaction was carried out in the same manner as in Example 6-(c) except for using 3.94 g (7.58 mmol) of 3-butyl-2-(3-cyclopropoxy-4-difluoromethoxyphenyl)-5-(2-trimethylsilylethoxymethyl)-1,5-dihydropyrrolo[2,3-d]-pyridazin-4-one obtained in Example 8-(b) in place of 2-(3-cyclopropoxy-4-difluoromethoxyphenyl)-3-propyl-5-(2-trimethylsilylethoxymethyl)-1,5-dihydropyrrolo[2,3-d]pyridazin-4-one, and post treatment was carried out except for using ethanol in place of methanol, whereby 2.81 g of the title compound was obtained as a white solid. (Yield: 95%)

Melting point: 192-194° C.

Mass Spectrum (CI, m/z): 390 (M$^+$+1).

$^1$H-NMR Spectrum (DMSO-d$_6$, δ ppm): 0.75-0.86 (m, 4H), 0.86 (t, J=7.3 Hz, 3H), 1.26-1.39 (m, 2H), 1.57-1.69 (m, 2H), 2.87-2.95 (m, 2H), 3.95-4.02 (m, 1H), 7.10 (t, J=74.3 Hz, 1H), 7.18 (dd, J=8.4, 2.1 Hz, 1H), 7.32 (d, J=8.4 Hz, 1H), 7.58 (d, J=2.1 Hz, 1H), 8.07 (s, 1H), 12.10 (brs, 1H), 12.15 (brs, 1H).

IR Spectrum (KBr, cm$^{-1}$): 1641.

Example 9

2-(3-Cyclopropoxy-4-difluoromethoxyphenyl)-3-isobutyl-1,5-dihydropyrrolo[2,3-d]pyridazin-4-one (Exemplary compound No. 1-9)

9-(a) 2-(3-Cyclopropoxy-4-difluoromethoxyphenyl)-3-isobutyl-1,5-bis(2-trimethylsilylethoxymethyl)-1,5-dihydropyrrolo[2,3-d]pyridazin-4-one Reaction and post treatment were carried out in the same manner as in Example 4-(a) except for using 4.77 g (9.00 mmol) of 2-bromo-3-isobutyl-1,5-bis(2-trimethylsilylethoxymethyl)-1,5-dihydropyrrolo[2,3-d]pyridazin-4-one obtained in the following Reference example 23-(b) in place of 2-bromo-3-methyl-1,5-bis(2-trimethylsilylethoxymethyl)-1,5-dihydropyrrolo[2,3-d]pyridazin-4-one, whereby 6.23 g of the title compound was obtained as a pale yellowish oil substantially quantitatively.

Mass Spectrum (CI, m/z): 650 (M$^+$+1).

$^1$H-NMR Spectrum (CDCl$_3$, δ ppm): −0.06 (s, 9H), −0.01 (s, 9H), 0.76-0.86 (m, 6H), 0.79 (d, J=6.8 Hz, 6H), 0.96-1.04 (m, 2H), 2.01-2.13 (m, 1H), 2.67 (d, J=7.1 Hz, 2H), 3.35-3.44 (m, 2H), 3.69-3.82 (m, 3H), 5.28 (s, 2H), 5.60 (s, 2H), 6.61 (t, J=74.7 Hz, 1H), 6.95 (dd, J=8.1, 2.0 Hz, 1H), 7.25 (d, J=8.1 Hz, 1H), 7.32 (d, J=2.0 Hz, 1H), 8.18 (s, 1H).

9-(b) 2-(3-Cyclopropoxy-4-difluoromethoxyphenyl)-3-isobutyl-5-(2-trimethylsilylethoxymethyl)-1,5-dihydropyrrolo-[2,3-d]pyridazin-4-one Reaction and post treatment were carried out in the same manner as in Example 4-(b) except for using 6.14 g (containing an amount corresponding to 9.00 mmol) of 2-(3-cyclopropoxy-4-difluoromethoxyphenyl)-3-isobutyl-1,5-bis(2-trimethylsilylethoxymethyl)-1,5-dihydropyrrolo[2,3-d]pyridazin-4-one obtained in Example 9-(a) in place of 2-(3-cyclopropoxy-4-difluoromethoxyphenyl)-3-methyl-1,5-bis(2-trimethylsilylethoxymethyl)-1,5-dihydropyrrolo[2,3-d]-pyridazin-4-one, whereby 5.74 g the title compound was obtained as a white foam substantially quantitatively.

Mass Spectrum (CI, m/z): 520 ($M^+$+1).
$^1$H-NMR Spectrum (CDCl$_3$, δ ppm): −0.02 (s, 9H), 0.82-0.88 (m, 4H), 0.85 (d, J=6.6 Hz, 6H), 0.94-1.03 (m, 2H), 2.03-2.19 (m, 1H), 2.90 (d, J=7.3 Hz, 2H), 3.69-3.77 (m, 2H), 3.80-3.87 (m, 1H), 5.59 (s, 2H), 6.57 (t, J=74.7 Hz, 1H), 7.05 (dd, J=8.2, 2.1 Hz, 1H), 7.24 (d, J=8.3 Hz, 1H), 7.49 (d, J=2.0 Hz, 1H), 8.07 (s, 1H), 8.60 (brs, 1H).

9-(c) 2-(3-Cyclopropoxy-4-difluoromethoxyphenyl)-3-isobutyl-1,5-dihydropyrrolo[2,3-d]pyridazin-4-one Reaction and post treatment were carried out in the same manner as in Example 6-(c) except for using 5.74 g (containing an amount corresponding to 9.00 mmol) of 2-(3-cyclopropoxy-4-difluoromethoxyphenyl)-3-isobutyl-5-(2-trimethylsilylethoxymethyl)-1,5-dihydropyrrolo[2,3-d]pyridazin-4-one obtained in Example 9-(b) in place of 2-(3-cyclopropoxy-4-difluoromethoxyphenyl)-5-(2-trimethylsilylethoxymethyl)-3-propyl-1,5-dihydropyrrolo[2,3-d]pyridazin-4-one, whereby 2.81 g of the title compound was obtained as a white solid. (Yield: 80%)

Melting point: 239-241° C.
Mass Spectrum (CI, m/z): 390 ($M^+$+1).
$^1$H-NMR Spectrum (DMSO-d$_6$, δ ppm): 0.73-0.88 (m, 4H), 0.80 (d, J=6.8 Hz, 6H), 1.92-2.06 (m, 1H), 2.89 (d, J=7.1 Hz, 2H), 3.96-4.03 (m, 1H), 7.10 (t, J=74.3 Hz, 1H), 7.20 (dd, J=8.3, 2.0 Hz, 1H), 7.30 (d, J=8.3 Hz, 1H), 7.61 (d, J=2.0 Hz, 1H), 8.07 (s, 1H), 12.08 (brs, 1H), 12.15 (brs, 1H).
IR Spectrum (KBr, cm$^{-1}$): 1648.

Example 10

2-(3-Cyclopropoxy-4-difluoromethoxyphenyl)-3-hydroxymethyl-1,5-dihydropyrrolo[2,3-d]pyridazin-4-one (Exemplary compound No. 1-32)

10-(a) 2-(3-Cyclopropoxy-4-difluoromethoxyphenyl)-3-formyl-1-(2-trimethylsilylethoxymethyl)-1,5-dihydropyrrolo[2,3-d]-pyridazin-4-one Reaction and post treatment were carried out in the same manner as in Example 1-(a) except for using 993 mg (2.66 mmol) of 2-bromo-3-formyl-1-(2-trimethylsilylethoxymethyl)-1,5-dihydropyrrolo[2,3-d]pyridazin-4-one obtained in the following Reference example 24-(g) in place of 2-bromo-1-(2-trimethylsilylethoxymethyl)-1,5-dihydropyrrolo[2,3-d]pyridazin-4-one, whereby 966 mg of the title compound was obtained as a yellowish foam. (Yield: 74%)

Mass Spectrum (CI, m/z): 492 ($M^+$+1).
$^1$H-NMR Spectrum (CDCl$_3$, δ ppm): −0.03 (s, 9H), 0.76-0.90 (m, 6H), 3.42-3.50 (m, 2H), 3.76-3.83 (m, 1H), 5.37 (s, 2H), 6.62 (t, J=74.5 Hz, 1H), 7.06 (dd, J=8.3, 2.1 Hz, 1H), 7.28 (d, J=8.3 Hz, 1H), 7.48 (d, J=2.1 Hz, 1H), 8.29 (s, 1H), 10.50 (brs, 1H), 10.67 (s, 1H).

10-(b) 2-(3-Cyclopropoxy-4-difluoromethoxyphenyl)-3-hydroxymethyl-1-(2-trimethylsilylethoxymethyl)-1,5-dihydropyrrolo[2,3-d]pyridazin-4-one To 3 ml of tetrahydrofuran solution containing 221 mg (0.450 mmol) of 2-(3-cyclopropoxy-4-difluoromethoxyphenyl)-3-formyl-1-(2-trimethylsilylethoxymethyl)-1,5-dihydropyrrolo[2,3-d]pyridazin-4-one obtained in Example 10-(a) was added 58 mg (1.53 mmol) of sodium borohydride under ice-cooling, and the reaction mixture was raised to room temperature. After completion of the reaction, water was added to the reaction mixture, and the mixture was extracted with ethyl acetate. The organic layer after separation was washed successively with water and then with a saturated aqueous solution of sodium chloride, dried over anhydrous magnesium sulfate, and then concentrated under reduced pressure. The obtained residue was applied to silica gel column chromatography (Eluent; hexane:ethyl acetate=1:1 (V/V)), and the fractions containing the desired compound were concentrated under reduced pressure to obtain 155 mg of the title compound as a pale yellowish foam. (Yield: 70%)

Mass Spectrum (EI, m/z): 493 ($M^+$+1).
$^1$H-NMR Spectrum (CDCl$_3$, δ ppm): −0.03 (s, 9H), 0.77-0.91 (m, 6H), 3.42-3.52 (m, 2H), 3.76-3.83 (m, 1H), 4.73 (s, 2H), 5.37 (s, 2H), 6.60 (t, J=74.6 Hz, 1H), 6.98 (dd, J=8.1, 2.0 Hz, 1H), 7.28 (d, J=8.1 Hz, 1H), 7.39 (d, J=2.0 Hz, 1H), 8.28 (s, 1H), 10.45 (brs, 1H).
IR Spectrum (KBr, cm$^{-1}$): 1645.

10-(c) 2-(3-Cyclopropoxy-4-difluoromethoxyphenyl)-3-hydroxymethyl-1,5-dihydropyrrolo[2,3-d]pyridazin-4-one Reaction was carried out in the same manner as in Example 1-(b) except for using 80 mg (0.16 mmol) of 2-(3-cyclopropoxy-4-difluoromethoxyphenyl)-3-hydroxymethyl-1-(2-trimethylsilylethoxymethyl)-1,5-dihydropyrrolo[2,3-d]pyridazin-4-one obtained in Example 10-(b) in place of 2-(3-cyclopropoxy-4-difluoromethoxyphenyl)-1-(2-trimethylsilylethoxymethyl)-1,5-dihydropyrrolo[2,3-d]pyridazin-4-one. After completion of the reaction, water was added to the reaction mixture and the precipitated solid was collected by filtration. The obtained solid was washed with water and dried under reduced pressure to obtain 50 mg of the title compound as a white solid. (Yield: 85%)

Melting point: 190-191° C.
Mass Spectrum (EI, m/z): 363 ($M^+$+1).
$^1$H-NMR Spectrum (DMSO-d$_6$, δ ppm): 0.70-0.91 (m, 4H), 3.93-4.01 (m, 1H), 4.78 (d, J=5.2 Hz, 2H), 5.60 (t, J=5.2 Hz, 1H), 7.09 (t, J=74.3 Hz, 1H), 7.28 (dd, J=8.3, 1.6 Hz, 1H) 7.32 (d, J=8.3 Hz, 1H), 7.79 (d, J=1.6 Hz, 1H), 8.19 (s, 1H), 12.46 (brs, 1H).
IR Spectrum (KBr, cm$^{-1}$): 1626.

Example 11

2-(3-Cyclopropoxy-4-difluoromethoxyphenyl)-3-methoxymethyl-1,5-dihydropyrrolo[2,3-d]pyridazin-4-one (Exemplary compound No. 1-50)

11-(a) 2-(3-Cyclopropoxy-4-difluoromethoxyphenyl)-3-methoxymethyl-1,5-bis(2-trimethylsilylethoxymethyl)-1,5-dihydropyrrolo[2,3-d]pyridazin-4-one Reaction and post treatment were carried out in the same manner as in Example 4-(a) except for using 219 mg (0.422 mmol) of 2-bromo-3-methoxymethyl-1,5-bis(2-trimethylsilylethoxymethyl)-1,5-dihydropyrrolo[2,3-d]pyridazin-4-one obtained in the following Reference example 25-(b) in place of 2-bromo-3-methyl-1,5-bis(2-trimethylsilylethoxymethyl)-1,5-dihydropyrrolo[2,3-d]pyridazin-4-one, whereby 224 mg of the title compound was obtained as a yellowish oil (Yield: 83%).

Mass Spectrum (CI, m/z): 638 ($M^+$+1).

$^1$H-NMR Spectrum (CDCl$_3$, δ ppm): −0.03 (s, 9H), 0.00 (s, 9H), 0.79-0.92 (m, 6H), 0.95-1.04 (m, 2H), 3.45-3.55 (m, 2H), 3.47 (s, 3H), 3.70-3.83 (m, 3H), 4.63 (s, 2H), 5.37 (s, 2H), 5.61 (s, 2H), 6.61 (t, J=74.7 Hz, 1H), 7.15 (dd, J=8.3, 2.0 Hz, 1H), 7.27 (d, J=8.3 Hz, 1H), 7.66 (d, J=2.0 Hz, 1H), 8.21 (s, 1H).

IR Spectrum (neat, cm$^{-1}$): 1667.

11-(b) 2-(3-Cyclopropoxy-4-difluoromethoxyphenyl)-3-methoxymethyl-5-(2-trimethylsilylethoxymethyl)-1,5-dihydropyrrolo[2,3-d]pyridazin-4-one Reaction and post treatment were carried out in the same manner as in Example 4-(b) except for using 239 mg (0.375 mmol) of 2-(3-cyclopropoxy-4-difluoromethoxyphenyl)-3-methoxymethyl-1,5-bis(2-trimethylsilylethoxymethyl)-1,5-dihydropyrrolo[2,3-d]pyridazin-4-one obtained in Example 11-(a) in place of 2-(3-cyclopropoxy-4-difluoromethoxyphenyl)-3-methyl-1,5-bis(2-trimethylsilylethoxymethyl)-1,5-dihydropyrrolo[2,3-d]pyridazin-4-one, whereby 174 mg of the title compound was obtained as a white solid. (Yield: 91%)

Mass Spectrum (CI, m/z): 508 ($M^+$+1).

$^1$H-NMR Spectrum (acetone-d$_6$, δ ppm): −0.02 (s, 9H), 0.76-0.83 (m, 2H), 0.84-0.95 (m, 4H), 3.43 (s, 3H), 3.70-3.77 (m, 2H), 3.93-4.00 (m, 1H), 4.85 (s, 2H), 5.50 (s, 2H), 6.89 (t, J=75.1 Hz, 1H), 7.30 (d, J=8.4 Hz, 1H), 7.42 (dd, J=8.4, 2.1 Hz, 1H), 8.05 (d, J=2.1 Hz, 1H), 8.13 (s, 1H), 11.51 (brs, 1H).

IR Spectrum (KBr, cm$^{-1}$): 1633.

11-(c) 2-(3-Cyclopropoxy-4-difluoromethoxyphenyl)-3-methoxymethyl-1,5-dihydropyrrolo[2,3-d]pyridazin-4-one To 8 ml of methanol was added 1.3 ml (18.3 mmol) of acetyl chloride, and the mixture was stirred at 50° C. for 15 minutes, and then, cooled to room temperature. To the solution was added 140 mg (0.276 mmol) of 2-(3-cyclopropoxy-4-difluoromethoxyphenyl)-3-methoxymethyl-5-(2-trimethylsilylethoxymethyl)-1,5-dihydropyrrolo[2,3-d]pyridazin-4-one obtained in Example 11-(b), and the resulting mixture was stirred at room temperature for 3 hours. After completion of the reaction, to the reaction mixture were successively added 18.4 ml of methanol solution containing 1M sodium methoxide and then water, and the mixture was extracted with a mixed solvent (chloroform:methanol=9:1 (UV)). The organic layer after separation of liquids was washed with water, dried over anhydrous magnesium sulfate and then concentrated under reduced pressure. Water was added to the obtained concentrate, and precipitated solid was collected by filtration and dried under reduced pressure to obtain 58 mg of the title compound as a white solid.

(Yield: 56%)

Melting point: 104-107° C.

Mass Spectrum (CI, m/z): 378($M^+$+1).

$^1$H-NMR Spectrum (acetone-d$_6$, δ ppm): 0.76-0.92 (m, 4H), 3.42 (s, 3H), 3.92-4.00 (m, 1H), 4.84 (s, 2H), 6.89 (t, J=75.2 Hz, 1H), 7.30 (d, J=8.4 Hz, 1H), 7.42 (dd, J=8.4, 2.0 Hz, 1H), 8.05 (d, J=2.0 Hz, 1H), 8.11 (s, 1H), 11.41 (brs, 1H), 11.50 (brs, 1H).

IR Spectrum (KBr, cm$^{-1}$): 1639.

Example 12

2-(3-Cyclopropoxy-4-difluoromethoxyphenyl)-3-ethoxymethyl-1,5-dihydropyrrolo[2,3-d]pyridazin-4-one (Exemplary compound No. 1-60)

12-(a) 2-(3-Cyclopropoxy-4-difluoromethoxyphenyl)-3-ethoxymethyl-1-(2-trimethylsilylethoxymethyl)-1,5-dihydropyrrolo-[2,3-d]pyridazin-4-one Reaction and post treatment were carried out in the same manner as in Example 1-(a) except for using 245 mg (0.609 mmol) of 2-bromo-3-ethoxymethyl-1-(2-trimethylsilylethoxymethyl)-1,5-dihydropyrrolo[2,3-d]pyridazin-4-one obtained in the following Reference example 26 in place of 2-bromo-1-(2-trimethylsilylethoxymethyl)-1,5-dihydropyrrolo[2,3-d]pyridazin-4-one, whereby 185 mg of the title compound was obtained as a yellowish foam. (Yield: 58%)

Mass Spectrum (CI, m/z): 522 ($M^+$+1).

$^1$H-NMR Spectrum (DMSO-d$_6$, δ ppm): −0.11 (s, 9H), 0.70-0.85 (m, 6H), 1.05 (t, J=7.0 Hz, 3H), 3.38-3.45 (m, 2H), 3.48 (q, J=7.0 Hz, 2H), 3.88-3.95 (m, 1H), 4.57 (s, 2H), 5.52 (s, 2H), 7.14 (t, J=74.2 Hz, 1H), 7.24 (dd, J=8.3, 2.0 Hz, 1H), 7.34 (d, J=8.3 Hz, 1H), 7.69 (d, J=2.0 Hz, 1H), 8.50 (s, 1H), 12.41 (brs, 1H).

12-(b) 2-(3-Cyclopropoxy-4-difluoromethoxyphenyl)-3-ethoxymethyl-1,5-dihydropyrrolo[2,3-d]pyridazin-4-one Reaction was carried out in the same manner as in Example 1-(b) except for using 184 mg (0.353 mmol) of 2-(3-cyclopropoxy-4-difluoromethoxyphenyl)-3-ethoxymethyl-1-(2-trimethylsilylethoxymethyl)-1,5-dihydropyrrolo[2,3-d]pyridazin-4-one obtained in Example 12-(a) in place of 2-(3-cyclopropoxy-4-difluoromethoxyphenyl)-1-(2-trimethylsilylethoxymethyl)-1,5-dihydropyrrolo[2,3-d]pyridazin-4-one. After completion of the reaction, water was added to the reaction mixture, and the mixture was extracted with ethyl acetate. The organic layer after separation was washed successively with water and then with a saturated aqueous solution of sodium chloride, dried over anhydrous magnesium sulfate and then concentrated under reduced pressure. To the obtained concentrate was added a small amount of tetrahydrofuran to dissolve the concentrate, hexane was then added thereto, and the mixture was subjected to ultrasonic wave treatment whereby the precipitated solid was collected by filtration. The obtained solid was washed with water and dried under reduced pressure to obtain 52 mg of the title compound as a white solid. (Yield: 38%)

Melting point: 141-143° C.

Mass Spectrum (CI, m/z): 392 ($M^+$+1).

$^1$H-NMR Spectrum (DMSO-d$_6$, δ ppm): 0.73-0.90 (m, 4H), 1.12 (t, J=7.0 Hz, 3H), 3.58 (q, J=7.0 Hz, 2H), 3.90-3.99 (m, 1H), 4.78 (s, 2H), 7.10 (t, J=74.5 Hz, 1H), 7.34 (d, J=8.4 Hz, 1H), 7.39 (dd, J=8.4, 1.9 Hz, 1H), 7.92 (d, J=1.9 Hz, 1H), 8.15 (s, 1H), 12.24 (brs, 1H), 12.46 (brs, 1H).

IR Spectrum (KBr, cm$^{-1}$): 1643.

Example 13

3-Cyclobutoxymethyl-2-(3-cyclopropoxy-4-difluoromethoxyphenyl)-1,5-dihydropyrrolo[2,3-d]pyridazin-4-one (Exemplary compound No. 1-102)

13-(a) 3-Cyclobutoxymethyl-2-(3-cyclopropoxy-4-difluoromethoxyphenyl)-1,5-bis(2-trimethylsilylethoxymethyl)-1,5-dihydropyrrolo[2,3-d]pyridazin-4-one Reaction and post treatment were carried out in the same manner as in Example 4-(a) except for using 500 mg (0.895 mmol) of 2-bromo-3-cyclobutoxymethyl-1,5-bis(2-trimethylsilylethoxymethyl)-1,5-dihydropyrrolo[2,3-d]pyridazin-4-one obtained in the following Reference example 27 in place of 2-bromo-3-methyl-1,5-bis(2-trimethylsilylethoxymethyl)-1,5-dihydropyrrolo[2,3-d]pyridazin-4-one, whereby 502 mg of the title compound was obtained as a slightly yellowish oil. (Yield: 83%)

$^1$H-NMR Spectrum (CDCl$_3$, δ ppm): −0.03 (s, 9H), 0.00 (s, 9H), 0.78-0.92 (m, 6H), 0.95-1.03 (m, 2H), 1.41-1.58 (m, 1H), 1.60-1.74 (m, 1H), 1.88-2.04 (m, 2H), 2.12-2.25 (m, 2H), 3.47-3.55 (m, 2H), 3.68-3.76 (m, 2H), 3.77-3.84 (m, 1H), 4.11-4.23 (m, 1H), 4.58 (s, 2H), 5.35 (s, 2H), 5.61 (s, 2H), 6.60 (t, J=74.7 Hz, 1H), 7.17 (dd, J=8.3, 2.0 Hz, 1H), 7.27 (d, J=8.3 Hz, 1H), 7.69 (d, J=2.0 Hz, 1H), 8.19 (s, 1H).

13-(b) 3-Cyclobutoxymethyl-2-(3-cyclopropoxy-4-difluoromethoxyphenyl)-5-(2-trimethylsilylethoxymethyl)-1,5-dihydropyrrolo[2,3-d]pyridazin-4-one Reaction and post treatment were carried out in the same manner as in Example 4-(b) except for using 479 mg (0.696 mmol) of 3-cyclobutoxymethyl-2-(3-cyclopropoxy-4-difluoromethoxyphenyl)-1,5-bis(2-trimethylsilylethoxymethyl)-1,5-dihydropyrrolo[2,3-d]pyridazin-4-one obtained in Example 13-(a) in place of 2-(3-cyclopropoxy-4-difluoromethoxyphenyl)-3-methyl-1,5-bis(2-trimethylsilylethoxymethyl)-1,5-dihydropyrrolo[2,3-d]pyridazin-4-one, whereby 369 mg of the title compound was obtained as a white foam. (Yield: 97%)

Mass Spectrum (CI, m/z): 548 (M$^+$+1).

$^1$H-NMR Spectrum (DMSO-d$_6$, δ ppm): −0.05 (s, 9H), 0.71-0.91 (m, 6H), 1.35-1.51 (m, 1H), 1.53-1.69 (m, 1H), 1.79-1.95 (m, 2H), 2.04-2.17 (m, 2H), 3.60-3.69 (m, 2H), 3.90-3.98 (m, 2H), 4.08-4.20 (m, 2H), 4.69 (s, 1H), 5.43 (s, 1H), 7.10 (t, J=74.3 Hz, 1H), 7.34 (d, J=8.2 Hz, 1H), 7.38 (dd, J=8.2, 1.7 Hz, 1H), 7.93 (d, J=1.7 Hz, 1H), 8.20 (s, 1H), 12.57 (brs, 1H).

13-(c) 3-Cyclobutoxymethyl-2-(3-cyclopropoxy-4-difluoromethoxyphenyl)-1,5-dihydropyrrolo[2,3-d]pyridazin-4-one To 1 ml of N,N-dimethylformamide containing 193 mg (0.352 mmol) of 3-cyclobutoxymethyl-2-(3-cyclopropoxy-4-difluoromethoxyphenyl)-5-(2-trimethylsilylethoxymethyl)-1,5-dihydropyrrolo[2,3-d]pyridazin-4-one obtained in Example 13-(b) were added 38.2 mg (0.440 mmol) of lithium bromide, 10 µl of ethylenediamine and 3 ml of tetrahydrofuran solution containing 1M tetrabutylammonium fluoride, and the mixture was stirred at 100° C. for 8 hours while removing tetrahydrofuran. After completion of the reaction, water was added to the reaction mixture, and the precipitated solid was collected by filtration. The obtained crude solid was applied to silica gel column chromatography (Eluent; chloroform:ethyl acetate=1:0→0:1 (V/V)), the fractions containing the desired compound were concentrated under reduced pressure, and recrystallized from a mixed solvent of ethanol and water to obtain 70 mg of the title compound as a white solid. (Yield: 47%)

Melting point: 95-100° C.

Mass Spectrum (CI, m/z): 418 (M$^+$+1).

$^1$H-NMR Spectrum (DMSO-d$_6$, δ ppm): 0.72-0.90 (m, 4H), 1.34-1.52 (m, 1H), 1.53-1.67 (m, 1H), 1.77-1.94 (m, 2H), 2.04-2.17 (m, 2H), 3.89-3.98 (m, 1H), 4.08-4.19 (m, 1H), 4.69 (s, 2H), 7.09 (t, J=74.3 Hz, 1H), 7.32 (d, J=8.3 Hz, 1H), 7.38 (dd, J=8.3, 1.8 Hz, 1H), 7.93 (d, J=2.0 Hz, 1H), 8.13 (s, 1H), 12.21 (brs, 1H).

IR Spectrum (KBr, cm$^{-1}$): 1646.

Example 14

2-(3-Cyclopropoxy-4-difluoromethoxyphenyl)-3-cyclopropyl-1,5-dihydropyrrolo[2,3-d]pyridazin-4-one (Exemplary compound No. 1-207)

14-(a) 2-(3-Cyclopropoxy-4-difluoromethoxyphenyl)-3-cyclopropyl-1,5-bis(2-trimethylsilylethoxymethyl)-1,5-dihydropyrrolo[2,3-d]pyridazin-4-one Reaction and post treatment were carried out in the same manner as in Example 1-(a) except for using 2.00 g (3.88 mmol) of 2-bromo-3-cyclopropyl-1,5-bis(2-trimethylsilylethoxymethyl)-1,5-dihydropyrrolo[2,3-d]pyridazin-4-one obtained in the following Reference example 28-(b) in place of 2-bromo-1-(2-trimethylsilylethoxymethyl)-1,5-dihydropyrrolo[2,3-d]pyridazin-4-one, whereby 2.72 g of the title compound was obtained as a pale yellowish oil substantially quantitatively.

Mass Spectrum (CI, m/z): 634 (M$^+$+1).

$^1$H-NMR Spectrum (CDCl$_3$, δ ppm): −0.04 (s, 9H), 0.00 (s, 9H), 0.68-0.89 (m, 10H), 0.96-1.03 (m, 2H), 1.96-2.03 (m, 1H), 3.41-3.48 (m, 2H), 3.70-3.82 (m, 3H), 5.27 (s, 2H), 5.60 (s, 2H), 6.61 (t, J=74.7 Hz, 1H), 7.04 (dd, J=8.1, 2.0 Hz, 1H), 7.25 (d, J=8.1 Hz, 1H), 7.44 (d, J=2.0 Hz, 1H), 8.16 (s, 1H).

14-(b) 2-(3-Cyclopropoxy-4-difluoromethoxyphenyl)-3-cyclopropyl-5-(2-trimethylsilylethoxymethyl)-1,5-dihydropyrrolo-[2,3-d]pyridazin-4-one Reaction and post treatment were carried out in the same manner as in Example 4-(b) except for using 2.72 g (containing an amount corresponding to 3.88 mmol) of 2-(3-cyclopropoxy-4-difluoromethoxyphenyl)-3-cyclopropyl-1,5-bis(2-trimethylsilylethoxymethyl)-1,5-dihydropyrrolo[2,3-d]pyridazin-4-one obtained in Example 14-(a) in place of 2-(3-cyclopropoxy-4-difluoromethoxyphenyl)-3-methyl-1,5-bis(2-trimethylsilylethoxymethyl)-1,5-dihydropyrrolo[2,3-d]pyridazin-4-one, whereby 3.95 g of the title compound was obtained as a white solid. (Yield: 93%)

Mass Spectrum (CI, m/z): 504 (M$^+$+1).

$^1$H-NMR Spectrum (CDCl$_3$, δ ppm): −0.02 (s, 9H), 0.66-0.73 (m, 2H), 0.81-0.89 (m, 4H), 0.91-1.01 (m, 4H), 1.99-2.11 (m, 1H), 3.69-3.76 (m, 2H), 3.80-3.87 (m, 1H), 5.59 (s, 2H), 6.57 (t, J=74.8 Hz, 1H), 7.14 (dd, J=8.3, 2.1 Hz, 1H), 7.23 (d, J=8.3 Hz, 1H), 7.64 (d, J=2.1 Hz, 1H), 8.06 (s, 1H), 8.78 (brs, 1H).

IR Spectrum (KBr, cm$^{-1}$): 1630.

14-(c) 2-(3-Cyclopropoxy-4-difluoromethoxyphenyl)-3-cyclopropyl-1,5-dihydropyrrolo[2,3-d]pyridazin-4-one Reaction and post treatment were carried out in the same manner as in Example 4-(c) except for using 1.80 g (3.57 mmol) of 2-(3-cyclopropoxy-4-difluoromethoxyphenyl)-3-cyclopropyl-5-(2-trimethylsilylethoxymethyl)-1,5-dihydropyrrolo[2,3-d]pyridazin-4-one obtained in Example 14-(b) in place of 2-(3-cyclopropoxy-4-difluoromethoxyphenyl)-3-methyl-5-(2-trimethylsilylethoxymethyl)-1,5-dihydropyrrolo-[2,3-d]pyridazin-4-one, whereby 1.21 g of the title compound was obtained as a white solid. (Yield: 91%)

Melting point: 248-249° C.

Mass Spectrum (CI, m/z): 374 ($M^+$+1).

$^1$H-NMR Spectrum (DMSO-$d_6$, δ ppm): 0.72-0.92 (m, 8H), 1.95-2.07 (m, 1H), 3.96-4.04 (m, 1H), 7.10 (t, J=74.3 Hz, 1H), 7.26-7.33 (m, 2H), 7.76 (s, 1H), 8.05 (s, 1H), 12.08 (brs, 1H), 12.17 (brs, 1H).

IR Spectrum (KBr, $cm^{-1}$): 1642.

Example 15

2-(3-Cyclopropoxy-4-difluoromethoxyphenyl)-3-cyclopropylmethyl-1,5-dihydropyrrolo[2,3-d]pyridazin-4-one (Exemplary compound No. 1-208)

15-(a) 2-(3-Cyclopropoxy-4-difluoromethoxyphenyl)-3-formyl-1,5-bis(2-trimethylsilylethoxymethyl)-1,5-dihydropyrrolo-[2,3-d]pyridazin-4-one Reaction and post treatment were carried out in the same manner as in Example 4-(a) except for using 7.82 g (15.6 mmol) of 2-bromo-3-formyl-1,5-bis(2-trimethylsilylethoxymethyl)-1,5-dihydropyrrolo[2,3-d]pyridazin-4-one obtained in the following Reference example 29 in place of 2-bromo-3-methyl-1,5-bis(2-trimethylsilylethoxymethyl)-1,5-dihydropyrrolo[2,3-d]pyridazin-4-one, whereby 5.57 g of the title compound was obtained as a brown solid substantially quantitatively.

Mass Spectrum (CI, m/z): 622 ($M^+$+1).

$^1$H-NMR Spectrum (CDCl$_3$, δ ppm): −0.03 (s, 9H), 0.01 (s, 9H), 0.75-0.92 (m, 6H), 0.96-1.05 (m, 2H), 3.41-3.51 (m, 2H), 3.71-3.84 (m, 3H), 5.36 (s, 2H), 5.65 (s, 2H), 6.61 (t, J=74.5 Hz, 1H), 7.05 (dd, J=8.3, 2.1 Hz, 1H), 7.27 (d, J=8.3 Hz, 1H), 7.47 (d, J=2.1 Hz, 1H), 8.28 (s, 1H), 10.72 (s, 1H).

IR Spectrum (KBr, $cm^{-1}$): 1693.

15-(b) 2-(3-Cyclopropoxy-4-difluoromethoxyphenyl)-3-cyclopropylhydroxymethyl-1,5-bis(2-trimethylsilylethoxymethyl)-1,5-dihydropyrrolo[2,3-d]pyridazin-4-one To 50 ml of tetrahydrofuran solution containing 10.3 g (116 mmol) of 2-(3-cyclopropoxy-4-difluoromethoxyphenyl)-4-formyl-1,5-bis(2-trimethylsilylethoxymethyl)-1,5-dihydropyrrolo[2,3-d]pyridazin-4-one obtained in Example 15-(a) was added 47 ml of tetrahydrofuran solution containing 0.5M cyclopropyl magnesium bromide by dividing it into 5 times, then, the mixture was stirred at room temperature for 2 hours. After completion of the reaction, the reaction mixture was poured into a saturated aqueous solution of ammonium chloride, water was added thereto and the mixture was extracted with ethyl acetate. The organic layer after separation was washed successively with water and then with a saturated aqueous solution of sodium chloride, dried over anhydrous magnesium sulfate and then concentrated under reduced pressure to obtain 11.6 g of the title compound as a yellowish oil substantially quantitatively.

Mass Spectrum (CI, m/z): 664 ($M^+$+1).

$^1$H-NMR Spectrum (CDCl$_3$, δ ppm): −0.04 (s, 9H), 0.00 (s, 9H), 0.25-0.36 (m, 1H), 0.37-0.47 (m, 1H), 0.47-0.58 (m, 1H), 0.75-0.89 (m, 7H), 0.97-1.04 (m, 2H), 1.29-1.41 (m, 1H), 3.34-3.50 (m, 2H), 3.71-3.81 (m, 3H), 3.96 (dd, J=11.6, 7.9 Hz, 1H), 5.25 (d, J=10.7 Hz, 1H), 5.31 (d, J=10.7 Hz, 1H), 5.64 (d, J=9.8 Hz, 1H), 5.68 (d, J=9.8 Hz, 1H), 6.05 (d, J=11.7 Hz, 1H), 6.60 (t, J=74.5 Hz, 1H), 6.99 (dd, J=8.1, 2.0 Hz, 1H), 7.26 (d, J=8.1 Hz, 1H), 7.37 (d, J=2.0 Hz, 1H), 8.28 (s, 1H).

IR Spectrum (neat, $cm^{-1}$): 1638.

15-(c) 2-(3-Cyclopropoxy-4-difluoromethoxyphenyl)-3-cyclopropylmethyl-1,5-bis(2-trimethylsilylethoxymethyl)-1,5-dihydropyrrolo[2,3-d]pyridazin-4-one To 200 ml of dichloromethane solution containing 11.6 g (containing an amount corresponding to 16.6 mmol) of 2-(3-cyclopropoxy-4-difluoromethoxyphenyl)-3-cyclopropylhydroxymethyl-1,5-bis(2-trimethylsilylethoxymethyl)-1,5-dihydropyrrolo[2,3-d]pyridazin-4-one obtained in Example 15-(b) was added 3.35 ml (21.0 mmol) of triethylsilane at −15° C. Then, 5 ml of trifluoroacetic acid was gradually added dropwise to the mixture at the same temperature, and after completion of dropwise addition, a temperature of the mixture was gradually raised to room temperature, and the mixture was stirred at room temperature for further 1 hour. After completion of the reaction, the reaction mixture was poured into a saturated aqueous solution of sodium hydrogencarbonate, the organic layer after separating the liquids was dried over anhydrous magnesium sulfate and then concentrated under reduced pressure. The obtained residue was applied to silica gel column chromatography (Eluent; hexane:ethyl acetate=4:1 (V/V)), and the fractions containing the desired compound were concentrated under reduced pressure to obtain 6.14 g of the title compound as a yellowish oil. (Yield: 57%)

Mass Spectrum (CI, m/z): 648 ($M^+$+1).

$^1$H-NMR Spectrum (CDCl$_3$, δ ppm): −0.05 (s, 9H), 0.00 (s, 9H), 0.05-0.11 (m, 2H), 0.27-0.35 (m, 2H), 0.78-0.88 (m, 6H), 0.96-1.04 (m, 2H), 1.05-1.16 (m, 1H), 2.74 (d, J=6.8 Hz, 2H), 3.38-3.46 (m, 2H), 3.70-3.82 (m, 3H), 5.27 (s, 2H), 5.61 (s, 2H), 6.60 (t, J=74.7 Hz, 1H), 6.98 (dd, J=8.2, 2.0 Hz, 1H), 7.25 (d, J=8.2 Hz, 1H), 7.35 (d, J=2.0 Hz, 1H), 8.19 (s, 1H).

IR Spectrum (neat, $cm^{-1}$): 1665.

15-(d) 2-(3-Cyclopropoxy-4-difluoromethoxyphenyl)-3-cyclopropylmethyl-5-(2-trimethylsilylethoxymethyl)-1,5-dihydropyrrolo[2,3-d]pyridazin-4-one Reaction and post treatment were carried out in the same manner as in Example 4-(b) except for using 6.14 g (9.48 mmol) of 2-(3-cyclopropoxy-4-difluoromethoxyphenyl)-3-cyclopropylmethyl-1,5-bis(2-trimethylsilylethoxymethyl)-1,5-dihydropyrrolo[2,3-d]pyridazin-4-one obtained in Example 15-(c) in place of 2-(3-cyclopropoxy-4-difluoromethoxyphenyl)-3-methyl-1,5-bis(2-trimethylsilylethoxymethyl)-1,5-dihydropyrrolo[2,3-d]pyridazin-4-one, whereby 3.41 g of the title compound was obtained as a white solid. (Yield: 70%)

Mass Spectrum (CI, m/z): 518 ($M^+$+1).

$^1$H-NMR Spectrum (CDCl$_3$, δ ppm): −0.02 (s, 9H), 0.18-0.25 (m, 2H), 0.31-0.39 (m, 2H), 0.83-0.87 (m, 4H), 0.92-1.00 (m, 2H), 1.10-1.21 (m, 1H), 2.99 (d, J=6.6 Hz, 2H), 3.68-3.76 (m, 2H), 3.79-3.86 (m, 1H), 5.59 (s, 2H), 6.56 (t, J=74.8 Hz, 1H), 7.09 (dd, J=8.3, 2.1 Hz, 1H), 7.23 (d, J=8.3 Hz, 1H), 7.55 (d, J=2.1 Hz, 1H), 8.09 (s, 1H), 9.04 (brs, 1H).

IR Spectrum (KBr, $cm^{-1}$): 1634.

15-(e) 2-(3-Cyclopropoxy-4-difluoromethoxyphenyl)-3-cyclopropylmethyl-1,5-dihydropyrrolo[2,3-d]pyridazin-4-one Reaction and post treatment were carried out in the same manner as in Example 6-(c) except for using 3.40 g (3.13 mmol) of 2-(3-cyclopropoxy-4-difluoromethoxyphenyl)-3-cyclopropylmethyl-5-(2-trimethylsilylethoxymethyl)-1,5-dihydropyrrolo[2,3-d]pyridazin-4-one obtained in Example 15-(d) in place of 2-(3-cyclopropoxy-4-difluoromethoxyphenyl)-3-propyl-5-(2-trimethylsilylethoxymethyl)-1,5-dihydropyrrolo[2,3-d]pyridazin-4-one, whereby 2.50 g of the title compound was obtained as a white solid. (Yield: 93%)

Melting point: 204-206° C.
Mass Spectrum (CI, m/z): 387 (M$^+$+1).
$^1$H-NMR Spectrum (DMSO-d$_6$, δ ppm): 0.16-0.35 (m, 4H), 0.73-0.90 (m, 4H), 1.05-1.16 (m, 1H), 2.95 (d, J=6.3 Hz, 2H), 3.96-4.04 (m, 1H), 7.10 (t, J=74.3 Hz, 1H), 7.24 (dd, J=8.4, 2.0 Hz, 1H), 7.32 (d, J=8.4 Hz, 1H), 7.67 (d, J=2.0 Hz, 1H), 8.09 (s, 1H), 12.13 (brs, 1H), 12.18 (brs, 1H).
IR Spectrum (KBr, cm$^{-1}$): 1634.

Example 16

2-(3-Cyclopropoxy-4-difluoromethoxyphenyl)-3-ethynyl-1,5-dihydropyrrolo[2,3-d]pyridazin-4-one (Exemplary compound No. 1-231)

16-(a) 2-(3-Cyclopropoxy-4-difluoromethoxyphenyl)-3-triethylsilylethynyl-1-(2-trimethylsilylethoxymethyl)-1,5-dihydropyrrolo[2,3-d]pyridazin-4-one Reaction and post treatment were carried out in the same manner as in Example 1-(a) except for using 42 mg (0.095 mmol) of 2-chloro-3-triethylsilylethynyl-1-(2-trimethylsilylethoxymethyl)-1,5-dihydropyrrolo[2,3-d]pyridazin-4-one obtained in the following Reference example 30-(c) in place of 2-bromo-1-(2-trimethylsilylethoxymethyl)-1,5-dihydropyrrolo[2,3-d]pyridazin-4-one, whereby 36 mg of the title compound was obtained as a yellow solid. (Yield: 64%)

Mass Spectrum (CI, m/z): 602 (M$^+$+1).
$^1$H-NMR Spectrum (CDCl$_3$, δ ppm): −0.03 (s, 9H), 0.61 (q, J=7.8 Hz, 6H), 0.79-0.91 (m, 6H), 0.97 (t, J=7.8 Hz, 9H), 3.44-3.52 (m, 2H), 3.77-3.84 (m, 1H), 5.40 (s, 2H), 6.58 (t, J=74.7 Hz, 1H), 7.23 (dd, J=8.3, 1.7 Hz, 1H), 7.27 (d, J=8.3 Hz, 1H), 7.61 (d, J=1.7 Hz, 1H), 8.16 (s, 1H), 9.79 (brs, 1H).
IR Spectrum (KBr, cm$^{-1}$): 1663.

16-(b) 2-(3-Cyclopropoxy-4-difluoromethoxyphenyl)-3-ethynyl-1,5-dihydropyrrolo[2,3-d]pyridazin-4-one Reaction was carried out in the same manner as in Example 4-(b) except for using 32 mg (0.053 mmol) of 2-(3-cyclopropoxy-4-difluoromethoxyphenyl)-3-triethylsilylethynyl-1-(2-trimethylsilylethoxymethyl)-1,5-dihydropyrrolo[2,3-d]pyridazin-4-one obtained in Example 16-(a) in place of 2-(3-cyclopropoxy-4-difluoromethoxyphenyl)-3-methyl-1,5-bis(2-trimethylsilylethoxymethyl)-1,5-dihydropyrrolo[2,3-d]pyridazin-4-one. After completion of the reaction, water was added to the reaction mixture, and the mixture was extracted with ethyl acetate. The organic layer after separation was washed successively with water and then with a saturated aqueous solution of sodium chloride, dried over anhydrous magnesium sulfate, and then concentrated under reduced pressure. To the obtained concentrate were added methanol and water, and the mixture was subjected to ultrasonic wave treatment and the precipitated solid was collected by filtration. The obtained solid was washed successively with water and then with diethyl ether and dried under reduced pressure to obtain 10 mg of the title compound as a beige solid. (Yield: 51%)

Melting point: >300° C.
Mass Spectrum (CI, m/z): 358 (M$^+$+1).
$^1$H-NMR Spectrum (DMSO-d$_6$, δ ppm): 0.72-0.81 (m, 2H), 0.82-0.93 (m, 2H), 3.90-3.98 (m, 1H), 4.35 (s, 1H), 7.11 (t, J=74.2 Hz, 1H), 7.33 (d, J=8.4 Hz, 1H), 7.57 (dd, J=8.4, 2.0 Hz, 1H), 8.13 (s, 1H), 8.30 (d, J=2.0 Hz, 1H), 12.31 (brs, 1H), 12.73 (brs, 1H).

Example 17

2-(3-Cyclopropoxy-4-difluoromethoxyphenyl)-3-phenyl-1,5-dihydropyrrolo[2,3-d]pyridazin-4-one (Exemplary compound No. 1-245)

17-(a) 2-(3-Cyclopropoxy-4-difluoromethoxyphenyl)-3-phenyl-1-(2-trimethylsilylethoxymethyl)-1,5-dihydropyrrolo[2,3-d]-pyridazin-4-one Reaction and post treatment were carried out in the same manner as in Example 1-(a) except for using 144 mg (0.383 mmol) of 2-chloro-3-phenyl-1-(2-trimethylsilylethoxymethyl)-1,5-dihydropyrrolo[2,3-d]pyridazin-4-one obtained in the following Reference example 31 in place of 2-bromo-1-(2-trimethylsilylethoxymethyl)-1,5-dihydropyrrolo[2,3-d]pyridazin-4-one, whereby 91 mg of the title compound was obtained as a yellowish oil. (Yield: 44%)

Mass Spectrum (CI, m/z): 540 (M$^+$+1).
$^1$H-NMR Spectrum (CDCl$_3$, δ ppm): −0.02 (s, 9H), 0.53-0.57 (m, 4H), 0.87-0.94 (m, 2H), 3.41-3.49 (m, 1H), 3.50-3.57 (m, 2H), 5.43 (s, 2H), 6.55 (t, J=74.7 Hz, 1H), 7.01 (dd, J=8.3, 2.1 Hz, 1H), 7.12 (d, J=2.1 Hz, 1H), 7.19 (d, J=8.3 Hz, 1H), 7.21-7.34 (m, 5H), 8.25 (s, 1H), 9.81 (brs, 1H).

17-(b) 2-(3-Cyclopropoxy-4-difluoromethoxyphenyl)-3-phenyl-1,5-dihydropyrrolo[2,3-d]pyridazin-4-one Reaction was carried out in the same manner as in Example 1-(b) except for using 86 mg (0.16 mmol) of 2-(3-cyclopropoxy-4-difluoromethoxyphenyl)-3-phenyl-1-(2-trimethylsilylethoxymethyl)-1,5-dihydropyrrolo[2,3-d]pyridazin-4-one obtained in Example 17-(a) in place of 2-(3-cyclopropoxy-4-difluoromethoxyphenyl)-1-(2-trimethylsilylethoxymethyl)-1,5-dihydropyrrolo[2,3-d]pyridazin-4-one. After completion of the reaction, water was added to the reaction mixture, and the precipitated solid was collected by filtration. The obtained solid was applied to silica gel column chromatography (Eluent; ethyl acetate), and the fractions containing the desired compound were concentrated under reduced pressure to obtain 14 mg of the title compound as a pale beige solid. (Yield: 21%)

Melting point: 138-143° C.
Mass Spectrum (CI, m/z): 410 (M$^+$+1).
$^1$H-NMR Spectrum (DMSO-d$_6$, δ ppm): 0.45-0.53 (m, 4H), 3.44-3.52 (m, 1H), 7.05 (t, J=74.2 Hz, 1H), 7.10 (dd, J=8.4, 2.1 Hz, 1H), 7.21 (d, J=2.1 Hz, 1H), 7.21 (d, J=8.4 Hz, 1H), 7.27-7.37 (m, 5H), 8.16 (s, 1H), 12.19 (brs, 1H), 12.53 (brs, 1H).
IR Spectrum (KBr, cm$^{-1}$): 1641.

Example 18

2-(3-Cyclopropoxy-4-difluoromethoxyphenyl)-3-(4-pyrazolyl)-1,5-dihydropyrrolo[2,3-d]pyridazin-4-one (Exemplary compound No. 1-334)

18-(a) 2-(3-Cyclopropoxy-4-difluoromethoxyphenyl)-1,5-bis(2-trimethylsilylethoxymethyl)-3-[1-(2-trimethylsilylethoxymethyl)-4-pyrazolyl]-1,5-dihydropyrrolo[2,3-d]pyridazin-4-one Reaction and post treatment were carried out in the same manner as in Example 4-(a) except for using 185 mg (0.276 mmol) of 2-bromo-1,5-bis(2-trimethylsilylethoxymethyl)-3-[1-(2-trimethylsilylethoxymethyl)-4-pyrazolyl]-1,5-dihydropyrrolo[2,3-d]pyridazin-4-one obtained in the following Reference example 32-(c) in place of 2-bromo-3-methyl-1,5-bis(2-trimethylsilylethoxymethyl)-1,5-dihydropyrrolo[2,3-d]pyridazin-4-one, whereby 173 mg of the title compound was obtained as a yellowish oil. (Yield: 83%)

$^1$H-NMR Spectrum (CDCl$_3$, δ ppm): −0.04 (s, 9H), −0.03 (s, 9H), 0.01 (s, 9H), 0.69-0.94 (m, 8H), 0.96-1.06 (m, 2H), 3.42-3.50 (m, 2H), 3.53-3.61 (m, 2H), 3.64-3.73 (m, 1H), 3.70-3.78 (m, 2H), 5.31 (s, 2H), 5.37 (s, 2H), 5.61 (s, 2H), 6.60 (t, J=74.6 Hz, 1H), 7.00 (dd, J=8.1, 2.0 Hz, 1H), 7.10 (d, J=0.5 Hz, 1H), 7.26 (d, J=8.1 Hz, 1H), 7.34 (d, J=2.0 Hz, 1H), 8.22 (s, 1H), 8.42 (d, J=0.5 Hz, 1H).

IR Spectrum (neat, cm$^{-1}$): 1662.

18-(b) 2-(3-Cyclopropoxy-4-difluoromethoxyphenyl)-3-(4-pyrazolyl)-5-(2-trimethylsilylethoxymethyl)-1,5-dihydropyrrolo[2,3-d]pyridazin-4-one Reaction and post treatment were carried out in the same manner as in Example 4-(b) except for using 190 mg (0.241 mmol) of 2-(3-cyclopropoxy-4-difluoromethoxyphenyl)-1,5-bis(2-trimethylsilylethoxymethyl)-3-[1-(2-trimethylsilylethoxymethyl)-1H-pyrazol-4-yl]-1,5-dihydropyrrolo[2,3-d]pyridazin-4-one obtained in Example 18-(a) in place of 2-(3-cyclopropoxy-4-difluoromethoxyphenyl)-3-methyl-1,5-bis(2-trimethylsilylethoxymethyl)-1,5-dihydropyrrolo[2,3-d]pyridazin-4-one, whereby 101 mg of the title compound was obtained as a white solid. (Yield: 79%)

Mass Spectrum (CI, m/z): 530 (M$^+$+1).

$^1$H-NMR Spectrum (CDCl$_3$, δ ppm): −0.01 (s, 9H), 0.66-0.75 (m, 4H), 0.94-1.01 (m, 2H), 3.59-3.66 (m, 1H), 3.68-3.76 (m, 2H), 5.58 (s, 2H), 6.56 (t, J=74.7 Hz, 1H), 7.06 (dd, J=8.3, 2.0 Hz, 1H), 7.20 (d, J=8.3 Hz, 1H), 7.41 (d, J=2.0 Hz, 1H), 7.86 (s, 2H), 8.11 (s, 1H), 9.08 (brs, 1H).

IR Spectrum (KBr, cm$^{-1}$): 1639.

18-(c) 2-(3-Cyclopropoxy-4-difluoromethoxyphenyl)-3-(4-pyrazolyl)-1,5-dihydropyrrolo[2,3-d]pyridazin-4-one Reaction and post treatment were carried out in the same manner as in Example 6-(c) except for using 100 mg (0.189 mmol) of 2-(3-cyclopropoxy-4-difluoromethoxyphenyl)-3-(4-pyrazolyl)-5-(2-trimethylsilylethoxymethyl)-1,5-dihydropyrrolo[2,3-d]pyridazin-4-one obtained in Example 18-(b) in place of 2-(3-cyclopropoxy-4-difluoromethoxyphenyl)-3-propyl-5-(2-trimethylsilylethoxymethyl)-1,5-dihydropyrrolo[2,3-d]pyridazin-4-one, whereby 76 mg of the title compound was obtained as a pale yellowish solid substantially quantitatively.

Melting point: 294-297° C.

Mass Spectrum (CI, m/z): 400 (M$^+$+1).

$^1$H-NMR Spectrum (DMSO-d$_6$, δ ppm): 0.60-0.70 (m, 4H), 3.69-3.78 (m, 1H), 7.09 (t, J=74.3 Hz, 1H), 7.16 (dd, J=8.3, 2.0 Hz, 1H), 7.26 (d, J=8.3 Hz, 1H), 7.42 (brs, 1H), 7.50 (d, J=2.0 Hz, 1H), 7.92 (brs, 1H), 8.11 (s, 1H), 12.16 (brs, 1H), 12.39 (brs, 1H), 12.73 (brs, 1H).

IR Spectrum (KBr, cm$^{-1}$): 1642.

Example 19

3-Benzyl-2-(3-cyclopropoxy-4-difluoromethoxyphenyl)-1,5-dihydropyrrolo[2,3-d]pyridazin-4-one (Exemplary compound No. 1-378)

19-(a) 3-Benzyl-1-benzyloxymethyl-2-(3-cyclopropoxy-4-difluoromethoxyphenyl)-5-(2-trimethylsilylethoxymethyl)-5-1,5-dihydropyrrolo[2,3-d]pyridazin-4-one Reaction and post treatment were carried out in the same manner as in Example 4-(a) except for using 278 mg (0.501 mmol) of 3-benzyl-1-benzyloxymethyl-2-bromo-5-(2-trimethylsilylethoxymethyl)-1,5-dihydropyrrolo[2,3-d]pyridazin-4-one obtained in the following Reference example 33-(h) in place of 2-bromo-3-methyl-1,5-bis(2-trimethylsilylethoxymethyl)-1,5-dihydropyrrolo[2,3-d]pyridazin-4-one, whereby 278 mg of the title compound was obtained as a colorless oil. (Yield: 83%)

Mass Spectrum (CI, m/z): 674 (M$^+$+1).

$^1$H-NMR Spectrum (CDCl$_3$, δ ppm): 0.00 (s, 9H), 0.47-0.55 (m, 2H), 0.62-0.69 (m, 2H), 0.96-1.03 (m, 2H), 3.40-3.48 (m, 1H), 3.70-3.77 (m, 2H), 4.26 (s, 2H), 4.47 (s, 2H), 5.36 (s, 2H), 5.60 (s, 2H), 6.57 (t, J=74.7 Hz, 1H), 6.93 (dd, J=8.2, 2.1 Hz, 1H), 7.05-7.34 (m, 12H), 8.13 (s, 1H).

19-(b) 3-Benzyl-1-benzyloxymethyl-2-(3-cyclopropoxy-4-difluoromethoxyphenyl)-1,5-dihydropyrrolo[2,3-d]pyridazin-4-one To 278 mg (0.413 mmol) of 3-benzyl-1-benzyloxymethyl-2-(3-cyclopropoxy-4-difluoromethoxyphenyl)-5-(2-trimethylsilylethoxymethyl)-1,5-dihydropyrrolo[2,3-d]pyridazin-4-one obtained in Example 19-(a) was added 3.3 ml of 1,4-dioxane solution containing 4N hydrogen chloride, and the mixture was stirred at room temperature for 3 hours. After completion of the reaction, the reaction mixture was concentrated under reduced pressure, to the obtained solid were added 8.6 ml of methanol and 4.3 ml of 28% aqueous ammonia, and the mixture was stirred at room temperature for 1 hour. Then, the solution was concentrated under reduced pressure, water was added to the obtained concentrate, and the precipitated solid was collected by filtration. The obtained solid was washed with water and dried under reduced pressure to obtain 198 mg of the title compound as a white solid. (Yield: 88%)

Mass Spectrum (CI, m/z): 544 (M$^+$+1).

$^1$H-NMR Spectrum (CDCl$_3$, δ ppm): 0.49-0.57 (m, 2H), 0.64-0.71 (m, 2H), 3.43-3.50 (m, 1H), 4.24 (s, 2H), 4.46 (s, 2H), 5.37 (s, 2H), 6.58 (t, J=74.7 Hz, 1H), 6.93 (dd, J=8.3, 2.0 Hz, 1H), 7.06-7.34 (m, 12H), 8.10 (s, 1H), 9.79 (brs, 1H).

19-(c) 3-Benzyl-2-(3-cyclopropoxy-4-difluoromethoxyphenyl)-1,5-dihydropyrrolo[2,3-d]pyridazin-4-one To 20 ml of ethanol solution containing 198 mg (0.364 mmol) of 3-benzyl-1-benzyloxymethyl-2-(3-cyclopropoxy-4-difluoromethoxyphenyl)-1,5-dihydropyrrolo[2,3-d]pyridazin-4-one obtained in Example 19-(b), then, 28 mg of 5% palladium-active carbon and 0.36 ml of 1N hydrochloric acid were added thereto, and the mixture was stirred under 1 atm hydrogen atmosphere at 50° C. for 3.8 hours. After completion of the reaction, the reaction mixture was filtered, the filtrate was concentrated under reduced pressure, 8.6 ml of methanol and 4.3 ml of 28% aqueous ammonia were added to the obtained solid and the mixture was stirred at room temperature for 1 hour. Then, the solution was concentrated under reduced pressure, water was added to the obtained concentrate, and the precipitated solid was collected by filtration. The obtained solid was washed successively with water and then with diisopropyl ether and dried under reduced pressure to obtain 128 mg of the title compound as a white solid. (Yield: 84%)

Melting point: 215-217° C.

Mass Spectrum (CI, m/z): 424 ($M^+$+1).

$^1$H-NMR Spectrum (DMSO-$d_6$, δ ppm): 0.43-0.61 (m, 4H), 3.60-3.67 (m, 1H), 4.40 (s, 2H), 7.05 (t, J=74.3 Hz, 1H), 7.09-7.30 (m, 7H), 7.38 (d, J=2.2 Hz, 1H), 8.15 (s, 1H), 12.18 (brs, 1H), 12.34 (brs, 1H).

IR Spectrum (KBr, $cm^{-1}$): 1637.

Example 20

2-(3-Cyclopropoxy-4-difluoromethoxyphenyl)-3-hydroxyphenylmethyl-1,5-dihydropyrrolo[2,3-d]pyridazin-4-one (Exemplary compound No. 1-476)

20-(a) 2-(3-Cyclopropoxy-4-difluoromethoxyphenyl)-3-hydroxyphenylmethyl-1-(2-trimethylsilylethoxymethyl)-1,5-dihydropyrrolo[2,3-d]pyridazin-4-one Reaction and post treatment were carried out in the same manner as in Example 1-(a) except for using 79 mg (0.18 mmol) of 2-bromo-3-hydroxyphenylmethyl-1-(2-trimethylsilylethoxymethyl)-1,5-dihydropyrrolo[2,3-d]pyridazin-4-one obtained in the following Reference example 34 in place of 2-bromo-1-(2-trimethylsilylethoxymethyl)-1,5-dihydropyrrolo[2,3-d]pyridazin-4-one, whereby 51 mg of the title compound was obtained as a pale yellowish oil. (Yield: 50%)

Mass Spectrum (EI, m/z): 569 ($M^+$).

20-(b) 2-(3-Cyclopropoxy-4-difluoromethoxyphenyl)-3-hydroxyphenylmethyl-1,5-dihydropyrrolo[2,3-d]pyridazin-4-one Reaction was carried out in the same manner as in Example 1-(b) except for using 51 mg (0.090 mmol) of 2-(3-cyclopropoxy-4-difluoromethoxyphenyl)-3-hydroxyphenylmethyl-1-(2-trimethylsilylethoxymethyl)-1,5-dihydropyrrolo-[2,3-d]pyridazin-4-one obtained in Example 20-(a) in place of 2-(3-cyclopropoxy-4-difluoromethoxyphenyl)-1-(2-trimethylsilylethoxymethyl)-1,5-dihydropyrrolo[2,3-d]pyridazin-4-one. After completion of the reaction, water was added to the reaction mixture, and the mixture was extracted with a mixed solvent (chloroform:methanol=9:1 (V/V)). The organic layer after separating the liquids was dried over anhydrous magnesium sulfate and then concentrated under reduced pressure. The obtained residue was applied to silica gel column chromatography (Eluent; hexane:ethyl acetate=9:1 (V/V)), and the fractions containing the desired compound were concentrated under reduced pressure to obtain 17 mg of the title compound as a white solid. (Yield: 42%)

Melting point: >3000C.

Mass Spectrum (EI, m/z): 439 ($M^+$).

$^1$H-NMR Spectrum (DMSO-$d_6$, δ ppm): 0.26-0.73 (m, 4H), 3.61-3.69 (m, 1H), 5.90 (d, J=11.0 Hz, 1H), 7.07 (t, J=73.7 Hz, 1H), 7.12 (d, J=11.0 Hz, 1H), 7.14 (dd, J=8.3, 2.0 Hz, 1H), 7.17-7.34 (m, 7H), 8.31 (s, 1H), 12.75 (brs, 1H).

Example 21

2-(3-Cyclopropoxy-4-difluoromethoxyphenyl)-3-phenethyl-1,5-dihydropyrrolo[2,3-d]pyridazin-4-one (Exemplary compound No. 1-460)

21-(a) 2-(3-Cyclopropoxy-4-difluoromethoxyphenyl)-3-phenethyl-1,5-bis(2-trimethylsilylethoxymethyl)-1,5-dihydropyrrolo[2,3-d]pyridazin-4-one Reaction and post treatment were carried out in the same manner as in Example 4-(a) except for using 602 mg (1.04 mmol) of 2-bromo-3-phenethyl-1,5-bis(2-trimethylsilylethoxymethyl)-1,5-dihydropyrrolo[2,3-d]pyridazin-4-one obtained in the following Reference example 35-(b) in place of 2-bromo-3-methyl-1,5-bis(2-trimethylsilylethoxymethyl)-1,5-dihydropyrrolo[2,3-d]pyridazin-4-one, whereby 509 mg of the title compound was obtained as an orange oil. (Yield: 73%)

Mass Spectrum (CI, m/z): 698 ($M^+$+1).

$^1$H-NMR Spectrum (CDCl$_3$, δ ppm): −0.05 (s, 9H), 0.01 (s, 9H), 0.75-0.86 (m, 6H), 0.98-1.06 (m, 2H), 2.95-3.10 (m, 4H), 3.34-3.42 (m, 2H), 3.69-3.81 (m, 3H), 5.24 (s, 2H), 5.65 (s, 2H), 6.56 (dd, J=8.2, 2.1 Hz, 1H), 6.58 (t, J=75.1 Hz, 1H), 6.99-7.03 (m, 2H), 7.08-7.20 (m, 5H), 8.20 (s, 1H).

21-(b) 2-(3-cyclopropoxy-4-difluoromethoxyphenyl)-3-phenethyl-5-(2-trimethylsilylethoxymethyl)-1,5-dihydropyrrolo[2,3-d]pyridazin-4-one Reaction and post treatment were carried out in the same manner as in Example 4-(b) except for using 509 mg (0.729 mmol) of 2-(3-cyclopropoxy-4-difluoromethoxyphenyl)-3-phenethyl-1,5-bis(2-trimethylsilylethoxymethyl)-1,5-dihydropyrrolo[2,3-d]pyridazin-4-one obtained in Example 21-(a) in place of 2-(3-cyclopropoxy-4-difluoromethoxyphenyl)-3-methyl-1,5-bis(2-trimethylsilylethoxymethyl)-1,5-dihydropyrrolo[2,3-d]pyridazin-4-one, whereby 365 mg of the title compound was obtained as a pale yellowish foam. (Yield: 88%)

Mass Spectrum (CI, m/z): 568 ($M^+$+1).

$^1$H-NMR Spectrum (CDCl$_3$, δ ppm): 0.00 (s, 9H), 0.76-0.84 (m, 4H), 0.97-1.04 (m, 2H), 3.06 (dd, J=9.4, 6.4 Hz, 2H), 3.27 (dd, J=9.4, 6.4 Hz, 2H), 3.67-3.80 (m, 3H), 5.63 (s, 2H), 6.54 (t, J=74.8 Hz, 1H), 6.80 (dd, J=8.1, 2.2 Hz, 1H), 7.07-7.22 (m, 6H), 7.28 (d, J=2.2 Hz, 1H), 8.09 (s, 1H), 8.55 (brs, 1H).

21-(c) 2-(3-Cyclopropoxy-4-difluoromethoxyphenyl)-3-phenethyl-1,5-dihydropyrrolo[2,3-d]pyridazin-4-one Reaction was carried out in the same manner as in Example 6-(c) except for using 364 mg (0.641 mmol) of 2-(3-cyclopropoxy-4-difluoromethoxyphenyl)-3-phenethyl-5-(2-trimethylsilylethoxymethyl)-1,5-dihydropyrrolo[2,3-d]pyridazin-4-one obtained in Example 21-(b) in place of 2-(3-cyclopropoxy-4-difluoromethoxyphenyl)-5-(2-trimethylsilylethoxymethyl)-3-propyl-1,5-dihydropyrrolo[2,3-d]pyridazin-4-one. After completion of the reaction, the solid was collected by filtration from the reaction suspension and washed with 1,4-dioxane. To the obtained solid were added methanol and 28% aqueous ammonia, and the mixture was stirred at room temperature for 16 hours. Then, water was added to the solution, and the precipitated solid was collected by filtration. The obtained solid was washed with water and dried under reduced pressure to obtain 224 mg of the title compound as a white solid. (Yield: 80%)

Melting point: 199-201° C.

Mass Spectrum (CI, m/z): 438 ($M^+$+1).

$^1$H-NMR Spectrum (DMSO-$d_6$, δ ppm): 0.70-0.79 (m, 4H), 2.99 (dd, J=10.2, 5.9 Hz, 2H), 3.18 (dd, J=10.2, 5.9 Hz, 2H), 3.91-3.98 (m, 1H), 7.05-7.30 (m, 7H), 7.08 (t, J=74.3 Hz, 1H), 7.49 (d, J=2.0 Hz, 1H), 8.11 (s, 1H), 12.18 (brs, 1H) 12.19 (brs, 1H).

IR Spectrum (KBr, $cm^{-1}$): 1641.

Example 22

2-(3-Cyclopropoxy-4-difluoromethoxyphenyl)-3-(2-fluorobenzyl)-1,5-dihydropyrrolo[2,3-d]pyridazin-4-one (Exemplary compound No. 1-379)

22-(a) 1-Benzyloxymethyl-2-(3-cyclopropoxy-4-difluoromethoxyphenyl)-3-(2-fluorobenzyl)-1,5-dihydropyrrolo[2,3-d]pyridazin-4-one To 46 ml of ethylene glycol solution containing 5.01 g (8.44 mmol) of ethyl 1-benzyloxymethyl-5-(3-cyclopropoxy-4-difluoromethoxyphenyl)-4-(2-fluorobenzyl)-2-formyl-1H-pyrrol-3-carboxylate obtained in the following Reference example 36-(f) was added 2.13 ml (42.5 mmol) of hydrazine monohydrate at 60° C., and then the mixture was stirred at 130° C. for 8.5 hours. After completion of the reaction, water was added to the reaction mixture, and the mixture was extracted with ethyl acetate. The organic layer after separation was washed successively with water and then with a saturated aqueous solution of sodium chloride, dried over anhydrous magnesium sulfate and then concentrated under reduced pressure. The obtained residue was applied to silica gel column chromatography (Eluent; hexane:ethyl acetate=1:1→1:2 (V/V)), and the fractions containing the desired compound were concentrated under reduced pressure to obtain 4.28 g of the title compound as a white solid. (Yield: 90%)

Mass Spectrum (EI, m/z): 561 ($M^+$).

$^1$H-NMR Spectrum (CDCl$_3$, δ ppm): 0.48-0.56 (m, 2H), 0.64-0.70 (m, 2H), 3.43-3.49 (m, 1H), 4.26 (s, 2H), 4.46 (s, 2H), 5.38 (s, 2H), 6.55 (t, J=74.7 Hz, 1H), 6.85-7.34 (m, 12H), 8.12 (s, 1H), 9.80 (brs, 1H)

IR Spectrum (KBr, $cm^{-1}$): 1651.

22-(b) 2-(3-Cyclopropoxy-4-difluoromethoxyphenyl)-3-(2-fluorobenzyl)-1,5-dihydropyrrolo[2,3-d]pyridazin-4-one To 330 ml of ethanol solution containing 4.28 g (7.62 mmol) of 1-benzyloxymethyl-2-(3-cyclopropoxy-4-difluoromethoxyphenyl)-3-(2-fluorobenzyl)-1,5-dihydropyrrolo[2,3-d]pyridazin-4-one obtained in Example 22-(a) were added 1.50 g of 5% palladium-active carbon and 3.8 ml of 2N hydrochloric acid, and then the mixture was stirred under 1 atm hydrogen atmosphere at 50° C. for 1 hour. After completion of the reaction, the reaction mixture was filtered, the filtrate was concentrated under reduced pressure, methanol and 28% aqueous ammonia were added to the obtained solid, and the mixture was stirred for 1 hour. Then, the solution was concentrated under reduced pressure, water was added to the obtained concentrate, and the precipitated solid was collected by filtration. The obtained solid was washed with water and dried under reduced pressure to obtain 2.99 g of the title compound as a white solid. (Yield: 89%)

Melting point: 202-204° C.

Mass Spectrum (EI, m/z): 441 ($M^+$).

$^1$H-NMR Spectrum (DMSO-$d_6$, δ ppm): 0.42-0.63 (m, 4H), 3.54-3.63 (m, 1H), 4.37 (s, 2H), 6.87-7.40 (m, 7H), 7.04 (t, J=74.3 Hz, 1H), 8.16 (s, 1H), 12.17 (brs, 1H).

IR Spectrum (KBr, $cm^{-1}$): 1628.

Example 23

2-(3-Cyclopropoxy-4-difluoromethoxyphenyl)-3-(3-fluorobenzyl)-1,5-dihydropyrrolo[2,3-d]pyridazin-4-one (Exemplary compound No. 1-380)

23-(a) 1-Benzyloxymethyl-2-(3-cyclopropoxy-4-difluoromethoxyphenyl)-3-(3-fluorobenzyl)-1,5-dihydropyrrolo[2,3-d]pyridazin-4-one Reaction and post treatment were carried out in the same manner as in Example 1-(a) except for using 300 mg (0.678 mmol) of 1-benzyloxymethyl-2-bromo-3-(3-fluorobenzyl)-1,5-dihydropyrrolo[2,3-d]pyridazin-4-one obtained in the following Reference example 37-(c) in place of 2-bromo-1-(2-trimethylsilylethoxymethyl)-1,5-dihydropyrrolo-[2,3-d]pyridazin-4-one, whereby 298 mg of the title compound was obtained as a brownish oil. (Yield: 78%)

Mass Spectrum (EI, m/z): 561 ($M^+$).

$^1$H-NMR Spectrum (CDCl$_3$, δ ppm): 0.51-0.60 (m, 2H), 0.65-0.72 (m, 2H), 3.45-3.53 (m, 1H), 4.23 (s, 2H), 4.47 (s, 2H), 5.37 (s, 2H), 6.58 (t, J=74.6 Hz, 1H), 6.74-7.35 (m, 12H), 8.13 (brs, 1H), 9.90 (brs, 1H).

23-(b) 2-(3-Cyclopropoxy-4-difluoromethoxyphenyl)-3-(3-fluorobenzyl)-1,5-dihydropyrrolo[2,3-d]pyridazin-4-one Reaction and post treatment were carried out in the same manner as in Example 22-(b) except for using 298 mg (0.531 mmol) of 1-benzyloxymethyl-2-(3-cyclopropoxy-4-difluoromethoxyphenyl)-3-(3-fluorobenzyl)-1,5-dihydropyrrolo[2,3-d]pyridazin-4-one obtained in Example 23-(a) in place of 1-benzyloxymethyl-2-(3-cyclopropoxy-4-difluoromethoxyphenyl)-3-(2-fluorobenzyl)-1,5-dihydropyrrolo[2,3-d]pyridazin-4-one, whereby 69 mg of the title compound was obtained as a white solid. (Yield: 56%)

Melting point: 208-210° C.

Mass Spectrum (FAB, m/z): 442 ($M^+$+1).

$^1$H-NMR Spectrum (DMSO-$d_6$, δ ppm): 0.49-0.57 (m, 2H), 0.58-0.65 (m, 2H), 3.67-3.75 (m, 1H), 4.41 (s, 2H), 6.91-7.01 (m, 3H), 7.06 (t, J=74.3 Hz, 1H), 7.16 (dd, J=8.4, 1.9 Hz, 1H), 7.23-7.29 (m, 2H), 7.40 (d, J=1.9 Hz, 1H), 8.14 (s, 1H), 12.13 (brs, 1H), 12.40 (brs, 1H).

IR Spectrum (KBr, $cm^{-1}$): 1626.

Example 24

2-(3-Cyclopropoxy-4-difluoromethoxyphenyl)-3-(4-fluorobenzyl)-1,5-dihydropyrrolo[2,3-d]pyridazin-4-one (Exemplary compound No. 1-381)

24-(a) 1-Benzyloxymethyl-2-(3-cyclopropoxy-4-difluoromethoxyphenyl)-3-(4-fluorobenzyl)-1,5-dihydropyrrolo[2,3-d]pyridazin-4-one Reaction and post treatment were carried out in the same manner as in Example 1-(a) except for using 300 mg (0.678 mmol) of 1-benzyloxymethyl-2-bromo-3-(4-fluorobenzyl)-1,5-dihydropyrrolo[2,3-d]pyridazin-4-one obtained in the following Reference example 38-(c) in place of 2-bromo-1-(2-trimethylsilylethoxymethyl)-1,5-dihydropyrrolo-[2,3-d]pyridazin-4-one, whereby 185 mg of the title compound was obtained as a brownish oil. (Yield: 49%)

Mass Spectrum (EI, m/z): 561 (M$^+$).

$^1$H-NMR Spectrum (CDCl$_3$, δ ppm): 0.54-0.62 (m, 2H), 0.66-0.73 (m, 2H), 3.48-3.56 (m, 1H), 4.19 (s, 2H), 4.46 (s, 2H), 5.36 (s, 2H), 6.59 (t, J=74.6 Hz, 1H), 6.81-7.35 (m, 12H), 8.12 (brs, 1H), 9.85 (brs, 1H).

24-(b) 2-(3-Cyclopropoxy-4-difluoromethoxyphenyl)-3-(4-fluorobenzyl)-1,5-dihydropyrrolo[2,3-d]pyridazin-4-one Reaction and post treatment were carried out in the same manner as in Example 22-(b) except for using 184 mg (0.531 mmol) of 1-benzyloxymethyl-2-(3-cyclopropoxy-4-difluoromethoxyphenyl)-3-(4-fluorobenzyl)-1,5-dihydropyrrolo[2,3-d]pyridazin-4-one obtained in Example 24-(a) in place of 1-benzyloxymethyl-2-(3-cyclopropoxy-4-difluoromethoxyphenyl)-3-(2-fluorobenzyl)-1,5-dihydropyrrolo[2,3-d]pyridazin-4-one, whereby 69 mg of the title compound was obtained as a white solid. (Yield: 24%)

Melting point: 193-195° C.

Mass Spectrum (CI, m/z): 442 (M$^+$+1).

$^1$H-NMR Spectrum (DMSO-d$_6$, δ ppm): 0.49-0.66 (m, 4H), 3.67-3.76 (m, 1H), 4.37 (s, 2H), 7.01-7.19 (m, 5H), 7.06 (t, J=74.2 Hz, 1H), 7.28 (d, J=8.3 Hz, 1H), 7.39 (d, J=2.0 Hz, 1H), 8.15 (s, 1H), 12.21 (brs, 1H), 12.37 (brs, 1H)

IR Spectrum (KBr, cm$^{-1}$): 1638.

Example 25

3-(2-Cyanobenzyl)-2-(3-cyclopropoxy-4-difluoromethoxyphenyl)-1,5-dihydropyrrolo[2,3-d]pyridazin-4-one (Exemplary compound No. 1-389)

25-(a) 1-Benzyloxymethyl-3-(2-cyanobenzyl)-2-(3-cyclopropoxy-4-difluoromethoxyphenyl)-1,5-dihydropyrrolo[2,3-d]-pyridazin-4-one Reaction and post treatment were carried out in the same manner as in Example 22-(a) except for using 900 mg (1.50 mmol) of ethyl 1-benzyloxymethyl-4-(2-cyanobenzyl)-5-(3-cyclopropoxy-4-difluoromethoxyphenyl)-2-formyl-1H-pyrrol-3-carboxylate obtained in the following Reference example 39-(c) in place of ethyl 1-benzyloxymethyl-5-(3-cyclopropoxy-4-difluoromethoxyphenyl)-4-(2-fluorobenzyl)-2-formyl-1H-pyrrol-3-carboxylate, whereby 549 mg of the title compound was obtained as a yellowish foam. (Yield: 64%)

Mass Spectrum (CI, m/z): 569 (M$^+$+1).

$^1$H-NMR Spectrum (DMSO-d$_6$, δ ppm): 0.43-0.59 (m, 4H), 3.56-3.63 (m, 1H), 4.33 (s, 2H), 4.47 (s, 2H), 5.57 (s, 2H), 6.97 (dd, J=8.2, 1.8 Hz, 1H), 7.05 (t, J=74.1 Hz, 1H), 7.08 (d, J=8.2 Hz, 1H), 7.12-7.17 (m, 2H), 7.20-7.36 (m, 6H), 7.52 (td, J=7.7, 1.4 Hz, 1H), 7.72 (dd, J=7.7, 1.4 Hz, 1H), 8.54 (s, 1H), 12.42 (brs, 1H).

IR Spectrum (KBr, cm$^{-1}$): 1655.

25-(b) 3-(2-Cyanobenzyl)-2-(3-cyclopropoxy-4-difluoromethoxyphenyl)-1,5-dihydropyrrolo[2,3-d]pyridazin-4-one Reaction and post treatment were carried out in the same manner as in Example 22-(b) except for using 548 mg (0.964 mmol) of 1-benzyloxymethyl-3-(2-cyanobenzyl)-2-(3-cyclopropoxy-4-difluoromethoxyphenyl)-1,5-dihydropyrrolo-[2,3-d]pyridazin-4-one obtained in Example 25-(a) in place of 1-benzyloxymethyl-2-(3-cyclopropoxy-4-difluoromethoxyphenyl)-3-(2-fluorobenzyl)-1,5-dihydropyrrolo[2,3-d]pyridazin-4-one, whereby 374 mg of the title compound was obtained as a white solid. (Yield: 87%)

Melting point: >300° C.

Mass Spectrum (CI, m/z): 449 (M$^+$+1).

$^1$H-NMR Spectrum (DMSO-d$_6$, δ ppm): 0.43-0.64 (m, 4H), 3.59-3.67 (m, 1H), 4.55 (s, 2H), 7.04 (t, J=74.2 Hz, 1H), 7.05 (d, J=7.8 Hz, 1H), 7.10 (dd, J=8.3, 2.0 Hz, 1H), 7.27 (d, J=8.3 Hz, 1H), 7.32 (d, J=2.0 Hz, 1H), 7.38 (t, J=7.8 Hz, 1H), 7.55 (td, J=7.7, 1.4 Hz, 1H), 7.83 (dd, J=7.7, 1.4 Hz, 1H), 8.18 (s, 1H), 12.18 (brs, 1H).

IR Spectrum (KBr, cm$^{-1}$): 1624.

Example 26

3-(3-Cyanobenzyl)-2-(3-cyclopropoxy-4-difluoromethoxyphenyl)-1,5-dihydropyrrolo[2,3-d]pyridazin-4-one (Exemplary compound No. 1-390)

26-(a) 1-Benzyloxymethyl-3-(3-cyanobenzyl)-2-(3-cyclopropoxy-4-difluoromethoxyphenyl)-1,5-dihydropyrrolo[2,3-d]-pyridazin-4-one Reaction and post treatment were carried out in the same manner as in Example 22-(a) except for using 258 mg (0.430 mmol) of ethyl 1-benzyloxymethyl-4-(3-cyanobenzyl)-5-(3-cyclopropoxy-4-difluoromethoxyphenyl)-2-formyl-1H-pyrrol-3-carboxylate obtained in the following Reference example 40-(c) in place of ethyl 1-benzyloxymethyl-5-(3-cyclopropoxy-4-difluoromethoxyphenyl)-4-(2-fluorobenzyl)-2-formyl-1H-pyrrol-3-carboxylate, whereby 111 mg of the title compound was obtained as a white foam. (Yield: 45%)

Mass Spectrum (CI, m/z): 569 (M$^+$+1).

$^1$H-NMR Spectrum (CDCl$_3$, δ ppm): 0.55-0.76 (m, 4H), 3.50-3.58 (m, 1H), 4.26 (s, 2H), 4.49 (s, 2H), 5.37 (s, 2H), 6.60 (t, J=74.5 Hz, 1H), 6.90 (dd, J=8.3, 2.0 Hz, 1H), 7.16-7.45 (m, 11H), 8.12 (s, 1H), 9.90 (brs, 1H).

26-(b) 3-(3-Cyanobenzyl)-2-(3-cyclopropoxy-4-difluoromethoxyphenyl)-1,5-dihydropyrrolo[2,3-d]pyridazin-4-one Reaction was carried out in the same manner as in Example 22-(b) except for using 110 mg (0.193 mmol) of 1-benzyloxymethyl-3-(3-cyanobenzyl)-2-(3-cyclopropoxy-4-difluoromethoxyphenyl)-1,5-dihydropyrrolo[2,3-d]pyridazin-4-one obtained in Example 26-(a) in place of 1-benzyloxymethyl-2-(3-cyclopropoxy-4-difluoromethoxyphenyl)-3-(2-fluorobenzyl)-1,5-dihydropyrrolo[2,3-d]pyridazin-4-one. After completion of the reaction, the reaction suspension was filtered, the filtrate was concentrated under reduced pressure, methanol and 28% aqueous ammonia were added to the obtained solid, and the mixture was stirred for 1 hour. Then, the solution was concentrated under reduced pressure and the obtained residue was applied to silica gel column chromatography (Eluent; hexane:ethyl acetate=9:1→0:1 (V/V)), and the fractions containing the desired compound were concentrated under reduced pressure to obtain 18 mg of the title compound as a white solid. (Yield: 20%)

Melting point: 130-135° C.

Mass Spectrum (CI, m/z): 449 (M$^+$+1).

¹H-NMR Spectrum (DMSO-d₆, δ ppm): 0.49-0.68 (m, 4H), 3.73-3.80 (m, 1H), 4.43 (s, 2H), 7.06 (t, J=74.2 Hz, 1H), 7.14 (dd, J=8.3, 2.0 Hz, 1H), 7.30 (d, J=8.3 Hz, 1H), 7.36 (d, J=2.0 Hz, 1H), 7.42-7.51 (m, 2H), 7.59 (s, 1H), 7.61-7.65 (m, 1H), 8.17 (s, 1H), 12.24 (brs, 1H), 12.33 (brs, 1H).

IR Spectrum (KBr, cm⁻¹): 1642.

Example 27

3-(3-Carboxybenzyl)-2-(3-cyclopropoxy-4-difluoromethoxyphenyl)-1,5-dihydropyrrolo[2,3-d]pyridazin-4-one (Exemplary compound No. 1-393)

27-(a) 1-Benzyloxymethyl-3-(3-carboxybenzyl)-2-(3-cyclopropoxy-4-difluoromethoxyphenyl)-1,5-dihydropyrrolo[2,3-d]-pyridazin-4-one Reaction and post treatment were carried out in the same manner as in Example 22-(a) except for using 1.21 g (1.95 mmol) of ethyl 1-benzyloxymethyl-4-(3-carboxybenzyl)-5-(3-cyclopropoxy-4-difluoromethoxyphenyl)-2-formyl-1H-pyrrol-3-carboxylate obtained in the following Reference example 41-(d) in place of ethyl 1-benzyloxymethyl-5-(3-cyclopropoxy-4-difluoromethoxyphenyl)-4-(2-fluorobenzyl)-2-formyl-1H-pyrrol-3-carboxylate at the time of the reaction, and adjusting a pH of the aqueous layer to 2 at the time of extraction with ethyl acetate in the post treatment, whereby 1.05 g of the title compound as a pale yellowish solid. (Yield: 92%)

Mass Spectrum (CI, m/z): 588 (M⁺+1).

¹H-NMR Spectrum (CDCl₃, δ ppm): 0.68-0.76 (m, 2H), 0.76-0.84 (m, 2H), 3.66-3.74 (m, 1H), 4.24 (s, 2H), 4.41 (s, 2H), 5.33 (s, 2H), 6.65 (t, J=74.6 Hz, 1H), 6.89-6.93 (m, 1H), 7.05 (dd, J=8.2, 2.0 Hz, 1H), 7.11-7.16 (m, 2H), 7.20 (t, J=7.7 Hz, 1H), 7.27-7.30 (m, 4H), 7.33 (d, J=8.2 Hz, 1H), 7.38 (d, J=2.0 Hz, 1H), 7.91 (dt, J=7.6, 1.3 Hz, 1H), 8.14 (s, 1H), 8.76 (brs, 1H), 12.58 (brs, 1H).

27-(b) 3-(3-Carboxybenzyl)-2-(3-cyclopropoxy-4-difluoromethoxyphenyl)-1,5-dihydropyrrolo[2,3-d]pyridazin-4-one Reaction was carried out in the same manner as in Example 22-(b) except for using 1.05 g (1.79 mmol) of 1-benzyloxymethyl-3-(3-carboxybenzyl)-2-(3-cyclopropoxy-4-difluoromethoxyphenyl)-1,5-dihydropyrrolo[2,3-d]pyridazin-4-one obtained in Example 27-(a) in place of 1-benzyloxymethyl-2-(3-cyclopropoxy-4-difluoromethoxyphenyl)-3-(2-fluorobenzyl)-1,5-dihydropyrrolo[2,3-d]pyridazin-4-one. After completion of the reaction, the reaction mixture was extracted with an alkaline aqueous solution with a pH 10, washed with diethyl ether, and after adjusting a pH of the aqueous layer to 2, the precipitated solid was collected by filtration. The obtained solid was washed with water and dried under reduced pressure to obtain 0.68 g of the title compound as a beige solid. (Yield: 82%)

Melting point: 155-163° C.

Mass Spectrum (CI, m/z): 468 (M⁺+1).

¹H-NMR Spectrum (DMSO-d₆, δ ppm): 0.41-0.50 (m, 2H), 0.53-0.62 (m, 2H), 3.62-3.70 (m, 1H), 4.46 (s, 2H), 7.05 (t, J=74.3 Hz, 1H), 7.16 (dd, J=8.2, 2.0 Hz, 1H), 7.28 (d, J=8.2 Hz, 1H), 7.33-7.43 (m, 3H), 7.69-7.76 (m, 2H), 8.17 (s, 1H), 12.23 (brs, 1H), 12.43 (brs, 1H)

IR Spectrum (KBr, cm⁻¹): 1638.

Example 28

2-(3-Cyclopropoxy-4-difluoromethoxyphenyl)-3-(6-methoxy-2-pyridylmethyl)-1,5-dihydropyrrolo[2,3-d]pyridazin-4-one (Exemplary compound No. 1-439)

28-(a) 1-Benzyloxymethyl-2-(3-cyclopropoxy-4-difluoromethoxyphenyl)-3-(6-methoxy-2-pyridylmethyl)-1,5-dihydropyrrolo[2,3-d]pyridazin-4-one Reaction and post treatment were carried out in the same manner as in Example 22-(a) except for using 1.11 g (1.82 mmol) of ethyl 1-benzyloxymethyl-5-(3-cyclopropoxy-4-difluoromethoxyphenyl)-2-formyl-4-(6-methoxy-2-pyridylmethyl)-1H-pyrrol-3-carboxylate obtained in the following Reference example 42-(c) in place of ethyl 1-benzyloxymethyl-5-(3-cyclopropoxy-4-difluoromethoxyphenyl)-4-(2-fluorobenzyl)-2-formyl-1H-pyrrol-3-carboxylate, whereby 712 mg of the title compound was obtained as a white foam. (Yield: 68%)

Mass Spectrum (EI, m/z): 574 (M⁺).

¹H-NMR Spectrum (CDCl₃, δ ppm): 0.49-0.57 (m, 2H), 0.65-0.72 (m, 2H), 3.51-3.59 (m, 1H), 3.75 (s, 3H), 4.30 (s, 2H), 4.47 (s, 2H), 5.43 (s, 2H), 6.50 (d, J=8.1 Hz, 1H), 6.56 (t, J=74.7 Hz, 1H), 6.90 (d, J=7.3 Hz, 1H), 7.15-7.22 (m, 4H), 7.28-7.37 (m, 3H), 7.41-7.49 (m, 2H), 8.11 (s, 1H), 9.84 (brs, 1H).

28-(b) 2-(3-Cyclopropoxy-4-difluoromethoxyphenyl)-3-(6-methoxy-2-pyridylmethyl)-1,5-dihydropyrrolo[2,3-d]pyridazin-4-one Reaction was carried out in the same manner as in Example 22-(b) except for using 227 mg (0.396 mmol) of 1-benzyloxymethyl-2-(3-cyclopropoxy-4-difluoromethoxyphenyl)-3-(6-methoxy-2-pyridylmethyl)-1,5-dihydropyrrolo[2,3-d]-pyridazin-4-one obtained in Example 28-(a) in place of 1-benzyloxymethyl-2-(3-cyclopropoxy-4-difluoromethoxyphenyl)-3-(2-fluorobenzyl)-1,5-dihydropyrrolo[2,3-d]pyridazin-4-one. After completion of the reaction, the reaction suspension was filtered, the filtrate was concentrated under reduced pressure, methanol and 28% aqueous ammonia were added to the obtained solid, and the mixture was stirred for 1 hour. Then, the solution was concentrated under reduced pressure and the obtained residue was applied to silica gel column chromatography (Eluent; chloroform:ethyl acetate=1:1 (V/V)), and the fractions containing the desired compound were concentrated under reduced pressure to obtain 39 mg of the title compound as a white solid. (Yield: 22%)

Melting point: 224-226° C.

Mass Spectrum (EI, m/z): 454 (M⁺).

¹H-NMR Spectrum (DMSO-d₆, δ ppm): 0.50-0.69 (m, 4H), 3.70-3.80 (m, 1H), 3.75 (s, 3H), 4.40 (s, 2H), 6.59 (d, J=7.7 Hz, 1H), 6.81 (d, J=7.7 Hz, 1H), 7.06 (t, J=74.3 Hz, 1H), 7.28 (d, J=8.4 Hz, 1H), 7.46 (dd, J=8.4, 2.0 Hz, 1H), 7.56 (t, J=7.7 Hz, 1H), 7.57 (d, J=2.0 Hz, 1H), 8.14 (s, 1H), 12.14 (brs, 1H).

IR Spectrum (KBr, cm⁻¹): 1634.

Example 29

2-(3-Cyclopropoxy-4-difluoromethoxyphenyl)-3-(6-methoxy-3-pyridylmethyl)-1,5-dihydropyrrolo[2,3-d]pyridazin-4-one (Exemplary compound No. 1-445)

29-(a) 1-Benzyloxymethyl-2-(3-cyclopropoxy-4-difluoromethoxyphenyl)-3-(6-methoxy-3-pyridylmethyl)-1,5-dihydropyrrolo[2,3-d]pyridazin-4-one Reaction and post treatment were carried out in the same manner as in Example 22-(a) except for using 380 mg (0.626 mmol) of ethyl 1-benzyloxymethyl-5-(3-cyclopropoxy-4-difluoromethoxyphenyl)-2-formyl-4-(6-methoxy-3-pyridylmethyl)-1H-pyrrol-3-carboxylate obtained in the following Reference example 43-(c) in place of ethyl 1-benzyloxymethyl-5-(3-cyclopropoxy-4-difluoromethoxyphenyl)-4-(2-fluorobenzyl)-2-formyl-1H-pyrrol-3-carboxylate, whereby 267 mg of the title compound was obtained as a slightly yellowish oil. (Yield: 74%)

Mass Spectrum (CI, m/z): 575 ($M^+$+1).

$^1$H-NMR Spectrum (CDCl$_3$, δ ppm): 0.56-0.77 (m, 4H), 3.54-3.62 (m, 1H), 3.85 (s, 3H), 4.13 (s, 2H), 4.45 (s, 2H), 5.35 (s, 2H), 6.59 (dd, J=8.4, 0.6 Hz, 1H), 6.60 (t, J=74.6 Hz, 1H), 6.92 (dd, J=8.2, 2.1 Hz, 1H), 7.14-7.33 (m, 7H), 7.52 (dd, J=8.4, 2.5 Hz, 1H), 7.78 (dd, J=2.5, 0.6 Hz, 1H), 8.09 (s, 1H), 9.80 (brs, 1H).

29-(b) 2-(3-Cyclopropoxy-4-difluoromethoxyphenyl)-3-(6-methoxy-3-pyridylmethyl)-1,5-dihydropyrrolo[2,3-d]-pyridazin-4-one Reaction was carried out in the same manner as in Example 22-(b) except for using 265 mg (1.79 mmol) of 1-benzyloxymethyl-2-(3-cyclopropoxy-4-difluoromethoxyphenyl)-3-(6-methoxy-3-pyridylmethyl)-1,5-dihydropyrrolo[2,3-d]-pyridazin-4-one obtained in Example 29-(a) in place of 1-benzyloxymethyl-2-(3-cyclopropoxy-4-difluoromethoxyphenyl)-3-(2-fluorobenzyl)-1,5-dihydropyrrolo[2,3-d]pyridazin-4-one. After completion of the reaction, the reaction suspension was filtered, the filtrate was concentrated under reduced pressure, methanol and 28% aqueous ammonia were added to the obtained solid, and the mixture was stirred for 1 hour. Then, the solution was concentrated under reduced pressure and the obtained residue was applied to silica gel column chromatography (Eluent; ethyl acetate), and the fractions containing the desired compound were concentrated under reduced pressure to obtain 146 mg of the title compound as a white solid. (Yield: 69%)

Melting point: 220-221° C.

Mass Spectrum (CI, m/z): 455 ($M^+$+1).

$^1$H-NMR Spectrum (DMSO-d$_6$, δ ppm): 0.58-0.67 (m, 4H), 3.76 (s, 3H), 3.77-3.84 (m, 1H), 4.30 (s, 2H), 6.68 (d, J=8.5 Hz, 1H), 7.07 (t, J=74.3 Hz, 1H), 7.16 (dd, J=8.4, 2.1 Hz, 1H), 7.30 (d, J=8.4 Hz, 1H), 7.43 (d, J=2.1 Hz, 1H), 7.47 (dd, J=8.5, 2.2 Hz, 1H), 7.93 (d, J=2.2 Hz, 1H), 8.14 (s, 1H), 12.20 (brs, 1H).

IR Spectrum (KBr, cm$^{-1}$): 1625.

Example 30

2-(3-Cyclopropoxy-4-difluoromethoxyphenyl)-3-dimethylaminomethyl-1,5-dihydropyrrolo[2,3-d]pyridazin-4-one (Exemplary compound No. 1-197)

30-(a) 2-(3-Cyclopropoxy-4-difluoromethoxyphenyl)-3-dimethylaminomethyl-1-(2-trimethylsilylethoxymethyl)-1,5-dihydropyrrolo[2,3-d]pyridazin-4-one To 133 mg (0.270 mmol) of 2-(3-cyclopropoxy-4-difluoromethoxyphenyl)-3-formyl-1-(2-trimethylsilylethoxymethyl)-1,5-dihydropyrrolo[2,3-d]pyridazin-4-one obtained in Example 10-(a) and 112 mg of Molecular sieve (3A) was added 5 ml of tetrahydrofuran solution containing 2M dimethylamine at room temperature, and the mixture was stirred for 10 minutes. Then, 156 mg (0.740 mmol) of sodium triacetoxyborohydride was added to the mixture, and the mixture was stirred for further 17 hours. After completion of the reaction, water was added to the reaction mixture, and the mixture was extracted with ethyl acetate. The organic layer after separation was washed successively with water and then with a saturated aqueous solution of sodium chloride, dried over anhydrous magnesium sulfate and then concentrated under reduced pressure. The obtained residue was applied to silica gel column chromatography (Eluent; ethyl acetate→chloroform:methanol=4:1 (V/V)), and the fractions containing the desired compound were concentrated under reduced pressure to obtain 74 mg of the title compound as a pale yellowish solid. (Yield: 53%)

Mass Spectrum (CI, m/z): 521 ($M^+$+1).

$^1$H-NMR Spectrum (CDCl$_3$, δ ppm): −0.04 (s, 9H), 0.76-0.90 (m, 6H), 2.24 (s, 6H), 3.41-3.49 (m, 2H), 3.68 (s, 2H), 3.77-3.85 (m, 1H), 5.37 (s, 2H), 6.61 (t, J=74.7 Hz, 1H), 7.16 (dd, J=8.2, 2.0 Hz, 1H), 7.26 (d, J=8.2 Hz, 1H), 7.75 (d, J=2.0 Hz, 1H), 8.19 (s, 1H), 9.94 (brs, 1H).

IR Spectrum (KBr, cm$^{-1}$): 1646.

30-(b) 2-(3-Cyclopropoxy-4-difluoromethoxyphenyl)-3-dimethylaminomethyl-1,5-dihydropyrrolo[2,3-d]pyridazin-4-one Reaction was carried out in the same manner as in Example 1-(b) except for using 70 mg (0.14 mmol) of 2-(3-cyclopropoxy-4-difluoromethoxyphenyl)-3-dimethylaminomethyl-1-(2-trimethylsilylethoxymethyl)-1,5-dihydropyrrolo[2,3-d]pyridazin-4-one obtained in Example 30-(a) in place of 2-(3-cyclopropoxy-4-difluoromethoxyphenyl)-1-(2-trimethylsilylethoxymethyl)-1,5-dihydropyrrolo[2,3-d]pyridazin-4-one. After completion of the reaction, water was added to the reaction mixture to precipitate a solid, and the precipitated solid was collected by filtration. The obtained solid was washed with water and dried under reduced pressure to obtain 36 mg of the title compound as a gray solid. (Yield: 68%)

Melting point: 154-157° C.

$^1$H-NMR Spectrum (DMSO-d$_6$, δ ppm): 0.72-0.88 (m, 4H), 2.23 (s, 6H), 3.73 (s, 2H), 3.93-4.00 (m, 1H), 7.08 (t, J=74.5 Hz, 1H), 7.30 (d, J=8.5 Hz, 1H), 7.49 (dd, J=8.5, 2.0 Hz, 1H), 8.12 (s, 1H), 8.27 (d, J=2.0 Hz, 1H), 12.16 (brs, 1H), 12.36 (brs, 1H).

IR Spectrum (KBr, cm$^{-1}$): 1639.

Example 31

2-(3-Cyclobutoxy-4-difluoromethoxyphenyl)-1,5-dihydropyrrolo[2,3-d]pyridazin-4-one (Exemplary compound No. 1-850)

31-(a) 2-(3-Cyclobutoxy-4-difluoromethoxyphenyl)-1-(2-trimethylsilylethoxymethyl)-1,5-dihydropyrrolo[2,3-d]pyridazin-4-one Reaction and post treatment were carried out in the same manner as in Example 1-(a) except for using 0.50 g (1.5 mmol) of 2-(3-cyclobutoxy-4-difluoromethoxyphenyl)-4,4,5,5-tetramethyl-[1,3,2]dioxaborolane obtained in the following Reference example 1-(b) in place of 2-(3-cyclopropoxy-4-difluoromethoxyphenyl)-4,4,5,5-tetramethyl-[1,3,2]dioxaborolane, whereby 0.46 g of the title compound was obtained as a pale yellowish foam. (Yield: 80%)

Mass Spectrum (CI, m/z): 478 ($M^+$+1).
$^1$H-NMR Spectrum (CDCl$_3$, δ ppm): −0.02 (s, 9H), 0.88-0.97 (m, 2H), 1.64-1.78 (m, 1H), 1.84-1.97 (m, 1H), 2.16-2.32 (m, 2H), 2.42-2.55 (m, 2H), 3.51-3.60 (m, 2H), 4.63-4.76 (m, 1H), 5.43 (s, 2H), 6.66 (t, J=75.1 Hz, 1H), 6.93 (s, 1H), 7.06 (d, J=2.0 Hz, 1H), 7.12 (dd, J=8.3, 2.0 Hz, 1H), 7.26 (d, J=8.3 Hz, 1H), 8.24 (s, 1H), 10.61 (brs, 1H).

31-(b) 2-(3-Cyclobutoxy-4-difluoromethoxyphenyl)-1,5-dihydropyrrolo[2,3-d]pyridazin-4-one Reaction was carried out in the same manner as in Example 2-(b) except for using 0.46 g (0.96 mmol) of 2-(3-cyclobutoxy-4-difluoromethoxyphenyl)-1-(2-trimethylsilylethoxymethyl)-1,5-dihydropyrrolo[2,3-d]pyridazin-4-one obtained in Example 31-(a) in place of 3-chloro-2-(3-cyclopropoxy-4-difluoromethoxyphenyl)-1-(2-trimethylsilylethoxymethyl)-1,5-dihydropyrrolo[2,3-d]pyridazin-4-one. After completion of the reaction, to the reaction mixture was added a saturated aqueous solution of sodium hydrogencarbonate to neutralize the mixture, and the mixture was extracted with a mixed solvent (chloroform/methanol=9/1 (V/V)). The organic layer after separation was washed with a saturated aqueous solution of sodium chloride, dried over anhydrous magnesium sulfate and then concentrated under reduced pressure. To the obtained solid were added methanol and 28% aqueous ammonia, and the mixture was stirred under room temperature for 3 hours. Then, the solution was concentrated under reduced pressure and the obtained solid was washed with chloroform and dried under reduced pressure to obtain 199 mg of the title compound as a white solid. (Yield: 60%)

Melting point: 289-291° C.
Mass Spectrum (CI, m/z): 348 ($M^+$+1).
$^1$H-NMR Spectrum (DMSO-d$_6$, δ ppm): 1.58-1.75 (m, 1H), 1.76-1.90 (m, 1H), 2.02-2.18 (m, 2H), 2.45-2.60 (m, 2H), 4.84-4.97 (m, 1H), 7.11 (t, J=74.5 Hz, 1H), 7.20 (d, J=0.6 Hz, 1H), 7.27 (d, J=8.3 Hz, 1H), 7.42 (d, J=2.1 Hz, 1H), 7.45 (dd, J=8.3, 2.1 Hz, 1H), 8.16 (d, J=0.6 Hz, 1H), 12.26 (brs, 1H), 12.45 (brs, 1H).

Example 32

3-Chloro-2-(3-cyclobutoxy-4-difluoromethoxyphenyl)-1,5-dihydropyrrolo[2,3-d]pyridazin-4-one (Exemplary compound No. 1-851)

32-(a) 3-Chloro-2-(3-cyclobutoxy-4-difluoromethoxyphenyl)-1-(2-trimethylsilylethoxymethyl)-1,5-dihydropyrrolo[2,3-d]-pyridazin-4-one Reaction and post treatment were carried out in the same manner as in Example 31-(a) except for using 0.40 g (1.1 mmol) of 2-bromo-3-chloro-1-(2-trimethylsilylethoxymethyl)-1,5-dihydropyrrolo[2,3-d]pyridazin-4-one obtained in the following Reference example 16-(d) in place of 2-bromo-1-(2-trimethylsilylethoxymethyl)-1,5-dihydropyrrolo-[2,3-d]pyridazin-4-one, whereby 263 mg of the title compound was obtained as a white solid. (Yield: 48%)

Mass Spectrum (CI, m/z): 512 ($M^+$+1).
$^1$H-NMR Spectrum (CDCl$_3$, δ ppm): −0.03 (s, 9H), 0.82-0.93 (m, 2H), 1.61-1.78 (m, 1H), 1.84-1.98 (m, 1H), 2.16-2.32 (m, 2H), 2.42-2.54 (m, 2H), 3.42-3.52 (m, 2H), 4.63-4.74 (m, 1H), 5.35 (s, 2H), 6.68 (t, J=74.8 Hz, 1H), 7.00 (d, J=2.2 Hz, 1H), 7.06 (dd, J=8.2, 2.2 Hz, 1H), 7.30 (d, J=8.2 Hz, 1H), 8.19 (s, 1H), 10.08 (brs, 1H).

32-(b) 3-Chloro-2-(3-cyclobutoxy-4-difluoromethoxyphenyl)-1,5-dihydropyrrolo[2,3-d]pyridazin-4-one Reaction was carried out in the same manner as in Example 2-(b) except for using 0.26 g (0.51 mmol) of 3-chloro-2-(3-cyclobutoxy-4-difluoromethoxyphenyl)-1-(2-trimethylsilylethoxymethyl)-1,5-dihydropyrrolo[2,3-d]pyridazin-4-one obtained in Example 32-(a) in place of 3-chloro-2-(3-cyclopropoxy-4-difluoromethoxyphenyl)-1-(2-trimethylsilylethoxymethyl)-1,5-dihydropyrrolo[2,3-d]pyridazin-4-one. After completion of the reaction, to the reaction mixture were added diisopropyl ether and cyclohexane, and the precipitated solid was collected by filtration and washed with cyclohexane. To the obtained solid were added methanol and 28% aqueous ammonia, and the mixture was stirred at room temperature for 3 hours. Then, the solution was concentrated under reduced pressure, and the obtained solid was washed with chloroform and dried under reduced pressure to obtain 120 mg of the title compound as a white solid. (Yield: 62%)

Melting point: 273-275° C.
Mass Spectrum (CI, m/z): 382 ($M^+$+1).
$^1$H-NMR Spectrum (DMSO-d$_6$, δ ppm): 1.59-1.90 (m, 2H), 2.06-2.22 (m, 2H), 2.43-2.57 (m, 2H), 4.77-4.88 (m, 1H), 7.16 (t, J=74.2 Hz, 1H), 7.35 (d, J=8.5 Hz, 1H), 7.38-7.43 (m, 2H), 8.15 (s, 1H), 12.35 (brs, 1H).
IR Spectrum (KBr, cm$^{-1}$): 1635.

Example 33

3-Bromo-2-(3-cyclobutoxy-4-difluoromethoxyphenyl)-1,5-dihydropyrrolo[2,3-d]pyridazin-4-one (Exemplary compound No. 1-852)

33-(a) 3-Bromo-2-(3-cyclobutoxy-4-difluoromethoxyphenyl)-1-(2-trimethylsilylethoxymethyl)-1,5-dihydropyrrolo[2,3-d]-pyridazin-4-one Reaction and post treatment were carried out in the same manner as in Example 31-(a) except for using 51 mg (0.12 mmol) of 2,3-dibromo-1-(2-trimethylsilylethoxymethyl)-1,5-dihydropyrrolo[2,3-d]pyridazin-4-one obtained in the following Reference example 44 in place of 2-bromo-1-(2-trimethylsilylethoxymethyl)-1,5-dihydropyrrolo[2,3-d]-pyridazin-4-one, whereby 57 mg of the title compound was obtained as a pale yellowish solid. (Yield: 84%)

$^1$H-NMR Spectrum (CDCl$_3$, δ ppm): −0.03 (s, 9H), 0.82-0.91 (m, 2H), 1.63-1.78 (m, 1H), 1.84-1.98 (m, 1H), 2.16-2.33 (m, 2H), 2.42-2.55 (m, 2H), 3.41-3.50 (m, 2H), 4.63-4.74 (m, 1H), 5.34 (s, 2H), 6.68 (t, J=74.8 Hz, 1H), 6.98 (d, J=2.1 Hz, 1H), 7.04 (dd, J=8.2, 2.1 Hz, 1H), 7.30 (d, J=8.1 Hz, 1H), 8.20 (s, 1H), 9.89 (brs, 1H).

33-(b) 3-Bromo-2-(3-cyclobutoxy-4-difluoromethoxyphenyl)-1,5-dihydropyrrolo[2,3-d]pyridazin-4-one Reaction and post treatment were carried out in the same manner as in Example 32-(b) except for using 54 mg (0.097 mmol) of 3-bromo-2-(3-cyclobutoxy-4-difluoromethoxyphenyl)-1-(2-trimethylsilylethoxymethyl)-1,5-dihydropyrrolo[2,3-d]pyridazin-4-one obtained in Example 33-(a) in place of 3-chloro-2-(3-cyclobutoxy-4-difluoromethoxyphenyl)-1-(2-trimethylsilylethoxymethyl)-1,5-dihydropyrrolo[2,3-d]pyridazin-4-one, whereby 27 mg of the title compound was obtained as a beige solid. (65%)

Melting point: 234-238° C.
Mass Spectrum (CI, m/z): 426 ($M^+$+1).
$^1$H-NMR Spectrum (DMSO-$d_6$, δ ppm): 1.58-1.94 (m, 2H), 2.06-2.23 (m, 2H), 2.43-2.59 (m, 2H), 4.75-4.90 (m, 1H), 7.17 (t, J=74.2 Hz, 1H), 7.31-7.45 (m, 3H), 8.15 (s, 1H), 12.33 (brs, 1H).
IR Spectrum (KBr, $cm^{-1}$): 1652.

Example 34

2-(3-Cyclobutoxy-4-difluoromethoxyphenyl)-3-phenyl-1,5-dihydropyrrolo[2,3-d]pyridazin-4-one (Exemplary compound No. 1-870)

34-(a) 2-(3-Cyclobutoxy-4-difluoromethoxyphenyl)-3-iodo-1-(2-trimethylsilylethoxymethyl)-1,5-dihydropyrrolo[2,3-d]-pyridazin-4-one To 283 mg (0.593 mmol) of 2-(3-cyclobutoxy-4-difluoromethoxyphenyl)-1-(2-trimethylsilylethoxymethyl)-1,5-dihydropyrrolo[2,3-d]pyridazin-4-one obtained in Example 31-(a) were added 1.6 ml of dichloromethane and 5 ml of acetonitrile, then, 167 mg of sodium hydrogencarbonate and 367 mg of anhydrous magnesium sulfate were added to the mixture, and the resulting mixture was stirred at room temperature for 30 minutes. Then, 3 ml of dichloromethane solution containing 267 mg of iodine chloride was added to the same, and the resulting mixture was further stirred at room temperature for 4 hours. After completion of the reaction, a filtrate obtained by removing insoluble material in the reaction suspension by filtration and a washed solution obtained by washing the filtered solid with ethyl acetate were combined and the combined solution was washed successively with 5% aqueous sodium thiosulfate solution and then with a saturated aqueous solution of sodium chloride. The organic layer after washing was dried over anhydrous magnesium sulfate and then concentrated under reduced pressure. The obtained residue was applied to silica gel column chromatography (Eluent; hexane:ethyl acetate=9:1→0:1 (V/V)), and the fractions containing the desired compound were concentrated under reduced pressure to obtain 314 mg of the title compound as a pale yellowish foam. (Yield: 88%)

Mass Spectrum (CI, m/z): 604 ($M^+$+1).
$^1$H-NMR Spectrum (CDCl$_3$, δ ppm): −0.03 (s, 9H), 0.80-0.90 (m, 2H), 1.62-1.78 (m, 1H), 1.84-1.98 (m, 1H), 2.17-2.34 (m, 2H), 2.43-2.56 (m, 2H), 3.38-3.47 (m, 2H), 4.64-4.74 (m, 1H), 5.34 (s, 2H), 6.69 (t, J=74.7 Hz, 1H), 6.93 (d, J=2.0 Hz, 1H), 6.99 (dd, J=8.3, 2.0 Hz, 1H), 7.29 (d, J=8.3 Hz, 1H), 8.22 (s, 1H), 9.95 (brs, 1H).
IR Spectrum (KBr, $cm^{-1}$): 1659.

34-(b) 2-(3-Cyclobutoxy-4-difluoromethoxyphenyl)-3-phenyl-1-(2-trimethylsilylethoxymethyl)-1,5-dihydropyrrolo[2,3-d]-pyridazin-4-one Reaction and post treatment were carried out in the same manner as in Example 1-(a) except for using 299 mg (0.495 mmol) of 2-(3-cyclobutoxy-4-difluoromethoxyphenyl)-3-iodo-1-(2-trimethylsilylethoxymethyl)-1,5-dihydropyrrolo-[2,3-d]pyridazin-4-one obtained in Example 34-(a) in place of 2-bromo-1-(2-trimethylsilylethoxymethyl)-1,5-dihydropyrrolo[2,3-d]pyridazin-4-one, and using 95 mg (0.779 mmol) of phenylboronic acid in place of 2-(3-cyclopropoxy-4-difluoromethoxyphenyl)-4,4,5,5-tetramethyl-[1,3,2]dioxaborolane obtained in the following Reference example 1-(a), whereby 151 mg of the title compound was obtained as a pale beige solid. (Yield: 89%)

Mass Spectrum (CI, m/z): 554 ($M^+$+1).
$^1$H-NMR Spectrum (CDCl$_3$, δ ppm): −0.02 (s, 9H), 0.86-0.95 (m, 2H), 1.46-1.63 (m, 1H), 1.71-1.85 (m, 1H), 1.91-2.07 (m, 2H), 2.07-2.20 (m, 2H), 3.47-3.56 (m, 2H), 4.25-4.37 (m, 1H), 5.39 (s, 2H), 6.62 (d, J=2.1 Hz, 1H), 6.62 (t, J=75.0 Hz, 1H), 6.95 (dd, J=8.3, 2.1 Hz, 1H), 7.18 (d, J=8.3 Hz, 1H), 7.20-7.32 (m, 5H), 8.24 (s, 1H), 9.87 (brs, 1H).
IR Spectrum (KBr, $cm^{-1}$): 1654.

34-(c) 2-(3-Cyclobutoxy-4-difluoromethoxyphenyl)-3-phenyl-1,5-dihydropyrrolo[2,3-d]pyridazin-4-one Reaction was carried out in the same manner as in Example 1-(b) except for using 145 mg (0.261 mmol) of 2-(3-cyclobutoxy-4-difluoromethoxyphenyl)-3-phenyl-1-(2-trimethylsilylethoxymethyl)-1,5-dihydropyrrolo[2,3-d]pyridazin-4-one obtained in Example 34-(b) in place of 2-(3-cyclopropoxy-4-difluoromethoxyphenyl)-1-(2-trimethylsilylethoxymethyl)-1,5-dihydropyrrolo[2,3-d]pyridazin-4-one. After completion of the reaction, the reaction mixture was concentrated under reduced pressure, water was added to the obtained concentrate, and the mixture was extracted with ethyl acetate. The organic layer after separation was dried over anhydrous magnesium sulfate and then concentrated under reduced pressure. The obtained solid was dissolved by adding ethyl acetate, followed by addition of diisopropyl ether and hexane, and the precipitated solid was collected by filtration. The obtained solid was dried under reduced pressure to obtain 93 mg of the title compound as a beige solid. (Yield: 84%)

Melting point: 280-284° C.
Mass Spectrum (CI, m/z): 424 ($M^+$+1).
$^1$H-NMR Spectrum (DMSO-$d_6$, δ ppm): 1.37-1.55 (m, 1H), 1.62-1.76 (m, 1H), 1.81-2.10 (m, 4H), 4.18-4.29 (m, 1H), 6.73 (d, J=2.1 Hz, 1H), 7.07 (dd, J=8.4, 2.1 Hz, 1H), 7.08 (t, J=73.4 Hz, 1H), 7.21 (d, J=8.4 Hz, 1H), 7.28-7.40 (m, 5H), 8.15 (s, 1H), 12.17 (brs, 1H), 12.47 (brs, 1H).
IR Spectrum (KBr, $cm^{-1}$): 1624.

Example 35

2-(3-Cyclopropylmethoxy-4-difluoromethoxyphenyl)-1,5-dihydropyrrolo[2,3-d]pyridazin-4-one (Exemplary compound No. 1-482)

Reaction was carried out in the same manner as in Example 22-(a) except for using 114 mg (0.30 mmol) of ethyl 5-(3-cyclopropylmethoxy-4-difluoromethoxyphenyl)-2-formyl-1H-pyrrol-3-carboxylate obtained in the following Reference example 45-(d) in place of ethyl 1-benzyloxymethyl-5-(3-cyclopropoxy-4-difluoromethoxyphenyl)-4-(2-fluorobenzyl)-2-formyl-1H-pyrrol-3-carboxylate. After completion of the reaction, water was added to the reaction mixture, and the mixture was extracted with a mixed solvent (chloroform:methanol=9:1 (V/V)). The organic layer after separation was washed with a saturated aqueous solution of sodium chloride, dried over anhydrous magnesium sulfate and then concentrated under reduced pressure. The obtained residue was applied to silica gel column chromatography (Eluent; chloroform:methanol=9:1 (V/V)), and the fractions containing the desired compound were concentrated under reduced pressure to obtain 49 mg of the title compound as a white solid. (Yield: 47%)

Melting point: 294-295° C.

Mass Spectrum (CI, m/z): 348 (M$^+$+1).

$^1$H-NMR Spectrum (DMSO-d$_6$, δ ppm): 0.34-0.40 (m, 2H), 0.58-0.64 (m, 2H), 1.23-1.34 (m, 1H), 4.01 (d, J=6.8 Hz, 2H), 7.12 (t, J=74.7 Hz, 1H), 7.21 (d, J=0.7 Hz, 1H), 7.26 (d, J=8.3 Hz, 1H), 7.45 (dd, J=8.3, 2.0 Hz, 1H), 7.62 (d, J=2.0 Hz, 1H), 8.16 (d, J=0.7 Hz, 1H), 12.21 (s, 1H), 12.46 (brs, 1H).

Example 36

3-Chloro-2-(3-cyclopropylmethoxy-4-difluoromethoxyphenyl)-1,5-dihydropyrrolo[2,3-d]pyridazin-4-one (Exemplary compound No. 1-483)

36-(a) 3-Chloro-2-(3-cyclopropylmethoxy-4-difluoromethoxyphenyl)-1-(2-trimethylsilylethoxymethyl)-1,5-dihydropyrrolo[2,3-d]pyridazin-4-one Reaction and post treatment were carried out in the same manner as in Example 1-(a) except for using 0.40 g (1.1 mmol) of 2-bromo-3-chloro-1-(2-trimethylsilylethoxymethyl)-1,5-dihydropyrrolo[2,3-d]pyridazin-4-one obtained in the following Reference example 16-(d) in place of 2-bromo-1-(2-trimethylsilylethoxymethyl)-1,5-dihydropyrrolo-[2,3-d]pyridazin-4-one, and using 0.55 g (2.1 mmol) of 3-cyclopropylmethoxy-4-difluoromethoxyphenylboronic acid obtained in the following Reference example 3-(b) in place of 2-(3-cyclopropoxy-4-difluoromethoxyphenyl)-4,4,5,5-tetramethyl-[1,3,2]dioxaborolane, whereby 254 mg of the title compound was obtained as a white solid. (Yield: 46%)

Mass Spectrum (CI, m/z): 512 (M$^+$+1).

$^1$H-NMR Spectrum (CDCl$_3$, δ ppm): −0.03 (s, 9H), 0.33-0.40 (m, 2H), 0.63-0.71 (m, 2H), 0.82-0.91 (m, 2H), 1.24-1.39 (m, 1H), 3.42-3.50 (m, 2H), 3.90 (d, J=6.8 Hz, 2H), 5.34 (s, 2H), 6.73 (t, J=75.1 Hz, 1H), 7.08 (dd, J=8.1, 2.0 Hz, 1H), 7.13 (d, J=2.0 Hz, 1H), 7.31 (d, J=8.1 Hz, 1H), 8.19 (s, 1H), 10.11 (brs, 1H)

36-(b) 3-Chloro-2-(3-cyclopropylmethoxy-4-difluoromethoxyphenyl)-1,5-dihydropyrrolo[2,3-d]pyridazin-4-one Reaction was carried out in the same manner as in Example 2-(b) except for using 254 mg (0.496 mmol) of 3-chloro-2-(3-cyclopropylmethoxy-4-difluoromethoxyphenyl)-1-(2-trimethylsilylethoxymethyl)-1,5-dihydropyrrolo[2,3-d]-pyridazin-4-one obtained in Example 36-(a) in place of 3-chloro-2-(3-cyclopropoxy-4-difluoromethoxyphenyl)-1-(2-trimethylsilylethoxymethyl)-1,5-dihydropyrrolo[2,3-d]pyridazin-4-one. After completion of the reaction, diisopropyl ether and cyclohexane were added to the reaction mixture, and the precipitated solid was collected by filtration. The obtained crude solid was applied to silica gel column chromatography (Eluent; chloroform:methanol=9:1 (V/V)), the fractions containing the desired compound were concentrated, methanol and 28% aqueous ammonia were added to the obtained solid, and the mixture was stirred at room temperature for 3 hours. Then, the solution was concentrated under reduced pressure, and the obtained solid was washed with diisopropyl ether and dried under reduced pressure to obtain 100 mg of the title compound as a white solid. (Yield: 58%)

Melting point: 258-260° C.

Mass Spectrum (CI, m/z): 382 (M$^+$+1).

$^1$H-NMR Spectrum (DMSO-d$_6$, δ ppm): 0.34-0.41 (m, 2H), 0.56-0.65 (m, 2H), 1.23-1.38 (m, 1H), 3.99 (d, J=7.1 Hz, 2H), 7.17 (t, J=74.5 Hz, 1H), 7.35 (d, J=8.4 Hz, 1H), 7.44 (dd, J=8.4, 2.1 Hz, 1H), 7.51 (d, J=2.1 Hz, 1H), 8.14 (s, 1H), 12.35 (brs, 1H).

Example 37

2-(3-Cyclopropylmethoxy-4-difluoromethoxyphenyl)-3-ethyl-1,5-dihydropyrrolo[2,3-d]pyridazin-4-one HCl adduct (Exemplary compound No. 1-486)

37-(a) 2-(3-Cyclopropylmethoxy-4-difluoromethoxyphenyl)-3-ethyl-1,5-bis(2-trimethylsilylethoxymethyl)-1,5-dihydropyrrolo[2,3-d]pyridazin-4-one Reaction and post treatment were carried out in the same manner as in Example 36-(a) except for using 105 mg (0.19 mmol) of 3-ethyl-2-iodo-1,5-bis(2-trimethylsilylethoxymethyl)-1,5-dihydropyrrolo[2,3-d]pyridazin-4-one obtained in the following Reference example 46 in place of 2-bromo-3-chloro-1-(2-trimethylsilylethoxymethyl)-1,5-dihydropyrrolo[2,3-d]pyridazin-4-one, whereby 91 mg of the title compound was obtained as a yellowish oil. (Yield: 75%)

$^1$H-NMR Spectrum (CDCl$_3$, δ ppm): −0.04 (s, 9H), 0.00 (s, 9H), 0.32-0.39 (m, 2H), 0.61-0.70 (m, 2H), 0.81-0.88 (m, 2H), 0.97-1.04 (m, 2H), 1.22 (t, J=7.4 Hz, 3H), 1.23-1.34 (m, 1H), 2.77 (q, J=7.4 Hz, 2H), 3.39-3.46 (m, 2H), 3.71-3.78 (m, 2H), 3.88 (d, J=7.1 Hz, 2H), 5.26 (s, 2H), 5.61 (s, 2H), 6.34 (dd, J=8.5, 2.8 Hz, 1H), 6.46 (d, J=2.8 Hz, 1H), 6.51 (t, J=76.0 Hz, 1H), 7.02 (d, J=8.5 Hz, 1H), 8.16 (s, 1H).

IR Spectrum (neat, cm$^{-1}$): 1643.

37-(b) 2-(3-Cyclopropylmethoxy-4-difluoromethoxyphenyl)-3-ethyl-5-(2-trimethylsilylethoxymethyl)-1,5-dihydropyrrolo-[2,3-d]pyridazin-4-one Reaction and post treatment were carried out in the same manner as in Example 4-(b) except for using 615 mg (0.967 mmol) of 2-(3-cyclopropylmethoxy-4-difluoromethoxyphenyl)-3-ethyl-1,5-bis(2-trimethylsilylethoxymethyl)-1,5-dihydropyrrolo[2,3-d]pyridazin-4-one obtained in Example 37-(a) in place of 2-(3-cyclopropoxy-4-difluoromethoxyphenyl)-3-methyl-1,5-bis(2-trimethylsilylethoxymethyl)-1,5-dihydropyrrolo[2,3-d]pyridazin-4-one, whereby 440 mg of the title compound was obtained as a white solid. (Yield: 90%)

Mass Spectrum (CI, m/z): 506 (M$^+$+1).

$^1$H-NMR Spectrum (CDCl$_3$, δ ppm): −0.01 (s, 9H), 0.34-0.41 (m, 2H), 0.64-0.71 (m, 2H), 0.94-1.02 (m, 2H), 1.24-1.37 (m, 1H), 1.33 (t, J=7.4 Hz, 3H), 2.96 (q, J=7.4 Hz, 2H), 3.69-3.77 (m, 2H), 3.92 (d, J=7.1 Hz, 2H), 5.59 (s, 2H), 6.69 (t, J=75.2 Hz, 1H), 7.04 (dd, J=8.2, 2.1 Hz, 1H), 7.07 (d, J=2.1 Hz, 1H), 7.27 (d, J=8.2 Hz, 1H), 8.06 (s, 1H), 8.56 (brs, 1H).

IR Spectrum (KBr, cm$^{-1}$): 1630.

37-(c) 2-(3-Cyclopropylmethoxy-4-difluoromethoxyphenyl)-3-ethyl-1,5-dihydropyrrolo[2,3-d]pyridazin-4-one HCl adduct Reaction was carried out in the same manner as in Example 6-(c) except for using 476 mg (0.941 mmol) of 2-(3-cyclopropylmethoxy-4-difluoromethoxyphenyl)-3-ethyl-5-(2-trimethylsilylethoxymethyl)-1,5-dihydropyrrolo[2,3-d]pyridazin-4-one obtained in Example 37-(b) in place of 2-(3- cyclopropoxy-4-difluoromethoxyphenyl)-3-propyl-5-(2-trimethylsilylethoxymethyl)-1,5-dihydropyrrolo[2,3-d]pyridazin-4-one. After completion of the reaction, the solid obtained by filtrating the reaction suspension was washed with diisopropyl ether and dried under reduced pressure to obtain 352 mg of the title compound as a white solid. (Yield: 91%)

Melting point: 224-227° C.

Mass Spectrum (CI, m/z): 376 (M$^+$+1).

$^1$H-NMR Spectrum (DMSO-d$_6$, δ ppm): 0.33-0.40 (m, 2H), 0.56-0.64 (m, 2H), 1.19-1.37 (m, 1H), 1.23 (t, J=7.4 Hz, 3H), 2.88 (q, J=7.4 Hz, 2H), 3.98 (d, J=6.8 Hz, 2H), 7.14 (dd, J=8.3, 2.0 Hz, 1H), 7.16 (t, J=74.5 Hz, 1H), 7.27 (d, J=2.0 Hz, 1H), 7.32 (d, J=8.3 Hz, 1H), 8.08 (s, 1H), 12.12 (brs, 1H), 12.14 (brs, 1H).

IR Spectrum (KBr, cm$^{-1}$): 1502.

Example 38

2-(3-Cyclopropylmethoxy-4-difluoromethoxyphenyl)-3-phenyl-1,5-dihydropyrrolo[2,3-d]pyridazin-4-one (Exemplary compound No. 1-545)

38-(a) 2-(3-Cyclopropylmethoxy-4-difluoromethoxyphenyl)-1-(2-trimethylsilylethoxymethyl)-1,5-dihydropyrrolo[2,3-d]-pyridazin-4-one Reaction and post treatment were carried out in the same manner as in Example 1-(a) except for using 500 mg (1.47 mmol) of 2-(3-cyclopropylmethoxy-4-difluoromethoxyphenyl)-4,4,5,5-tetramethyl-[1,3,2]dioxaborolane obtained in the following Reference example 1-(c) in place of 2-(3-cyclopropoxy-4-difluoromethoxyphenyl)-4,4,5,5-tetramethyl-[1,3,2]dioxaborolane, whereby 448 mg of the title compound was obtained as a yellowish oil. (Yield: 76%)

Mass Spectrum (CI, m/z): 478 (M$^+$+1).

$^1$H-NMR Spectrum (CDCl$_3$, δ ppm): −0.02 (s, 9H), 0.33-0.40 (m, 2H), 0.64-0.71 (m, 2H), 0.86-0.95 (m, 2H), 1.23-1.39 (m, 1H), 3.50-3.58 (m, 2H), 3.91 (d, J=6.8 Hz, 2H), 5.43 (s, 2H), 6.71 (t, J=75.1 Hz, 1H), 6.93 (d, J=0.5 Hz, 1H), 7.13 (dd, J=8.3, 2.1 Hz, 1H), 7.20 (d, J=2.1 Hz, 1H), 7.28 (d, J=8.3 Hz, 1H), 8.22 (d, J=0.5 Hz, 1H), 10.18 (brs, 1H).

IR Spectrum (KBr, cm$^{-1}$): 1660.

38-(b) 2-(3-Cyclopropoxy-4-difluoromethoxyphenyl)-3-iodo-1-(2-trimethylsilylethoxymethyl)-1,5-dihydropyrrolo[2,3-d]-pyridazin-4-one Reaction and post treatment were carried out in the same manner as in Example 34-(a) except for using 403 mg (0.845 mmol) of 2-(3-cyclopropylmethoxy-4-difluoromethoxyphenyl)-1-(2-trimethylsilylethoxymethyl)-1,5-dihydropyrrolo[2,3-d]pyridazin-4-one obtained in Example 38-(a) in place of 2-(3-cyclobutoxy-4-difluoromethoxyphenyl)-1-(2-trimethylsilylethoxymethyl)-1,5-dihydropyrrolo[2,3-d]pyridazin-4-one, whereby 464 mg of the title compound was obtained as a pale yellowish foam. (Yield: 91%)

Mass Spectrum (CI, m/z): 604 (M$^+$+1).

$^1$H-NMR Spectrum (CDCl$_3$, δ ppm): −0.04 (s, 9H), 0.34-0.40 (m, 2H), 0.63-0.71 (m, 2H), 0.80-0.88 (m, 2H), 1.23-1.39 (m, 1H), 3.39-3.46 (m, 2H), 3.91 (d, J=6.8 Hz, 2H), 5.34 (s, 2H), 6.74 (t, J=75.0 Hz, 1H), 7.01 (dd, J=8.2, 2.0 Hz, 1H), 7.06 (d, J=2.0 Hz, 1H), 7.31 (d, J=8.2 Hz, 1H), 8.22 (s, 1H), 9.99 (brs, 1H).

IR Spectrum (KBr, cm$^{-1}$): 1658.

38-(c) 5-Benzyl-2-(3-cyclopropylmethoxy-4-difluoromethoxyphenyl)-3-iodo-1-(2-trimethylsilylethoxymethyl)-1,5-dihydropyrrolo[2,3-d]pyridazin-4-one To 452 mg (0.749 mmol) of 2-(3-cyclopropylmethoxy-4-difluoromethoxyphenyl)-3-iodo-1-(2-trimethylsilylethoxymethyl)-1,5-dihydropyrrolo[2,3-d]pyridazin-4-one obtained in Example 38-(b) and 126 mg of potassium carbonate was added 4 ml of dehydrated N,N-dimethylformamide, then 0.1 ml of benzyl bromide was added to the mixture, and the resulting mixture was stirred at room temperature for 16 hours. Moreover, 36 mg of sodium hydride (55% dispersed material in mineral oil) and 0.1 ml of benzyl bromide were further added to the mixture, and the resulting mixture was stirred for 2 hours. After completion of the reaction, a saturated aqueous solution of ammonium chloride was added to the reaction mixture, and the mixture was extracted with toluene. The organic layer after separation was washed successively with water and then with a saturated aqueous solution of sodium chloride, dried over anhydrous magnesium sulfate and then concentrated under reduced pressure. The obtained residue was applied to silica gel column chromatography (Eluent; hexane:ethyl acetate=19:1→1:1 (V/V)), and the fractions containing the desired compound were concentrated under reduced pressure to obtain 389 mg of the title compound as a pale yellowish foam. (Yield: 75%)

Mass Spectrum (CI, m/z): 694 (M$^+$+1).

$^1$H-NMR Spectrum (CDCl$_3$, δ ppm): −0.05 (s, 9H), 0.33-0.40 (m, 2H), 0.62-0.70 (m, 2H), 0.79-0.86 (m, 2H), 1.24-1.39 (m, 1H), 3.37-3.44 (m, 2H), 3.90 (d, J=7.1 Hz, 2H), 5.30 (s, 2H), 5.42 (s, 2H), 6.73 (t, J=75.0 Hz, 1H), 6.99 (dd, J=8.2, 2.1 Hz, 1H), 7.05 (d, J=2.1 Hz, 1H), 7.21-7.38 (m, 4H), 7.45-7.50 (m, 2H), 8.19 (s, 1H).

IR Spectrum (KBr, cm$^{-1}$): 1662.

38-(d) 5-Benzyl-2-(3-cyclopropylmethoxy-4-difluoromethoxyphenyl)-3-phenyl-1-(2-trimethylsilylethoxymethyl)-1,5-dihydropyrrolo[2,3-d]pyridazin-4-one Reaction and post treatment were carried out in the same manner as in Example 1-(a) except for using 383 mg (0.552 mmol) of 5-benzyl-2-(3-cyclopropylmethoxy-4-difluoromethoxyphenyl)-3-iodo-1-(2-trimethylsilylethoxymethyl)-1,5-dihydropyrrolo[2,3-d]pyridazin-4-one obtained in Example 38-(c) in place of 2-bromo-1-(2-trimethylsilylethoxymethyl)-1,5-dihydropyrrolo[2,3-d]pyridazin-4-one, using 84 mg (0.69 mmol) of phenylboronic acid in place of 2-(3-cyclopropoxy-4-difluoromethoxyphenyl)-4,4,5,5-tetramethyl-[1,3,2]dioxaborolane, and using 55 μl of tetrahydrofuran solution containing 100 mM palladium complex prepared previously from 231 mg (1.03 mmol) of palladium acetate and 846 mg of 2-dicyclohexylphosphino-2',6'-dimethoxybiphenyl in place of tetrakis(triphenylphosphine) palladium, whereby 330 mg of the title compound was obtained as a pale brownish foam. (Yield: 93%)

$^1$H-NMR Spectrum (CDCl$_3$, δ ppm): −0.03 (s, 9H), 0.19-0.25 (m, 2H), 0.50-0.58 (m, 2H), 0.85-0.92 (m, 2H), 0.93-1.05 (m, 1H), 3.46-3.54 (m, 2H), 3.58 (d, J=7.1 Hz, 2H), 5.37 (s, 2H), 5.43 (s, 2H), 6.65 (t, J=75.1 Hz, 1H), 6.77 (d, J=2.0 Hz, 1H), 6.93 (dd, J=8.3, 2.0 Hz, 1H), 7.14-7.50 (m, 10H), 7.16 (d, J=8.3 Hz, 1H), 8.23 (s, 1H).

38-(e) 5-Benzyl-2-(3-cyclopropylmethoxy-4-difluoromethoxyphenyl)-3-phenyl-1,5-dihydropyrrolo[2,3-d]pyridazin-4-one Reaction and post treatment were carried out in the same manner as in Example 4-(b) except for using 328 mg (0.501 mmol) of 5-benzyl-2-(3-cyclopropylmethoxy-4-difluoromethoxyphenyl)-3-phenyl-1-(2-trimethylsilylethoxymethyl)-1,5-dihydropyrrolo[2,3-d]pyridazin-4-one obtained in Example 38-(d) in place of 2-(3-cyclopropoxy-4-difluoromethoxyphenyl)-3-methyl-1,5-bis(2-trimethylsilylethoxymethyl)-1,5-dihydropyrrolo[2,3-d]pyridazin-4-one, whereby 207 mg of the title compound was obtained as a white solid. (81%)

Mass Spectrum (CI, m/z): 514 (M$^+$+1).

$^1$H-NMR Spectrum (CDCl$_3$, δ ppm): 0.10-0.18 (m, 2H), 0.46-0.55 (m, 2H), 0.85-1.04 (m, 1H), 3.36 (d, J=6.8 Hz, 2H), 5.40 (s, 2H), 6.59 (t, J=75.3 Hz, 1H), 6.66 (d, J=2.1 Hz, 1H), 6.81 (dd, J=8.3, 2.1 Hz, 1H), 7.02 (d, J=8.3 Hz, 1H), 7.09-7.41 (m, 10H), 7.99 (s, 1H), 9.37 (brs, 1H).

IR Spectrum (KBr, cm$^{-1}$): 1622.

38-(f) 2-(3-Cyclopropylmethoxy-4-difluoromethoxyphenyl)-3-phenyl-1,5-dihydropyrrolo[2,3-d]pyridazin-4-one To 15 ml of acetic acid solution containing 205 mg (0.399 mmol) of 5-benzyl-2-(3-cyclopropylmethoxy-4-difluoromethoxyphenyl)-3-phenyl-1,5-dihydropyrrolo[2,3-d]-pyridazin-4-one obtained in Example 38-(e) was added 103 mg of 10% palladium-active carbon, and under 1 atm hydrogen atmosphere, the mixture was stirred at 95° C. for 31.5 hours. After completion of the reaction, insoluble material was removed from the reaction suspension by filtration, and the filtrate was concentrated under reduced pressure. The obtained residue was applied to silica gel column chromatography (Eluent; hexane:ethyl acetate=4:1→0:1 (V/V)), and the fractions containing the desired compound were concentrated under reduced pressure. The obtained crude solid was purified by high performance liquid chromatography (column; Kromacil™ 100-5-C18 (20×250 mm (manufactured by EKA CHEMICALS), Eluent; acetonitrile:water:trifluoroacetic acid=1500:1000:2.5 (V/V/V), Flow rate; 10 ml/min) to obtain 30 mg of the title compound as a white solid. (Yield: 18%)

Melting point: 249-251° C.

Mass Spectrum (CI, m/z): 424 (M$^+$+1).

$^1$H-NMR Spectrum (DMSO-d$_6$, δ ppm): 0.18-0.27 (m, 2H), 0.46-0.56 (m, 2H), 0.97-1.10 (m, 1H), 3.58 (d, J=6.8 Hz, 2H), 6.92-7.00 (m, 2H), 7.09 (t, J=73.6 Hz, 1H), 7.16 (d, J=8.8 Hz, 1H), 7.23-7.40 (m, 5H), 8.15 (s, 1H), 12.15 (brs, 1H), 12.48 (brs, 1H).

IR Spectrum (KBr, cm$^{-1}$): 1618.

Example 39

2-(4-Difluoromethoxy-3-isopropoxyphenyl)-1,5-dihydropyrrolo[2,3-d]pyridazin-4-one (Exemplary compound No. 1-666)

39-(a) 2-(4-Difluoromethoxy-3-isopropoxyphenyl)-1-(2-trimethylsilylethoxymethyl)-1,5-dihydropyrrolo[2,3-d]pyridazin-4-one Reaction and post treatment were carried out in the same manner as in Example 1-(a) except for using 125 mg (0.382 mmol) of 2-(4-difluoromethoxy-3-isopropoxyphenyl)-4,4,5,5-tetramethyl-[1,3,2]dioxaborolane obtained in the following Reference example 1-(d) in place of 2-(3-cyclopropoxy-4-difluoromethoxyphenyl)-4,4,5,5-tetramethyl-[1,3,2]dioxaborolane, whereby 108 mg of the title compound was obtained as a pale yellowish solid substantially quantitatively.

$^1$H-NMR Spectrum (CDCl$_3$, δ ppm): −0.02 (s, 9H), 0.88-0.94 (m, 2H), 1.40 (d, J=6.1 Hz, 6H), 3.52-3.58 (m, 2H), 4.55-4.64 (m, 1H), 5.44 (s, 2H), 6.64 (t, J=75.0 Hz, 1H), 6.94 (d, J=0.5 Hz, 1H), 7.12 (dd, J=8.1, 2.1 Hz, 1H), 7.22 (d, J=2.1 Hz, 1H), 7.27 (d, J=8.1 Hz, 1H), 8.22 (d, J=0.5 Hz, 1H), 10.11 (brs, 1H).

39-(b) 2-(4-Difluoromethoxy-3-isopropoxyphenyl)-1,5-dihydropyrrolo[2,3-d]pyridazin-4-one To 2 ml of dichloromethane solution containing 99 mg (0.21 mmol) of 2-(4-difluoromethoxy-3-isopropoxyphenyl)-1-(2-trimethylsilylethoxymethyl)-1,5-dihydropyrrolo[2,3-d]-pyridazin-4-one obtained in Example 39-(a) was added 0.1 ml of boron trifluoride diethyl ether complex under ice-cooling, and the mixture was reacted at room temperature for 3 hours. After completion of the reaction, methanol and 28% aqueous ammonia were added to the solid obtained by filtrating the reaction suspension, and the mixture was stirred at room temperature for 12 hours. Then, the solution was concentrated under reduced pressure, and the obtained solid was washed with chloroform and dried under reduced pressure to obtain 29 mg of the title compound as a white solid. (Yield: 42%)

Melting point: 269-273° C.

Mass Spectrum (CI, m/z): 336 (M$^+$+1)

$^1$H-NMR Spectrum (DMSO-d$_6$, δ ppm): 1.33 (d, J=5.9 Hz, 6H) 4.77-4.85 (m, 1H), 7.07 (t, J=74.7 Hz, 1H), 7.20 (d, J=0.6 Hz, 1H), 7.25 (d, J=8.4 Hz, H=1), 7.45 (dd, J=8.4, 2.1 Hz, 1H), 7.64 (d, J=2.1 Hz, 1H), 8.16 (d, J=0.6 Hz, 1H), 12.23 (brs, 1H), 12.45 (brs, 1H).

IR Spectrum (KBr, cm$^{-1}$): 1645.

Example 40

3-Chloro-2-(4-difluoromethoxy-3-isopropoxyphenyl)-1,5-dihydropyrrolo[2,3-d]pyridazin-4-one (Exemplary compound No. 1-667)

40-(a) 3-Chloro-2-(4-difluoromethoxy-3-isopropoxyphenyl)-1-(2-trimethylsilylethoxymethyl)-1,5-dihydropyrrolo[2,3-d]-pyridazin-4-one Reaction and post treatment were carried out in the same manner as in Example 39-(a) except for using 405 mg (1.09 mmol) of 2-bromo-3-chloro-1-(2-trimethylsilylethoxymethyl)-1,5-dihydropyrrolo[2,3-d]pyridazin-4-one obtained in the following Reference example 16-(d) in place of 2-bromo-1-(2-trimethylsilylethoxymethyl)-1,5-dihydropyrrolo-[2,3-d]pyridazin-4-one, whereby 249 mg of the title compound was obtained as a white solid. (Yield: 46%)

Mass Spectrum (CI, m/z): 500 (M$^+$+1).

$^1$H-NMR Spectrum (CDCl$_3$, δ ppm): −0.03 (s, 9H), 0.83-0.91 (m, 2H), 1.40 (d, J=6.1 Hz, 6H), 3.42-3.51 (m, 2H), 4.51-4.63 (m, 1H), 5.36 (s, 2H), 6.66 (t, J=75.1 Hz, 1H), 7.06 (dd, J=8.3, 2.1 Hz, 1H), 7.15 (d, J=2.1 Hz, 1H), 7.30 (d, J=8.3 Hz, 1H), 8.19 (s, 1H), 10.00 (brs, 1H).

40-(b) 3-Chloro-2-(4-difluoromethoxy-3-isopropoxyphenyl)-1,5-dihydropyrrolo[2,3-d]pyridazin-4-one Reaction was carried out in the same manner as in Example 1-(b) except for using 247 mg (0.495 mmol) of 3-chloro-2-(4-difluoromethoxy-3-isopropoxyphenyl)-1-(2-trimethylsilylethoxymethyl)-1,5-dihydropyrrolo[2,3-d]pyridazin-4-one obtained in Example 40-(a) in place of 2-(3-cyclopropoxy-4- difluoromethoxyphenyl)-1-(2-trimethylsilylethoxymethyl)-1,5-dihydropyrrolo[2,3-d]pyridazin-4-one. After completion of the reaction, active carbon was added to the reaction suspension, and the mixture was stirred at room temperature for further 2 hours, and insoluble material was removed by filtration. The filtrate was concentrated under reduced pressure, the obtained solid was dissolved by adding a small amount of tetrahydrofuran, followed by addition of water, and the solid precipitated by ultrasonic wave treatment was collected by filtration. The obtained solid was washed with water and dried under reduced pressure to obtain 175 mg of the title compound as a white solid. (Yield: 96%)

Melting point: 248-262° C.

Mass Spectrum (CI, m/z): 370 ($M^++1$).

$^1$H-NMR Spectrum (DMSO-$d_6$, δ ppm): 1.35 (d, J=6.1 Hz, 6H) 4.63-4.77 (m, 1H), 7.11 (t, J=74.5 Hz, 1H), 7.32 (d, J=8.4 Hz, 1H), 7.44 (dd, J=8.4, 2.1 Hz, 1H), 7.56 (d, J=2.1 Hz, 1H), 8.12 (s, 1H), 12.24 (brs, 1H).

IR Spectrum (KBr, $cm^{-1}$): 1635.

Example 41

3-Bromo-2-(4-difluoromethoxy-3-isopropoxyphenyl)-1,5-dihydropyrrolo[2,3-d]pyridazin-4-one (Exemplary compound No. 1-668)

41-(a) 3-Bromo-2-(4-difluoromethoxy-3-isopropoxyphenyl)-1-(2-trimethylsilylethoxymethyl)-1,5-dihydropyrrolo[2,3-d]-pyridazin-4-one Reaction and post treatment were carried out in the same manner as in Example 39-(a) except for using 30 mg (0.070 mmol) of 2,3-dibromo-1-(2-trimethylsilylethoxymethyl)-1,5-dihydropyrrolo[2,3-d]pyridazin-4-one obtained in the following Reference example 44 in place of 2-bromo-1-(2-trimethylsilylethoxymethyl)-1,5-dihydropyrrolo[2,3-d]-pyridazin-4-one, whereby 24 mg of the title compound was obtained as a pale yellowish solid. (Yield: 64%)

$^1$H-NMR Spectrum (CDCl$_3$, δ ppm): -0.03 (s, 9H), 0.82-0.90 (m, 2H), 1.40 (d, J=6.1 Hz, 6H), 3.41-3.49 (m, 2H), 4.52-4.64 (m, 1H), 5.35 (s, 2H), 6.67 (t, J=75.0 Hz, 1H), 7.03 (dd, J=8.3, 2.1 Hz, 1H), 7.13 (d, J=2.1 Hz, 1H), 7.30 (d, J=8.3 Hz, 1H), 8.20 (s, 1H), 9.90 (brs, 1H).

41-(b) 3-Bromo-2-(4-difluoromethoxy-3-isopropoxyphenyl)-1,5-dihydropyrrolo[2,3-d]pyridazin-4-one Reaction and post treatment were carried out in the same manner as in Example 32-(b) except for using 22 mg (0.040 mmol) of 3-bromo-2-(4-difluoromethoxy-3-isopropoxyphenyl)-1-(2-trimethylsilylethoxymethyl)-1,5-dihydropyrrolo[2,3-d]pyridazin-4-one obtained in Example 41-(a) in place of 3-chloro-2-(3-cyclobutoxy-4-difluoromethoxyphenyl)-1-(2-trimethylsilylethoxymethyl)-1,5-dihydropyrrolo[2,3-d]pyridazin-4-one, whereby 7 mg of the title compound was obtained as a white solid. (Yield: 40%)

Melting point: 250-256° C. (decomposed).

$^1$H-NMR Spectrum (DMSO-$d_6$, δ ppm): 1.35 (d, J=5.9 Hz, 6H) 4.64-4.78 (m, 1H), 7.13 (t, J=74.3 Hz, 1H), 7.34 (d, J=8.3 Hz, 1H), 7.38 (dd, J=8.3, 2.0 Hz, 1H), 7.53 (d, J=2.0 Hz, 1H), 8.16 (s, 1H), 12.35 (brs, 1H), 12.79 (brs, 1H)

Example 42

3-Chloro-2-(3-cyclopropoxy-4-methoxyphenyl)-1,5-dihydropyrrolo[2,3-d]pyridazin-4-one (Exemplary compound No. 1-917)

42-(a) 3-Chloro-2-(3-cyclopropoxy-4-methoxyphenyl)-1-(2-trimethylsilylethoxymethyl)-1,5-dihydropyrrolo[2,3-d]-pyridazin-4-one Reaction and post treatment were carried out in the same manner as in Example 1-(a) except for using 400 mg (1.07 mmol) of 2-bromo-3-chloro-1-(2-trimethylsilylethoxymethyl)-1,5-dihydropyrrolo[2,3-d]pyridazin-4-one obtained in the following Reference example 16-(d) in place of 2-bromo-1-(2-trimethylsilylethoxymethyl)-1,5-dihydropyrrolo-[2,3-d]pyridazin-4-one, and using 468 mg (1.61 mmol) of 2-(3-cyclopropoxy-4-methoxyphenyl)-4,4,5,5-tetramethyl-[1,3,2]dioxaborolane obtained in the following Reference example 1-(e) in place of 2-(3-cyclopropoxy-4-difluoromethoxyphenyl)-4,4,5,5-tetramethyl-[1,3,2]dioxaborolane, whereby 322 mg of the title compound was obtained as a pale yellowish solid. (Yield: 65%)

Mass Spectrum (CI, m/z): 462 ($M^++1$).

$^1$H-NMR Spectrum (CDCl$_3$, δ ppm): -0.04 (s, 9H), 0.77-0.93 (m, 6H), 3.41-3.49 (m, 2H), 3.72-3.80 (m, 1H), 3.93 (s, 3H), 5.39 (s, 2H), 7.00 (d, J=8.3 Hz, 1H), 7.09 (dd, J=8.3, 2.1 Hz, 1H), 7.41 (d, J=2.1 Hz, 1H), 8.19 (s, 1H), 9.84 (brs, 1H).

IR Spectrum (KBr, $cm^{-1}$): 1663.

42-(b) 3-Chloro-2-(3-cyclopropoxy-4-methoxyphenyl)-1,5-dihydropyrrolo[2,3-d]pyridazin-4-one Reaction was carried out in the same manner as in Example 1-(b) except for using 313 mg (0.677 mmol) of 3-chloro-2-(3-cyclopropoxy-4-methoxyphenyl)-1-(2-trimethylsilylethoxymethyl)-1,5-dihydropyrrolo[2,3-d]pyridazin-4-one obtained in Example 42-(a) in place of 2-(3-cyclopropoxy-4-difluoromethoxyphenyl)-1-(2-trimethylsilylethoxymethyl)-1,5-dihydropyrrolo[2,3-d]pyridazin-4-one. After completion of the reaction, water was added to the reaction mixture, and the precipitated solid was collected by filtration. The obtained crude solid was dissolved by adding small amounts of tetrahydrofuran and methanol, followed by addition of water, and the solid precipitated by ultrasonic wave treatment was collected by filtration. The obtained solid was washed with water and dried under reduced pressure to obtain 136 mg of the title compound as a white solid. (Yield: 61%)

Melting point: 293-294° C.

Mass Spectrum (CI, m/z): 332 ($M^++1$).

$^1$H-NMR Spectrum (DMSO-$d_6$, δ ppm): 0.66-0.77 (m, 2H), 0.77-0.86 (m, 2H), 3.80 (s, 3H), 3.84-3.92 (m, 1H), 7.12 (d, J=8.5 Hz, 1H), 7.40 (dd, J=8.5, 2.2 Hz, 1H), 7.75 (d, J=2.2 Hz, 1H), 8.10 (s, 1H), 12.23 (brs, 1H).

IR Spectrum (KBr, $cm^{-1}$): 1628.

Example 43

3-Bromo-2-(3-cyclopropoxy-4-methoxyphenyl)-1,5-dihydropyrrolo[2,3-d]pyridazin-4-one (Exemplary compound No. 1-918)

43-(a) 3-Bromo-2-(3-cyclopropoxy-4-methoxyphenyl)-1-(2-trimethylsilylethoxymethyl)-1,5-dihydropyrrolo[2,3-d]-pyridazin-4-one Reaction and post treatment were carried out in the same manner as in Example 42-(a) except for using 227 mg (0.536 mmol) of 2,3-dibromo-1-(2-trimethylsilylethoxymethyl)-1,5-dihydropyrrolo[2,3-d]pyridazin-4-one obtained in the following Reference example 44 in place of 2-bromo-3-chloro-1-(2-trimethylsilylethoxymethyl)-1,5-dihydropyrrolo[2,3-d]pyridazin-4-one, whereby 241 mg of the title compound was obtained as a pale yellowish solid. (Yield: 90%)

$^1$H-NMR Spectrum (CDCl$_3$, δ ppm): −0.04 (s, 9H), 0.77-0.95 (m, 6H), 3.39-3.47 (m, 2H), 3.72-3.80 (m, 1H), 3.93 (s, 3H), 5.39 (s, 2H), 6.99 (d, J=8.3 Hz, 1H), 7.07 (dd, J=8.3, 2.0 Hz, 1H), 7.39 (d, J=2.0 Hz, 1H), 8.21 (s, 1H), 9.97 (brs, 1H).

43-(b) 3-Bromo-2-(3-cyclopropoxy-4-methoxyphenyl)-1,5-dihydropyrrolo[2,3-d]pyridazin-4-one To 1 ml of dichloromethane solution containing 186 mg (0.367 mmol) of 3-bromo-2-(3-cyclopropoxy-4-methoxyphenyl)-1-(2-trimethylsilylethoxymethyl)-1,5-dihydropyrrolo[2,3-d]-pyridazin-4-one obtained in Example 43-(a) was added 6 ml of 1,4-dioxane solution containing 4N hydrogen chloride, and the mixture was stirred at room temperature for 8 hours. After completion of the reaction, the solid obtained from the reaction suspension by filtration was washed with diisopropyl ether. To the obtained crude solid were added methanol and 28% aqueous ammonia, and the mixture was stirred at room temperature for 5 hours. Then, the solution was concentrated under reduced pressure and the obtained solid was washed with ethyl acetate and dried under reduced pressure to obtain 85 mg of the title compound as a white solid. (Yield: 62%)

Melting point: 293-296° C. (decomposed).
Mass Spectrum (CI, m/z): 376 (M$^+$+1).
$^1$H-NMR Spectrum (DMSO-d$_6$, δ ppm): 0.68-0.87 (m, 4H), 3.81 (s, 3H), 3.85-3.92 (m, 1H), 7.13 (d, J=8.5 Hz, 1H), 7.38 (dd, J=8.5, 2.2 Hz, 1H), 7.76 (d, J=2.2 Hz, 1H), 8.14 (s, 1H), 12.32 (brs, 1H), 12.78 (brs, 1H).
IR Spectrum (KBr, cm$^{-1}$): 1634.

Example 44

3-Butyl-2-(3-cyclopropoxy-4-methoxyphenyl)-1,5-dihydropyrrolo[2,3-d]pyridazin-4-one (Exemplary compound No. 1-923)

44-(a) 3-Butyl-2-(3-cyclopropoxy-4-methoxyphenyl)-1,5-bis(2-trimethylsilylethoxymethyl)-1,5-dihydropyrrolo[2,3-d]-pyridazin-4-one Reaction and post treatment were carried out in the same manner as in Example 4-(a) except for using 530 mg (0.999 mmol) of 2-bromo-3-butyl-1,5-bis(2-trimethylsilylethoxymethyl)-1,5-dihydropyrrolo[2,3-d]pyridazin-4-one obtained in the following Reference example 22-(b) in place of 2-bromo-3-methyl-1,5-bis(2-trimethylsilylethoxymethyl)-1,5-dihydropyrrolo[2,3-d]pyridazin-4-one, and using 435 mg (1.50 mmol) of 2-(3-cyclopropoxy-4-methoxyphenyl)-4,4,5,5-tetramethyl-[1,3,2]dioxaborolane obtained in the following Reference Example 1-(e) in place of 2-(3-cyclopropoxy-4-difluoromethoxyphenyl)-4,4,5,5-tetramethyl-[1,3,2]dioxaborolane, whereby 537 mg of the title compound was obtained as a brownish oil. (Yield: 88%)

Mass Spectrum (CI, m/z): 614 (M$^+$+1).
$^1$H-NMR Spectrum (CDCl$_3$, δ ppm): −0.05 (s, 9H), 0.00 (s, 9H) 0.76-0.92 (m, 6H), 0.83 (t, J=7.3 Hz, 3H), 0.95-1.04 (m, 2H), 1.22-1.35 (m, 2H), 1.56-1.68 (m, 2H), 2.73-2.81 (m, 2H), 3.36-3.43 (m, 2H), 3.69-3.79 (m, 3H), 3.93 (s, 3H), 5.30 (s, 2H), 5.61 (s, 2H), 6.93-6.99 (m, 2H), 7.25-7.27 (m, 1H), 8.17 (s, 1H).

44-(b) 3-Butyl-2-(3-cyclopropoxy-4-methoxyphenyl)-5-(2-trimethylsilylethoxymethyl)-1,5-dihydropyrrolo[2,3-d]-pyridazin-4-one Reaction and post treatment were carried out in the same manner as in Example 4-(b) except for using 536 mg (0.873 mmol) of 3-butyl-2-(3-cyclopropoxy-4-methoxyphenyl)-1,5-bis(2-trimethylsilylethoxymethyl)-1,5-dihydropyrrolo-[2,3-d]pyridazin-4-one obtained in Example 44-(a) in place of 2-(3-cyclopropoxy-4-difluoromethoxyphenyl)-3-methyl-1,5-bis(2-trimethylsilylethoxymethyl)-1,5-dihydropyrrolo[2,3-d]pyridazin-4-one, whereby 329 mg of the title compound was obtained as a white solid. (Yield: 78%)

Mass Spectrum (CI, m/z): 484 (M$^+$+1).
$^1$H-NMR Spectrum (CDCl$_3$, δ ppm): −0.01 (s, 9H), 0.78-0.94 (m, 4H), 0.89 (t, J=7.3 Hz, 3H), 0.95-1.03 (m, 2H), 1.33-1.47 (m, 2H), 1.66-1.78 (m, 2H), 2.93-3.02 (m, 2H), 3.68-3.81 (m, 3H), 3.91 (s, 3H), 5.60 (s, 2H), 6.96 (d, J=8.3 Hz, 1H), 7.05 (dd, J=8.3, 2.1 Hz, 1H), 7.41 (d, J=2.1 Hz, 1H), 8.06 (s, 1H), 8.53 (brs, 1H).
IR Spectrum (KBr, cm$^{-1}$): 1628.

44-(c) 3-Butyl-2-(3-cyclopropoxy-4-difluoromethoxyphenyl)-1,5-dihydropyrrolo[2,3-d]pyridazin-4-one Reaction and post treatment were carried out in the same manner as in Example 6-(c) except for using 328 mg (0.678 mmol) of 3-butyl-2-(3-cyclopropoxy-4-methoxyphenyl)-5-(2-trimethylsilylethoxymethyl)-1,5-dihydropyrrolo[2,3-d]-pyridazin-4-one obtained in Example 44-(b) in place of 2-(3-cyclopropoxy-4-difluoromethoxyphenyl)-3-propyl-5-(2-trimethylsilylethoxymethyl)-1,5-dihydropyrrolo[2,3-d]pyridazin-4-one, whereby 222 mg of the title compound was obtained as a white solid. (Yield: 93%)

Melting point: 198-200° C.
Mass Spectrum (CI, m/z): 354 (M$^+$+1).
$^1$H-NMR Spectrum (DMSO-d$_6$, δ ppm): 0.69-0.82 (m, 4H), 0.86 (t, J=7.3 Hz, 3H), 1.25-1.38 (m, 2H), 1.56-1.69 (m, 2H), 2.85-2.94 (m, 2H), 3.79 (s, 3H), 3.82-3.91 (m, 1H), 7.07-7.16 (m, 2H), 7.43 (d, J=1.2 Hz, 1H), 8.04 (s, 1H), 12.01 (brs, 1H), 12.05 (brs, 1H).
IR Spectrum (KBr, cm$^{-1}$): 1641.

Example 45

3-Chloro-2-(3-cyclobutoxy-4-methoxyphenyl)-1,5-dihydropyrrolo[2,3-d]pyridazin-4-one (Exemplary compound No. 1-1224)

45-(a) 3-Chloro-2-(3-cyclobutoxy-4-methoxyphenyl)-1-(2-trimethylsilylethoxymethyl)-1,5-dihydropyrrolo[2,3-d]pyridazin-4-one Reaction and post treatment were carried out in the same manner as in Example 1-(a) except for using 0.40 g (1.1 mmol) of 2-bromo-3-chloro-1-(2-trimethylsilylethoxymethyl)-1,5-dihydropyrrolo[2,3-d]pyridazin-4-one obtained in the following Reference example 16-(d) in place of 2-bromo-1-(2-trimethylsilylethoxymethyl)-1,5-dihydropyrrolo-[2,3-d]pyridazin-4-one, and using 0.49 g (1.6 mmol) of 2-(3-cyclobutoxy-4-methoxyphenyl)-4,4,5,5-tetramethyl-[1,3,2]dioxaborolane obtained in the following Reference example 1-(f) in place of 2-(3-cyclopropoxy-4-difluoromethoxyphenyl)-4,4,5,5-tetramethyl-[1,3,2]dioxaborolane, whereby 339 mg of the title compound was obtained as a pale yellowish solid. (Yield: 67%)

Mass Spectrum (CI, m/z): 476 (M$^+$+1).

$^1$H-NMR Spectrum (CDCl$_3$, δ ppm): −0.04 (s, 9H), 0.81-0.90 (m, 2H), 1.55-1.75 (m, 1H), 1.81-1.95 (m, 1H), 2.21-2.36 (m, 2H), 2.42-2.54 (m, 2H), 3.40-3.47 (m, 2H), 3.94 (s, 3H), 4.61-4.72 (m, 1H), 5.36 (s, 2H), 6.89 (d, J=2.0 Hz, 1H), 6.99 (d, J=8.3 Hz, 1H), 7.05 (dd, J=8.3, 2.0 Hz, 1H), 8.19 (s, 1H), 10.16 (brs, 1H).

45-(b) 3-Chloro-2-(3-cyclobutoxy-4-methoxyphenyl)-1,5-dihydropyrrolo[2,3-d]pyridazin-4-one Reaction and post treatment were carried out in the same manner as in Example 32-(b) except for using 335 mg (0.70 mmol) of 3-chloro-2-(3-cyclobutoxy-4-methoxyphenyl)-1-(2-trimethylsilylethoxymethyl)-1,5-dihydropyrrolo[2,3-d]-pyridazin-4-one obtained in Example 45-(a) in place of 3-chloro-2-(3-cyclobutoxy-4-difluoromethoxyphenyl)-1-(2-trimethylsilylethoxymethyl)-1,5-dihydropyrrolo[2,3-d]pyridazin-4-one, whereby 204 mg of the title compound was obtained as a white solid. (Yield: 84%)
Melting point: 285-287° C.
Mass Spectrum (CI, m/z): 346 (M$^+$+1).
$^1$H-NMR Spectrum (DMSO-d$_6$, δ ppm): 1.57-1.74 (m, 1H), 1.74-1.88 (m, 1H), 2.03-2.18 (m, 2H), 2.40-2.49 (m, 2H), 3.83 (s, 3H), 4.66-4.78 (m, 1H), 7.13 (d, J=8.5 Hz, 1H), 7.25 (d, J=2.1 Hz, 1H), 7.37 (dd, J=8.5, 2.1 Hz, 1H), 8.11 (s, 1H), 12.31 (brs, 1H).

Example 46

2-(3-Cyclopentoxy-4-methoxyphenyl)-1,5-dihydropyrrolo[2,3-d]pyridazin-4-one (Exemplary compound No. 1-1256)

Reaction was carried out in the same manner as in Example 22-(a) except for using 107 mg (0.30 mmol) of ethyl 5-(3-cyclopentoxy-4-methoxyphenyl)-2-formyl-1H-pyrrol-3-carboxylate obtained in the following Reference example 47-(e) in place of ethyl 1-benzyloxymethyl-5-(3-cyclopropoxy-4-difluoromethoxyphenyl)-4-(2-fluorobenzyl)-2-formyl-1H-pyrrol-3-carboxylate. After completion of the reaction, the solid obtained from the reaction suspension by filtration was washed successively with ethanol, water and then with diisopropyl ether, and dried under reduced pressure to obtain 44 mg of the title compound as a white solid. (Yield: 45%)
Melting point: 290° C. (decomposed).
Mass Spectrum (CI, m/z): 326 (M$^+$+1).
$^1$H-NMR Spectrum (DMSO-d$_6$, δ ppm): 1.52-1.66 (m, 2H), 1.66-1.79 (m, 4H), 1.86-2.01 (m, 2H), 3.78 (s, 3H), 4.90-4.96 (m, 1H), 7.03 (s, 1H), 7.03 (d, J=8.3 Hz, 1H), 7.37-7.43 (m, 2H), 8.12 (s, 1H), 12.17 (brs, 1H), 12.37 (brs, 1H).
IR Spectrum (KBr, cm$^{-1}$): 1644.

Example 47

3-Chloro-2-(3-cyclopropylmethoxy-4-methoxyphenyl)-1,5-dihydropyrrolo[2,3-d]pyridazin-4-one (Exemplary compound No. 1-1101)

47-(a) 3-Chloro-2-(3-cyclopropylmethoxy-4-methoxyphenyl)-1-(2-trimethylsilylethoxymethyl)-1,5-dihydropyrrolo[2,3-d]-pyridazin-4-one Reaction and post treatment were carried out in the same manner as in Example 1-(a) except for using 0.40 g (1.1 mmol) of 2-bromo-3-chloro-1-(2-trimethylsilylethoxymethyl)-1,5-dihydropyrrolo[2,3-d]pyridazin-4-one obtained in the following Reference example 16-(d) in place of 2-bromo-1-(2-trimethylsilylethoxymethyl)-1,5-dihydropyrrolo-[2,3-d]pyridazin-4-one, and using 0.57 g (1.9 mmol) of 2-(3-cyclopropylmethoxy-4-methoxyphenyl)-4,4,5,5-tetramethyl-[1,3,2]dioxaborolane obtained in the following Reference example 2-(a) in place of 2-(3-cyclopropoxy-4-difluoromethoxyphenyl)-4,4,5,5-tetramethyl-[1,3,2]dioxaborolane, whereby 0.34 g of the title compound was obtained as a pale yellowish solid. (Yield: 67%)
Mass Spectrum (CI, m/z): 476 (M$^+$+1).
$^1$H-NMR Spectrum (CDCl$_3$, δ ppm): −0.04 (s, 9H), 0.33-0.40 (m, 2H), 0.62-0.70 (m, 2H), 0.80-0.88 (m, 2H), 1.29-1.41 (m, 1H), 3.39-3.47 (m, 2H), 3.88 (d, J=6.8 Hz, 2H), 3.95 (s, 3H), 5.35 (s, 2H), 7.01 (d, J=8.2 Hz, 1H), 7.02 (d, J=1.9 Hz, 1H), 7.07 (dd, J=8.2, 1.9 Hz, 1H), 8.18 (s, 1H), 10.10 (brs, 1H).

47-(b) 3-Chloro-2-(3-cyclopropylmethoxy-4-methoxyphenyl)-1,5-dihydropyrrolo[2,3-d]pyridazin-4-one Reaction and post treatment were carried out in the same manner as in Example 32-(b) except for using 340 mg (0.71 mmol) of 3-chloro-2-(3-cyclopropylmethoxy-4-methoxyphenyl)-1-(2-trimethylsilylethoxymethyl)-1,5-dihydropyrrolo[2,3-d]pyridazin-4-one obtained in Example 47-(a) in place of 3-chloro-2-(3-cyclobutoxy-4-difluoromethoxyphenyl)-1-(2-trimethylsilylethoxymethyl)-1,5-dihydropyrrolo[2,3-d]pyridazin-4-one, whereby 134 mg of the title compound was obtained as a white solid. (Yield: 55%)
Melting point: 256-258° C.
Mass Spectrum (CI, m/z): 346 (M$^+$+1).
$^1$H-NMR Spectrum (DMSO-d$_6$, δ ppm): 0.30-0.38 (m, 2H), 0.55-0.64 (m, 2H), 1.20-1.35 (m, 1H), 3.84 (s, 3H), 3.88 (d, J=6.8 Hz, 2H), 7.13 (d, J=8.5 Hz, 1H), 7.34 (d, J=2.1 Hz, 1H), 7.42 (dd, J=8.5, 2.1 Hz, 1H), 8.11 (s, 1H), 12.30 (brs, 1H).

Example 48

3-Chloro-2-(3-isopropoxy-4-methoxyphenyl)-1,5-dihydropyrrolo[2,3-d]pyridazin-4-one (Exemplary compound No. 1-1191)

48-(a) 3-Chloro-2-(3-isopropoxy-4-methoxyphenyl)-1-(2-trimethylsilylethoxymethyl)-1,5-dihydropyrrolo[2,3-d]pyridazin-4-one Reaction and post treatment were carried out in the same manner as in Example 1-(a) except for using 409 mg (1.10 mmol) of 2-bromo-3-chloro-1-(2-trimethylsilylethoxymethyl)-1,5-dihydropyrrolo[2,3-d]pyridazin-4-one obtained in the following Reference example 16-(d) in place of 2-bromo-1-(2-trimethylsilylethoxymethyl)-1,5-dihydropyrrolo-[2,3-d]pyridazin-4-one, and using 714 mg (2.44 mmol) of 2-(3-isopropoxy-4-methoxyphenyl)-4,4,5,5-tetramethyl-[1,3,2]dioxaborolane obtained in the following Reference example 1-(g) in place of 2-(3-cyclopropoxy-4-difluoromethoxyphenyl)-4,4,5,5-tetramethyl-[1,3,2]dioxaborolane, whereby 315 mg of the title compound was obtained as a white solid. (Yield: 62%)
Mass Spectrum (CI, m/z): 464 (M$^+$+1).
$^1$H-NMR Spectrum (CDCl$_3$, δ ppm): −0.04 (s, 9H), 0.81-0.88 (m, 2H), 1.40 (d, J=6.1 Hz, 6H), 3.39-3.47 (m, 2H), 3.93 (s, 3H), 4.50-4.59 (m, 1H), 5.37 (s, 2H), 7.01 (d, J=8.5 Hz, 1H), 7.03-7.08 (m, 2H), 8.18 (s, 1H), 9.94 (brs, 1H).

48-(b) 3-Chloro-2-(3-isopropoxy-4-methoxyphenyl)-1,5-dihydropyrrolo[2,3-d]pyridazin-4-one Reaction and post treatment were carried out in the same manner as in Example 40-(b) except for using 305 mg (0.657 mmol) of 3-chloro-2-(3-isopropoxy-4-methoxyphenyl)-1-(2-trimethylsilylethoxymethyl)-1,5-dihydropyrrolo[2,3-d]-pyridazin-4-one obtained in Example 48-(a) in place of 3-chloro-2-(4-difluoromethoxy-3-isopropoxyphenyl)-1-(2-trimethylsilylethoxymethyl)-1,5-dihydropyrrolo[2,3-d]pyridazin-4-one, whereby 164 mg of the title compound was obtained as a white solid. (Yield: 75%)

Melting point: 291-299° C.
Mass Spectrum (CI, m/z): 334 (M$^+$+1).
$^1$H-NMR Spectrum (DMSO-d$_6$, δ ppm): 1.31 (d, J=5.9 Hz, 6H), 3.82 (s, 3H), 4.54-4.67 (m, 1H), 7.14 (d, J=8.3 Hz, 1H), 7.37-7.44 (m, 2H), 8.11 (s, 1H), 12.30 (brs, 1H), 12.56 (brs, 1H).
IR Spectrum (KBr, cm$^{-1}$): 1633.

Example 49

2-(7-Difluoromethoxy-2,3-dihydrobenzofuran-2-spiro-1'-cyclopentan-4-yl)-1,5-dihydropyrrolo[2,3-d]pyridazin-4-one (Exemplary compound No. 5-67)

To 1 ml of ethylene glycol solution containing 41 mg (0.1 mmol) of ethyl 5-(7-difluoromethoxy-2,3-dihydrobenzofuran-2-spiro-1'-cyclopentan-4-yl)-2-formyl-1H-pyrrol-3-carboxylate obtained in the following Reference example 48-(e) was added 24 μl (0.5 mmol) of hydrazine monohydrate, and the mixture was stirred at 130° C. for 16 hours. After completion of the reaction, the reaction mixture was poured into water, and the precipitated solid was collected by filtration. The obtained crude solid was applied to silica gel column chromatography (Eluent; chloroform:methanol=20:1→10:1 (V/V)), and the fractions containing the desired compound were concentrated under reduced pressure to obtain 22 mg of the title compound as a pale yellowish solid. (Yield: 59%)

Melting point: 290-295° C.
Mass Spectrum (CI, m/z): 374 (M$^+$+1).
$^1$H-NMR Spectrum (DMSO-d$_6$, δ ppm): 1.70-1.89 (m, 6H), 1.99-2.08 (m, 2H), 3.52 (s, 2H), 6.85 (s, 1H), 7.14 (d, J=8.8 Hz, 1H), 7.15 (t, J=74.2 Hz, 1H), 7.25 (d, J=8.8 Hz, 1H), 8.15 (s, 1H), 12.22 (brs, 1H), 12.35 (brs, 1H).
IR Spectrum (KBr, cm$^{-1}$): 1634.

Example 50

2-(2,3-Dihydro-7-methoxybenzofuran-2-spiro-1'-cyclopentan-4-yl)-1,5-dihydropyrrolo[2,3-d]pyridazin-4-one (Exemplary compound No. 5-166)

To 3 ml of ethylene glycol solution containing 111 mg (0.3 mmol) of ethyl 2-formyl-5-(2,3-dihydro-7-methoxybenzofuran-2-spiro-1'-cyclopentan-4-yl)-1H-pyrrol-3-carboxylate obtained in the following Reference example 49-(e) was added 73 μl (1.5 mmol) of hydrazine monohydrate, and the mixture was stirred at 130° C. for 5 hours. After completion of the reaction, the reaction mixture was poured into water, and the mixture was extracted with a mixed solvent (chloroform:methanol=5:1 (V/V)). The organic layer after separation was washed with a saturated aqueous solution of sodium chloride, dried over anhydrous magnesium sulfate and then concentrated under reduced pressure. The obtained residue was applied to silica gel column chromatography (Eluent; chloroform:methanol=20:1 (V/V)), and the fractions containing the desired compound were concentrated under reduced pressure to obtain 82 mg of the title compound as a white solid. (Yield: 81%)

Melting point: 265° C. (decomposed).
Mass Spectrum (CI, m/z): 338 (M$^+$+1).
$^1$H-NMR Spectrum (DMSO-d$_6$, δ ppm): 1.68-1.88 (m, 6H), 1.91-2.06 (m, 2H), 3.45 (s, 2H), 3.81 (s, 3H), 6.74 (d, J=0.6 Hz, 1H), 6.97 (d, J=8.5 Hz, 1H), 7.21 (d, J=8.5 Hz, 1H), 8.14 (d, J=0.6 Hz, 1H), 12.22 (brs, 2H).
IR Spectrum (KBr, cm$^{-1}$): 1645.

Example 51

3-Chloro-2-(2,3-dihydro-7-methoxybenzofuran-2-spiro-1'-cyclopentan-4-yl)-1,5-dihydropyrrolo[2,3-d]pyridazin-4-one (Exemplary compound No. 5-167)

51-(a) 3-Chloro-2-(2,3-dihydro-7-methoxybenzofuran-2-spiro-1'-cyclopentan-4-yl)-1-(2-trimethylsilylethoxymethyl)-1,5-dihydropyrrolo[2,3-d]pyridazin-4-one Reaction and post treatment were carried out in the same manner as in Example 1-(a) except for using 201 mg (pure content: 84.6%, 0.450 mmol) of 2-bromo-3-chloro-1-(2-trimethylsilylethoxymethyl)-1,5-dihydropyrrolo[2,3-d]pyridazin-4-one obtained in the following Reference example 16-(d) in place of 2-bromo-1-(2-trimethylsilylethoxymethyl)-1,5-dihydropyrrolo[2,3-d]pyridazin-4-one, and using 220 mg (0.665 mmol) of 2-(2,3-dihydro-7-methoxybenzofuran-2-spiro-1'-cyclopentan-4-yl)-4,4,5,5-tetramethyl-[1,3,2]dioxaborolane obtained in the following Reference example 1-(h) in place of 2-(3-cyclopropoxy-4-difluoromethoxyphenyl)-4,4,5,5-tetramethyl-[1,3,2]dioxaborolane, whereby 253 mg of the title compound was obtained as pale yellowish foam substantially quantitatively.

$^1$H-NMR Spectrum (CDCl$_3$, δ ppm): −0.05 (s, 9H), 0.77-0.85 (m, 2H), 1.61-1.84 (m, 4H), 1.86-2.00 (m, 2H), 2.11-2.25 (m, 2H), 2.86 (d, J=15.9 Hz, 1H), 3.25 (d, J=15.9 Hz, 1H), 3.30-3.37 (m, 2H), 3.94 (s, 3H), 5.26 (d, J=10.7 Hz, 1H), 5.35 (d, J=10.7 Hz, 1H), 6.76 (d, J=8.3 Hz, 1H), 6.87 (d, J=8.3 Hz, 1H), 8.20 (s, 1H), 10.11 (brs, 1H).

51-(b) 3-Chloro-2-(2,3-dihydro-7-methoxybenzofuran-2-spiro-1'-cyclopentan-4-yl)-1,5-dihydropyrrolo[2,3-d]pyridazin-4-one Reaction and post treatment were carried out in the same manner as in Example 32-(b) except for using 233 mg (containing an amount corresponding to 0.450 mmol) of 3-chloro-2-(2,3-dihydro-7-methoxybenzofuran-2-spiro-1'-cyclopentan-4-yl)-1-(2-trimethylsilylethoxymethyl)-1,5-dihydropyrrolo[2,3-d]pyridazin-4-one obtained in Example 51-(a) in place of 3-chloro-2-(3-cyclobutoxy-4-difluoromethoxyphenyl)-1-(2-trimethylsilylethoxymethyl)-1,5-dihydropyrrolo[2,3-d]pyridazin-4-one, whereby 127 mg of the title compound was obtained as a white solid. (Yield: 74%)

Melting point: >300° C.
Mass Spectrum (CI, m/z): 372 (M$^+$+1).
$^1$H-NMR Spectrum (DMSO-d$_6$, δ ppm): 1.64-1.86 (m, 6H), 1.90-2.05 (m, 2H), 3.29 (s, 2H), 3.82 (s, 3H), 6.97 (d, J=8.5 Hz, 1H), 7.00 (d, J=8.5 Hz, 1H), 8.11 (s, 1H), 12.32 (brs, 1H).
IR Spectrum (KBr, cm$^{-1}$): 1625.

Example 52

3-Chloro-2-(8-difluoromethoxy-2,2-dimethyl-2H-chromen-5-yl)-1,5-dihydropyrrolo[2,3-d]pyridazin-4-one (Exemplary compound No. 2-2)

52-(a) 3-Chloro-2-(8-difluoromethoxy-2,2-dimethyl-2H-chromen-5-yl)-1-(2-trimethylsilylethoxymethyl)-1,5-dihydropyrrolo[2,3-d]pyridazin-4-one Reaction and post treatment were carried out in the same manner as in Example 1-(a) except for using 189 mg (0.500 mmol) of 2-bromo-3-chloro-1-(2-trimethylsilylethoxymethyl)-1,5-dihydropyrrolo[2,3-d]pyridazin-4-one obtained in the following Reference example 16-(d) in place of 2-bromo-1-(2-trimethylsilylethoxymethyl)-1,5-dihydropyrrolo-[2,3-d]pyridazin-4-one, and using 352 mg (1.00 mmol) of 2-(8-difluoromethoxy-2,2-dimethyl-2H-chromen-5-yl)-4,4,5,5-tetramethyl-[1,3,2]dioxaborolane obtained in the following Reference example 1-(i) in place of 2-(3-cyclopropoxy-4-difluoromethoxyphenyl)-4,4,5,5-tetramethyl-[1,3,2]dioxaborolane, whereby 183 mg of the title compound was obtained as a pale yellowish foam. (Yield: 70%)

Mass Spectrum (CI, m/z): 524 ($M^+$+1).

$^1$H-NMR Spectrum (CDCl$_3$, δ ppm): −0.07 (s, 9H), 0.75-0.82 (m, 2H), 1.50 (s, 3H), 1.51 (s, 3H), 3.25-3.32 (m, 2H), 5.23 (d, J=11.0 Hz, 1H), 5.30 (d, J=11.0 Hz, 1H), 5.72 (d, J=10.0 Hz, 1H), 5.96 (d, J=10.0 Hz, 1H), 6.68 (t, J=74.7 Hz, 1H), 6.81 (d, J=8.3 Hz, 1H), 7.15 (d, J=8.3 Hz, 1H), 8.21 (s, 1H), 9.87 (brs, 1H).

52-(b) 3-Chloro-2-(8-difluoromethoxy-2,2-dimethyl-2H-chromen-5-yl)-1,5-dihydropyrrolo[2,3-d]pyridazin-4-one Reaction was carried out in the same manner as in Example 1-(b) except for using 180 mg (0.34 mmol) of 3-chloro-2-(8-difluoromethoxy-2,2-dimethyl-2H-chromen-5-yl)-1-1-(2-trimethylsilylethoxymethyl)-1,5-dihydropyrrolo[2,3-d]pyridazin-4-one obtained in Example 52-(a) in place of 2-(3-cyclopropoxy-4-difluoromethoxyphenyl)-1-(2-trimethylsilylethoxymethyl)-1,5-dihydropyrrolo[2,3-d]pyridazin-4-one. After completion of the reaction, water was added to the reaction mixture and the precipitated solid was collected by filtration. The obtained solid was dissolved by adding a small amount of isopropanol, followed by addition of water, and the precipitated solid was collected by filtration. The obtained solid was washed with water and dried under reduced pressure to obtain 98 mg of the title compound as a white solid. (Yield: 73%)

Melting point: 226-234° C.

Mass Spectrum (FAB, m/z): 394 ($M^+$+1).

$^1$H-NMR Spectrum (DMSO-d$_6$, δ ppm): 1.45 (s, 6H), 5.89 (d, J=9.9 Hz, 1H), 6.19 (d, J=9.9 Hz, 1H), 7.00 (d, J=8.4 Hz, 1H), 7.15 (t, J=74.2 Hz, 1H), 7.19 (d, J=8.4 Hz, 1H), 8.10 (s, 1H), 12.27 (brs, 1H).

IR Spectrum (KBr, cm$^{-1}$): 1649.

Example 53

2-(8-Difluoromethoxy-2,2-dimethyl-2H-chromen-5-yl)-3-methyl-1,5-dihydropyrrolo[2,3-d]pyridazin-4-one HCl adduct (Exemplary compound No. 2-4)

53-(a) 2-(8-Difluoromethoxy-2,2-dimethyl-2H-chromen-5-yl)-3-methyl-1,5-bis(2-trimethylsilylethoxymethyl)-1,5-dihydropyrrolo[2,3-d]pyridazin-4-one Reaction and post treatment were carried out in the same manner as in Example 4-(a) except for using 525 mg (1.49 mmol) of 2-(8-difluoromethoxy-2,2-dimethyl-2H-chromen-5-yl)-4,4,5,5-tetramethyl-[1,3,2]dioxaborolane obtained in the following Reference example 1-(i) in place of 2-(3-cyclopropoxy-4-difluoromethoxyphenyl)-4,4,5,5-tetramethyl-[1,3,2]dioxaborolane, whereby 574 mg of the title compound was obtained as a brownish oil substantially quantitatively.

Mass Spectrum (CI, m/z): 634 ($M^+$+1).

$^1$H-NMR Spectrum (CDCl$_3$, δ ppm): −0.08 (s, 9H), 0.01 (s, 9H), 0.73-0.80 (m, 2H), 0.97-1.04 (m, 2H), 1.49 (s, 3H), 1.50 (s, 3H), 2.27 (s, 3H), 3.22-3.30 (m, 2H), 3.71-3.79 (m, 2H), 5.17 (d, J=10.9 Hz, 1H), 5.26 (d, J=10.9 Hz, 1H), 5.59 (s, 2H), 5.68 (d, J=10.0 Hz, 1H), 5.92 (d, J=10.0 Hz, 1H), 6.67 (t, J=75.0 Hz, 1H), 6.77 (d, J=8.3 Hz, 1H), 7.12 (d, J=8.3 Hz, 1H), 8.18 (s, 1H).

53-(b) 2-(8-Difluoromethoxy-2,2-dimethyl-2H-chromen-5-yl)-3-methyl-5-(2-trimethylsilylethoxymethyl)-1,5-dihydropyrrolo[2,3-d]pyridazin-4-one Reaction and post treatment were carried out in the same manner as in Example 4-(b) except for using 574 mg (containing an amount corresponding to 0.754 mmol) of 2-(8-difluoromethoxy-2,2-dimethyl-2H-chromen-5-yl)-3-methyl-1,5-bis(2-trimethylsilylethoxymethyl)-1,5-dihydropyrrolo[2,3-d]pyridazin-4-one obtained in Example 53-(a) in place of 2-(3-cyclopropoxy-4-difluoromethoxyphenyl)-3-methyl-1,5-bis(2-trimethylsilylethoxymethyl)-1,5-dihydropyrrolo[2,3-d]-pyridazin-4-one, whereby 163 mg of the title compound was obtained as a white solid. (Yield: 43%)

Mass Spectrum (CI, m/z): 504 ($M^+$+1).

$^1$H-NMR Spectrum (DMSO-d$_6$, δ ppm): −0.02 (s, 9H), 0.82-0.91 (m, 2H), 1.45 (s, 6H), 2.21 (s, 3H), 3.60-3.69 (m, 2H), 5.41 (s, 2H), 5.90 (d, J=10.2 Hz, 1H), 6.11 (d, J=10.2 Hz, 1H), 6.95 (d, J=8.4 Hz, 1H), 7.14 (t, J=74.3 Hz, 1H), 7.19 (d, J=8.4 Hz, 1H), 8.12 (s, 1H), 12.19 (brs, 1H).

IR Spectrum (KBr, cm$^{-1}$): 1631.

53-(c) 2-(8-Difluoromethoxy-2,2-dimethyl-2H-chromen-5-yl)-3-methyl-1,5-dihydropyrrolo[2,3-d]pyridazin-4-one HCl adduct Reaction was carried out in the same manner as in Example 6-(c) except for using 163 mg (0.323 mmol) of 2-(8-difluoromethoxy-2,2-dimethyl-2H-chromen-5-yl)-3-methyl-5-(2-trimethylsilylethoxymethyl)-1,5-dihydropyrrolo[2,3-d]-pyridazin-4-one obtained in Example 53-(b) in place of 3-chloro-2-(3-cyclopropoxy-4-difluoromethoxyphenyl)-1-(2-trimethylsilylethoxymethyl)-1,5-dihydropyrrolo[2,3-d]pyridazin-4-one. After completion of the reaction, the solid obtained from the reaction suspension by filtration was washed with diisopropyl ether and dried under reduced pressure to obtain 112 mg of the title compound as a white solid. (Yield: 84.6%)

Melting point: >300° C.
Mass Spectrum (CI, m/z): 374 (M$^+$+1).
$^1$H-NMR Spectrum (DMSO-d$_6$, δ ppm): 1.45 (s, 6H), 2.20 (s, 3H), 5.89 (d, J=10.0 Hz, 1H), 6.11 (d, J=10.0 Hz, 1H), 6.94 (d, J=8.4 Hz, 1H), 7.14 (t, J=74.5 Hz, 1H), 7.18 (d, J=8.4 Hz, 1H), 8.06 (s, 1H), 12.09 (brs, 1H), 12.14 (brs, 1H).
IR Spectrum (KBr, cm$^{-1}$): 1505.

Example 54

2-(8-Difluoromethoxy-2,2-dimethyl-2H-chromen-5-yl)-3-ethyl-1,5-dihydropyrrolo[2,3-d]pyridazin-4-one HCl adduct (Exemplary compound No. 2-5)

54-(a) 2-(8-Difluoromethoxy-2,2-dimethyl-2H-chromen-5-yl)-3-ethyl-1,5-bis(2-trimethylsilylethoxymethyl)-1,5-dihydropyrrolo[2,3-d]pyridazin-4-one Reaction and post treatment were carried out in the same manner as in Example 4-(a) except for using 794 mg (1.57 mmol) of 2-bromo-3-ethyl-1,5-bis(2-trimethylsilylethoxymethyl)-1,5-dihydropyrrolo[2,3-d]pyridazin-4-one obtained in the following Reference example 19-(d) in place of 2-bromo-3-methyl-1,5-bis(2-trimethylsilylethoxymethyl)-1,5-dihydropyrrolo[2,3-d]pyridazin-4-one, using 1.08 g (3.06 mmol) of 2-(8-difluoromethoxy-2,2-dimethyl-2H-chromen-5-yl)-4,4,5,5-tetramethyl-[1,3,2]dioxaborolane obtained in the following Reference example 1-(i) in place of 2-(3-cyclopropoxy-4-difluoromethoxyphenyl)-4,4,5,5-tetramethyl-[1,3,2]dioxaborolane, and using 57 mg of tricyclohexylphosphine in place of butyl-di-1-adamantylphosphine, whereby 1.03 g of the title compound was obtained as a brownish oil substantially quantitatively.
Mass Spectrum (CI, m/z): 648 (M$^+$+1).
$^1$H-NMR Spectrum (CDCl$_3$, δ ppm): −0.08 (s, 9H), 0.00 (s, 9H) 0.73-0.80 (m, 2H), 0.97-1.05 (m, 2H), 1.12 (t, J=7.4 Hz, 3H), 1.49 (s, 6H), 2.56 (dq, J=13.7, 7.4 Hz, 1H), 2.76 (dq, J=13.7, 7.4 Hz, 1H), 3.22-3.30 (m, 2H), 3.72-3.80 (m, 2H), 5.10 (d, J=10.9 Hz, 1H), 5.23 (d, J=10.9 Hz, 1H), 5.61 (s, 2H), 5.66 (d, J=10.0 Hz, 1H), 5.90 (d, J=10.0 Hz, 1H), 6.68 (t, J=75.0 Hz, 1H), 6.77 (d, J=8.3 Hz, 1H), 7.11 (d, J=8.3 Hz, 1H), 8.19 (s, 1H).

54-(b) 2-(8-Difluoromethoxy-2,2-dimethyl-2H-chromen-5-yl)-3-ethyl-5-(2-trimethylsilylethoxymethyl)-1,5-dihydropyrrolo[2,3-d]pyridazin-4-one Reaction and post treatment were carried out in the same manner as in Example 4-(b) except for using 1.02 g (containing an amount corresponding to 1.57 mmol) of 2-(8-difluoromethoxy-2,2-dimethyl-2H-chromen-5-yl)-3-ethyl-1,5-bis(2-trimethylsilylethoxymethyl)-1,5-dihydropyrrolo[2,3-d]pyridazin-4-one obtained in Example 54-(a) in place of 2-(3-cyclopropoxy-4-difluoromethoxyphenyl)-3-methyl-1,5-bis(2-trimethylsilylethoxymethyl)-1,5-dihydropyrrolo[2,3-d]-pyridazin-4-one, whereby 626 mg of the title compound was obtained as a yellowish white solid. (Yield: 77%)
Mass Spectrum (CI, m/z): 518 (M$^+$+1).
$^1$H-NMR Spectrum (CDCl$_3$, δ ppm): 0.00 (s, 9H), 0.96-1.04 (m, 2H), 1.18 (t, J=7.4 Hz, 3H), 1.50 (s, 6H), 2.75 (q, J=7.4 Hz, 2H), 3.71-3.79 (m, 2H), 5.60 (s, 2H), 5.70 (d, J=10.0 Hz, 1H), 6.13 (d, J=10.0 Hz, 1H), 6.66 (t, J=75.0 Hz, 1H), 6.85 (d, J=8.3 Hz, 1H), 7.10 (d, J=8.3 Hz, 1H), 8.05 (s, 1H), 8.38 (brs, 1H).
IR Spectrum (KBr, cm$^{-1}$): 1633.

54-(c) 2-(8-Difluoromethoxy-2,2-dimethyl-2H-chromen-5-yl)-3-ethyl-1,5-dihydropyrrolo[2,3-d]pyridazin-4-one HCl adduct Reaction was carried out in the same manner as in Example 6-(c) except for using 613 mg (1.18 mmol) of 2-(8-difluoromethoxy-2,2-dimethyl-2H-chromen-5-yl)-3-ethyl-5-(2-trimethylsilylethoxymethyl)-1,5-dihydropyrrolo[2,3-d]pyridazin-4-one obtained in Example 54-(b) in place of 3-chloro-2-(3-cyclopropoxy-4-difluoromethoxyphenyl)-1-(2-trimethylsilylethoxymethyl)-1,5-dihydropyrrolo[2,3-d]pyridazin-4-one. After completion of the reaction, the solid obtained from the reaction suspension by filtration was washed with hexane and dried under reduced pressure to obtain 467 mg of the title compound as a white solid. (Yield: 93%)
Melting point: >3000C.
Mass Spectrum (CI, m/z): 388 (M$^+$+1).
$^1$H-NMR Spectrum (DMSO-d$_6$, δ ppm): 1.08 (t, J=7.4 Hz, 3H), 1.45 (s, 6H), 2.58 (q, J=7.4 Hz, 2H), 5.87 (d, J=10.0 Hz, 1H), 6.07 (d, J=10.0 Hz, 1H), 6.92 (d, J=8.3 Hz, 1H), 7.15 (t, J=74.3 Hz, 1H), 7.17 (d, J=8.3 Hz, 1H), 8.05 (s, 1H) 12.06 (brs, 1H), 12.15 (brs, 1H).
IR Spectrum (KBr, cm$^{-1}$): 1498.

Example 55

3-Cyclopropyl-2-(8-difluoromethoxy-2,2-dimethyl-2H-chromen-5-yl)-1,5-dihydropyrrolo[2,3-d]pyridazin-4-one HCl adduct (Exemplary compound No. 2-38)

55-(a) 3-Cyclopropyl-2-(8-difluoromethoxy-2,2-dimethyl-2H-chromen-5-yl)-1,5-bis(2-trimethylsilylethoxymethyl)-1,5-dihydropyrrolo[2,3-d]pyridazin-4-one Reaction and post treatment were carried out in the same manner as in Example 4-(a) except for using 1.03 g (2.0 mmol) of 2-bromo-3-cyclopropyl-1,5-bis(2-trimethylsilylethoxymethyl)-1,5-dihydropyrrolo[2,3-d]pyridazin-4-one obtained in the following Reference example 28-(b) in place of 2-bromo-3-methyl-1,5-bis(2-trimethylsilylethoxymethyl)-1,5-dihydropyrrolo[2,3-d]pyridazin-4-one, and using 1.40 g (3.97 mmol) of 2-(8-difluoromethoxy-2,2-dimethyl-2H-chromen-5-yl)-4,4,5,5-tetramethyl-[1,3,2]dioxaborolane obtained in the following Reference example 1-(i) in place of 2-(3-cyclopropoxy-4-difluoromethoxyphenyl)-4,4,5,5-tetramethyl-[1,3,2]dioxaborolane, whereby 1.35 g of the title compound was obtained as a yellowish oil substantially quantitatively.
Mass Spectrum (CI, m/z): 660 (M$^+$+1).
$^1$H-NMR Spectrum (CDCl$_3$, δ ppm): −0.07 (s, 9H), 0.01 (s, 9H) 0.60-0.84 (m, 6H), 0.97-1.04 (m, 2H), 1.48 (s, 3H), 1.50 (s, 3H), 1.86-1.96 (m, 1H), 3.22-3.30 (m, 2H), 3.71-3.79 (m, 2H), 5.12 (d, J=10.7 Hz, 1H), 5.21 (d, J=10.7 Hz, 1H), 5.60 (s, 2H), 5.68 (d, J=10.0 Hz, 1H), 5.99 (d, J=10.0 Hz, 1H), 6.69 (t, J=75.0 Hz, 1H), 6.79 (d, J=8.3 Hz, 1H), 7.11 (d, J=8.3 Hz, 1H), 8.17 (s, 1H).

55-(b) 3-Cyclopropyl-2-(8-difluoromethoxy-2,2-dimethyl-2H-chromen-5-yl)-5-(2-trimethylsilylethoxymethyl)-1,5-dihydropyrrolo[2,3-d]pyridazin-4-one Reaction and post treatment were carried out in the same manner as in Example 4-(b) except for using 1.35 g (containing an amount corresponding to 2.00 mmol) of 3-cyclopropyl-2-(8-difluoromethoxy-2,2-dimethyl-2H-chromen-5-yl)-1,5-bis(2-trimethylsilylethoxymethyl)-1,5-dihydropyrrolo[2,3-d]pyridazin-4-one obtained in Example 55-(a) in place of 2-(3-cyclopropoxy-4-difluoromethoxyphenyl)-3-methyl-1,5-bis(2-trimethylsilylethoxymethyl)-1,5-dihydropyrrolo[2,3-d]pyridazin-4-one, whereby 907 mg of the title compound was obtained as a pale yellowish solid. (Yield: 84%)

Mass Spectrum (CI, m/z): 530 ($M^+$+1).

$^1$H-NMR Spectrum (CDCl$_3$, δ ppm): −0.01 (s, 9H), 0.62-0.69 (m, 2H), 0.71-0.80 (m, 2H), 0.93-1.02 (m, 2H), 1.50 (s, 6H), 1.84-1.95 (m, 1H), 3.69-3.77 (m, 2H), 5.58 (s, 2H), 5.71 (d, J=10.0 Hz, 1H), 6.25 (d, J=10.0 Hz, 1H), 6.66 (t, J=75.1 Hz, 1H), 6.87 (d, J=8.3 Hz, 1H), 7.08 (d, J=8.3 Hz, 1H), 8.04 (s, 1H), 8.61 (brs, 1H).

IR Spectrum (KBr, cm$^{-1}$): 1647.

55-(c) 3-Cyclopropyl-2-(8-difluoromethoxy-2,2-dimethyl-2H-chromen-5-yl)-1,5-dihydropyrrolo[2,3-d]pyridazin-4-one HCl adduct Reaction was carried out in the same manner as in Example 6-(c) except for using 900 mg (1.70 mmol) of 3-cyclopropyl-2-(8-difluoromethoxy-2,2-dimethyl-2H-chromen-5-yl)-5-(2-trimethylsilylethoxymethyl)-1,5-dihydropyrrolo-[2,3-d]pyridazin-4-one obtained in Example 55-(b) in place of 3-chloro-2-(3-cyclopropoxy-4-difluoromethoxyphenyl)-1-(2-trimethylsilylethoxymethyl)-1,5-dihydropyrrolo[2,3-d]-pyridazin-4-one. After completion of the reaction, the solid obtained from the reaction suspension by filtration was washed with 1,4-dioxane and dried under reduced pressure to obtain 739 mg of the title compound as a white solid substantially quantitatively.

Melting point: >300° C.

Mass Spectrum (CI, m/z): 400 ($M^+$+1).

$^1$H-NMR Spectrum (DMSO-d$_6$, δ ppm): 0.64-0.71 (m, 2H), 0.76-0.83 (m, 2H), 1.44 (s, 6H), 1.68-1.80 (m, 1H), 5.88 (d, J=10.2 Hz, 1H), 6.16 (d, J=10.2 Hz, 1H), 6.96 (d, J=8.3 Hz, 1H), 7.15 (t, J=74.5 Hz, 1H), 7.17 (d, J=8.3 Hz, 1H), 8.02 (s, 1H), 12.11 (brs, 2H).

IR Spectrum (KBr, cm$^{-1}$): 1499.

Example 56

3-Chloro-2-(8-difluoromethoxy-2H-chromen-2-spiro-1'-cyclobutan-5-yl)-1,5-dihydropyrrolo[2,3-d]pyridazin-4-one (Exemplary compound No. 4-35)

Reaction and post treatment were carried out in the same manner as in Example 1-(a) except for using 0.34 g (0.90 mmol) of 2-bromo-3-chloro-1-(2-trimethylsilylethoxymethyl)-1,5-dihydropyrrolo[2,3-d]pyridazin-4-one obtained in the following Reference example 16-(d) in place of 2-bromo-1-(2-trimethylsilylethoxymethyl)-1,5-dihydropyrrolo-[2,3-d]pyridazin-4-one, and using 0.49 g (1.3 mmol) of 2-(8-difluoromethoxy-2H-chromen-2-spiro-1'-cyclobutan-5-yl)-4,4,5,5-tetramethyl-[1,3,2]dioxaborolane obtained in the following Reference example 1-(j) in place of 2-(3-cyclopropoxy-4-difluoromethoxyphenyl)-4,4,5,5-tetramethyl-[1,3,2]dioxaborolane, whereby 249 mg of a pale yellowish foam was obtained.

Then, the reaction was carried out in the same manner as in Example 1-(b) except for using the above-mentioned pale yellowish foam in place of 2-(3-cyclopropoxy-4-difluoromethoxyphenyl)-1-(2-trimethylsilylethoxymethyl)-1,5-dihydropyrrolo[2,3-d]pyridazin-4-one. After completion of the reaction, water was added to the reaction mixture and the precipitated solid was collected by filtration. The obtained crude solid was purified by high performance liquid chromatography (column; Kromacil™ 100-5-C18 (20×250 mm (manufactured by EKA CHEMICALS), Eluent; acetonitrile:water:trifluoroacetic acid=600:400:1 (V/V/V), Flow rate; 10 ml/min) to obtain 90 mg of the title compound as a white solid. (Yield: 24%)

Melting point: 289-291° C.

Mass Spectrum (CI, m/z): 406 ($M^+$+1).

$^1$H-NMR Spectrum (DMSO-d$_6$, δ ppm): 1.68-1.92 (m, 2H), 2.19-2.29 (m, 2H), 2.38-2.51 (m, 2H), 6.18 (d, J=10.2 Hz, 1H), 6.30 (d, J=10.2 Hz, 1H), 7.01 (d, J=8.5 Hz, 1H), 7.21 (d, J=8.5 Hz, 1H), 7.21 (t, J=74.2 Hz, 1H), 8.12 (s, 1H), 12.36 (brs, 1H), 12.68 (brs, 1H).

Example 57

3-Chloro-2-(8-difluoromethoxy-2H-chromen-2-spiro-1'-cyclopentan-5-yl)-1,5-dihydropyrrolo[2,3-d]pyridazin-4-one (Exemplary compound No. 4-68)

57-(a) 3-Chloro-2-(8-difluoromethoxy-2H-chromen-2-spiro-1'-cyclopentan-5-yl)-1-(2-trimethylsilylethoxymethyl)-1,5-dihydropyrrolo[2,3-d]pyridazin-4-one Reaction and post treatment were carried out in the same manner as in Example 1-(a) except for using 0.34 g (0.90 mmol) of 2-bromo-3-chloro-1-(2-trimethylsilylethoxymethyl)-1,5-dihydropyrrolo[2,3-d]pyridazin-4-one obtained in the following Reference example 16-(d) in place of 2-bromo-1-(2-trimethylsilylethoxymethyl)-1,5-dihydropyrrolo-[2,3-d]pyridazin-4-one, and using 0.51 g (1.34 mmol) of 2-(8-difluoromethoxy-2H-chromen-2-spiro-1'-cyclopentan-5-yl)-4,4,5,5-tetramethyl-[1,3,2]dioxaborolane obtained in the following Reference example 1-(k) in place of 2-(3-cyclopropoxy-4-difluoromethoxyphenyl)-4,4,5,5-tetramethyl-[1,3,2]dioxaborolane, whereby 290 mg of the title compound was obtained as a pale yellowish foam. (Yield: 59%)

$^1$H-NMR Spectrum (CDCl$_3$, δ ppm): −0.07 (s, 9H), 0.74-0.82 (m, 2H), 1.56-1.83 (m, 4H), 1.88-2.06 (m, 2H), 2.12-2.34 (m, 2H), 3.25-3.32 (m, 2H), 5.22 (d, J=10.9 Hz, 1H), 5.30 (d, J=10.9 Hz, 1H), 5.76 (d, J=10.0 Hz, 1H), 5.99 (d, J=10.0 Hz, 1H), 6.64 (t, J=74.7 Hz, 1H), 6.80 (d, J=8.4 Hz, 1H) 7.13 (d, J=8.4 Hz, 1H), 8.21 (s, 1H), 9.88 (brs, 1H).

57-(b) 3-Chloro-2-(8-difluoromethoxy-2H-chromen-2-spiro-1'-cyclopentan-5-yl)-1,5-dihydropyrrolo[2,3-d]pyridazin-4-one Reaction was carried out in the same manner as in Example 1-(b) except for using 0.29 g (0.53 mmol) of 3-chloro-2-(8-difluoromethoxy-2H-chromen-2-spiro-1'-cyclopentan-5-yl)-1-(2-trimethylsilylethoxymethyl)-1,5-dihydropyrrolo[2,3-d]pyridazin-4-one obtained in Example 57-(a) in place of 2-(3-cyclopropoxy-4-difluoromethoxyphenyl)1-(2-trimethylsilylethoxymethyl)-1,5-dihydropyrrolo[2,3-d]pyridazin-4-one. After completion of the reaction, water was added to the reaction mixture and the precipitated solid was collected by filtration. The obtained solid was washed with a mixed solvent (acetonitrile:water=1:1 (V/V)) and dried under reduced pressure to obtain 66 mg of the title compound as a white solid. (Yield: 30%)

Melting point: >300° C.

Mass Spectrum (CI, m/z): 420 ($M^+$+1).

$^1$H-NMR Spectrum (DMSO-d$_6$, δ ppm): 1.62-1.77 (m, 4H), 1.78-1.92 (m, 2H), 2.04-2.16 (m, 2H), 5.97 (d, J=10.0

Hz, 1H), 6.20 (d, J=10.0 Hz, 1H), 6.99 (d, J=8.3 Hz, 1H), 7.10 (t, J=74.1 Hz, 1H), 7.19 (d, J=8.3 Hz, 1H), 8.12 (s, 1H), 12.36 (brs, 1H), 12.70 (brs, 1H).

Example 58

2-(2-Cyclopropyl-8-difluoromethoxy-2H-chromen-5-yl)-1,5-dihydropyrrolo[2,3-d]pyridazin-4-one (Exemplary compound No. 3-1)

58-(a) 2-(2-Cyclopropyl-8-difluoromethoxy-2H-chromen-5-yl)-1-(2-trimethylsilylethoxymethyl)-1,5-dihydropyrrolo[2,3-d]-pyridazin-4-one Reaction and post treatment were carried out in the same manner as in Example 1-(a) except for using 0.30 g (0.82 mmol) of 2-(2-cyclopropyl-8-difluoromethoxy-2H-chromen-5-yl)-4,4,5,5-tetramethyl-[1,3,2]dioxaborolane-obtained in the following Reference example 1-(1) in place of 2-(3-cyclopropoxy-4-difluoromethoxyphenyl)-4,4,5,5-tetramethyl-[1,3,2]dioxaborolane, whereby 206 mg of the title compound was obtained as a slightly yellowish oil. (Yield: 60%)

Mass Spectrum (CI, m/z): 502 ($M^+$+1).

$^1$H-NMR Spectrum (CDCl$_3$, δ ppm): −0.08 (s, 9H), 0.33-0.42 (m, 1H), 0.48-0.57 (m, 1H), 0.58-0.69 (m, 2H), 0.75-0.84 (m, 2H), 1.19-1.34 (m, 1H), 3.24-3.34 (m, 2H), 4.30-4.37 (m, 1H), 5.31 (s, 2H), 5.83 (dd, J=10.1, 3.7 Hz, 1H), 6.22 (dd, J=10.1, 1.6 Hz, 1H), 6.73 (t, J=75.1 Hz, 1H), 6.83 (d, J=0.7 Hz, 1H), 6.86 (d, J=8.3 Hz, 1H), 7.12 (d, J=8.3 Hz, 1H), 8.26 (d, J=0.7 Hz, 1H), 10.43 (brs, 1H)

58-(b) 2-(2-Cyclopropyl-8-difluoromethoxy-2H-chromen-5-yl)-1,5-dihydropyrrolo[2,3-d]pyridazin-4-one Reaction was carried out in the same manner as in Example 31-(b) except for using 194 mg (0.387 mmol) of 2-(2-cyclopropyl-8-difluoromethoxy-2H-chromen-5-yl)-1-(2-trimethylsilylethoxymethyl)-1,5-dihydropyrrolo[2,3-d]pyridazin-4-one obtained in Example 58-(a) in place of 2-(3-cyclobutoxy-4-difluoromethoxyphenyl)-1-(2-trimethylsilylethoxymethyl)-1,5-dihydropyrrolo[2,3-d]pyridazin-4-one. After completion of the reaction, the reaction mixture was neutralized with a saturated aqueous solution of sodium hydrogencarbonate and the mixture was extracted with a mixed solvent (chloroform/methanol=9/1 (V/V)). The organic layer after separation was washed with a saturated aqueous solution of sodium chloride, dried over anhydrous magnesium sulfate and then concentrated under reduced pressure. To the obtained solid were added methanol and 28% aqueous ammonia, and the mixture was stirred under room temperature for 3 hours. Then, the solution was concentrated under reduced pressure and the obtained residue was applied to silica gel column chromatography (Eluent; chloroform:methanol=9:1 (V/V)), and the fractions containing the desired compound were concentrated under reduced pressure to obtain 81 mg of the title compound as a white solid. (Yield: 56%)

Melting point: 232-242° C.

Mass Spectrum (CI, m/z): 372 ($M^+$+1).

$^1$H-NMR Spectrum (DMSO-d$_6$, δ ppm): 0.37-0.63 (m, 4H), 1.22-1.33 (m, 1H), 4.44 (ddd, J=8.1, 3.7, 1.5 Hz, 1H), 6.04 (dd, J=10.0, 3.7 Hz, 1H), 6.65 (d, J=0.6 Hz, 1H), 6.68 (dd, J=10.0, 1.5 Hz, 1H), 7.09 (d, J=8.4 Hz, 1H), 7.14 (t, J=74.5 Hz, 1H), 7.20 (d, J=8.4 Hz, 1H), 8.16 (d, J=0.6 Hz, 1H), 12.31 (brs, 1H), 12.40 (brs, 1H).

Example 59

2-(3-Cyclopropoxy-4-difluoromethoxyphenyl)-3-cyclopropylmethoxymethyl-1,5-dihydropyrrolo[2,3-d]pyridazin-4-one (Exemplary Compound No. 1-112)

59-(a) 2-(3-Cyclopropoxy-4-difluoromethoxyphenyl)-3-cyclopropylmethoxymethyl-1-(2-trimethylsilylethoxymethyl)-1,5-dihydropyrrolo[2,3-d]pyridazin-4-one Reaction and post treatment were carried out in the same manner as in Example 1-(a) except for using 610 mg (1.42 mmol) of 2-bromo-3-cyclopropylmethoxymethyl-1-(2-trimethylsilylethoxymethyl)-1,5-dihydropyrrolo[2,3-d]pyridazin-4-one obtained in the following Reference example 50 in place of 2-bromo-1-(2-trimethylsilylethoxymethyl)-1,5-dihydropyrrolo[2,3-d]pyridazin-4-one, whereby 590 mg of the title compound was obtained as a pale yellowish foam. (Yield: 76%)

Mass Spectrum (CI, m/z): 548 ($M^+$+1).

$^1$H-NMR Spectrum (DMSO-d$_6$, δ ppm): −0.12 (s, 9H), 0.03-0.10 (m, 2H), 0.33-0.41 (m, 2H), 0.67-0.86 (m, 6H), 0.86-0.98 (m, 1H), 3.26 (d, J=6.8 Hz, 2H), 3.36-3.45 (m, 2H), 3.88-3.96 (m, 1H), 4.58 (s, 2H), 5.52 (s, 2H), 7.14 (t, J=74.2 Hz, 1H), 7.25 (dd, J=8.3, 2.0 Hz, 1H), 7.33 (d, J=8.3 Hz, 1H), 7.69 (d, J=2.0 Hz, 1H), 8.50 (s, 1H), 12.41 (brs, 1H).

59-(b) 2-(3-Cyclopropoxy-4-difluoromethoxyphenyl)-3-cyclopropylmethoxymethyl-1,5-dihydropyrrolo[2,3-d]pyridazin-4-one Reaction was carried out in the same manner as in Example 1-(b) except for using 581 mg (1.06 mmol) of 2-(3-cyclopropoxy-4-difluoromethoxyphenyl)-3-cyclopropylmethoxymethyl-1-(2-trimethylsilylethoxymethyl)-1,5-dihydropyrrolo[2,3-d]pyridazin-4-one obtained in Example 59-(a) in place of 2-(3-cyclopropoxy-4-difluoromethoxyphenyl)-1-(2-trimethylsilylethoxymethyl)-1,5-dihydropyrrolo[2,3-d]pyridazin-4-one. After completion of the reaction, the reaction mixture was concentrated under reduced pressure, water was added to the obtained concentrate, and precipitated solid was collected by filtration and washed with water. The obtained crude solid was applied to silica gel column chromatography (Eluent; ethyl acetate), and the fractions containing the desired compound were concentrated under reduced pressure to obtain 287 mg of the title compound as a white solid. (Yield: 65%)

Melting point: 170-172° C.

Mass Spectrum (CI, m/z): 418 ($M^+$+1).

$^1$H-NMR Spectrum (DMSO-d$_6$, δ ppm): 0.10-0.16 (m, 2H), 0.38-0.46 (m, 2H), 0.73-0.82 (m, 2H), 0.83-0.91 (m, 2H), 0.96-1.07 (m, 1H), 3.37 (d, J=6.8 Hz, 2H), 3.93-4.00 (m, 1H), 4.80 (s, 2H), 7.11 (t, J=74.3 Hz, 1H), 7.34 (d, J=8.4 Hz, 1H), 7.43 (dd, J=8.4, 2.0 Hz, 1H), 7.94 (d, J=2.0 Hz, 1H) 8.15 (s, 1H), 12.24 (brs, 1H), 12.48 (brs, 1H)

IR Spectrum (KBr, cm$^{-1}$): 1645. .

Example 60

2-(3-Cyclopropoxy-4-difluoromethoxyphenyl)-3-isopropoxymethyl-1,5-dihydropyrrolo[2,3-d]pyridazin-4-one (Exemplary compound No. 1-86)

60-(a) 2-(3-Cyclopropoxy-4-difluoromethoxyphenyl)-3-isopropoxymethyl-1,5-bis(2-trimethylsilylethoxymethyl)-1,5-dihydropyrrolo[2,3-d]pyridazin-4-one Reaction and post treatment were carried out in the same manner as in Example 4-(a) except for using 171 mg (0.314 mmol) of 2-bromo-3-isopropoxymethyl-1,5-bis(2-trimethylsilylethoxymethyl)-1,5-dihydropyrrolo[2,3-d]pyridazin-4-one obtained in the following Reference example 51 in place of 2-bromo-3-methyl-1,5-bis(2-trimethylsilylethoxymethyl)-1,5-dihydropyrrolo[2,3-d]pyridazin-4-one, whereby 196 mg of the title compound was obtained as a slightly yellowish oil. (Yield: 94%)

Mass Spectrum (CI, m/z): 666 ($M^+$+1).
$^1$H-NMR Spectrum (CDCl$_3$, δ ppm): −0.02 (s, 9H), 0.00 (s, 9H), 0.79-1.03 (m, 8H), 1.18 (d, J=6.1 Hz, 6H), 3.47-3.56 (m, 2H), 3.68-3.77 (m, 2H), 3.78-3.90 (m, 2H), 4.68 (s, 2H), 5.34 (s, 2H), 5.60 (s, 2H), 6.60 (t, J=74.8 Hz, 1H), 7.19 (dd, J=8.3, 1.9 Hz, 1H), 7.26 (d, J=8.3 Hz, 1H), 7.64 (d, J=1.9 Hz, 1H), 8.19 (s, 1H).
IR Spectrum (neat, cm$^{-1}$): 1667.

60-(b) 2-(3-Cyclopropoxy-4-difluoromethoxyphenyl)-3-isopropoxymethyl-5-(2-trimethylsilylethoxymethyl)-1,5-dihydropyrrolo[2,3-d]pyridazin-4-one Reaction and post treatment were carried out in the same manner as in Example 4-(b) except for using 191 mg (0.287 mmol) of 2-(3-cyclopropoxy-4-difluoromethoxyphenyl)-3-isopropoxymethyl-1,5-bis(2-trimethylsilylethoxymethyl)-1,5-dihydropyrrolo[2,3-d]pyridazin-4-one obtained in Example 60-(a) in place of 2-(3-cyclopropoxy-4-difluoromethoxyphenyl)-3-methyl-1,5-bis(2-trimethylsilylethoxymethyl)-1,5-dihydropyrrolo[2,3-d]pyridazin-4-one, whereby 135 mg of the title compound was obtained as a white solid. (Yield: 88%)

Mass Spectrum (CI, m/z): 536 ($M^+$+1).
$^1$H-NMR Spectrum (CDCl$_3$, δ ppm): −0.02 (s, 9H), 0.80-0.90 (m, 4H), 0.91-1.00 (m, 2H), 1.22 (d, J=6.1 Hz, 6H), 3.66-3.75 (m, 2H), 3.84-3.99 (m, 2H), 4.85 (s, 2H), 5.59 (s, 2H), 6.56 (t, J=74.8 Hz, 1H), 7.20-7.25 (m, 1H), 7.26 (d, J=8.3 Hz, 1H), 7.83 (d, J=1.2 Hz, 1H), 8.09 (s, 1H), 9.11 (brs, 1H).
IR Spectrum (KBr, cm$^{-1}$): 1627.

60-(c) 2-(3-Cyclopropoxy-4-difluoromethoxyphenyl)-3-isopropoxymethyl-1,5-dihydropyrrolo[2,3-d]pyridazin-4-one Reaction and post treatment were carried out in the same manner as in Example 13-(c) except for using 1.22 g (2.28 mmol) of 2-(3-cyclopropoxy-4-difluoromethoxyphenyl)-3-isopropoxymethyl-5-(2-trimethylsilylethoxymethyl)-1,5-dihydropyrrolo[2,3-d]pyridazin-4-one obtained in the same manner as in Example 60-(b) in place of 3-cyclobutoxymethyl-2-(3-cyclopropoxy-4-difluoromethoxyphenyl)-5-(2-trimethylsilylethoxymethyl)-1,5-dihydropyrrolo[2,3-d]-pyridazin-4-one, whereby 619 mg of the title compound was obtained as a white solid. (Yield: 67%)

Melting point: 196-197° C.
Mass Spectrum (CI, m/z): 406 ($M^+$+1).
$^1$H-NMR Spectrum (DMSO-d$_6$, δ ppm): 0.75-0.80 (m, 2H), 0.83-0.88 (m, 2H), 1.13 (d, J=6.1 Hz, 6H), 3.76-3.84 (m, 1H), 3.93-3.98 (m, 1H), 4.79 (s, 2H), 7.10 (t, J=74.3 Hz, 1H), 7.33 (d, J=8.4 Hz, 1H), 7.43 (dd, J=8.4, 2.0 Hz, 1H), 7.93 (d, J=2.0 Hz, 1H), 8.15 (s, 1H), 12.23 (brs, 1H).
IR Spectrum (KBr, cm$^{-1}$): 1657.

Example 61

2-(3-Cyclopropoxy-4-difluoromethoxyphenyl)-3-(2-fluoroethoxymethyl)-1,5-dihydropyrrolo[2,3-d]pyridazin-4-one (Exemplary compound No. 1-90)

61-(a) 2-(3-Cyclopropoxy-4-difluoromethoxyphenyl)-3-(2-fluoroethoxymethyl)-1,5-bis(2-trimethylsilylethoxymethyl)-1,5-dihydropyrrolo[2,3-d]pyridazin-4-one Reaction and post treatment were carried out in the same manner as in Example 4-(a) except for using 400 mg (0.726 mmol) of 2-bromo-3-(2-fluoroethoxymethyl)-1,5-bis(2-trimethylsilylethoxymethyl)-1,5-dihydropyrrolo[2,3-d]pyridazin-4-one obtained in the following Reference example 52 in place of 2-bromo-3-methyl-1,5-bis(2-trimethylsilylethoxymethyl)-1,5-dihydropyrrolo[2,3-d]pyridazin-4-one, whereby 436 mg of the title compound was obtained as a colorless oil. (Yield: 90%)

$^1$H-NMR Spectrum (CDCl$_3$, δ ppm): −0.03 (s, 9H), −0.01 (s, 9H), 0.76-0.85 (m, 4H), 0.85-0.93 (m, 2H), 0.95-1.03 (m, 2H), 3.47-3.57 (m, 2H), 3.68-3.77 (m, 2H), 3.80-3.88 (m, 2H), 3.92-3.98 (m, 1H), 4.44-4.49 (m, 1H), 4.60-4.65 (m, 1H), 4.76 (s, 2H), 5.37 (s, 2H), 5.60 (s, 2H), 6.60 (t, J=74.7 Hz, 1H), 7.16 (dd, J=8.3, 2.0 Hz, 1H), 7.27 (d, J=8.3 Hz, 1H), 7.70 (d, J=2.0 Hz, 1H), 8.22 (s, 1H).

61-(b) 2-(3-Cyclopropoxy-4-difluoromethoxyphenyl)-3-(2-fluoroethoxymethyl)-5-(2-trimethylsilylethoxymethyl)-1,5-dihydropyrrolo[2,3-d]pyridazin-4-one Reaction and post treatment were carried out in the same manner as in Example 4-(b) except for using 406 mg (0.606 mmol) of 2-(3-cyclopropoxy-4-difluoromethoxyphenyl)-3-(2-fluoroethoxymethyl)-1,5-bis(2-trimethylsilylethoxymethyl)-1,5-dihydropyrrolo[2,3-d]pyridazin-4-one obtained in Example 61-(a) in place of 2-(3-cyclopropoxy-4-difluoromethoxyphenyl)-3-methyl-1,5-bis(2-trimethylsilylethoxymethyl)-1,5-dihydropyrrolo[2,3-d]pyridazin-4-one, whereby 280 mg of the title compound was obtained as a white solid. (Yield: 86%)

Mass Spectrum (CI, m/z): 540 ($M^+$+1).
$^1$H-NMR Spectrum (DMSO-d$_6$, δ ppm): −0.05 (s, 9H), 0.71-0.80 (m, 2H), 0.80-0.90 (m, 4H), 3.60-3.68 (m, 2H), 3.70-3.75 (m, 1H), 3.80-3.86 (m, 1H), 3.91-3.99 (m, 1H), 4.43-4.48 (m, 1H), 4.59-4.64 (m, 1H), 4.84 (s, 2H), 5.43 (s, 2H), 7.10 (t, J=74.2 Hz, 1H), 7.33 (d, J=8.3 Hz, 1H), 7.38 (dd, J=8.3, 1.9 Hz, 1H), 7.92 (d, J=1.9 Hz, 1H), 8.22 (s, 1H), 12.62 (brs, 1H).

61-(c) 2-(3-Cyclopropoxy-4-difluoromethoxyphenyl)-3-(2-fluoroethoxymethyl)-1,5-dihydropyrrolo[2,3-d]pyridazin-4-one Reaction and post treatment were carried out in the same manner as in Example 13-(c) except for using 248 mg (0.460 mmol) of 2-(3-cyclopropoxy-4-difluoromethoxyphenyl)-3-(2-fluoroethoxymethyl)-5-(2-trimethylsilylethoxymethyl)-1,5-dihydropyrrolo[2,3-d]pyridazin-4-one obtained in Example 61-(b) in place of 3-cyclobutoxymethyl-2-(3-cyclopropoxy-4-difluoromethoxyphenyl)-5-(2-trimethylsilylethoxymethyl)-1,5-dihydropyrrolo[2,3-d]pyridazin-4-one, whereby 60 mg of the title compound was obtained as a gray solid. (Yield: 32%)

Melting point: 139-140° C.

$^1$H-NMR Spectrum (DMSO-d$_6$, δ ppm): 0.67-0.90 (m, 4H), 3.67-3.76 (m, 1H), 3.78-3.87 (m, 1H), 3.90-3.99 (m, 1H), 4.42-4.51 (m, 1H), 4.56-4.67 (m, 1H), 4.84 (s, 2H), 7.09 (t, J=74.1 Hz, 1H), 7.32 (d, J=8.5 Hz, 1H), 7.39 (d, J=8.8 Hz, 1H), 7.92 (s, 1H), 8.15 (s, 1H), 12.27 (brs, 1H).

IR Spectrum (KBr, cm$^{-1}$): 1639.

Example 62

2-(3-Cyclopropoxy-4-difluoromethoxyphenyl)-3-isobutoxymethyl-1,5-dihydropyrrolo[2,3-d]pyridazin-4-one (Exemplary compound No. 1-1289)

62-(a) 2-(3-Cyclopropoxy-4-difluoromethoxyphenyl)-3-isobutoxymethyl-1,5-bis(2-trimethylsilylethoxymethyl)-1,5-dihydropyrrolo[2,3-d]pyridazin-4-one Reaction and post treatment were carried out in the same manner as in Example 4-(a) except for using 1.22 g (2.18 mmol) of 2-bromo-3-isobutoxymethyl-1,5-bis(2-trimethylsilylethoxymethyl)-1,5-dihydropyrrolo[2,3-d]pyridazin-4-one obtained in the same manner as in the following Reference example 53 in place of 2-bromo-3-methyl-1,5-bis(2-trimethylsilylethoxymethyl)-1,5-dihydropyrrolo[2,3-d]pyridazin-4-one, whereby 1.35 g of the title compound was obtained as a slightly yellowish oil. (Yield: 91%)

Mass Spectrum (CI, m/z): 680 (M$^+$+1).

$^1$H-NMR Spectrum (CDCl$_3$, δ ppm): −0.03 (s, 9H), −0.01 (s, 9H), 0.79-0.85 (m, 4H), 0.85-0.90 (m, 2H), 0.85 (d, J=6.7 Hz, 6H), 0.96-1.01 (m, 2H), 1.80-1.89 (m, 1H), 3.35 (d, J=6.7 Hz, 2H), 3.48-3.53 (m, 2H), 3.71-3.75 (m, 2H), 3.79-3.84 (m, 1H), 4.69 (s, 2H), 5.36 (s, 2H), 5.61 (s, 2H), 6.59 (t, J=74.7 Hz, 1H), 7.19 (dd, J=8.3, 1.9 Hz, 1H), 7.26 (d, J=8.3 Hz, 1H), 7.62 (d, J=1.9 Hz, 1H), 8.20 (s, 1H).

62-(b) 2-(3-Cyclopropoxy-4-difluoromethoxyphenyl)-3-isobutoxymethyl-5-(2-trimethylsilylethoxymethyl)-1,5-dihydropyrrolo[2,3-d]pyridazin-4-one Reaction and post treatment were carried out in the same manner as in Example 4-(b) except for using 1.35 g (1.99 mmol) of 2-(3-cyclopropoxy-4-difluoromethoxyphenyl)-3-isobutoxymethyl-1,5-bis(2-trimethylsilylethoxymethyl)-1,5-dihydropyrrolo[2,3-d]pyridazin-4-one obtained in Example 62-(a) in place of 2-(3-cyclopropoxy-4-difluoromethoxyphenyl)-3-methyl-1,5-bis(2-trimethylsilylethoxymethyl)-1,5-dihydropyrrolo[2,3-d]pyridazin-4-one, whereby 0.84 g of the title compound was obtained as a white foam. (Yield: 77%)

Mass Spectrum (CI, m/z): 550 (M$^+$+1).

$^1$H-NMR Spectrum (CDCl$_3$, δ ppm): −0.02 (s, 9H), 0.83-0.87 (m, 4H), 0.87 (d, J=6.7 Hz, 6H), 0.93-0.99 (m, 2H), 1.82-1.91 (m, 1H), 3.41 (d, J=6.7 Hz, 2H), 3.70-3.74 (m, 2H), 3.85-3.89 (m, 1H), 4.86 (s, 2H), 5.59 (s, 2H), 6.56 (t, J=74.8 Hz, 1H), 7.23 (d, J=8.3 Hz, 1H), 7.26 (dd, J=8.3, 1.9 Hz, 1H), 7.83 (d, J=1.9 Hz, 1H), 8.11 (s, 1H), 9.03 (brs, 1H).

62-(c) 2-(3-Cyclopropoxy-4-difluoromethoxyphenyl)-3-isobutoxymethyl-1,5-dihydropyrrolo[2,3-d]pyridazin-4-one Reaction and post treatment were carried out in the same manner as in Example 13-(c) except for using 0.83 g (1.51 mmol) of 2-(3-cyclopropoxy-4-difluoromethoxyphenyl)-3-isobutoxymethyl-5-(2-trimethylsilylethoxymethyl)-1,5-dihydropyrrolo[2,3-d]pyridazin-4-one obtained in Example 62-(b) in place of 3-cyclobutoxymethyl-2-(3-cyclopropoxy-4-difluoromethoxyphenyl)-5-(2-trimethylsilylethoxymethyl)-1,5-dihydropyrrolo[2,3-d]pyridazin-4-one, whereby 402 mg of the title compound was obtained as a white solid. (Yield: 64%)

Melting point: 162-164° C.

Mass Spectrum (CI, m/z): 420 (M$^+$+1).

$^1$H-NMR Spectrum (DMSO-d$_6$, δ ppm): 0.73-0.89 (m, 4H), 0.82 (d, J=6.7 Hz, 6H), 1.71-1.86 (m, 1H), 3.30 (d, J=6.7 Hz, 2H), 3.91-4.00 (m, 1H), 4.80 (s, 2H), 7.10 (t, J=74.3 Hz, 1H), 7.32 (d, J=8.4 Hz, 1H), 7.43 (dd, J=8.4, 2.0 Hz, 1H), 7.91 (d, J=2.0 Hz, 1H), 8.15 (s, 1H), 12.21 (brs, 1H).

IR Spectrum (KBr, cm$^{-1}$): 1645.

Example 63

3-(sec-Butoxymethyl)-2-(3-cyclopropoxy-4-difluoromethoxyphenyl)-1,5-dihydropyrrolo[2,3-d]pyridazin-4-one (Exemplary compound No. 1-1299)

63-(a) 3-(sec-Butoxymethyl)-2-(3-cyclopropoxy-4-difluoromethoxyphenyl)-1,5-bis(2-trimethylsilylethoxymethyl)-1,5-dihydropyrrolo[2,3-d]pyridazin-4-one Reaction and post treatment were carried out in the same manner as in Example 4-(a) except for using 0.81 g (1.44 mmol) of 2-bromo-3-(sec-butoxymethyl)-1,5-bis(2-trimethylsilylethoxymethyl)-1,5-dihydropyrrolo[2,3-d]pyridazin-4-one obtained in the same manner as in the following Reference example 54 in place of 2-bromo-3-methyl-1,5-bis(2-trimethylsilylethoxymethyl)-1,5-dihydropyrrolo[2,3-d]pyridazin-4-one, whereby 0.88 g of the title compound was obtained as a pale yellowish solid. (Yield: 90%)

Mass Spectrum (CI, m/z): 680 (M$^+$+1).

$^1$H-NMR Spectrum (CDCl$_3$, δ ppm): −0.03 (s, 9H), −0.01 (s, 9H), 0.78-0.91 (m, 6H), 0.83 (t, J=7.2 Hz, 3H), 0.94-1.03 (m, 2H), 1.16 (d, J=6.1 Hz, 3H), 1.34-1.49 (m, 1H), 1.50-1.65 (m, 1H), 3.47-3.55 (m, 2H), 3.53-3.64 (m, 1H), 3.69-3.76 (m, 2H), 3.78-3.85 (m, 1H), 4.67 (d, J=10.3 Hz, 1H), 4.73 (d, J=10.3 Hz, 1H), 5.34 (s, 2H), 5.59 (d, J=9.8 Hz, 1H), 5.62 (d, J=9.8 Hz, 1H), 6.59 (t, J=74.7 Hz, 1H), 7.20 (dd, J=8.3, 1.9 Hz, 1H), 7.26 (d, J=8.3 Hz, 1H), 7.62 (d, J=1.9 Hz, 1H), 8.19 (s, 1H).

63-(b) 3-(sec-Butoxymethyl)-2-(3-cyclopropoxy-4-difluoromethoxyphenyl)-5-(2-trimethylsilylethoxymethyl)-1,5-dihydropyrrolo[2,3-d]pyridazin-4-one Reaction and post treatment were carried out in the same manner as in Example 4-(b) except for using 0.88 g (1.30 mmol) of 3-(sec-butoxymethyl)-2-(3-cyclopropoxy-4-difluoromethoxyphenyl)-1,5-bis(2-trimethylsilylethoxymethyl)-1,5-dihydropyrrolo[2,3-d]pyridazin-4-one obtained in Example 63-(a) in place of 2-(3-cyclopropoxy-4-difluoromethoxyphenyl)-3-methyl-1,5-bis(2-trimethylsilylethoxymethyl)-1,5-dihydropyrrolo[2,3-d]pyridazin-4-one, whereby 0.64 g of the title compound was obtained as a white foam. (Yield: 90%)

Mass Spectrum (CI, m/z): 550 ($M^+$+1).

$^1$H-NMR Spectrum (CDCl$_3$, δ ppm): −0.02 (s, 9H), 0.81-0.89 (m, 4H), 0.85 (t, J=7.4 Hz, 3H), 0.92-1.01 (m, 2H), 1.21 (d, J=6.1 Hz, 3H), 1.38-1.54 (m, 1H), 1.54-1.71 (m, 1H), 3.63-3.75 (m, 3H), 3.84-3.91 (m, 1H), 4.85 (d, J=10.7 Hz, 1H), 4.89 (d, J=10.7 Hz, 1H), 5.60 (s, 2H), 6.57 (t, J=74.8 Hz, 1H), 7.23 (d, J=8.3 Hz, 1H), 7.29 (dd, J=8.3, 2.0 Hz, 1H), 7.82 (d, J=2.0 Hz, 1H), 8.10 (s, 1H), 8.93 (brs, 1H).

63-(c) 3-(sec-Butoxymethyl)-2-(3-cyclopropoxy-4-difluoromethoxyphenyl)-1,5-dihydropyrrolo[2,3-d]pyridazin-4-one Reaction and post treatment were carried out in the same manner as in Example 13-(c) except for using 0.64 g (1.16 mmol) of 3-(sec-butoxymethyl)-2-(3-cyclopropoxy-4-difluoromethoxyphenyl)-5-(2-trimethylsilylethoxymethyl)-1,5-dihydropyrrolo[2,3-d]pyridazin-4-one obtained in Example 63-(b) in place of 3-cyclobutoxymethyl-2-(3-cyclopropoxy-4-difluoromethoxyphenyl)-5-(2-trimethylsilylethoxymethyl)-1,5-dihydropyrrolo[2,3-d]pyridazin-4-one, whereby 303 mg of the title compound was obtained as a white solid. (Yield: 61%)

Melting point: 103-106° C.

Mass Spectrum (CI, m/z): 420 ($M^+$+1).

$^1$H-NMR Spectrum (DMSO-d$_6$, δ ppm): 0.72-0.90 (m, 4H), 0.77 (t, J=7.4 Hz, 3H), 1.11 (d, J=6.1 Hz, 3H), 1.31-1.56 (m, 2H), 3.53-3.65 (m, 1H), 3.91-3.99 (m, 1H), 4.78 (d, J=11.1 Hz, 1H), 4.83 (d, J=11.1 Hz, 1H), 7.10 (t, J=74.5 Hz, 1H), 7.32 (d, J=8.4 Hz, 1H), 7.46 (dd, J=8.4, 2.1 Hz, 1H), 7.94 (d, J=2.1 Hz, 1H), 8.14 (s, 1H), 12.20 (brs, 1H).

IR Spectrum (KBr, cm$^{-1}$): 1643.

Example 64

3-(tert-Butoxymethyl)-2-(3-cyclopropoxy-4-difluoromethoxyphenyl)-1,5-dihydropyrrolo[2,3-d]pyridazin-4-one (Exemplary compound No. 1-1309)

64-(a) 3-(tert-Butoxymethyl)-2-(3-cyclopropoxy-4-difluoromethoxyphenyl)-1,5-bis(2-trimethylsilylethoxymethyl)-1,5-dihydropyrrolo[2,3-d]pyridazin-4-one Reaction and post treatment were carried out in the same manner as in Example 4-(a) except for using 0.83 g (1.48 mmol) of 2-bromo-3-(tert-butoxymethyl)-1,5-bis(2-trimethylsilylethoxymethyl)-1,5-dihydropyrrolo[2,3-d]-pyridazin-4-one obtained in the same manner as in the following Reference example 55 in place of 2-bromo-3-methyl-1,5-bis(2-trimethylsilylethoxymethyl)-1,5-dihydropyrrolo[2,3-d]pyridazin-4-one, whereby 0.90 g of the title compound was obtained as a slightly yellowish oil. (Yield: 89%)

Mass Spectrum (CI, m/z): 680 ($M^+$+1).

$^1$H-NMR Spectrum (CDCl$_3$, δ ppm): −0.02 (s, 9H), 0.00 (s, 9H), 0.78-0.92 (m, 6H), 0.95-1.03 (m, 2H), 1.35 (s, 9H), 3.48-3.57 (m, 2H), 3.68-3.76 (m, 2H), 3.80-3.87 (m, 1H), 4.64 (s, 2H), 5.31 (s, 2H), 5.60 (s, 2H), 6.59 (t, J=74.7 Hz, 1H), 7.22 (dd, J=8.3, 1.7 Hz, 1H), 7.26 (d, J=8.3 Hz, 1H), 7.61 (d, J=1.7 Hz, 1H), 8.17 (s, 1H).

64-(b) 3-(tert-Butoxymethyl)-2-(3-cyclopropoxy-4-difluoromethoxyphenyl)-5-(2-trimethylsilylethoxymethyl)-1,5-dihydropyrrolo[2,3-d]pyridazin-4-one Reaction and post treatment were carried out in the same manner as in Example 4-(b) except for using 0.90 g (1.33 mmol) of 3-(tert-butoxymethyl)-2-(3-cyclopropoxy-4-difluoromethoxyphenyl)-1,5-bis(2-trimethylsilylethoxymethyl)-1,5-dihydropyrrolo[2,3-d]pyridazin-4-one obtained in Example 64-(a) in place of 2-(3-cyclopropoxy-4-difluoromethoxyphenyl)-3-methyl-1,5-bis(2-trimethylsilylethoxymethyl)-1,5-dihydropyrrolo[2,3-d]pyridazin-4-one, whereby 0.51 g of the title compound was obtained as a white solid. (Yield: 70%)

Mass Spectrum (CI, m/z): 550 ($M^+$+1).

$^1$H-NMR Spectrum (CDCl$_3$, δ ppm): −0.01 (s, 9H), 0.81-0.87 (m, 4H), 0.93-1.00 (m, 2H), 1.35 (s, 9H), 3.66-3.74 (m, 2H), 3.87-3.94 (m, 1H), 4.80 (s, 2H), 5.59 (s, 2H), 6.56 (t, J=74.7 Hz, 1H), 7.24 (d, J=8.3 Hz, 1H), 7.33 (dd, J=8.3, 2.1 Hz, 1H), 7.73 (d, J=2.1 Hz, 1H), 8.07 (s, 1H), 8.83 (brs, 1H).

64-(c) 3-(tert-Butoxymethyl)-2-(3-cyclopropoxy-4-difluoromethoxyphenyl)-1,5-dihydropyrrolo[2,3-d]pyridazin-4-one Reaction and post treatment were carried out in the same manner as in Example 13-(c) except for using 0.48 g (0.87 mmol) of 3-(tert-butoxymethyl)-2-(3-cyclopropoxy-4-difluoromethoxyphenyl)-5-(2-trimethylsilylethoxymethyl)-1,5-dihydropyrrolo[2,3-d]pyridazin-4-one obtained in Example 64-(b) in place of 3-cyclobutoxymethyl-2-(3-cyclopropoxy-4-difluoromethoxyphenyl)-5-(2-trimethylsilylethoxymethyl)-1,5-dihydropyrrolo[2,3-d]pyridazin-4-one, whereby 183 mg of the title compound was obtained as a white solid. (Yield: 50%)

Melting point: >300° C.

Mass Spectrum (CI, m/z): 420 ($M^+$+1).

$^1$H-NMR Spectrum (DMSO-d$_6$, δ ppm): 0.73-0.90 (m, 4H), 1.26 (s, 9H), 3.95-4.03 (m, 1H), 4.71 (s, 2H), 7.10 (t, J=74.2 Hz, 1H), 7.33 (d, J=8.4 Hz, 1H), 7.49 (dd, J=8.4, 2.1 Hz, 1H), 7.83 (d, J=2.1 Hz, 1H), 8.13 (s, 1H), 12.17 (brs, 1H).

IR Spectrum (KBr, cm$^{-1}$): 1656.

Example 65

2-(3-Cyclopropoxy-4-difluoromethoxyphenyl)-3-(1-ethylpropoxymethyl)-1,5-dihydropyrrolo[2,3-d]pyridazin-4-one (Exemplary compound No. 1-1319)

65-(a) 2-(3-Cyclopropoxy-4-difluoromethoxyphenyl)-3-(1-ethylpropoxymethyl)-1,5-bis(2-trimethylsilylethoxymethyl)-1,5-dihydropyrrolo[2,3-d]pyridazin-4-one Reaction and post treatment were carried out in the same manner as in Example 4-(a) except for using 0.65 g (1.13 mmol) of 2-bromo-3-(1-ethylpropoxymethyl)-1,5-bis(2-trimethylsilylethoxymethyl)-1,5-dihydropyrrolo[2,3-d]pyridazin-4-one obtained in the following Reference example 56 in place of 2-bromo-3-methyl-1,5-bis(2-trimethylsilylethoxymethyl)-1,5-dihydropyrrolo[2,3-d]pyridazin-4-one, whereby 0.70 g of the title compound was obtained as a slightly yellowish oil. (Yield: 89%)

Mass Spectrum (CI, m/z): 694 ($M^+$+1).

$^1$H-NMR Spectrum (CDCl$_3$, δ ppm): −0.03 (s, 9H), −0.01 (s, 9H), 0.81-1.00 (m, 8H), 0.82 (t, J=7.4 Hz, 6H), 1.47-1.54 (m, 4H), 3.34-3.40 (m, 1H), 3.47-3.51 (m, 2H), 3.70-3.75 (m, 2H), 3.78-3.83 (m, 1H), 4.71 (s, 2H), 5.34 (s, 2H), 5.61 (s, 2H), 6.59 (t, J=74.7 Hz, 1H), 7.20 (dd, J=8.2, 2.0 Hz, 1H), 7.25 (d, J=8.2 Hz, 1H), 7.61 (d, J=2.0 Hz, 1H), 8.20 (s, 1H).

65-(b) 2-(3-Cyclopropoxy-4-difluoromethoxyphenyl)-3-(1-ethylpropoxymethyl)-5-(2-trimethylsilylethoxymethyl)-1,5-dihydropyrrolo[2,3-d]pyridazin-4-one Reaction and post treatment were carried out in the same manner as in Example 4-(b) except for using 0.70 g (1.01 mmol) of 2-(3-cyclopropoxy-4-difluoromethoxyphenyl)-3-(1-ethylpropoxymethyl)-1,5-bis(2-trimethylsilylethoxymethyl)-1,5-dihydropyrrolo[2,3-d]pyridazin-4-one obtained in Example 65-(a) in place of 2-(3-cyclopropoxy-4-difluoromethoxyphenyl)-3-methyl-1,5-bis(2-trimethylsilylethoxymethyl)-1,5-dihydropyrrolo[2,3-d]pyridazin-4-one, whereby 0.27 g of the title compound was obtained as a white solid. (Yield: 476)

Mass Spectrum (CI, m/z): 564 (M$^+$+1).
$^1$H-NMR Spectrum (DMSO-d$_6$, δ ppm): −0.06 (s, 9H), 0.74 (t, J=7.4 Hz, 6H), 0.75-0.87 (m, 6H), 1.40-1.49 (m, 4H), 3.40-3.45 (m, 1H), 3.61-3.66 (m, 2H), 3.91-3.96 (m, 1H), 4.81 (s, 2H), 5.43 (s, 2H), 7.09 (t, J=74.4 Hz, 1H), 7.31 (d, J=8.4 Hz, 1H), 7.46 (dd, J=8.4, 2.0 Hz, 1H), 7.94 (d, J=2.0 Hz, 1H), 8.20 (s, 1H), 12.56 (brs, 1H).

65-(c) 2-(3-Cyclopropoxy-4-difluoromethoxyphenyl)-3-(1-ethylpropoxymethyl)-1,5-dihydropyrrolo[2,3-d]pyridazin-4-one Reaction and post treatment were carried out in the same manner as in Example 13-(c) except for using 0.26 g (0.46 mmol) of 2-(3-cyclopropoxy-4-difluoromethoxyphenyl)-3-(1-ethylpropoxymethyl)-5-(2-trimethylsilylethoxymethyl)-1,5-dihydropyrrolo[2,3-d]pyridazin-4-one obtained in Example 65-(b) in place of 3-cyclobutoxymethyl-2-(3-cyclopropoxy-4-difluoromethoxyphenyl)-5-(2-trimethylsilylethoxymethyl)-1,5-dihydropyrrolo[2,3-d]pyridazin-4-one, whereby 69 mg of the title compound was obtained as a white solid. (Yield: 35%)

Melting point: 133-162° C.
Mass Spectrum (CI, m/z): 434 (M$^+$+1).
$^1$H-NMR Spectrum (DMSO-d$_6$, δ ppm): 0.72-0.81 (m, 2H), 0.75 (t, J=7.3 Hz, 6H), 0.82-0.90 (m, 2H), 1.38-1.53 (m, 4H), 3.39-3.48 (m, 1H), 3.91-3.99 (m, 1H), 4.82 (s, 2H), 7.10 (t, J=74.3 Hz, 1H), 7.32 (d, J=8.3 Hz, 1H), 7.47 (dd, J=8.3, 2.0 Hz, 1H), 7.95 (d, J=2.0 Hz, 1H), 8.15 (s, 1H), 12.22 (brs, 1H).
IR Spectrum (KBr, cm$^{-1}$): 1643.

Example 66

2-(3-Cyclopropoxy-4-difluoromethoxyphenyl)-3-(2-methoxyethyl)-1,5-dihydropyrrolo[2,3-d]pyridazin-4-one (Exemplary compound No. 1-51)

66-(a) 2-(3-Cyclopropoxy-4-difluoromethoxyphenyl)-3-(2-methoxyethyl)-1,5-bis(2-trimethylsilylethoxymethyl)-1,5-dihydropyrrolo[2,3-d]pyridazin-4-one Reaction and post treatment were carried out in the same manner as in Example 4-(a) except for using 1.12 g (2.10 mmol) of 2-bromo-3-(2-methoxyethyl)-1,5-bis(2-trimethylsilylethoxymethyl)-1,5-dihydropyrrolo[2,3-d]pyridazin-4-one obtained in the following Reference example 57-(g) in place of 2-bromo-3-methyl-1,5-bis(2-trimethylsilylethoxymethyl)-1,5-dihydropyrrolo[2,3-d]pyridazin-4-one, whereby 1.35 g of the title compound was obtained as a pale brownish oil. (Yield: 99%)

Mass Spectrum (CI, m/z): 652 (M$^+$+1).
$^1$H-NMR Spectrum (CDCl$_3$, δ ppm): −0.04 (s, 9H), 0.00 (s, 9H), 0.75-0.90 (m, 6H), 0.95-1.05 (m, 2H), 3.03 (t, J=6.3 Hz, 2H), 3.25 (s, 3H), 3.40-3.48 (m, 2H), 3.69-3.85 (m, 3H), 3.77 (t, J=6.3 Hz, 2H), 5.30 (s, 2H), 5.60 (s, 2H), 6.59 (t, J=74.8 Hz, 1H), 7.07 (dd, J=8.4, 2.0 Hz, 1H), 7.25 (d, J=8.4 Hz, 1H), 7.58 (d, J=2.0 Hz, 1H), 8.18 (s, 1H).

66-(b) 2-(3-Cyclopropoxy-4-difluoromethoxyphenyl)-3-(2-methoxyethyl)-5-(2-trimethylsilylethoxymethyl)-1,5-dihydropyrrolo[2,3-d]pyridazin-4-one Reaction and post treatment were carried out in the same manner as in Example 4-(b) except for using 1.34 g (2.06 mmol) of 2-(3-cyclopropoxy-4-difluoromethoxyphenyl)-3-(2-methoxyethyl)-1,5-bis(2-trimethylsilylethoxymethyl)-1,5-dihydropyrrolo[2,3-d]pyridazin-4-one obtained in Example 66-(a) in place of 2-(3-cyclopropoxy-4-difluoromethoxyphenyl)-3-methyl-1,5-bis(2-trimethylsilylethoxymethyl)-1,5-dihydropyrrolo[2,3-d]pyridazin-4-one, whereby 0.90 g of the title compound was obtained as a white solid. (Yield: 84%)

Mass Spectrum (CI, m/z): 522 (M$^+$+1).
$^1$H-NMR Spectrum (CDCl$_3$, δ ppm): −0.02 (s, 9H), 0.80-0.87 (m, 4H), 0.93-1.01 (m, 2H), 3.19 (t, J=6.2 Hz, 2H), 3.29 (s, 3H), 3.68-3.76 (m, 2H), 3.80-3.89 (m, 1H), 3.86 (t, J=6.2 Hz, 2H), 5.58 (s, 2H), 6.55 (t, J=74.8 Hz, 1H), 7.12 (dd, J=8.3, 2.1 Hz, 1H), 7.21 (d, J=8.3 Hz, 1H), 7.82 (d, J=2.1 Hz, 1H), 8.07 (s, 1H), 8.98 (brs, 1H)

66-(c) 2-(3-Cyclopropoxy-4-difluoromethoxyphenyl)-3-(2-methoxyethyl)-1,5-dihydropyrrolo[2,3-d]pyridazin-4-one Reaction and post treatment were carried out in the same manner as in Example 13-(c) except for using 0.90 g (1.73 mmol) of 2-(3-cyclopropoxy-4-difluoromethoxyphenyl)-3-(2-methoxyethyl)-5-(2-trimethylsilylethoxymethyl)-1,5-dihydropyrrolo[2,3-d]pyridazin-4-one obtained in Example 66-(b) in place of 3-cyclobutoxymethyl-2-(3-cyclopropoxy-4-difluoromethoxyphenyl)-5-(2-trimethylsilylethoxymethyl)-1,5-dihydropyrrolo[2,3-d]pyridazin-4-one, whereby 412 mg of the title compound was obtained as a white solid. (Yield: 61%)

Melting point: 215-217° C.
Mass Spectrum (CI, m/z): 392 (M$^+$+1).
$^1$H-NMR Spectrum (DMSO-d$_6$, δ ppm): 0.73-0.80 (m, 2H), 0.81-0.89 (m, 2H), 3.10 (t, J=6.7 Hz, 2H), 3.21 (s, 3H), 3.70 (t, J=6.7 Hz, 2H), 3.93-4.00 (m, 1H), 7.10 (t, J=74.3 Hz, 1H), 7.25 (dd, J=8.4, 1.9 Hz, 1H), 7.32 (d, J=8.4 Hz, 1H) 7.78 (d, J=1.9 Hz, 1H), 8.10 (s, 1H), 12.19 (brs, 1H).
IR Spectrum (KBr, cm$^{-1}$): 1642.

Example 67

2-(3-Cyclopropoxy-4-difluoromethoxyphenyl)-3-(2-ethoxyethyl)-1,5-dihydropyrrolo[2,3-d]pyridazin-4-one (Exemplary compound No. 1-61)

67-(a) 2-(3-Cyclopropoxy-4-difluoromethoxyphenyl)-3-(2-ethoxyethyl)-1,5-bis(2-trimethylsilylethoxymethyl)-1,5-dihydropyrrolo[2,3-d]pyridazin-4-one Reaction and post treatment were carried out in the same manner as in Example 4-(a) except for using 850 mg (1.55 mmol) of 2-bromo-3-(2-ethoxyethyl)-1,5-bis(2-trimethylsilylethoxymethyl)-1,5-dihydropyrrolo[2,3-d]pyridazin-4-one obtained in the following Reference example 58-(b) in place of 2-bromo-3-methyl-1,5-bis(2-trimethylsilylethoxymethyl)-1,5-dihydropyrrolo[2,3-d]pyridazin-4-one, whereby 0.91 g of the title compound was obtained as a pale brownish oil. (Yield: 88%)

Mass Spectrum (CI, m/z): 666 ($M^+$+1).

$^1$H-NMR Spectrum (CDCl$_3$, δ ppm): −0.05 (s, 9H), 0.00 (s, 9H), 0.77-0.88 (m, 6H), 0.96-1.04 (m, 2H), 1.09 (t, J=7.0 Hz, 3H), 3.03 (t, J=6.6 Hz, 2H), 3.39-3.47 (m, 2H), 3.42 (q, J=7.0 Hz, 2H), 3.70-3.85 (m, 2H), 3.78 (t, J=6.6 Hz, 2H), 5.31 (s, 2H), 5.60 (s, 2H), 6.59 (t, J=74.7 Hz, 1H), 7.09 (dd, J=8.3, 2.1 Hz, 1H), 7.25 (d, J=8.3 Hz, 1H), 7.50 (d, J=2.1 Hz, 1H), 8.19 (s, 1H).

67-(b) 2-(3-Cyclopropoxy-4-difluoromethoxyphenyl)-3-(2-ethoxyethyl)-5-(2-trimethylsilylethoxymethyl)-1,5-dihydropyrrolo[2,3-d]pyridazin-4-one Reaction and post treatment were carried out in the same manner as in Example 4-(b) except for using 0.90 g (1.35 mmol) of 2-(3-cyclopropoxy-4-difluoromethoxyphenyl)-3-(2-ethoxyethyl)-1,5-bis(2-trimethylsilylethoxymethyl)-1,5-dihydropyrrolo[2,3-d]pyridazin-4-one obtained in Example 67-(a) in place of 2-(3-cyclopropoxy-4-difluoromethoxyphenyl)-3-methyl-1,5-bis(2-trimethylsilylethoxymethyl)-1,5-dihydropyrrolo[2,3-d]pyridazin-4-one, whereby 0.65 g of the title compound was obtained as a white solid. (Yield: 90%)

Mass Spectrum (CI, m/z): 536 ($M^+$+1).

$^1$H-NMR Spectrum (CDCl$_3$, δ ppm): −0.01 (s, 9H), 0.80-0.87 (m, 4H), 0.94-1.01 (m, 2H), 1.08 (t, J=7.0 Hz, 3H), 3.20 (t, J=6.4 Hz, 2H), 3.44 (q, J=7.0 Hz, 2H), 3.68-3.76 (m, 2H), 3.82-3.91 (m, 1H), 3.87 (t, J=6.4 Hz, 2H), 5.58 (s, 2H), 6.56 (t, J=74.8 Hz, 1H), 7.17 (dd, J=8.3, 2.0 Hz, 1H), 7.22 (d, J=8.3 Hz, 1H), 7.74 (d, J=2.0 Hz, 1H), 8.08 (s, 1H), 8.84 (s, 1H).

67-(c) 2-(3-Cyclopropoxy-4-difluoromethoxyphenyl)-3-(2-ethoxyethyl)-1,5-dihydropyrrolo[2,3-d]pyridazin-4-one Reaction and post treatment were carried out in the same manner as in Example 13-(c) except for using 0.65 g (1.20 mmol) of 2-(3-cyclopropoxy-4-difluoromethoxyphenyl)-3-(2-ethoxyethyl)-5-(2-trimethylsilylethoxymethyl)-1,5-dihydropyrrolo[2,3-d]pyridazin-4-one obtained in Example 67-(b) in place of 3-cyclobutoxymethyl-2-(3-cyclopropoxy-4-difluoromethoxyphenyl)-5-(2-trimethylsilylethoxymethyl)-1,5-dihydropyrrolo[2,3-d]pyridazin-4-one, whereby 279 mg of the title compound was obtained as a white solid. (Yield: 57%)

Melting point: 201-203° C.

Mass Spectrum (CI, m/z): 406 ($M^+$+1).

$^1$H-NMR Spectrum (DMSO-d$_6$, δ ppm): 0.73-0.90 (m, 4H), 1.04 (t, J=7.0 Hz, 3H), 3.11 (t, J=7.0 Hz, 2H), 3.39 (q, J=7.0 Hz, 2H), 3.72 (t, J=7.0 Hz, 2H), 3.94-4.02 (m, 1H), 7.10 (t, J=74.3 Hz, 1H), 7.28 (dd, J=8.5, 1.9 Hz, 1H), 7.32 (d, J=8.5 Hz, 1H), 7.74 (d, J=1.9 Hz, 1H), 8.10 (s, 1H), 12.19 (brs, 1H).

IR Spectrum (KBr, cm$^{-1}$): 1643.

Example 68

2-(3-Cyclopropoxy-4-difluoromethoxyphenyl)-3-pentyl-1,5-dihydropyrrolo[2,3-d]pyridazin-4-one (Exemplary compound No. 1-10)

68-(a) 2-(3-Cyclopropoxy-4-difluoromethoxyphenyl)-3-(1-pentenyl)-1,5-bis(2-trimethylsilylethoxymethyl)-1,5-dihydropyrrolo[2,3-d]pyridazin-4-one To 10 ml of tetrahydrofuran solution containing 1.20 g (3.00 mmol) of butyltriphenylphosphonium bromide was added 0.38 g (3.40 mmol) of potassium tert-butoxide under room temperature, and the mixture was stirred at the same temperature for 30 minutes. Then, to the mixture was added 0.62 g (1.00 mmol) of 2-(3-cyclopropoxy-4-difluoromethoxyphenyl)-3-formyl-1,5-bis(2-trimethylsilylethoxymethyl)-1,5-dihydropyrrolo[2,3-d]pyridazin-4-one obtained in the same method as in Example 15-(a), and the mixture was stirred for further 4 hours. After completion of the reaction, the reaction suspension was filtered, and the filtrate was concentrated under reduced pressure. The residue was applied to silica gel column chromatography (Eluent; hexane:ethyl acetate=1:3 (V/V)), and the fractions containing the desired compound were concentrated under reduced pressure to obtain 0.35 g of the title compound as a slightly yellowish oil. (Yield: 53%).

Mass Spectrum (CI, m/z): 662 ($M^+$+1).

$^1$H-NMR Spectrum (CDCl$_3$, δ ppm): −0.05 (s, 9H), 0.00 (s, 9H), 0.78-0.89 (m, 9H), 0.95-1.05 (m, 2H), 1.30-1.45 (m, 2H), 2.02-2.12 (m, 2H), 3.38-3.46 (m, 2H), 3.69-3.80 (m, 3H), 5.28 (s, 2H), 5.61 (s, 2H), 6.51 (dd, J=16.2, 3.3 Hz, 1H), 6.58 (dt, J=16.2, 5.1 Hz, 1H), 6.60 (t, J=74.7 Hz, 1H), 7.00 (dd, J=8.1, 2.0 Hz, 1H), 7.27 (d, J=8.1 Hz, 1H), 7.38 (d, J=2.0 Hz, 1H), 8.17 (s, 1H).

68-(b) 2-(3-Cyclopropoxy-4-difluoromethoxyphenyl)-3-pentyl-1,5-bis(2-trimethylsilylethoxymethyl)-1,5-dihydropyrrolo-[2,3-d]pyridazin-4-one To 26 ml of ethanol solution containing 1.08 g (1.60 mmol) of 2-(3-cyclopropoxy-4-difluoromethoxyphenyl)-3-(1-pentenyl)-1,5-bis(2-trimethylsilylethoxymethyl)-1,5-dihydropyrrolo[2,3-d]pyridazin-4-one obtained in the same manner as in Example 68-(a) was added 43.8 mg of platinum oxide, and the mixture was stirred under 1 atm hydrogen atmosphere at room temperature for 3 hours. After completion of the reaction, the insoluble material was filtered off from the reaction mixture, and the filtrate was concentrated under reduced pressure. The residue was applied to silica gel column chromatography (Eluent; hexane:ethyl acetate=1:3 (V/V)), and the fractions containing the desired compound were concentrated under reduced pressure to obtain 0.66 g of the title compound as a colorless oil. (Yield: 626).

Mass Spectrum (CI, m/z): 664 ($M^+$+1).

$^1$H-NMR Spectrum (CDCl$_3$, δ ppm): −0.05 (s, 9H), −0.01 (s, 9H), 0.76-0.89 (m, 9H), 0.95-1.04 (m, 2H), 1.16-1.31 (m, 4H), 1.57-1.69 (m, 2H), 2.70-2.82 (m, 2H), 3.38-3.46 (m, 2H), 3.69-3.81 (m, 3H), 5.29 (s, 2H), 5.60 (s, 2H), 6.60 (t, J=74.7 Hz, 1H), 6.97 (dd, J=8.2, 2.1 Hz, 1H), 7.26 (d, J=8.2 Hz, 1H), 7.35 (d, J=2.1 Hz, 1H), 8.17 (s, 1H).

68-(c) 2-(3-Cyclopropoxy-4-difluoromethoxyphenyl)-3-pentyl-5-(2-trimethylsilylethoxymethyl)-1,5-dihydropyrrolo[2,3-d]-pyridazin-4-one Reaction and post treatment were carried out in the same manner as in Example 4-(b) except for using 0.65 g (0.98 mmol) of 2-(3-cyclopropoxy-4-difluoromethoxyphenyl)-3-pentyl-1,5-bis(2-trimethylsilylethoxymethyl)-1,5-dihydropyrrolo[2,3-d]pyridazin-4-one obtained in Example 68-(b) in place of 2-(3-cyclopropoxy-4-difluoromethoxyphenyl)-3-methyl-1,5-bis(2-trimethylsilylethoxymethyl)-1,5-dihydropyrrolo[2,3-d]pyridazin-4-one, whereby 0.33 g of the title compound was obtained as a white solid. (Yield: 62%)

Mass Spectrum (CI, m/z): 534 ($M^+$+1).

$^1$H-NMR Spectrum (CDCl$_3$, δ ppm): −0.04 (s, 9H), 0.77-0.87 (m, 4H), 0.81 (t, J=7.2 Hz, 3H), 0.90-0.98 (m, 2H), 1.19-1.37 (m, 4H), 1.62-1.79 (m, 2H), 2.88-2.98 (m, 2H), 3.66-3.75 (m, 2H), 3.76-3.84 (m, 1H), 5.58 (s, 2H), 6.55 (t, J=74.8 Hz, 1H), 7.06 (dd, J=8.3, 2.0 Hz, 1H), 7.21 (d, J=8.3 Hz, 1H), 7.47 (d, J=2.0 Hz, 1H), 8.07 (s, 1H), 9.25 (brs, 1H)

68-(d) 2-(3-Cyclopropoxy-4-difluoromethoxyphenyl)-3-pentyl-1,5-dihydropyrrolo[2,3-d]pyridazin-4-one Reaction and post treatment were carried out in the same manner as in Example 6-(c) except for using 0.32 g (0.60 mmol) of 2-(3-cyclopropoxy-4-difluoromethoxyphenyl)-3-pentyl-5-(2-trimethylsilylethoxymethyl)-1,5-dihydropyrrolo[2,3-d]pyridazin-4-one obtained in Example 68-(c) in place of 2-(3-cyclopropoxy-4-difluoromethoxyphenyl)-3-propyl-5-(2-trimethylsilylethoxymethyl)-1,5-dihydropyrrolo-[2,3-d]pyridazin-4-one, whereby 99 mg of the title compound was obtained as a white solid. (Yield: 41%)

Melting point: 191-193° C.
Mass Spectrum (CI, m/z): 404 (M$^+$+1).
$^1$H-NMR Spectrum (DMSO-d$_6$, δ ppm): 0.73-0.88 (m, 7H), 1.19-1.35 (m, 4H), 1.57-1.73 (m, 2H), 2.85-2.96 (m, 2H), 3.95-4.03 (m, 1H), 7.10 (t, J=74.3 Hz, 1H), 7.17 (dd, J=8.3, 2.0 Hz, 1H), 7.32 (d, J=8.3 Hz, 1H), 7.58 (d, J=2.0 Hz, 1H), 8.07 (s, 1H), 12.10 (brs, 1H).
IR Spectrum (KBr, cm$^{-1}$): 1641.

Example 69

2-(3-Cyclopropoxy-4-difluoromethoxyphenyl)-3-hexyl-1,5-dihydropyrrolo[2,3-d]pyridazin-4-one (Exemplary compound No. 1-12)

69-(a) 2-(3-Cyclopropoxy-4-difluoromethoxyphenyl)-3-(1-hexenyl)-1,5-bis(2-trimethylsilylethoxymethyl)-1,5-dihydropyrrolo[2,3-d]pyridazin-4-one Reaction and post treatment were carried out in the same manner as in Example 68-(a) except for using 2.00 g (3.22 mmol) of 2-(3-cyclopropoxy-4-difluoromethoxyphenyl)-3-formyl-1,5-bis(2-trimethylsilylethoxymethyl)-1,5-dihydropyrrolo[2,3-d]pyridazin-4-one obtained in the same manner as in Example 15-(a), and using 4.00 g (9.68 mmol) of pentyltriphenylphosphonium bromide in place of butyltriphenylphosphonium bromide, whereby 1.07 g of the title compound was obtained as a slightly yellowish oil. (Yield: 49%)

Mass Spectrum (CI, m/z): 676 (M$^+$+1).
$^1$H-NMR Spectrum (CDCl$_3$, δ ppm): −0.05 (s, 9H), 0.00 (s, 9H), 0.76-0.88 (m, 9H), 0.96-1.04 (m, 2H), 1.20-1.39 (m, 6H), 2.02-2.15 (m, 2H), 3.38-3.46 (m, 2H), 3.60-3.80 (m, 5H), 5.28 (s, 2H), 5.61 (s, 2H), 6.51 (dd, J=15.8, 2.7 Hz, 1H), 6.58 (dt, J=15.8, 5.1 Hz, 1H), 6.61 (t, J=74.7 Hz, 1H), 7.00 (dd, J=8.2, 2.0 Hz, 1H), 7.27 (d, J=8.2 Hz, 1H), 7.38 (d, J=2.0 Hz, 1H), 8.17 (s, 1H).

69-(b) 2-(3-Cyclopropoxy-4-difluoromethoxyphenyl)-3-hexyl-1,5-bis(2-trimethylsilylethoxymethyl)-1,5-dihydropyrrolo-[2,3-d]pyridazin-4-one Reaction and post treatment were carried out in the same manner as in Example 68-(b) except for using 1.05 g (1.55 mmol) of 2-(3-cyclopropoxy-4-difluoromethoxyphenyl)-3-(1-hexenyl)-1,5-bis(2-trimethylsilylethoxymethyl)-1,5-dihydropyrrolo[2,3-d]pyridazin-4-one obtained in Example 69-(a) in place of 2-(3-cyclopropoxy-4-difluoromethoxyphenyl)-3-(1-pentenyl)-1,5-bis(2-trimethylsilylethoxymethyl)-1,5-dihydropyrrolo[2,3-d]pyridazin-4-one, whereby 0.62 g of the title compound was obtained as a colorless oil. (Yield: 59%)

Mass Spectrum (CI, m/z): 678 (M$^+$+1).
$^1$H-NMR Spectrum (CDCl$_3$, δ ppm): −0.05 (s, 9H), 0.00 (s, 9H), 0.77-0.90 (m, 9H), 0.96-1.03 (m, 2H), 1.15-1.32 (m, 6H), 1.56-1.69 (m, 2H), 2.72-2.81 (m, 2H), 3.39-3.46 (m, 2H), 3.70-3.81 (m, 3H), 5.29 (s, 2H), 5.60 (s, 2H), 6.60 (t, J=74.7 Hz, 1H), 6.97 (dd, J=8.3, 2.0 Hz, 1H), 7.26 (d, J=8.3 Hz, 1H), 7.35 (d, J=2.0 Hz, 1H), 8.17 (s, 1H).

69-(c) 2-(3-Cyclopropoxy-4-difluoromethoxyphenyl)-3-hexyl-5-(2-trimethylsilylethoxymethyl)-1,5-dihydropyrrolo[2,3-d]-pyridazin-4-one Reaction and post treatment were carried out in the same manner as in Example 4-(b) except for using 0.61 g (0.90 mmol) of 2-(3-cyclopropoxy-4-difluoromethoxyphenyl)-3-hexyl-1,5-bis(2-trimethylsilylethoxymethyl)-1,5-dihydropyrrolo[2,3-d]pyridazin-4-one obtained in Example 69-(b) in place of 2-(3-cyclopropoxy-4-difluoromethoxyphenyl)-3-methyl-1,5-bis(2-trimethylsilylethoxymethyl)-1,5-dihydropyrrolo[2,3-d]pyridazin-4-one, whereby 0.43 g of the title compound was obtained as a white solid. (Yield: 87%)

Mass Spectrum (CI, m/z): 548 (M$^+$+1).
$^1$H-NMR Spectrum (CDCl$_3$, δ ppm): −0.03 (s, 9H), 0.78-0.87 (m, 7H), 0.92-0.99 (m, 2H), 1.16-1.27 (m, 6H), 1.27-1.39 (m, 2H), 1.64-1.77 (m, 2H), 2.88-3.00 (m, 2H), 3.67-3.76 (m, 2H), 3.77-3.85 (m, 1H), 5.58 (s, 2H), 6.56 (t, J=74.8 Hz, 1H), 7.05 (dd, J=8.3, 2.0 Hz, 1H), 7.22 (d, J=8.3 Hz, 1H), 7.47 (d, J=2.0 Hz, 1H), 8.07 (s, 1H), 9.01 (brs, 1H)

69-(d) 2-(3-Cyclopropoxy-4-difluoromethoxyphenyl)-3-hexyl-1,5-dihydropyrrolo[2,3-d]pyridazin-4-one Reaction and post treatment were carried out in the same manner as in Example 6-(c) except for using 0.41 g (0.75 mmol) of 2-(3-cyclopropoxy-4-difluoromethoxyphenyl)-3-hexyl-5-(2-trimethylsilylethoxymethyl)-1,5-dihydropyrrolo[2,3-d]pyridazin-4-one obtained in Example 69-(c) in place of 2-(3-cyclopropoxy-4-difluoromethoxyphenyl)-3-propyl-5-(2-trimethylsilylethoxymethyl)-1,5-dihydropyrrolo-[2,3-d]pyridazin-4-one, whereby 210 mg of the title compound was obtained as a white solid. (Yield: 67%)

Melting point: 186-188° C.
Mass Spectrum (CI, m/z): 418 (M$^+$+1).
$^1$H-NMR Spectrum (DMSO-d$_6$, δ ppm): 0.72-0.88 (m, 7H), 1.15-1.36 (m, 6H), 1.56-1.71 (m, 2H), 2.85-2.97 (m, 2H), 3.95-4.02 (m, 1H), 7.09 (t, J=74.3 Hz, 1H), 7.17 (dd, J=8.4, 2.2 Hz, 1H), 7.32 (d, J=8.4 Hz, 1H), 7.57 (d, J=2.2 Hz, 1H), 8.07 (s, 1H), 12.10 (brs, 1H).
IR Spectrum (KBr, cm$^{-1}$): 1640.

Example 70

2-(3-cyclopropoxy-4-difluoromethoxyphenyl)-3-(2-cyclopropylethyl)-1,5-dihydropyrrolo[2,3-d]pyridazin-4-one (Exemplary compound No. 1-216)

70-(a) 2-(3-Cyclopropoxy-4-difluoromethoxyphenyl)-3-(2-cyclopropylvinyl)-1,5-bis(2-trimethylsilylethoxymethyl)-1,5-dihydropyrrolo[2,3-d]pyridazin-4-one Reaction and post treatment were carried out in the same manner as in Example 68-(a) except for using 0.62 g (1.00 mmol) of 2-(3-cyclopropoxy-4-difluoromethoxyphenyl)-3-formyl-1,5-bis(2-trimethylsilylethoxymethyl)-1,5-dihydropyrrolo[2,3-d]pyridazin-4-one obtained in the same manner as in Example 15-(a), and using 1.19 g (3.00 mmol) of cyclopropylmethyltriphenylphosphonium bromide in place of butyltriphenylphosphonium bromide, whereby 0.47 g of the title compound was obtained as a colorless oil. (Yield: 71%)

Mass Spectrum (CI, m/z): 660 (M$^+$+1).

$^1$H-NMR Spectrum (CDCl$_3$, δ ppm): −0.05 (s, 9H), 0.00 (s, 9H), 0.38-0.45 (m, 2H), 0.67-0.75 (m, 2H), 0.78-0.88 (m, 6H), 0.96-1.04 (m, 2H), 1.36-1.49 (m, 1H), 3.38-3.45 (m, 2H), 3.68-3.82 (m, 3H), 5.28 (s, 2H), 5.60 (s, 2H), 6.29 (dd, J=15.9, 9.0 Hz, 1H), 6.55 (d, J=15.9 Hz, 1H), 6.61 (t, J=74.7 Hz, 1H), 7.01 (dd, J=8.2, 2.0 Hz, 1H), 7.27 (d, J=8.2 Hz, 1H), 7.38 (d, J=2.0 Hz, 1H), 8.16 (s, 1H).

70-(b) 2-(3-Cyclopropoxy-4-difluoromethoxyphenyl)-3-(2-cyclopropylethyl)-1,5-bis(2-trimethylsilylethoxymethyl)-1,5-dihydropyrrolo[2,3-d]pyridazin-4-one Reaction and post treatment were carried out in the same manner as in Example 68-(b) except for using 0.47 g (0.71 mmol) of 2-(3-cyclopropoxy-4-difluoromethoxyphenyl)-3-(2-cyclopropylvinyl)-1,5-bis(2-trimethylsilylethoxymethyl)-1,5-dihydropyrrolo[2,3-d]pyridazin-4-one obtained in Example 70-(a) in place of 2-(3-cyclopropoxy-4-difluoromethoxyphenyl)-3-(1-pentenyl)-1,5-bis(2-trimethylsilylethoxymethyl)-1,5-dihydropyrrolo[2,3-d]pyridazin-4-one, whereby 0.44 g of the title compound was obtained as a colorless oil. (Yield: 94%)

Mass Spectrum (CI, m/z): 662 (M$^+$+1).

$^1$H-NMR Spectrum (CDCl$_3$, δ ppm): −0.05 (s, 9H), 0.00 (s, 9H), 0.25-0.33 (m, 2H), 0.55-0.69 (m, 1H), 0.77-0.89 (m, 7H), 0.95-1.04 (m, 2H), 1.50-1.61 (m, 3H), 2.84-2.93 (m, 2H), 3.38-3.47 (m, 2H), 3.69-3.82 (m, 3H), 5.29 (s, 2H), 5.60 (s, 2H), 6.60 (t, J=74.7 Hz, 1H), 6.98 (dd, J=8.0, 2.0 Hz, 1H), 7.26 (d, J=8.0 Hz, 1H), 7.36 (d, J=2.0 Hz, 1H), 8.17 (s, 1H).

70-(c) 2-(3-Cyclopropoxy-4-difluoromethoxyphenyl)-3-(2-cyclopropylethyl)-5-(2-trimethylsilylethoxymethyl)-1,5-dihydropyrrolo[2,3-d]pyridazin-4-one Reaction and post treatment were carried out in the same manner as in Example 4-(b) except for using 0.44 g (0.66 mmol) of 2-(3-cyclopropoxy-4-difluoromethoxyphenyl)-3-(2-cyclopropylethyl)-1,5-bis(2-trimethylsilylethoxymethyl)-1,5-dihydropyrrolo[2,3-d]pyridazin-4-one obtained in Example 70-(b) in place of 2-(3-cyclopropoxy-4-difluoromethoxyphenyl)-3-methyl-1,5-bis(2-trimethylsilylethoxymethyl)-1,5-dihydropyrrolo[2,3-d]pyridazin-4-one, whereby 0.29 g of the title compound was obtained as a white foam. (Yield: 83%)

Mass Spectrum (CI, m/z): 532 (M$^+$+1).

$^1$H-NMR Spectrum (CDCl$_3$, δ ppm): −0.01 (s, 9H), 0.00-0.06 (m, 2H), 0.30-0.37 (m, 2H), 0.63-0.76 (m, 1H), 0.80-0.91 (m, 4H), 0.94-1.02 (m, 2H), 1.58-1.69 (m, 2H), 3.03-3.12 (m, 2H), 3.68-3.77 (m, 2H), 3.79-3.88 (m, 1H), 5.58 (s, 2H), 6.57 (t, J=74.8 Hz, 1H), 7.07 (dd, J=8.3, 2.0 Hz, 1H), 7.25 (d, J=8.3 Hz, 1H), 7.47 (d, J=2.0 Hz, 1H), 8.06 (s, 1H), 8.64 (brs, 1H).

70-(d) 2-(3-Cyclopropoxy-4-difluoromethoxyphenyl)-3-(2-cyclopropylethyl)-1,5-dihydropyrrolo[2,3-d]pyridazin-4-one Reaction and post treatment were carried out in the same manner as in Example 6-(c) except for using 0.29 g (0.54 mmol) of 2-(3-cyclopropoxy-4-difluoromethoxyphenyl)-3-(2-cyclopropylethyl)-5-(2-trimethylsilylethoxymethyl)-1,5-dihydropyrrolo[2,3-d]pyridazin-4-one obtained in Example 70-(c) in place of 2-(3-cyclopropoxy-4-difluoromethoxyphenyl)-3-propyl-5-(2-trimethylsilylethoxymethyl)-1,5-dihydropyrrolo[2,3-d]pyridazin-4-one, whereby 209 mg of the title compound was obtained as a white solid. (Yield: 96%)

Melting point: 194-197° C.

Mass Spectrum (CI, m/z): 402 (M$^+$+1).

$^1$H-NMR Spectrum (DMSO-d$_6$, δ ppm): −0.05-0.07 (m, 2H), 0.29-0.39 (m, 2H), 0.62-0.91 (m, 5H), 1.49-1.64 (m, 2H), 2.95-3.04 (m, 2H), 3.96-4.04 (m, 1H), 7.10 (t, J=74.3 Hz, 1H), 7.19 (dd, J=8.3, 2.0 Hz, 1H), 7.32 (d, J=8.3 Hz, 1H), 7.59 (d, J=2.0 Hz, 1H), 8.07 (s, 1H), 12.09 (brs, 1H).

IR Spectrum (KBr, cm$^{-1}$): 1643.

Example 71

2-(3-Cyclopropoxy-4-difluoromethoxyphenyl)-3-(2-propynyl)-1,5-dihydropyrrolo[2,3-d]pyridazin-4-one (Exemplary compound No. 1-232)

71-(a) 2-(3-Cyclopropoxy-4-difluoromethoxyphenyl)-3-(1-hydroxy-2-propynyl)-1,5-bis(2-trimethylsilylethoxymethyl)-1,5-dihydropyrrolo[2,3-d]pyridazin-4-one To 25 ml of tetrahydrofuran solution containing 1.01 g (1.62 mmol) of 2-(3-cyclopropoxy-4-difluoromethoxyphenyl)-3-formyl-1,5-bis(2-trimethylsilylethoxymethyl)-1,5-dihydropyrrolo[2,3-d]pyridazin-4-one obtained in the same manner as in Example 15-(a) was added dropwise 3.6 ml of tetrahydrofuran solution containing 0.5M ethynyl magnesium bromide at 60° C., and the mixture was stirred at the same temperature for 30 minutes. After completion of the reaction, the reaction mixture was poured into a saturated ammonium chloride solution, and extracted with toluene. The organic layer after separation was washed successively with water, and then, with a saturated aqueous solution of sodium chloride, dried over anhydrous magnesium sulfate and then concentrated under reduced pressure. The obtained residue was applied to silica gel column chromatography (Eluent; hexane:ethyl acetate=7:3 (V/V)), and the fractions containing the desired compound were concentrated under reduced pressure to obtain 1.11 g of the title compound as a yellowish oil. (Yield: 96%)

Mass Spectrum (CI, m/z): 647 (M$^+$+1).

$^1$H-NMR Spectrum (CDCl$_3$, δ ppm): −0.03 (s, 9H), 0.00 (s, 9H), 0.75-0.94 (m, 6H), 0.95-1.05 (m, 2H), 2.58 (d, J=2.3 Hz, 1H), 3.43-3.57 (m, 2H), 3.71-3.84 (m, 3H), 5.26 (dd, J=11.6, 2.3 Hz, 1H), 5.34 (d, J=11.0 Hz, 1H), 5.38 (d, J=11.0 Hz, 1H), 5.56 (d, J=9.9 Hz, 1H), 5.79 (d, J=9.9 Hz, 1H), 6.61 (t, J=74.5 Hz, 1H), 6.96 (d, J=11.6 Hz, 1H), 7.09 (dd, J=8.3, 2.1 Hz, 1H), 7.29 (d, J=8.3 Hz, 1H), 7.50 (d, J=2.1 Hz, 1H), 8.29 (s, 1H).

71-(b) 2-(3-Cyclopropoxy-4-difluoromethoxyphenyl)-3-(1-hydroxy-2-propynyl)-5-(2-trimethylsilylethoxymethyl)-1,5-dihydropyrrolo[2,3-d]pyridazin-4-one Reaction and post treatment were carried out in the same manner as in Example 4-(b) except for using 0.73 g (1.13 mmol) of 2-(3-cyclopropoxy-4-difluoromethoxyphenyl)-3-(1-hydroxy-2-propynyl)-1,5-bis(2-trimethylsilylethoxymethyl)-1,5-dihydropyrrolo[2,3-d]pyridazin-4-one obtained in Example 71-(a) in place of 2-(3-cyclopropoxy-4-difluoromethoxyphenyl)-3-methyl-1,5-bis(2-trimethylsilylethoxymethyl)-1,5-dihydropyrrolo[2,3-d]pyridazin-4-one, whereby 0.48 g of the title compound was obtained as a beige solid. (Yield: 81%)

Mass Spectrum (CI, m/z): 518 (M$^+$+1).

$^1$H-NMR Spectrum (CDCl$_3$, δ ppm): −0.01 (s, 9H), 0.78-0.94 (m, 4H), 0.94-1.02 (m, 2H), 2.62 (d, J=2.4 Hz, 1H), 3.71-3.78 (m, 2H), 3.80-3.87 (m, 1H), 5.51 (dd, J=11.7, 2.4 Hz, 1H), 5.56 (d, J=9.9 Hz, 1H), 5.74 (d, J=9.9 Hz, 1H), 6.58 (t, J=74.6 Hz, 1H), 7.07 (dd, J=8.3, 2.1 Hz, 1H), 7.26 (d, J=8.3 Hz, 1H), 7.29 (d, J=11.7 Hz, 1H), 7.55 (d, J=2.1 Hz, 1H), 8.19 (s, 1H), 9.13 (brs, 1H).

71-(c) 2-(3-Cyclopropoxy-4-difluoromethoxyphenyl)-3-(2-propynyl)-5-(2-trimethylsilylethoxymethyl)-1,5-dihydropyrrolo[2,3-d]pyridazin-4-one Reaction and post treatment were carried out in the same manner as in Example 15-(c) except for using 0.41 g (0.79 mmol) of 2-(3-cyclopropoxy-4-difluoromethoxyphenyl)-3-(1-hydroxy-2-propynyl)-5-(2-trimethylsilylethoxymethyl)-1,5-dihydropyrrolo[2,3-d]pyridazin-4-one obtained in Example 71-(b) in place of 2-(3-cyclopropoxy-4-difluoromethoxyphenyl)-3-cyclopropylhydroxymethyl-1,5-bis(2-trimethylsilylethoxymethyl)-1,5-dihydropyrrolo[2,3-d]pyridazin-4-one, whereby 0.14 g of the title compound was obtained as a pale yellowish solid. (Yield: 35%)

Mass Spectrum (CI, m/z): 502 (M$^+$+1).

$^1$H-NMR Spectrum (CDCl$_3$, δ ppm): −0.02 (s, 9H), 0.81-0.92 (m, 4H), 0.92-1.00 (m, 2H), 2.05 (t, J=2.7 Hz, 1H), 3.67-3.76 (m, 2H), 3.83-3.91 (m, 1H), 3.95 (d, J=2.7 Hz, 2H), 5.58 (s, 2H), 6.57 (t, J=74.8 Hz, 1H), 7.16 (dd, J=8.3, 2.0 Hz, 1H), 7.25 (d, J=8.3 Hz, 1H), 7.76 (d, J=2.0 Hz, 1H), 8.10 (s, 1H), 9.14 (brs, 1H).

71-(d) 2-(3-Cyclopropoxy-4-difluoromethoxyphenyl)-3-(2-propynyl)-1,5-dihydropyrrolo[2,3-d]pyridazin-4-one Reaction and post treatment were carried out in the same manner as in Example 6-(c) except for using 151 mg (0.30 mmol) of 2-(3-cyclopropoxy-4-difluoromethoxyphenyl)-3-(2-propynyl)-5-(2-trimethylsilylethoxymethyl)-1,5-dihydropyrrolo[2,3-d]pyridazin-4-one obtained in Example 71-(c) in place of 2-(3-cyclopropoxy-4-difluoromethoxyphenyl)-3-propyl-5-(2-trimethylsilylethoxymethyl)-1,5-dihydropyrrolo[2,3-d]pyridazin-4-one, whereby 56 mg of the title compound was obtained as a pale brownish solid. (Yield: 50%)

Melting point: 245-246° C.

Mass Spectrum (CI, m/z): 372 (M$^+$+1).

$^1$H-NMR Spectrum (DMSO-d$_6$, δ ppm): 0.74-0.83 (m, 2H), 0.84-0.93 (m, 2H), 2.92 (t, J=2.5 Hz, 1H), 3.93 (d, J=2.5 Hz, 2H), 3.93-4.02 (m, 1H), 7.11 (t, J=74.3 Hz, 1H), 7.32 (dd, J=8.5, 1.6 Hz, 1H), 7.35 (d, J=8.5 Hz, 1H), 7.84 (d, J=1.6 Hz, 1H), 8.13 (s, 1H), 12.25 (brs, 1H).

IR Spectrum (KBr, cm$^{-1}$): 1634.

Example 72

3-(2-Butynyl)-2-(3-cyclopropoxy-4-difluoromethoxyphenyl)-1,5-dihydropyrrolo[2,3-d]pyridazin-4-one (Exemplary compound No. 1-233)

72-(a) 2-(3-Cyclopropoxy-4-difluoromethoxyphenyl)-3-(1-hydroxy-2-butynyl)-1,5-bis(2-trimethylsilylethoxymethyl)-1,5-dihydropyrrolo[2,3-d]pyridazin-4-one Reaction and post treatment were carried out in the same manner as in Example 71-(a) except for using 1.01 g (1.62 mmol) of 2-(3-cyclopropoxy-4-difluoromethoxyphenyl)-3-formyl-1,5-bis(2-trimethylsilylethoxymethyl)-1,5-dihydropyrrolo[2,3-d]pyridazin-4-one obtained in the same manner as in Example 15-(a), and using 3.6 ml of tetrahydrofuran solution containing 0.5M propynyl magnesium bromide in place of tetrahydrofuran solution containing ethynyl magnesium bromide, whereby 1.07 g of the title compound was obtained as a pale brownish foam substantially quantitatively.

Mass Spectrum (CI, m/z): 662 (M$^+$+1).

$^1$H-NMR Spectrum (CDCl$_3$, δ ppm): −0.03 (s, 9H), 0.00 (s, 9H), 0.76-0.95 (m, 6H), 0.96-1.05 (m, 2H), 1.80 (d, J=2.2 Hz, 3H), 3.42-3.57 (m, 2H), 3.71-3.85 (m, 3H), 5.24 (dq, J=11.5, 2.2 Hz, 1H), 5.36 (s, 2H), 5.59 (d, J=9.8 Hz, 1H), 5.75 (d, J=9.8 Hz, 1H), 6.60 (t, J=74.6 Hz, 1H), 6.85 (d, J=11.5 Hz, 1H), 7.10 (dd, J=8.2, 2.0 Hz, 1H), 7.29 (d, J=8.2 Hz, 1H), 7.52 (d, J=2.0 Hz, 1H), 8.28 (s, 1H).

72-(b) 2-(3-Cyclopropoxy-4-difluoromethoxyphenyl)-3-(2-butynyl)-1,5-bis(2-trimethylsilylethoxymethyl)-1,5-dihydropyrrolo[2,3-d]pyridazin-4-one Reaction and post treatment were carried out in the same manner as in Example 15-(c) except for using 1.57 g (2.37 mmol) of 2-(3-cyclopropoxy-4-difluoromethoxyphenyl)-3-(1-hydroxy-2-butynyl)-1,5-bis(2-trimethylsilylethoxymethyl)-1,5-dihydropyrrolo[2,3-d]pyridazin-4-one obtained in the same manner as in Example 71-(b) in place of 2-(3-cyclopropoxy-4-difluoromethoxyphenyl)-3-cyclopropylhydroxymethyl-1,5-bis(2-trimethylsilylethoxymethyl)-1,5-dihydropyrrolo[2,3-d]pyridazin-4-one, whereby 1.04 g of the title compound was obtained as a yellowish oil. (Yield: 68%)

Mass Spectrum (CI, m/z): 646 (M$^+$+1).

$^1$H-NMR Spectrum (CDCl$_3$, δ ppm): −0.03 (s, 9H), 0.00 (s, 9H), 0.77-0.92 (m, 6H), 0.95-1.05 (m, 2H), 1.68 (t, J=2.4 Hz, 3H), 3.45-3.54 (m, 2H), 3.70-3.79 (m, 4H), 3.80-3.88 (m, 1H), 5.33 (s, 2H), 5.61 (s, 2H), 6.60 (t, J=74.7 Hz, 1H), 7.13 (dd, J=8.3, 2.0 Hz, 1H), 7.28 (d, J=8.3 Hz, 1H), 7.61 (d, J=2.0 Hz, 1H), 8.18 (s, 1H).

72-(c) 3-(2-Butynyl)-2-(3-cyclopropoxy-4-difluoromethoxyphenyl)-1,5-dihydropyrrolo[2,3-d]pyridazin-4-one (Exemplary compound No. 1-233)

Reaction and post treatment were carried out in the same manner as in Example 6-(c) except for using 1.02 g (1.58 mmol) of 2-(3-cyclopropoxy-4-difluoromethoxyphenyl)-3-(2-butynyl)-1,5-bis(2-trimethylsilylethoxymethyl)-1,5-dihydropyrrolo[2,3-d]pyridazin-4-one obtained in Example 72-(b) in place of 2-(3-cyclopropoxy-4-difluoromethoxyphenyl)-3-propyl-5-(2-trimethylsilylethoxymethyl)-1,5-dihydropyrrolo[2,3-d]pyridazin-4-one, whereby 205 mg of the title compound was obtained as a pale yellowish solid. (Yield: 34%)

Melting point: 231-236° C.

Mass Spectrum (CI, m/z): 386 (M$^+$+1).

$^1$H-NMR Spectrum (DMSO-d$_6$, δ ppm): 0.74-0.92 (m, 4H), 1.69 (t, J=2.4 Hz, 3H), 3.86 (q, J=2.4 Hz, 2H), 3.95-4.02 (m, 1H), 7.11 (t, J=74.3 Hz, 1H), 7.30-7.37 (m, 2H), 7.84-7.87 (m, 1H), 8.11 (s, 1H), 12.22 (brs, 1H)

IR Spectrum (KBr, cm$^{-1}$): 1642.

Example 73

2-(3-cyclopropoxy-4-difluoromethoxyphenyl)-3-(4-methyl-2-pentynyl)-1,5-dihydropyrrolo[2,3-d]pyridazin-4-one (Exemplary compound No. 1-236)

73-(a) 2-(3-Cyclopropoxy-4-difluoromethoxyphenyl)-3-(1-hydroxy-4-methyl-2-pentynyl)-1,5-bis(2-trimethylsilylethoxymethyl)-1,5-dihydropyrrolo[2,3-d]pyridazin-4-one Reaction and post treatment were carried out in the same manner as in Example 71-(a) except for using 1.74 g (2.80 mmol) of 2-(3-cyclopropoxy-4-difluoromethoxyphenyl)-3-formyl-1,5-bis(2-trimethylsilylethoxymethyl)-1,5-dihydropyrrolo[2,3-d]pyridazin-4-one obtained in the same manner as in Example 15-(a), and using 6 ml of toluene solution containing 27w % 27 wt % 3-methyl-1-butynyl magnesium bromide prepared from ethyl magnesium bromide and 3-methyl-1-butyne in place of tetrahydrofuran solution containing ethynyl magnesium bromide, whereby 1.30 g of the title compound was obtained as a white foam. (Yield: 67%)

Mass Spectrum (CI, m/z): 690 ($M^+$+1).

$^1$H-NMR Spectrum (CDCl$_3$, δ ppm): −0.03 (s, 9H), 0.00 (s, 9H), 0.76-0.93 (m, 6H), 0.96-1.04 (m, 2H), 1.08 (d, J=6.8 Hz, 3H), 1.11 (d, J=6.8 Hz, 3H), 2.47-2.59 (m, 1H), 3.41-3.56 (m, 2H), 3.70-3.87 (m, 3H), 5.26 (dd, J=11.5, 2.0 Hz, 1H), 5.36 (s, 2H), 5.62 (d, J=9.9 Hz, 1H), 5.71 (d, J=9.9 Hz, 1H), 6.60 (t, J=74.5 Hz, 1H), 6.82 (d, J=11.5 Hz, 1H), 7.10 (dd, J=8.3, 2.0 Hz, 1H), 7.28 (d, J=8.3 Hz, 1H), 7.49 (d, J=2.0 Hz, 1H), 8.28 (s, 1H).

73-(b) 2-(3-Cyclopropoxy-4-difluoromethoxyphenyl)-3-(4-methyl-2-pentynyl)-1,5-bis(2-trimethylsilylethoxymethyl)-1,5-dihydropyrrolo[2,3-d]pyridazin-4-one Reaction and post treatment were carried out in the same manner as in Example 15-(c) except for using 1.72 g (2.49 mmol) of 2-(3-cyclopropoxy-4-difluoromethoxyphenyl)-3-(1-hydroxy-4-methyl-2-pentynyl)-1,5-bis(2-trimethylsilylethoxymethyl)-1,5-dihydropyrrolo[2,3-d]pyridazin-4-one obtained in the same manner as in Example 73-(a) in place of 2-(3-cyclopropoxy-4-difluoromethoxyphenyl)-3-cyclopropylhydroxymethyl-1,5-bis(2-trimethylsilylethoxymethyl)-1,5-dihydropyrrolo[2,3-d]pyridazin-4-one, whereby 1.43 g of the title compound was obtained as a slightly yellowish oil. (Yield: 85%)

Mass Spectrum (CI, m/z): 674 ($M^+$+1).

$^1$H-NMR Spectrum (CDCl$_3$, δ ppm): −0.03 (s, 9H), 0.00 (s, 9H) 0.81-0.90 (m, 6H), 0.95-1.04 (m, 2H), 0.99 (d, J=6.8 Hz, 6H), 2.31-2.43 (m, 1H), 3.43-3.52 (m, 2H), 3.70-3.78 (m, 2H), 3.81-3.88 (m, 1H), 3.84 (d, J=2.2 Hz, 2H), 5.34 (s, 2H), 5.60 (s, 2H), 6.60 (t, J=74.8 Hz, 1H), 7.15 (dd, J=8.2, 1.9 Hz, 1H), 7.27 (d, J=8.2 Hz, 1H), 7.53 (d, J=1.9 Hz, 1H), 8.18 (s, 1H).

73-(c) 2-(3-Cyclopropoxy-4-difluoromethoxyphenyl)-3-(4-methyl-2-pentynyl)-5-(2-trimethylsilylethoxymethyl)-1,5-dihydropyrrolo[2,3-d]pyridazin-4-one Reaction and post treatment were carried out in the same manner as in Example 4-(b) except for using 1.43 g (2.12 mmol) of 2-(3-cyclopropoxy-4-difluoromethoxyphenyl)-3-(4-methyl-2-pentynyl)-1,5-bis(2-trimethylsilylethoxymethyl)-1,5-dihydropyrrolo[2,3-d]pyridazin-4-one obtained in Example 73-(b) in place of 2-(3-cyclopropoxy-4-difluoromethoxyphenyl)-3-methyl-1,5-bis(2-trimethylsilylethoxymethyl)-1,5-dihydropyrrolo[2,3-d]pyridazin-4-one, whereby 0.99 g of the title compound was obtained as a pale beige foam. (Yield: 86%)

Mass Spectrum (CI, m/z): 544 ($M^+$+1).

$^1$H-NMR Spectrum (CDCl$_3$, δ ppm): −0.02 (s, 9H), 0.83-0.92 (m, 4H), 0.92-1.01 (m, 2H), 0.98 (d, J=6.8 Hz, 6H), 2.31-2.46 (m, 1H), 3.68-3.76 (m, 2H), 3.86-3.94 (m, 1H), 3.99 (d, J=2.2 Hz, 2H), 5.57 (s, 2H), 6.56 (t, J=74.8 Hz, 1H), 7.20 (dd, J=8.4, 1.9 Hz, 1H), 7.24 (d, J=8.4 Hz, 1H), 7.73 (d, J=1.9 Hz, 1H), 8.09 (s, 1H), 9.05 (brs, 1H).

73-(d) 2-(3-Cyclopropoxy-4-difluoromethoxyphenyl)-3-(4-methyl-2-pentynyl)-1,5-dihydropyrrolo[2,3-d]pyridazin-4-one Reaction and post treatment were carried out in the same manner as in Example 6-(c) except for using 0.99 g (1.82 mmol) of 2-(3-cyclopropoxy-4-difluoromethoxyphenyl)-3-(4-methyl-2-pentynyl)-5-(2-trimethylsilylethoxymethyl)-1,5-dihydropyrrolo[2,3-d]pyridazin-4-one obtained in Example 73-(c) in place of 2-(3-cyclopropoxy-4-difluoromethoxyphenyl)-3-propyl-5-(2-trimethylsilylethoxymethyl)-1,5-dihydropyrrolo[2,3-d]pyridazin-4-one, whereby 544 mg of the title compound was obtained as a white solid. (Yield: 72%)

Melting point: 139-143° C.

Mass Spectrum (CI, m/z): 414 ($M^+$+1).

$^1$H-NMR Spectrum (DMSO-d$_6$, δ ppm): 0.73-0.84 (m, 2H), 0.85-0.98 (m, 2H), 0.94 (d, J=6.8 Hz, 6H), 2.35-2.47 (m, 1H), 3.93-4.02 (m, 1H), 3.95 (d, J=2.0 Hz, 2H), 7.10 (t, J=74.3 Hz, 1H), 7.33 (d, J=8.3 Hz, 1H), 7.37 (dd, J=8.3, 1.9 Hz, 1H), 7.77 (d, J=1.9 Hz, 1H), 8.12 (s, 1H), 12.22 (brs, 1H).

IR Spectrum (KBr, cm$^{-1}$): 1641.

Example 74

2-(3-Cyclopropoxy-4-difluoromethoxyphenyl)-3-(2-propenyl)-1,5-dihydropyrrolo[2,3-d]pyridazin-4-one (Exemplary compound No. 1-220)

To 5 ml of mixed solvent (ethyl acetate:tetrahydrofuran=4:1 (V/V)) solution containing 63.2 mg (0.17 mmol) of 2-(3-cyclopropoxy-4-difluoromethoxyphenyl)-3-(2-propynyl)-1,5-dihydropyrrolo[2,3-d]pyridazin-4-one obtained in Example 73-(c) was added 32.2 mg of 5% Lindlar catalyst, and the mixture was stirred under 1 atm hydrogen atmosphere at room temperature for 2 hours. After completion of the reaction, the insoluble material was removed from the reaction mixture by filtration, and the filtrate was concentrated under reduced pressure. The residue was purified by high performance liquid chromatography (column; Sunfire Prep C18 OBD™ (19 mm×250 mm (manufactured by Waters Co.), Eluent; acetonitrile:water:trifluoroacetic acid=600:400:1 (V/V/V), Flow rate; 10 ml/min) to obtain 17.6 mg of the title compound as a white solid. (Yield: 28%)

Melting point: 176-179° C.

Mass Spectrum (CI, m/z): 374 ($M^+$+1).

$^1$H-NMR Spectrum (DMSO-d$_6$, δ ppm): 0.71-0.88 (m, 4H), 3.72 (d, J=5.4 Hz, 2H), 3.91-3.98 (m, 1H), 4.92 (dd, J=17.1, 2.0 Hz, 1H), 5.01 (dd, J=10.0, 2.0 Hz, 1H), 6.13 (ddt, J=17.1, 10.3, 5.5 Hz, 1H), 7.08 (t, J=74.3 Hz, 1H), 7.21 (dd, J=8.5, 2.2 Hz, 1H), 7.31 (d, J=8.5 Hz, 1H), 7.61 (d, J=2.2 Hz, 1H), 8.10 (s, 1H), 12.13 (brs, 1H)

IR Spectrum (KBr, cm$^{-1}$): 1633. .

Example 75

2-(3-Cyclopropoxy-4-difluoromethoxyphenyl)-3-(1-hydroxy-2-propenyl)-1,5-dihydropyrrolo[2,3-d]pyridazin-4-one (Exemplary compound No. 1-237)

75-(a) 2-(3-Cyclopropoxy-4-difluoromethoxyphenyl)-3-(1-hydroxy-2-propenyl)-1,5-bis(2-trimethylsilylethoxymethyl)-1,5-dihydropyrrolo[2,3-d]pyridazin-4-one Reaction and post treatment were carried out in the same manner as in Example 71-(a) except for using 1.02 g (1.64 mmol) of 2-(3-cyclopropoxy-4-difluoromethoxyphenyl)-3-formyl-1,5-bis(2-trimethylsilylethoxymethyl)-1,5-dihydropyrrolo[2,3-d]pyridazin-4-one obtained in the same manner as in Example 15-(a), and using 4 ml of tetrahydrofuran solution containing 1M ethynyl magnesium bromide in place of tetrahydrofuran solution containing ethynyl magnesium bromide, whereby 1.01 g of the title compound was obtained as a yellowish oil substantially quantitatively.

Mass Spectrum (EI, m/z): 649 ($M^+$).

$^1$H-NMR Spectrum (CDCl$_3$, δ ppm): −0.04 (s, 9H), 0.00 (s, 9H) 0.76-0.89 (m, 6H), 0.95-1.04 (m, 2H), 3.41-3.49 (m, 2H), 3.69-3.79 (m, 3H), 5.00-5.08 (m, 1H), 5.01 (dt, J=17.3, 1.5 Hz, 1H), 5.09 (dt, J=10.3, 1.5 Hz, 1H), 5.34 (s, 2H), 5.57 (d, J=9.8 Hz, 1H), 5.71 (d, J=9.8 Hz, 1H), 6.24 (ddd, J=17.3, 10.3, 5.1 Hz, 1H), 6.31 (d, J=11.7 Hz, 1H), 6.60 (t, J=74.6 Hz, 1H), 6.99 (dd, J=8.2, 1.9 Hz, 1H), 7.26 (d, J=8.2 Hz, 1H), 7.38 (d, J=1.9 Hz, 1H), 8.28 (s, 1H)

75-(b) 2-(3-Cyclopropoxy-4-difluoromethoxyphenyl)-3-(1-hydroxy-2-propenyl)-5-(2-trimethylsilylethoxymethyl)-1,5-dihydropyrrolo[2,3-d]pyridazin-4-one Reaction and post treatment were carried out in the same manner as in Example 4-(b) except for using 0.31 g (0.48 mmol) of 2-(3-cyclopropoxy-4-difluoromethoxyphenyl)-3-(1-hydroxy-2-propenyl)-1,5-bis(2-trimethylsilylethoxymethyl)-1,5-dihydropyrrolo[2,3-d]pyridazin-4-one obtained in Example 75-(a) in place of 2-(3-cyclopropoxy-4-difluoromethoxyphenyl)-3-methyl-1,5-bis(2-trimethylsilylethoxymethyl)-1,5-dihydropyrrolo[2,3-d]pyridazin-4-one, whereby 0.20 g of the title compound was obtained as a pale yellowish solid. (Yield: 81%)

$^1$H-NMR Spectrum (CDCl$_3$, δ ppm): −0.02 (s, 9H), 0.74-0.89 (m, 4H), 0.92-1.01 (m, 2H), 3.68-3.79 (m, 3H), 5.06 (dt, J=17.2, 1.4 Hz, 1H), 5.16 (dt, J=10.3, 1.4 Hz, 1H), 5.32 (ddt, J=11.5, 5.1, 1.4 Hz, 1H), 5.57 (d, J=9.8 Hz, 1H), 5.67 (d, J=9.8 Hz, 1H), 6.33 (ddd, J=17.2, 10.3, 5.1 Hz, 1H), 6.56 (t, J=74.6 Hz, 1H), 6.65 (d, J=11.5 Hz, 1H), 6.99 (dd, J=8.3, 2.0 Hz, 1H), 7.20 (d, J=8.3 Hz, 1H), 7.39 (d, J=2.0 Hz, 1H), 8.15 (s, 1H), 9.33 (brs, 1H)

75-(c) 2-(3-Cyclopropoxy-4-difluoromethoxyphenyl)-3-(1-hydroxy-2-propenyl)-1,5-bis(2-trimethylsilylethoxymethyl)-1,5-dihydropyrrolo[2,3-d]pyridazin-4-one Reaction and post treatment were carried out in the same manner as in Example 13-(c) except for using 0.18 g (0.35 mmol) of 2-(3-cyclopropoxy-4-difluoromethoxyphenyl)-3-(1-hydroxy-2-propenyl)-5-(2-trimethylsilylethoxymethyl)-1,5-dihydropyrrolo[2,3-d]pyridazin-4-one obtained in Example 75-(b) in place of 3-cyclobutoxymethyl-2-(3-cyclopropoxy-4-difluoromethoxyphenyl)-5-(2-trimethylsilylethoxymethyl)-1,5-dihydropyrrolo[2,3-d]pyridazin-4-one, whereby 68 mg of the title compound was obtained as a white solid. (Yield: 50%)

Melting point: 202-203° C.

Mass Spectrum (CI, m/z): 390 ($M^+$+1).

$^1$H-NMR Spectrum (DMSO-d$_6$, δ ppm): 0.67-0.90 (m, 4H), 3.92-4.00 (m, 1H), 5.01 (dt, J=17.1, 1.5 Hz, 1H), 5.07 (dt, J=10.3, 1.5 Hz, 1H), 5.24-5.32 (m, 1H), 6.23 (ddd, J=17.1, 10.3, 5.1 Hz, 1H), 6.58 (dd, J=10.7, 2.9 Hz, 1H), 7.11 (t, J=74.2 Hz, 1H), 7.18 (dd, J=8.3, 2.0 Hz, 1H), 7.34 (d, J=8.3 Hz, 1H), 7.57 (d, J=2.0 Hz, 1H), 8.26 (s, 1H), 12.73 (brs, 1H).

IR Spectrum (KBr, cm$^{-1}$): 1617.

The substituted catechol boronic acid derivative used in Examples was synthesized as follows.

Reference Example 1-(a)

2-(3-Cyclopropoxy-4-difluoromethoxyphenyl)-4,4,5,5-tetramethyl-[1,3,2]dioxaborolane 2 L of dehydrated 1,4-dioxane solution containing 128 g (457 mmol) of 4-bromo-2-cyclopropoxy-1-difluoromethoxybenzene was degassed by blowing argon into the mixture to make argon atmosphere. Then, to the solution were added 174 g (685 mmol) of bis(pinacolato)diboron, 37.3 g (45.7 mmol) of 1,1'-bis(diphenylphosphino)ferrocene palladium chloride dichloromethane complex and 135 g (1.38 mol) of potassium acetate, and the mixture was stirred at 80° C. for 12 hours. After completion of the reaction, to the reaction mixture were added 1 L of ethyl acetate and 1.2 L of a saturated aqueous solution of ammonium chloride, then, the insoluble material was removed by filtration using 70 g of Celite (trade name), and the resulting solid was washed with 1.5 L of ethyl acetate. The organic layer after separation was washed successively with water, and then, with a saturated aqueous solution of sodium chloride, dried over anhydrous magnesium sulfate and then concentrated under reduced pressure. To the obtained solid were added 1.2 L of cyclohexane and 22 g of activated carbon, the mixture was stirred at 50° C., then cooled to room temperature, and the insoluble material was removed by filtration. The obtained filtrate and the washing solution obtained by washing the filtered material with cyclohexane were combined and the solution was concentrated under reduced pressure. The obtained residue was applied to silica gel column chromatography (Eluent; hexane:ethyl acetate=50:1→9:1 (V/V)), and the fractions containing the desired compound were concentrated under reduced pressure to obtain 150 g of the title compound as a white solid substantially quantitatively.

Mass Spectrum (CI, m/z): 327 ($M^+$+1).

$^1$H-NMR Spectrum (CDCl$_3$, δ ppm): 0.80-0.85 (m, 4H), 1.35 (s, 12H), 3.84-3.91 (m, 1H), 6.53 (t, J=75.1 Hz, 1H), 7.12 (d, J=8.0 Hz, 1H), 7.41 (dd, J=8.0, 1.4 Hz, 1H), 7.69 (d, J=1.4 Hz, 1H).

In the following, the following substituted catechol boronic acids were synthesized in the same manner by using various bromo-substituted catechols.

Reference Example 1-(b)

2-(3-Cyclobutoxy-4-difluoromethoxyphenyl)-4,4,5,5-tetramethyl-[1,3,2]dioxaborolane Characteristics: pale yellowish oil (Yield: 73%).
$^1$H-NMR Spectrum (CDCl$_3$, δ ppm): 1.33 (s, 12H), 1.60-1.77 (m, 1H), 1.80-1.94 (m, 1H), 2.12-2.29 (m, 2H), 2.42-2.56 (m, 2H), 4.67-4.83 (m, 1H), 6.61 (t, J=75.4 Hz, 1H), 7.13 (d, J=8.0 Hz, 1H), 7.23 (d, J=1.3 Hz, 1H), 7.37 (dd, J=8.0, 1.3 Hz, 1H).

Reference Example 1-(c)

2-(3-Cyclopropylmethoxy-4-difluoromethoxyphenyl)-4,4,5,5-tetramethyl-[1,3,2]dioxaborolane Characteristics: pale yellowish oil (Yield: 73%).
$^1$H-NMR Spectrum (CDCl$_3$, δ ppm): 0.31-0.38 (m, 2H), 0.60-0.67 (m, 2H), 1.23-1.32 (m, 1H), 1.34 (s, 12H), 3.91 (d, J=7.1 Hz, 2H), 6.67 (t, J=75.7 Hz, 1H), 7.14 (d, J=7.9 Hz, 1H), 7.35 (d, J=1.3 Hz, 1H), 7.39 (dd, J=7.9, 1.3 Hz, 1H).

Reference Example 1-(d)

2-(4-Difluoromethoxy-3-isopropoxyphenyl)-4,4,5,5-tetramethyl-[1,3,2]dioxaborolane Characteristics: yellowish brown oil (Yield: 71%).
Mass Spectrum (CI, m/z): 329 (M$^+$+1).
$^1$H-NMR Spectrum (CDCl$_3$, δ ppm): 1.34 (s, 12H), 1.36 (d, J=6.1 Hz, 6H), 4.57-4.71 (m, 1H), 6.60 (t, J=75.6 Hz, 1H), 7.14 (dd, J=7.4, 0.6 Hz, 1H), 7.36-7.41 (m, 2H).

Reference Example 1-(e)

2-(3-Cyclopropoxy-4-methoxyphenyl)-4,4,5,5-tetramethyl-[1,3,2]dioxaborolane

Characteristics: white solid (Yield: 62%).
Mass Spectrum (CI, m/z): 291 (M$^+$+1).
$^1$H-NMR Spectrum (CDCl$_3$, δ ppm): 0.79-0.87 (m, 4H), 1.34 (s, 12H), 3.80-3.91 (m, 1H), 3.87 (s, 3H), 6.87 (d, J=8.0 Hz, 1H), 7.44 (dd, J=8.0, 1.6 Hz, 1H), 7.62 (d, J=1.6 Hz, 1H).

Reference Example 1-(f)

2-(3-Cyclobutoxy-4-methoxyphenyl)-4,4,5,5-tetramethyl-[1,3,2]dioxaborolane

Characteristics: colorless oil (Yield: 81%).
$^1$H-NMR Spectrum (CDCl$_3$, δ ppm): 1.33 (s, 12H), 1.59-1.76 (m, 1H), 1.78-1.91 (m, 1H), 2.19-2.32 (m, 2H), 2.44-2.57 (m, 2H), 3.89 (s, 3H), 4.69-4.81 (m, 1H), 6.87 (d, J=7.9 Hz, 1H), 7.15 (d, J=1.4 Hz, 1H), 7.40 (dd, J=7.9, 1.4 Hz, 1H).

Reference Example 1-(g)

2-(3-Isopropoxy-4-methoxyphenyl)-4,4,5,5-tetramethyl-[1,3,2]dioxaborolane

Characteristics: white solid (Yield: 76%).
Mass Spectrum (EI, m/z): 292 (M$^+$).
$^1$H-NMR Spectrum (CDCl$_3$, δ ppm): 1.33 (s, 12H), 1.36 (d, J=6.1 Hz, 6H), 3.87 (s, 3H), 4.53-4.67 (m, 1H), 6.88 (d, J=8.1 Hz, 1H), 7.33 (d, J=1.5 Hz, 1H), 7.41 (dd, J=8.1, 1.5 Hz, 1H).

Reference Example 1-(h)

2-(2,3-Dihydro-7-methoxybenzofuran-2-spiro-1'-cyclopentan-4-yl)-4,4,5,5-tetramethyl-[1,3,2]dioxaborolane Characteristics: white solid (Yield: 69%).
Mass Spectrum (EI, m/z): 330 (M$^+$).
$^1$H-NMR Spectrum (CDCl$_3$, δ ppm): 1.32 (s, 12H), 1.69-1.82 (m, 4H), 1.86-1.99 (m, 2H), 2.08-2.21 (m, 2H), 3.35 (s, 2H), 3.87 (s, 3H), 6.73 (d, J=8.3 Hz, 1H), 7.26 (d, J=8.3 Hz, 1H).

Reference Example 1-(i)

2-(8-Difluoromethoxy-2,2-dimethyl-2H-chromen-5-yl)-4,4,5,5-tetramethyl-[1,3,2]dioxaborolane Characteristics: yellowish oil (Yield: 90%).
Mass Spectrum (CI, m/z): 353 (M$^+$+1).
$^1$H-NMR Spectrum (CDCl$_3$, δ ppm): 1.34 (s, 12H), 1.45 (s, 6H), 5.69 (d, J=10.2 Hz, 1H), 6.61 (t, J=75.6 Hz, 1H), 6.97 (d, J=8.1 Hz, 1H), 7.17 (d, J=10.2 Hz, 1H), 7.31 (d, J=8.1 Hz, 1H).

Reference Example 1-(j)

2-(8-difluoromethoxy-2H-chromen-2-spiro-1'-cyclobutan-5-yl)-4,4,5,5-tetramethyl-[1,3,2]dioxaborolane Characteristics: slightly yellowish oil (Yield: 77%).
Mass Spectrum (CI, m/z): 365 (M$^+$+1).
$^1$H-NMR Spectrum (CDCl$_3$, δ ppm): 1.33 (s, 12H), 1.60-1.77 (m, 1H), 1.80-1.96 (m, 1H), 2.18-2.29 (m, 2H), 2.42-2.55 (m, 2H), 6.05 (d, J=10.2 Hz, 1H), 6.64 (t, J=75.4 Hz, 1H), 6.96 (d, J=8.2 Hz, 1H), 7.19 (d, J=10.2 Hz, 1H), 7.31 (d, J=8.2 Hz, 1H).

Reference Example 1-(k)

2-(8-Difluoromethoxy-2H-chromen-2-spiro-1'-cyclopentan-5-yl)-4,4,5,5-tetramethyl-[1,3,2]dioxaborolane Characteristics: pale yellowish oil (Yield: 80%).
Mass Spectrum (EI, m/z): 378(M$^+$).
$^1$H-NMR Spectrum (CDCl$_3$, δ ppm): 1.34 (s, 12H), 1.52-1.79 (m, 4H), 1.85-2.01 (m, 2H), 2.09-2.23 (m, 2H), 5.73 (d, J=10.2 Hz, 1H), 6.57 (t, J=75.4 Hz, 1H), 6.96 (d, J=8.2 Hz, 1H), 7.20 (d, J=10.2 Hz, 1H), 7.30 (d, J=8.2 Hz, 1H).

Reference Example 1-(l)

2-(2-cyclopropyl-8-difluoromethoxy-2H-chromen-5-yl)-4,4,5,5-tetramethyl-[1,3,2]dioxaborolane Characteristics: pale yellowish solid (Yield: 56%).
Mass Spectrum (EI, m/z): 364 (M$^+$).
$^1$H-NMR Spectrum (CDCl$_3$, δ ppm): 0.31-0.39 (m, 1H), 0.45-0.53 (m, 1H), 0.53-0.64 (m, 2H), 1.20-1.37 (m, 1H), 1.34 (s, 12H), 4.24 (ddd, J=8.1, 3.6, 1.7 Hz, 1H), 5.84 (dd, J=10.2, 3.5 Hz, 1H), 6.68 (dd, J=76.4, 74.7 Hz, 1H), 6.98 (d, J=8.2 Hz, 1H), 7.27 (dd, J=10.2, 1.7 Hz, 1H), 7.32 (d, J=8.2 Hz, 1H).

Reference Example 2-(a)

2-(3-Cyclopropylmethoxy-4-methoxyphenyl)-4,4,5,5-tetramethyl-[1,3,2]dioxaborolane To 60 ml of dehydrated tetrahydrofuran solution containing 3.64 g (14.2 mmol) of 4-bromo-2-cyclopropylmethoxy-1-methoxybenzene was added dropwise 18.0 ml of tetrahydrofuran solution containing 0.97M sec-butyl lithium at −70° C. under argon atmosphere, and the mixture was stirred at the same temperature for 50 minutes. Then, 3.70 ml (19.2 mmol) of 2-isopropoxy-4,4,5,5-tetramethyl-[1,3,2]-dioxaborolane was added to the mixture, and the resulting mixture was raised to room temperature. After completion of the reaction, a saturated aqueous solution of ammonium chloride was added to the reaction mixture, and after adjusting a pH thereof to 2 with 1N hydrochloric acid, the mixture was extracted with ethyl acetate. The organic layer after separation was washed with a saturated aqueous solution of sodium chloride, dried over anhydrous magnesium sulfate, and then, concentrated under reduced pressure to obtain 4.78 g (purity: 84.7%) of the title compound as a slightly yellowish oil. (Yield: 94%)

Mass Spectrum (EI, m/z): 304 (M$^+$).
$^1$H-NMR Spectrum (CDCl$_3$, δ ppm): 0.30-0.42 (m, 2H), 0.58-0.67 (m, 2H), 1.22-1.44 (m, 1H), 1.33 (s, 12H), 3.89 (d, J=7.1 Hz, 2H), 3.89 (s, 3H), 6.88 (d, J=8.1 Hz, 1H), 7.27 (d, J=1.5 Hz, 1H), 7.41 (dd, J=8.1, 1.5 Hz, 1H).

Reference Example 2-(b)

2-(3-Cyclopentoxy-4-methoxyphenyl)-4,4,5,5-tetramethyl-[1,3,2]dioxaborolane

Reaction and post treatment were carried out in the same manner as in Reference Example 2-(a) except for using 2.66 g (9.81 mmol) of 4-bromo-2-cyclopentoxy-1-methoxybenzene in place of 4-bromo-2-cyclopropylmethoxy-1-methoxybenzene, whereby 3.35 g (purity: 85%) of the title compound was obtained as a pale yellowish oil. (Yield: 91%)

Mass Spectrum (EI, m/z): 318 (M$^+$).
$^1$H-NMR Spectrum (CDCl$_3$, δ ppm): 1.33 (s, 12H), 1.54-1.65 (m, 2H), 1.80-1.98 (m, 6H), 3.86 (s, 3H), 4.82-4.88 (m, 1H), 6.87 (d, J=8.1 Hz, 1H), 7.30 (d, J=1.5 Hz, 1H), 7.39 (dd, J=8.1, 1.5 Hz, 1H).

Reference Example 3

3-Cyclopropylmethoxy-4-difluoromethoxyphenylboronic acid

3-(a) 2-(3-cyclopropylmethoxy-4-difluoromethoxyphenyl)-[1,3,6,2]dioxoazaborocane To 90 ml of isopropanol solution containing 32.0 g (purity: 53.5%, 50.3 mmol) of 2-(3-cyclopropylmethoxy-4-difluoromethoxyphenyl)-4,4,5,5-tetramethyl-[1,3,2]dioxaborolane obtained in Reference Example 1-(c) was added 32.8 g of diethanolamine, and the mixture was stirred at room temperature for 63 hours. After completion of the reaction, 150 ml of hexane was added to the reaction mixture, and the precipitated solid was collected by filtration.

The obtained solid was washed with hexane and then with isopropanol, and dried under reduced pressure to obtain 14.2 g of the title compound as a white solid. (Yield: 86%)

Mass Spectrum (CI, m/z): 328 (M$^+$+1).
$^1$H-NMR Spectrum (CDCl$_3$, δ ppm): 0.29-0.36 (m, 2H), 0.57-0.65 (m, 2H), 1.19-1.35 (m, 1H), 2.76-2.93 (m, 2H), 3.17-3.36 (m, 2H), 3.88 (d, J=6.8 Hz, 2H), 3.92-4.16 (m, 4H), 4.38-4.50 (m, 1H), 6.61 (t, J=76.2 Hz, 1H), 7.06 (d, J=7.9 Hz, 1H), 7.10 (dd, J=7.9, 1.0 Hz, 1H), 7.21 (d, J=1.0 Hz, 1H)

3-(b) 3-Cyclopropylmethoxy-4-difluoromethoxyphenylboronic acid

To 20 ml of tetrahydrofuran solution containing 2.56 g (7.81 mmol) of 2-(3-cyclopropylmethoxy-4-difluoromethoxyphenyl)-[1,3,6,2]dioxoazaborocane obtained in Reference example 3-(a) was added 40 ml of 2N hydrochloric acid, and the mixture was reacted at room temperature for 2 hours. After completion of the reaction, the reaction mixture was extracted with ethyl acetate, and the organic layer after separating the liquids was extracted with 1N aqueous solution of sodium hydroxide. The aqueous layer was adjusted a pH to 1.6 by conc. hydrochloric acid and extracted with ethyl acetate. The obtained organic layer was dried over anhydrous magnesium sulfate, and concentrated under reduced pressure to obtain 1.63 g of the title compound as a white solid. (Yield: 81%)

$^1$H-NMR Spectrum (CDCl$_3$+CD$_3$OD, δ ppm): 0.34-0.40 (m, 2H), 0.60-0.68 (m, 2H), 1.23-1.36 (m, 1H), 3.92 (d, J=6.8 Hz, 2H), 6.70 (t, J=75.6 Hz, 1H), 7.05-7.46 (m, 3H).

The substituted bromobenzene derivatives used in Reference examples 1 and 2 are known compounds or can be synthesized according to the following Reference examples. As the known compounds, 4-bromo-2-cyclopropylmethoxy-1-difluoromethoxybenzene (Reference Example 1-(c) starting material: see WO 2004/033430), 4-bromo-2-cyclopropylmethoxy-1-methoxybenzene (Reference Example 2-(a) starting material: see WO 95/27692), 4-bromo-2-isopropoxy-1-methoxybenzene (Reference Example 1-(g) starting material: see Organic Letters, 17, 2881 (2002)), 4-bromo-2-cyclopentoxy-1-methoxybenzene (Reference Example 2-(b) starting material: see Tetrahedron Letters, 41, 811 (2000)), and 4-bromo-2,3-dihydro-7-methoxybenzofuran-2-spiro-1'-cyclopentane (Reference Example 1-(h) starting material: see J. Med. Chem., 44, 2523 (2001)) were used.

Reference Example 4

4-Bromo-2-cyclopropoxy-1-difluoromethoxybenzene

To 1.5 L of toluene solution containing 116 g (508 mmol) of 4-bromo-2-cyclopropoxyphenol (see J. Org. Chem., 2005, 70, 3021-3030) were added 81.9 g (254 mmol) of tetrabutylammonium bromide, and 900 ml of 15% aqueous solution of sodium hydroxide previously degassed under argon atmosphere. Then, the mixture was heated to 80° C. by blowing 86 g of chlorodifluoromethane therein, and the mixture was stirred at the same temperature for 30 minutes. After completion of the reaction, 1 L of water was added to the reaction mixture, and the resulting mixture was extracted with toluene. The organic layer after separation was washed successively with water, and then, with a saturated aqueous solution of sodium chloride, dried over anhydrous magnesium sulfate and then concentrated under reduced pressure. The obtained concentrate was applied to distillation under reduced pressure (93 to 98° C./60 to 110 Pa) to obtain 127.6 g of the title compound as a colorless oil. (Yield: 90%)

Mass Spectrum (EI, m/z): 278 (M$^+$).
$^1$H-NMR Spectrum (CDCl$_3$, δ ppm): 0.81-0.87 (m, 4H), 3.74-3.81 (m, 1H), 6.46 (t, J=74.7 Hz, 1H), 7.01 (d, J=8.5 Hz, 1H), 7.07 (dd, J=8.5, 2.2 Hz, 1H), 7.44 (d, J=2.2 Hz, 1H).

Reference Example 5

4-Bromo-2-cyclopropoxy-1-difluoromethoxybenzene

5-(a) 5-Bromo-2-methoxymethoxybenzaldehyde

To 600 ml of acetone solution containing 30.0 g (0.15 mol) of 5-bromo-2-hydroxybenzaldehyde was added 20.6 g (0.15 mol) of potassium carbonate, and then, 12.5 ml (0.17 mol) of chloromethylmethyl ether was added dropwise to the mixture over 30 minutes under ice-cooling. After stirring the mixture at the same temperature for 30 minutes, the mixture was further stirred at room temperature for 5 hours. After completion of the reaction, 600 ml of water was added to the reaction mixture. A pH of the mixture was adjusted to 7.6 with conc. hydrochloric acid, and extracted with ethyl acetate. The organic layer after separation was washed with a saturated aqueous solution of sodium chloride, dried over anhydrous sodium sulfate, and concentrated under reduced pressure to obtain 28.4 g of the title compound as a pale yellowish oil. (Yield: 77%)

Mass Spectrum (EI, m/z): 244(M$^+$).
$^1$H-NMR Spectrum (CDCl$_3$, δ ppm): 3.52 (s, 3H), 5.29 (s, 2H), 7.14 (d, J=8.8 Hz, 1H), 7.61 (dd, J=8.8, 2.6 Hz, 1H), 7.94 (d, J=2.6 Hz, 1H), 10.42 (s, 1H).

5-(b) 5-Bromo-2-methoxymethoxyphenol

To 660 ml of dichloromethane solution containing 27.9 g (0.11 mol) of 5-bromo-2-methoxymethoxybenzaldehyde obtained in Reference example 5-(a) was added 42.9 g (0.132 mol) of m-chloroperbenzoic acid (purity: 53%), and the mixture was stirred at room temperature for 3 days. After completion of the reaction, the precipitated solid was removed from the reaction suspension by filtration, 97 ml of 2M aqueous sodium thiosulfate solution was added to the filtrate, and the mixture was stirred at room temperature for 2 hours. The organic layer after separation was concentrated under reduced pressure and the obtained solid was dissolved in diethyl ether. The solution was washed successively with 1M aqueous sodium thiosulfate solution, a saturated aqueous solution of sodium hydrogencarbonate and a saturated aqueous solution of sodium chloride, dried over anhydrous sodium sulfate and then concentrated under reduced pressure. The obtained residue was applied to silica gel column chromatography (Eluent; hexane:ethyl acetate=4:1 (V/V)), and the fractions containing the desired compound were concentrated under reduced pressure to obtain 20.3 g of the title compound as a colorless oil. (Yield: 79%)

Mass Spectrum (EI, m/z): 232 (M$^+$).
$^1$H-NMR Spectrum (CDCl$_3$, δ ppm): 3.46 (s, 3H), 5.16 (s, 2H) 7.13 (d, J=8.8 Hz, 1H), 7.26 (d, J=2.2 Hz, 1H), 7.33 (dd, J=8.8, 2.2 Hz, 1H), 8.24 (s, 1H).

5-(c) 4-Bromo-2-cyclobutoxy-1-methoxymethoxybenzene

To 10 ml of N,N-dimethylformamide solution containing 1.73 g (7.4 mmol) of 5-bromo-2-methoxymethoxyphenol obtained in Reference example 5-(b) were added 1.0 g (7.2 mmol) of potassium carbonate and 1.0 g (7.4 mmol) of cyclobutyl bromide, and the mixture was stirred at 100° C. for 5 hours. After completion of the reaction, 10 ml of water was added to the reaction mixture, and the mixture was extracted with ethyl acetate. The organic layer after separation was washed with a saturated aqueous solution of sodium chloride, dried over anhydrous sodium sulfate and then concentrated under reduced pressure. The obtained residue was applied to silica gel column chromatography (Eluent; hexane:ethyl acetate=9:1 (V/V)), and the fractions containing the desired compound were concentrated under reduced pressure to obtain 1.4 g of the title compound as a colorless oil. (Yield: 66%)

Mass Spectrum (EI, m/z): 286 (M$^+$).
$^1$H-NMR Spectrum (CDCl$_3$, δ ppm): 1.60-1.76 (m, 1H), 1.80-1.93 (m, 1H), 2.15-2.30 (m, 2H), 2.40-2.53 (m, 2H), 3.51 (s, 3H), 4.56-4.67 (m, 1H), 5.16 (s, 2H), 6.86 (d, J=1.8 Hz, 1H), 6.97 (dd, J=8.6, 1.8 Hz, 1H), 7.00 (d, J=8.6 Hz, 1H).

5-(d) 4-Bromo-2-cyclobutoxyphenol

To 7.26 g (25.3 mmol) of 4-bromo-2-cyclobutoxy-1-methoxymethoxybenzene obtained in Reference Example 5-(c) was added 30 ml of 1,4-dioxane solution containing 4N hydrogen chloride, and the mixture was stirred at room temperature for 24 hours. After completion of the reaction, 100 ml of water was added to the reaction mixture, and the mixture was extracted with diethyl ether. The organic layer after separation was washed with a saturated aqueous solution of sodium chloride, dried over anhydrous sodium sulfate and then concentrated under reduced pressure. The obtained residue was applied to silica gel column chromatography (Eluent; hexane:ethyl acetate=9:1 (V/V)), and the fractions containing the desired compound were concentrated under reduced pressure to obtain 3.07 g of the title compound as a pale yellowish oil. (Yield: 50%)

$^1$H-NMR Spectrum (CDCl$_3$, δ ppm): 1.62-1.79 (m, 1H), 1.82-1.95 (m, 1H), 2.11-2.26 (m, 2H), 2.42-2.54 (m, 2H), 4.60-4.70 (m, 1H), 5.56 (s, 1H), 6.79 (d, J=8.4 Hz, 1H), 6.82 (d, J=2.3 Hz, 1H), 6.96 (dd, J=8.4, 2.3 Hz, 1H).

5-(e) 4-Bromo-2-cyclobutoxy-1-difluoromethoxybenzene

Reaction and post treatment were carried out in the same manner as in Reference Example 4 except for using 3.07 g (12.6 mmol) of 4-bromo-2-cyclobutoxyphenol obtained in Reference Example 5-(d) in place of 4-bromo-2-cyclopropoxyphenol, and the obtained residue was applied to silica gel column chromatography (Eluent; hexane:ethyl acetate=9:1 (V/V)), and the fractions containing the desired compound were concentrated under reduced pressure to obtain 4.11 g of the title compound as a colorless oil. (Yield: 78%)

$^1$H-NMR Spectrum (CDCl$_3$, δ ppm): 1.61-1.79 (m, 1H), 1.81-1.96 (m, 1H), 2.12-2.28 (m, 2H), 2.40-2.54 (m, 2H), 4.56-4.70 (m, 1H), 6.53 (t, J=75.1 Hz, 1H), 6.92-6.94 (m, 1H), 6.99-7.06 (m, 2H).

Reference Example 6

4-Bromo-1-difluoromethoxy-2-isopropoxybenzene

6-(a) 4-Bromo-2-isopropoxyphenol

To 200 ml of dichloromethane solution containing 27.2 g (0.179 mol) of 2-isopropoxyphenol was added dropwise 50 ml of dichloromethane solution containing 28.4 g (0.177 mol) of bromine at −70° C. or lower. After completion of the dropwise addition, the mixture was stirred at the same temperature 1 hour, and gradually raised to −10° C. After completion of the reaction, the reaction mixture was poured into ice-water, the mixture was neutralized with a saturated aqueous solution of sodium hydrogencarbonate, and then extracted with chloroform. The organic layer after separation was washed with a saturated aqueous solution of sodium chloride, dried over anhydrous magnesium sulfate and then concentrated under reduced pressure. The obtained residue was applied to silica gel column chromatography (Eluent; hexane:ethyl acetate=9:1 (V/V)), and the fractions containing the desired compound were concentrated under reduced pressure to obtain 38.8 g of the title compound as a colorless oil. (Yield: 94%)

$^1$H-NMR Spectrum (CDCl$_3$, δ ppm): 1.37 (d, J=6.1 Hz, 6H), 4.49-4.62 (m, 1H), 5.62 (s, 1H), 6.80 (d, J=8.8 Hz, 1H), 6.94-6.99 (m, 2H).

6-(b)
4-Bromo-1-difluoromethoxy-2-isopropoxybenzene

To 21.9 g (94.9 mmol) of 4-bromo-2-isopropoxyphenol obtained in Reference Example 6-(a) were added 2.01 g (9.56 mmol) of tetraethylammonium bromide, 150 ml of 1,4-dioxane, 11.2 g (275 mmol) of sodium hydroxide and 10 ml of water, and the mixture was stirred at 80° C. Then, the mixture was stirred at the same temperature for 1 hour while blowing 40.4 g of chlorodifluoromethane therein. After completion of the reaction, water was added to the reaction mixture, a pH of the mixture was adjusted to 7 with conc. hydrochloric acid, and extracted with ethyl acetate. The organic layer after separation was washed with a saturated aqueous solution of sodium chloride, dried over anhydrous magnesium sulfate and then concentrated under reduced pressure. The obtained residue was applied to silica gel column chromatography (Eluent; hexane:ethyl acetate=100:1→25:1 (V/V)), and the obtained crude oil containing the desired compound was applied to distillation under reduced pressure (105 to 110° C./7 Pa) to obtain 8.27 g of the title compound as a colorless oil. (Yield: 31%)

$^1$H-NMR Spectrum (CDCl$_3$, δ ppm): 1.36 (d, J=6.1 Hz, 6H), 4.46-4.60 (m, 1H), 6.51 (t, J=75.2 Hz, 1H), 7.00-7.07 (m, 2H), 7.09-7.11 (m, 1H).

Reference Example 7

4-Bromo-2-cyclopropoxy-1-methoxybenzene 7-(a) 4-Bromo-2-(2-chloroethoxy)-1-methoxybenzene To 1.2 L of N,N-dimethylformamide solution containing 159 g (0.79 mol) of 5-bromo-2-methoxyphenol (see WO 01019785) were added 340 g (2.37 mol) of 1-bromo-2-chloroethane and 120 g (0.868 mol) of potassium carbonate, and the mixture was stirred at 70° C. for 5 hours. Then, 220 g (1.53 mol) of 1-bromo-2-chloroethane and 80 g (0.58 mol) of potassium carbonate were additionally added thereto twice by dividing them to two portions during the reaction, and the mixture was further stirred for 7 hours. After completion of the reaction, the reaction mixture was poured into water, and extracted with toluene. The organic layer after separation was washed with water, dried over anhydrous magnesium sulfate, and concentrated under reduced pressure to obtain 217 g of the title compound as a dark brownish solid substantially quantitatively.

Mass Spectrum (EI, m/z): 264 (M$^+$).

$^1$H-NMR Spectrum (CDCl$_3$, δ ppm): 3.83 (t, J=6.1 Hz, 2H), 3.85 (s, 3H), 4.25 (t, J=6.1 Hz, 2H), 6.76 (d, J=8.5 Hz, 1H), 7.02 (d, J=2.2 Hz, 1H), 7.08 (dd, J=8.5, 2.2 Hz, 1H).

7-(b) 4-Bromo-2-vinyloxy-1-methoxybenzene

To 2 L of toluene solution containing 217 g (containing an amount corresponding to 790 mmol) of 4-bromo-2-(2-chloroethoxy)-1-methoxybenzene obtained in Reference example 7-(a) were added 780 ml of 50% aqueous solution of sodium hydroxide and 268 g (789 mmol) of tetrabutylammonium hydrogensulfate under ice-cooling, and the mixture was stirred at room temperature for 3 hours. After completion of the reaction, the reaction mixture was poured into water, the organic layer after separation was washed successively with water and then with a saturated aqueous solution of sodium chloride, dried over anhydrous magnesium sulfate and then concentrated under reduced pressure. The obtained concentrate was applied to distillation under reduced pressure (79 to 83° C./100 Pa) to obtain 122 g of the title compound as a colorless oil. (Yield: 68%)

Mass Spectrum (CI, m/z): 229 (M$^+$+1).

$^1$H-NMR Spectrum (CDCl$_3$, δ ppm): 3.86 (s, 3H), 4.47 (dd, J=6.1, 2.1 Hz, 1H), 4.76 (dd, J=13.7, 2.1 Hz, 1H), 6.56 (dd, J=13.7, 6.1 Hz, 1H), 6.81 (d, J=8.7 Hz, 1H), 7.12 (d, J=2.4 Hz, 1H), 7.17 (dd, J=8.7, 2.4 Hz, 1H).

7-(c) 4-Bromo-2-cyclopropoxy-1-methoxybenzene

To 60 ml of dehydrated toluene solution containing 30.0 g (131 mmol) of 4-bromo-2-vinyl-1-methoxybenzene obtained in Reference Example 7-(a) was added dropwise 200 ml of toluene solution containing 1.1M diethyl zinc at −40° C., followed by addition of 46.2 g (262 mmol) of chloroiodomethane dropwisely at the same temperature. After stirring at the same temperature for 15 minutes, the mixture was raised to room temperature, and stirred for 28 hours. After completion of the reaction, the reaction mixture was poured into a saturated aqueous solution of ammonium chloride, and extracted with toluene. The organic layer after separation was washed with a saturated aqueous solution of sodium chloride, dried over anhydrous magnesium sulfate, and concentrated under reduced pressure to obtain 33.7 g of the title compound as a white solid substantially quantitatively.

Mass Spectrum (CI, m/z): 243 (M$^+$+1).

$^1$H-NMR Spectrum (CDCl$_3$, δ ppm): 0.79-0.88 (m, 4H), 3.69-3.77 (m, 1H), 3.83 (s, 3H), 6.73 (d, J=8.7 Hz, 1H), 7.04 (dd, J=8.7, 2.2 Hz, 1H), 7.35 (d, J=2.2 Hz, 1H).

Reference Example 8

4-Bromo-2-cyclopropoxyphenol

To 300 ml of dehydrated dichloromethane solution containing 60.0 g (247 mmol) of 4-bromo-2-cyclopropoxy-1-methoxybenzene obtained in Reference Example 7-(c) was added 300 ml of dichloromethane solution containing 1M boron tribromide under argon atmosphere at −70° C. After completion of the addition, the mixture was gradually raised to 0° C., and stirred at the same temperature for 30 minutes. After completion of the reaction, the reaction mixture was poured into ice-water, and extracted with toluene. The organic layer after separation was washed with a saturated aqueous solution of sodium chloride, dried over anhydrous magnesium sulfate, and concentrated under reduced pressure to obtain 58.6 g of the title compound as a blue-greenish solid substantially quantitatively.

Mass Spectrum (CI, m/z): 229 (M$^+$+1).

$^1$H-NMR Spectrum (CDCl$_3$, δ ppm): 0.80-0.86 (m, 4H), 3.75-3.82 (m, 1H), 5.37 (s, 1H), 6.78 (d, J=8.4 Hz, 1H), 7.00 (dd, J=8.4, 2.2 Hz, 1H), 7.29 (d, J=2.2 Hz, 1H).

Reference Example 9

4-Bromo-2-cyclobutoxy-1-methoxybenzene

To 60 ml of N,N-dimethylformamide solution containing 6.22 g (25.6 mmol) of 4-bromo-2-cyclobutoxyphenol obtained in Reference Example 5-(d) were successively added 3.54 g of potassium carbonate and 3.2 ml of methyl iodide, and the mixture was stirred at room temperature for 6 hours. After completion of the reaction, water was added to the reaction mixture, and the mixture was extracted with toluene. The organic layer after separation was washed with a saturated aqueous solution of sodium chloride, dried over anhydrous magnesium sulfate and then concentrated under reduced pressure. The obtained residue was applied to silica gel column chromatography (Eluent; toluene), and the obtained crude solid was recrystallized from hexane to obtain 3.90 g of the title compound as a colorless solid. (Yield: 59%)

$^1$H-NMR Spectrum (CDCl$_3$, δ ppm): 1.60-1.77 (m, 1H), 1.80-1.94 (m, 1H), 2.17-2.32 (m, 2H), 2.42-2.54 (m, 2H), 3.84 (s, 3H), 4.57-4.68 (m, 1H), 6.73 (d, J=8.6 Hz, 1H), 6.83 (d, J=2.3 Hz, 1H), 7.00 (dd, J=8.6, 2.3 Hz, 1H).

Reference Example 10

4-Bromo-2-isopropoxy-1-methoxybenzene

Reaction and post treatment were carried out in the same manner as in Reference Example 7-(a) except for using 10.1 g (49.8 mmol) of 5-bromo-2-methoxyphenol, and using 15 ml of isopropyl iodide in place of 1-bromo-2-chloroethane, whereby 10.4 g of the title compound was obtained as a pale yellowish solid. (Yield: 86%)

Mass Spectrum (EI, m/z): 244 (M$^+$).

$^1$H-NMR Spectrum (CDCl$_3$, δ ppm): 1.37 (d, J=6.1 Hz, 6H), 3.82 (s, 3H), 4.43-4.56 (m, 1H), 6.71-6.76 (m, 1H), 7.00-7.04 (m, 2H).

Reference Example 11

5-Bromo-8-difluoromethoxy-2,2-dimethyl-2H-chromene 11-(a) 5-Bromo-2-difluoromethoxy-phenol To 60 ml of methanol solution containing 5.80 g (19.7 mmol) of 4-bromo-2-cyclopropylmethoxy-1-difluoromethoxybenzene (see WO 2004033430) was added 60 ml of conc. hydrochloric acid, and the mixture was refluxed for 5 hours. After completion of the reaction, 60 ml of water was added to the reaction mixture, and the mixture was extracted with diethyl ether. The organic layer after separation was washed with a saturated aqueous solution of sodium chloride, dried over anhydrous sodium sulfate and then concentrated under reduced pressure. The obtained residue was applied to silica gel column chromatography (Eluent; hexane:ethyl acetate=4:1 (V/V)), and the fractions containing the desired compound were concentrated under reduced pressure to obtain 4.80 g of the title compound as a slightly yellowish oil substantially quantitatively.

Mass Spectrum (EI, m/z): 238 (M$^+$).

$^1$H-NMR Spectrum (CDCl$_3$, δ ppm): 5.70 (brs, 1H), 6.51 (t, J=73.2 Hz, 1H), 6.98 (dd, J=8.6, 0.6 Hz, 1H), 7.02 (dd, J=8.6, 2.0 Hz, 1H), 7.19 (dd, J=2.0, 0.6 Hz, 1H).

11-(b) 4-Bromo-1-difluoromethoxy-2-(1,1-dimethyl-2-propynyloxy)benzene

To 30 ml of acetonitrile solution containing 7.31 g (30.6 mmol) of 5-bromo-2-difluoromethoxyphenol obtained in Reference example 11-(a) were added 6.4 mg of cuprous chloride and 6.43 ml of 1,8-diazabicyclo[5$_7$O 5.4.0]-7-undecene at −10° C., and the mixture was stirred at the same temperature for 30 minutes. To the reaction mixture was added dropwise 30 ml of acetonitrile solution containing 6.18 g (73.5 mmol) of 2-methyl-3-butyn-2-ol which further contains 7.34 ml of 1,8-diazabicyclo[5.4.0]-7-undecene and 5.05 ml of trifluoroacetic anhydride at −10° C. After completion of the dropwise addition, the mixture was stirred at the same temperature for 1.5 hours, and further at 0° C. for 2 hours. After completion of the reaction, water was added to the reaction mixture, and extracted with toluene. The organic layer after separation was washed successively with 2N hydrochloric acid, a saturated aqueous solution of sodium hydrogencarbonate and a saturated aqueous solution of sodium chloride, dried over anhydrous sodium sulfate and then concentrated under reduced pressure. The obtained residue was applied to silica gel column chromatography (Eluent; hexane:ethyl acetate=9:1 (V/V)), and the fractions containing the desired compound were concentrated under reduced pressure to obtain 4.88 g of the title compound as a colorless oil. (Yield: 52%)

$^1$H-NMR Spectrum (CDCl$_3$, δ ppm): 1.67 (s, 6H), 2.64 (s, 1H), 6.48 (t, J=74.8 Hz, 1H), 7.04 (d, J=8.6 Hz, 1H), 7.18 (dd, J=8.6, 2.3 Hz, 1H), 7.72 (d, J=2.3 Hz, 1H).

11-(c)
5-Bromo-8-difluoromethoxy-2,2-dimethyl-2H-chromene

To 4.86 g (15.9 mmol) of 4-bromo-1-difluoromethoxy-2-(1,1-dimethyl-2-propynyloxy)benzene obtained in Reference example 11-(b) was added 47 ml of N,N-diethylaniline, and the mixture was stirred at 200° C. for 2 hours. After completion of the reaction, the reaction mixture was concentrated under reduced pressure, and the obtained concentrate was washed successively with 1N hydrochloric acid, a saturated aqueous solution of sodium hydrogencarbonate and a saturated aqueous solution of sodium chloride, dried over anhydrous magnesium sulfate and then concentrated under reduced pressure. The obtained residue was applied to silica gel column chromatography (Eluent; hexane:ethyl acetate=9:1 (V/V)), and the fractions containing the desired compound were concentrated under reduced pressure to obtain 3.76 g of the title compound as a yellowish oil. (Yield: 78%)

Mass Spectrum (EI, m/z): 304 (M$^+$).

$^1$H-NMR Spectrum (CDCl$_3$, δ ppm): 1.47 (s, 6H), 5.76 (d, J=10.2 Hz, 1H), 6.54 (t, J=75.1 Hz, 1H), 6.63 (d, J=10.2 Hz, 1H), 6.88 (d, J=8.7 Hz, 1H), 7.04 (d, J=8.7 Hz, 1H)

Reference Example 12

5-Bromo-8-difluoromethoxy-2H-chromen-2-spiro-1'-cyclobutane 12-(a) 1-Bromo-2-cyclopropylmethoxy-3-methoxymethoxybenzene To 200 ml of N,N-dimethylformamide solution containing 23.3 g (0.10 mol) of 2-bromo-6-methoxymethoxyphenol (see Synthesis, 2001, 741-744) were added 13.8 g (0.10 mol) of potassium carbonate and 19.5 ml (0.20 mol) of cyclopropylmethyl bromide, and the mixture was stirred at 80° C. for 2 hours. After completion of the reaction, water was added to the reaction mixture, and extracted with toluene. The organic layer after separation was washed with a saturated aqueous solution of sodium chloride, dried over anhydrous sodium sulfate and then concentrated under reduced pressure. The obtained residue was applied to silica gel column chromatography (Eluent; hexane:ethyl acetate=9:1 (V/V)), and the fractions containing the desired compound were concentrated under reduced pressure to obtain 24.1 g of the title compound as a colorless oil. (Yield: 84%)

$^1$H-NMR Spectrum (CDCl$_3$, δ ppm): 0.29-0.37 (m, 2H), 0.56-0.64 (m, 2H), 1.27-1.40 (m, 1H), 3.51 (s, 3H), 3.86 (d, J=7.1 Hz, 2H), 5.19 (s, 2H), 6.88 (t, J=8.1 Hz, 1H), 7.07 (dd, J=8.1, 1.6 Hz, 1H), 7.19 (dd, J=8.1, 1.6 Hz, 1H).

12-(b) 2-Cyclopropylmethoxy-1-iodo-3-methoxymethoxybenzene

To 76 ml of diethyl ether solution containing 24.1 g (84 mmol) of 1-bromo-2-cyclopropylmethoxy-3-methoxymethoxybenzene obtained in Reference example 12-(a) was added dropwise 53.4 ml (84 mmol) of 1.58M n-butyl lithium hexane solution at −60° C. or lower under argon atmosphere. The mixture was stirred at the same temperature for further 30 minutes, raised to −30° C., and then, 50 ml of diethyl ether solution containing 21.3 g (84 mmol) of iodine was added dropwise to the mixture. After completion of the dropwise addition, the mixture was stirred at the same temperature for 30 minutes, and then, gradually raised to room temperature. After completion of the reaction, to the reaction mixture was added 95 ml of 2% aqueous sodium thiosulfate solution, and the mixture was stirred for 1 hour. The organic layer after separation was washed with a saturated aqueous solution of sodium chloride, dried over dried over anhydrous sodium sulfate, and concentrated under reduced pressure to obtain 29.8 g of the title compound as a reddish oil substantially quantitatively.

Mass Spectrum (EI, m/z): 334 (M$^+$).

$^1$H-NMR Spectrum (CDCl$_3$, δ ppm): 0.31-0.39 (m, 2H), 0.58-0.66 (m, 2H), 1.29-1.42 (m, 1H), 3.50 (s, 3H), 3.85 (d, J=7.1 Hz, 2H), 5.18 (s, 2H), 6.75 (t, J=8.1 Hz, 1H), 7.09 (dd, J=8.1, 1.5 Hz, 1H), 7.42 (dd, J=8.1, 1.5 Hz, 1H).

12-(c) 2-Cyclopropylmethoxy-3-iodophenol

To 100 ml of 1,4-dioxane solution containing 33.9 g (0.10 mol) of 2-cyclopropylmethoxy-1-iodo-3-methoxymethoxybenzene obtained in Reference example 12-(b) was added 150 ml of 1,4-dioxane solution containing 4N hydrogen chloride, and the mixture was stirred at room temperature for 6 hours. After completion of the reaction, 100 ml of water was added to the reaction mixture, and the resulting mixture was extracted with diethyl ether. The organic layer after separation was washed with a saturated aqueous solution of sodium chloride, dried over anhydrous sodium sulfate and then concentrated under reduced pressure. The obtained residue was applied to silica gel column chromatography (Eluent; hexane:ethyl acetate=9:1 (V/V)), and the fractions containing the desired compound were concentrated under reduced pressure to obtain 22.3 g of the title compound as a colorless oil. (Yield: 77%)

Mass Spectrum (EI, m/z): 290 (M$^+$).

$^1$H-NMR Spectrum (CDCl$_3$, δ ppm): 0.33-0.40 (m, 2H), 0.62-0.71 (m, 2H), 1.24-1.37 (m, 1H), 3.88 (d, J=7.3 Hz, 2H), 5.84 (s, 1H), 6.75 (t, J=8.0 Hz, 1H), 6.92 (dd, J=8.0, 1.6 Hz, 1H), 7.27 (dd, J=8.0, 1.6 Hz, 1H).

12-(d) 4-Bromo-2-cyclopropylmethoxy-3-iodophenol

To 15 ml of 1,4-dioxane solution containing 1.62 g (5.6 mmol) of 2-cyclopropylmethoxy-3-iodophenol obtained in Reference example 12-(c) was added dropwise 10 ml of 1,4-dioxane solution containing 1,4-dioxane-bromine complex adjusted to 0.56M at 10° C. After completion of the dropwise addition, the mixture was stirred at the same temperature for 10 minutes. After completion of the reaction, 20 ml of ice-water was added to the reaction mixture, and after adjusting a pH thereof to 7 with sodium hydrogencarbonate, then, the mixture was extracted with ethyl acetate. The organic layer after separation was washed with a saturated aqueous solution of sodium chloride, dried over anhydrous sodium sulfate and then concentrated under reduced pressure. The obtained residue was applied to silica gel column chromatography (Eluent; hexane:ethyl acetate=4:1 (V/V)), and the fractions containing the desired compound were concentrated under reduced pressure to obtain 465 mg of the title compound as a colorless oil. (Yield: 15%)

Mass Spectrum (CI, m/z): 368 (M$^+$).

$^1$H-NMR Spectrum (CDCl$_3$, δ ppm): 0.33-0.41 (m, 2H), 0.63-0.72 (m, 2H), 1.23-1.37 (m, 1H), 3.87 (d, J=7.3 Hz, 2H), 5.85 (s, 1H), 6.86 (d, J=8.7 Hz, 1H), 7.31 (d, J=8.7 Hz, 1H).

12-(e) 1-Bromo-3-cyclopropylmethoxy-4-difluoromethoxy-2-iodobenzene

To 20 ml of toluene solution containing 1.84 g (5.0 mmol) of 4-bromo-2-cyclopropylmethoxy-3-iodophenol obtained in Reference example 12-(d) were added 0.8 g (2.5 mmol) of tetrabutylammonium bromide and 10 ml of 35% aqueous solution of sodium hydroxide, and then, 5.0 g (62 mmol) of chlorodifluoromethane was blown thereinto at 80° C. over 30 minutes. After completion of the reaction, 2N hydrochloric acid was added to the reaction mixture to adjust a pH thereof to 5. The organic layer after separation was washed with a saturated aqueous solution of sodium chloride, dried over anhydrous sodium sulfate and then concentrated under reduced pressure. The obtained residue was applied to silica gel column chromatography (Eluent; hexane:ethyl acetate=9:1 (V/V)), and the fractions containing the desired compound were concentrated under reduced pressure to obtain 1.93 g of the title compound as a colorless oil. (Yield: 92%)

Mass Spectrum (EI, m/z): 418 (M$^+$).

$^1$H-NMR Spectrum (CDCl$_3$, δ ppm): 0.32-0.40 (m, 2H), 0.59-0.68 (m, 2H), 1.28-1.43 (m, 1H), 3.86 (d, J=7.3 Hz, 2H), 6.52 (t, J=74.3 Hz, 1H), 7.07 (dt, J=8.8, 0.7 Hz, 1H), 7.40 (d, J=8.8 Hz, 1H).

12-(f) 3-Bromo-6-difluoromethoxy-2-iodophenol

To 59.5 ml of methanol solution containing 8.1 g (22 mmol) of 1-bromo-3-cyclopropylmethoxy-4-difluoromethoxy-2-iodobenzene obtained in Reference example 12-(e) was added 59.5 ml of conc. hydrochloric acid, and the mixture was refluxed for 4 hours. After completion of the reaction, water was added to the reaction mixture, and the mixture was extracted with diethyl ether. The organic layer after separation was washed with a saturated aqueous solution of sodium chloride, dried over anhydrous sodium sulfate and then concentrated under reduced pressure. The obtained residue was applied to silica gel column chromatography (Eluent; hexane:ethyl acetate=9:1 (V/V)), and the fractions containing the desired compound were concentrated under reduced pressure to obtain 6.9 g of the title compound as a colorless solid. (Yield: 87%)

Mass Spectrum (CI, m/z): 364 (M$^+$).

$^1$H-NMR Spectrum (CDCl$_3$, δ ppm): 6.13 (s, 1H), 6.54 (t, J=73.1 Hz, 1H), 7.06 (dt, J=8.9, 0.9 Hz, 1H), 7.24 (d, J=8.9 Hz, 1H).

12-(g) 5-Bromo-8-difluoromethoxy-2H-chromen-2-spiro-1'-cyclobutane

To 48 ml of N,N-dimethylformamide solution containing 10.0 g (27.5 mmol) of 3-bromo-6-difluoromethoxy-2-iodophenol obtained in Reference example 12-(f) were added 0.62 g (2.8 mmol) of palladium acetate, 9.2 g (110 mmol) of sodium hydrogencarbonate and 3.23 g (32.9 mmol) of 1-vinylcyclobutanol (see J. Org. Chem., 1977, 42, 300-305) under argon atmosphere, and the mixture was stirred at 140° C. for 4 hours. After completion of the reaction, water was added to the reaction mixture, and the mixture was extracted with toluene. The organic layer after separation was washed with a saturated aqueous solution of sodium chloride, dried over anhydrous sodium sulfate and then concentrated under reduced pressure. The obtained residue was applied to silica gel column chromatography (Eluent; hexane:ethyl acetate=9:1 (V/V)), and the fractions containing the desired compound were concentrated under reduced pressure to obtain 0.61 g of the title compound as a pale yellowish oil. (Yield: 70%)

Mass Spectrum (CI, m/z): 317 ($M^+$+1).

$^1$H-NMR Spectrum (CDCl$_3$, δ ppm): 1.65-1.78 (m, 1H), 1.83-1.97 (m, 1H), 2.20-2.31 (m, 2H), 2.45-2.58 (m, 2H), 6.11 (d, J=10.0 Hz, 1H), 6.57 (t, J=75.0 Hz, 1H), 6.63 (d, J=10.0 Hz, 1H), 6.87 (d, J=8.7 Hz, 1H), 7.03 (d, J=8.7 Hz, 1H)

Reference Example 13

5-Bromo-8-difluoromethoxy-2H-chromen-2-spiro-1'-cyclopentane

Reaction and post treatment were carried out in the same manner as in Reference example 12-(g) except for using 5.10 g (45.5 mmol) of 1-vinylcyclopentanol (see J. Org. Chem., 1977, 42, 682-685) in place of 1-vinylcyclobutanol, whereby 1.60 g of the title compound was obtained as a yellowish oil. (Yield: 11%)

$^1$H-NMR Spectrum (CDCl$_3$, δ ppm): 1.57-1.80 (m, 4H), 1.86-1.98 (m, 2H), 2.11-2.23 (m, 2H), 5.80 (d, J=10.0 Hz, 1H), 6.50 (t, J=75.0 Hz, 1H), 6.65 (d, J=10.0 Hz, 1H), 6.86 (d, J=8.7 Hz, 1H), 7.03 (d, J=8.7 Hz, 1H).

Reference Example 14

5-Bromo-2-cyclopropyl-8-difluoromethoxy-2H-chromene 14-(a) 4-Bromo-2-(1-cyclopropyl-3-trimethylsilyl-2-propynyloxy)-1-difluoromethoxybenzene To 23 ml of toluene solution containing 3.8 g (16 mmol) of 5-bromo-2-difluoromethoxy-phenol obtained in Reference example 11-(a) were added 4.14 g (15.8 mmol) of triphenylphosphine and 2.74 g (16.2 mmol) of 1-cyclopropyl-3-trimethylsilyl-2-propyn-1-ol (see J. Org. Chem., 1999, 64, 5321-5324), and then, 2.3 ml of diethyl azodicarboxylate (40% toluene solution) was gradually added dropwise to the mixture at 5° C. under argon atmosphere. The mixture was stirred at the same temperature for 30 minutes, and further stirred at room temperature for 3 hours. After completion of the reaction, the reaction mixture was applied to silica gel column chromatography (Eluent; hexane:ethyl acetate=9:1 (V/V)), and the fractions containing the desired compound were concentrated under reduced pressure to obtain 4.07 g of the title compound as pale yellowish liquid. (Yield: 66%)

Mass Spectrum (CI, m/z): 389 ($M^+$+1).

$^1$H-NMR Spectrum (CDCl$_3$, δ ppm): 0.13-0.21 (m, 1H), 0.15 (s, 9H), 0.48-0.57 (m, 1H), 0.58-0.71 (m, 2H), 1.36-1.48 (m, 1H), 4.59 (d, J=6.3 Hz, 1H), 6.57 (dd, J=76.0, 74.3 Hz, 1H), 7.03 (d, J=8.5 Hz, 1H), 7.11 (dd, J=8.5, 2.2 Hz, 1H) 7.37 (d, J=2.2 Hz, 1H).

14-(b) 4-Bromo-2-(1-cyclopropyl-2-propynyloxy)-1-difluoromethoxybenzene

To 34 ml of methanol solution containing 4.05 g (10.5 mmol) of 4-bromo-2-(1-cyclopropyl-3-trimethylsilyl-2-propynyloxy)-1-difluoromethoxybenzene obtained in Reference example 14-(a) was added 0.48 g (3.5 mmol) of potassium carbonate, and the mixture was stirred at room temperature for 5 hours. After completion of the reaction, 50 ml of water was added to the reaction mixture, and the mixture was extracted with ethyl acetate. The organic layer after separation was washed with a saturated aqueous solution of sodium chloride, dried over anhydrous sodium sulfate and then concentrated under reduced pressure. The obtained residue was applied to silica gel column chromatography (Eluent; hexane:ethyl acetate=9:1 (V/V)), and the fractions containing the desired compound were concentrated under reduced pressure to obtain 2.8 g of the title compound as colorless liquid. (Yield: 84%)

Mass Spectrum (EI, m/z): 316 ($M^+$).

$^1$H-NMR Spectrum (CDCl$_3$, δ ppm): 0.51-0.73 (m, 4H), 1.40-1.51 (m, 1H), 2.53 (d, J=2.0 Hz, 1H), 4.59 (dd, J=6.6, 2.0 Hz, 1H), 6.55 (dd, J=75.7, 74.2 Hz, 1H), 7.04 (d, J=8.5 Hz, 1H), 7.12 (dd, J=8.5, 2.2 Hz, 1H), 7.30 (d, J=2.2 Hz, 1H).

14-(c) 5-Bromo-2-cyclopropyl-8-difluoromethoxy-2H-chromene

To 545 mg (1.7 mmol) of 4-bromo-2-(1-cyclopropyl-2-propynyloxy)-1-difluoromethoxybenzene obtained in Reference example 14-(b) was added 5 ml of N,N-diethylaniline, and the mixture was stirred at 200° C. for 2 hours. After completion of the reaction, water was added to the reaction mixture, and then, a pH of the mixture was adjusted to 1 with conc. hydrochloric acid, and the mixture was extracted with diethyl ether. The organic layer after separation was washed with a saturated aqueous solution of sodium chloride, dried over anhydrous sodium sulfate and then concentrated under reduced pressure. The obtained residue was applied to silica gel column chromatography (Eluent; hexane:ethyl acetate=9:1 (V/V)), and the fractions containing the desired compound were concentrated under reduced pressure to obtain 339 mg of the title compound as yellowish liquid. (Yield: 63%)

Mass Spectrum (EI, m/z): 316 ($M^+$).

$^1$H-NMR Spectrum (CDCl$_3$, δ ppm): 0.32-0.40 (m, 1H), 0.45-0.53 (m, 1H), 0.54-0.67 (m, 2H), 1.18-1.31 (m, 1H), 4.29 (ddd, J=8.3, 3.7, 1.6 Hz, 1H), 5.90 (dd, J=10.0, 3.7 Hz, 1H), 6.60 (dd, J=75.7, 74.5 Hz, 1H), 6.73 (dd, J=10.1, 1.6 Hz, 1H), 6.89 (d, J=8.7 Hz, 1H), 7.05 (d, J=8.7 Hz, 1H)

Pyrrolopyridazinone compounds and ethyl 2-formyl-1H-pyrrol-3-carboxylate derivatives used in Examples as starting substances were synthesized as follows.

Reference Example 15

2-Bromo-1-(2-trimethylsilylethoxymethyl)-1,5-dihydropyrrolo[2,3-d]pyridazin-4-one

15-(a) Potassium 4,4-diethoxy-2-ethoxycarbonylbutanoate

To 15 L of dehydrated ethanol solution containing 2.48 Kg (purity: 95.1%., 8.54 mol) of diethyl 2-(2,2-diethoxyethyl)

malonate was added 564 g (purity: 85%, 8.54 mol) of potassium hydroxide under argon gas atmosphere, and the mixture was stirred at room temperature for 4 hours. After completion of the reaction, the reaction mixture was concentrated under reduced pressure, 2 L of toluene was added to the obtained concentrate and the mixture was concentrated under reduced pressure. This operation of azeotropic dehydration with toluene was repeated three times to obtain 2.45 Kg of the title compound as a yellowish high-viscous oil substantially quantitatively.

$^1$H-NMR Spectrum (D$_2$O, δ ppm): 1.19 (t, J=7.1 Hz, 3H), 1.19 (t, J=7.1 Hz, 3H), 1.28 (t, J=7.1 Hz, 3H), 2.00-2.25 (m, 2H), 3.36 (dd, J=8.5, 6.1 Hz, 1H), 3.54-3.67 (m, 2H), 3.68-3.81 (m, 2H), 4.20 (q, J=7.1 Hz, 2H), 4.63 (dd, J=6.2, 5.2 Hz, 1H).

15-(b) Ethyl 2-(2,2-diethoxyethyl)-4-methoxy-3-oxobutanoate

To 11 L of dehydrated ethyl acetate solution containing 2.45 Kg (8.54 mol) of potassium 4,4-diethoxy-2-ethoxycarbonylbutanoate obtained in Reference example 15-(a) were added 1.63 Kg (17.1 mol) of anhydrous magnesium chloride and 3.12 L (22.2 mol) of triethylamine under argon atmosphere, and the mixture was stirred at 75° C. for 1 hour. Then, 974 g (8.97 mol) of methoxyacetyl chloride was added dropwise to the mixture at 15° C. or lower under cooling in ice-bath, and the mixture was further stirred at room temperature for 6 hours. After completion of the reaction, the reaction mixture was poured into 10 L of ice-water, neutralized with 20% aqueous potassium hydrogen sulfate solution and extracted with ethyl acetate. The organic layer after separation was washed with a saturated aqueous solution of sodium chloride, dried over anhydrous magnesium sulfate, and concentrated under reduced pressure to obtain 1.68 kg (purity: 66.4%) of the title compound as a yellowish oil. (Yield: 47.3%)

Mass Spectrum (FAB, m/z) 231 (M$^+$–45).

$^1$H-NMR Spectrum (CDCl$_3$, δ ppm): 1.17 (t, J=7.1 Hz, 3H), 1.18 (t, J=7.1 Hz, 3H), 1.26 (t, J=7.1 Hz, 3H), 2.10-2.34 (m, 2H), 3.37-3.52 (m, 2H), 3.42 (s, 3H), 3.55-3.69 (m, 2H), 3.77 (dd, J=8.2, 5.7 Hz, 1H), 4.17 (q, J=7.1 Hz, 2H), 4.19, 4.20 (each s, 2H in total), 4.51 (t, J=5.1 Hz, 1H).

15-(c) Ethyl 2-methoxymethyl-1H-pyrrol-3-carboxylate

To 1.68 kg (purity: 66.4%, 4.04 mol) of ethyl 2-(2,2-diethoxyethyl)-4-methoxy-3-oxobutanoate obtained in Reference example 15-(b) was added 1.38 L of cold water, then, added 1.38 L of 85% phosphoric acid at 10° C. or lower, and the mixture was stirred at the same temperature for 3 hours. After completion of the reaction, the reaction mixture was poured into ice-water, neutralized with 20% aqueous solution of sodium hydroxide, and extracted with chloroform. The obtained organic layer was washed with a saturated aqueous solution of sodium chloride, dried over anhydrous magnesium sulfate, and concentrated under reduced pressure to obtain 1.31 Kg of a deacetalated product as a reddish brown oil.

To 10 L of ethanol solution containing 1.31 Kg of the obtained deacetalated product was added 3.11 Kg (40.4 mol) of ammonium acetate, and the mixture was refluxed for 3 hours. After completion of the reaction, the reaction mixture was poured into ice-water, and extracted with toluene. The organic layer after separation was washed with a saturated aqueous solution of sodium chloride, dried over anhydrous magnesium sulfate, 15 g of activated carbon was added to the mixture, and the mixture was stirred at room temperature for 1 hour. The insoluble material was filtered off, the filtrate was concentrated under reduced pressure, and the obtained crude solid was recrystallized from 800 ml of cyclohexane to obtain 384 g (purity: 95%) of the title compound as a pale brownish solid. (Yield: 52%)

$^1$H-NMR Spectrum (CDCl$_3$, δ ppm): 1.34 (t, J=7.2 Hz, 3H), 3.46 (s, 3H), 4.27 (q, J=7.2 Hz, 2H), 4.82 (s, 2H), 6.59 (t, J=2.8 Hz, 1H), 6.67 (t, J=2.8 Hz, 1H), 8.79 (brs, 1H).

15-(d) Ethyl 2-methoxymethyl-1-(2-trimethylsilylethoxymethyl)-1H-pyrrol-3-carboxylate To 1250 ml of dehydrated N,N-dimethylformamide solution containing 63.1 g (1.45 mol) of sodium hydride (55% dispersed material in mineral oil) which had been washed three times with each 500 ml of dehydrated heptane was added dropwise 750 ml of dehydrated N,N-dimethylformamide solution containing 263 g (purity: 95%, 1.36 mol) of ethyl 2-methoxymethyl-1H-pyrrol-3-carboxylate obtained in Reference example 15-(c) at room temperature under argon atmosphere, and the mixture was stirred for 30 minutes. Then, 242 g (1.45 mol) of (2-trimethylsilylethoxy)methyl chloride was added dropwise to the mixture under ice-cooling, and the mixture was further stirred at room temperature for 3 hours. After completion of the reaction, the reaction mixture was poured into ice-water, neutralized with 30% aqueous potassium hydrogen sulfate solution, and extracted with toluene. The organic layer after separation was washed successively with water, and then, with a saturated aqueous solution of sodium chloride, dried over anhydrous magnesium sulfate, and concentrated under reduced pressure to obtain 420 g (purity: 98.6%) of the title compound as a yellowish oil. (Yield: 96%)

Mass Spectrum (EI, m/z): 313 (M$^+$).

$^1$H-NMR Spectrum (CDCl$_3$, δ ppm): –0.02 (s, 9H), 0.86-0.94 (m, 2H), 1.35 (t, J=7.2 Hz, 3H), 3.34 (s, 3H), 3.44-3.52 (m, 2H), 4.28 (q, J=7.2 Hz, 2H), 4.90 (s, 2H), 5.31 (s, 2H), 6.57 (d, J=3.2 Hz, 1H), 6.71 (d, J=3.2 Hz, 1H).

15-(e) Ethyl 5-bromo-2-methoxymethyl-1-(2-trimethylsilylethoxymethyl)-1H-pyrrol-3-carboxylate To 2.5 L of acetonitrile solution containing 420 g (purity: 98.6%, 1.32 mol) of ethyl 2-methoxymethyl-1-(2-trimethylsilylethoxymethyl)-1H-pyrrol-3-carboxylate obtained in Reference example 15-(d) was added 223 g (1.25 mol) of N-bromosuccineimide at –10° C. or lower by dividing it into several portions, and the mixture was stirred for 2 hours. 12.5 g (0.07 mol) of N-bromosuccineimide was additionally added to the mixture, and the mixture was stirred at the same temperature for 1.5 hours. After completion of the reaction, the reaction mixture was poured into a saturated aqueous solution of sodium hydrogencarbonate, and extracted with toluene. The organic layer after separation was washed successively with 5% aqueous sodium thiosulfate solution and then with a saturated aqueous solution of sodium chloride, dried over anhydrous magnesium sulfate and then concentrated under reduced pressure. The obtained residue was applied to silica gel column chromatography (Eluent; hexane: ethyl acetate=9:1 (V/V)), and the fractions containing the desired compound were concentrated under reduced pressure to obtain 460 g of the title compound as a colorless oil. (Yield: 89%)

¹H-NMR Spectrum (CDCl₃, δ ppm): −0.01 (s, 9H), 0.86-0.95 (m, 2H), 1.34 (t, J=7.1 Hz, 3H), 3.35 (s, 3H), 3.51-3.60 (m, 2H), 4.27 (q, J=7.1 Hz, 2H), 4.91 (s, 2H), 5.42 (s, 2H), 6.61 (s, 1H).

15-(f) Ethyl 5-bromo-2-formyl-1-(2-trimethylsilylethoxymethyl)-1H-pyrrol-3-carboxylate To 450 g (1.15 mol) of ethyl 5-bromo-2-methoxymethyl-1-(2-trimethylsilylethoxymethyl)-1H-pyrrol-3-carboxylate obtained in Reference example 15-(e) were added 5.4 L of dichloromethane and 540 ml of water, and then, 363 g (1.60 mol) of 2,3-dichloro-5,6-dicyano-1,4-benzoquinone was added to the mixture by dividing it into several portions at room temperature. The mixture was stirred at room temperature for 30 minutes, and then, refluxed for 6 hours. After completion of the reaction, 450 g of Celite and 2.5 L of toluene were added to the reaction suspension, the mixture was stirred at room temperature for 30 minutes, and insoluble material was removed by filtration. The organic layer obtained by separating the filtrate was washed successively with a saturated aqueous solution of sodium hydrogencarbonate, and with a saturated aqueous solution of sodium chloride, dried over anhydrous magnesium sulfate, and concentrated under reduced pressure to obtain 430 g of the title compound as a pale brownish oil substantially quantitatively.

¹H-NMR Spectrum (CDCl₃, δ ppm): −0.03 (s, 9H), 0.86-0.94 (m, 2H), 1.38 (t, J=7.2 Hz, 3H), 3.55-3.63 (m, 2H), 4.35 (q, J=7.2 Hz, 2H), 5.86 (s, 2H), 6.78 (s, 1H), 10.32 (s, 1H)

15-(g) 2-Bromo-1-(2-trimethylsilylethoxymethyl)-1,5-dihydropyrrolo[2,3-d]pyridazin-4-one To 2.1 L of ethylene glycol solution containing 430 g (1.14 mol) of ethyl 5-bromo-2-formyl-1-(2-trimethylsilylethoxymethyl)-1H-pyrrol-3-carboxylate obtained in Reference example 15-(f) was added 290 ml (5.98 mol) of hydrazine monohydrate at 60° C., and the mixture was stirred at 125° C. for 2 hours. After completion of the reaction, the reaction mixture was poured into water, and precipitated solid was collected by filtration and washed with water. The obtained crude solid was recrystallized from 3 L of a mixed solvent (toluene/cyclohexane=1/1 (V/V)) to obtain 289 g of the title compound as a beige solid. (Yield: 74%)

¹H-NMR Spectrum (CDCl₃, δ ppm): −0.03 (s, 9H), 0.86-0.96 (m, 2H), 3.52-3.61 (m, 2H), 5.55 (s, 2H), 6.95 (d, J=0.6 Hz, 1H), 8.18 (d, J=0.6 Hz, 1H), 10.62 (brs, 1H).

Reference Example 16

2-Bromo-3-chloro-1-(2-trimethylsilylethoxymethyl)-1,5-dihydropyrrolo[2,3-d]pyridazin-4-one

16-(a) Ethyl 2-formyl-1-(2-trimethylsilylethoxymethyl)-1H-pyrrol-3-carboxylate Reaction was carried out in the same manner as in Reference example 15-(f) except for using 42.1 g (0.134 mol) of ethyl 2-methoxymethyl-1-(2-trimethylsilylethoxymethyl)-1H-pyrrol-3-carboxylate obtained in Reference example 15-(d) in place of ethyl 5-bromo-2-methoxymethyl-1-(2-trimethylsilylethoxymethyl)-1H-pyrrol-3-carboxylate. After completion of the reaction, 45 g of Celite and 200 ml of toluene were added to the reaction suspension, the mixture was stirred at room temperature for 30 minutes, and insoluble material was removed by filtration. The organic layer obtained by separating the filtrate was washed successively with a saturated aqueous solution of sodium hydrogencarbonate and then with a saturated aqueous solution of sodium chloride, dried over anhydrous magnesium sulfate and then concentrated under reduced pressure. The obtained residue was applied to silica gel column chromatography (Eluent; hexane:ethyl acetate=9:1→7:3 (V/V)), and the fractions containing the desired compound were concentrated under reduced pressure to obtain 37.7 g of the title compound as a colorless oil. (Yield: 95%)

Mass Spectrum (CI, m/z): 298 (M⁺+1).

¹H-NMR Spectrum (CDCl₃, δ ppm): −0.02 (s, 9H), 0.86-0.96 (m, 2H), 1.38 (t, J=7.2 Hz, 3H), 3.50-3.60 (m, 2H), 4.35 (q, J=7.2 Hz, 2H), 5.74 (s, 2H), 6.72 (d, J=2.9 Hz, 1H), 7.08 (dd, J=2.9, 0.8 Hz, 1H), 10.42 (d, J=0.8 Hz, 1H).

16-(b) 1-(2-Trimethylsilylethoxymethyl)-1,5-dihydropyrrolo-[2,3-d]pyridazin-4-one Reaction and post treatment were carried out in the same manner as in Reference example 15-(g) except for using 37.6 g (0.127 mol) of ethyl 2-formyl-1-(2-trimethylsilylethoxymethyl)-1H-pyrrol-3-carboxylate obtained in Reference example 16-(a) in place of ethyl 5-bromo-2-formyl-1-(2-trimethylsilylethoxymethyl)-1H-pyrrol-3-carboxylate, whereby 28.7 g of the title compound was obtained as a pale yellowish solid. (Yield: 85%)

Melting point: 147-148° C.

¹H-NMR Spectrum (CDCl₃, δ ppm): −0.04 (s, 9H), 0.85-0.95 (m, 2H), 3.43-3.54 (m, 2H), 5.47 (s, 2H), 6.90 (dd, J=3.2, 0.6 Hz, 1H), 7.15 (d, J=3.2 Hz, 1H), 8.22 (d, J=0.6 Hz, 1H), 10.67 (brs, 1H).

16-(c) 3-Chloro-1-(2-trimethylsilylethoxymethyl)-1,5-dihydropyrrolo[2,3-d]pyridazin-4-one To 150 ml of acetonitrile solution containing 2.99 g (11.3 mmol) of 1-(2-trimethylsilylethoxymethyl)-1,5-dihydropyrrolo[2,3-d]pyridazin-4-one obtained in Reference example 16-(b) was added 1.42 g (10.6 mmol) of N-chlorosuccineimide, the mixture was stirred at room temperature for 3.5 hours, 0.53 g (4.0 mmol) of N-chlorosuccineimide was further added to the mixture and the resulting mixture was stirred for 24 hours. After completion of the reaction, to the reaction mixture were added a saturated aqueous solution of sodium hydrogencarbonate, 5% sodium hydrogen sulfite and ethyl acetate, and the mixture was stirred for 1 hour. Then, a saturated aqueous solution of sodium chloride was added to the solution and the liquids were separated. The organic layer after separation was further washed with a saturated aqueous solution of sodium chloride, dried over anhydrous magnesium sulfate and then concentrated under reduced pressure. The obtained residue was applied to silica gel column chromatography (Eluent; toluene:ethyl acetate=9:1→7:3 (V/V)), and the fractions containing the desired compound were concentrated under reduced pressure to obtain 2.20 g of the title compound as a white solid. (Yield: 65%)

¹H-NMR Spectrum (CDCl₃, δ ppm): −0.03 (s, 9H), 0.86-0.96 (m, 2H), 3.45-3.55 (m, 2H), 5.41 (s, 2H), 7.11 (s, 1H), 8.16 (s, 1H), 10.60 (brs, 1H).

16-(d) 2-Bromo-3-chloro-1-(2-trimethylsilylethoxymethyl)-1,5-dihydropyrrolo[2,3-d]pyridazin-4-one To 30 ml of acetonitrile solution containing 903 mg (3.00 mmol) of 3-chloro-1-(2-trimethylsilylethoxymethyl)-1,5-dihydropyrrolo[2,3-d]pyridazin-4-one obtained in Reference example 16-(c) was added 703 mg (3.95 mmol) of N-bromosuccinimide at room temperature, and the mixture was stirred for 8.5 hours. After completion of the reaction, ethyl acetate was added to the reaction mixture, and the mixture was washed successively with a saturated aqueous solution of sodium hydrogencarbonate, 5% aqueous sodium hydrogen sulfite solution and then a saturated aqueous solution of sodium chloride, dried over anhydrous magnesium sulfate and concentrated under reduced pressure. To the obtained concentrate were added diisopropyl ether and cyclohexane, precipitated solid was collected by filtration. The obtained solid was washed with cyclohexane and then with hexane, and dried under reduced pressure to obtain 943 mg of the title compound as a pale yellowish solid. (Yield: 83%)

Mass Spectrum (EI, m/z): 377 (M$^+$).

$^1$H-NMR Spectrum (CDCl$_3$, δ ppm): −0.01 (s, 9H), 0.88-0.97 (m, 2H), 3.53-3.61 (m, 2H), 5.56 (s, 2H), 8.14 (s, 1H), 9.95 (brs, 1H).

Reference Example 17

1-Benzyloxymethyl-2-bromo-1,5-dihydropyrrolo[2,3-d]pyridazin-4-one 17-(a) Ethyl 1-benzyloxymethyl-2-methoxymethyl-1H-pyrrol-3-carboxylate Reaction and post treatment were carried out in the same manner as in Reference example 15-(d) except for using 453 g (2.89 mol) of benzyloxymethyl chloride in place of (2-trimethylsilylethoxy)methyl chloride, whereby 880 g (purity: 93.5%) of the title compound was obtained as a brownish oil. (Yield: 99%)

Mass Spectrum (EI, m/z): 303 (M$^+$).

$^1$H-NMR Spectrum (CDCl$_3$, δ ppm): 1.36 (t, J=7.2 Hz, 3H), 3.33 (s, 3H), 4.29 (q, J=7.2 Hz, 2H), 4.44 (s, 2H), 4.89 (s, 2H), 5.39 (s, 2H), 6.60 (d, J=3.1 Hz, 1H), 6.73 (d, J=3.1 Hz, 1H), 7.25-7.39 (m, 5H).

17-(b) Ethyl 1-benzyloxymethyl-5-bromo-2-methoxymethyl-1H-pyrrol-3-carboxylate

Reaction and post treatment were carried out in the same manner as in Reference example 15-(e) except for using 880 g (purity: 93.5%, 2.71 mol) of ethyl 1-benzyloxymethyl-2-methoxymethyl-1H-pyrrol-3-carboxylate obtained in Reference example 17-(a) in place of ethyl 2-methoxymethyl-1-(2-trimethylsilylethoxymethyl)-1H-pyrrol-3-carboxylate, whereby 1.10 kg (purity: 85.1%) of the title compound was obtained as a brownish oil. (Yield: 90%)

Mass Spectrum (EI, m/z): 381 (M$^+$).

$^1$H-NMR Spectrum (CDCl$_3$, δ ppm): 1.34 (t, J=7.1 Hz, 3H), 3.32 (s, 3H), 4.28 (q, J=7.1 Hz, 2H), 4.53 (s, 2H), 4.89 (s, 2H), 5.51 (s, 2H), 6.63 (s, 1H), 7.25-7.39 (m, 5H)

17-(c) Ethyl 1-benzyloxymethyl-5-bromo-2-formyl-1H-pyrrol-3-carboxylate

Reaction and post treatment were carried out in the same manner as in Reference example 15-(f) except for using 895 g (purity: 85.1%, 1.99 mol) of ethyl 1-benzyloxymethyl-5-bromo-2-methoxymethyl-1H-pyrrol-3-carboxylate obtained in Reference example 17-(b) in place of ethyl 5-bromo-2-methoxymethyl-1-(2-trimethylsilylethoxymethyl)-1H-pyrrol-3-carboxylate, whereby 805 g (purity: 86.3%) of the title compound was obtained as a brownish oil. (Yield: 95%)

Mass Spectrum (CI, m/z): 366 (M$^+$+1).

$^1$H-NMR Spectrum (CDCl$_3$, δ ppm): 1.38 (t, J=7.1 Hz, 3H), 4.35 (q, J=7.1 Hz, 2H), 4.60 (s, 2H), 5.98 (s, 2H), 6.78 (s, 1H), 7.22-7.36 (m, 5H), 10.31 (s, 1H).

IR Spectrum (KBr, cm$^{-1}$): 1665, 1713.

17-(d) 1-Benzyloxymethyl-2-bromo-1,5-dihydropyrrolo[2,3-d]-pyridazin-4-one

Reaction and post treatment were carried out in the same manner as in Reference example 15-(g) except for using 600 g (purity: 86.3%, 1.41 mol) of ethyl 1-benzyloxymethyl-5-bromo-2-formyl-1H-pyrrol-3-carboxylate obtained in Reference example 17-(c) in place of ethyl 5-bromo-2-formyl-1-(2-trimethylsilylethoxymethyl)-1H-pyrrol-3-carboxylate, whereby 407 g (purity: 96.9%) of the title compound was obtained as a pale brownish solid. (Yield: 83%)

Mass Spectrum (EI, m/z): 333 (M$^+$).

$^1$H-NMR Spectrum (CDCl$_3$, δ ppm): 4.54 (s, 2H), 5.62 (s, 2H) 6.94 (d, J=0.6 Hz, 1H), 7.25-7.38 (m, 5H), 8.11 (d, J=0.6 Hz, 1H), 10.12 (brs, 1H).

IR Spectrum (KBr, cm$^{-1}$): 1667.

Reference Example 18

2-Bromo-3-methyl-1,5-bis(2-trimethylsilylethoxymethyl)-1,5-dihydropyrrolo[2,3-d]pyridazin-4-one 18-(a) 1,5-Bis(2-trimethylsilylethoxymethyl)-1,5-dihydropyrrolo[2,3-d]pyridazin-4-one To 1.5 L of dehydrated N,N-dimethylformamide solution containing 107 g (0.403 mol) of 1-(2-trimethylsilylethoxymethyl)-1,5-dihydropyrrolo[2,3-d]pyridazin-4-one obtained in Reference example 16-(b) was added 22.2 g (0.509 mol) of sodium hydride (55% dispersed material in mineral oil) by dividing it into several portions under argon atmosphere and under ice-cooling, and the mixture was stirred at room temperature for 1 hour. Then, 85.9 g (0.515 mol) of (2-trimethylsilylethoxy)methyl chloride was added dropwise to the mixture under ice-cooling, and the mixture was stirred at room temperature for 5 hours. After completion of the reaction, the reaction mixture was poured into ice-water, neutralized with a saturated aqueous solution of ammonium chloride, and extracted with toluene. The organic layer after separation was washed successively with water and then a saturated aqueous solution of sodium chloride, dried over anhydrous magnesium sulfate and then concentrated under reduced pressure. The obtained concentrate was recrystallized from 400 ml of cyclohexane to obtain 76.2 g of the title compound as a white solid. (Yield: 48%)

Mass Spectrum (CI, m/z): 396(M$^+$+1).

$^1$H-NMR Spectrum (CDCl$_3$, δ ppm): −0.04 (s, 9H), −0.02 (s, 9H), 0.86-0.94 (m, 2H), 0.94-1.02 (m, 2H), 3.44-3.53 (m, 2H), 3.68-3.77 (m, 2H), 5.45 (s, 2H), 5.61 (s, 2H), 6.89 (dd, J=3.0, 0.6 Hz, 1H), 7.12 (d, J=3.0 Hz, 1H), 8.20 (d, J=0.6 Hz, 1H).

IR Spectrum (KBr, cm$^{-1}$): 1645.

18-(b) 3-Iodo-1,5-bis(2-trimethylsilylethoxymethyl)-1,5-dihydropyrrolo[2,3-d]pyridazin-4-one To 65 ml of acetonitrile solution containing 7.0 g (18 mmol) of 1,5-bis(2-trimethylsilylethoxymethyl)-1,5-dihydropyrrolo[2,3-d]pyridazin-4-one obtained in Reference example 18-(a) were added 6.0 g (71 mmol) of sodium hydrogencarbonate and 12.4 g (103 mmol) of anhydrous magnesium sulfate under argon atmosphere, and the mixture was stirred at room temperature for 1 hour. Then, 4.0 g (36 mmol) of s-caprolactam and 35.5 ml (35.5 mmol) of dichloromethane solution containing 1M iodine chloride were added to the mixture, and the mixture was further stirred for 3 hours. After completion of the reaction, water was added to the reaction mixture, and the mixture was extracted with ethyl acetate. The organic layer after separation was washed successively with 5% aqueous sodium hydrogen sulfite solution and then a saturated aqueous solution of sodium chloride, dried over anhydrous magnesium sulfate, and then, concentrated under reduced pressure. The obtained residue was applied to silica gel column chromatography (Eluent; hexane: ethyl acetate=5:1 (V/V)), and the fractions containing the desired compound were concentrated under reduced pressure to obtain 7.3 g of the title compound as a brownish solid. (Yield: 79%)

Mass Spectrum (CI, m/z): 522 ($M^++1$).
$^1$H-NMR Spectrum (CDCl$_3$, δ ppm): −0.02 (s, 9H), −0.01 (s, 9H), 0.87-0.94 (m, 2H), 0.94-1.02 (m, 2H), 3.45-3.53 (m, 2H), 3.69-3.77 (m, 2H), 5.41 (s, 2H), 5.55 (s, 2H), 7.20 (s, 1H), 8.18 (s, 1H).
IR Spectrum (KBr, cm$^{-1}$): 1651.

18-(c) 3-Methyl-1,5-bis(2-trimethylsilylethoxymethyl)-1,5-dihydropyrrolo[2,3-d]pyridazin-4-one 1 ml of tetrahydrofuran was added to 34 mg (0.15 mmol) of palladium acetate and 126 mg (0.306 mmol) of 2-dicyclohexylphosphino-2',6'-dimethoxybiphenyl, the mixture was degassed under reduced pressure and replaced with argon. Then, the mixture was stirred at room temperature for 30 minutes. Thereafter, 1.59 g (3.04 mmol) of 3-iodo-1,5-bis(2-trimethylsilylethoxymethyl)-1,5-dihydropyrrolo[2,3-d]pyridazin-4-one obtained in Reference example 18-(b), 551 mg (9.20 mmol) of methylboronic acid, 2.62 g (12.3 mmol) of potassium phosphate and 9 ml of toluene were added to the mixture, and after the resulting mixture was again degassed under reduced pressure and replaced with argon, the mixture was stirred at 100° C. for 4 hours. After completion of the reaction, water was added to the reaction mixture, and the mixture was extracted with ethyl acetate. The organic layer after separation was washed with a saturated aqueous solution of sodium chloride, dried over anhydrous magnesium sulfate and then concentrated under reduced pressure. The obtained residue was applied to silica gel column chromatography (Eluent; hexane:ethyl acetate=19:1→3:2 (V/V)), and the fractions containing the desired compound were concentrated under reduced pressure to obtain 1.15 g of the title compound as a yellowish solid. (Yield: 92%)

Mass Spectrum (CI, m/z): 410 ($M^++1$).
$^1$H-NMR Spectrum (CDCl$_3$, δ ppm): −0.03 (s, 9H), −0.01 (s, 9H), 0.85-0.94 (m, 2H), 0.94-1.02 (m, 2H), 2.47 (d, J=1.0 Hz, 3H), 3.43-3.50 (m, 2H), 3.68-3.76 (m, 2H), 5.37 (s, 2H), 5.56 (s, 2H), 6.86 (d, J=1.0 Hz, 1H), 8.11 (s, 1H).
IR Spectrum (KBr, cm$^{-1}$): 1648.

18-(d) 2-Bromo-3-methyl-1,5-bis(2-trimethylsilylethoxymethyl)-1,5-dihydropyrrolo[2,3-d]pyridazin-4-one To 25 ml of acetonitrile solution containing 1.13 g (2.76 mmol) of 3-methyl-1,5-bis(2-trimethylsilylethoxymethyl)-1,5-dihydropyrrolo[2,3-d]pyridazin-4-one obtained in Reference example 18-(c) was added 516 mg (2.90 mmol) of N-bromosuccineimide, and the mixture was stirred at room temperature for 3 hours. After completion of the reaction, ethyl acetate was added to the reaction mixture, and the mixture was washed successively with 5% aqueous sodium hydrogen sulfite solution, a saturated aqueous solution of sodium hydrogencarbonate and a saturated aqueous solution of sodium chloride, dried over anhydrous magnesium sulfate and then concentrated under reduced pressure. The obtained residue was applied to silica gel column chromatography (Eluent; hexane:ethyl acetate=1:0→7:3 (V/V)), and the fractions containing the desired compound were concentrated under reduced pressure to obtain 1.31 g of the title compound as a pale yellowish solid. (Yield: 97%)

Mass Spectrum (CI, m/z): 488 ($M^++1$).
$^1$H-NMR Spectrum (CDCl$_3$, δ ppm): −0.03 (s, 9H), −0.01 (s, 9H), 0.87-0.94 (m, 2H), 0.95-1.02 (m, 2H), 2.46 (s, 3H), 3.51-3.58 (m, 2H), 3.67-3.75 (m, 2H), 5.51 (s, 2H), 5.55 (s, 2H), 8.11 (s, 1H).
IR Spectrum (KBr, cm$^{-1}$): 1669.

Reference Example 19

2-Bromo-3-ethyl-1,5-bis(2-trimethylsilylethoxymethyl)-1,5-dihydropyrrolo[2,3-d]pyridazin-4-one 19-(a) 1,5-Bis(2-trimethylsilylethoxymethyl)-3-trimethylsilylethynyl-1,5-dihydropyrrolo[2,3-d]pyridazin-4-one To 50 ml of tetrahydrofuran solution containing 16.6 g (purity: 78.4%, 25.0 mmol) of 3-iodo-1,5-bis(2-trimethylsilylethoxymethyl)-1,5-dihydropyrrolo[2,3-d]pyridazin-4-one obtained in Reference example 18-(b) were added 880 mg (1.25 mmol) of bis(triphenylphosphine)palladium dichloride, 620 mg (3.25 mmol) of cuprous iodide, 1.31 g (5.00 mmol) of triphenylphosphine and 10.5 ml (75.3 mmol) of triethylamine, and the mixture was degassed under reduced pressure and replaced with argon. Then, 11 ml of trimethylsilylacetylene was added to the mixture, and the mixture was stirred at 60° C. for 24 hours. After completion of the reaction, water was added to the reaction mixture, and the mixture was extracted with toluene. The organic layer after separation was washed successively with a saturated aqueous solution of ammonium chloride and a saturated aqueous solution of sodium chloride, dried over anhydrous magnesium sulfate, and concentrated under reduced pressure. The obtained residue was applied to silica gel column chromatography (Eluent; hexane:ethyl acetate=9:1→4:1 (V/V)), and the fractions containing the desired compound were concentrated under reduced pressure to obtain 10.8 g of the title compound as a yellowish solid. (Yield: 88%)

Mass Spectrum (CI, m/z): 492 ($M^++1$).
$^1$H-NMR Spectrum (CDCl$_3$, δ ppm): −0.03 (s, 9H), −0.01 (s, 9H), 0.27 (s, 9H), 0.85-0.94 (m, 2H), 0.94-1.02 (m, 2H), 3.42-3.50 (m, 2H), 3.67-3.75 (m, 2H), 5.40 (s, 2H), 5.57 (s, 2H), 7.26 (s, 1H), 8.14 (s, 1H).
IR Spectrum (KBr, cm$^{-1}$): 1669.

19-(b) 3-Ethynyl-1,5-bis(2-trimethylsilylethoxymethyl)-1,5-dihydropyrrolo[2,3-d]pyridazin-4-one To 150 ml of methanol solution containing 10.8 g (22.0 mmol) of 1,5-bis(2-trimethylsilylethoxymethyl)-3-trimethylsilylethynyl-1,5-dihydropyrrolo[2,3-d]pyridazin-4-one obtained in Reference example 19-(a) was added 1.00 g (7.23 mmol) of potassium carbonate, and the mixture was stirred at room temperature for 3.5 hours. After completion of the reaction, water and a saturated aqueous solution of sodium chloride were added to the reaction mixture, and the mixture was extracted with ethyl acetate. The organic layer after separation was washed with a saturated aqueous solution of sodium chloride, dried over anhydrous magnesium sulfate and concentrated under reduced pressure. The obtained residue was applied to silica gel column chromatography (Eluent; hexane: ethyl acetate=7:3 (V/V)), and the fractions containing the desired compound were concentrated under reduced pressure to obtain 8.58 g of the title compound as a pale yellowish solid. (Yield: 93%)

Mass Spectrum (CI, m/z): 420 ($M^+$+1).

$^1$H-NMR Spectrum (CDCl$_3$, δ ppm): −0.03 (s, 9H), −0.01 (s, 9H), 0.86-1.01 (m, 4H), 3.25 (s, 1H), 3.45-3.53 (m, 2H), 3.69-3.77 (m, 2H), 5.42 (s, 2H), 5.58 (s, 2H), 7.32 (s, 1H), 8.17 (s, 1H).

IR Spectrum (KBr, cm$^{-1}$): 1658.

19-(c) 3-Ethyl-1,5-bis(2-trimethylsilylethoxymethyl)-1,5-dihydropyrrolo[2,3-d]pyridazin-4-one To 8.56 g (20.4 mmol) of 3-ethynyl-1,5-bis(2-trimethylsilylethoxymethyl)-1,5-dihydropyrrolo[2,3-d]pyridazin-4-one obtained in Reference example 19-(b) were added 300 ml of ethanol and 200 ml of tetrahydrofuran, then, 2.0 g of 5% palladium-active carbon was added to the mixture, and the mixture was stirred under 1 atm hydrogen atmosphere at room temperature for 15 hours. After completion of the reaction, insoluble material was removed from the reaction suspension by filtration, and the filtrate was concentrated under reduced pressure. The obtained residue was applied to silica gel column chromatography (Eluent; hexane:ethyl acetate=9: 1→4:1 (V/V)), and the fractions containing the desired compound were concentrated under reduced pressure to obtain 8.00 g of the title compound as a pale yellowish solid. (Yield: 93%)

Mass Spectrum (CI, m/z): 424 ($M^+$+1).

$^1$H-NMR Spectrum (CDCl$_3$, δ ppm): −0.04 (s, 9H), −0.02 (s, 9H), 0.85-0.94 (m, 2H), 0.94-1.02 (m, 2H), 1.29 (t, J=7.5 Hz, 3H), 2.93 (qd, J=7.5, 1.0 Hz, 2H), 3.44-3.51 (m, 2H), 3.68-3.76 (m, 2H), 5.38 (s, 2H), 5.57 (s, 2H), 6.88 (t, J=1.0 Hz, 1H), 8.12 (s, 1H).

IR Spectrum (KBr, cm$^{-1}$): 1648.

19-(d) 2-Bromo-3-ethyl-1,5-bis(2-trimethylsilylethoxymethyl)-1,5-dihydropyrrolo[2,3-d]pyridazin-4-one Reaction and post treatment were carried out in the same manner as in Reference example 18-(d) except for using 6.61 g (15.6 mmol) of 3-ethyl-1,5-bis-(2-trimethylsilylethoxymethyl)-1,5-dihydropyrrolo[2,3-d]pyridazin-4-one obtained in Reference example 19-(c) in place of 3-methyl-1,5-bis(2-trimethylsilylethoxymethyl)-1,5-dihydropyrrolo-[2,3-d]pyridazin-4-one, whereby 7.91 g of the title compound was obtained as a white solid substantially quantitatively.

Mass Spectrum (EI, m/z): 501 ($M^+$).

$^1$H-NMR Spectrum (CDCl$_3$, δ ppm): −0.03 (s, 9H), −0.02 (s, 9H), 0.86-1.02 (m, 4H), 1.23 (t, J=7.5 Hz, 3H), 2.89 (q, J=7.5 Hz, 2H), 3.51-3.59 (m, 2H), 3.68-3.76 (m, 2H), 5.52 (s, 2H), 5.56 (s, 2H), 8.11 (s, 1H).

IR Spectrum (KBr, cm$^{-1}$): 1649.

Reference Example 20

2-Bromo-3-propyl-1,5-bis(2-trimethylsilylethoxymethyl)-1,5-dihydropyrrolo[2,3-d]pyridazin-4-one

20-(a) 3-Bromo-1,5-bis(2-trimethylsilylethoxymethyl)-1,5-dihydropyrrolo[2,3-d]pyridazin-4-one To 1 L of acetonitrile solution containing 109 g (0.274 mol) of 1,5-bis(2-trimethylsilylethoxymethyl)-1,5-dihydropyrrolo[2,3-d]pyridazin-4-one obtained in Reference example 18-(a) was added 58.6 g (0.329 mol) of N-bromosuccineimide by dividing it into several portions at room temperature, and the mixture was stirred at 35° C. for 9 hours. After completion of the reaction, to the reaction mixture were added 5% aqueous sodium thiosulfate solution and a saturated aqueous solution of sodium hydrogencarbonate, and the mixture was extracted with ethyl acetate. The organic layer after separation was washed successively with a saturated aqueous solution of sodium hydrogencarbonate and a saturated aqueous solution of sodium chloride, dried over anhydrous magnesium sulfate and concentrated under reduced pressure. The obtained crude solid was recrystallized from 600 ml of a mixed solvent (cyclohexane:hexane=1:2 (V/V)) to obtain 105 g of the title compound as a pale reddish solid. (Yield: 80%)

Mass Spectrum (CI, m/z): 474 ($M^+$+1).

$^1$H-NMR Spectrum (CDCl$_3$, δ ppm): −0.02 (s, 9H), −0.01 (s, 9H), 0.87-1.02 (m, 4H), 3.45-3.54 (m, 2H), 3.69-3.77 (m, 2H), 5.40 (s, 2H), 5.56 (s, 2H), 7.13 (s, 1H), 8.16 (s, 1H).

IR Spectrum (KBr, cm$^{-1}$): 1649.

20-(b) 3-Propyl-1,5-bis(2-trimethylsilylethoxymethyl)-1,5-dihydropyrrolo[2,3-d]pyridazin-4-one To 2.37 g (5.00 mmol) of 3-bromo-1,5-bis(2-trimethylsilylethoxymethyl)-1,5-dihydropyrrolo[2,3-d]pyridazin-4-one obtained in Reference example 20-(a) were added 1.76 g (20 mmol) of propylboronic acid, 4.25 g (20 mmol) of potassium phosphate, 15.8 ml of toluene, 0.95 ml of water, 56 mg of palladium acetate and 179 mg of butyl-di-1-adamantylphosphine, and the mixture was degassed under reduced pressure, replaced with argon and stirred at 100° C. for 5.5 hours. After completion of the reaction, water was added to the reaction mixture, and the mixture was extracted with toluene. The organic layer after separation was washed with a saturated aqueous solution of sodium chloride, dried over anhydrous magnesium sulfate and concentrated under reduced pressure. The obtained residue was applied to silica gel column chromatography (Eluent; hexane:ethyl acetate=7:1→5:1 (V/V)), and the fractions containing the desired compound were concentrated under reduced pressure to obtain 834 mg of the title compound as a pale brownish solid. (Yield: 38%)

Mass Spectrum (CI, m/z): 438 ($M^+$+1).

$^1$H-NMR Spectrum (CDCl$_3$, δ ppm): −0.04 (s, 9H), −0.02 (s, 9H), 0.85-0.93 (m, 2H), 0.93-1.03 (m, 2H), 0.96 (t, J=7.5 Hz, 3H), 1.65-1.78 (m, 2H), 2.86 (td, J=7.5, 0.6 Hz, 2H), 3.43-3.51 (m, 2H), 3.68-3.75 (m, 2H), 5.38 (s, 2H), 5.57 (s, 2H), 6.87 (t, J=0.6 Hz, 1H), 8.12 (s, 1H).

20-(c) 2-Bromo-3-propyl-1,5-bis(2-trimethylsilylethoxymethyl)-1,5-dihydropyrrolo[2,3-d]pyridazin-4-one Reaction and post treatment were carried out in the same manner as in Reference example 18-(d) except for using 833 mg (1:90 mmol) of 3-propyl-1,5-bis(2-trimethylsilylethoxymethyl)-1,5-dihydropyrrolo[2,3-d]pyridazin-4-one obtained in Reference example 20-(b) in place of 3-methyl-1,5-bis(2-trimethylsilylethoxymethyl)-1,5-dihydropyrrolo-[2,3-d]pyridazin-4-one, whereby 901 mg of the title compound was obtained as a white solid. (Yield: 92%)

Mass Spectrum (CI, m/z): 516 ($M^+$+1).

$^1$H-NMR Spectrum (CDCl$_3$, δ ppm): −0.04 (s, 9H), −0.02 (s, 9H), 0.86-1.01 (m, 4H), 0.95 (t, J=7.2 Hz, 3H), 1.62-1.76 (m, 2H), 2.80-2.88 (m, 2H), 3.50-3.58 (m, 2H), 3.67-3.76 (m, 2H), 5.52 (s, 2H), 5.56 (s, 2H), 8.11 (s, 1H)

IR Spectrum (KBr, cm$^{-1}$): 1650. .

Reference Example 21

1-Benzyloxymethyl-2-bromo-3-isopropyl-5-(2-trimethylsilylethoxymethyl)-1,5-dihydropyrrolo[2,3-d]pyridazin-4-one 21-(a) 1-Benzyloxymethyl-1,5-dihydropyrrolo[2,3-d]pyridazin-4-one To 33.4 g (100 mmol) of 1-benzyloxymethyl-2-bromo-1,5-dihydropyrrolo[2,3-d]pyridazin-4-one obtained in Reference example 17-(d) were added 4.5 g of 5% palladium-active carbon, 330 ml of toluene, 330 ml of tetrahydrofuran and 21 ml (121 mmol) of N,N-diisopropylethylamine, and the mixture was stirred under 1 atm hydrogen atmosphere at 60° C. for 1 hour. After completion of the reaction, the insoluble material in the reaction suspension was removed by filtration, followed by washing with 300 ml of a mixed solution (chloroform/methanol=1/1 (V/V)), and the filtrate and the washing solution were combined, then concentrated under reduced pressure. To the obtained concentrate was added 400 ml of water, and the mixture was extracted with a mixed solvent comprising 500 ml of chloroform and 30 ml of ethanol. The organic layer after separation was washed successively with water and a saturated aqueous solution of sodium chloride, dried over anhydrous magnesium sulfate, and concentrated under reduced pressure to obtain 24.3 g of the title compound as a yellowish brown solid. (Yield: 95%)

Mass Spectrum (CI, m/z): 376 ($M^+$+1).

$^1$H-NMR Spectrum (CDCl$_3$, δ ppm): 4.46 (s, 2H), 5.52 (s, 2H), 6.91 (dd, J=3.0, 0.7 Hz, 1H), 7.14 (d, J=3.0 Hz, 1H), 7.23-7.41 (m, 5H), 8.16 (d, J=0.7 Hz, 1H), 10.10 (brs, 1H).

21-(b) 1-Benzyloxymethyl-3-iodo-1,5-dihydropyrrolo[2,3-d]-pyridazin-4-one

Reaction and post treatment were carried out in the same manner as in Reference example 18-(b) except for using 5.38 g (21.1 mmol) of 1-benzyloxymethyl-1,5-dihydropyrrolo-[2,3-d]pyridazin-4-one obtained in Reference example 21-(a) in place of 1,5-bis(2-trimethylsilylethoxymethyl)-1,5-dihydropyrrolo[2,3-d]pyridazin-4-one, whereby 5.43 g of the title compound was obtained as a beige solid. (Yield: 68%)

Mass Spectrum (CI, m/z): 382 ($M^+$+1).

$^1$H-NMR Spectrum (DMSO-d$_6$, δ ppm): 4.50 (s, 2H), 5.69 (s, 2H), 7.21-7.36 (m, 5H), 7.74 (s, 1H), 8.41 (s, 1H), 12.40 (brs, 1H).

21-(c) 3-Acetyl-1-benzyloxymethyl-1,5-dihydropyrrolo[2,3-d]pyridazin-4-one

To 43 ml of dehydrated N,N-dimethylformamide solution containing 6.48 g (17.0 mmol) of 1-benzyloxymethyl-3-iodo-1,5-dihydropyrrolo[2,3-d]pyridazin-4-one obtained in Reference example 21-(b) were added 0.19 g (0.46 mmol) of 1,3-bis(diphenylphosphino)propane, 94 mg (0.42 mmol) of palladium acetate and 8.4 g (83.9 mmol) of butyl-vinyl ether, and after degassing under reduced pressure, 4.7 ml of triethylamine was further added to the mixture under nitrogen atmosphere, and the mixture was stirred at 100° C. for 7.5 hours. After completion of the reaction, the reaction mixture was concentrated under reduced pressure, the obtained residue was applied to silica gel column chromatography (Eluent; toluene:ethyl acetate=7:3 (V/V)), and the fractions containing the desired compound were concentrated under reduced pressure to obtain 2.02 g of the title compound as a pale yellowish solid. (Yield: 40%)

Mass Spectrum (CI, m/z): 298 ($M^+$+1).

$^1$H-NMR Spectrum (DMSO-d$_6$, δ ppm): 2.77 (s, 3H), 4.52 (s, 2H), 5.78 (s, 2H), 7.20-7.36 (m, 5H), 8.15 (s, 1H), 8.45 (s, 1H), 12.63 (brs, 1H).

21-(d) 1-Benzyloxymethyl-3-(1-hydroxy-1-methylethyl)-1,5-dihydropyrrolo[2,3-d]pyridazin-4-one To 87 ml of tetrahydrofuran solution containing 1.69 g (5.7 mmol) of 3-acetyl-1-benzyloxymethyl-1,5-dihydropyrrolo[2,3-d]pyridazin-4-one obtained in Reference example 21-(c) was added dropwise 7.5 ml of 3M methyl magnesium bromide in diethyl ether solution under ice-cooling, and the mixture was stirred at room temperature for 3 hours. After completion of the reaction, a saturated aqueous solution of ammonium chloride was added to the reaction mixture, and the mixture was extracted with ethyl acetate. The organic layer after separation was washed with a saturated aqueous solution of sodium chloride, dried over anhydrous magnesium sulfate and concentrated under reduced pressure. The obtained residue was applied to silica gel column chromatography (Eluent; toluene:ethyl acetate=7:3 (V/V)), and the fractions containing the desired compound were concentrated under reduced pressure to obtain 1.66 g of the title compound as a white solid. (Yield: 93%)

Mass Spectrum (CI, m/z): 314 ($M^+$+1).

$^1$H-NMR Spectrum (CDCl$_3$, δ ppm): 1.64 (s, 6H), 4.47 (s, 2H), 5.48 (s, 2H), 6.26 (brs, 1H), 6.94 (s, 1H), 7.21-7.42 (m, 5H), 8.17 (s, 1H), 10.55 (brs, 1H).

21-(e) 1-Benzyloxymethyl-3-isopropyl-1,5-dihydropyrrolo-[2,3-d]pyridazin-4-one

To 13 ml of dichloromethane solution containing 2.47 g of triethylsilane was added 1.31 ml of boron trifluoride diethyl ether complex under ice-cooling, then 30 ml of dichloromethane solution containing 1.65 g (5.3 mmol) of 1-benzyloxymethyl-3-(1-hydroxy-1-methylethyl)-1,5-dihydropyrrolo[2,3-d]pyridazin-4-one obtained in Reference example 21-(d) was added dropwise to the mixture, and the mixture was stirred at room temperature for 22 hours. After completion of the reaction, a saturated aqueous solution of sodium hydrogencarbonate was added to the reaction mixture, and the mixture was extracted with chloroform. The organic layer after separation was washed with a saturated aqueous solution of sodium chloride, dried over anhydrous magnesium sulfate and concentrated under reduced pressure. The obtained residue was applied to silica gel column chromatography (Eluent; toluene:ethyl acetate=7:3 (V/V)), and the fractions containing the desired compound were concentrated under reduced pressure to obtain 0.98 g of the title compound as a white solid. (Yield: 62%)

Mass Spectrum (CI, m/z): 298 ($M^+$+1).

$^1$H-NMR Spectrum (CDCl$_3$, δ ppm): 1.33 (d, J=6.8 Hz, 6H), 3.41-3.55 (m, 1H), 4.46 (s, 2H), 5.45 (s, 2H), 6.88 (d, J=0.7 Hz, 1H), 7.22-7.41 (m, 5H), 8.07 (s, 1H), 9.85 (brs, 1H).

21-(f) 1-Benzyloxymethyl-3-isopropyl-5-(2-trimethylsilylethoxymethyl)-1,5-dihydropyrrolo[2,3-d]pyridazin-4-one Reaction was carried out in the same manner as in Reference example 18-(a) except for using 0.98 g (3.3 mmol) of 1-benzyloxymethyl-3-isopropyl-1,5-dihydropyrrolo[2,3-d]-pyridazin-4-one obtained in Reference example 21-(e) in place of 1-(2-trimethylsilylethoxymethyl)-1,5-dihydropyrrolo[2,3-d]pyridazin-4-one. After completion of the reaction, the reaction mixture was poured into ice-water, neutralized with a saturated aqueous solution of ammonium chloride and extracted with toluene. The organic layer after separation was washed successively with water and a saturated aqueous solution of sodium chloride, dried over anhydrous magnesium sulfate and concentrated under reduced pressure. The obtained residue was applied to silica gel column chromatography (Eluent; hexane:ethyl acetate=3:2 (V/V)), and the fractions containing the desired compound were concentrated under reduced pressure to obtain 0.87 g of the title compound as a slightly yellowish oil. (Yield: 62%)

Mass Spectrum (CI, m/z): 428 ($M^+$+1).

$^1$H-NMR Spectrum (CDCl$_3$, δ ppm): −0.01 (s, 9H), 0.93-1.04 (m, 2H), 1.32 (d, J=6.8 Hz, 6H), 3.45-3.59 (m, 1H), 3.69-3.78 (m, 2H), 4.45 (s, 2H), 5.43 (s, 2H), 5.58 (s, 2H), 6.86 (d, J=0.7 Hz, 1H), 7.23-7.40 (m, 5H), 8.07 (s, 1H).

21-(g) 1-Benzyloxymethyl-2-bromo-3-isopropyl-5-(2-trimethylsilylethoxymethyl)-1,5-dihydropyrrolo[2,3-d]pyridazin-4-one Reaction and post treatment were carried out in the same manner as in Reference example 18-(d) except for using 0.87 g (2.0 mmol) of 1-benzyloxymethyl-3-isopropyl-5-(2-trimethylsilylethoxymethyl)-1,5-dihydropyrrolo[2,3-d]pyridazin-4-one obtained in Reference example 21-(f) in place of 3-methyl-1,5-bis(2-trimethylsilylethoxymethyl)-1,5-dihydropyrrolo[2,3-d]pyridazin-4-one, whereby 932 mg of the title compound was obtained as a slightly yellowish oil. (Yield: 92%)

Mass Spectrum (CI, m/z): 506 ($M^+$+1).

$^1$H-NMR Spectrum (CDCl$_3$, δ ppm): −0.01 (s, 9H), 0.94-1.03 (m, 2H), 1.41 (d, J=7.1 Hz, 6H), 3.37-3.52 (m, 1H), 3.69-3.76 (m, 2H), 4.55 (s, 2H), 5.57 (s, 2H), 5.59 (s, 2H), 7.15-7.37 (m, 5H), 8.05 (s, 1H).

Reference Example 22

2-Bromo-3-butyl-1,5-bis(2-trimethylsilylethoxymethyl)-1,5-dihydropyrrolo[2,3-d]pyridazin-4-one 22-(a) 3-Butyl-1,5-bis(2-trimethylsilylethoxymethyl)-1,5-dihydropyrrolo[2,3-d]pyridazin-4-one Reaction and post treatment were carried out in the same manner as in Reference example 20-(b) except for using 430 mg (4.20 mmol) of butylboronic acid in place of propylboronic acid, whereby 550 mg of the title compound was obtained as a yellowish solid. (Yield: 58%)

Mass Spectrum (CI, m/z): 452 ($M^+$+1).

$^1$H-NMR Spectrum (CDCl$_3$, δ ppm): −0.04 (s, 9H), −0.02 (s, 9H), 0.85-0.93 (m, 2H), 0.93 (t, J=7.3 Hz, 3H), 0.94-1.02 (m, 2H), 1.32-1.46 (m, 2H), 1.59-1.73 (m, 2H), 2.89 (td, J=7.6, 0.6 Hz, 2H), 3.43-3.50 (m, 2H), 3.68-3.76 (m, 2H), 5.38 (s, 2H), 5.57 (s, 2H), 6.87 (t, J=0.6 Hz, 1H), 8.12 (s, 1H).

IR Spectrum (KBr, cm$^{-1}$): 1665.

22-(b) 2-Bromo-3-butyl-1,5-bis(2-trimethylsilylethoxymethyl)-1,5-dihydropyrrolo[2,3-d]pyridazin-4-one Reaction and post treatment were carried out in the same manner as in Reference example 18-(d) except for using 6.00 g (13.3 mmol) of 3-butyl-1,5-bis(2-trimethylsilylethoxymethyl)-1,5-dihydropyrrolo[2,3-d]pyridazin-4-one obtained in Reference example 22-(a) in place of 3-methyl-1,5-bis(2-trimethylsilylethoxymethyl)-1,5-dihydropyrrolo-[2,3-d]pyridazin-4-one, whereby 6.89 g of the title compound was obtained as a pale yellowish solid. (Yield: 98%)

Mass Spectrum (CI, m/z): 530 ($M^+$+1).

$^1$H-NMR Spectrum (CDCl$_3$, δ ppm): −0.04 (s, 9H), −0.02 (s, 9H), 0.86-1.02 (m, 4H), 0.92 (t, J=7.4 Hz, 3H), 1.30-1.44 (m, 2H), 1.58-1.69 (m, 2H), 2.87 (t, J=7.4 Hz, 2H), 3.50-3.58 (m, 2H), 3.67-3.75 (m, 2H), 5.52 (s, 2H), 5.56 (s, 2H), 8.11 (s, 1H).

IR Spectrum (KBr, cm$^{-1}$): 1658.

Reference Example 23

2-Bromo-3-isobutyl-1,5-bis(2-trimethylsilylethoxymethyl)-1,5-dihydropyrrolo[2,3-d]pyridazin-4-one 23-(a) 3-Isobutyl-1,5-bis(2-trimethylsilylethoxymethyl)-1,5-dihydropyrrolo[2,3-d]pyridazin-4-one Reaction and post treatment were carried out in the same manner as in Reference example 20-(b) except for using 3.87 g (37.9 mmol) of isobutylboronic acid in place of propylboronic acid, using 423 mg (1.27 mmol) of 2-dicyclohexylphosphino-2',6'-dimethoxybiphenyl in place of butyl-di-1-adamantylphosphine, and using toluene alone in place of toluene and water as a solvent, respectively, whereby 3.52 g of the title compound was obtained as a yellowish solid. (Yield: 67%)

Mass Spectrum (CI, m/z): 452 ($M^+$+1).

$^1$H-NMR Spectrum (CDCl$_3$, δ ppm): −0.04 (s, 9H), −0.02 (s, 9H), 0.85-0.92 (m, 2H), 0.92 (d, J=6.6 Hz, 6H), 0.95-1.01 (m, 2H), 1.96-2.10 (m, 1H), 2.74 (dd, J=7.1, 0.5 Hz, 2H), 3.42-3.50 (m, 2H), 3.67-3.76 (m, 2H), 5.39 (s, 2H), 5.57 (s, 2H), 6.86 (t, J=0.5 Hz, 1H), 8.13 (s, 1H).

IR Spectrum (KBr, cm$^{-1}$): 1664.

23-(b) 2-Bromo-3-isobutyl-1,5-bis(2-trimethylsilylethoxymethyl)-1,5-dihydropyrrolo[2,3-d]pyridazin-4-one Reaction and post treatment were carried out in the same manner as in Reference example 18-(d) except for using 4.46 g (9.87 mmol) of 3-isobutyl-1,5-bis(2-trimethylsilylethoxymethyl)-1,5-dihydropyrrolo[2,3-d]pyridazin-4-one obtained in Reference example 23-(a) in place of 3-methyl-1,5-bis(2-trimethylsilylethoxymethyl)-1,5-dihydropyrrolo-[2,3-d]pyridazin-4-one, whereby 4.82 g of the title compound was obtained as a pale yellowish solid. (Yield: 92%)

Mass Spectrum (CI, m/z): 530 ($M^+$+1).

$^1$H-NMR Spectrum (CDCl$_3$, δ ppm): −0.04 (s, 9H), −0.02 (s, 9H), 0.85-0.93 (m, 2H), 0.93 (d, J=6.6 Hz, 6H), 0.93-1.01 (m, 2H), 2.05-2.17 (m, 1H), 2.73 (d, J=7.3 Hz, 2H), 3.50-3.58 (m, 2H), 3.66-3.75 (m, 2H), 5.54 (s, 2H), 5.56 (s, 2H), 8.12 (s, 1H).

Reference Example 24

2-Bromo-3-formyl-1-(2-trimethylsilylethoxymethyl)-1,5-dihydropyrrolo[2,3-d]pyridazin-4-one 24-(a) 5-Benzyloxymethyl-1-(2-trimethylsilylethoxymethyl)-1,5-dihydropyrrolo[2,3-d]pyridazin-4-one Reaction was carried out in the same manner as in Reference example 18-(a) except for using 9.26 g (51.2 mmol) of benzyloxymethyl chloride in place of (2-trimethylsilylethoxy)methyl chloride. After completion of the reaction, the reaction mixture was poured into ice-water, neutralized with a saturated aqueous solution of ammonium chloride and extracted with toluene. The organic layer after separation was washed successively with water and a saturated aqueous solution of sodium chloride, dried over anhydrous magnesium sulfate and concentrated under reduced pressure. The obtained residue was applied to silica gel column chromatography (Eluent; hexane:ethyl acetate=3:2 (V/V)), and the fractions containing the desired compound were concentrated under reduced pressure to obtain 10.5 g of the title compound as a pale yellowish solid. (Yield: 69%)

$^1$H-NMR Spectrum (DMSO-$d_6$, δ ppm): −0.10 (s, 9H), 0.77-0.85 (m, 2H), 3.43-3.51 (m, 2H), 4.61 (s, 2H), 5.54 (s, 2H), 5.61 (s, 2H), 6.74 (dd, J=3.0, 0.7 Hz, 1H), 7.21-7.35 (m, 5H), 7.58 (d, J=3.0 Hz, 1H), 8.48 (d, J=0.7 Hz, 1H).

24-(b) 5-Benzyloxymethyl-3-bromo-1-(2-trimethylsilylethoxymethyl)-1,5-dihydropyrrolo[2,3-d]pyridazin-4-one Reaction and post treatment were carried out in the same manner as in Reference example 20-(a) except for using 27.2 g (71 mmol) of 5-benzyloxymethyl-1-(2-trimethylsilylethoxymethyl)-1,5-dihydropyrrolo[2,3-d]pyridazin-4-one obtained in Reference example 24-(a) in place of 1,5-bis(2-trimethylsilylethoxymethyl)-1,5-dihydropyrrolo[2,3-d]pyridazin-4-one, whereby 30.8 g of the title compound was obtained as a gray solid. (Yield: 93%)

$^1$H-NMR Spectrum (DMSO-$d_6$, δ ppm): −0.08 (s, 9H), 0.78-0.87 (m, 2H), 3.44-3.54 (m, 2H), 4.62 (s, 2H), 5.50 (s, 2H), 5.57 (s, 2H), 7.21-7.35 (m, 5H), 7.78 (s, 1H), 8.49 (s, 1H).

24-(c) 5-Benzyloxymethyl-3-methyl-1-(2-trimethylsilylethoxymethyl)-1,5-dihydropyrrolo[2,3-d]pyridazin-4-one Reaction and post treatment were carried out in the same manner as in Reference example 20-(b) except for using 30.8 g (66.3 mmol) of 5-benzyloxymethyl-3-bromo-1-(2-trimethylsilylethoxymethyl)-1,5-dihydropyrrolo[2,3-d]pyridazin-4-one obtained in Reference example 24-(b) in place of 3-bromo-1,5-bis(2-trimethylsilylethoxymethyl)-1,5-dihydropyrrolo[2,3-d]pyridazin-4-one, and using 12.0 g (200 mmol) of methylboronic acid in place of propylboronic acid, respectively, whereby 25.3 g of the title compound was obtained as a brownish oil. (Yield: 96%)

$^1$H-NMR Spectrum (DMSO-$d_6$, δ ppm): −0.09 (s, 9H), 0.76-0.86 (m, 2H), 2.34 (d, J=1.0 Hz, 3H), 3.41-3.51 (m, 2H), 4.61 (s, 2H), 5.50 (s, 2H), 5.52 (s, 2H), 7.21-7.35 (m, 6H), 8.40 (s, 1H).

24-(d) 3-Methyl-1-(2-trimethylsilylethoxymethyl)-1,5-dihydropyrrolo[2,3-d]pyridazin-4-one To 380 ml of ethanol solution containing 25.3 g (65 mmol) of 5-benzyloxymethyl-3-methyl-1-(2-trimethylsilylethoxymethyl)-1,5-dihydropyrrolo[2,3-d]pyridazin-4-one obtained in Reference example 24-(c) was added 25 g of 5% palladium-active carbon, and the mixture was stirred under 1 atm hydrogen atmosphere at room temperature for 2.5 hours. After completion of the reaction, insoluble material was removed from the reaction suspension by filtration, 100 ml of 28% aqueous ammonia was added to the obtained filtrate, and the mixture was stirred at room temperature for 5 hours. Then, the solution was concentrated under reduced pressure, 500 ml of water was added to the obtained concentrate, and precipitated solid was collected by filtration. The obtained solid was washed with water, and dried under reduced pressure to obtain 14.3 g of the title compound as a pale yellowish solid. (Yield: 79%)

Mass Spectrum (CI, m/z): 280($M^+$+1).

$^1$H-NMR Spectrum (DMSO-$d_6$, δ ppm): −0.09 (s, 9H), 0.76-0.84 (m, 2H), 2.32 (d, J=1.0 Hz, 3H), 3.41-3.48 (m, 2H), 5.49 (s, 2H), 7.24 (d, J=1.0 Hz, 1H), 8.30 (s, 1H), 12.17 (brs, 1H).

24-(e) 2-Bromo-3-methyl-1-(2-trimethylsilylethoxymethyl)-1,5-dihydropyrrolo[2,3-d]pyridazin-4-one Reaction and post treatment were carried out in the same manner as in Reference example 18-(d) except for using 14.3 g (51.2 mmol) of 3-methyl-1-(2-trimethylsilylethoxymethyl)-1,5-dihydropyrrolo[2,3-d]pyridazin-4-one obtained in Reference example 24-(d) in place of 3-methyl-1,5-bis(2-trimethylsilylethoxymethyl)-1,5-dihydropyrrolo[2,3-d]pyridazin-4-one, whereby 16.7 g of the title compound was obtained as a white solid. (Yield: 91%)

Mass Spectrum (CI, m/z): 358 ($M^+$+1).

$^1$H-NMR Spectrum (DMSO-$d_6$, δ ppm): −0.09 (s, 9H), 0.77-0.86 (m, 2H), 2.30 (s, 3H), 3.46-3.55 (m, 2H), 5.58 (s, 2H), 8.40 (s, 1H), 12.38 (brs, 1H).

24-(f) 2-Bromo-3-bromomethyl-1-(2-trimethylsilylethoxymethyl)-1,5-dihydropyrrolo[2,3-d]pyridazin-4-one To 4 ml of 1,2-dichloroethane solution containing 100 mg (0.28 mmol) of 2-bromo-3-methyl-1-(2-trimethylsilylethoxymethyl)-1,5-dihydropyrrolo[2,3-d]pyridazin-4-one obtained in Reference example 24-(e) was added 50 mg (0.28 mmol) of N-bromosuccineimide, and the mixture was stirred at 40° C. for 4 hours under irradiation with a mercury lamp (300 WH). After completion of the reaction, a saturated aqueous solution of sodium hydrogencarbonate was added to the reaction mixture, and the mixture was extracted with chloroform. The organic layer after separation was washed with a saturated aqueous solution of sodium chloride, dried over anhydrous sodium sulfate and concentrated under reduced pressure. The obtained residue was applied to silica gel column chromatography (Eluent; hexane:ethyl acetate=1:1 (V/V)), and the fractions containing the desired compound were concentrated under reduced pressure to obtain 39.3 mg of the title compound as a pale yellowish solid. (Yield: 32%)

$^1$H-NMR Spectrum (CDCl$_3$, δ ppm): −0.02 (s, 9H), 0.87-0.95 (m, 2H), 3.52-3.61 (m, 2H), 4.86 (s, 2H), 5.55 (s, 2H), 8.15 (s, 1H), 10.14 (brs, 1H).

24-(g) 2-Bromo-3-formyl-1-(2-trimethylsilylethoxymethyl)-1,5-dihydropyrrolo[2,3-d]pyridazin-4-one To 370 mg (4.2 mmol) of 2-nitropropane were added 10 ml of dehydrated ethanol and 1.43 g (4.2 mmol) of 20% sodium ethoxide ethanol solution, then, 500 mg (0.84 mmol) of 2-bromo-3-bromomethyl-1-(2-trimethylsilylethoxymethyl)-1,5-dihydropyrrolo[2,3-d]pyridazin-4-one obtained in Reference example 24-(f) was added to the mixture at 5° C., and the mixture was stirred at the same temperature for 1 hour. After completion of the reaction, ice water was added to the reaction mixture, and the mixture was extracted with ethyl acetate. The organic layer after separation was washed with a saturated aqueous solution of sodium chloride, dried over anhydrous sodium sulfate and concentrated under reduced pressure. The obtained residue was applied to silica gel column chromatography (Eluent; hexane:ethyl acetate=1:1 (V/V)), and the fractions containing the desired compound were concentrated under reduced pressure to obtain 167 mg of the title compound as a white solid. (Yield: 32%)

Mass Spectrum (CI, m/z): 372($M^+$+1).

$^1$H-NMR Spectrum (DMSO-$d_6$, δ ppm): −0.09 (s, 9H), 0.79-0.88 (m, 2H), 3.52-3.61 (m, 2H), 5.72 (s, 2H), 8.58 (s, 1H), 10.48 (s, 1H), 12.90 (brs, 1H).

Reference Example 25

2-Bromo-3-methoxymethyl-1,5-bis(2-trimethylsilylethoxymethyl)-1,5-dihydropyrrolo[2,3-d]pyridazin-4-one 25-(a) 2-Bromo-3-bromomethyl-1,5-bis(2-trimethylsilylethoxymethyl)-1,5-dihydropyrrolo[2,3-d]pyridazin-4-one To 250 ml of 1,2-dichloroethane solution containing 15.6 g (38.0 mmol) of 3-methyl-1,5-bis(2-trimethylsilylethoxymethyl)-1,5-dihydropyrrolo[2,3-d]pyridazin-4-one obtained in Reference example 18-(c) was added 15.9 g (89.3 mmol) of N-bromosuccineimide, and the mixture was stirred at room temperature for 4 hours under irradiation with a mercury lamp (300 WH). After completion of the reaction, water and a saturated aqueous solution of sodium hydrogencarbonate were added to the reaction mixture, and the mixture was extracted with ethyl acetate. The organic layer after separation was washed successively with a saturated aqueous solution of sodium hydrogencarbonate, water and a saturated aqueous solution of sodium chloride, dried over anhydrous magnesium sulfate and concentrated under reduced pressure. The obtained residue was applied to silica gel column chromatography (Eluent; toluene:ethyl acetate=4:1 (V/V)), and the fractions containing the desired compound were concentrated under reduced pressure to obtain 15.5 g of the title compound as a pale reddish solid. (Yield: 72%)

Mass Spectrum (CI, m/z): 566 ($M^+$+1).

$^1$H-NMR Spectrum (CDCl$_3$, δ ppm): −0.02 (s, 9H), −0.01 (s, 9H), 0.86-1.03 (m, 4H), 3.52-3.61 (m, 2H), 3.68-3.77 (m, 2H), 4.88 (s, 2H), 5.54 (s, 2H), 5.57 (s, 2H), 8.14 (s, 1H).

IR Spectrum (KBr, cm$^{-1}$): 1658.

25-(b) 2-Bromo-3-methoxymethyl-1,5-bis(2-trimethylsilylethoxymethyl)-1,5-dihydropyrrolo[2,3-d]pyridazin-4-one To 4 ml of tetrahydrofuran solution containing 459 mg (0.81 mmol) of 2-bromo-3-bromomethyl-1,5-bis(2-trimethylsilylethoxymethyl)-1,5-dihydropyrrolo[2,3-d]pyridazin-4-one obtained in Reference example 25-(a) was added 4 ml of 28% sodium methoxide methanol solution, and the mixture was stirred at room temperature for 2 hours. After completion of the reaction, water was added to the reaction mixture, and the mixture was extracted with ethyl acetate. The organic layer after separation was washed successively with water and a saturated aqueous solution of sodium chloride, dried over anhydrous magnesium sulfate and concentrated under reduced pressure. The obtained residue was applied to silica gel column chromatography (Eluent; hexane:ethyl acetate=4:1 (V/V)), and the fractions containing the desired compound were concentrated under reduced pressure to obtain 359 mg of the title compound as a colorless oil. (Yield: 86%)

Mass Spectrum (CI, m/z): 518 ($M^+$+1)

$^1$H-NMR Spectrum (CDCl$_3$, δ ppm): −0.03 (s, 9H), −0.02 (s, 9H), 0.85-1.02 (m, 4H), 3.44 (s, 3H), 3.53-3.61 (m, 2H), 3.67-3.75 (m, 2H), 4.76 (s, 2H), 5.55 (s, 2H), 5.57 (s, 2H), 8.15 (s, 1H).

IR Spectrum (KBr, cm$^{-1}$): 1668.

Reference Example 26

2-Bromo-3-ethoxymethyl-1-(2-trimethylsilylethoxymethyl)-1,5-dihydropyrrolo[2,3-d]pyridazin-4-one To 23 ml of ethanol solution containing 1.06 g (2.42 mmol) of 2-bromo-3-bromomethyl-1-(2-trimethylsilylethoxymethyl)-1,5-dihydropyrrolo[2,3-d]pyridazin-4-one obtained in Reference example 24-(f) was added 3.33 g (9.78 mmol) of 20% sodium ethoxide ethanol solution, and the mixture was stirred at room temperature for 1 hour. After completion of the reaction, water was added to the reaction mixture, and the mixture was extracted with ethyl acetate. The organic layer after separation was dried over anhydrous magnesium sulfate and concentrated under reduced pressure. The obtained residue was applied to silica gel column chromatography (Eluent; hexane:ethyl acetate=2:1→1:1 (V/V)), and the fractions containing the desired compound were concentrated under reduced pressure to obtain 549 mg of the title compound as a white solid. (Yield: 56%)

$^1$H-NMR Spectrum (CDCl$_3$, δ ppm): −0.02 (s, 9H), 0.88-0.95 (m, 2H), 1.23 (t, J=7.1 Hz, 3H), 3.54-3.61 (m, 2H), 3.64 (q, J=7.1 Hz, 2H), 4.80 (s, 2H), 5.56 (s, 2H), 8.14 (s, 1H) 9.94 (brs, 1H).

Reference Example 27

2-Bromo-3-cyclobutoxymethyl-1,5-bis(2-trimethylsilylethoxymethyl)-1,5-dihydropyrrolo[2,3-d]pyridazin-4-one To 10 ml of dehydrated tetrahydrofuran solution containing 0.89 g (12 mmol) of cyclobutanol was added 0.25 g (6.2 mmol) of sodium hydride (60% dispersed material in mineral oil) under ice-cooling, and the mixture was stirred at room temperature for 30 minutes. To the mixture was further added 0.70 g (1.2 mmol) of 2-bromo-3-bromomethyl-1,5-bis(2-trimethylsilylethoxymethyl)-1,5-dihydropyrrolo-[2,3-d]pyridazin-4-one obtained in Reference example 25-(a), and the mixture was stirred at 45° C. for 1 hour. After completion of the reaction, water was added to the reaction mixture, and the mixture was extracted with ethyl acetate. The organic layer after separation was washed with a saturated aqueous solution of sodium chloride, dried over anhydrous magnesium sulfate and concentrated under reduced pressure. The obtained residue was applied to silica gel column chromatography (Eluent; hexane:ethyl acetate=7:3 (V/V)), and the fractions containing the desired compound were concentrated under reduced pressure to obtain 561 mg of the title compound as a pale yellowish oil. (Yield: 82%)

$^1$H-NMR Spectrum (CDCl$_3$, δ ppm): −0.03 (s, 9H), −0.02 (s, 9H), 0.86-1.02 (m, 4H), 1.40-1.57 (m, 1H), 1.60-1.75 (m, 1H), 1.90-2.06 (m, 2H), 2.13-2.27 (m, 2H), 3.52-3.60 (m, 2H), 3.66-3.75 (m, 2H), 4.08-4.19 (m, 1H), 4.71 (s, 2H), 5.53 (s, 2H), 5.56 (s, 2H), 8.13 (s, 1H).

Reference Example 28

2-Bromo-3-cyclopropyl-1,5-bis(2-trimethylsilylethoxymethyl)-1,5-dihydropyrrolo[2,3-d]pyridazin-4-one

28-(a) 3-Cyclopropyl-1,5-bis(2-trimethylsilylethoxymethyl)-1,5-dihydropyrrolo[2,3-d]pyridazin-4-one Reaction and post treatment were carried out in the same manner as in Reference example 20-(b) except for using 7.00 g (purity: 78.4%, 10.5 mmol) of 3-iodo-1,5-bis(2-trimethylsilylethoxymethyl)-1,5-dihydropyrrolo[2,3-d]pyridazin-4-one obtained in Reference example 18-(b) in place of 3-bromo-1,5-bis(2-trimethylsilylethoxymethyl)-1,5-dihydropyrrolo[2,3-d]pyridazin-4-one, and using 589 mg (2.10 mmol) of tricyclohexylphosphine in place of butyl-di-1-adamantylphosphine, respectively, whereby 3.60 g of the title compound was obtained as a white solid. (Yield: 79%)

Mass Spectrum (CI, m/z): 436 ($M^+$+1).
$^1$H-NMR Spectrum (CDCl$_3$, δ ppm): −0.04 (s, 9H), −0.01 (s, 9H), 0.59-0.65 (m, 2H), 0.84-0.92 (m, 2H), 0.95-1.03 (m, 4H), 2.41-2.52 (m, 1H), 3.42-3.49 (m, 2H), 3.69-3.77 (m, 2H), 5.35 (s, 2H), 5.58 (s, 2H), 6.68 (d, J=0.7 Hz, 1H), 8.11 (s, 1H).
IR Spectrum (KBr, cm$^{-1}$): 1648.

28-(b) 2-Bromo-3-cyclopropyl-1,5-bis(2-trimethylsilylethoxymethyl)-1,5-dihydropyrrolo[2,3-d]pyridazin-4-one Reaction and post treatment were carried out in the same manner as in Reference example 18-(d) except for using 3.60 g (8.26 mmol) of 3-cyclopropyl-1,5-bis(2-trimethylsilylethoxymethyl)-1,5-dihydropyrrolo[2,3-d]pyridazin-4-one obtained in Reference example 28-(a) except for using 3-methyl-1,5-bis(2-trimethylsilylethoxymethyl)-1,5-dihydropyrrolo[2,3-d]pyridazin-4-one, whereby 4.11 g of the title compound was obtained as a pale yellowish solid. (Yield: 97%)

Mass Spectrum (CI, m/z): 514 ($M^+$+1).
$^1$H-NMR Spectrum (CDCl$_3$, δ ppm): −0.03 (s, 9H), −0.01 (s, 9H), 0.86-1.03 (m, 6H), 1.10-1.17 (m, 2H), 2.00-2.11 (m, 1H), 3.51-3.59 (m, 2H), 3.67-3.74 (m, 2H), 5.51 (s, 2H), 5.55 (s, 2H), 8.10 (s, 1H).
IR Spectrum (KBr, cm$^{-1}$): 1651.

Reference Example 29

2-Bromo-3-formyl-1,5-bis(2-trimethylsilylethoxymethyl)-1,5-dihydropyrrolo[2,3-d]pyridazin-4-one Reaction and post treatment were carried out in the same manner as in Reference example 24-(g) except for using 5.70 g (10.0 mmol) of 2-bromo-3-bromomethyl-1,5-bis(2-trimethylsilylethoxymethyl)-1,5-dihydropyrrolo[2,3-d]pyridazin-4-one obtained in Reference example 25-(a) in place of 2-bromo-3-bromomethyl-1-(2-trimethylsilylethoxymethyl)-1,5-dihydropyrrolo[2,3-d]pyridazin-4-one, whereby 3.38 g of the title compound was obtained as a white solid. (Yield: 67%)

Mass Spectrum (CI, m/z): 502($M^+$+1).
$^1$H-NMR Spectrum (CDCl$_3$, δ ppm): −0.02 (s, 9H), −0.01 (s, 9H), 0.88-1.03 (m, 4H), 3.53-3.64 (m, 2H), 3.69-3.77 (m, 2H), 5.61 (s, 2H), 5.65 (s, 2H), 8.24 (s, 1H), 10.70 (s, 1H)
IR Spectrum (KBr, cm$^{-1}$): 1686, 1664.

Reference Example 30

2-Chloro-3-triethylsilylethynyl-1-(2-trimethylsilylethoxymethyl)-1,5-dihydropyrrolo[2,3-d]pyridazin-4-one

30-(a) 3-Iodo-1-(2-trimethylsilylethoxymethyl)-1,5-dihydropyrrolo[2,3-d]pyridazin-4-one Reaction and post treatment were carried out in the same manner as in Reference example 18-(b) except for using 3.81 g (14.4 mmol) of 1-(2-trimethylsilylethoxymethyl)-1,5-dihydropyrrolo[2,3-d]pyridazin-4-one obtained in Reference example 16-(b) in place of 1,5-bis(2-trimethylsilylethoxymethyl)-1,5-dihydropyrrolo[2,3-d]pyridazin-4-one, whereby 4.28 g of the title compound was obtained as a beige solid. (Yield: 76%)

Mass Spectrum (CI, m/z): 392 ($M^+$+1).
$^1$H-NMR Spectrum (CDCl$_3$, δ ppm): −0.02 (s, 9H), 0.87-0.95 (m, 2H), 3.46-3.54 (m, 2H), 5.42 (s, 2H), 7.21 (s, 1H), 8.19 (s, 1H), 10.00 (brs, 1H).
IR Spectrum (KBr, cm$^{-1}$): 1659.

30-(b) 2-Chloro-3-iodo-1-(2-trimethylsilylethoxymethyl)-1,5-dihydropyrrolo[2,3-d]pyridazin-4-one To 40 ml of acetonitrile solution containing 3.00 g (7.66 mmol) of 3-iodo-1-(2-trimethylsilylethoxymethyl)-1,5-dihydropyrrolo[2,3-d]pyridazin-4-one obtained in Reference example 30-(a) was added 4.04 g (30.3 mmol) of N-chlorosuccineimide, and the mixture was stirred at 80° C. for 12 hours. After completion of the reaction, water was added to the reaction mixture, and the mixture was extracted with ethyl acetate. The organic layer after separation was washed successively with 5% aqueous sodium hydrogen sulfite solution, a saturated aqueous solution of sodium hydrogencarbonate and a saturated aqueous solution of sodium chloride, dried over anhydrous magnesium sulfate and concentrated under reduced pressure. The obtained residue was applied to silica gel column chromatography (Eluent; chloroform:ethyl acetate=7:3→1:1 (V/V)), and the fractions containing the desired compound were concentrated under reduced pressure to obtain 1.87 g of the title compound as a pale yellowish solid. (Yield: 57%)

$^1$H-NMR Spectrum (CDCl$_3$, δ ppm): −0.02 (s, 9H), 0.87-0.96 (m, 2H), 3.53-3.60 (m, 2H), 5.58 (s, 2H), 8.16 (s, 1H), 10.00 (brs, 1H).

30-(c) 2-Chloro-3-triethylsilylethynyl-1-(2-trimethylsilylethoxymethyl)-1,5-dihydropyrrolo[2,3-d]pyridazin-4-one To 61 mg (0.14 mmol) of 2-chloro-3-iodo-1-(2-trimethylsilylethoxymethyl)-1,5-dihydropyrrolo[2,3-d]pyridazin-4-one obtained in Reference example 30-(b) were added 5 mg of bis(triphenylphosphine)palladium dichloride, 4 mg of cuprous iodide, 8 mg of triphenylphosphine, 1 ml of diisopropylamine, 0.04 ml of triethylsilylacetylene and 0.4 ml of N,N-dimethylformamide, the mixture was degassed under reduced pressure and replaced with argon, and the mixture was stirred at 80° C. for 1.5 hours. After completion of the reaction, toluene was added to the reaction mixture, and the mixture was washed successively with 5% aqueous sodium hydrogen sulfite solution, a saturated aqueous solution of sodium hydrogencarbonate and a saturated aqueous solution of sodium chloride. The organic layer after separation was dried over anhydrous magnesium sulfate and concentrated under reduced pressure. The obtained residue was applied to silica gel column chromatography (Eluent; hexane:ethyl acetate=7:3→1:1 (V/V)), and the fractions containing the desired compound were concentrated under reduced pressure to obtain 47 mg of the title compound as a yellowish solid. (Yield: 75%)

Mass Spectrum (CI, m/z): 438 ($M^+$+1).

$^1$H-NMR Spectrum (CDCl$_3$, δ ppm): −0.02 (s, 9H), 0.72 (q, J=7.8 Hz, 6H), 0.87-0.95 (m, 2H), 1.09 (t, J=7.8 Hz, 9H), 3.51-3.59 (m, 2H), 5.53 (s, 2H), 8.10 (s, 1H), 9.89 (brs, 1H).

Reference Example 31

2-Chloro-3-phenyl-1-(2-trimethylsilylethoxymethyl)-1,5-dihydropyrrolo[2,3-d]pyridazin-4-one To 206 mg (0.484 mmol) of 2-chloro-3-iodo-1-(2-trimethylsilylethoxymethyl)-1,5-dihydropyrrolo[2,3-d]pyridazin-4-one obtained in Reference example 30-(b) were added 71 mg (0.58 mmol) of phenylboronic acid, 54 mg of tetrakistriphenylphosphine palladium, 6 ml of toluene, 4 ml of ethanol and 1 ml of 2M aqueous sodium carbonate solution, the mixture was degassed under reduced pressure and replaced with argon, and the mixture was stirred at 80° C. for 16 hours. After completion of the reaction, a saturated aqueous solution of sodium chloride was added to the reaction mixture, and the mixture was extracted with ethyl acetate. The organic layer after separation was dried over anhydrous magnesium sulfate and then concentrated under reduced pressure. The obtained residue was applied to silica gel column chromatography (Eluent; toluene:ethyl acetate=1:1 (V/V)), and the fractions containing the desired compound were concentrated under reduced pressure to obtain 152 mg of the title compound as a pale yellowish solid. (Yield: 84%)

Mass Spectrum (CI, m/z): 376 ($M^+$+1).

$^1$H-NMR Spectrum (CDCl$_3$, δ ppm): −0.01 (s, 9H), 0.90-1.00 (m, 2H), 3.59-3.67 (m, 2H), 5.62 (s, 2H), 7.33-7.67 (m, 5H), 8.19 (s, 1H), 9.91 (brs, 1H).

IR Spectrum (KBr, cm$^{-1}$): 1661.

Reference Example 32

2-Bromo-1,5-bis(2-trimethylsilylethoxymethyl)-3-[1-(2-trimethylsilylethoxymethyl)-4-pyrazolyl]-1,5-dihydropyrrolo-[2,3-d]pyridazin-4-one 32-(a) 4-(4,4,5,5-Tetramethyl-[1,3,2]dioxaborolan-2-yl)-1-(2-trimethylsilylethoxymethyl)-1H-pyrazole Under argon atmosphere, to 20 ml of tetrahydrofuran solution containing 1.09 g (5.62 mmol) of 4-(4,4,5,5-tetramethyl-[1,3,2]dioxaborolan-2-yl)-1H-pyrazole was added 443 mg (11.1 mmol) of 60% sodium hydride under ice-cooling, and the mixture was stirred for 5 minutes. Then, 3 ml (17.0 mmol) of (2-trimethylsilylethoxy)methyl chloride was added dropwise to the mixture, and the mixture was reacted at room temperature for 2 hours. After completion of the reaction, water was added to the reaction mixture, and the mixture was extracted with ethyl acetate. The organic layer was separated, and the solutions were washed successively with water and then with a saturated aqueous solution of sodium chloride, dried over anhydrous magnesium sulfate and then concentrated under reduced pressure. The obtained residue was applied to silica gel column chromatography (Eluent; hexane:ethyl acetate=9:1 (V/V)), and the fractions containing the desired compound were concentrated under reduced pressure to obtain 832 mg of the title compound as a colorless oil. (Yield: 46%)

Mass Spectrum (CI, m/z): 325 ($M^+$+1).

$^1$H-NMR Spectrum (CDCl$_3$, δ ppm): −0.03 (s, 9H), 0.86-0.94 (m, 2H), 1.32 (s, 12H), 3.51-3.59 (m, 2H), 5.43 (s, 2H), 7.81 (d, J=0.5 Hz, 1H), 7.86 (d, J=0.5 Hz, 1H).

32-(b) 1,5-Bis(2-trimethylsilylethoxymethyl)-3-[1-(2-trimethylsilylethoxymethyl)-4-pyrazolyl]-1,5-dihydropyrrolo-[2,3-d]pyridazin-4-one Reaction and post treatment were carried out in the same manner as in Reference example 31 except for using 289 mg (0.61 mmol) of 3-bromo-1,5-bis(2-trimethylsilylethoxymethyl)-1,5-dihydropyrrolo[2,3-d]pyridazin-4-one obtained in Reference example 20-(a) in place of 2-chloro-3-iodo-1-(2-trimethylsilylethoxymethyl)-1,5-dihydropyrrolo[2,3-d]-pyridazin-4-one, and using 619 mg (1.91 mmol) of 4-(4,4,5,5-tetramethyl-[1,3,2]dioxaborolan-2-yl)-1-(2-trimethylsilylethoxymethyl)-1H-pyrazole obtained in Reference example 32-(a) in place of phenylboronic acid, respectively, whereby 166 mg of the title compound was obtained as a slightly yellowish oil. (Yield: 46%)

Mass Spectrum (CI, m/z): 592 ($M^+$+1).

$^1$H-NMR Spectrum (CDCl$_3$, δ ppm): −0.02 (s, 18H), −0.01 (s, 9H), 0.88-1.04 (m, 6H), 3.49-3.56 (m, 2H), 3.57-3.64 (m, 2H), 3.69-3.77 (m, 2H), 5.44 (s, 2H), 5.46 (s, 2H), 5.60 (s, 2H), 7.31 (s, 1H), 7.87 (d, J=0.6 Hz, 1H), 8.17 (s, 1H), 8.74 (d, J=0.6 Hz, 1H).

IR Spectrum (neat, cm$^{-1}$): 1664.

32-(c) 2-Bromo-1,5-bis(2-trimethylsilylethoxymethyl)-3-[1-(2-trimethylsilylethoxymethyl)-4-pyrazolyl]-1,5-dihydropyrrolo[2,3-d]pyridazin-4-one Reaction and post treatment were carried out in the same manner as in Reference example 18-(d) except for using 192 mg (0.369 mmol) of 1,5-bis(2-trimethylsilylethoxymethyl)-3-[1-(2-trimethylsilylethoxymethyl)-4-pyrazolyl]-1,5-dihydropyrrolo[2,3-d]pyridazin-4-one obtained in Reference example 32-(b) in place of 3-methyl-1,5-bis(2-trimethylsilylethoxymethyl)-1,5-dihydropyrrolo[2,3-d]pyridazin-4-one, whereby 198 mg of the title compound was obtained as a yellowish oil. (Yield: 80%)

Mass Spectrum (CI, m/z): 670 ($M^+$+1).

$^1$H-NMR Spectrum (CDCl$_3$, δ ppm): −0.02 (s, 9H), −0.01 (s, 9H), −0.01 (s, 9H), 0.89-1.03 (m, 6H), 3.55-3.76 (m, 6H), 5.48 (s, 2H), 5.57 (s, 2H), 5.61 (s, 2H), 8.17 (s, 1H), 8.20 (d, J=0.6 Hz, 1H), 8.47 (d, J=0.6 Hz, 1H).

IR Spectrum (neat, cm$^{-1}$): 1667.

Reference Example 33

3-Benzyl-1-benzyloxymethyl-2-bromo-5-(2-trimethylsilylethoxymethyl)-1,5-dihydropyrrolo[2,3-d]pyridazin-4-one 33-(a) 1-Benzyloxymethyl-2-bromo-5-(2-trimethylsilylethoxymethyl)-1,5-dihydropyrrolo[2,3-d]pyridazin-4-one To 300 ml of dichloromethane solution containing 33.4 g (0.100 mol) of 1-benzyloxymethyl-2-bromo-1,5-dihydropyrrolo[2,3-d]pyridazin-4-one obtained in Reference example 17-(d) was added 25.8 g (0.200 mol) of N,N-diisopropylethylamine, and 25.0 g (0.15 mol) of (2-trimethylsilylethoxy)

methyl chloride was added dropwise to the mixture under ice-cooling. After completion of the dropwise addition, the mixture was stirred at 40° C. for 3 hours. After completion of the reaction, the reaction mixture was washed successively with 1N hydrochloric acid, a saturated aqueous solution of sodium hydrogencarbonate and a saturated aqueous solution of sodium chloride, dried over anhydrous magnesium sulfate and concentrated under reduced pressure. To the obtained concentrate was added 300 ml of cyclohexane, and precipitated solid was collected by filtration. The obtained solid was washed with cyclohexane, and dried under reduced pressure to obtain 33.1 g of the title compound as a beige solid. (Yield: 71%)

Mass Spectrum (CI, m/z): 464 ($M^+$+1).

$^1$H-NMR Spectrum (DMSO-$d_6$, δ ppm): −0.07 (s, 9H), 0.79-0.88 (m, 2H), 3.57-3.66 (m, 2H), 4.54 (s, 2H), 5.40 (s, 2H), 5.75 (s, 2H), 6.95 (d, J=0.6 Hz, 1H), 7.20-7.33 (m, 5H), 8.52 (d, J=0.6 Hz, 1H).

33-(b) 1-Benzyloxymethyl-5-(2-trimethylsilylethoxymethyl)-1,5-dihydropyrrolo[2,3-d]pyridazin-4-one To 5.00 g (10.8 mmol) of 1-benzyloxymethyl-2-bromo-5-(2-trimethylsilylethoxymethyl)-1,5-dihydropyrrolo[2,3-d]-pyridazin-4-one obtained in Reference example 33-(a) were added 50 ml of methanol, 30 ml of toluene, 1.5 g of potassium carbonate and 2.5 g of 51 palladium-active carbonate, and the mixture was stirred under 1 atm hydrogen atmosphere at room temperature for 3 hours. After completion of the reaction, insoluble material of the reaction suspension was removed by filtration, and the filtrate was concentrated under reduced pressure. The obtained residue was applied to silica gel column chromatography (Eluent; toluene:ethyl acetate=1:1 (V/V)), and the fractions containing the desired compound were concentrated under reduced pressure to obtain 8.15 g of the title compound as a pale yellowish solid. (Yield: 77%)

$^1$H-NMR Spectrum (DMSO-$d_6$, δ ppm): −0.07 (s, 9H), 0.79-0.88 (m, 2H), 3.58-3.67 (m, 2H), 4.47 (s, 2H), 5.41 (s, 2H), 5.73 (s, 2H), 6.73 (dd, J=2.9, 0.5 Hz, 1H), 7.12-7.34 (m, 5H), 7.60 (d, J=2.9 Hz, 1H), 8.46 (d, J=0.5 Hz, 1H).

33-(c) 1-Benzyloxymethyl-3-iodo-5-(2-trimethylsilylethoxymethyl)-1,5-dihydropyrrolo[2,3-d]pyridazin-4-one Reaction and post treatment were carried out in the same manner as in Reference example 18-(b) except for using 39.1 g (0.104 mmol) of 1-benzyloxymethyl-5-(2-trimethylsilylethoxymethyl)-1,5-dihydropyrrolo[2,3-d]pyridazin-4-one obtained in Reference example 33-(b) in place of 1,5-bis(2-trimethylsilylethoxymethyl)-1,5-dihydropyrrolo[2,3-d]pyridazin-4-one, whereby 45.3 g of the title compound was obtained as a brownish solid. (Yield: 89%)

$^1$H-NMR Spectrum (DMSO-$d_6$, δ ppm): −0.05 (s, 9H), 0.81-0.89 (m, 2H), 3.58-3.65 (m, 2H), 4.49 (s, 2H), 5.37 (s, 2H), 5.69 (s, 2H), 7.19-7.33 (m, 5H), 7.76 (s, 1H), 8.46 (s, 1H).

33-(d) 1-Benzyloxymethyl-3-formyl-5-(2-trimethylsilylethoxymethyl)-1,5-dihydropyrrolo[2,3-d]pyridazin-4-one In 500 ml of an autoclave made of stainless were charged 45.3 g (86.8 mmol) of 1-benzyloxymethyl-3-iodo-5-(2-trimethylsilylethoxymethyl)-1,5-dihydropyrrolo[2,3-d]pyridazin-4-one obtained in Reference example 33-(c), 390 mg (1.74 mmol) of palladium acetate, 1.92 g (3.47 mmol) of 1,1'-bis(diphenylphosphino)ferrocene, 30.2 ml (220 mmol) of triethylamine, 27.7 ml (170 mmol) of triethylsilane and 300 ml of N,N-dimethylformamide, and the mixture was stirred at 80° C. for 8 hours under carbon monoxide atmosphere of 15 atm. After completion of the reaction, water was added to the reaction mixture, and the mixture was extracted with toluene. The organic layer after separation was washed with a saturated aqueous solution of sodium chloride, dried over anhydrous magnesium sulfate and concentrated under reduced pressure. The obtained residue was applied to silica gel column chromatography (Eluent; hexane:ethyl acetate=4:1 (V/V)), and the fractions containing the desired compound were concentrated under reduced pressure to obtain 14.2 g of the title compound as a brownish solid. (Yield: 40%)

Mass Spectrum (CI, m/z): 414 ($M^+$+1).

$^1$H-NMR Spectrum (CDCl$_3$, δ ppm): 0.00 (s, 9H), 0.96-1.04 (m, 2H), 3.70-3.79 (m, 2H), 4.50 (s, 2H), 5.54 (s, 2H), 5.62 (s, 2H), 7.23-7.40 (m, 5H), 7.76 (s, 1H), 8.21 (s, 1H), 10.58 (s, 1H).

IR Spectrum (KBr, cm$^{-1}$): 1682, 1667.

33-(e) 1-Benzyloxymethyl-3-hydroxyphenylmethyl-5-(2-trimethylsilylethoxymethyl)-1,5-dihydropyrrolo[2,3-d]pyridazin-4-one To 87 ml of dehydrated tetrahydrofuran solution containing 3.60 g (8.71 mmol) of 1-benzyloxymethyl-3-formyl-5-(2-trimethylsilylethoxymethyl)-1,5-dihydropyrrolo-[2,3-d]pyridazin-4-one obtained in Reference example 33-(d) were added 12.2 ml of 1M phenyl magnesium bromide tetrahydrofuran solution under ice-cooling and under argon atmosphere, and the mixture was stirred at room temperature for 1 hour. After completion of the reaction, to the reaction mixture were added a saturated aqueous solution of ammonium chloride and a saturated aqueous solution of sodium chloride, and the mixture was extracted with ethyl acetate. The organic layer after separation was dried over anhydrous magnesium sulfate and concentrated under reduced pressure. The obtained residue was applied to silica gel column chromatography (Eluent; hexane:ethyl acetate=4:1→1:1 (V/V)), and the fractions containing the desired compound were concentrated under reduced pressure to obtain 3.12 g of the title compound as a yellowish oil. (Yield: 73%)

$^1$H-NMR Spectrum (CDCl$_3$, δ ppm): 0.00 (s, 9H), 0.95-1.04 (m, 2H), 3.70-3.78 (m, 2H), 4.38 (d, J=12.1 Hz, 1H), 4.43 (d, J=12.1 Hz, 1H), 5.37 (s, 2H), 5.60 (d, J=9.9 Hz, 1H), 5.65 (d, J=9.9 Hz, 1H), 6.00 (d, J=5.5 Hz, 1H), 6.53 (d, J=0.7 Hz, 1H), 6.54 (d, J=5.5 Hz, 1H), 7.17-7.23 (m, 2H), 7.28-7.41 (m, 6H), 7.45-7.52 (m, 2H), 8.17 (s, 1H).

33-(f) 3-Benzyl-1-benzyloxymethyl-5-hydroxymethyl-1,5-dihydropyrrolo[2,3-d]pyridazin-4-one Reaction and post treatment were carried out in the same manner as in Reference example 21-(e) except for using 3.08 g (6.26 mmol) of 1-benzyloxymethyl-3-hydroxyphenylmethyl-5-(2-trimethylsilylethoxymethyl)-1,5-dihydropyrrolo-[2,3-d]pyridazin-4-one obtained in Reference example 33-(e) in place of 1-benzyloxymethyl-3-(1-hydroxy-1-methylethyl)-1,5-dihydropyrrolo[2,3-d]pyridazin-4-one, whereby 1.68 g of the title compound was obtained as a pale yellowish solid. (Yield: 71%)

¹H-NMR Spectrum (CDCl₃, δ ppm): 4.02 (brs, 1H), 4.28 (d, J=0.8 Hz, 2H), 4.40 (s, 2H), 5.38 (s, 2H), 5.65 (s, 2H), 6.67 (t, J=0.8 Hz, 1H), 7.18-7.25 (m, 3H), 7.28-7.38 (m, 7H), 8.06 (s, 1H).

IR Spectrum (KBr, cm⁻¹): 1655.

33-(g) 3-Benzyl-1-benzyloxymethyl-5-(2-trimethylsilylethoxymethyl)-1,5-dihydropyrrolo[2,3-d]pyridazin-4-one Reaction was carried out in the same manner as in Reference example 33-(a) except for using 1.66 g (4.82 mmol) of 3-benzyl-1-benzyloxymethyl-5-hydroxymethyl-1,5-dihydropyrrolo[2,3-d]pyridazin-4-one obtained in Reference example 33-(f) in place of 1-benzyloxymethyl-2-bromo-1,5-dihydropyrrolo[2,3-d]pyridazin-4-one. After completion of the reaction, the reaction mixture was washed successively with 1N hydrochloric acid, a saturated aqueous solution of sodium hydrogencarbonate and a saturated aqueous solution of sodium chloride, dried over anhydrous magnesium sulfate and concentrated under reduced pressure. The obtained residue was applied to silica gel column chromatography (Eluent; hexane:ethyl acetate=7:1→1:1 (V/V)), and the fractions containing the desired compound were concentrated under reduced pressure to obtain 0.66 g of the title compound as a yellowish oil. (Yield: 29%)

Mass Spectrum (CI, m/z): 476 (M⁺+1).

¹H-NMR Spectrum (CDCl₃, δ ppm): 0.01 (s, 9H), 0.96-1.03 (m, 2H), 3.71-3.77 (m, 2H), 4.30 (brs, 2H), 4.40 (s, 2H), 5.37 (s, 2H), 5.58 (s, 2H), 6.63 (t, J=0.6 Hz, 1H), 7.18-7.37 (m, 10H), 8.07 (s, 1H).

33-(h) 3-Benzyl-1-benzyloxymethyl-2-bromo-5-(2-trimethylsilylethoxymethyl)-1,5-dihydropyrrolo[2,3-d]pyridazin-4-one Reaction and post treatment were carried out in the same manner as in Reference example 18-(d) except for using 0.64 g (1.35 mmol) of 3-benzyl-1-benzyloxymethyl-5-(2-trimethylsilylethoxymethyl)-1,5-dihydropyrrolo[2,3-d]pyridazin-4-one obtained in Reference example 33-(g) in place of 3-methyl-1,5-bis(2-trimethylsilylethoxymethyl)-1,5-dihydropyrrolo[2,3-d]pyridazin-4-one, whereby 0.70 g of the title compound was obtained as a yellowish oil. (Yield: 94%)

Mass Spectrum (CI, m/z): 554 (M⁺+1).

¹H-NMR Spectrum (CDCl₃, δ ppm): -0.01 (s, 9H), 0.95-1.02 (m, 2H), 3.68-3.75 (m, 2H), 4.27 (s, 2H), 4.53 (s, 2H), 5.56 (s, 2H), 5.58 (s, 2H), 7.12-7.19 (m, 1H), 7.21-7.35 (m, 7H), 7.41-7.47 (m, 2H), 8.05 (s, 1H).

Reference Example 34

2-Bromo-3-hydroxyphenylmethyl-1-(2-trimethylsilylethoxymethyl)-1,5-dihydropyrrolo[2,3-d]pyridazin-4-one Reaction and post treatment were carried out in the same manner as in Reference example 33-(e) except for using 200 mg (0.54 mmol) of 2-bromo-3-formyl-1-(2-trimethylsilylethoxymethyl)-1,5-dihydropyrrolo[2,3-d]pyridazin-4-one obtained in Reference example 24-(g) in place of 1-benzyloxymethyl-3-formyl-5-(2-trimethylsilylethoxymethyl)-1,5-dihydropyrrolo[2,3-d]pyridazin-4-one, whereby 78.5 mg of the title compound was obtained as a pale yellowish solid. (Yield: 32%)

Mass Spectrum (EI, m/z): 449 (M⁺).

¹H-NMR Spectrum (DMSO-d₆, δ ppm): -0.13 (s, 9H), 0.74-0.82 (m, 2H), 3.48-3.56 (m, 2H), 5.62 (d, J=11.9 Hz, 1H), 5.66 (d, J=11.9 Hz, 1H), 5.78 (d, J=10.9 Hz, 1H), 7.07 (d, J=10.9 Hz, 1H), 7.19 (tt, J=7.1, 1.8 Hz, 1H), 7.24-7.31 (m, 2H), 7.33-7.40 (m, 2H), 8.61 (s, 1H), 13.01 (brs, 1H).

Reference Example 35

2-Bromo-3-phenethyl-1,5-bis(2-trimethylsilylethoxymethyl)-1,5-dihydropyrrolo[2,3-d]pyridazin-4-one

35-(a) 3-Phenethyl-1,5-bis(2-trimethylsilylethoxymethyl)-1,5-dihydropyrrolo[2,3-d]pyridazin-4-one Reaction and post treatment were carried out in the same manner as in Reference example 18-(c) except for using 855 mg (1.80 mmol) of 3-bromo-1,5-bis(2-trimethylsilylethoxymethyl)-1,5-dihydropyrrolo[2,3-d]pyridazin-4-one obtained in Reference example 20-(a) in place of 3-iodo-1,5-bis(2-trimethylsilylethoxymethyl)-1,5-dihydropyrrolo-[2,3-d]pyridazin-4-one, and using 965 mg (6.43 mmol) of phenethylboronic acid in place of methylboronic acid, respectively, whereby 698 mg of the title compound was obtained as an orange oil. (Yield: 78%)

Mass Spectrum (CI, m/z): 500 (M⁺+1).

¹H-NMR Spectrum (CDCl₃, δ ppm): -0.03 (s, 9H), -0.01 (s, 9H), 0.84-0.91 (m, 2H), 0.96-1.04 (m, 2H), 3.02 (dd, J=8.8, 6.3 Hz, 2H), 3.20 (dd, J=8.8, 6.3 Hz, 2H), 3.37-3.45 (m, 2H), 3.70-3.78 (m, 2H), 5.33 (s, 2H), 5.60 (s, 2H), 6.71 (s, 1H), 7.12-7.39 (m, 5H), 8.13 (s, 1H).

35-(b) 2-Bromo-3-phenethyl-1,5-bis(2-trimethylsilylethoxymethyl)-1,5-dihydropyrrolo[2,3-d]pyridazin-4-one Reaction and post treatment were carried out in the same manner as in Reference example 18-(d) except for using 755 mg (1.51 mmol) of 3-phenethyl-1,5-bis(2-trimethylsilylethoxymethyl)-1,5-dihydropyrrolo[2,3-d]pyridazin-4-one obtained in Reference example 35-(a) in place of 3-methyl-1,5-bis(2-trimethylsilylethoxymethyl)-1,5-dihydropyrrolo-[2,3-d]pyridazin-4-one, whereby 605 mg of the title compound was obtained as a yellowish oil. (Yield: 69%)

Mass Spectrum (CI, m/z): 578 (M⁺+1).

¹H-NMR Spectrum (CDCl₃, δ ppm): -0.03 (s, 9H), -0.01 (s, 9H), 0.86-0.93 (m, 2H), 0.96-1.04 (m, 2H), 2.93-3.01 (m, 2H), 3.11-3.20 (m, 2H), 3.46-3.56 (m, 2H), 3.69-3.78 (m, 2H), 5.49 (s, 2H), 5.59 (s, 2H), 7.13-7.31 (m, 5H), 8.12 (s, 1H).

Reference Example 36

Ethyl 1-benzyloxymethyl-5-(3-cyclopropoxy-4-difluoromethoxyphenyl)-4-(2-fluorobenzyl)-2-formyl-1H-pyrrol-3-carboxylate

36-(a) Ethyl 1-benzyloxymethyl-2-formyl-1H-pyrrol-3-carboxylate

To 43 ml of toluene solution containing 3.66 g (10.0 mmol) of ethyl 1-benzyloxymethyl-5-bromo-2-formyl-1H-pyrrol-3-carboxylate obtained in Reference example 17-(c) were added 2.1 ml of N,N-diisopropylethylamine and 0.4 g of 5% palladium-active carbon, and the mixture was stirred under 1 atm hydrogen atmosphere at room temperature for 6 hours. After completion of the reaction, insoluble material was removed by filtration from the reaction mixture, ethyl acetate was added to the filtrate, and the filtrate was washed successively with water and a saturated aqueous solution of sodium chloride. The organic layer after separation was dried over anhydrous magnesium sulfate, and concentrated under reduced pressure to obtain 2.96 g the title compound as a pale yellowish solid substantially quantitatively.

Mass Spectrum (CI, m/z): 288 ($M^+$+1).

$^1$H-NMR Spectrum (CDCl$_3$, δ ppm): 1.39 (t, J=7.1 Hz, 3H), 4.36 (q, J=7.1 Hz, 2H), 4.54 (s, 2H), 5.83 (s, 2H), 6.73 (d, J=2.8 Hz, 1H), 7.07 (dd, J=2.8, 0.7 Hz, 1H), 7.26-7.38 (m, 5H), 10.44 (d, J=0.7 Hz, 1H).

IR Spectrum (KBr, cm$^{-1}$): 1713, 1660.

36-(b) Ethyl 1-benzyloxymethyl-4-bromo-2-formyl-1H-pyrrol-3-carboxylate

To 10 ml of acetonitrile solution containing 1.00 g (3.48 mmol) of ethyl 1-benzyloxymethyl-2-formyl-1H-pyrrol-3-carboxylate obtained in Reference example 36-(a) was added 0.62 g (3.48 mmol) of N-bromosuccineimide under ice-cooling, and the mixture was stirred at room temperature for 4.5 hours. After completion of the reaction, a saturated aqueous solution of sodium hydrogencarbonate was added to the reaction mixture, and the mixture was extracted with ethyl acetate. The organic layer after separation was washed successively with a saturated aqueous solution of sodium hydrogencarbonate and a saturated aqueous solution of sodium chloride, dried over anhydrous magnesium sulfate and concentrated under reduced pressure. The obtained residue was applied to silica gel column chromatography (Eluent; hexane:ethyl acetate=9:1→4:1 (V/V)), and the fractions containing the desired compound were concentrated under reduced pressure to obtain 1.00 g of the title compound as a pale yellowish solid. (Yield: 78%)

Mass Spectrum (CI, m/z): 366 ($M^+$+1).

$^1$H-NMR Spectrum (CDCl$_3$, δ ppm): 1.42 (t, J=7.2 Hz, 3H), 4.41 (q, J=7.2 Hz, 2H), 4.56 (s, 2H), 5.79 (s, 2H), 7.15 (d, J=0.9 Hz, 1H), 7.26-7.39 (m, 5H), 10.27 (d, J=0.9 Hz, 1H).

36-(c) Ethyl 1-benzyloxymethyl-2-formyl-4-(4,4,5,5-tetramethyl-[1,3,2]dioxaborolan-2-yl)-1H-pyrrol-3-carboxylate Reaction and post treatment were carried out in the same manner as in Reference example 1-(a) except for using 366 mg (1.00 mmol) of ethyl 1-benzyloxymethyl-4-bromo-2-formyl-1H-pyrrol-3-carboxylate obtained in Reference example 36-(b) in place of 4-bromo-2-cyclopropoxy-1-difluoromethoxybenzene, whereby 439 mg (purity: 55%) of the title compound was obtained as a brownish oil. (Yield: 58%)

$^1$H-NMR Spectrum (CDCl$_3$, δ ppm): 1.35 (s, 12H), 1.40 (t, J=7.2 Hz, 3H), 4.38 (q, J=7.2 Hz, 2H), 4.53 (s, 2H), 5.79 (s, 2H), 7.26-7.37 (m, 5H), 7.34 (d, J=1.0 Hz, 1H), 10.27 (d, J=1.0 Hz, 1H).

36-(d) Ethyl 1-benzyloxymethyl-4-(2-fluorobenzyl)-2-formyl-1H-pyrrol-3-carboxylate To 100 ml of 1,2-dimethoxyethane solution containing 4.38 g (10.6 mmol) of ethyl 1-benzyloxymethyl-2-formyl-4-(4,4,5,5-tetramethyl-[1,3,2]dioxaborolan-2-yl)-1H-pyrrol-3-carboxylate obtained in Reference example 36-(c) were added 2.60 ml (21.4 mmol) of 2-fluorobenzyl bromide and 100 ml of 2M sodium carbonate aqueous solution, the mixture was degassed under reduced pressure and replaced with argon. Further, 2.47 g (2.14 mmol) of tetrakistriphenylphosphine palladium was added to the mixture, and the resulting mixture was stirred at 50° C. for 3 hours. After completion of the reaction, to the reaction mixture were added water and a saturated aqueous solution of sodium chloride, and the mixture was extracted with ethyl acetate. The organic layer after separation was washed with a saturated aqueous solution of sodium chloride, dried over anhydrous magnesium sulfate and concentrated under reduced pressure. The obtained residue was applied to silica gel column chromatography (Eluent; hexane:ethyl acetate=9:1→4:1 (V/V)), and the fractions containing the desired compound were concentrated under reduced pressure to obtain 3.80 g of the title compound as a yellowish oil. (Yield: 91%)

Mass Spectrum (CI, m/z): 396 ($M^+$+1).

$^1$H-NMR Spectrum (CDCl$_3$, δ ppm): 1.33 (t, J=7.2 Hz, 3H), 4.10 (brs, 2H), 4.34 (q, J=7.2 Hz, 2H), 4.49 (s, 5H), 5.73 (s, 2H), 6.71 (brs, 1H), 7.00-7.10 (m, 2H), 7.11-7.37 (m, 7H), 10.36 (d, J=0.7 Hz, 1H).

36-(e) Ethyl 1-benzyloxymethyl-5-bromo-4-(2-fluorobenzyl)-2-formyl-1H-pyrrol-3-carboxylate Reaction and post treatment were carried out in the same manner as in Reference example 18-(d) except for using 3.80 g (9.61 mmol) of ethyl 1-benzyloxymethyl-4-(2-fluorobenzyl)-2-formyl-1H-pyrrol-3-carboxylate obtained in Reference example 36-(d) in place of 3-methyl-1,5-bis(2-trimethylsilylethoxymethyl)-1,5-dihydropyrrolo[2,3-d]pyridazin-4-one, whereby 4.05 g of the title compound was obtained as a slightly yellowish oil. (Yield: 89%)

Mass Spectrum (CI, m/z): 474 ($M^+$+1).

$^1$H-NMR Spectrum (CDCl$_3$, δ ppm): 1.18 (t, J=7.2 Hz, 3H), 4.14 (s, 2H), 4.23 (q, J=7.2 Hz, 2H), 4.63 (s, 2H), 6.03 (s, 2H), 6.81-6.88 (m, 1H), 6.95-7.06 (m, 2H), 7.12-7.22 (m, 1H), 7.23-7.36 (m, 5H), 10.22 (s, 1H).

36-(f) Ethyl 1-benzyloxymethyl-5-(3-cyclopropoxy-4-difluoromethoxyphenyl)-4-(2-fluorobenzyl)-2-formyl-1H-pyrrol-3-carboxylate To 4.04 g (8.52 mmol) of ethyl 1-benzyloxymethyl-5-bromo-4-(2-fluorobenzyl)-2-formyl-1H-pyrrol-3-carboxylate obtained in Reference example 36-(e) were added 3.62 g (11.1 mmol) of 2-(3-cyclopropoxy-4-difluoromethoxyphenyl)-4,4,5,5-tetramethyl-[1,3,2]dioxaborolane obtained in Reference example 1-(a), 7.23 g (34.0 mmol) of potassium phosphate, 60 ml of toluene and 3.6 ml of water, the mixture was degassed under reduced pressure and replaced with argon. Further, 40 mg (0.178 mmol) of palladium acetate and 128 mg (0.356 mmol) of butyl-di-1-adamantylphosphine were added to the mixture, and the mixture was stirred at 100° C. for 2 hours. After completion of the reaction, water was added to the reaction mixture, and the mixture was extracted with ethyl acetate. The organic layer after separation was washed with a saturated aqueous solution of sodium chloride, dried over anhydrous magnesium sulfate and concentrated under reduced pressure. The obtained residue was applied to silica gel column chromatography (Eluent; hexane:ethyl acetate=19:1→9:1 (V/V)), and the fractions containing the desired compound were concentrated under reduced pressure to obtain 5.01 g of the title compound as a yellowish oil substantially quantitatively.

Mass Spectrum (CI, m/z): 594 ($M^+$+1).

$^1$H-NMR Spectrum (CDCl$_3$, δ ppm): 0.36-0.45 (m, 2H), 0.55-0.64 (m, 2H), 1.13 (t, J=7.2 Hz, 3H), 3.31-3.38 (m, 1H), 4.01 (s, 2H), 4.21 (q, J=7.2 Hz, 2H), 4.62 (s, 2H), 5.71 (s, 2H), 6.52 (t, J=74.7 Hz, 1H), 6.82-6.89 (m, 1H), 6.90-7.00 (m, 2H), 6.93 (dd, J=8.2, 2.1 Hz, 1H), 7.08-7.17 (m, 1H), 7.13 (d, J=8.1 Hz, 1H), 7.20-7.33 (m, 5H), 7.22 (d, J=2.1 Hz, 1H), 10.46 (s, 1H).

Reference Example 37

1-Benzyloxymethyl-2-bromo-3-(3-fluorobenzyl)-1,5-dihydropyrrolo[2,3-d]pyridazin-4-one

37-(a) 1-Benzyloxymethyl-3-[(3-fluorophenyl)hydroxymethyl]-5-(2-trimethylsilylethoxymethyl)-1,5-dihydropyrrolo[2,3-d]-pyridazin-4-one Reaction and post treatment were carried out in the same manner as in Reference example 33-(e) except for using 6.2 ml of 1M 3-fluorophenyl magnesium bromide tetrahydrofuran solution in place of phenyl magnesium bromide, whereby 2.60 g of the title compound was obtained as a brownish oil. (Yield: 82%)

Mass Spectrum (CI, m/z): 510 ($M^+$+1).
$^1$H-NMR Spectrum (CDCl$_3$, δ ppm): 0.00 (s, 9H), 0.95-1.04 (m, 2H), 3.69-3.78 (m, 2H), 4.40 (d, J=12.0 Hz, 1H), 4.45 (d, J=12.0 Hz, 1H), 5.40 (s, 2H), 5.60 (d, J=9.8 Hz, 1H), 5.64 (d, J=9.8 Hz, 1H), 5.97 (brs, 1H), 6.57 (d, J=0.7 Hz, 1H), 6.95-7.04 (m, 1H), 7.17-7.39 (m, 8H), 8.17 (s, 1H).

37-(b) 1-Benzyloxymethyl-3-(3-fluorobenzyl)-1,5-dihydropyrrolo[2,3-d]pyridazin-4-one Reaction and post treatment were carried out in the same manner as in Reference example 21-(e) except for using 2.60 g (5.10 mmol) of 1-benzyloxymethyl-3-[(3-fluorophenyl)hydroxymethyl]-5-(2-trimethylsilylethoxymethyl)-1,5-dihydropyrrolo[2,3-d]pyridazin-4-one obtained in Reference example 37-(a) in place of 1-benzyloxymethyl-3-(1-hydroxy-1-methylethyl)-1,5-dihydropyrrolo[2,3-d]pyridazin-4-one, whereby 1.07 g of the title compound was obtained as a white solid. (Yield: 58%)

Mass Spectrum (CI, m/z): 364 ($M^+$+1).
$^1$H-NMR Spectrum (CDCl$_3$, δ ppm): 4.27 (brs, 2H), 4.43 (s, 2H), 5.41 (s, 2H), 6.71 (t, J=1.0 Hz, 1H), 6.87-6.95 (m, 1H), 6.99-7.05 (m, 1H), 7.10-7.15 (m, 1H), 7.18-7.39 (m, 6H), 8.10 (s, 1H), 9.96 (brs, 1H).
IR Spectrum (KBr, cm$^{-1}$): 1652.

37-(c) 1-Benzyloxymethyl-2-bromo-3-(3-fluorobenzyl)-1,5-dihydropyrrolo[2,3-d]pyridazin-4-one To 1.07 g (2.94 mmol) of 1-benzyloxymethyl-3-(3-fluorobenzyl)-1,5-dihydropyrrolo[2,3-d]pyridazin-4-one obtained in Reference example 37-(b) were added 30 ml of acetonitrile and 30 ml of dichloromethane, then, 612 mg (3.44 mmol) of N-bromosuccineimide was added to the mixture, and the mixture was stirred at 50° C. for 2 hours. After completion of the reaction, water was added to the reaction mixture, and the mixture was extracted with chloroform. The organic layer after separation was washed successively with a saturated aqueous solution of sodium hydrogencarbonate and a saturated aqueous solution of sodium chloride, dried over anhydrous magnesium sulfate and concentrated under reduced pressure. The obtained residue was applied to silica gel column chromatography (Eluent; hexane:ethyl acetate=4:1→2:1→1:1 (V/V)), and the fractions containing the desired compound were concentrated under reduced pressure to obtain 1.18 g of the title compound as a white solid. (Yield: 91%)

Mass Spectrum (CI, m/z): 442 ($M^+$+1).
$^1$H-NMR Spectrum (CDCl$_3$, δ ppm): 4.24 (s, 2H), 4.53 (s, 2H), 5.60 (s, 2H), 6.81-6.92 (m, 1H), 7.08-7.16 (m, 1H), 7.19-7.36 (m, 8H).
IR Spectrum (KBr, cm$^{-1}$): 1655.

Reference Example 38

1-Benzyloxymethyl-2-bromo-3-(4-fluorobenzyl)-1,5-dihydropyrrolo[2,3-d]pyridazin-4-one

38-(a) 1-Benzyloxymethyl-3-[(4-fluorophenyl)hydroxymethyl]-5-(2-trimethylsilylethoxymethyl)-1,5-dihydropyrrolo[2,3-d]-pyridazin-4-one Reaction and post treatment were carried out in the same manner as in Reference example 33-(e) except for using 6.1 ml of 1M 4-fluorophenyl magnesium bromide tetrahydrofuran solution in place of phenyl magnesium bromide, whereby 2.73 g of the title compound was obtained as a brownish oil. (Yield: 88%)

Mass Spectrum (CI, m/z): 510 ($M^+$+1).
$^1$H-NMR Spectrum (CDCl$_3$, δ ppm): 0.00 (s, 9H), 0.95-1.04 (m, 2H), 3.70-3.77 (m, 2H), 4.40 (d, J=11.9 Hz, 1H), 4.45 (d, J=11.9 Hz, 1H), 5.39 (s, 2H), 5.60 (d, J=9.8 Hz, 1H), 5.64 (d, J=9.8 Hz, 1H), 5.97 (brs, 1H), 6.51 (d, J=0.7 Hz, 1H), 7.06 (tt, J=8.8, 2.4 Hz, 2H), 7.18-7.23 (m, 2H), 7.29-7.36 (m, 3H), 7.41-7.49 (m, 2H), 8.17 (s, 1H).

38-(b) 1-Benzyloxymethyl-3-(4-fluorobenzyl)-1,5-dihydropyrrolo[2,3-d]pyridazin-4-one Reaction and post treatment were carried out in the same manner as in Reference example 21-(e) except for using 2.73 g (5.36 mmol) of 1-benzyloxymethyl-3-[(4-fluorophenyl)hydroxymethyl]-5-(2-trimethylsilylethoxymethyl)-1,5-dihydropyrrolo[2,3-d]pyridazin-4-one obtained in Reference example 38-(a) in place of 1-benzyloxymethyl-3-(1-hydroxy-1-methylethyl)-1,5-dihydropyrrolo[2,3-d]pyridazin-4-one, whereby 1.73 g of the title compound was obtained as a pale yellowish solid. (Yield: 89%)

Mass Spectrum (CI, m/z): 364 ($M^+$+1).
$^1$H-NMR Spectrum (CDCl$_3$, δ ppm): 4.24 (brs, 2H), 4.42 (s, 2H), 5.40 (s, 2H), 6.67 (t, J=0.9 Hz, 1H), 6.95-7.03 (m, 2H), 7.18-7.36 (m, 7H), 8.07 (s, 1H), 9.81 (brs, 1H).
IR Spectrum (KBr, cm$^{-1}$): 1653.

38-(c) 1-Benzyloxymethyl-2-bromo-3-(4-fluorobenzyl)-1,5-dihydropyrrolo[2,3-d]pyridazin-4-one Reaction and post treatment were carried out in the same manner as in Reference example 37-(c) except for using 1.73 g (4.78 mmol) of 1-benzyloxymethyl-3-(4-fluorobenzyl)-1,5-dihydropyrrolo[2,3-d]pyridazin-4-one obtained in Reference example 38-(b) in place of 1-benzyloxymethyl-3-(3-fluorobenzyl)-1,5-dihydropyrrolo[2,3-d]pyridazin-4-one, whereby 473 mg of the title compound was obtained as a white solid. (Yield: 22%)

Mass Spectrum (CI, m/z): 442 ($M^+$+1).
$^1$H-NMR Spectrum (CDCl$_3$, δ ppm): 4.24 (brs, 2H), 4.42 (s, 2H), 5.40 (s, 2H), 6.67 (t, J=0.9 Hz, 1H), 6.95-7.03 (m, 2H), 7.18-7.36 (m, 7H), 8.07 (s, 1H), 9.81 (brs, 1H).

Reference Example 39

Ethyl 1-benzyloxymethyl-4-(2-cyanobenzyl)-5-(3-cyclopropoxy-4-difluoromethoxyphenyl)-2-formyl-1H-pyrrol-3-carboxylate 39-(a) Ethyl 1-benzyloxymethyl-4-(2-cyanobenzyl)-2-formyl-1H-pyrrol-3-carboxylate Reaction and post treatment were carried out in the same manner as in Reference example 36-(d) except for using 195 mg (3.73 mmol) of 2-cyanobenzyl bromide in place of 2-fluorobenzyl bromide, whereby 817 mg of the title compound was obtained as a yellowish solid. (Yield: 54%)
Mass Spectrum (CI, m/z): 403 ($M^+$+1).
$^1$H-NMR Spectrum (CDCl$_3$, δ ppm): 1.29 (t, J=7.1 Hz, 3H), 4.32 (brs, 2H), 4.32 (q, J=7.1 Hz, 2H), 4.53 (s, 2H), 6.80 (d, J=0.9 Hz, 1H), 7.22-7.36 (m, 9H), 7.50 (td, J=7.7, 1.3 Hz, 1H), 7.66 (dd, J=7.7, 1.3 Hz, 1H), 10.38 (d, J=0.9 Hz, 1H).

39-(b) Ethyl 1-benzyloxymethyl-5-bromo-4-(2-cyanobenzyl)-2-formyl-1H-pyrrol-3-carboxylate Reaction and post treatment were carried out in the same manner as in Reference example 18-(d) except for using 779 mg (1.94 mmol) of ethyl 1-benzyloxymethyl-4-(2-cyanobenzyl)-2-formyl-1H-pyrrol-3-carboxylate obtained in Reference example 39-(a) in place of 3-methyl-1,5-bis(2-trimethylsilylethoxymethyl)-1,5-dihydropyrrolo[2,3-d]pyridazin-4-one, whereby 809 mg of the title compound was obtained as a slightly yellowish oil. (Yield: 87%)
Mass Spectrum (CI, m/z): 481 ($M^+$+1).
$^1$H-NMR Spectrum (CDCl$_3$, δ ppm): 1.15 (t, J=7.2 Hz, 3H), 4.23 (q, J=7.2 Hz, 2H), 4.36 (s, 2H), 4.65 (s, 2H), 6.04 (s, 2H), 6.89 (d, J=8.1 Hz, 1H), 7.24-7.39 (m, 6H), 7.43 (td, J=7.7, 1.4 Hz, 1H), 7.66 (dd, J=7.7, 1.4 Hz, 1H), 10.28 (s, 1H).

39-(c) Ethyl 1-benzyloxymethyl-4-(2-cyanobenzyl)-5-(3-cyclopropoxy-4-difluoromethoxyphenyl)-2-formyl-1H-pyrrol-3-carboxylate Reaction and post treatment were carried out in the same manner as in Reference example 36-(f) except for using 796 mg (1.65 mmol) of ethyl 1-benzyloxymethyl-5-bromo-4-(2-cyanobenzyl)-2-formyl-1H-pyrrol-3-carboxylate obtained in Reference example 39-(b) in place of ethyl 1-benzyloxymethyl-5-bromo-4-(2-fluorobenzyl)-2-formyl-1H-pyrrol-3-carboxylate, whereby 900 mg of the title compound was obtained as a yellowish brown oil. (Yield: 91%)
Mass Spectrum (CI, m/z): 601 ($M^+$+1).
$^1$H-NMR Spectrum (CDCl$_3$, δ ppm): 0.40-0.48 (m, 2H), 0.58-0.66 (m, 2H), 1.12 (t, J=7.2 Hz, 3H), 3.37-3.44 (m, 1H), 4.21 (q, J=7.2 Hz, 2H), 4.24 (s, 2H), 4.63 (s, 2H), 5.71 (s, 2H), 6.53 (t, J=74.7 Hz, 1H), 6.85 (dd, J=8.2, 2.1 Hz, 1H), 7.02 (dd, J=8.2, 0.7 Hz, 1H), 7.12 (d, J=8.2 Hz, 1H), 7.20-7.33 (m, 7H), 7.43 (td, J=7.8, 1.3 Hz, 1H), 7.58 (dd, J=7.8, 1.3 Hz, 1H), 10.50 (s, 1H).

Reference Example 40

Ethyl 1-benzyloxymethyl-4-(3-cyanobenzyl)-5-(3-cyclopropoxy-4-difluoromethoxyphenyl)-2-formyl-1H-pyrrol-3-carboxylate 40-(a) Ethyl 1-benzyloxymethyl-4-(3-cyanobenzyl)-2-formyl-1H-pyrrol-3-carboxylate Reaction and post treatment were carried out in the same manner as in Reference example 36-(d) except for using 195 mg (0.993 mmol) of 3-cyanobenzyl bromide in place of 2-fluorobenzyl bromide, whereby 390 mg of the title compound was obtained as a yellowish oil. (Yield: 97%)
Mass Spectrum (CI, m/z): 403 ($M^+$+1).
$^1$H-NMR Spectrum (CDCl$_3$, δ ppm): 1.30 (t, J=7.2 Hz, 3H), 4.11 (s, 2H), 4.32 (q, J=7.2 Hz, 2H), 4.54 (s, 2H), 5.78 (s, 2H), 6.75 (s, 1H), 7.21-7.54 (m, 9H), 10.37 (d, J=0.7 Hz, 1H).

40-(b) Ethyl 1-benzyloxymethyl-5-bromo-4-(3-cyanobenzyl)-2-formyl-1H-pyrrol-3-carboxylate Reaction and post treatment were carried out in the same manner as in Reference example 18-(d) except for using 362 mg (0.900 mmol) of ethyl 1-benzyloxymethyl-4-(3-cyanobenzyl)-2-formyl-1H-pyrrol-3-carboxylate obtained in Reference example 40-(a) in place of 3-methyl-1,5-bis(2-trimethylsilylethoxymethyl)-1,5-dihydropyrrolo[2,3-d]-pyridazin-4-one, whereby 252 mg of the title compound was obtained as a colorless oil. (Yield: 58%)
Mass Spectrum (CI, m/z): 481 ($M^+$+1).
$^1$H-NMR Spectrum (CDCl$_3$, δ ppm): 1.26 (t, J=7.2 Hz, 3H), 4.15 (s, 2H), 4.29 (q, J=7.2 Hz, 2H), 4.63 (s, 2H), 6.02 (s, 2H), 7.22-7.52 (m, 9H), 10.23 (s, 1H).

40-(c) Ethyl 1-benzyloxymethyl-4-(3-cyanobenzyl)-5-(3-cyclopropoxy-4-difluoromethoxyphenyl)-2-formyl-1H-pyrrol-3-carboxylate Reaction and post treatment were carried out in the same manner as in Reference example 36-(f) except for using 223 mg (0.685 mmol) of ethyl 1-benzyloxymethyl-5-bromo-4-(3-cyanobenzyl)-2-formyl-1H-pyrrol-3-carboxylate obtained in Reference example 40-(b) in place of ethyl 1-benzyloxymethyl-5-bromo-4-(2-fluorobenzyl)-2-formyl-1H-pyrrol-3-carboxylate, whereby 261 mg of the title compound was obtained as a yellowish brown oil. (Yield: 86%)
Mass Spectrum (CI, m/z): 601 ($M^+$+1).
$^1$H-NMR Spectrum (CDCl$_3$, δ ppm): 0.41-0.50 (m, 2H), 0.58-0.66 (m, 2H), 1.21 (t, J=7.2 Hz, 3H), 3.34-3.41 (m, 1H), 4.05 (s, 2H), 4.27 (q, J=7.2 Hz, 2H), 4.63 (s, 2H), 5.70 (s, 2H), 6.55 (t, J=74.6 Hz, 1H), 6.87 (dd, J=8.3, 2.0 Hz, 1H), 7.16 (d, J=8.3 Hz, 1H), 7.20-7.54 (m, 10H), 10.46 (s, 1H).

Reference Example 41

Ethyl 1-benzyloxymethyl-4-(3-carboxybenzyl)-5-(3-cyclopropoxy-4-difluoromethoxyphenyl)-2-formyl-1H-pyrrol-3-carboxylate 41-(a) Ethyl 1-benzyloxymethyl-4-(3-tert-butoxycarbonylbenzyl)-2-formyl-1H-pyrrol-3-carboxylate Reaction and post treatment were carried out in the same manner as in Reference example 36-(d) except for using 1.43 g (5.27 mmol) of 3-tert-butoxycarbonylbenzyl bromide in place of 2-fluorobenzyl bromide, whereby 1.55 g of the title compound was obtained as a yellowish solid. (Yield: 62%)
Mass Spectrum (EI, m/z): 477 ($M^+$).
$^1$H-NMR Spectrum (CDCl$_3$, δ ppm): 1.34 (t, J=7.2 Hz, 3H), 1.58 (s, 9H), 4.11 (s, 2H), 4.34 (q, J=7.2 Hz, 2H), 4.50 (s, 2H), 5.73 (s, 2H), 6.65 (d, J=0.6 Hz, 1H), 7.19-7.42 (m, 7H), 7.81-7.90 (m, 2H), 10.37 (d, J=0.6 Hz, 1H).

41-(b) Ethyl 1-benzyloxymethyl-5-bromo-4-(3-tert-butoxycarbonylbenzyl)-2-formyl-1H-pyrrol-3-carboxylate Reaction and post treatment were carried out in the same manner as in Reference example 18-(d) except for using 1.55 g (3.25 mmol) of ethyl 1-benzyloxymethyl-4-(3-tert-butoxycarbonylbenzyl)-2-formyl-1H-pyrrol-3-carboxylate obtained in Reference example 41-(a) in place of 3-methyl-1,5-bis(2-trimethylsilylethoxymethyl)-1,5-dihydropyrrolo-[2,3-d]pyridazin-4-one, whereby 1.22 g of the title compound was obtained as a slightly yellowish oil. (Yield: 67%)

Mass Spectrum (CI, m/z): 557 (M$^+$+1).

$^1$H-NMR Spectrum (CDCl$_3$, δ ppm): 1.26 (t, J=7.2 Hz, 3H), 1.57 (s, 9H), 4.16 (s, 2H), 4.28 (q, J=7.2 Hz, 2H), 4.62 (s, 2H), 6.02 (s, 2H), 7.21-7.36 (m, 7H), 7.77-7.83 (m, 1H) 7.85 (d, J=0.7 Hz, 1H), 10.21 (s, 1H)

41-(c) Ethyl 1-benzyloxymethyl-4-(3-tert-butoxycarbonylbenzyl)-5-(3-cyclopropoxy-4-difluoromethoxyphenyl)-2-formyl-1H-pyrrol-3-carboxylate Reaction and post treatment were carried out in the same manner as in Reference example 36-(f) except for using 1.20 g (2.16 mmol) of ethyl 1-benzyloxymethyl-5-bromo-4-(3-tert-butoxycarbonylbenzyl)-2-formyl-1H-pyrrol-3-carboxylate obtained in Reference example 41-(b) in place of ethyl 1-benzyloxymethyl-5-bromo-4-(2-fluorobenzyl)-2-formyl-1H-pyrrol-3-carboxylate, whereby 1.26 g of the title compound was obtained as an orange oil. (Yield: 86%)

Mass Spectrum (CI, m/z): 676 (M$^+$+1).

$^1$H-NMR Spectrum (CDCl$_3$, δ ppm): 0.37-0.46 (m, 2H), 0.55-0.62 (m, 2H), 1.20 (t, J=7.2 Hz, 3H), 1.56 (s, 9H), 3.30-3.37 (m, 1H), 4.06 (s, 2H), 4.26 (q, J=7.2 Hz, 2H), 4.61 (s, 2H), 5.70 (s, 2H), 6.54 (t, J=74.8 Hz, 1H), 6.92 (dd, J=8.2, 2.1 Hz, 1H), 7.10-7.32 (m, 9H), 7.64 (t, J=1.3 Hz, 1H), 7.74 (dt, J=7.7, 1.3 Hz, 1H), 10.45 (s, 1H).

41-(d) Ethyl 1-benzyloxymethyl-4-(3-carboxybenzyl)-5-(3-cyclopropoxy-4-difluoromethoxyphenyl)-2-formyl-1H-pyrrol-3-carboxylate To 25 ml of dichloromethane solution containing 1.24 g (1.84 mmol) of ethyl 1-benzyloxymethyl-4-(3-tert-butoxycarbonylbenzyl)-5-(3-cyclopropoxy-4-difluoromethoxyphenyl)-2-formyl-1H-pyrrol-3-carboxylate obtained in Reference example 41-(c) was added 5 ml of trifluoroacetic acid, and the mixture was stirred at room temperature for 3 hours. After completion of the reaction, the reaction mixture was concentrated under reduced pressure, and azeotropic dehydration with toluene was further carried out, and then the residue was dried under reduced pressure to obtain 1.21 g of the title compound as a yellowish oil substantially quantitatively.

Mass Spectrum (CI, m/z): 620 (M$^+$+1).

$^1$H-NMR Spectrum (CDCl$_3$, δ ppm): 0.37-0.47 (m, 2H), 0.55-0.64 (m, 2H), 1.20 (t, J=7.2 Hz, 3H), 2.36 (s, 1H), 3.32-3.40 (m, 1H), 4.09 (s, 2H), 4.26 (q, J=7.2 Hz, 2H), 4.62 (s, 2H), 5.71 (s, 2H), 6.53 (t, J=74.7 Hz, 1H), 6.91 (dd, J=8.3, 2.0 Hz, 1H), 7.12-7.38 (m, 9H), 7.73 (t, J=1.5 Hz, 1H), 7.87 (dt, J=7.2, 1.5 Hz, 1H), 10.45 (s, 1H).

Reference Example 42

Ethyl 1-benzyloxymethyl-5-(3-cyclopropoxy-4-difluoromethoxyphenyl)-2-formyl-4-(6-methoxy-2-pyridylmethyl)-1H-pyrrol-3-carboxylate

42-(a) Ethyl 1-benzyloxymethyl-2-formyl-4-(6-methoxy-2-pyridylmethyl)-1H-pyrrol-3-carboxylate Reaction and post treatment were carried out in the same manner as in Reference example 36-(d) except for using 0.99 g (4.90 mmol) of 2-bromomethyl-6-methoxypyridine in place of 2-fluorobenzyl bromide, whereby 1.02 g of the title compound was obtained as a yellowish oil. (Yield: 89%)

Mass Spectrum (CI, m/z): 409 (M$^+$+1).

$^1$H-NMR Spectrum (CDCl$_3$, δ ppm): 1.30 (t, J=7.2 Hz, 3H), 3.87 (s, 3H), 4.16 (s, 2H), 4.32 (q, J=7.2 Hz, 2H), 4.52 (s, 2H), 5.78 (s, 2H), 6.58 (d, J=8.2 Hz, 1H), 6.71 (d, J=7.3 Hz, 1H), 6.94 (d, J=0.6 Hz, 1H), 7.22-7.35 (m, 5H), 7.48 (dd, J=8.2, 7.3 Hz, 1H), 10.35 (d, J=0.6 Hz, 1H).

42-(b) Ethyl 1-benzyloxymethyl-5-bromo-2-formyl-4-(6-methoxy-2-pyridylmethyl)-1H-pyrrol-3-carboxylate Reaction and post treatment were carried out in the same manner as in Reference example 18-(d) except for using 1.02 g (2.50 mmol) of ethyl 1-benzyloxymethyl-2-formyl-4-(6-methoxy-2-pyridylmethyl)-1H-pyrrol-3-carboxylate obtained in Reference example 42-(a) in place of 3-methyl-1,5-bis(2-trimethylsilylethoxymethyl)-1,5-dihydropyrrolo-[2,3-d]pyridazin-4-one, whereby 897 mg of the title compound was obtained as a slightly yellowish oil. (Yield: 74%)

Mass Spectrum (CI, m/z): 487 (M$^+$+1).

$^1$H-NMR Spectrum (CDCl$_3$, δ ppm): 1.22 (t, J=7.1 Hz, 3H), 3.84 (s, 3H), 4.22 (s, 2H), 4.25 (q, J=7.1 Hz, 2H), 4.61 (s, 2H), 6.03 (s, 2H), 6.55 (d, J=7.7 Hz, 1H), 6.58 (d, J=7.7 Hz, 1H), 7.21-7.35 (m, 5H), 7.45 (t, J=7.7 Hz, 1H), 10.21 (s, 1H).

42-(c) Ethyl 1-benzyloxymethyl-5-(3-cyclopropoxy-4-difluoromethoxyphenyl)-2-formyl-4-(6-methoxy-2-pyridylmethyl)-1H-pyrrol-3-carboxylate Reaction and post treatment were carried out in the same manner as in Reference example 31 except for using 875 mg (1.80 mmol) of ethyl 1-benzyloxymethyl-5-bromo-2-formyl-4-(6-methoxy-2-pyridylmethyl)-1H-pyrrol-3-carboxylate obtained in Reference example 42-(b) in place of 2-chloro-3-iodo-1-(2-trimethylsilylethoxymethyl)-1,5-dihydropyrrolo-[2,3-d]pyridazin-4-one, and using 880 mg (2.70 mmol) of 2-(3-cyclopropoxy-4-difluoromethoxyphenyl)-4,4,5,5-tetramethyl-[1,3,2]dioxaborolane obtained in Reference example 1-(a) in place of phenylboronic acid, respectively, whereby 1.15 g of the title compound was obtained as a yellowish oil substantially quantitatively.

Mass Spectrum (CI, m/z): 607 (M$^+$+1).

$^1$H-NMR Spectrum (CDCl$_3$, δ ppm): 0.37-0.46 (m, 2H), 0.57-0.65 (m, 2H), 1.17 (t, J=7.2 Hz, 3H), 3.36-3.43 (m, 1H), 3.79 (s, 3H), 4.08 (s, 2H), 4.23 (q, J=7.2 Hz, 2H), 4.61 (s, 2H), 5.74 (s, 2H), 6.50 (d, J=8.2 Hz, 1H), 6.53 (t, J=74.7 Hz, 1H), 6.55 (d, J=7.4 Hz, 1H), 7.03 (dd, J=8.2, 2.0 Hz, 1H), 7.15 (d, J=8.2 Hz, 1H), 7.19-7.32 (m, 5H), 7.35 (d, J=2.0 Hz, 1H), 7.42 (dd, J=8.2, 7.4 Hz, 1H), 10.45 (s, 1H).

Reference Example 43

Ethyl 1-benzyloxymethyl-5-(3-cyclopropoxy-4-difluoromethoxyphenyl)-2-formyl-4-(6-methoxy-3-pyridylmethyl)-1H-pyrrol-3-carboxylate

43-(a) Ethyl 1-benzyloxymethyl-2-formyl-4-(6-methoxy-3-pyridylmethyl)-1H-pyrrol-3-carboxylate Reaction and post treatment were carried out in the same manner as in Reference example 36-(d) except for using 1.16 g (5.44 mmol) of 3-bromomethyl-6-methoxypyridine in place of 2-fluorobenzyl bromide, whereby 617 mg of the title compound was obtained as a greenish oil. (Yield: 54%)

Mass Spectrum (CI, m/z): 409 (M$^+$+1).

$^1$H-NMR Spectrum (CDCl$_3$, δ ppm): 1.35 (t, J=7.1 Hz, 3H), 3.93 (s, 3H), 3.99 (s, 2H), 4.35 (q, J=7.1 Hz, 2H), 4.51 (s, 2H), 5.74 (s, 2H), 6.67 (d, J=0.7 Hz, 1H), 6.69 (dd, J=8.5, 0.7 Hz, 1H), 7.19-7.37 (m, 5H), 7.41 (dd, J=8.5, 2.4 Hz, 1H), 8.02 (dd, J=2.4, 0.7 Hz, 1H), 10.36 (d, J=0.7 Hz, 1H)

43-(b) Ethyl 1-benzyloxymethyl-5-bromo-2-formyl-4-(6-methoxy-3-pyridylmethyl)-1H-pyrrol-3-carboxylate Reaction and post treatment were carried out in the same manner as in Reference example 18-(d) except for using 617 mg (1.51 mmol) of ethyl 1-benzyloxymethyl-2-formyl-4-(6-methoxy-3-pyridylmethyl)-1H-pyrrol-3-carboxylate obtained in Reference example 43-(a) in place of 3-methyl-1,5-bis(2-trimethylsilylethoxymethyl)-1,5-dihydropyrrolo-[2,3-d]pyridazin-4-one, whereby 322 mg of the title compound was obtained as a yellowish oil. (Yield: 44%)

Mass Spectrum (CI, m/z): 487 (M$^+$+1).

$^1$H-NMR Spectrum (CDCl$_3$, δ ppm): 1.30 (t, J=7.1 Hz, 3H), 3.90 (s, 3H), 4.03 (s, 2H), 4.32 (q, J=7.1 Hz, 2H), 4.61 (s, 2H), 6.00 (s, 2H), 6.64 (dd, J=8.5, 0.5 Hz, 1H), 7.22-7.35 (m, 5H), 7.40 (dd, J=8.5, 2.5 Hz, 1H), 8.02 (dd, J=2.5, 0.5 Hz, 1H), 10.20 (s, 1H).

43-(c) Ethyl 1-benzyloxymethyl-5-(3-cyclopropoxy-4-difluoromethoxyphenyl)-2-formyl-4-(6-methoxy-3-pyridylmethyl)-1H-pyrrol-3-carboxylate Reaction and post treatment were carried out in the same manner as in Reference example 31 except for using 322 mg (0.66 mmol) of ethyl 1-benzyloxymethyl-5-bromo-2-formyl-4-(6-methoxy-3-pyridylmethyl)-1H-pyrrol-3-carboxylate obtained in Reference example 43-(b) in place of 2-chloro-3-iodo-1-(2-trimethylsilylethoxymethyl)-1,5-dihydropyrrolo-[2,3-d]pyridazin-4-one, and using 323 mg (0.96 mmol) of 2-(3-cyclopropoxy-4-difluoromethoxyphenyl)-4,4,5,5-tetramethyl-[1,3,2]dioxaborolane obtained in Reference example 1-(a) in place of phenylboronic acid, respectively, whereby 383 mg of the title compound was obtained as a slightly yellowish oil. (Yield: 96%)

Mass Spectrum (CI, m/z): 607 (M$^+$+1).

$^1$H-NMR Spectrum (CDCl$_3$, δ ppm): 0.44-0.52 (m, 2H), 0.59-0.67 (m, 2H), 1.26 (t, J=7.1 Hz, 3H), 3.38-3.46 (m, 1H), 3.87 (s, 3H), 3.93 (s, 2H), 4.30 (q, J=7.1 Hz, 2H), 4.60 (s, 2H), 5.68 (s, 2H), 6.55 (t, J=74.7 Hz, 1H), 6.60 (dd, J=8.4, 0.5 Hz, 1H), 6.90 (dd, J=8.4, 2.0 Hz, 1H), 7.13-7.33 (m, 9H), 10.43 (s, 1H).

Reference Example 44

2,3-Dibromo-1-(2-trimethylsilylethoxymethyl)-1,5-dihydropyrrolo[2,3-d]pyridazin-4-one 11.6 g of a concentrate of the mother liquor at the time of recrystallization of 2-bromo-1-(2-trimethylsilylethoxymethyl)-1,5-dihydropyrrolo[2,3-d]pyridazin-4-one in Reference example 15-(g) was applied to silica gel column chromatography (Eluent; toluene:ethyl acetate=2:1 (V/V)) to obtain 0.81 g of the title compound was obtained as a gray solid.

$^1$H-NMR Spectrum (CDCl$_3$, δ ppm): −0.02 (s, 9H), 0.87-0.98 (m, 2H), 3.52-3.63 (m, 2H), 5.58 (s, 2H), 8.16 (s, 1H), 10.25 (brs, 1H).

Reference Example 45

Ethyl 5-(3-Cyclopropylmethoxy-4-difluoromethoxyphenyl)-2-formyl-1H-pyrrol-3-carboxylate

45-(a) 2-Bromo-1-(3-cyclopropylmethoxy-4-difluoromethoxyphenyl)ethanone

To 250 ml of isopropanol solution containing 10.8 g (42.3 mmol) of 1-(3-cyclopropylmethoxy-4-difluoromethoxyphenyl)ethanone (see WO 9206963) was added 36.5 g (97.1 mmol) of trimethylphenylammonium tribromide at room temperature, and the mixture was stirred at room temperature for 5 hours. After completion of the reaction, a saturated aqueous solution of sodium hydrogencarbonate was added to the reaction mixture, and the mixture was extracted with ethyl acetate. The organic layer after separation was washed with a saturated aqueous solution of sodium chloride, dried over anhydrous magnesium sulfate, and then, concentrated under reduced pressure to obtain 16.5 g of the title compound as a pale yellowish solid substantially quantitatively.

$^1$H-NMR Spectrum (CDCl$_3$, δ ppm): 0.30-0.42 (m, 2H), 0.59-0.72 (m, 2H), 1.24-1.38 (m, 1H), 3.95 (d, J=7.1 Hz, 2H), 4.40 (s, 2H), 6.75 (t, J=74.7 Hz, 1H), 7.24 (d, J=8.3 Hz, 1H), 7.55 (dd, J=8.3, 2.0 Hz, 1H), 7.59 (d, J=2.0 Hz, 1H).

45-(b) Ethyl 2-[2-(3-cyclopropylmethoxy-4-difluoromethoxyphenyl)-2-oxoethyl]-4-(4-methoxybenzyloxy)-3-oxobutyrate To 460 ml of an ethanol solution containing 13.5 g (50.7 mmol) of ethyl 4-(4-methoxybenzyloxy)-3-oxobutyrate (see WO 2004060890) was added 18.9 ml (50.6 mmol) of 21% sodium ethoxide-ethanol solution under ice-cooling, and the mixture was stirred at room temperature for 1 hour. Then, to the above mixture was added dropwise 300 ml of ethanol solution containing 16.5 g (42.3 mmol) of 2-bromo-1-(3-cyclopropylmethoxy-4-difluoromethoxyphenyl)ethanone obtained in Reference example 45-(a) under ice-cooling, and the mixture was further stirred at 10° C. or lower for 2.5 hours. After completion of the reaction, water was added to the reaction mixture, and the mixture was extracted with chloroform. The organic layer after separation was washed with a saturated aqueous solution of sodium chloride, dried over anhydrous magnesium sulfate and then concentrated under reduced pressure. The obtained residue was applied to silica gel column chromatography (Eluent; hexane:ethyl acetate=4:1→7:3 (V/V)), and the fractions containing the desired compound were concentrated under reduced pressure to obtain 14.0 g of the title compound as a pale yellowish oil. (Yield: 63%)

$^1$H-NMR Spectrum (CDCl$_3$, δ ppm): 0.31-0.41 (m, 2H), 0.59-0.70 (m, 2H), 1.12-1.36 (m, 1H), 1.23 (t, J=7.1 Hz, 3H), 3.49 (dd, J=18.3, 4.9 Hz, 1H), 3.71 (dd, J=18.3, 9.0 Hz, 1H), 3.80 (s, 3H), 3.92 (d, J=7.1 Hz, 1H), 4.17 (q, J=7.1 Hz, 2H), 4.33 (dd, J=9.0, 4.9 Hz, 1H), 4.39 (s, 2H), 4.58 (s, 2H), 6.72 (t, J=74.8 Hz, 1H), 6.82-6.93 (m, 2H), 7.19-7.36 (m, 2H), 7.22 (d, J=8.3 Hz, 1H), 7.52 (d, J=2.0 Hz, 1H), 7.57 (dd, J=8.3, 2.0 Hz, 1H).

45-(q) Ethyl 5-(3-cyclopropylmethoxy-4-difluoromethoxyphenyl)-2-(4-methoxybenzyloxymethyl)-1H-pyrrol-3-carboxylate To 100 ml of ethanol solution containing 14.0 g (26.8 mmol) of ethyl 2-[2-(3-cyclopropylmethoxy-4-difluoromethoxyphenyl)-2-oxoethyl]-4-(4-methoxybenzyloxy)-3- oxobutyrate obtained in Reference example 45-(b) was added 10.3 g (134 mmol) of ammonium acetate, the mixture was stirred at room temperature for 1 hour, and further stirred at 80° C. for 4 hours. After completion of the reaction, to the reaction mixture were added water and a saturated aqueous solution of sodium chloride, and the mixture was extracted with chloroform. The organic layer after separation was washed with a saturated aqueous solution of sodium chloride, dried over anhydrous magnesium sulfate and then concentrated under reduced pressure. The obtained residue was applied to silica gel column chromatography (Eluent; hexane: ethyl acetate=7:3 (V/V)), and the fractions containing the desired compound were concentrated under reduced pressure to obtain 10.3 g of the title compound as a beige solid. (Yield: 77%)

$^1$H-NMR Spectrum (CDCl$_3$, δ ppm): 0.29-0.43 (m, 2H), 0.56-0.72 (m, 2H), 1.18-1.40 (m, 1H), 1.34 (t, J=7.1 Hz, 3H), 3.81 (s, 3H), 3.91 (d, J=7.1 Hz, 2H), 4.28 (q, J=7.1 Hz, 2H), 4.60 (s, 2H), 4.93 (s, 2H), 6.62 (t, J=75.6 Hz, 1H), 6.78 (d, J=2.9 Hz, 1H), 6.86-6.93 (m, 2H), 6.95 (dd, J=8.3, 2.2 Hz, 1H), 7.03 (d, J=2.2 Hz, 1H), 7.15 (d, J=8.3 Hz, 1H), 7.23-7.35 (m, 2H), 8.89 (brs, 1H).

45-(d) Ethyl 5-(3-cyclopropylmethoxy-4-difluoromethoxyphenyl)-2-formyl-1H-pyrrol-3-carboxylate To 10.3 g (20.6 mmol) of ethyl 5-(3-cyclopropylmethoxy-4-difluoromethoxyphenyl)-2-(4-methoxybenzyloxymethyl)-1H-pyrrol-3-carboxylate obtained in Reference example 45-(c) were added 100 ml of dichloromethane and 10 ml of water, then, 5.15 g (22.7 mmol) of 2,3-dichloro-5,6-dicyano-1,4-benzoquinone was added to the mixture under ice-cooling, and the mixture was stirred at room temperature for 3 hours. After completion of the reaction, the reaction suspension was filtered through Celite, the filtrate was successively washed with a saturated aqueous solution of sodium hydrogencarbonate, and then, with a saturated aqueous solution of sodium chloride. The organic layer after separation was dried over anhydrous magnesium sulfate and then concentrated under reduced pressure. To the obtained concentrate was added 100 ml of a mixed solvent (diisopropyl ether/hexane=1/1 (V/V)), and the precipitated solid was collected by filtration. The obtained solid was washed with diisopropyl ether, and dried under reduced pressure to obtain 3.98 g of the title compound as a pale yellowish solid. (Yield: 49%)

$^1$H-NMR Spectrum (CDCl$_3$, δ ppm): 0.33-0.44 (m, 2H), 0.59-0.72 (m, 2H), 1.25-1.48 (m, 1H), 1.42 (t, J=7.1 Hz, 3H), 3.95 (d, J=6.8 Hz, 2H), 4.41 (q, J=7.1 Hz, 2H), 6.67 (t, J=75.2 Hz, 1H), 7.00 (d, J=2.0 Hz, 1H), 7.19 (dd, J=8.1, 2.0 Hz, 1H), 7.22 (s, 1H), 7.24 (d, J=8.1 Hz, 1H), 10.10 (brs, 1H), 10.26 (s, 1H).

Reference Example 46

3-Ethyl-2-iodo-1,5-bis(2-trimethylsilylethoxymethyl)-1,5-dihydropyrrolo[2,3-d]pyridazin-4-one Reaction and post treatment were carried out in the same manner as in Reference example 18-(b) except for using 1.01 g (2.40 mmol) of 3-ethyl-1,5-bis(2-trimethylsilylethoxymethyl)-1,5-dihydropyrrolo[2,3-d]pyridazin-4-one obtained in Reference example 19-(c) in place of 1,5-bis(2-trimethylsilylethoxymethyl)-1,5-dihydropyrrolo[2,3-d]pyridazin-4-one, whereby 1.12 g of the title compound was obtained as a white solid. (Yield: 85%)

Mass Spectrum (CI, m/z): 550 (M$^+$+1).

$^1$H-NMR Spectrum (CDCl$_3$, δ ppm): −0.04, −0.03 (each s, 9H in total, rotational isomer), −0.02 (s, 9H), 0.86-1.02 (m, 4H), 1.21, 1.24 (each t, J=7.4 Hz, 3H in total), 2.89, 2.90 (each q, J=7.4 Hz, 2H in total), 3.51-3.59 (m, 2H), 3.68-3.76 (m, 2H), 5.50 (s, 2H), 5.56 (s, 2H), 8.10, 8.13 (s, 1H).

Reference Example 47

Ethyl 5-(3-cyclopentoxy-4-methoxyphenyl)-2-formyl-1H-pyrrol-3-carboxylate

47-(a) 2-Bromo-1-(3-cyclopentoxy-4-methoxyphenyl)ethanone

To 200 ml of methanol solution containing 11.6 g (49.5 mmol) of 1-(3-cyclopentoxy-4-methoxyphenyl)ethanone (see Bioorg. Med. Chem. Lett. 2003, 13, 2355) was added 20.47 g (54.5 mmol) of trimethylphenylammonium tribromide at room temperature, and the mixture was stirred at room temperature for 40 minutes. After completion of the reaction, water was added to the reaction mixture, and the mixture was neutralized with a saturated aqueous solution of sodium hydrogencarbonate and then extracted with chloroform. The organic layer after separation was washed with a saturated aqueous solution of sodium chloride, dried over anhydrous magnesium sulfate and then concentrated under reduced pressure. To the obtained concentrate was added 50 ml of a mixed solvent (diisopropyl ether/hexane=1/2 (V/V)), and precipitated solid was collected by filtration. The obtained solid was washed with diisopropyl ether, and dried under reduced pressure to obtain 6.47 g of the title compound as a white solid. (Yield: 41%)

$^1$H-NMR Spectrum (CDCl$_3$, δ ppm): 1.48-2.00 (m, 8H), 3.92 (s, 3H), 4.40 (s, 2H), 4.81-4.91 (m, 1H), 6.89 (t, J=8.5 Hz, 1H), 7.54 (d, J=2.2 Hz, 1H), 7.58 (dd, J=8.5, 2.2 Hz, 1H).

47-(b) Ethyl 4-benzyloxy-2-[2-(3-cyclopentoxy-4-methoxyphenyl)-2-oxoethyl]-3-oxobutyrate Reaction and post treatment were carried out in the same manner as in Reference example 45-(b) except for using 7.65 g (32.4 mmol) of ethyl 4-benzyloxy-3-oxobutyrate in place of ethyl 4-(4-methoxybenzyloxy)-3-oxobutyrate, and using 8.45 g (27 mmol) of 2-bromo-1-(3-cyclopentoxy-4-methoxyphenyl)ethanone obtained in Reference example 47-(a) in place of 2-bromo-1-(3-cyclopropylmethoxy-4-difluoromethoxyphenyl)ethanone, respectively, whereby 9.49 g of the title compound was obtained as a yellowish oil. (Yield: 75%)

$^1$H-NMR Spectrum (CDCl$_3$, δ ppm): 1.23 (t, J=7.1 Hz, 3H), 1.52-2.06 (m, 8H), 3.51 (dd, J=18.1, 4.6 Hz, 1H), 3.75 (dd, J=18.1, 9.3 Hz, 1H), 3.91 (s, 3H), 4.17 (q, J=7.1 Hz, 2H), 4.32 (dd, J=9.3, 4.6 Hz, 1H), 4.45 (s, 2H), 4.66 (s, 2H), 4.78-4.88 (m, 1H), 6.88 (d, J=8.5 Hz, 1H), 7.24-7.44 (m, 5H), 7.48 (d, J=2.0 Hz, 1H), 7.60 (dd, J=8.5, 2.0 Hz, 1H).

47-(c) Ethyl 2-benzyloxymethyl-5-(3-cyclopentoxy-4-methoxyphenyl)-1H-pyrrol-3-carboxylate Reaction and post treatment were carried out in the same manner as in Reference example 45-(c) except for using 9.37 g (20 mmol) of ethyl 4-benzyloxy-2-[2-(3-cyclopentoxy-4-methoxyphenyl)-2-oxoethyl]-3-oxobutyrate obtained in Reference example 47-(b) in place of ethyl 2-[2-(3-cyclopropylmethoxy-4-difluoromethoxyphenyl)-2-oxoethyl]-4-(4-methoxybenzyloxy)-3-oxobutyrate, whereby 7.27 g of the title compound was obtained as a reddish solid. (Yield: 80%)

¹H-NMR Spectrum (CDCl₃, δ ppm): 1.34 (t, J=7.1 Hz, 3H), 1.52-2.04 (m, 8H), 3.86 (s, 3H), 4.28 (q, J=7.1 Hz, 2H), 4.66 (s, 2H), 4.78-4.88 (m, 1H), 4.97 (s, 2H), 6.71 (d, J=2.9 Hz, 1H), 6.86 (d, J=8.3 Hz, 1H), 6.94 (d, J=2.2 Hz, 1H), 6.99 (dd, J=8.3, 2.2 Hz, 1H), 7.25-7.45 (m, 5H), 8.87 (brs, 1H).

47-(d) Ethyl 5-(3-cyclopentoxy-4-methoxyphenyl)-2-hydroxymethyl-1H-pyrrol-3-carboxylate To 280 ml of ethanol solution containing 3.15 g (7.0 mmol) of ethyl 2-benzyloxymethyl-5-(3-cyclopentoxy-4-methoxyphenyl)-1H-pyrrol-3-carboxylate obtained in Reference example 47-(c) was added 600 mg of 10% palladium-active carbon, and the mixture was stirred under 1 atm hydrogen atmosphere at room temperature for 11 hours. Then, the mixture was stirred at 30° C. for 1.25 hours, and further at 40° C. for 13 hours. After completion of the reaction, the reaction suspension was filtered through Celite, and the filtrate was concentrated under reduced pressure. The obtained residue was applied to silica gel column chromatography (Eluent; hexane:ethyl acetate=7:3→1:1 (V/V)), and the fractions containing the desired compound were concentrated under reduced pressure to obtain 1.09 g of the title compound as a yellowish oil. (Yield: 43%)

¹H-NMR Spectrum (CDCl₃, δ ppm): 1.38 (t, J=7.1 Hz, 3H), 1.50-2.03 (m, 8H), 3.50 (t, J=6.2 Hz, 1H), 3.86 (s, 3H), 4.32 (q, J=7.1 Hz, 2H), 4.80-4.95 (m, 3H), 6.70 (d, J=2.9 Hz, 1H), 6.87 (d, J=8.1 Hz, 1H), 6.98 (dd, J=8.1, 2.0 Hz, 1H), 7.01 (d, J=2.0 Hz, 1H), 8.86 (brs, 1H).

47-(e) Ethyl 5-(3-cyclopentoxy-4-methoxyphenyl)-2-formyl-1H-pyrrol-3-carboxylate To 30 ml of dichloromethane solution containing 1.08 g (3.0 mmol) of ethyl 5-(3-cyclopentoxy-4-methoxyphenyl)-2-hydroxymethyl-1H-pyrrol-3-carboxylate obtained in Reference example 47-(d) was added 3.13 g (36 mmol) of manganese dioxide, and the mixture was stirred at room temperature for 1.2 hours. After completion of the reaction, the reaction suspension was filtered through Celite, and the obtained filtrate was concentrated under reduced pressure to obtain 1.05 g of the title compound as a yellowish solid. (Yield: 97%)

Mass Spectrum (CI, m/z): 358(M⁺+1).

¹H-NMR Spectrum (DMSO-d₆, δ ppm): 1.33 (t, J=7.3 Hz, 3H), 1.54-1.79 (m, 6H), 1.85-2.00 (m, 2H), 3.77 (s, 3H), 4.31 (q, J=7.3 Hz, 2H), 4.94-5.01 (m, 1H), 6.98 (d, J=8.3 Hz, 1H), 7.05 (s, 1H), 7.47 (dd, J=8.3, 2.0 Hz, 1H), 7.56 (d, J=2.0 Hz, 1H), 10.11 (s, 1H).

Reference Example 48

Ethyl 5-(7-difluoromethoxy-2,3-dihydrobenzofuran-2-spiro-1'-cyclopentan-4-yl)-2-formyl-1H-pyrrol-3-carboxylate 48-(a) 1-(7-Difluoromethoxy-2,3-dihydrobenzofuran-2-spiro-1'-cyclopentan-4-yl)ethanone To 80 ml of tetrahydrofuran solution containing 4.55 g (16 mmol) of 7-difluoromethoxy-2,3-dihydrobenzofuran-2-spiro-1'-cyclopentan-4-carboxylic acid (see WO 96/03399) was added 38 ml (43.3 mmol) of diethyl ether solution containing 1.14M methyl lithium under ice-cooling, and the mixture was stirred at room temperature for 7.5 hours. After completion of the reaction, 2N hydrochloric acid was added to the reaction mixture, and the mixture was extracted with ethyl acetate. The organic layer after separation was washed successively with a saturated aqueous solution of sodium hydrogencarbonate and then with a saturated aqueous solution of sodium chloride, dried over anhydrous magnesium sulfate, and then, concentrated under reduced pressure. The obtained residue was applied to silica gel column chromatography (Eluent; hexane:ethyl acetate=4:1→1:1 (V/V)), and the fractions containing the desired compound were concentrated under reduced pressure to obtain 1.32 g of the title compound as a yellowish oil. (Yield: 29%)

¹H-NMR Spectrum (CDCl₃, δ ppm): 1.68-2.19 (m, 8H), 2.56 (s, 3H), 3.55 (s, 2H), 6.81 (t, J=74.7 Hz, 1H), 7.03 (d, J=8.4 Hz, 1H), 7.35 (d, J=8.4 Hz, 1H).

48-(b) 2-Bromo-1-(7-difluoromethoxy-2,3-dihydrobenzofuran-2-spiro-1'-cyclopentan-4-yl)ethanone To 100 ml of tetrahydrofuran solution containing 1.43 g (5.1 mmol) of 1-(7-difluoromethoxy-2,3-dihydrobenzofuran-2-spiro-1'-cyclopentan-4-yl)ethanone obtained in Reference example 48-(a) was added 1.71 g (4.5 mmol) of trimethylphenylammonium tribromide under ice-cooling, and the mixture was stirred at room temperature for 3 hours. After completion of the reaction, to the reaction mixture was added a saturated aqueous solution of sodium hydrogencarbonate, and the mixture was extracted with ethyl acetate. The organic layer after separation was washed with a saturated aqueous solution of sodium chloride, dried over anhydrous magnesium sulfate and then concentrated under reduced pressure. The obtained residue was applied to silica gel column chromatography (Eluent; hexane:ethyl acetate=19:1 (V/V)), and the fractions containing the desired compound were concentrated under reduced pressure to obtain 1.25 g of the title compound as an oil. (Yield: 67%)

¹H-NMR Spectrum (CDCl₃, δ ppm): 1.69-2.19 (m, 8H), 3.55 (s, 2H), 4.40 (s, 2H), 6.83 (t, J=74.3 Hz, 1H), 7.05 (d, J=8.7 Hz, 1H), 7.36 (d, J=8.7 Hz, 1H).

48-(c) Ethyl 2-[2-(7-difluoromethoxy-2,3-dihydrobenzofuran-2-spiro-1'-cyclopentan-4-yl)-2-oxoethyl]-4-(4-methoxybenzyloxy)-3-oxobutyrate Reaction and post treatment were carried out in the same manner as in Reference example 45-(b) except for using 792 mg (2.20 mmol) of 2-bromo-1-(7-difluoromethoxy-2,3-dihydrobenzofuran-2-spiro-1'-cyclopentan-4-yl)ethanone obtained in Reference example 48-(b) in place of 2-bromo-1-(3-cyclopropylmethoxy-4-difluoromethoxyphenyl)ethanone, whereby 1.08 g of the title compound as a yellowish oil. (Yield: 75%)

¹H-NMR Spectrum (CDCl₃, δ ppm): 1.23 (t, J=7.1 Hz, 3H), 1.65-2.16 (m, 8H), 3.47 (dd, J=18.3, 4.6 Hz, 1H), 3.49 (s, 2H), 3.70 (dd, J=18.3, 9.0 Hz, 1H), 3.81 (s, 3H), 4.15 (q, J=7.1 Hz, 2H), 4.28 (dd, J=9.0, 4.6 Hz, 1H), 4.39 (s, 2H), 4.58 (s, 2H), 6.81 (t, J=74.6 Hz, 1H), 6.87-6.91 (m, 2H), 7.04 (d, J=8.5 Hz, 1H), 7.27-7.34 (m, 2H), 7.42 (d, J=8.5 Hz, 1H).

48-(d) Ethyl 5-(7-difluoromethoxy-2,3-dihydrobenzofuran-2-spiro-1'-cyclopentan-4-yl)-2-(4-methoxybenzyloxymethyl)-1H-pyrrol-3-carboxylate Reaction and post treatment were carried out in the same manner as in Reference example 45-(c) except for using 1.43 g (2.62 mmol) of ethyl 2-[2-(7-difluoromethoxy-2,3-dihydrobenzofuran-2-spiro-1'-cyclopentan-4-yl)-2-oxoethyl]-4-(4-methoxybenzyloxy)-3-oxobutyrate obtained in Reference example 48-(c), whereby 1.23 g of the title compound was obtained as a brownish oil. (Yield: 89%)

¹H-NMR Spectrum (CDCl₃, δ ppm): 1.34 (t, J=7.1 Hz, 3H), 1.67-2.22 (m, 8H), 3.34 (s, 2H), 3.81 (s, 3H), 4.28 (q, J=7.1 Hz, 2H), 4.60 (s, 2H), 4.93 (s, 2H), 6.65 (d, J=3.2 Hz, 1H), 6.68 (t, J=75.1 Hz, 1H), 6.80 (d, J=8.5 Hz, 1H), 6.87-6.93 (m, 2H), 6.99 (d, J=8.5 Hz, 1H), 7.27-7.32 (m, 2H), 8.91 (brs, 1H).

48-(e) Ethyl 5-(7-difluoromethoxy-2,3-dihydrobenzofuran-2-spiro-1'-cyclopentan-4-yl)-2-formyl-1H-pyrrol-3-carboxylate Reaction was carried out in the same manner as in Reference example 45-(d) except for using 1.22 g (2.31 mmol) of ethyl 5-(7-difluoromethoxy-2,3-dihydrobenzofuran-2-spiro-1'-cyclopentan-4-yl)-2-(4-methoxybenzyloxymethyl)-1H-pyrrol-3-carboxylate obtained in Reference example 48-(d) in place of ethyl 5-(3-cyclopropylmethoxy-4-difluoromethoxyphenyl)-2-(4-methoxybenzyloxymethyl)-1H-pyrrol-3-carboxylate. After completion of the reaction, the reaction suspension was filtered through Celite, and the filtrate was successively washed with a saturated aqueous solution of sodium hydrogencarbonate and the with a saturated aqueous solution of sodium chloride. The organic layer after separation was dried over anhydrous magnesium sulfate and then concentrated under reduced pressure. The obtained residue was applied to silica gel column chromatography (Eluent; hexane:ethyl acetate=9:1→4:1 (V/V)), and the fractions containing the desired compound were concentrated under reduced pressure to obtain 630 mg of the title compound as a yellowish solid. (Yield: 67%)

Mass Spectrum (CI, m/z): 406 (M⁺+1).
¹H-NMR Spectrum (CDCl₃, δ ppm): 1.42 (t, J=7.1 Hz, 3H), 1.70-2.25 (m, 8H), 3.41 (d, J=0.5 Hz, 2H), 4.41 (q, J=7.1 Hz, 2H), 6.72 (t, J=74.7 Hz, 1H), 6.87 (d, J=2.9 Hz, 1H), 6.98 (d, J=8.3 Hz, 1H), 7.07 (d, J=8.3 Hz, 1H), 9.48 (brs, 1H), 10.22 (s, 1H).

Reference Example 49

Ethyl 2-formyl-5-(2,3-dihydro-7-methoxybenzofuran-2-spiro-1'-cyclopentan-4-yl)-1H-pyrrol-3-carboxylate 49-(a) 1-(2,3-Dihydro-7-methoxybenzofuran-2-spiro-1'-cyclopentan-4-yl)ethanone To 250 ml of 1,2-dichloroethane solution containing 61.8 g (0.25-mol) of 2,3-dihydro-7-methoxybenzofuran-2-spiro-1'-cyclopentan-4-carboxylic acid (see WO 9603399) were added 36.5 ml (0.5 mol) of thionyl chloride and 2.5 ml of N,N-dimethylformamide, and the mixture was stirred at 80° C. for 1.7 hours. The reaction mixture was concentrated under reduced pressure, to the residue was added 100 ml of 1,2-dichloroethane, and the obtained solution was added dropwise to 1.5 L of dichloromethane solution containing a mixture comprising 122 g (1.25 mol) of N,O-dimethylhydroxylamine hydrochloride and 350 ml (2.5 mol) of triethylamine under ice-cooling. After completion of the dropwise addition, the mixture was further stirred at room temperature for 1 hour. After completion of the reaction, water was added to the reaction mixture, and the mixture was extracted with chloroform. The organic layer after separation was washed with a saturated aqueous solution of sodium chloride, dried over anhydrous magnesium sulfate, and then, concentrated under reduced pressure to obtain 77.8 g of a black oily material. To 77.8 g of the black oily material obtained as mentioned above were added 500 ml of diethyl ether and 500 ml of tetrahydrofuran, 200 ml of diethyl ether solution containing 3M methyl magnesium bromide was added to the mixture under ice-cooling, and the mixture was stirred at room temperature for 2 hours. After completion of the reaction, ice-water was added to the reaction mixture, followed by adjusting a pH thereof to 1 with 4N hydrochloric acid, and the mixture was extracted with ethyl acetate. The organic layer after separation was washed successively with a saturated aqueous solution of sodium hydrogencarbonate and then with a saturated aqueous solution of sodium chloride, dried over anhydrous magnesium sulfate, and then, concentrated under reduced pressure.

The obtained residue was applied to silica gel column chromatography (Eluent; hexane:ethyl acetate=9:1 (V/V)), and the fractions containing the desired compound were concentrated under reduced pressure to obtain 56.1 g of the title compound as a pale yellowish solid. (Yield: 91%)
¹H-NMR Spectrum (CDCl₃, δ ppm): 1.67-2.20 (m, 8H), 2.54 (s, 3H), 3.54 (s, 2H), 3.93 (s, 3H), 6.77 (d, J=8.5 Hz, 1H), 7.40 (d, J=8.5 Hz, 1H).

49-(b) 2-Bromo-1-(2,3-dihydro-7-methoxybenzofuran-2-spiro-1'-cyclopentan-4-yl)ethanone Reaction was carried out in the same manner as in Reference example 45-(a) except for using 246 mg (1.0 mmol) of 1-(2,3-dihydro-7-methoxybenzofuran-2-spiro-1'-cyclopentan-4-yl)ethanone obtained in Reference example 49-(a) in place of 1-(3-cyclopropylmethoxy-4-difluoromethoxyphenyl)ethanone. After completion of the reaction, to the reaction mixture was added a saturated aqueous solution of sodium hydrogencarbonate, and the mixture was extracted with ethyl acetate. The organic layer after separation was washed with a saturated aqueous solution of sodium chloride, dried over anhydrous magnesium sulfate and then concentrated under reduced pressure. The obtained residue was applied to silica gel column chromatography (Eluent; hexane:ethyl acetate=9:1 (V/V)), and the fractions containing the desired compound were concentrated under reduced pressure to obtain 287 mg of the title compound as a yellowish oil. (Yield: 88%)

Mass Spectrum (CI, m/z): 326 (M⁺+1).
¹H-NMR Spectrum (CDCl₃, δ ppm): 1.68-2.20 (m, 8H), 3.54 (d, J=0.5 Hz, 2H), 3.94 (s, 3H), 4.41 (s, 2H), 6.79 (d, J=8.7 Hz, 1H), 7.42 (d, J=8.7 Hz, 1H)

49-(c) Ethyl 2-[2-(2,3-dihydro-7-methoxybenzofuran-2-spiro-1'-cyclopentan-4-yl)-2-oxoethyl]-4-(4-methoxybenzyloxy)-3-oxobutyrate Reaction and post treatment were carried out in the same manner as in Reference example 45-(b) except for using 860 mg (2.64 mmol) of 2-bromo-1-(2,3-dihydro-7-methoxybenzofuran-2-spiro-1'-cyclopentan-4-yl)ethanone obtained in Reference example 49-(b) in place of 2-bromo-1-(3-cyclopropylmethoxy-4-difluoromethoxyphenyl)ethanone, whereby 906 mg of the title compound was obtained as a yellowish oil. (Yield: 67%)

Mass Spectrum (CI, m/z): 511 (M⁺+1).
¹H-NMR Spectrum (CDCl₃, δ ppm): 1.23 (t, J=7.1 Hz, 3H), 1.66-2.19 (m, 8H), 3.48 (dd, J=18.0, 4.6 Hz, 1H), 3.48 (s, 2H), 3.72 (dd, J=18.0, 9.0 Hz, 1H), 3.81 (s, 3H), 3.93 (s, 3H), 4.17 (q, J=7.1 Hz, 2H), 4.27 (dd, J=9.0, 4.6 Hz, 1H), 4.41 (s, 2H), 4.58 (s, 2H), 6.78 (d, J=8.5 Hz, 1H), 6.85-6.91 (m, 2H), 7.27-7.34 (m, 2H), 7.47 (d, J=8.5 Hz, 1H).

49-(d) Ethyl 5-(2,3-dihydro-7-methoxybenzofuran-2-spiro-1'-cyclopentan-4-yl)-2-(4-methoxybenzyloxymethyl)-1H-pyrrol-3-carboxylate Reaction and post treatment were carried out in the same manner as in Reference example 45-(c) except for using 903 mg (1.77 mmol) of ethyl 2-[2-(2,3-dihydro-7-methoxybenzofuran-2-spiro-1'-cyclopentan-4-yl)-2-oxoethyl]-4-(4-methoxybenzyloxy)-3-oxobutyrate obtained in Reference example 49-(c) in place of ethyl 2-[2-(3-cyclopropylmethoxy-4-difluoromethoxyphenyl)-2-oxoethyl]-4-(4-methoxybenzyloxy)-3-oxobutyrate, whereby 786 mg of the title compound was obtained as a yellowish foam. (Yield: 90%)

Mass Spectrum (CI, m/z): 492 ($M^+$+1).

$^1$H-NMR Spectrum (CDCl$_3$, δ ppm): 1.34 (t, J=7.1 Hz, 3H), 1.67-2.25 (m, 8H), 3.33 (s, 2H), 3.81 (s, 3H), 3.88 (s, 3H), 4.28 (q, J=7.1 Hz, 2H), 4.59 (s, 2H), 4.93 (s, 2H), 6.59 (d, J=2.9 Hz, 1H), 6.77 (d, J=8.3 Hz, 1H), 6.82 (d, J=8.3 Hz, 1H), 6.87-6.93 (m, 2H), 7.26-7.33 (m, 2H), 8.85 (brs, 1H).

49-(e) Ethyl 2-formyl-5-(2,3-dihydro-7-methoxybenzofuran-2-spiro-1'-cyclopentan-4-yl)-1H-pyrrol-3-carboxylate Reaction and post treatment were carried out in the same manner as in Reference example 45-(d) except for using 783 mg (1.59 mmol) of ethyl 5-(2,3-dihydro-7-methoxybenzofuran-2-spiro-1'-cyclopentan-4-yl)-2-(4-methoxybenzyloxymethyl)-1H-pyrrol-3-carboxylate obtained in Reference example 49-(d) in place of ethyl 5-(3-cyclopropylmethoxy-4-difluoromethoxyphenyl)-2-(4-methoxybenzyloxymethyl)-1H-pyrrol-3-carboxylate. After completion of the reaction, the reaction suspension was filtered through Celite, and the filtrate was successively washed with a saturated aqueous solution of sodium hydrogencarbonate and then with a saturated aqueous solution of sodium chloride. The organic layer after separation was dried over anhydrous magnesium sulfate and then concentrated under reduced pressure. The obtained residue was applied to silica gel column chromatography (Eluent; hexane:ethyl acetate=4:1 (V/V)), and the fractions containing the desired compound were concentrated under reduced pressure to obtain 450 mg of the title compound as a greenish solid. (Yield: 76%)

Mass Spectrum (CI, m/z): 370 ($M^+$+1).

$^1$H-NMR Spectrum (CDCl$_3$, δ ppm): 1.42 (t, J=7.1 Hz, 3H), 1.68-2.27 (m, 8H), 3.39 (s, 2H), 3.91 (s, 3H), 4.41 (q, J=7.1 Hz, 2H), 6.83 (d, J=2.9 Hz, 1H), 6.83 (d, J=8.5 Hz, 1H), 7.00 (d, J=8.5 Hz, 1H), 9.47 (brs, 1H), 10.20 (s, 1H).

Reference Example 50

2-Bromo-3-cyclopropylmethoxymethyl-1-(2-trimethylsilylethoxymethyl)-1,5-dihydropyrrolo[2,3-d]pyridazin-4-one To 10 ml of dehydrated tetrahydrofuran solution containing 0.92 g (13 mmol) of cyclopropylmethanol was added 0.25 g (6.2 mmol) of sodium hydride (60% dispersed material in mineral oil) under ice-cooling, the mixture was stirred at room temperature for 30 minutes, then, 10 ml of dehydrated tetrahydrofuran solution containing 0.56 g (1.3 mmol) of 2-bromo-3-bromomethyl-1-(2-trimethylsilylethoxymethyl)-1,5-dihydropyrrolo[2,3-d]pyridazin-4-one obtained in Reference example 24-(f) was further added to the mixture, and the mixture was stirred at room temperature for 2 hours. After completion of the reaction, water was added to the reaction mixture, and the mixture was extracted with ethyl acetate. The organic layer after separation was washed with a saturated aqueous solution of sodium chloride, dried over anhydrous magnesium sulfate and then concentrated under reduced pressure. The obtained residue was applied to silica gel column chromatography (Eluent; hexane:ethyl acetate=2:3 (V/V)), and the fractions containing the desired compound were concentrated under reduced pressure to obtain 157 mg of the title compound as a pale yellowish solid. (Yield: 29%)

Mass Spectrum (CI, m/z): 428($M^+$+1).

$^1$H-NMR Spectrum (DMSO-d$_6$, δ ppm): −0.10 (s, 9H), 0.08-0.16 (m, 2H), 0.37-0.45 (m, 2H), 0.77-0.85 (m, 2H), 0.90-1.04 (m, 1H), 3.25 (d, J=6.8 Hz, 2H), 3.48-3.57 (m, 2H), 4.64 (s, 2H), 5.63 (s, 2H), 8.45 (s, 1H), 12.47 (brs, 1H).

Reference Example 51

2-Bromo-3-isopropoxymethyl-1,5-bis(2-trimethylsilylethoxymethyl)-1,5-dihydropyrrolo[2,3-d]pyridazin-4-one To 2 ml of dehydrated tetrahydrofuran solution containing 1 ml of isopropanol was added 155 mg of sodium hydride (55% dispersed material in mineral oil), the mixture was stirred at room temperature for 20 minutes, then, 272 mg (0.48 mmol) of 2-bromo-3-bromomethyl-1,5-bis(2-trimethylsilylethoxymethyl)-1,5-dihydropyrrolo[2,3-d]pyridazin-4-one obtained in Reference example 25-(a) was further added to the mixture, and the mixture was stirred at room temperature for 1 hour. After completion of the reaction, water was added to the reaction mixture, and the mixture was extracted with ethyl acetate. The organic layer after separation was washed successively with water and then with a saturated aqueous solution of sodium chloride, dried over anhydrous magnesium sulfate, and then, concentrated under reduced pressure. The obtained residue was applied to silica gel column chromatography (Eluent; hexane:ethyl acetate=9:1 (V/V)), and the fractions containing the desired compound were concentrated under reduced pressure to obtain 176 mg of the title compound as a colorless oil. (Yield: 67%)

Mass Spectrum (CI, m/z): 546 ($M^+$+1).

$^1$H-NMR Spectrum (CDCl$_3$, δ ppm): −0.02 (s, 9H), −0.02 (s, 9H), 0.87-1.02 (m, 4H), 1.22 (d, J=6.1 Hz, 6H), 3.53-3.61 (m, 2H), 3.66-3.74 (m, 2H), 3.77-3.86 (m, 1H), 4.80 (s, 2H), 5.53 (s, 2H), 5.56 (s, 2H), 8.14 (s, 1H).

IR Spectrum (KBr, cm$^{-1}$): 1669.

Reference Example 52

2-Bromo-3-(2-fluoroethoxymethyl)-1,5-bis(2-trimethylsilylethoxymethyl)-1,5-dihydropyrrolo[2,3-d]pyridazin-4-one To 15 ml of dehydrated tetrahydrofuran solution containing 1.02 g (16 mmol) of 2-fluoroethanol was added 0.32 g (8.0 mmol) of sodium hydride (60% dispersed material in mineral oil) under ice-cooling, and the mixture was stirred at room temperature for 30 minutes. Then, 0.90 g (1.6 mmol) of 2-bromo-3-bromomethyl-1,5-bis(2-trimethylsilylethoxymethyl)-1,5-dihydropyrrolo[2,3-d]pyridazin-4-one obtained in Reference example 25-(a) was further added to the mixture, and the mixture was stirred at room temperature for 3 hours. After completion of the reaction, water was added to the reaction mixture, and the mixture was extracted with ethyl acetate. The organic layer after separation was washed with a saturated aqueous solution of sodium chloride, dried over anhydrous magnesium sulfate, and then, concentrated under reduced pressure. The obtained residue was applied to silica gel column chromatography (Eluent; hexane:ethyl acetate=7:3 (V/V)), and the fractions containing the desired compound were concentrated under reduced pressure to obtain 802 mg of the title compound as a white solid. (Yield: 91%)

$^1$H-NMR Spectrum (CDCl$_3$, δ ppm): −0.03 (s, 9H), −0.02 (s, 9H), 0.87-1.01 (m, 4H), 3.53-3.61 (m, 2H), 3.66-3.74 (m, 2H), 3.77-3.82 (m, 1H), 3.87-3.92 (m, 1H), 4.46-4.51 (m, 1H), 4.62-4.67 (m, 1H), 4.89 (s, 2H), 5.55 (s, 2H), 5.56 (s, 2H), 8.15 (s, 1H).

Reference Example 53

2-Bromo-3-isobutoxymethyl-1,5-bis(2-trimethylsilylethoxymethyl)-1,5-dihydropyrrolo[2,3-d]pyridazin-4-one To 5 ml of dehydrated tetrahydrofuran solution containing 1 ml of isobutanol was added 0.49 g of sodium hydride (60% dispersed material in mineral oil) under cooling in ice-bath, and the mixture was stirred at room temperature for 15 minutes. Then, 0.99 g (1.75 mmol) of 2-bromo-3-bromomethyl-1,5-bis(2-trimethylsilylethoxymethyl)-1,5-dihydropyrrolo[2,3-d]pyridazin-4-one obtained in Reference example 25-(a) was added to the mixture under cooling in ice-bath, and the mixture was stirred at the same temperature for 1 hour. After completion of the reaction, water was added to the reaction mixture, and the mixture was extracted with ethyl acetate. The organic layer after separation was washed with a saturated aqueous solution of sodium chloride, dried over anhydrous magnesium sulfate, and then, concentrated under reduced pressure. The obtained residue was applied to silica gel column chromatography (Eluent; hexane:ethyl acetate=9:1→4:1 (V/V)), and the fractions containing the desired compound were concentrated under reduced pressure to obtain 0.66 g of the title compound as a colorless oil. (Yield: 67%)

Mass Spectrum (CI, m/z): 562 (M$^+$+1).

$^1$H-NMR Spectrum (CDCl$_3$, δ ppm): −0.03 (s, 9H), −0.02 (s, 9H), 0.86-1.01 (m, 4H), 0.89 (d, J=6.7 Hz, 6H), 1.82-1.97 (m, 1H), 3.32 (d, J=6.7 Hz, 2H), 3.53-3.60 (m, 2H), 3.67-3.74 (m, 2H), 4.80 (s, 2H), 5.55 (s, 2H), 5.56 (s, 2H), 8.15 (s, 1H).

Reference Example 54

2-Bromo-3-(sec-butoxymethyl)-1,5-bis(2-trimethylsilylethoxymethyl)-1,5-dihydropyrrolo[2,3-d]pyridazin-4-one To 4 ml of dehydrated tetrahydrofuran solution containing 0.96 ml of 2-butanol was added 0.30 g of sodium hydride (60% dispersed material in mineral oil), and the mixture was stirred at room temperature for 3 hours. Then, 0.85 g (1.50 mmol) of 2-bromo-3-bromomethyl-1,5-bis(2-trimethylsilylethoxymethyl)-1,5-dihydropyrrolo[2,3-d]pyridazin-4-one obtained in Reference example 25-(a) was added to the mixture under cooling in ice-bath, and the mixture was stirred at the same temperature for 1 hour. After completion of the reaction, water was added to the reaction mixture, and the mixture was extracted with ethyl acetate. The organic layer after separation was washed successively with water and then with a saturated aqueous solution of sodium chloride, dried over anhydrous magnesium sulfate, and then, concentrated under reduced pressure. The obtained residue was applied to silica gel column chromatography (Eluent; hexane:ethyl acetate=9:1→4:1 (V/V)), and the fractions containing the desired compound were concentrated under reduced pressure to obtain 0.46 g of the title compound as a colorless oil. (Yield: 55%)

Mass Spectrum (CI, m/z): 562 (M$^+$+1).

$^1$H-NMR Spectrum (CDCl$_3$, δ ppm): −0.02 (s, 9H), −0.02 (s, 9H), 0.89 (t, J=7.4 Hz, 3H), 0.90-0.94 (m, 2H), 0.95-0.99 (m, 2H), 1.21 (d, J=6.1 Hz, 3H), 1.42-1.51 (m, 1H), 1.54-1.64 (m, 1H), 3.51-3.59 (m, 3H), 3.68-3.72 (m, 2H), 4.77 (d, J=10.8 Hz, 1H), 4.84 (d, J=10.8 Hz, 1H), 5.54 (s, 2H), 5.55 (d, J=9.8 Hz, 1H), 5.58 (d, J=9.8 Hz, 1H), 8.14 (s, 1H).

Reference Example 55

2-bromo-3-(tert-butoxymethyl)-1,5-bis(2-trimethylsilylethoxymethyl)-1,5-dihydropyrrolo[2,3-d]pyridazin-4-one To 50 ml of N,N-dimethylformamide solution containing 2.52 g (4.44 mmol) of 2-bromo-3-bromomethyl-1,5-bis(2-trimethylsilylethoxymethyl)-1,5-dihydropyrrolo[2,3-d]pyridazin-4-one obtained in Reference example 25-(a) was added 0.43 g (4.44 mmol) of sodium tert-butoxide at −10° C., and the mixture was stirred at the same temperature for 3 hours. The mixture was further stirred at 0° C. for 10 hours. After completion of the reaction, water was added to the reaction mixture, and the mixture was extracted with toluene. The organic layer after separation was washed successively with water and then with a saturated aqueous solution of sodium chloride, dried over anhydrous magnesium sulfate and then concentrated under reduced pressure. The obtained residue was applied to silica gel column chromatography (Eluent; hexane:ethyl acetate=98:2→65:35 (V/V)), and the fractions containing the desired compound were concentrated under reduced pressure to obtain 0.61 g of the title compound as a pale yellowish solid. (Yield: 25%)

Mass Spectrum (CI, m/z): 562 (M$^+$+1).

$^1$H-NMR Spectrum (CDCl$_3$, δ ppm): −0.02 (s, 18H), 0.87-1.02 (m, 4H), 1.33 (s, 9H), 3.54-3.61 (m, 2H), 3.66-3.73 (m, 2H), 4.75 (s, 2H), 5.52 (s, 2H), 5.56 (s, 2H), 8.12 (s, 1H).

Reference Example 56

2-Bromo-3-(1-ethylpropoxymethyl)-1,5-bis(2-trimethylsilylethoxymethyl)-1,5-dihydropyrrolo[2,3-d]pyridazin-4-one To 15 ml of dehydrated tetrahydrofuran solution containing 1.90 ml of 3-pentanol was added 0.38 g of sodium hydride (55% dispersed material in mineral oil) under cooling in ice-bath, and the mixture was stirred at room temperature for 3 hours. Then, 0.99 g (1.75 mmol) of 2-bromo-3-bromomethyl-1,5-bis(2-trimethylsilylethoxymethyl)-1,5-dihydropyrrolo[2,3-d]pyridazin-4-one obtained in Reference example 25-(a) was added to the mixture, and the mixture was stirred at 45° C. for 2 hours. After completion of the reaction, water was added to the reaction mixture, and the mixture was extracted with ethyl acetate. The organic layer was washed with a saturated aqueous solution of sodium chloride, dried over anhydrous magnesium sulfate, and then, concentrated under reduced pressure. The obtained residue was applied to silica gel column chromatography (Eluent; hexane:ethyl acetate=7:3 (V/V)), and the fractions containing the desired compound were concentrated under reduced pressure to obtain 0.66 g of the title compound as a slightly yellowish oil. (Yield: 65%)

Mass Spectrum (CI, m/z): 576(M$^+$+1).

¹H-NMR Spectrum (CDCl₃, δ ppm): −0.03 (s, 18H), 0.86-1.00 (m, 4H), 0.90 (t, J=3.7 Hz, 6H), 1.51-1.64 (m, 4H), 3.29-3.39 (m, 1H), 3.52-3.60 (m, 2H), 3.65-3.74 (m, 2H), 4.81 (s, 2H), 5.54 (s, 2H), 5.56 (s, 2H), 8.14 (s, 1H).

Reference Example 57

2-Bromo-3-(2-methoxyethyl)-1,5-bis(2-trimethylsilylethoxymethyl)-1,5-dihydropyrrolo[2,3-d]pyridazin-4-one 57-(a) 3-(1-Butoxyvinyl)-1,5-bis(2-trimethylsilylethoxymethyl)-1,5-dihydropyrrolo[2,3-d]pyridazin-4-one To 215 ml of N,N-dimethylformamide solution containing 10.1 g (21.2 mmol) of 3-bromo-1,5-bis(2-trimethylsilylethoxymethyl)-1,5-dihydropyrrolo[2,3-d]pyridazin-4-one obtained in Reference example 20-(a) were added 13.9 ml (108 mmol) of butyl vinyl ether, 5.59 g (21.2 mmol) of thallium acetate, 6.24 ml (36.7 mmol) of N,N-diisopropylethylamine, 482 mg (2.15 mmol) of palladium acetate and 1.86 g (4.51 mmol) of 1,3-bis(diphenylphosphino)propane in this order, and after degassing under reduced pressure, the atmosphere was replaced by a nitrogen gas, and the mixture was stirred at 100° C. for 2 hours. After completion of the reaction, water was added to the reaction mixture, and extracted with toluene. The organic layer was washed with a saturated aqueous solution of sodium chloride, dried over anhydrous magnesium sulfate, and then, concentrated under reduced pressure. The obtained residue was applied to silica gel column chromatography (Eluent; hexane:ethyl acetate=1:1 (V/V)), and the fractions containing the desired compound were concentrated under reduced pressure to obtain 8.80 g of the title compound as a pale brownish oil. (Yield: 84%)

Mass Spectrum (CI, m/z): 494 (M⁺+1).
¹H-NMR Spectrum (CDCl₃, δ ppm): −0.03 (s, 9H), −0.02 (s, 9H), 0.88-0.92 (m, 2H), 0.96-1.00 (m, 2H), 0.98 (t, J=7.4 Hz, 3H), 1.45-1.53 (m, 2H), 1.73-1.79 (m, 2H), 3.47-3.52 (m, 2H), 3.70-3.74 (m, 2H), 3.87 (t, J=6.5 Hz, 2H), 4.48 (d, J=2.4 Hz, 1H), 5.42 (s, 2H), 5.59 (s, 2H), 6.08 (d, J=2.4 Hz, 1H), 7.37 (s, 1H), 8.16 (s, 1H).

57-(b) 3-(2-Bromoacetyl)-1,5-bis(2-trimethylsilylethoxymethyl)-1,5-dihydropyrrolo[2,3-d]pyridazin-4-one To 8.80 g (17.8 mmol) of 3-(1-butoxyvinyl)-1,5-bis(2-trimethylsilylethoxymethyl)-1,5-dihydropyrrolo[2,3-d]pyridazin-4-one obtained in Reference example 57-(a) were added 21.1 ml of water and 341 ml of tetrahydrofuran, and 100 ml of tetrahydrofuran solution containing 4.70 g (26.4 mmol) of N-bromosuccinimide was added dropwise to the mixture under cooling in ice-bath. After the dropwise addition, the mixture was stirred at the same temperature 2 hours. After completion of the reaction, the reaction mixture was concentrated under reduced pressure. The residue was applied to silica gel column chromatography (Eluent; hexane: ethyl acetate=1:3 (V/V)), and the fractions containing the desired compound were concentrated under reduced pressure to obtain 6.64 g of the title compound as a white solid. (Yield: 72%)

Mass Spectrum (CI, m/z): 518 (M⁺+1).
¹H-NMR Spectrum (CDCl₃, δ ppm): −0.02 (s, 9H), −0.01 (s, 9H), 0.90-0.95 (m, 2H), 0.97-1.02 (m, 2H), 3.50-3.54 (m, 2H), 3.71-3.76 (m, 2H), 5.14 (s, 2H), 5.49 (s, 2H), 5.62 (s, 2H), 7.87 (s, 1H), 8.26 (s, 1H).

57-(c) 3-(2-Bromo-1-hydroxyethyl)-1,5-bis(2-trimethylsilylethoxymethyl)-1,5-dihydropyrrolo[2,3-d]pyridazin-4-one To 150 ml of dehydrated tetrahydrofuran solution containing 6.64 g (12.9 mmol) of 3-(2-bromoacetyl)-1,5-bis(2-trimethylsilylethoxymethyl)-1,5-dihydropyrrolo[2,3-d]pyridazin-4-one obtained in Reference example 57-(b) was added dropwise 100 ml of tetrahydrofuran solution containing 486 mg (12.8 mmol) of sodium borohydride under cooling in ice-bath. After dropwise addition, the mixture was stirred at the same temperature for 2 hours. After completion of the reaction, to the reaction mixture was added a saturated aqueous solution of sodium hydrogencarbonate, and the mixture was extracted with ethyl acetate. The organic layer was washed with a saturated aqueous solution of sodium chloride, dried over anhydrous magnesium sulfate, and then, concentrated under reduced pressure. The obtained residue was applied to silica gel column chromatography (Eluent; hexane: ethyl acetate=7:3 (V/V)), and the fractions containing the desired compound were concentrated under reduced pressure to obtain 5.67 g of the title compound as a white solid. (Yield: 85%)

Mass Spectrum (CI, m/z): 520(M⁺+1).
¹H-NMR Spectrum (CDCl₃, δ ppm): −0.03 (s, 9H), −0.01 (s, 9H), 0.88-0.93 (m, 2H), 0.96-1.01 (m, 2H), 3.47-3.52 (m, 2H), 3.55 (dd, J=9.9, 8.4 Hz, 1H), 3.70-3.75 (m, 2H), 3.79 (dd, J=9.9, 5.4 Hz, 1H), 4.94 (ddd, J=10.5, 8.4, 5.4 Hz, 1H), 5.44 (d, J=11.0 Hz, 1H), 5.47 (d, J=11.0 Hz, 1H), 5.61 (s, 2H), 6.21 (d, J=10.5 Hz, 1H), 7.15 (s, 1H), 8.25 (s, 1H).

57-(d) 3-(1-Hydroxy-2-methoxyethyl)-1,5-bis(2-trimethylsilylethoxymethyl)-1,5-dihydropyrrolo[2,3-d]pyridazin-4-one To 60 ml of dehydrated tetrahydrofuran solution containing 5.66 g (10.9 mmol) of 3-(2-bromo-1-hydroxyethyl)-1,5-bis(2-trimethylsilylethoxymethyl)-1,5-dihydropyrrolo[2,3-d]pyridazin-4-one obtained in Reference example 57-(c) was added 1.22 g (10.9 mmol) of potassium tert-butoxide under ice-cooling, and the mixture was stirred at the same temperature for 1 hour. After completion of the reaction, to the reaction mixture were added ice-water and a saturated aqueous solution of ammonium chloride, and the mixture was extracted with ethyl acetate. The organic layer was washed with a saturated aqueous solution of sodium chloride, dried over anhydrous magnesium sulfate, and then, concentrated under reduced pressure to obtain 4.63 g of 3-oxylanyl-1,5-bis(2-trimethylsilylethoxymethyl)-1,5-dihydropyrrolo[2,3-d]pyridazin-4-one as a colorless oil.

To 2.33 g (5.32 mmol) of the obtained 3-oxylanyl-1,5-bis(2-trimethylsilylethoxymethyl)-1,5-dihydropyrrolo[2,3-d]pyridazin-4-one was added 50 ml of dehydrated methanol, and the mixture was stirred at room temperature for 24 hours. After completion of the reaction, the reaction mixture was concentrated under reduced pressure to obtain 2.50 g of the title compound as a pale yellowish oil substantially quantitatively.

Mass Spectrum (CI, m/z): 470 (M⁺+1).
¹H-NMR Spectrum (CDCl₃, δ ppm): −0.04 (s, 9H), −0.02 (s, 9H), 0.87-0.94 (m, 2H), 0.94-1.02 (m, 2H), 2.88 (dd, J=7.1, 5.4 Hz, 1H), 3.44 (s, 3H), 3.46-3.55 (m, 2H), 3.68-3.76 (m, 2H), 3.78-3.92 (m, 2H), 5.07 (ddd, J=5.7, 4.8, 0.7 Hz, 1H), 5.41 (d, J=11.0 Hz, 1H), 5.45 (d, J=11.0 Hz, 1H), 5.55 (d, J=9.8 Hz, 1H), 5.59 (d, J=9.8 Hz, 1H), 7.18 (d, J=0.7 Hz, 1H), 8.19 (s, 1H)

57-(e) 3-(2-Hydroxyethyl)-1,5-bis(2-trimethylsilylethoxymethyl)-1,5-dihydropyrrolo[2,3-d]pyridazin-4-one To 40 ml of acetic acid solution containing 2.30 g (4.90 mmol) of 3-(1-hydroxy-2-methoxyethyl)-1,5-bis(2-trimethylsilylethoxymethyl)-1,5-dihydropyrrolo[2,3-d]pyridazin-4-one obtained in Reference example 57-(d) was added 1.0 g of 10% palladium-carbon, and the mixture was stirred under 1 atm hydrogen atmosphere at 80° C. for 2.5 hours. After completion of the reaction, insoluble material was filtered off from the reaction mixture, and the filtrate was concentrated under reduced pressure. Water was added to the residue, the mixture was neutralized with a saturated aqueous solution of sodium hydrogencarbonate, and extracted with ethyl acetate. The organic layer was washed with a saturated aqueous solution of sodium chloride, dried over anhydrous magnesium sulfate, and then, concentrated under reduced pressure. The obtained residue was applied to silica gel column chromatography (Eluent; hexane:ethyl acetate=3:7 (V/V)), and the fractions containing the desired compound were concentrated under reduced pressure to obtain 1.43 g of the title compound as a colorless oil. (Yield: 66%)

Mass Spectrum (CI, m/z): 440 (M$^+$+1).
$^1$H-NMR Spectrum (CDCl$_3$, δ ppm): −0.03 (s, 9H), −0.01 (s, 9H), 0.86-0.94 (m, 2H), 0.94-1.02 (m, 2H), 3.13 (t, J=5.4 Hz, 2H), 3.46-3.54 (m, 2H), 3.68-3.76 (m, 2H), 3.80-3.93 (m, 3H), 5.40 (s, 2H), 5.58 (s, 2H), 6.98 (s, 1H), 8.19 (s, 1H).

57-(f) 3-(2-Methoxyethyl)-1,5-bis(2-trimethylsilylethoxymethyl)-1,5-dihydropyrrolo[2,3-d]pyridazin-4-one To 5 ml of mixed solvent (dehydrated tetrahydrofuran:N,N-dimethylformamide=3:1 (V/V)) solution containing 1.29 g (2.93 mmol) of 3-(2-hydroxyethyl)-1,5-bis(2-trimethylsilylethoxymethyl)-1,5-dihydropyrrolo[2,3-d]pyridazin-4-one obtained in Reference example 57-(e) was added 0.56 g (5.83 mmol) of sodium tert-butoxide under room temperature, and the mixture was stirred at the same temperature for 2 hours. Then, 1.1 ml (17.7 mmol) of methyl iodide was added to the mixture, and the mixture was further stirred for 16-hours. After completion of the reaction, water was added to the reaction mixture, and the mixture was extracted with ethyl acetate. The organic layer was washed with a saturated aqueous solution of sodium chloride, dried over anhydrous magnesium sulfate, and then, concentrated under reduced pressure. The obtained residue was applied to silica gel column chromatography (Eluent; hexane:ethyl acetate=1:1 (V/V)), and the fractions containing the desired compound were concentrated under reduced pressure to obtain 1.18 g of the title compound as a slightly yellowish oil. (Yield: 89%)

Mass Spectrum (CI, m/z): 454(M$^+$+1).
$^1$H-NMR Spectrum (CDCl$_3$, δ ppm): −0.04 (s, 9H), −0.01 (s, 9H), 0.85-0.94 (m, 2H), 0.94-1.03 (m, 2H), 3.17 (td, J=6.3, 0.6 Hz, 2H), 3.35 (s, 3H), 3.44-3.51 (m, 2H), 3.70-3.75 (m, 2H), 3.71 (t, J=6.3 Hz, 2H), 5.39 (s, 2H), 5.57 (s, 2H), 7.00 (t, J=0.6 Hz, 1H), 8.13 (s, 1H).

57-(g) 2-Bromo-3-(2-methoxyethyl)-1,5-bis(2-trimethylsilylethoxymethyl)-1,5-dihydropyrrolo[2,3-d]pyridazin-4-one Reaction and post treatment were carried out in the same manner as in Reference example 18-(d) except for using 1.12 g (2.47 mmol) of 3-(2-methoxyethyl)-1,5-bis(2-trimethylsilylethoxymethyl)-1,5-dihydropyrrolo[2,3-d]pyridazin-4-one obtained in Reference example 57-(f) in place of 3-methyl-1,5-bis(2-trimethylsilylethoxymethyl)-1,5-dihydropyrrolo[2,3-d]pyridazin-4-one, whereby 1.13 g of the title compound was obtained as a pale yellowish solid. (Yield: 86%)

Mass Spectrum (CI, m/z): 534 (M$^+$+1).
$^1$H-NMR Spectrum (CDCl$_3$, δ ppm): −0.03 (s, 9H), −0.02 (s, 9H), 0.86-0.94 (m, 2H), 0.94-1.02 (m, 2H), 3.15 (t, J=6.8 Hz, 2H), 3.35 (s, 3H), 3.52-3.59 (m, 2H), 3.68-3.75 (m, 2H), 3.69 (t, J=6.8 Hz, 2H), 5.52 (s, 2H), 5.56 (s, 2H), 8.12 (s, 1H).

Reference Example 58

2-Bromo-3-(2-ethoxyethyl)-1,5-bis(2-trimethylsilylethoxymethyl)-1,5-dihydropyrrolo[2,3-d]pyridazin-4-one

58-(a) 3-(2-Ethoxyethyl)-1,5-bis(2-trimethylsilylethoxymethyl)-1,5-dihydropyrrolo[2,3-d]pyridazin-4-one Reaction and post treatment were carried out in the same manner as in Reference example 57-(f) except for using 1.15 g (2.61 mmol) of 3-(2-hydroxyethyl)-1,5-bis(2-trimethylsilylethoxymethyl)-1,5-dihydropyrrolo[2,3-d]pyridazin-4-one obtained by the same manner as in Reference example 57-(e), and using 1.3 ml (18.7 mmol) of ethyl iodide in place of methyl iodide, whereby 0.77 g of the title compound was obtained as a slightly yellowish oil. (Yield: 63%)

Mass Spectrum (CI, m/z): 468 (M$^+$+1).
$^1$H-NMR Spectrum (CDCl$_3$, δ ppm): −0.04 (s, 9H), −0.02 (s, 9H), 0.86-0.94 (m, 2H), 0.94-1.02 (m, 2H), 1.18 (t, J=7.0 Hz, 3H), 3.17 (td, J=6.4, 0.5 Hz, 2H), 3.44-3.51 (m, 2H), 3.51 (q, J=7.0 Hz, 2H), 3.68-3.75 (m, 2H), 3.74 (t, J=6.4 Hz, 2H), 5.39 (s, 2H), 5.56 (s, 2H), 7.01 (t, J=0.5 Hz, 1H), 8.13 (s, 1H).

58-(b) 2-Bromo-3-(2-ethoxyethyl)-1,5-bis(2-trimethylsilylethoxymethyl)-1,5-dihydropyrrolo[2,3-d]pyridazin-4-one Reaction and post treatment were carried out in the same manner as in Reference example 18-(d) except for using 0.76 g (1.62 mmol) of 3-(2-ethoxyethyl)-1,5-bis(2-trimethylsilylethoxymethyl)-1,5-dihydropyrrolo[2,3-d]pyridazin-4-one obtained in Reference example 58-(a) in place of 3-methyl-1,5-bis(2-trimethylsilylethoxymethyl)-1,5-dihydropyrrolo[2,3-d]pyridazin-4-one, whereby 0.86 g of the title compound was obtained as a colorless oil. (Yield: 97%)

Mass Spectrum (CI, m/z): 548 (M$^+$+1).
$^1$H-NMR Spectrum (CDCl$_3$, δ ppm): −0.03 (s, 9H), −0.02 (s, 9H), 0.86-0.94 (m, 2H), 0.94-1.02 (m, 2H), 1.16 (t, J=7.1 Hz, 3H), 3.15 (t, J=7.1 Hz, 2H), 3.52-3.59 (m, 2H), 3.52 (q, J=7.1 Hz, 2H), 3.67-3.75 (m, 2H), 3.70 (t, J=7.1 Hz, 2H), 5.52 (s, 2H), 5.55 (s, 2H), 8.12 (s, 1H).

Test Example 1

Measurement of PDE4 Enzyme Inhibiting Action

Preparation of a PDE4 enzyme solution was carried out according to the method of Cooper et al. (Br. J. Pharmacol., 126, 1863 (1999)) by modifying a part thereof. Heparin-treated peripheral blood from healthy volunteer was stratified by a blood cell separating solution (Polymorphprep™, available from AXIS-SHIELD PoC AS CO.), and centrifugation was carried out at 20° C. with 1900 rpm for 27 minutes to obtain polymorphonuclear leukocytes. The polymorphonuclear leukocytes were washed with a Hanks' balanced salt solution, then, a mixed solution comprising 70% of 10 mM 3-morpholinopropane sulfonic acid buffer solution (pH 7.4) containing 1 mM EGTA, 1 mM magnesium acetate and 5 mM dithiothreitol and 30% of ethylene glycol was added thereto to dissolve the same under ice-cooling, and the obtained cell dissolved solution was used as a PDE4 enzyme solution.

Measurement of PDE4 activity was carried out according to the method of Owens, et al. (Biochem. J., 326, 53 (1997)) by modifying a part thereof. The PDE4 enzyme solution was incubated with a compound to be tested dissolved in dimethylsulfoxide in 80 mM Tris-HCl buffer solution (pH 7.4) containing 0.2 µM [$^3$H] cAMP, 0.1 mM cGMP, 20 mM MgCl$_2$ and 12 mM 2-mercaptoethanol at 30° C. for 30 minutes. Trifluoroacetic acid (final concentration: 1%) was added to the mixture to stop the reaction, and the reaction mixture was added to neutral alumina column (BOND ELUT™, available from VARIAN INC.). After the column was washed with 100 mM Tris-HCl buffer solution (pH 8.0), [$^3$H] 5'-AMP was eluted with 2N sodium hydroxide solution, and radioactivity of the eluent was measured by a liquid scintillation analyzer.

A concentration of the compound to be tested which inhibits 50% of PDE4 activity was calculated from the relation between the concentration of the compound to be tested which had been added and PDE4 activity as an IC$_{50}$ value. The test results are shown in Table 6.

TABLE 6

| Example No. of compound to be tested | PDE4 inhibition IC$_{50}$ value (nM) |
|---|---|
| Example 3 | 5.2 |
| Example 5 | 3.4 |
| Example 8 | 1.7 |
| Example 9 | 1.8 |
| Example 12 | 4.6 |
| Example 13 | 0.65 |
| Example 14 | 4.7 |
| Example 16 | 13 |
| Example 19 | 0.18 |
| Example 20 | 0.23 |
| Example 29 | 0.57 |
| Example 31 | 9.1 |
| Example 33 | 1.8 |
| Example 34 | 8.7 |
| Example 36 | 7.9 |
| Example 37 | 6.6 |
| Example 38 | 7.1 |
| Example 41 | 9.9 |
| Example 44 | 2.6 |
| Example 49 | 3.5 |
| Example 50 | 16 |
| Example 52 | 8.0 |
| Example 53 | 17 |
| Example 57 | 11 |
| Example 58 | 36 |
| Example 60 | 3.0 |
| Example 62 | 0.41 |
| Example 67 | 1.4 |
| Example 69 | 0.38 |
| Example 73 | 0.23 |
| Example 75 | 1.5 |

In the present test, Compound (1) of the present invention showed excellent PDE4 inhibitory activity.

Test Example 2

Pulmonary Neutrophil Infiltration-Inhibiting Activity in SD Rats

Inhalation of lipopolysaccharide (hereinafter abbreviated to as LPS) was carried out by modifying the method of Moraes et al. (Br. J. Pharmacol., 123, 631 (1998)). SD rats (male, 5-weeks old, supplied by CHARLES RIVER LABORATORIES JAPAN, INC.) fasted 24 hours before administration of a compound were kept in a plastic cage, and inhalated LPS (L2880-500MG, available from SIGMA Inc.) (0.1 mg/ml) dissolved in physiological saline for 30 minutes. An ultrasonic nebulizer (NE-U12, manufactured by Omron Corporation) was used for inhalation.

A compound to be tested is dissolved (10 ml/Kg) in mixed solution of polyethylene glycol (hereinafter abbreviated to as PEG) and water, and orally administered 15 minutes before the inhalation of LPS. For the control group, 50% PEG solution was administered.

Bronchoalveolar lavage (hereinafter abbreviated to as BAL) was carried out as mentioned below 4 hours after the inhalation of LPS. SD rats were anesthetized by sodium pentobarbital (64.8 mg/Kg, i.p.), then, inferior vena cava was cut open to carry out exsanguination, trachea was exposed, a peroral sonde (manufactured by Fuchigami Kikai Co.) for mouse was inserted therein, and the trachea was ligated and fixed. 3.5 ml of physiological saline containing heparin (1 U/ml) was injected by using a disposable injection syringe (5 ml volume, manufactured by Terumo Corporation), and immediately recovered. This operation was repeated four times to obtain a bronchioalveolar lavage fluid (hereinafter abbreviated to as BALF). BALF was centrifugated (at 2500 rpm, 10 minutes, 4° C.), and 1 ml of 0.5% hexadecyltrimethylammonium bromide (030-02105, available from Wako Pure Chemical Industries, Ltd.) was added to the precipitated cells. Thereafter, a freeze-thaw operation (−80° C./37° C.) was repeated three times to destroy the cells.

As an index of a number of neutrophil, measurement of myeloperoxidase (hereinafter abbreviated to as MPO) activity was carried out as follows. Measurement of MPO activity was carried out by partially modifying the method of Krawisz et al. (GASTROENTEROLOGY, 1344 (1984)). To cell dissolved solution was added 50 mM phosphate buffer solution (pH 6.0) containing o-dianisidine hydrochloride (0.2 mg/ml) and 0.005% hydrogen peroxide, and change in absorbance at 450 nm was measured. As a MPO standard substance, MPO from human sputum (available from Elastin Products Company Inc.) was used. Measurement of absorbance was carried out by using a Microplate Reader (MTP-32, manufactured by Corona Electric Co., Ltd.).

An inhibiting rate of the compound to be tested relative to the control was calculated. The test results are shown in Table 7.

TABLE 7

| Compound Example No. to be tested | Rat pulmonary neutrophil infiltration-inhibiting activity (%) @3 mg/Kg |
|---|---|
| Example 15 | 73 |
| Example 22 | 78 |
| Example 61 | 59 |
| Example 66 | 69 |
| Example 72 | 76 |

In the present test, Compound (1) of the present invention showed excellent pulmonary neutrophil infiltration-inhibiting activity.

Test Example 3

Emetic Action Test in Cynomulgus Monkey

To cynomulgus monkey (male, 3 to 5-years old, origin: China) fasted from the evening of the day before the administration was administered a compound to be tested, and presence or absence of emesis was observed for 24 hours. The compound to be tested was suspended in 0.5% aqueous methyl cellulose solution (5 ml/Kg), and administered nasally.

With respect to each dose, each administered to 3 or 4 monkeys, and a dose in which emesis had not been admitted in all monkeys was made a maximum non-emesis dose.

The test results are shown in Table 8.

TABLE 8

| Number of compound to be tested | Monkey Maximum non-emesis dose (mg/Kg) |
|---|---|
| Example 5 | >30 |
| Example 12 | 3 |
| Example 62 | >10 |
| Example 66 | >10 |
| Example 72 | >10 |
| compound A | 0.1 |

Compound A of a compound to be tested is N-(3,5-dichloro-4-pyridyl)-3-cyclopropylmethoxy-4-difluoromethoxybenzamide which is a compound of Example 5 mentioned in WO 95/01338, and is a control compound having a PDE4 inhibitory activity.

In this experiment, the compounds of the present invention showed low emesis causing action as compared with those of the control compound.

Preparation Example

Preparation Example 1

Hard Capsule 50 mg of powder state compound of Example 5, 128.7 mg of lactose, 70 mg of cellulose and 1.3 mg of magnesium stearate are mixed, passed through a sieve of 60 mesh, and then, the powder is charged in No. 3 gelatin capsule with 250 mg to prepare a capsule.

Preparation Example 2

Tablets 50 mg of the compound of Example 5, 124 mg of lactose, 25 mg of cellulose and 1 mg of magnesium stearate are mixed, and tabletted by a tabletting machine to prepare tablets each having 200 mg. This tablet may be sugar coated if necessary.

UTILIZABLILITY IN INDUSTRY

The pyrrolopyridazinone compound represented by the formula (1) or a pharmaceutically acceptable salt thereof of the present invention shows excellent PDE4 inhibiting activity, and also, has excellent properties as a medical compound in the points of oral absorbability, continuity of medical effects, less occurrence in side effects, etc., so that, it is suitably useful as a medicine for the treatment or prevention of a respiratory disease (for example, bronchitic asthma (including atopic asthma), COPD, chronic bronchitis, pneumonial disease, adult respiratory distress syndrome (ARDS), etc.) to which PDE4 pertains to, and further as a medicine for the treatment or prevention of a disease to which cytokine (IL-1, IL-4, IL-6 and TNF (tumor necrosis factor)), etc., pertains to (for example, chronic rheumatism, ulcerative colitis, Crohn's disease, sepsis, septic shock, endotoxin shock, Gram-negative bacterial sepsis, toxic shock syndrome, nephritis, hepatitis, infection (bacteria and virus), circulatory failure (cardiac insufficiency, arteriosclerosis, cardiac infarction, cerebral apoplexy), etc.), etc., which has been known to be participated in PDE4.

The invention claimed is:
1. A pyrrolopyridazinone compound represented by the formula (1):

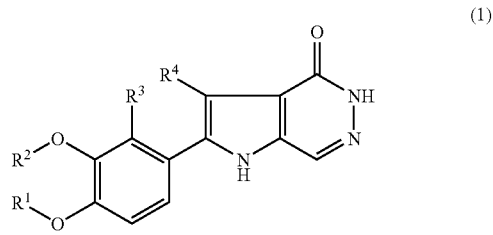

wherein
$R^1$ represents a $C_1$-$C_2$ alkyl group or a halogeno $C_1$-$C_2$ alkyl group,
$R^2$ represents a $C_3$-$C_5$ cycloalkyl group, a ($C_3$-$C_5$ cycloalkyl)$C_1$-$C_2$ alkyl group or a $C_1$-$C_3$ alkyl group, or a methylene group which constitutes a substituted tetrahydrofuran ring or 3,6-dihydro-2H-pyran ring in combination with a group $R^3$,
$R^3$ represents a hydrogen atom, or a methylene group or a cis-vinylene group each of which is a group for constituting a substituted tetrahydrofuran ring or 3,6-dihydro-2H-pyran ring in combination with a group —O—$R^2$,
$R^4$ represents a hydrogen atom; a halogen atom; a $C_1$-$C_8$ alkyl group; a $C_2$-$C_6$ alkenyl group; a $C_2$-$C_6$ alkynyl group; a hydroxy $C_3$-$C_6$ alkenyl group; a hydroxy $C_3$-$C_6$ alkynyl group; a $C_1$-$C_6$ alkyl group substituted by a substituent(s) selected from Substituent group (a); a $C_3$-$C_6$ cycloalkyl group which may be substituted by a substituent(s) selected from Substituent group (b); a $C_1$-$C_3$ alkyl group which is substituted by a $C_3$-$C_6$ cycloalkyl group which may be substituted by a substituent(s) selected from Substituent group (b), and which may be substituted by a hydroxy group; an aromatic ring group or heteroaromatic ring group each of which may be substituted by a substituent(s) selected from Substituent group (c); or a $C_1$-$C_2$ alkyl group which is substituted by an aromatic ring group or heteroaromatic ring group each of which may be substituted by a substituent(s) selected from Substituent group (c), and which may be substituted by a hydroxy group;
Substituent group (a) represents a halogen atom, a hydroxy group, a cyano group, a carboxy group, a $C_1$-$C_5$ alkoxy group, a halogeno $C_1$-$C_4$ alkoxy group, a $C_3$-$C_6$ cycloalkoxy group, a ($C_3$-$C_6$ cycloalkyl)$C_1$-$C_2$ alkoxy group, a $C_1$-$C_4$ alkoxycarbonyl group, a $C_2$-$C_4$ alkanoyl group, a $C_2$-$C_4$ alkanoyloxy group or a $C_1$-$C_4$ alkyl-substituted amino group,
Substituent group (b) represents a hydroxy group or a halogen atom,
Substituent group (c) represents a halogen atom, a hydroxy group, a cyano group, a nitro group, a carboxy group, a $C_1$-$C_5$ alkoxy group, a $C_1$-$C_4$ alkoxycarbonyl group, a $C_2$-$C_4$ alkanoyloxy group, a $C_1$-$C_4$ alkyl-substituted amino group or a $C_1$-$C_4$ alkyl group which may be substituted by a substituent(s) selected from the group consisting of a halogen atom, a hydroxy group and a carboxy group,
or a pharmaceutically acceptable salt thereof.

2. The pyrrolopyridazinone compound or a pharmaceutically acceptable salt thereof according to claim 1, wherein
$R^1$ represents a $C_1$-$C_2$ alkyl group or halogeno $C_1$-$C_2$ alkyl group,
$R^2$ represents a $C_3$-$C_5$ cycloalkyl group, ($C_3$-$C_5$ cycloalkyl) $C_1$-$C_2$ alkyl group or $C_1$-$C_3$ alkyl group,
$R^3$ represents a hydrogen atom, and
$R^4$ represents a hydrogen atom; a halogen atom; $C_1$-$C_8$ alkyl group; $C_2$-$C_6$ alkenyl group; $C_2$-$C_6$ alkynyl group; hydroxy $C_3$-$C_6$ alkenyl group; hydroxy $C_3$-$C_6$ alkynyl group; a $C_1$-$C_6$ alkyl group substituted by a substituent(s) selected from Substituent group (a); a $C_3$-$C_6$ cycloalkyl group which may be substituted by a substituent(s) selected from Substituent group (b); a $C_1$-$C_3$ alkyl group which is substituted by a $C_3$-$C_6$ cycloalkyl group which may be substituted by a substituent(s) selected from Substituent group (b), and which may be substituted by a hydroxy group; an aromatic ring group or heteroaromatic ring group each of which may be substituted by a substituent(s) selected from Substituent group (c); or a $C_1$-$C_2$ alkyl group which is substituted by an aromatic ring group or heteroaromatic ring group each of which may be substituted by a group(s) selected from Substituent group (c), and which may be substituted by a hydroxy group;
Substituent group (a) represents a halogen atom, a hydroxy group, a cyano group, a carboxy group, $C_1$-$C_5$ alkoxy group, halogeno $C_1$-$C_4$ alkoxy group, $C_3$-$C_6$ cycloalkoxy group, ($C_3$-$C_6$ cycloalkyl)$C_1$-$C_2$ alkoxy group, $C_1$-$C_4$ alkoxycarbonyl group, $C_2$-$C_4$ alkanoyl group, $C_2$-$C_4$ alkanoyloxy group or $C_1$-$C_4$ alkyl-substituted amino group,
Substituent group (b) represents a hydroxy group or a halogen atom,
Substituent group (c) represents a halogen atom, a hydroxy group, a cyano group, a nitro group, a carboxy group, $C_1$-$C_5$ alkoxy group, $C_1$-$C_4$ alkoxycarbonyl group, $C_2$-$C_4$ alkanoyloxy group, $C_1$-$C_4$ alkyl-substituted amino group or $C_1$-$C_4$ alkyl group which may be substituted by a substituent(s) selected from the group consisting of a halogen atom, a hydroxy group and a carboxy group.

3. The pyrrolopyridazinone compound or a pharmaceutically acceptable salt thereof according to claim 2, wherein
$R^1$ represents a methyl or difluoromethyl group,
$R^2$ represents a cyclopropyl, cyclobutyl, cyclopentyl, cyclopropylmethyl, cyclobutylmethyl, ethyl or isopropyl group,
$R^3$ represents a hydrogen atom, and
$R^4$ represents a hydrogen atom, chlorine atom, bromine atom, methyl, ethyl, propyl, isopropyl, butyl, isobutyl, pentyl, isopentyl, neopentyl, hexyl, 2-ethylbutyl, 2,2,2-trifluoroethyl, 3,3,3-trifluoropropyl, 2-chloroethyl, hydroxymethyl, methoxymethyl, ethoxymethyl, isopropoxy-methyl, 2-methoxyethyl, 2-ethoxyethyl, 2-isopropoxyethyl, isobutoxymethyl, sec-butoxymethyl, tert-butoxymethyl, 1-ethylpropoxymethyl, 2-fluoroethoxymethyl, cyclobutoxymethyl, cyclo-propylmethoxymethyl, dimethylaminomethyl, cyclopropyl, cyclobutyl, cyclopropylmethyl, cyclobutylmethyl, cyclopropylhydroxymethyl, cyclobutylhydroxymethyl, 2-cyclopropylethyl, 2-cyclobutylethyl, 2-propenyl, 2-butenyl, 2-methyl-2-propenyl, 2-methyl-2-butenyl, 3-methyl-2-butenyl, 2,3-dimethyl-2-butenyl, ethynyl, 2-propynyl, 2-butynyl, 4-methyl-2-pentynyl, 1-hydroxy-2-propenyl, phenyl, 2-fluorophenyl, 4-fluorophenyl, 2,4-difluorophenyl, 2-chlorophenyl, 4-chlorophenyl, 4-cyanophenyl, 2-thienyl, 3-thienyl, 4-thiazolyl, 5-thiazolyl, 4-pyrazolyl, 6-methoxy-2-pyridyl, 6-methoxy-3-pyridyl, benzyl, 2-fluorobenzyl, 3-fluorobenzyl, 4-fluorobenzyl, 2,4-difluorobenzyl, 3,4-difluorobenzyl, 2-chlorobenzyl, 3-chlorobenzyl, 2-cyanobenzyl, 3-cyanobenzyl, 3-carboxybenzyl, 4-carboxybenzyl, 2-thienylmethyl, 5-cyano-2-thienylmethyl, 5-carboxy-2-thienylmethyl, 3-thienylmethyl, 5-cyano-3-thienylmethyl, 5-carboxy-3-thienylmethyl, 2-carboxy-4-thiazolylmethyl, 6-cyano-2-pyridylmethyl, 6-carboxy-2-pyridylmethyl, 6-methoxy-2-pyridylmethyl, 6-cyano-3-pyridylmethyl, 6-carboxy-3-pyridylmethyl, 6-methoxy-3-pyridylmethyl, 2-cyano-3-pyridylmethyl, 2-carboxy-3-pyridylmethyl, 2-cyano-4-pyridylmethyl, 2-carboxy-4-pyridylmethyl, phenethyl, 2-fluorophenethyl, 3-fluorophenethyl, 4-fluorophenethyl, 3-cyanophenethyl, 2-(2-thienyl)ethyl, 2-(6-cyano-2-pyridyl)ethyl, 2-(6-cyano-3-pyridyl)ethyl, 2-(2-cyano-3-pyridyl) ethyl, hydroxyphenylmethyl, (2-fluorophenyl)hydroxymethyl, (3-fluorophenyl)hydroxymethyl or (4-fluorophenyl)hydroxymethyl group.

4. The pyrrolopyridazinone compound or a pharmaceutically acceptable salt thereof according to claim 2, wherein
$R^1$ represents a difluoromethyl group,
$R^2$ represents a cyclopropyl, cyclobutyl, cyclopentyl, cyclopropylmethyl or isopropyl group,
$R^3$ represents a hydrogen atom, and
$R^4$ represents a hydrogen atom, chlorine atom, bromine atom, methyl, ethyl, propyl, isopropyl, butyl, isobutyl, pentyl, isopentyl, neopentyl, hexyl, 2-ethylbutyl, 2,2,2-trifluoroethyl, 3,3,3-trifluoropropyl, 2-chloroethyl, hydroxymethyl, methoxymethyl, ethoxymethyl, isopropoxy-methyl, 2-methoxyethyl, 2-ethoxyethyl, 2-isopropoxyethyl, isobutoxymethyl, sec-butoxymethyl, tert-butoxymethyl, 1-ethylpropoxymethyl, 2-fluoroethoxymethyl, cyclobutoxymethyl, cyclo-propylmethoxymethyl, dimethylaminomethyl, cyclopropyl, cyclobutyl, cyclopropylmethyl, cyclobutylmethyl, cyclopropylhydroxymethyl, cyclobutylhydroxymethyl, 2-cyclopropylethyl, 2-cyclobutylethyl, 2-propenyl, 2-butenyl, 2-methyl-2-propenyl, 2-methyl-2-butenyl, 3-methyl-2-butenyl, 2,3-dimethyl-2-butenyl, ethynyl, 2-propynyl, 2-butynyl, 4-methyl-2-pentynyl, 1-hydroxy-2-propenyl, phenyl, 2-fluorophenyl, 4-fluorophenyl, 2,4-difluorophenyl, 2-chlorophenyl, 4-chlorophenyl, 4-cyanophenyl, 2-thienyl, 3-thienyl, 4-thiazolyl, 5-thiazolyl, 4-pyrazolyl, 6-methoxy-2-pyridyl, 6-methoxy-3-pyridyl, benzyl, 2-fluorobenzyl, 3-fluorobenzyl, 4-fluorobenzyl, 2,4-difluorobenzyl, 3,4-difluorobenzyl, 2-chlorobenzyl, 3-chlorobenzyl, 2-cyanobenzyl, 3-cyanobenzyl, 3-carboxybenzyl, 4-carboxybenzyl, 2-thienylmethyl, 5-cyano-2-thienylmethyl, 5-carboxy-2-thienylmethyl, 3-thienylmethyl, 5-cyano-3-thienylmethyl, 5-carboxy-3-thienylmethyl, 2-carboxy-4-thiazolylmethyl, 6-cyano-2-pyridylmethyl, 6-carboxy-2-pyridylmethyl, 6-methoxy-2-pyridylmethyl, 6-cyano-3-pyridylmethyl, 6-carboxy-3-pyridylmethyl, 6-methoxy-3-pyridylmethyl, 2-cyano-3-pyridylmethyl, 2-carboxy-3-pyridylmethyl, 2-cyano-4-pyridylmethyl, 2-carboxy-4-pyridylmethyl, phenethyl, 2-fluorophenethyl, 3-fluorophenethyl, 4-fluorophenethyl, 3-cyanophenethyl, 2-(2-thienyl)ethyl, 2-(6-cyano-2-pyridyl)ethyl, 2-(6-cyano-3-pyridyl)ethyl, 2-(2-cyano-3-pyridyl)

ethyl, hydroxyphenylmethyl, (2-fluorophenyl)hydroxymethyl, (3-fluorophenyl)hydroxymethyl or (4-fluorophenyl)hydroxymethyl group.

5. The pyrrolopyridazinone compound or a pharmaceutically acceptable salt thereof according to claim 2, wherein
$R^1$ represents a difluoromethyl group,
$R^2$ represents a cyclopropyl or cyclopropylmethyl group,
$R^3$ represents a hydrogen atom, and
$R^4$ represents a hydrogen atom, chlorine atom, bromine atom, methyl, ethyl, propyl, isopropyl, butyl, isobutyl, pentyl, isopentyl, hexyl, 2-ethylbutyl, 2,2,2-trifluoroethyl, 3,3,3-trifluoropropyl, 2-chloroethyl, hydroxymethyl, methoxymethyl, ethoxymethyl, isopropoxymethyl, 2-methoxyethyl, 2-ethoxyethyl, 2-isopropoxyethyl, isobutoxymethyl, sec-butoxymethyl, tert-butoxymethyl, 1-ethylpropoxymethyl, 2-fluoroethoxymethyl, cyclobutoxymethyl, cyclopropylmethoxymethyl, dimethylaminomethyl, cyclopropyl, cyclopropylmethyl, cyclopropylhydroxymethyl, 2-cyclopropylethyl, 2-propenyl, 2-butenyl, 2-methyl-2-propenyl, 2-methyl-2-butenyl, 3-methyl-2-butenyl, 2,3-dimethyl-2-butenyl, ethynyl, 2-propynyl, 2-butynyl, 4-methyl-2-pentynyl, 1-hydroxy-2-propenyl, phenyl, 2-thienyl, 3-thienyl, 4-pyrazolyl, benzyl, 2-fluorobenzyl, 3-fluorobenzyl, 4-fluorobenzyl, 2,4-difluorobenzyl, 3,4-difluorobenzyl, 2-chlorobenzyl, 3-chlorobenzyl, 2-cyanobenzyl, 3-cyanobenzyl, 3-carboxybenzyl, 2-thienylmethyl, 3-thienylmethyl, 6-methoxy-2-pyridylmethyl, 6-methoxy-3-pyridylmethyl, phenethyl, hydroxyphenylmethyl, (2-fluorophenyl)hydroxymethyl, (3-fluorophenyl)hydroxymethyl or (4-fluorophenyl)hydroxymethyl group.

6. The pyrrolopyridazinone compound or a pharmaceutically acceptable salt thereof according to claim 2, wherein
$R^1$ represents a difluoromethyl group,
$R^2$ represents a cyclopropyl or cyclopropylmethyl group,
$R^3$ represents a hydrogen atom, and
$R^4$ represents a hydrogen atom, chlorine atom, bromine atom, methyl, ethyl, propyl, isopropyl, butyl, isobutyl, pentyl, isopentyl, hexyl, hydroxymethyl, methoxymethyl, ethoxymethyl, isopropoxymethyl, 2-methoxyethyl, 2-ethoxyethyl, isobutoxymethyl, sec-butoxymethyl, tert-butoxymethyl, 1-ethylpropoxymethyl, 2-fluoroethoxymethyl, cyclobutoxymethyl, cyclopropylmethoxymethyl, dimethylaminomethyl, cyclopropyl, cyclopropylmethyl, 2-cyclopropylethyl, 2-propenyl, ethynyl, 2-propynyl, 2-butynyl, 4-methyl-2-pentynyl, 1-hydroxy-2-propenyl, phenyl, 4-pyrazolyl, benzyl, 2-fluorobenzyl, 3-fluorobenzyl, 4-fluorobenzyl, 2-cyanobenzyl, 3-cyanobenzyl, 3-carboxybenzyl, 6-methoxy-2-pyridylmethyl, 6-methoxy-3-pyridylmethyl, phenethyl or hydroxyphenylmethyl group.

7. The pyrrolopyridazinone compound or a pharmaceutically acceptable salt thereof according to claim 2, wherein the pyrrolopyridazinone compound is
2-(3-cyclopropoxy-4-difluoromethoxyphenyl)-1,5-dihydropyrrolo[2,3-d]pyridazin-4-one,
3-chloro-2-(3-cyclopropoxy-4-difluoromethoxyphenyl)-1,5-dihydropyrrolo[2,3-d]pyridazin-4-one,
3-bromo-2-(3-cyclopropoxy-4-difluoromethoxyphenyl)-1,5-dihydropyrrolo[2,3-d]pyridazin-4-one,
2-(3-cyclopropoxy-4-difluoromethoxyphenyl)-3-methyl-1,5-dihydropyrrolo[2,3-d]pyridazin-4-one,
2-(3-cyclopropoxy-4-difluoromethoxyphenyl)-3-ethyl-1,5-dihydropyrrolo[2,3-d]pyridazin-4-one,
2-(3-cyclopropoxy-4-difluoromethoxyphenyl)-3-propyl-1,5-dihydropyrrolo[2,3-d]pyridazin-4-one,
2-(3-cyclopropoxy-4-difluoromethoxyphenyl)-3-isopropyl-1,5-dihydropyrrolo[2,3-d]pyridazin-4-one,
3-butyl-2-(3-cyclopropoxy-4-difluoromethoxyphenyl)-1,5-dihydropyrrolo[2,3-d]pyridazin-4-one,
2-(3-cyclopropoxy-4-difluoromethoxyphenyl)-3-isobutyl-1,5-dihydropyrrolo[2,3-d]pyridazin-4-one,
2-(3-cyclopropoxy-4-difluoromethoxyphenyl)-3-pentyl-1,5-dihydropyrrolo[2,3-d]pyriBazin-4-one,
2-(3-cyclopropoxy-4-difluoromethoxyphenyl)-3-hexyl-1,5-dihydropyrrolo[2,3-d]pyridazin-4-one,
2-(3-cyclopropoxy-4-difluoromethoxyphenyl)-3-hydroxymethyl-1,5-dihydropyrrolo[2,3-d]-pyridazin-4-one,
2-(3-cyclopropoxy-4-difluoromethoxyphenyl)-3-methoxymethyl-1,5-dihydropyrrolo[2,3-d]-pyridazin-4-one,
2-(3-cyclopropoxy-4-difluoromethoxyphenyl)-3-(2-methoxyethyl)-1,5-dihydropyrrolo[2,3-d]-pyridazin-4-one,
2-(3-cyclopropoxy-4-difluoromethoxyphenyl)-3-ethoxymethyl-1,5-dihydropyrrolo[2,3-d]pyridazin-4-one,
2-(3-cyclopropoxy-4-difluoromethoxyphenyl)-3-(2-ethoxyethyl)-1,5-dihydropyrrolo[2,3-d]-pyridazin-4-one,
2-(3-cyclopropoxy-4-difluoromethoxyphenyl)-3-isopropoxymethyl-1,5-dihydropyrrolo[2,3-d]-pyridazin-4-one,
2-(3-cyclopropoxy-4-difluoromethoxyphenyl)-3-(2-fluoroethoxymethyl)-1,5-dihydropyrrolo[2,3-d]pyridazin-4-one,
3-cyclobutoxymethyl-2-(3-cyclopropoxy-4-difluoromethoxyphenyl)-1,5-dihydropyrrolo[2,3-d]-pyridazin-4-one,
2-(3-cyclopropoxy-4-difluoromethoxyphenyl)-3-cyclopropylmethoxymethyl-1,5-dihydropyrrolo-[2,3-d]pyridazin-4-one,
2-(3-cyclopropoxy-4-difluoromethoxyphenyl)-3-dimethylaminomethyl-1,5-dihydropyrrolo[2,3-d]pyridazin-4-one,
2-(3-cyclopropoxy-4-difluoromethoxyphenyl)-3-cyclopropyl-1,5-dihydropyrrolo[2,3-d]pyridazin-4-one,
2-(3-cyclopropoxy-4-difluoromethoxyphenyl)-3-cyclopropylmethyl-1,5-dihydropyrrolo[2,3-d]-pyridazin-4-one,
2-(3-cyclopropoxy-4-difluoromethoxyphenyl)-3-(2-cyclopropylethyl)-1,5-dihydropyrrolo[2,3-d]-pyridazin-4-one,
2-(3-cyclopropoxy-4-difluoromethoxyphenyl)-3-(2-propenyl)-1,5-dihydropyrrolo[2,3-d]pyridazin-4-one,
2-(3-cyclopropoxy-4-difluoromethoxyphenyl)-3-ethynyl-1,5-dihydropyrrolo[2,3-d]pyridazin-4-one,
2-(3-cyclopropoxy-4-difluoromethoxyphenyl)-3-(2-propynyl)-1,5-dihydropyrrolo[2,3-d]pyridazin-4-one,
3-(2-butynyl)-2-(3-cyclopropoxy-4-difluoromethoxyphenyl)-1,5-dihydropyrrolo[2,3-d]pyridazin-4-one,
2-(3-cyclopropoxy-4-difluoromethoxyphenyl)-3-(4-methyl-2-pentynyl)-1,5-dihydropyrrolo[2,3-d]pyridazin-4-one,
2-(3-cyclopropoxy-4-difluoromethoxyphenyl)-3-(1-hydroxy-2-propenyl)-1,5-dihydropyrrolo[2,3-d]pyridazin-4-one,
2-(3-cyclopropoxy-4-difluoromethoxyphenyl)-3-phenyl-1,5-dihydropyrrolo[2,3-d]pyridazin-4-one,
2-(3-cyclopropoxy-4-difluoromethoxyphenyl)-3-(4-pyrazolyl)-1,5-dihydropyrrolo[2,3-d]pyridazin-4-one,
3-benzyl-2-(3-cyclopropoxy-4-difluoromethoxyphenyl)-1,5-dihydropyrrolo[2,3-d]pyridazin-4-one, 2-(3-cyclopropoxy-4-difluoromethoxyphenyl)-3-(2-fluorobenzyl)-1,5-dihydropyrrolo[2,3-d]-pyridazin-4-one,
2-(3-cyclopropoxy-4-difluoromethoxyphenyl)-3-(3-fluorobenzyl)-1,5-dihydropyrrolo[2,3-d]-pyridazin-4-one,
2-(3-cyclopropoxy-4-difluoromethoxyphenyl)-3-(4-fluorobenzyl)-1,5-dihydropyrrolo[2,3-d]-pyridazin-4-one,
3-(2-cyanobenzyl)-2-(3-cyclopropoxy-4-difluoromethoxyphenyl)-1,5-dihydropyrrolo[2,3-d]-pyridazin-4-one,
3-(3-cyanobenzyl)-2-(3-cyclopropoxy-4-difluoromethoxyphenyl)-1,5-dihydropyrrolo[2,3-d]-pyridazin-4-one,
3-(3-carboxybenzyl)-2-(3-cyclopropoxy-4-difluoromethoxyphenyl)-1,5-dihydropyrrolo[2,3-d]-pyridazin-4-one,
2-(3-cyclopropoxy-4-difluoromethoxyphenyl)-3-(6-methoxy-2-pyridylmethyl)-1,5-dihydro-pyrrolo[2,3-d]pyridazin-4-one,
2-(3-cyclopropoxy-4-difluoromethoxyphenyl)-3-(6-methoxy-3-pyridylmethyl)-1,5-dihydro-pyrrolo[2,3-d]pyridazin-4-one,
2-(3-cyclopropoxy-4-difluoromethoxyphenyl)-3-phenethyl-1,5-dihydropyrrolo[2,3-d]pyridazin-4-one,
2-(3-cyclopropoxy-4-difluoromethoxyphenyl)-3-hydroxyphenylmethyl-1,5-dihydropyrrolo[2,3-d]pyridazin-4-one,
2-(3-cyclopropylmethoxy-4-difluoromethoxyphenyl)-1,5-dihydropyrrolo[2,3-d]pyridazin-4-one,
3-chloro-2-(3-cyclopropylmethoxy-4-difluoromethoxyphenyl)-1,5-dihydropyrrolo[2,3-d]pyridazin-4-one,
2-(3-cyclopropylmethoxy-4-difluoromethoxyphenyl)-3-ethyl-1,5-dihydropyrrolo[2,3-d]pyridazin-4-one,
2-(3-cyclopropylmethoxy-4-difluoromethoxyphenyl)-3-phenyl-1,5-dihydropyrrolo[2,3-d]pyridazin-4-one,
2-(4-difluoromethoxy-3-isopropoxyphenyl)-1,5-dihydropyrrolo[2,3-d]pyridazin-4-one,
3-chloro-2-(4-difluoromethoxy-3-isopropoxyphenyl)-1,5-dihydropyrrolo[2,3-d]pyridazin-4-one,
3-bromo-2-(4-difluoromethoxy-3-isopropoxyphenyl)-1,5-dihydropyrrolo[2,3-d]pyridazin-4-one,
2-(3-cyclobutoxy-4-difluoromethoxyphenyl)-1,5-dihydropyrrolo[2,3-d]pyridazin-4-one,
3-chloro-2-(3-cyclobutoxy-4-difluoromethoxyphenyl)-1,5-dihydropyrrolo[2,3-d]pyridazin-4-one,
3-bromo-2-(3-cyclobutoxy-4-difluoromethoxyphenyl)-1,5-dihydropyrrolo[2,3-d]pyridazin-4-one,
2-(3-cyclobutoxy-4-difluoromethoxyphenyl)-3-phenyl-1,5-dihydropyrrolo[2,3-d]pyridazin-4-one,
3-chloro-2-(3-cyclopropoxy-4-methoxyphenyl)-1,5-dihydropyrrolo[2,3-d]pyridazin-4-one,
3-bromo-2-(3-cyclopropoxy-4-methoxyphenyl)-1,5-dihydropyrrolo[2,3-d]pyridazin-4-one,
3-butyl-2-(3-cyclopropoxy-4-methoxyphenyl)-1,5-dihydropyrrolo[2,3-d]pyridazin-4-one,
3-chloro-2-(3-cyclopropylmethoxy-4-methoxyphenyl)-1,5-dihydropyrrolo[2,3-d]pyridazin-4-one,
3-chloro-2-(3-isopropoxy-4-methoxyphenyl)-1,5-dihydropyrrolo[2,3-d]pyridazin-4-one,
3-chloro-2-(3-cyclobutoxy-4-methoxyphenyl)-1,5-dihydropyrrolo[2,3-d]pyridazin-4-one,
2-(3-cyclopentoxy-4-methoxyphenyl)-1,5-dihydropyrrolo[2,3-d]pyridazin-4-one,
2-(3-cyclopropoxy-4-difluoromethoxyphenyl)-3-isobutoxymethyl-1,5-dihydropyrrolo[2,3-d]-pyridazin-4-one,
3-(sec-butoxymethyl)-2-(3-cyclopropoxy-4-difluoromethoxyphenyl)-1,5-dihydropyrrolo[2,3-d]-pyridazin-4-one,
3-(tert-butoxymethyl)-2-(3-cyclopropoxy-4-difluoromethoxyphenyl)-1,5-dihydropyrrolo[2,3-d]-pyridazin-4-one, or
2-(3-cyclopropoxy-4-difluoromethoxyphenyl)-3-(1-ethylpropoxymethyl)-1,5-dihydropyrrolo[2,3-d]pyridazin-4-one.

8. The pyrrolopyridazinone compound or a pharmaceutically acceptable salt thereof according to claim 1, wherein
$R^1$ represents a $C_1$-$C_2$ alkyl group or a halogeno $C_1$-$C_2$ alkyl group,
the substituted tetrahydrofuran ring or 3,6-dihydro-2H-pyran ring formed by $R^3$ in combination with the group —O—$R^2$ represents a 2,2-(1,2-ethylene)-tetrahydrofuran ring, 2,2-(1,3-propylene)-tetrahydrofuran ring, 2,2-(1,4-butylene)-tetrahydrofuran ring, 2-cyclopropyl-tetrahydrofuran ring, 2-cyclobutyl-tetrahydrofuran ring, 2,2-dimethyl-tetrahydrofuran ring, 6,6-(1,2-ethylene)-3,6-dihydro-2H-pyran ring, 6,6-(1,3-propylene)-3,6-dihydro-2H-pyran ring, 6,6-(1,4-butylene)-3,6-dihydro-2H-pyran ring, 6-cyclopropyl-3,6-dihydro-2H-pyran ring, 6-cyclobutyl-3,6-dihydro-2H-pyran ring or 6,6-dimethyl-3,6-dihydro-2H-pyran ring,
$R^4$ represents a hydrogen atom; a halogen atom; a $C_1$-$C_8$ alkyl group; a $C_2$-$C_6$ alkenyl group; a $C_2$-$C_6$ alkynyl group; a hydroxy $C_3$-$C_6$ alkenyl group; a hydroxy $C_3$-$C_6$ alkynyl group; a $C_1$-$C_6$ alkyl group which is substituted by a substituent(s) selected from Substituent group (a); a $C_3$-$C_6$ cycloalkyl group which may be substituted by a substituent(s) selected from Substituent group (b); a $C_1$-$C_3$ alkyl group which is substituted by a $C_3$-$C_6$ cycloalkyl group which may be substituted by a substituent(s) selected from Substituent group (b) and which may be substituted by a hydroxy group; an aromatic ring group or heteroaromatic ring group each of which may be substituted by a substituent(s) selected from Substituent group (c); or a $C_1$-$C_2$ alkyl group which is substituted by an aromatic ring group or heteroaromatic ring group which may be substituted by a group(s) selected from Substituent group (c), and which may be substituted by a hydroxy group;
Substituent group (a) represents a halogen atom, a hydroxy group, a cyano group, a carboxy group, $C_1$-$C_5$ alkoxy group, halogeno $C_1$-$C_4$ alkoxy group, $C_3$-$C_6$ cycloalkoxy group, ($C_3$-$C_6$ cycloalkyl)$C_1$-$C_2$ alkoxy group, $C_1$-$C_4$ alkoxycarbonyl group, $C_2$-$C_4$ alkanoyl group, $C_2$-$C_4$ alkanoyloxy group or $C_1$-$C_4$ alkyl-substituted amino group,
Substituent group (b) represents a hydroxy group or a halogen atom,
Substituent group (c) represents a halogen atom, a hydroxy group, a cyano group, a nitro group, a carboxy group, a $C_1$-$C_5$ alkoxy group, a $C_1$-$C_4$ alkoxycarbonyl group, a $C_2$-$C_4$ alkanoyloxy group, a $C_1$-$C_4$ alkyl-substituted amino group or a $C_1$-$C_4$ alkyl group which may be substituted by a substituent(s) selected from the group consisting of a halogen atom, a hydroxy group and a carboxy group.

9. The pyrrolopyridazinone compound or a pharmaceutically acceptable salt thereof according to claim 8, wherein
$R^1$ represents a methyl or difluoromethyl group,
the substituted tetrahydrofuran ring or 3,6-dihydro-2H-pyran ring formed by $R^3$ in combination with the group —O—$R^2$ represents a 2,2-(1,4-butylene)-tetrahydrofuran ring, 6,6-(1,3-propylene)-3,6-dihydro-2H-pyran ring, 6,6-(1,4-butylene)-3,6-dihydro-2H-pyran ring, 6-cyclopropyl-3,6-dihydro-2H-pyran ring or 6,6-dimethyl-3,6-dihydro-2H-pyran ring, R⁴ represents a hydrogen atom, chlorine atom, bromine atom, methyl, ethyl, propyl, isopropyl, butyl, isobutyl, pentyl, isopentyl, neopentyl, hexyl, 2-ethylbutyl, 2,2,2-trifluoroethyl, 3,3,3-trifluoropropyl, 2-chloroethyl, hydroxymethyl, methoxymethyl, ethoxymethyl, isopropoxy-methyl, 2-methoxyethyl, 2-ethoxyethyl, 2-isopropoxyethyl, isobutoxymethyl, sec-butoxymethyl, tert-butoxymethyl, 1-ethylpropoxymethyl, 2-fluoroethoxymethyl, cyclobutoxymethyl, cyclopropylmethoxymethyl, dimethylaminomethyl, cyclopropyl, cyclobutyl, cyclopropylmethyl, cyclobutylmethyl, cyclopropylhydroxymethyl, cyclobutylhydroxymethyl, 2-cyclopropylethyl, 2-cyclobutylethyl, 2-propenyl, 2-butenyl, 2-methyl-2-propenyl, 2-methyl-2-butenyl, 3-methyl-2-butenyl, 2,3-dimethyl-2-butenyl, ethynyl, 2-propynyl, 2-butynyl, 4-methyl-2-pentynyl, 1-hydroxy-2-propenyl, phenyl, 2-fluorophenyl, 4-fluorophenyl, 2,4-difluorophenyl, 2-chlorophenyl, 4-chlorophenyl, 4-cyanophenyl, 2-thienyl, 3-thienyl, 4-thiazolyl, 5-thiazolyl, 4-pyrazolyl, 6-methoxy-2-pyridyl, 6-methoxy-3-pyridyl, benzyl, 2-fluorobenzyl, 3-fluorobenzyl, 4-fluorobenzyl, 2,4-difluorobenzyl, 3,4-difluorobenzyl, 2-chlorobenzyl, 3-chlorobenzyl, 2-cyanobenzyl, 3-cyanobenzyl, 3-carboxybenzyl, 4-carboxybenzyl, 2-thienylmethyl, 5-cyano-2-thienylmethyl, 5-carboxy-2-thienylmethyl, 3-thienylmethyl, 5-cyano-3-thienylmethyl, 5-carboxy-3-thienylmethyl, 2-carboxy-4-thiazolylmethyl, 6-cyano-2-pyridylmethyl, 6-carboxy-2-pyridylmethyl, 6-methoxy-2-pyridylmethyl, 6-cyano-3-pyridylmethyl, 6-carboxy-3-pyridylmethyl, 6-methoxy-3-pyridylmethyl, 2-cyano-3-pyridylmethyl, 2-carboxy-3-pyridylmethyl, 2-cyano-4-pyridylmethyl, 2-carboxy-4-pyridylmethyl, phenethyl, 2-fluorophenethyl, 3-fluorophenethyl, 4-fluorophenethyl, 3-cyanophenethyl, 2-(2-thienyl)ethyl, 2-(6-cyano-2-pyridyl)ethyl, 2-(6-cyano-3-pyridyl)ethyl, 2-(2-cyano-3-pyridyl)ethyl, hydroxyphenylmethyl, (2-fluorophenyl)hydroxymethyl, (3-fluorophenyl)hydroxymethyl or (4-fluorophenyl)hydroxymethyl group.

10. The pyrrolopyridazinone compound or a pharmaceutically acceptable salt thereof according to claim 8, wherein
R¹ represents a methyl or difluoromethyl group,
the substituted tetrahydrofuran ring or 3,6-dihydro-2H-pyran ring formed by R³ in combination with the group —O—R² represents a 2,2-(1,4-butylene)-tetrahydrofuran ring, 6,6-(1,3-propylene)-3,6-dihydro-2H-pyran ring, 6,6-(1,4-butylene)-3,6-dihydro-2H-pyran ring, 6-cyclopropyl-3,6-dihydro-2H-pyran ring or 6,6-dimethyl-3,6-dihydro-2H-pyran ring,
R⁴ represents a hydrogen atom, chlorine atom, bromine atom, methyl, ethyl, propyl, isopropyl, butyl, isobutyl, pentyl, isopentyl, hexyl, 2-ethylbutyl, 2,2,2-trifluoroethyl, 3,3,3-trifluoropropyl, 2-chloroethyl, hydroxymethyl, methoxymethyl, ethoxymethyl, isopropoxymethyl, 2-methoxyethyl, 2-ethoxyethyl, 2-isopropoxyethyl, isobutoxymethyl, sec-butoxymethyl, tert-butoxymethyl, 1-ethylpropoxymethyl, 2-fluoroethoxymethyl, cyclobutoxymethyl, cyclopropylmethoxymethyl, dimethylaminomethyl, cyclopropyl, cyclopropylmethyl, cyclopropylhydroxymethyl, 2-cyclopropylethyl, 2-propenyl, 2-butenyl, 2-methyl-2-propenyl, 2-methyl-2-butenyl, 3-methyl-2-butenyl, 2,3-dimethyl-2-butenyl, ethynyl, 2-propynyl, 2-butynyl, 4-methyl-2-pentynyl, 1-hydroxy-2-propenyl, phenyl, 2-thienyl, 3-thienyl, 4-pyrazolyl, benzyl, 2-fluorobenzyl, 3-fluorobenzyl, 4-fluorobenzyl, 2,4-difluorobenzyl, 3,4-difluorobenzyl, 2-chlorobenzyl, 3-chlorobenzyl, 2-cyanobenzyl, 3-cyanobenzyl, 3-carboxybenzyl, 2-thienylmethyl, 3-thienylmethyl, 6-methoxy-2-pyridylmethyl, 6-methoxy-3-pyridylmethyl, phenethyl, hydroxyphenylmethyl, (2-fluorophenyl)hydroxymethyl, (3-fluorophenyl)hydroxymethyl or (4-fluorophenyl)hydroxymethyl group.

11. The pyrrolopyridazinone compound or a pharmaceutically acceptable salt thereof according to claim 8, wherein
R¹ represents a difluoromethyl group,
the substituted tetrahydrofuran ring or 3,6-dihydro-2H-pyran ring formed by R³ in combination with the group —O—R² represents a 2,2-(1,4-butylene)-tetrahydrofuran ring, 6,6-(1,3-propylene)-3,6-dihydro-2H-pyran ring, 6,6-(1,4-butylene)-3,6-dihydro-2H-pyran ring, 6-cyclopropyl-3,6-dihydro-2H-pyran ring or 6,6-dimethyl-3,6-dihydro-2H-pyran ring,
R⁴ represents a hydrogen atom, chlorine atom, bromine atom, methyl, ethyl, propyl, isopropyl, butyl, isobutyl, pentyl, isopentyl, hexyl, 2-ethylbutyl, 2,2,2-trifluoroethyl, 3,3,3-trifluoropropyl, 2-chloroethyl, hydroxymethyl, methoxymethyl, ethoxymethyl, isopropoxymethyl, 2-methoxyethyl, 2-ethoxyethyl, 2-isopropoxyethyl, isobutoxymethyl, sec-butoxymethyl, tert-butoxymethyl, 1-ethylpropoxymethyl, 2-fluoroethoxymethyl, cyclobutoxymethyl, cyclopropylmethoxymethyl, dimethylaminomethyl, cyclopropyl, cyclopropylmethyl, cyclopropylhydroxymethyl, 2-cyclopropylethyl, 2-propenyl, 2-butenyl, 2-methyl-2-propenyl, 2-methyl-2-butenyl, 3-methyl-2-butenyl, 2,3-dimethyl-2-butenyl, ethynyl, 2-propynyl, 2-butynyl, 4-methyl-2-pentynyl, 1-hydroxy-2-propenyl, phenyl, 2-thienyl, 3-thienyl, 4-pyrazolyl, benzyl, 2-fluorobenzyl, 3-fluorobenzyl, 4-fluorobenzyl, 2,4-difluorobenzyl, 3,4-difluorobenzyl, 2-chlorobenzyl, 3-chlorobenzyl, 2-cyanobenzyl, 3-cyanobenzyl, 3-carboxybenzyl, 2-thienylmethyl, 3-thienylmethyl, 6-methoxy-2-pyridylmethyl, 6-methoxy-3-pyridylmethyl, phenethyl, hydroxyphenylmethyl, (2-fluorophenyl)hydroxymethyl, (3-fluorophenyl)hydroxymethyl or (4-fluorophenyl)hydroxymethyl group.

12. The pyrrolopyridazinone compound or a pharmaceutically acceptable salt thereof according to claim 8, wherein
R¹ represents a difluoromethyl group,
the substituted tetrahydrofuran ring or 3,6-dihydro-2H-pyran ring formed by R³ in combination with the group —O—R² represents a 2,2-(1,4-butylene)-tetrahydrofuran ring, 6,6-(1,3-propylene)-3,6-dihydro-2H-pyran ring, 6,6-(1,4-butylene)-3,6-dihydro-2H-pyran ring, 6-cyclopropyl-3,6-dihydro-2H-pyran ring or 6,6-dimethyl-3,6-dihydro-2H-pyran ring, and
R⁴ represents a hydrogen atom, chlorine atom, bromine atom, methyl, ethyl, propyl, isopropyl, butyl, isobutyl, pentyl, isopentyl, hexyl, hydroxymethyl, methoxymethyl, ethoxymethyl, isopropoxymethyl, 2-methoxyethyl, 2-ethoxyethyl, isobutoxymethyl, sec-butoxymethyl, tert-butoxymethyl, 1-ethylpropoxymethyl, 2-fluoroethoxymethyl, cyclobutoxymethyl, cyclopropylmethoxymethyl, dimethylaminomethyl, cyclopropyl, cyclopropylmethyl, 2-cyclopropylethyl, 2-propenyl, ethynyl, 2-propynyl, 2-butynyl, 4-methyl-2-pentynyl, 1-hydroxy-2-propenyl, phenyl, 4-pyrazolyl, benzyl, 2-fluorobenzyl, 3-fluorobenzyl, 4-fluorobenzyl, 2-cyanobenzyl, 3-cyanobenzyl, 3-carboxybenzyl, 6-methoxy-2-pyridylmethyl, 6-methoxy-3-pyridylmethyl, phenethyl or hydroxyphenylmethyl group.

13. The pyrrolopyridazinone compound or a pharmaceutically acceptable salt thereof according to claim 8, wherein the pyrrolopyridazinone compound is 3-chloro-2-(8-difluoromethoxy-2,2-dimethyl-2H-chromen-5-yl)-1,5-dihydropyrrolo[2,3-d]-pyridazin-4-one, 2-(8-difluoromethoxy-2,2-dimethyl-2H-chromen-5-yl)-3-methyl-1,5-dihydropyrrolo[2,3-d]-pyridazin-4-one, 2-(8-difluoromethoxy-2,2-dimethyl-2H-chromen-5-yl)-3-ethyl-1,5-dihydropyrrolo[2,3-d]pyridazin-4-one, 3-cyclopropyl-2-(8-difluoromethoxy-2,2-dimethyl-2H-chromen-5-yl)-1,5-dihydropyrrolo[2,3-d]-pyridazin-4-one, 2-(2-cyclopropyl-8-difluoromethoxy-2H-chromen-5-yl)-1,5-dihydropyrrolo[2,3-d]pyridazin-4-one, 3-chloro-2-(8-difluoromethoxy-2H-chromen-2-spiro-1'-cyclobutan-5-yl)-1,5-dihydropyrrolo[2,3-d]pyridazin-4-one, 3-chloro-2-(8-difluoromethoxy-2H-chromen-2-spiro-1'-cyclopentan-5-yl)-1,5-dihydropyrrolo[2,3-d]pyridazin-4-one, 2-(7-difluoromethoxy-2,3-dihydrobenzofuran-2-spiro-1'-cyclopentan-4-yl)-1,5-dihydropyrrolo[2,3-d]pyridazin-4-one, 2-(2,3-dihydro-7-methoxybenzofuran-2-spiro-1'-cyclopentan-4-yl)-1,5-dihydropyrrolo[2,3-d]-pyridazin-4-one, or 3-chloro-2-(2,3-dihydro-7-methoxybenzofuran-2-spiro-1'-cyclopentan-4-yl)-1,5-dihydropyrrolo-[2,3-d]pyridazin-4-one.

14. A pharmaceutical composition which comprises the pyrrolopyridazinone compound according to any one of claim 1 or a -pharmaceutically acceptable salt thereof as an effective ingredient.

\* \* \* \* \*